(12) United States Patent
Dai et al.

(10) Patent No.: US 11,478,474 B2
(45) Date of Patent: Oct. 25, 2022

(54) 2-(3'-(HYDROXYMETHYL)-1-METHYL-5-((5-(2-METHYL-4-(OXETAN-3-YL)PIPERAZIN-1-YL)PYRIDIN-2-YL)AMINO)-6-OXO-1,6-DIHYDRO-[3,4'-BIPYRIDIN]-2'-YL)-7,7-DIMETHYL-7,8-DIHYDRO-2H-CYCLO-PENTA[4,5]PYRROLO[1,2-A]PYRAZIN-1(6H)-ONE AS A BTK INHIBITOR

(71) Applicant: HUTCHISON MEDIPHARMA LIMITED, Shanghai (CN)

(72) Inventors: Guangxiu Dai, Shanghai (CN); Kun Xiao, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 0 days.

(21) Appl. No.: 17/506,220

(22) Filed: Oct. 20, 2021

(65) Prior Publication Data

US 2022/0125785 A1    Apr. 28, 2022

Related U.S. Application Data

(63) Continuation of application No. PCT/CN2021/076869, filed on Feb. 19, 2021.

(30) Foreign Application Priority Data

Feb. 20, 2020  (CN) .......................... 202010104062.2
Feb. 7, 2021   (CN) .......................... 202110169142.0

(51) Int. Cl.
| | | |
|---|---|---|
| *A61K 31/4985* | (2006.01) | |
| *C07D 487/04* | (2006.01) | |
| *A61P 35/00* | (2006.01) | |
| *A61K 31/501* | (2006.01) | |
| *A61K 31/506* | (2006.01) | |
| *A61K 31/53* | (2006.01) | |
| *A61K 31/5377* | (2006.01) | |
| *A61K 45/06* | (2006.01) | |
| *C07D 487/14* | (2006.01) | |
| *C07D 519/00* | (2006.01) | |

(52) U.S. Cl.
CPC ........ *A61K 31/4985* (2013.01); *A61K 31/501* (2013.01); *A61K 31/506* (2013.01); *A61K 31/53* (2013.01); *A61K 31/5377* (2013.01); *A61K 45/06* (2013.01); *A61P 35/00* (2018.01); *C07D 487/04* (2013.01); *C07D 487/14* (2013.01); *C07D 519/00* (2013.01); *C07B 2200/05* (2013.01)

(58) Field of Classification Search
CPC .......................... A61K 31/4985; C07D 487/04
USPC ........................................... 514/250; 544/344
See application file for complete search history.

(56) References Cited

U.S. PATENT DOCUMENTS

2018/0194762 A1   7/2018  Atallah et al.

FOREIGN PATENT DOCUMENTS

| CN | 110256446 A | 9/2019 |
|---|---|---|
| WO | WO 2010/006947 A1 | 1/2010 |
| WO | WO 2011/140488 A1 | 11/2011 |
| WO | WO 2013/067260 A1 | 5/2013 |
| WO | WO 2013/067264 A1 | 5/2013 |
| WO | WO 2013/067274 A1 | 5/2013 |
| WO | WO 2013/067277 A1 | 5/2013 |
| WO | WO 2013/083666 A1 | 6/2013 |
| WO | WO 2015/000949 A1 | 1/2015 |
| WO | WO 2015/082583 A1 | 6/2015 |
| WO | WO 2016/050921 A1 | 4/2016 |
| WO | WO 2016/057500 A1 | 4/2016 |
| WO | WO 2018/035080 A1 | 2/2018 |
| WO | WO 2018/109050 A1 | 6/2018 |
| WO | WO 2019/161152 A1 | 8/2019 |
| WO | WO-2021164735 A1 * | 8/2021 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Crawford et al., "Discovery of GDC-0853: A Potent, Selective, and Noncovalent Bruton's Tyrosine Kinase Inhibitor in Early Clinical Development," *J. Med. Chem.*, (2018), 61, 2227-2245.
International Search Report issued in International Application No. PCT/CN2021/076869, dated Jun. 1, 2021, 7 pages.
Written Opinion of the International Searching Authority for International Application No. PCT/CN2021/076869 dated Jun. 1, 2021, 7 pages.

* cited by examiner

*Primary Examiner* — Douglas M Willis
(74) *Attorney, Agent, or Firm* — Hoxie & Associates LLC

(57) ABSTRACT

The present invention relates to heteroaryl heterocyclic compounds, e.g., the compound of the formula shown below, pharmaceutical compositions comprising same, methods for preparing same, and uses thereof.

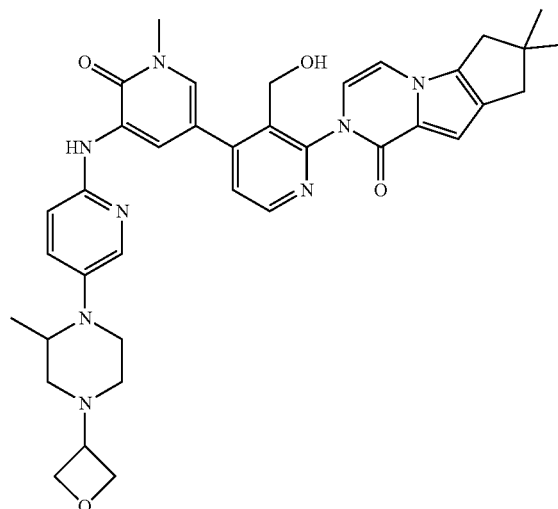

15 Claims, 3 Drawing Sheets

2-(3'-(HYDROXYMETHYL)-1-METHYL-5-((5-(2-METHYL-4-(OXETAN-3-YL)PIPERAZIN-1-YL)PYRIDIN-2-YL)AMINO)-6-OXO-1,6-DIHYDRO-[3,4'-BIPYRIDIN]-2'-YL)-7,7-DIMETHYL-7,8-DIHYDRO-2H-CYCLO-PENTA[4,5]PYRROLO[1,2-A]PYRAZIN-1(6H)-ONE AS A BTK INHIBITOR

CROSS REFERENCE TO RELATED APPLICATIONS

This application is a continuation of International Application No. PCT/CN2021/076869, filed on Feb. 19, 2021, which claims the benefit of Chinese Patent Application Nos. 202010104062.2 filed on Feb. 20, 2020, and 202110169142.0 filed on Feb. 7, 2021, the contents of each of which are incorporated herein by reference.

FIELD OF THE INVENTION

The present invention relates to heteroaryl heterocyclic compounds, pharmaceutical compositions comprising same, methods for preparing same, and uses thereof.

BACKGROUND OF THE INVENTION

Bruton's Tyrosine kinase (BTK), a member of non-receptor tyrosine protein Tec family (including BTK, LTK, TEC, BMX, TXK and the like), is widely expressed in hematopoietic cells except for T cells, NK cells and differentiated plasma cells. BTK plays an important role in signaling mediated by B cell antigen receptor (BCR) and Fcγ receptor (FcγR) in B cells and myeloid cells, respectively. It is a key regulator on the B cell development, activation, signaling and survival. BTK can control the development and differentiation of B cells by activating positive regulatory factors and differentiation factors of cell cycle, and can also control the survival and proliferation of B cells by regulating the expressions of pro-apoptotic proteins and anti-apoptotic proteins. BTK also plays an important role in the migration and adhesion of B lymphoma cells. In addition, BTK plays a role in many other hematopoietic signaling pathways, such as Toll-like receptor (TLR) and cytokine receptor-mediated TNF-α production in macrophages, signaling mediated by IgE receptor (FceRI) in mast cells, inhibition of Fas/APO-1 induced apoptotic signal in B-type lymphoid cells, and collagen induced platelet aggregation.

In humans, BTK gene mutation would lead to a hereditary immunodeficiency disease, X-linked agammaglobulinaemia (XLA). Point mutation of BTK gene is implicated in human XLA patients, associated with low to undetective BTK mRNA level and BTK protein expression, as a consequence, almost completely lack of the maturation and the development of B cells and immunoglobulins, and significant attenuation of persistent calcium signal in response to BCR stimulation. The effect of BTK mutation is only restricted on B cell populations, no significant development defects in other immune cells found in XLA patients. Spontaneous mutations of BTK gene were also found in X-linked immunodeficiency (xid) mice, showing a similar but less severe phenotype. In xid mice or mutation induced BTK gene knock-out mice, B cell differentiation was partially blocked at the B cell stage, with reduced number of mature B cells in blood circulation, and resistance to models of collagen-induced arthritis and *staphylococcus*-induced arthritis. It has been indicated by a large amount of evidences that BTK is abundantly expressed in the circulating B cells in the patients with autoimmune diseases such as rheumatoid arthritis (RA), primary Sjogren's syndrome (pSS) and systemic lupus erythematosus (SLE), as well as B-cell leukemia and lymphoma. The aberrant activation of BCR signaling has been confirmed in these autoimmune diseases and B cell related diseases. Inhibition of B cells, BCR signaling pathway and BTK may slow down the progression of the diseases to varying degrees.

Based on the key role of BTK in the development and functions of B cells, BTK is considered as a potential target for the treatment of B cell malignancies and autoimmune diseases. A variety of BTK inhibitors are being developed for the clinical research of hematologic malignancies and autoimmune diseases. Small molecule BTK inhibitors (such as ibrutinib, acalabrutinib, zanubrutinib, PRN1008, GDC-0853) have shown promising therapeutic efficacies. For example, ibrutinib, an irreversible BTK inhibitor, with a relatively high durable efficacy and low toxicity in clinical studies, has been approved by U.S. Food and Drug Administration (FDA) for the treatment of relapsed mantle cell lymphoma (MCL) in 2013, chronic lymphocytic leukemia (CLL) in 2014, Waldenström's macroglobulinaemia (WM) in 2015, and relapsed/refractory marginal zone lymphoma (MZL) in 2017. In particular, the approved indications were extended to chronic graft-versus-host disease (GVHD) in 2017, demonstrating the mechanism of BTK in the treatment of chronic autoimmune diseases. In addition, the irreversible BTK inhibitor acalabrutinib was approved for the treatment of adult MCL in 2017 and for CLL in 2019; zanubrutinib was approved by FDA for the treatment of MCL in November 2019; and a phase 3 study of PRN1008 against pemphigus is ongoing. Some irreversible BTK inhibitors (tirabrutinib, spebrutinib, and evobrutinib) and reversible BTK inhibitors (GDC-0853, ARQ-531 and LOXO-305) have been on the stage of pre-clinical and clinical development.

Therefore, BTK inhibitors represent attractive therapy for the treatment of related diseases, especially cancer, inflammatory diseases or autoimmune diseases.

SUMMARY OF THE INVENTION

Provided is a compound of formula (I):

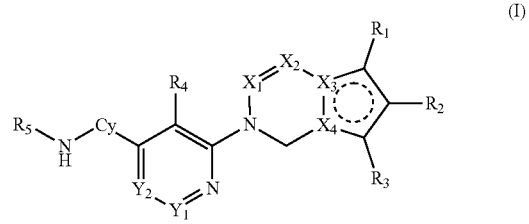

or a pharmaceutically acceptable salt thereof, or a solvate, a racemic mixture, an enantiomer, a diastereomer or a tautomer thereof, wherein $X_1$ and $X_2$ are each independently CH or N; or, $X_1$ is N, $X_2$ is $CR_{14}$, wherein $R_{14}$ is chosen from $C_{1-6}$ alkyl;

$X_3$ and $X_4$ are each independently C or N;

$Y_1$ and $Y_2$ are each independently $CR_{10}$ or N;

$R_1$ and $R_2$ are each independently chosen from hydrogen, deuterium, halogen, $C_{1-6}$ alkyl, $C_{2-6}$ alkynyl, $C_{1-6}$ haloalkyl, $C_{3-6}$ cycloalkyl and phenyl; or $R_1$ and $R_2$ together with the carbon atoms to which they are attached form the following structures:

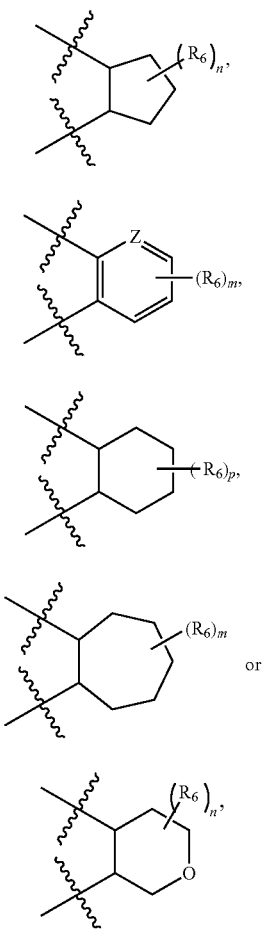

(I-1)

(I-2)

(I-3)

(I-4)

or (I-5)

wherein $R_6$ is independently chosen from deuterium, halogen, hydroxyl, $C_{1-6}$ alkyl, $C_{2-6}$ alkynyl, $C_{1-6}$ deuteroalkyl and $C_{1-6}$ haloalkyl; or two $R_6$ together with the carbon atoms to which they are attached form 3-6 membered cycloalkyl; m is 0, 1, 2, 3 or 4; p is 1, 2, 3 or 4; Z is N or $CR_7$; $R_7$ is chosen from hydrogen, deuterium, $C_{1-6}$ alkyl, halogen and $C_{1-6}$ haloalkyl;

or $R_1$ and $R_2$ together with the carbon atoms to which they are attached form

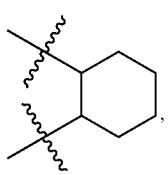

(I-6)

provided that $R_3$ is halogen, or both $X_1$ and $X_2$ are not CH at the same time;

$R_3$ is hydrogen, deuterium, halogen or $C_{1-6}$ haloalkyl;

$R_4$ is hydrogen, halogen, —CN, $C_{1-6}$ alkyl, $C_{2-6}$ alkynyl, —($C_{1-3}$ alkyl)-OH, —($C_{1-3}$ alkyl)-O—($C_{1-3}$ alkyl), —O—($C_{1-3}$ alkyl), —CHO, —C(O)NH$_2$, —C(O)NHCH$_3$, —C(O)N(CH$_3$)$_2$ or 3-hydroxyl-oxetan-3-yl, wherein the $C_{1-6}$ alkyl or $C_{1-3}$ alkyl is each optionally substituted with one or more deuterium or halo;

Cy is

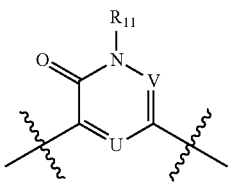 or 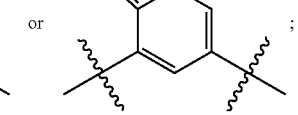

wherein $R_{11}$ is chosen from hydrogen, $C_{1-6}$ alkyl and $C_{3-6}$ cycloalkyl, wherein the $C_{1-6}$ alkyl is optionally substituted with one or more deuterium or halo;

U, V and W are each independently N or $CR_{12}$; $R_{12}$ is hydrogen, deuterium or halogen;

$R_5$ is hydrogen, $C_{1-6}$ alkyl, —C(O)—($C_{1-6}$ alkyl), —C(O)—($C_{3-6}$ cycloalkyl), —C(O)-phenyl, —C(O)NH—($C_{1-6}$ alkyl), —C(O)NH—($C_{3-6}$ cycloalkyl), —C(O)N($C_{1-6}$ alkyl)$_2$, phenyl, 5-6 membered monocyclic heteroaryl or 8-10 membered bicyclic heteroaryl, wherein the $C_{1-6}$ alkyl, $C_{3-6}$ cycloalkyl, phenyl, 5-6 membered monocyclic heteroaryl or 8-10 membered bicyclic heteroaryl is each optionally substituted with one or more groups chosen from:
  1) halogen;
  2) oxo;
  3) —CN;
  4) $C_{1-6}$ alkyl;
  5) $C_{2-6}$ alkenyl;
  6) $C_{2-6}$ alkynyl;
  7) $C_{1-6}$ alkoxy;
  8) $C_{1-6}$ haloalkyl;
  9) —($C_{1-6}$ alkyl)-OH;
  10) —($C_{1-6}$ alkyl)-O—($C_{1-6}$ alkyl);
  11) $C_{3-6}$ cycloalkyl;
  12) 3-12 membered heterocyclyl optionally substituted with one or more groups chosen from: deuterium, halogen, hydroxyl, oxo, —CN, $C_{1-6}$ alkyl, $C_{1-6}$ haloalkyl, $C_{3-6}$ cycloalkyl, $C_{2-6}$ alkynyl, $C_{1-6}$ alkoxy, —($C_{1-6}$ alkyl)-CN, —($C_{1-6}$ alkyl)-O—($C_{1-6}$ alkyl), —($C_{1-6}$ alkyl)-OH, 4-6 membered heterocyclyl and deuterated 4-6 membered heterocyclyl, wherein the $C_{1-6}$ alkyl, $C_{3-6}$ cycloalkyl or 4-6 membered heterocyclyl is each optionally substituted with one or more groups chosen from: deuterium, halogen, —NH$_2$, —OH, —NH($C_{1-6}$ alkyl), —N($C_{1-6}$ alkyl)$_2$ and —NH($C_{3-6}$ cycloalkyl);
  13) 5-6 membered monocyclic heteroaryl optionally substituted with one or more groups chosen from: halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O—($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and 4-6 membered heterocyclyl;
  14) phenyl optionally substituted with one or more groups chosen from: halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O—($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N—($C_{1-6}$ alkyl)$_2$, —($C_{1-6}$ alkyl)-NH($C_{3-6}$ cycloalkyl) and 4-6 membered heterocyclyl;
  15) —NR$_a$'R$_a$", wherein R$_a$' and R$_a$" are each independently chosen from hydrogen, $C_{1-6}$ alkyl, $C_{3-6}$ cycloalkyl, —($C_{1-6}$ alkyl)-O—($C_{1-6}$ alkyl) and 4-6 membered heterocyclyl, wherein the 4-6 membered heterocyclyl is optionally substituted with one or more substituents of —($C_{1-6}$ alkyl)-OH, the $C_{1-6}$ alkyl is optionally substituted with one or more —NR$_e$'R$_e$", and R$_e$' and R$_e$" are each independently chosen from hydrogen, C$_{1-6}$ alkyl, —(C$_{1-6}$ alkyl)-OH and 4-6 membered heterocyclyl;

16) —C(O)NR$_b$'R$_b$", wherein R$_b$' and R$_b$" together with the N atoms to which they are attached form 4-6 membered heterocyclyl optionally substituted with one or more groups chosen from: deuterium, halogen, —OH, C$_{1-6}$ alkyl, —(C$_{1-6}$ alkyl)-NH$_2$, —(C$_{1-6}$ alkyl)-NH(C$_{1-6}$ alkyl), —(C$_{1-6}$ alkyl)-N(C$_{1-6}$ alkyl)$_2$, —(C$_{1-6}$ alkyl)-NH(C$_{3-6}$ cycloalkyl), —NH$_2$, —NH(C$_{1-6}$ alkyl), —N(C$_{1-6}$ alkyl)$_2$, —NH(C$_{3-6}$ cycloalkyl) and —(C$_{1-6}$ alkyl)-OH; and 17) —C(O)R$_c$, wherein R$_c$ is chosen from hydrogen, C$_{1-6}$ alkyl, C$_{2-6}$ alkenyl, C$_{2-6}$ alkynyl, —(C$_{1-6}$ alkyl)-OH and —(C$_{1-6}$ alkyl)-O—(C$_{1-6}$ alkyl);

R$_{10}$ is hydrogen, deuterium, halogen, CN, C$_{1-6}$ alkyl or C$_{1-6}$ haloalkyl;

provided that if R$_1$ and R$_2$ together with the carbon atoms to which they are attached form the following structures:

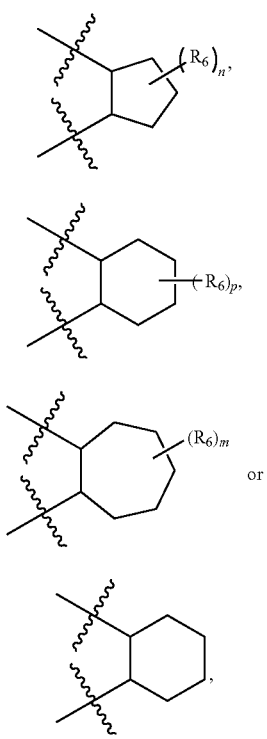

and Cy is

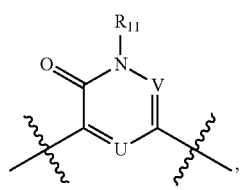

then the 3-12 membered heterocyclyl, when substituted, is not piperazin-1-yl substituted with C$_{1-6}$ alkyl at both 2- and 6-positions.

The above compounds and the active compounds (including general structural formula compounds and specific compounds) disclosed in the context of the present invention, including pharmaceutically acceptable salts thereof, or solvates, racemic mixtures, enantiomers, diastereomers or tautomers thereof, which are covered by the above scope, are collectively referred to herein as "compounds of the present invention".

Also provided is a pharmaceutical composition, comprising the compounds of the present invention, and optionally comprising a pharmaceutically acceptable excipient.

Also provided is a method of in vivo or in vitro inhibiting the activity of BTK, comprising contacting BTK with an effective amount of the compounds of the present invention.

Also provided is a method of treating or preventing a disease mediated by BTK or at least in part by BTK, comprising administering to the subject in need thereof an effective amount of the compounds of the present invention.

Also provided is a method of treating or preventing cancer, an inflammatory disease or autoimmune disease, comprising administering to the subject in need thereof an effective amount of the compounds of the present invention.

Also provided is a use of the compounds of the present invention for treating or preventing a disease mediated by BTK or at least in part by BTK.

Also provided is a use of the compounds of the present invention for treating or preventing cancer, an inflammatory disease or autoimmune disease.

Also provided is a use of the compounds of the present invention in the manufacture of a medicament for treating or preventing a disease mediated by BTK or at least in part by BTK.

Also provided is a use of the compounds of the present invention in the manufacture of a medicament for treating or preventing cancer, an inflammatory disease or autoimmune disease.

Also provided are the compounds of the present invention for in vivo or in vitro inhibiting the activity of BTK.

Also provided are the compounds of the present invention for use as a medicament.

Also provided is a use of the compounds of the present invention for use as a medicament for treating or preventing a disease mediated by BTK or at least in part by BTK, especially for treating or preventing cancer, an inflammatory disease or autoimmune disease.

Also provided is a pharmaceutical combination, comprising the compounds of the present invention and at least one additional therapeutic agent, wherein the therapeutic agent is preferably chosen from: an anti-inflammatory agent, an immunomodulator or an anti-tumor active agent, wherein the anti-tumor active agent includes a chemotherapeutic agent, an immune checkpoint inhibitor or agonist, and a targeted therapeutic agent.

Also provided is a kit for treating or preventing a disease mediated by BTK or at least in part by BTK. The kit can comprise the pharmaceutical composition of the present invention and instructions for use, and the pharmaceutical composition comprises the compounds of the present invention.

DETAILED DESCRIPTION OF THE INVENTION

Definitions

Figure 1:
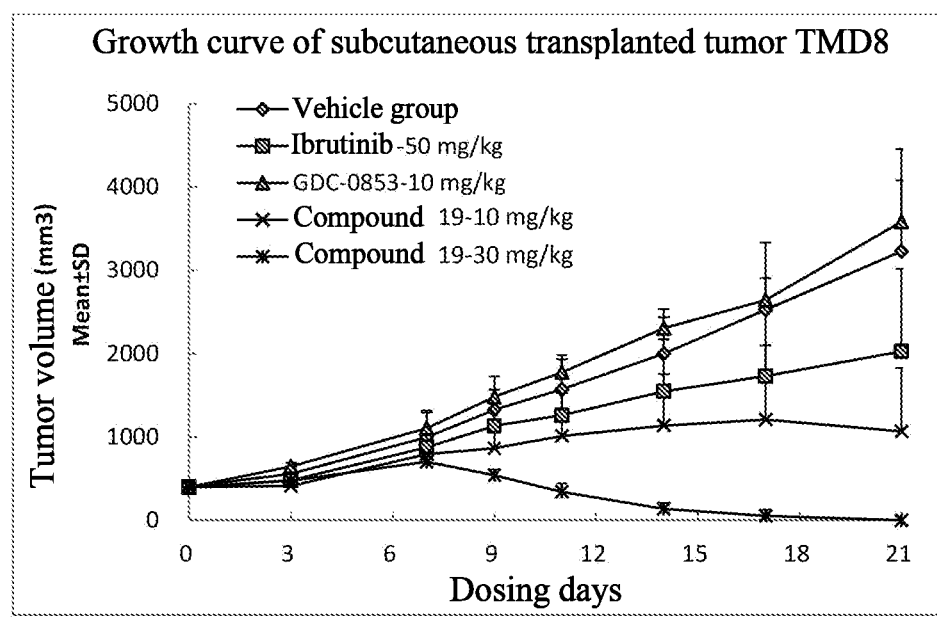
FIG. 1: Growth curve of subcutaneous transplanted tumor TMD8.

As used in the present application, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —$OR^3$ refers to the attachment of $R^3$ to the rest of the molecule through an oxygen atom.

The term "alkyl" as used herein refers to a straight or branched saturated hydrocarbon radical containing 1-18 carbon atoms ($C_{1-8}$), preferably 1-10 carbon atoms ($C_{1-10}$), more preferably 1-6 carbon atoms ($C_{1-6}$), and further more preferably 1-4 carbon atoms ($C_{1-4}$) or 1-3 carbon atoms ($C_{1-3}$). When the term "alkyl" is prefixed with "C", it means the number of carbon atoms. For example, "$C_{1-6}$ alkyl" refers to an alkyl containing 1-6 carbon atoms. "$C_{1-3}$ alkyl" refers to an alkyl containing 1-3 carbon atoms. Examples of $C_{1-6}$ alkyl include, but are not limited to, methyl, ethyl, propyl (e.g. n-propyl, i-propyl), butyl (eg. n-butyl, i-butyl, s-butyl and t-butyl), pentyl (e.g. n-pentyl, i-pentyl, neo-pentyl), and hexyl, and the like.

The term "alkenyl" as used herein refers to a straight or branched unsaturated hydrocarbon radical containing one or more, for example 1, 2, or 3 carbon-carbon double bonds (C=C) and 2-18 carbon atoms ($C_{2-18}$), preferably 2-10 carbon atoms ($C_{2-10}$), more preferably 2-6 carbon atoms ($C_{2-6}$), and further more preferably 2-4 carbon atoms ($C_{2-4}$). When the term "alkenyl" is prefixed with "C", it means the number of carbon atoms. For example, "$C_{2-6}$ alkenyl" refers to an alkenyl containing 2-6 carbon atoms. "$C_{2-4}$ alkenyl" refers to an alkenyl containing 2-4 carbon atoms. Examples of $C_{2-6}$ alkenyl include, but are not limited to, vinyl, propenyl (eg. 2-propenyl), and butenyl (eg. 2-butenyl), and the like. The point of attachment for the alkenyl can be on or not on the double bonds.

The term "alkynyl" as used herein refers to a straight or branched unsaturated hydrocarbon radical containing one or more, for example 1, 2, or 3, carbon-carbon triple bonds (C≡C) and 2-18 carbon atoms ($C_{2-18}$), preferably 2-10 carbon atoms ($C_{2-10}$), more preferably 2-6 carbon atoms ($C_{2-6}$), and further more preferably 2-4 carbon atoms ($C_{2-4}$). When the term "alkynyl" is prefixed with "C", it means the number of carbon atoms. For example, "$C_{2-6}$ alkynyl" refers to an alkynyl containing 2-6 carbon atoms. "$C_{2-4}$ alkynyl" refers to an alkynyl containing 2-4 carbon atoms. Examples of $C_{2-6}$ alkynyl include, but are not limited to, ethynyl, propynyl (eg. 2-propynyl), and butynyl (eg. 2-butynyl), and the like. The point of attachment for the alkynyl can be on or not on the triple bonds.

The term "halogen" or "halo" as used herein means fluoro, chloro, bromo, and iodo, preferably fluoro, chloro and bromo, more preferably fluoro and chloro.

The term "haloalkyl" as used herein refers to an alkyl radical, as defined herein, in which one or more, for example 1, 2, 3, 4, or 5, hydrogen atoms are replaced with halogen atom, and when more than one hydrogen atoms are replaced with halogen atoms, the halogen atoms may be the same or different from each other. In one embodiment, the term "haloalkyl" as used herein refers to an alkyl radical, as defined herein, in which two or more, such as 2, 3, 4, or 5 hydrogen atoms are replaced with halogen atoms, wherein the halogen atoms are identical to each other. In another embodiment, the term "haloalkyl" as used herein refers to an alkyl radical, as defined herein, in which two or more hydrogen atoms, such as 2, 3, 4, or 5 hydrogen atoms are replaced with halogen atoms, wherein the halogen atoms are different from each other. When the term "haloalkyl" is prefixed with "C", it means the number of carbon atoms. For example, "$C_{1-6}$ haloalkyl" refers to a haloalkyl as defined herein containing 1-6 carbon atoms. "$C_{1-4}$ haloalkyl" refers to a haloalkyl as defined herein containing 1-4 carbon atoms. Examples of $C_{1-6}$ haloalkyl include, but are not limited to —$CF_3$, —$CHF_2$, —$CH_2F$, —$CH_2CF_3$, —$CH(CF_3)_2$, and the like.

The term "cycloalkyl" as used herein refers to saturated or partially unsaturated cyclic hydrocarbon radical having 3-12 ring carbon atoms ($C_{3-12}$), such as 3-8 ring carbon atoms ($C_{3-8}$), 5-7 ring carbon atoms ($C_7$), 4-7 ring carbon atoms ($C_{4-7}$) or 3-6 ring carbon atoms ($C_{3-6}$), which may have one or more rings, such as 1, 2, or 3 rings, preferably 1 or 2 rings. When the term "cycloalkyl" is prefixed with "C", it means the number of carbon atoms. For example, "$C_{3-6}$ cycloalkyl" or "3-6 membered cycloalkyl" refers to a cycloalkyl containing 3-6 ring carbon atoms. The cycloalkyl may include a fused or bridged ring, or a spirocyclic ring. The rings of the cycloalkyl may be saturated or has one or more, for example, one or two double bonds (i.e. partially unsaturated), but not fully conjugated, and not an aryl as defined herein. Examples of $C_{3-6}$ cycloalkyl include, but are not limited to cyclopropyl, cyclobutyl, cyclopentyl, cyclohexyl, spiro[2.2]pentyl, cyclopropenyl, cyclobutenyl, cyclopentenyl, cyclopentadienyl, cyclohexenyl, etc.

The term "heterocyclyl" or "heterocyclic" as used herein can be used interchangeably and each refers to saturated or partially unsaturated cyclic radicals having 3-12 ring atoms, such as 3-8 ring atoms, 4-8 ring atoms, 4-6 ring atoms or 4-5 ring atoms, and containing one or more, for example 1, 2 or 3, preferably 1 or 2 heteroatoms independently chosen from N, O and S in the rings, with the remaining ring atoms being carbon; it may have one or more rings, for example 1, 2 or 3, preferably 1 or 2 rings. The heterocyclyl also includes those wherein the N or S heteroatom are optionally oxidized to various oxidation states. The point of attachment of heterocyclyl can be on the N heteroatom or carbon. For example, "4-8 membered heterocyclyl" represents a heterocyclyl having 4-8 (4, 5, 6, 7 or 8) ring atoms comprising at least one, such as 1, 2 or 3, preferably 1 or 2 heteroatoms independently chosen from N, O and S; "4-6 membered heterocyclyl" represents a heterocyclyl having 4-6 (4, 5 or 6) ring atoms comprising at least one, preferably 1 or 2 heteroatoms independently chosen from N, O and S (preferably N and O), which is preferably a monocyclic ring; and "4-5 membered heterocyclyl" represents a heterocyclyl having 4-5 ring atoms comprising at least one, preferably 1 or 2 heteroatoms independently chosen from N, O and S (preferably N and O), which is a monocyclic ring. The heterocyclyl also includes a fused or bridged ring, or a spirocyclic ring. The rings of the heterocyclyl may be saturated or has one or more, for example, one or two double bonds (i.e. partially unsaturated), but not fully conjugated, and not a heteroaryl as defined herein. Examples of heterocyclyl include, but are not limited to: 4-8 membered heterocyclyl, 4-6 membered heterocyclyl and 4-5 membered heterocyclyl, such as oxetanyl, azetidinyl, pyrrolidyl, tetrahydrofuranyl, dioxolanyl, tetrahydropyranyl, morpholinyl, thiomorpholinyl, piperidyl, piperazinyl, tetrahydropyridyl, pyrazinyl, pyrazolidinyl and oxaspiro[3.3]heptyl, preferably oxetanyl (such as oxetan-3-yl), azetidinyl, tetrahydropyranyl, morpholinyl (such as morpholino), piperazinyl (such as piperazin-1-yl), tetrahydropyridyl (such as 1,2,3,6-tetrahydropyridyl).

The term "aryl" or "aromatic ring" as used herein can be used interchangeably and each refers to carbocyclic hydrocarbon radical of 6 to 14 carbon atoms consisting of one ring or more fused rings, wherein at least one ring is an aromatic ring. Examples of aryl include, but are not limited to phenyl, naphthalenyl, 1,2,3,4-tetrahydronaphthalenyl, phenanthryl, indenyl, indanyl, azulenyl, preferably phenyl and naphthalenyl.

The term "heteroaryl" or "heteroaromatic ring" as used herein can be used interchangeably and each refers to: mono-, bi-, or tri-ring system having 5-15 ring atoms, preferably 5-12 ring atoms, more preferably 5-10 ring atoms, and most preferably 5-6 or 8-10 ring atoms, wherein at least one ring is 5- or 6-membered aromatic ring containing one or more, for example 1 to 4, heteroatoms independently chosen from N, O, and S, wherein S and N may be optionally oxidized to various oxidation states. When the total number of S and O atoms in the heteroaryl group exceeds 1, said S and O heteroatoms are not adjacent to one another. Preferably, the heteroaryl is 5-12 membered heteroaryl. For example, the heteroaryl includes: a 5-6 membered monocyclic heteroaryl, i.e., a monocyclic ring aromatic hydrocarbyl having 5 or 6 ring atoms, wherein the ring atoms include one or more, such as 1, 2 or 3 heteroatoms independently chosen from N, O and S (preferably N), and the remaining ring atoms are carbon atoms; and the heteroaryl is preferably triazolyl, pyridyl, pyrazinyl, pyrimidyl, pyrazolyl, imidazolyl, isoxazolyl, triazinyl, oxazolyl, thiadiazolyl, and pyridazinyl, more preferably triazolyl (such as 1H-1,2,3-triazole), pyridyl (such as pyridin-2-yl), pyrazinyl, and pyrimidyl, and a 8-10 membered bicyclic heteroaryl, i.e., a bicycle aromatic hydrocarbyl having 8, 9 or 10 ring atoms, wherein the ring atoms include one or more, such as 1, 2, 3 or 4, preferably 1, 2 or 3 heteroatoms independently chosen from N, O and S (preferably N), and the remaining ring atoms are carbon atoms, wherein at least one ring is an aromatic ring; which is preferably 4,5,6,7-tetrahydropyrazolo[1,5-a]pyrazine, such as 4,5,6,7-tetrahydropyrazolo[1,5-a]pyrazin-2-yl.

Examples of heteroaryl include, but are not limited to: 5-6 membered monocyclic heteroaryl, such as pyridyl, N-oxide pyridyl, pyrazinyl, pyrimidyl, triazinyl, pyrazolyl, imidazolyl, oxazolyl, isoxazolyl, oxadiazolyl (such as 1,2,4-oxadiazolyl, 1,2,5-oxadiazolyl and 1,3,4-oxadiazolyl), thiazolyl, isothiazolyl, thiadiazolyl, tetrazolyl, triazolyl, thienyl, furanyl, pyranyl, pyrrolyl, and pyridazinyl; and a 8-10 membered bicyclic heteroaryl, such as benzooxazolyl, benzisoxazolyl, benzothienyl, benzoisothienyl, benzothiazolyl, benzoisothiazolyl, imidazopyridyl (such as imidazo[1,2-a]pyridyl), imidazopyridazinyl (such as imidazo[1,2-b]pyridazinyl), pyrrolopyridyl (such as 1H-pyrrolo[2,3-b]pyridyl), pyrrolopyrimidyl (such as pyrrolo[3,4-d] pyrimidyl), pyrazolopyridyl (such as 1H-pyrazolo[3,4-b]pyridyl), pyrazolopyrimidyl (such as pyrazolo[1,5-a]pyrimidyl), triazolopyridyl (such as [1,2,4]triazolo[4,3-a]pyridyl and [1,2,4]triazolo[1,5-a]pyridyl), tetrazolopyridyl (such as tetrazolo[1,5-a]pyridyl), benzofuranyl, indolyl, indazolyl, purinyl, quinolyl, isoquinolinyl, and 6,7-dihydro-4H-pyrazolo[5,1-c][1,4]oxazine.

The term "—OH" as used herein refers to hydroxyl radical.

The term "—CN" as used herein refers to cyano radical.

The term "oxo" as used herein refers to =O.

Any asymmetric atom (e.g. carbon, etc.) of a compound of formula (I) may exist in an racemic or enantiomeric rich form, for example in (R)-, (S)- or (RS)-configuration. In some embodiments, asymmetric atoms have at least 50%, at least 60%, at least 70%, at least 80%, at least 90%, at least 95%, at least 99%, or 100% enantiomeric excess in (R)- or (S) configurations, respectively.

When a structural formula or chemical name herein contains "(RS)", it means any mixture of (R) configuration and (S) configuration of the compound.

The term "optional" or "optionally" as used herein means that the subsequently described event or circumstance may or may not occur, and the description includes instances wherein the event or circumstance occur and instances in which it does not occur. For example, "optionally substituted with one or more" includes unsubstituted and substituted with 1, 2, 3 or more substituents as described. It will be understood by those skilled in the art, with respect to any group containing one or more substituents, that such groups are not intended to introduce any substitution or substitution patterns that are sterically impractical, chemically incorrect, synthetically non-feasible and/or inherently unstable.

The term "substituted" or "substituted with . . . ", as used herein, means that one or more (such as, 1, 2, 3 or 4) hydrogens on the designated atom or group are replaced with one or more (such as 1, 2, 3 or 4) substituents, preferably the substituents chosen from the indicated group of substituents or radicals, provided that the designated atom's normal valence is not exceeded. The said substituents may be the same or different from each other. The term "substituted with one or more groups chosen from" or "substituted with one or more" as used herein means that one or more hydrogens on the designated atom or group are independently replaced with one or more radicals from the indicated group of substituents or radicals, wherein the said radicals may be the same or different from each other. Preferably, "substituted with one or more groups chosen from" or "substituted with one or more" means that the designated atom or group is substituted with 1, 2, 3, or 4 radicals independently chosen from the indicated group of substituents or radicals, wherein the said radicals may be the same or different from each other. In some embodiments, when a substituent is oxo (i.e., =O), then 2 hydrogens on a single atom are replaced by the oxo. An optional substituent can be any radicals, provided that combinations of substituents and/or variables result in a chemically correct and stable compound. A chemically correct and stable compound is meant to imply a compound that is sufficiently robust to survive sufficient isolation from a reaction mixture to be able to identify the chemical structure of the compound. Preferably, substituents are those exemplified in the compounds of the embodiment of the present application.

Unless otherwise specified, substituents are named into the core structure. For example, it is to be understood that when (cycloalkyl)alkyl is listed as a possible substituent, the point of attachment of this substituent to the core structure is in the alkyl portion.

It will be appreciated by the person of ordinary skill in the art ("POSITA") that some of the compounds of formula (I) may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the POSITA that the present invention includes all the individual stereoisomers (e.g. enantiomers), racemic mixtures or partially resolved mixtures of the compounds of formula (I) and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "Topics in Stereochemistry", Vol. 6, Wiley Interscience, 1971) and include physical methods such as chromatography using a chiral adsorbent. Individual isomers can be prepared in chiral form from chiral precursors. Alternatively, individual isomers can be separated chemically from a mixture by: forming diastereomeric salts with a chiral acid (such as the individual enantiomers of 10-camphorsulfonic acid, camphoric acid, alpha-bromocamphoric acid, tartaric acid, diacetyltartaric acid, malic acid, pyrrolidone-5-carboxylic acid, and the like), fractionally crystallizing the salts, and then freeing one or both of the resolved bases, optionally repeating the process, so as obtain either or both substantially free of the other; i.e., in a form having an optical purity of >95%. Alternatively, the racemates can be covalently linked to a chiral compound (auxiliary) to produce diastereomers which can be separated by chromatography or by fractional crystallization after which time the chiral auxiliary is chemically removed to afford the pure enantiomers, as is known to the POSITA.

The term "tautomer" as used herein refers to constitutional isomers of compounds generated by rapid movement of an atom in two positions in a molecule. Tautomers readily interconvert into each other, e.g., enol form and ketone form are tipical tautomers.

A "pharmaceutically acceptable salt" is intended to mean a salt of a free acid or base of a compound of Formula (I) that is non-toxic, biologically tolerable, or otherwise biologically suitable for administration to the subject. For example, an acid addition salt includes such as a salt derived from an inorganic acid and an organic acid. Said inorganic acid includes such as hydrochloric acid, hydrobromic acid, hydroiodic acid, sulfuric acid, phosphoric acid, and nitric acid; said organic acid includes such as p-toluenesulfonic acid, salicylic acid, methanesulfonic acid, oxalic acid, succinic acid, citric acid, malic acid, lactic acid, fumaric acid, and the like. For examples, see, generally, S. M. Berge, et al., "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002.

In addition, if a compound of the present invention herein is obtained as an acid addition salt, the free base can be obtained by basifying a solution of the acid addition salt. Conversely, if the product is a free base, an acid addition salt, particularly a pharmaceutically acceptable acid addition salt, may be produced by dissolving the free base in a suitable solvent and treating the solution with an acid, in accordance with conventional procedures for preparing acid addition salts from base compounds. The POSITA will recognize various synthetic methodologies that may be used without undue experimentation to prepare non-toxic pharmaceutically acceptable acid addition salts or base addition salts.

The term "deuterated compound" or "deuteride" refers to a compound in which one or more hydrogen atoms, such as 1, 2, 3, 4 or 5 hydrogen atoms, are replaced by deuterium atoms (D). The term "solvates" means solvent addition forms that contain either stoichiometric or non-stoichiometric amounts of solvent. Some compounds have a tendency to trap a fixed molar ratio of solvent molecules in the solid state, thus forming a solvate. If the solvent is water, the solvate formed is a hydrate, when the solvent is alcohol, the solvate formed is an alcoholate. Hydrates are formed by the combination of one or more molecules of water, or less than one molecule of water, with one molecule of the substances in which the water retains its molecular state as $H_2O$, such combination being able to form one or more hydrates, for example, hemihydrate, monohydrate, and dihydrate.

As used herein, the terms "group(s)" and "radical(s)" are synonymous and are intended to indicate functional groups or fragments of molecules attachable to other fragments of molecules.

The term "active ingredient" is used to indicate a chemical substance which has biological activity. In some embodiments, an "active ingredient" is a chemical substance having pharmaceutical utility.

The term "pharmaceutical combination" as used herein means a product obtained by mixing or combining two or more active ingredients, including fixed and non-fixed combinations of active ingredients, such as a kit, and a pharmaceutical composition. The term "fixed combination" means that two or more active ingredients (such as compounds of the present invention and additional therapeutic agents) are administered simultaneously to a patient in the form of a single entity or dose. The term "non-fixed combination" means that two or more active ingredients (such as compounds of the present invention and additional therapeutic agents) are administered simultaneously, in parallel or successively to a patient in separate entities, wherein the administration provides the patient with a therapeutically effective level of the compound.

The terms "treating" or "treatment" or "prevention" of a disease or disorder, in the context of achieving therapeutic benefit, refer to administering one or more pharmaceutical substances, especially a compound of formula (I) described herein to a subject that has the disease or disorder, or has a symptom of a disease or disorder, or has a predisposition toward a disease or disorder, with the purpose to cure, heal, alleviate, relieve, alter, remedy, ameliorate, improve, or affect the disease or disorder, the symptoms of the disease or disorder, or the predisposition toward the disease or disorder. In some embodiments, the disease or disorder is cancer, such as solid tumors or hematologic malignancies, including lymphoma, leukemia and myeloma. In another embodiment, the disease or disorder is an inflammatory diseases or autoimmune disease.

The terms "treating", "contacting" and "reacting," in the context of a chemical reaction, mean adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately lead to the formation of the indicated and/or the desired product.

The term "effective amount" as used herein refers to an amount or dose of an BTK inhibiting agent sufficient to generally bring about a therapeutic benefit in patients in need of treatment for a disease or disorder mediated by BTK or at least in part by BTK. Effective amounts or doses of the active ingredient of the present disclosure may be ascertained by methods such as modeling, dose escalation studies or clinical trials, and by taking into consideration factors, e.g., the mode or route of administration or drug delivery, the pharmacokinetics of the agent, the severity and course of the disease or disorder, the subject's previous or ongoing therapy, the subject's health status and response to drugs, and the judgment of the attending physician.

An exemplary dose is in the range of from about 0.0001 to about 200 mg of active agent per kg of subject's body weight per day, such as from about 0.001 to 100 mg/kg/day, or about 0.01 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 5 g/day. Once improvement of the patient's disease or disorder has occurred, the dose may be adjusted for maintenance treatment. For example, the dosage or the frequency of administration, or both, may be reduced as a function of the symptoms, to a level at which the desired therapeutic effect is maintained. Of course, if symptoms have been alleviated to an appropriate level, treatment may cease. Patients may, however, require intermittent treatment on a long-term basis upon any recurrence of symptoms.

The term "inhibition" or "inhibiting" indicates a decrease in the baseline activity of a biological activity or process. The term "inhibition of BTK activity" is a practical pharmaceutical activity for purposes of this disclosure and refers to a decrease in the activity of BTK as a direct or indirect response to the presence of the compound of the present invention, relative to the activity of BTK in the absence of the compound of the present invention. The decrease in activity may be due to the direct interaction of the compound of the present invention with BTK, or due to the interaction of the compound of the present invention, with one or more other factors that in turn affect the BTK activity. For example, the presence of the compound of the present invention may decrease the BTK activity by directly binding to the BTK, by causing (directly or indirectly) another factor to decrease the BTK activity, or by (directly or indirectly) decreasing the amount of BTK present in the cell or organism.

The term "subject" or "patient" as used herein means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" or "patient" does not denote a particular age or sex. In some embodiments, the subject or patient is a human.

In general, the term "about" is used herein to modify a numerical value above or below the stated value by a variance of 20%.

Technical and scientific terms used herein and not specifically defined have the meaning commonly understood by the POSITA to which the present disclosure pertains.

All numerical ranges herein shall be interpreted as disclosing each numerical value and subset of numerical values within the range, regardless of whether they are specifically otherwise disclosed. For example, when referring to any range of values, it should be regarded as referring to every value within the range of values, for example, every integer within the range of values. For example, $C_{1-6}$ as used herein represents the inclusion of 1, 2, 3, 4, 5 or 6 C. The invention relates to all values falling within the ranges, all smaller ranges and the upper or lower limits of the numerical range.

DETAILED DESCRIPTION OF EMBODIMENTS (I)

Embodiment 1. A compound of formula (I):

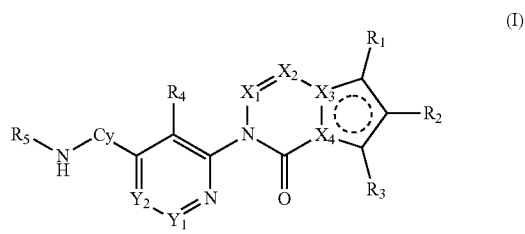

or a pharmaceutically acceptable salt thereof, or a solvate, a racemic mixture, an enantiomer, a diastereomer or a tautomer thereof, wherein $X_1$ and $X_2$ are each independently CH or N; or, $X_1$ is N, $X_2$ is $CR_{14}$, wherein $R_{14}$ is $C_{1-6}$ alkyl;

$X_3$ and $X_4$ are each independently C or N;

$Y_1$ and $Y_2$ are each independently $CR_{10}$ or N;

$R_1$ and $R_2$ are each independently chosen from hydrogen, deuterium, halogen, $C_{1-6}$ alkyl, $C_{2-6}$ alkynyl, $C_{1-6}$ haloalkyl, $C_{3-6}$ cycloalkyl and phenyl;

or $R_1$ and $R_2$ together with the carbon atoms to which they are attached form the following structures:

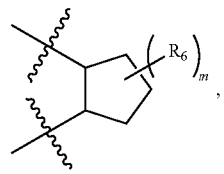

(I-1)

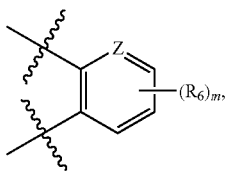

(I-2)

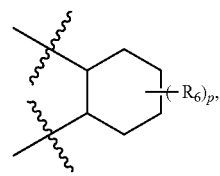

(I-3)

-continued

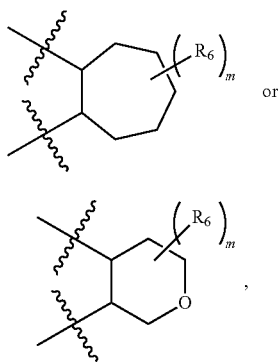

wherein R$_6$ is independently chosen from deuterium, halogen, hydroxyl, C$_{1-6}$ alkyl, C$_{2-6}$ alkynyl, C$_{1-6}$ deuteroalkyl and C$_{1-6}$ haloalkyl; or two R$_6$ together with the carbon atoms to which they are attached form 3-6 membered cycloalkyl; m is 0, 1, 2, 3 or 4; p is 1, 2, 3 or 4;

Z is N or CR$_7$; R$_7$ is chosen from hydrogen, deuterium, C$_{1-6}$ alkyl, halogen and C$_{1-6}$ haloalkyl or R$_1$ and R$_2$ together with the carbon atoms to which they are attached form

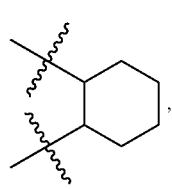

provided that R$_3$ is halogen, or both X$_1$ and X$_2$ are not CH at the same time;

R$_3$ is hydrogen, deuterium, halogen or C$_{1-6}$ haloalkyl;

R$_4$ is hydrogen, halogen, —CN, C$_{1-6}$ alkyl, C$_{2-6}$ alkynyl, —(C$_{1-3}$ alkyl)-OH, —(C$_{1-3}$ alkyl)-O—(C$_{1-3}$ alkyl), —O—(C$_{1-3}$ alkyl), —CHO, —C(O)NH$_2$, —C(O)NHCH$_3$, —C(O)N(CH$_3$)$_2$ or 3-hydroxyl-oxetan-3-yl, wherein the C$_{1-6}$ alkyl or C$_{1-3}$ alkyl is each optionally substituted with one or more deuterium or halo;

Cy is

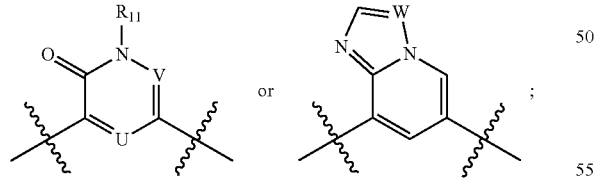

wherein R$_{11}$ is chosen from hydrogen, C$_{1-6}$ alkyl and C$_{3-6}$ cycloalkyl, wherein the C$_{1-6}$ alkyl is optionally substituted with one or more deuterium or halo;

U, V and W are each independently N or CR$_{12}$; R$_{12}$ is hydrogen, deuterium or halogen;

R$_5$ is hydrogen, C$_{1-6}$ alkyl, —C(O)—(C$_{1-6}$ alkyl), —C(O)—(C$_{3-6}$ cycloalkyl), —C(O)-phenyl, —C(O)NH—(C$_{1-6}$ alkyl), —C(O)NH—(C$_{3-6}$ cycloalkyl), —C(O)N(C$_{1-6}$ alkyl)$_2$, phenyl, 5-6 membered monocyclic heteroaryl or 8-10 membered bicyclic heteroaryl, wherein the C$_{1-6}$ alkyl, C$_{3-6}$ cycloalkyl, phenyl, 5-6 membered monocyclic heteroaryl or 8-10 membered bicyclic heteroaryl is each optionally substituted with one or more groups chosen from:
1) halogen;
2) oxo;
3) —CN;
4) C$_{1-6}$ alkyl;
5) C$_{2-6}$ alkenyl;
6) C$_{2-6}$ alkynyl;
7) C$_{1-6}$ alkoxy;
8) C$_{1-6}$ haloalkyl;
9) —(C$_{1-6}$ alkyl)-OH;
10) —(C$_{1-6}$ alkyl)-O—(C$_{1-6}$ alkyl);
11) C$_{3-6}$ cycloalkyl;
12) 3-12 membered heterocyclyl optionally substituted with one or more groups chosen from: deuterium, halogen, hydroxyl, oxo, —CN, C$_{1-6}$ alkyl, C$_{1-6}$ haloalkyl, C$_{3-6}$ cycloalkyl, C$_{2-6}$ alkynyl, C$_{1-6}$ alkoxy, —(C$_{1-6}$ alkyl)-CN, —(C$_{1-6}$ alkyl)-O—(C$_{1-6}$ alkyl), —(C$_{1-6}$ alkyl)-OH, 4-6 membered heterocyclyl and deuterated 4-6 membered heterocyclyl, wherein the C$_{1-6}$ alkyl, C$_{3-6}$ cycloalkyl or 4-6 membered heterocyclyl is each optionally substituted with one or more groups chosen from: deuterium, halogen, —NH$_2$, —OH, —NH(C$_{1-6}$ alkyl), —N(C$_{1-6}$ alkyl)$_2$ and —NH(C$_{3-6}$ cycloalkyl);
13) 5-6 membered monocyclic heteroaryl optionally substituted with one or more groups chosen from: halogen, —CN, —(C$_{1-6}$ alkyl)-CN, —(C$_{1-6}$ alkyl)-OH, C$_{1-6}$ alkyl, C$_{3-6}$ cycloalkyl, C$_{1-6}$ alkoxy, —(C$_{1-6}$ alkyl)-O—(C$_{1-6}$ alkyl), —(C$_{1-6}$ alkyl)-NH$_2$, —(C$_{1-6}$ alkyl)-NH(C$_{1-6}$ alkyl), —(C$_{1-6}$ alkyl)-N(C$_{1-6}$ alkyl)$_2$, —(C$_{1-6}$ alkyl)-NH(C$_{3-6}$ cycloalkyl) and 4-6 membered heterocyclyl;
14) phenyl optionally substituted with one or more groups chosen from: halogen, —CN, —(C$_{1-6}$ alkyl)-CN, —(C$_{1-6}$ alkyl)-OH, C$_{1-6}$ alkyl, C$_{3-6}$ cycloalkyl, C$_{1-6}$ alkoxy, —(C$_{1-6}$ alkyl)-O—(C$_{1-6}$ alkyl), —(C$_{1-6}$ alkyl)-NH$_2$, —(C$_{1-6}$ alkyl)-NH(C$_{1-6}$ alkyl), —(C$_{1-6}$ alkyl)-N—(C$_{1-6}$ alkyl)$_2$, —(C$_{1-6}$ alkyl)-NH(C$_{3-6}$ cycloalkyl) and 4-6 membered heterocyclyl;
15) —NR$_a$'R$_a$", wherein R$_a$' and R$_a$" are each independently chosen from hydrogen, C$_{1-6}$ alkyl, C$_{3-6}$ cycloalkyl, —(C$_{1-6}$ alkyl)-O—(C$_{1-6}$ alkyl) and 4-6 membered heterocyclyl, wherein the 4-6 membered heterocyclyl is optionally substituted with one or more substituents of —(C$_{1-6}$ alkyl)-OH, the C$_{1-6}$ alkyl is optionally substituted with one or more —NR$_e$'R$_e$", and R$_e$' and R$_e$" are each independently chosen from hydrogen, C$_{1-6}$ alkyl, —(C$_{1-6}$ alkyl)-OH and 4-6 membered heterocyclyl;
16) —C(O)NR$_b$'R$_b$", wherein R$_b$' and R$_b$" together with the N atoms to which they are attached form 4-6 membered heterocyclyl optionally substituted with one or more groups chosen from: deuterium, halogen, —OH, C$_{1-6}$ alkyl, —(C$_{1-6}$ alkyl)-NH$_2$, —(C$_{1-6}$ alkyl)-NH(C$_{1-6}$ alkyl), —(C$_{1-6}$ alkyl)-N(C$_{1-6}$ alkyl)$_2$, —(C$_{1-6}$ alkyl)-NH(C$_{3-6}$ cycloalkyl), —NH$_2$, —NH(C$_{1-6}$ alkyl), —N(C$_{1-6}$ alkyl)$_2$, —NH(C$_{3-6}$ cycloalkyl) and —(C$_{1-6}$ alkyl)-OH; and
17) —C(O)R$_c$, wherein R$_c$ is chosen from hydrogen, C$_{1-6}$ alkyl, C$_{2-6}$ alkenyl, C$_{2-6}$ alkynyl, —(C$_{1-6}$ alkyl)-OH and —(C$_{1-6}$ alkyl)-O—(C$_{1-6}$ alkyl);

R$_{10}$ is hydrogen, deuterium, halogen, CN, C$_{1-6}$ alkyl or C$_{1-6}$ haloalkyl;

provided that if R$_1$ and R$_2$ together with the carbon atoms to which they are attached form the following structures:

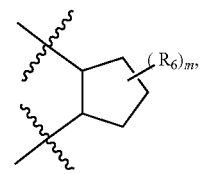 (I-1)

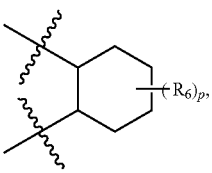 (I-3)

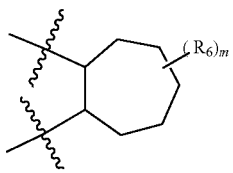 (I-4)

or 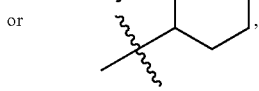 , (I-6)

and Cy is 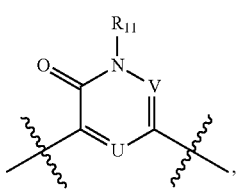 , then the 3-12 membered heterocyclyl, when substituted, is not piperazin-1-yl substituted with $C_{1-6}$ alkyl at both 2- and 6-positions;

for example, $X_1$ and $X_2$ are each independently CH or N; or, $X_1$ is N, $X_2$ is $CR_{14}$, wherein $R_{14}$ is $C_{1-6}$ alkyl; $X_3$ is N, and $X_4$ is C;
both $Y_1$ and $Y_2$ are CH;
$R_3$ is hydrogen, deuterium or halogen;
$R_1$ and $R_2$ together with the carbon atoms to which they are attached form the following structures:

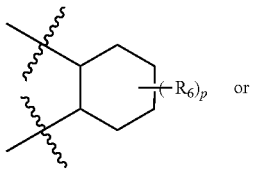 (I-3)

or

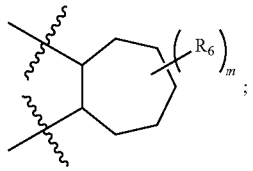 ; (I-4)

wherein $R_6$ is independently chosen from halogen, hydroxyl, $C_{1-6}$ alkyl and $C_{1-6}$ haloalkyl; m is 0, 1 or 2; p is 1, 2 or 3;

or $R_1$ and $R_2$ together with the carbon atoms to which they are attached form

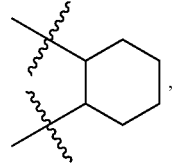 , (I-6)

provided that $R_3$ is halogen, or both $X_1$ and $X_2$ are not CH at the same time;
$R_4$ is —($C_{1-3}$ alkyl)-OH;
Cy is

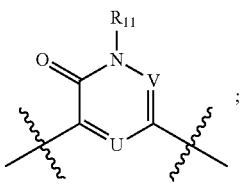 ;

herein $R_{11}$ is $C_{1-6}$ alkyl;
both U and V are CH; and
$R_5$ is chosen from

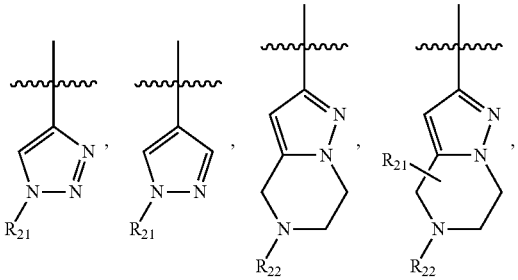

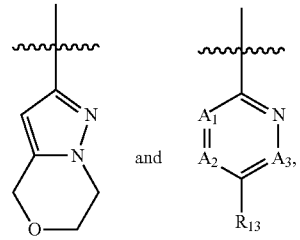

wherein
$R_{21}$ is chosen from $C_{1-6}$ alkyl;
$R_{22}$ is independently chosen from $C_{1-6}$ alkyl, —($C_{1-6}$ alkyl)-O—($C_{1-6}$ alkyl) or 4-6 membered heterocyclyl;
$A_1$, $A_2$ and $A_3$ are each independently CH; and $R_{13}$ is a 6 membered heterocyclyl optionally substituted with one or more substituents chosen from $C_{1-6}$ alkyl and 4 membered heterocyclyl;
provided that the 6 membered heterocyclyl, when substituted, is not a piperazin-1-yl substituted with $C_{1-6}$ alkyl at both 2- and -6 positions.
preferably, $R_1$ and $R_2$ together with the carbon atoms to which they are attached form

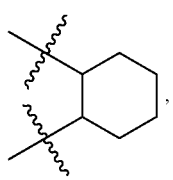
(I-6)

provided that R₃ is halogen, or both X₁ and X₂ are not CH at the same time;

for example, or R₁ and R₂ together with the carbon atoms to which they are attached form the following structure:

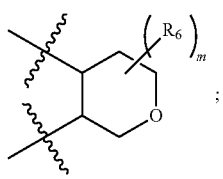
(I-5)

wherein R₆ is independently chosen from deuterium, halogen, hydroxyl, $C_{1-6}$ alkyl, $C_{2-6}$ alkynyl, $C_{1-6}$ deuteroalkyl and $C_{1-6}$ haloalkyl; m is 0, 1 or 2; preferably, m is 0.

Embodiment 2. The compound of embodiment 1, or a pharmaceutically acceptable salt thereof, or a solvate, a racemic mixture, an enantiomer, a diastereomer or a tautomer thereof, wherein R₁ and R₂ together with the carbon atoms to which they are attached form

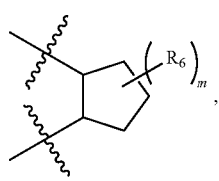
(I-1)

i.e. the compound is a compound of formula (IA):

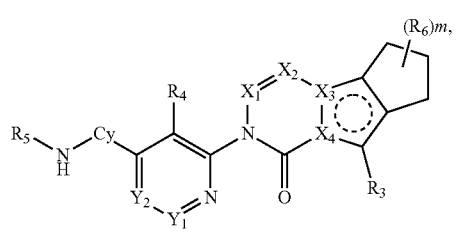
(IA)

Embodiment 3. The compound of embodiment 2, or a pharmaceutically acceptable salt thereof, or a solvate, a racemic mixture, an enantiomer, a diastereomer or a tautomer thereof, wherein R₁ and R₂ together with the carbon atoms to which they are attached form

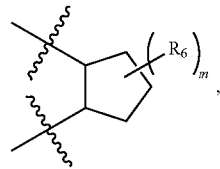
(I-1)

X₃ is N, X₄ is C, Y₁ is CH, Cy is

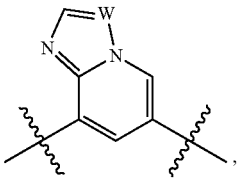

and the compound is a compound of formula (II):

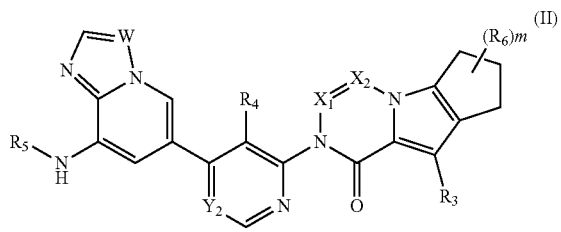
(II)

wherein
X₁ and X₂ are each independently CH or N; or, X₁ is N, X₂ is $CR_{14}$, wherein $R_{14}$ is chosen from $C_{1-6}$ alkyl;
Y₂ is CH or N;
R₃ is hydrogen, deuterium, halogen or $C_{1-6}$ haloalkyl;
R₄ is hydrogen, halogen, —CN, $C_{1-6}$ alkyl, —($C_{1-3}$ alkyl)-OH, —($C_{1-3}$ deuteroalkyl)-OH, —($C_{1-3}$ alkyl)-O—($C_{1-3}$ alkyl), —O—($C_{1-3}$ alkyl), —CHO, —C(O)NH₂, —C(O)NHCH₃, —C(O)N(CH₃)₂ or 3-hydroxyl-oxetan-3-yl, wherein the $C_{1-6}$ alkyl is optionally substituted with one or more halo;
W is N or $CR_{12}$, and $R_{12}$ is hydrogen or halogen;
R₅ is hydrogen, $C_{1-6}$ alkyl, —C(O)—($C_{1-6}$ alkyl), —C(O)—($C_{3-6}$ cycloalkyl), —C(O)-phenyl, —C(O)NH—($C_{1-6}$ alkyl), —C(O)NH—($C_{3-6}$ cycloalkyl), —C(O)N($C_{1-6}$ alkyl)₂, phenyl, 5-6 membered monocyclic heteroaryl or 8-10 membered bicyclic heteroaryl, wherein the $C_{1-6}$ alkyl, $C_{3-6}$ cycloalkyl, phenyl, 5-6 membered monocyclic heteroaryl or 8-10 membered bicyclic heteroaryl is each optionally substituted with one or more groups chosen from:
1) halogen;
2) oxo;
3) —CN;
4) $C_{1-6}$ alkyl;
5) $C_{2-6}$ alkenyl;
6) $C_{2-6}$ alkynyl;
7) $C_{1-6}$ alkoxy;
8) $C_{1-6}$ haloalkyl;
9) —($C_{1-6}$ alkyl)-OH;
10) —($C_{1-6}$ alkyl)-O—($C_{1-6}$ alkyl);
11) $C_{3-6}$ cycloalkyl;

12) 3-12 membered heterocyclyl optionally substituted with one or more substituents chosen from halogen, hydroxyl, oxo, —CN, $C_{1-6}$ alkyl, $C_{1-6}$ haloalkyl, $C_{3-6}$ cycloalkyl, $C_{2-6}$ alkynyl, $C_{1-6}$ alkoxy, —($C_{1-6}$ alkyl)-CN, —($C_{1-6}$ alkyl)-O—($C_{1-6}$ alkyl), —($C_{1-6}$ alkyl)-OH, 4-6 membered heterocyclyl, 4-6 membered fluoroheterocyclyl and deuterated 4-6 membered heterocyclyl, wherein the $C_{1-6}$ alkyl is optionally substituted with one or more —OH;

13) 5-6 membered monocyclic heteroaryl optionally substituted with one or more substituents chosen from halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O—($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and 4-6 membered heterocyclyl;

14) phenyl optionally substituted with one or more substituents chosen from halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and 4-6 membered heterocyclyl;

15) —NR$_a$'R$_a$", wherein R$_a$' and R$_a$" are each independently chosen from hydrogen, $C_{1-6}$ alkyl, $C_{3-6}$ cycloalkyl, —($C_{1-6}$ alkyl)-O—($C_{1-6}$ alkyl) and 4-6 membered heterocyclyl, wherein the 4-6 membered heterocyclyl is optionally substituted with one or more substituents of —($C_{1-6}$ alkyl)-OH, the $C_{1-6}$ alkyl is optionally substituted with one or more —NR$_e$'R$_e$", and R$_e$' and R$_e$" are each independently chosen from hydrogen, $C_{1-6}$ alkyl, —($C_{1-6}$ alkyl)-OH and 4-6 membered heterocyclyl;

16) —C(O)NR$_b$'R$_b$", wherein R$_b$' and R$_b$" together with the N atoms to which they are attached form 4-6 membered heterocyclyl, wherein the 4-6 membered heterocyclyl is optionally substituted with one or more substituents chosen from halogen, —OH, $C_{1-6}$ alkyl, —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and —($C_{1-6}$ alkyl)-OH; and 17) —C(O)R$_c$, wherein R$_c$ is chosen from hydrogen, $C_{1-6}$ alkyl, $C_{2-6}$ alkenyl, $C_{2-6}$ alkynyl and —($C_{1-6}$ alkyl)-O—($C_{1-6}$ alkyl);

$R_6$ is halogen, $C_{1-6}$ alkyl or hydroxyl; and m is 0, 1, 2 or 3;

preferably, W is N or CR$_{12}$, and R$_{12}$ is halogen; and/or preferably, R$_5$ is 5-6 membered monocyclic heteroaryl or 8-10 membered bicyclic heteroaryl optionally substituted with one or more groups chosen from:
1) $C_{1-6}$ alkyl; and
2) 4-6 membered heterocycloalkyl, which is optionally substituted with $C_{1-6}$ alkyl and 4-6 membered heterocyclyl;

preferably, 5-6 membered monocyclic heteroaryl is 5 membered monocyclic heteroaryl, more preferably triazolyl;

preferably, 8-10 membered bicyclic heteroaryl is 8 membered bicyclic heteroaryl, more preferably 4,5,6,7-tetrahydropyrazolo[1,5-a]pyrazinyl.

Embodiment 4. The compound of embodiment 2, or a pharmaceutically acceptable salt thereof, or a solvate, a racemic mixture, an enantiomer, a diastereomer or a tautomer thereof, wherein R$_1$ and R$_2$ together with the carbon atoms to which they are attached form

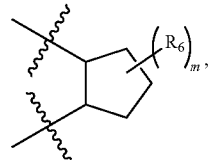

(I-1)

$X_3$ is N, $X_4$ is C, $Y_1$ is CH, Cy is

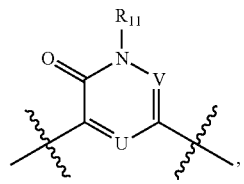

and the compound is a compound of formula (III):

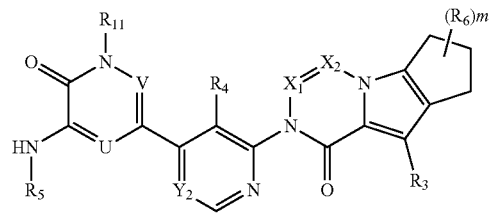

(III)

wherein
$X_1$ and $X_2$ are each independently CH or N; or, $X_1$ is N, $X_2$ is CR$_{14}$, wherein R$_{14}$ is chosen from $C_{1-6}$ alkyl;
$Y_2$ is CH or N;
$R_3$ is hydrogen, deuterium, halogen or $C_{1-6}$ haloalkyl;
$R_4$ is hydrogen, halogen, —CN, $C_{1-6}$ alkyl, —($C_{1-3}$ alkyl)-OH, —($C_{1-3}$ deuteroalkyl)-OH, —($C_{1-3}$ alkyl)-O—($C_{1-3}$ alkyl), —O—($C_{1-3}$ alkyl), —CHO, —C(O)NH$_2$, —C(O)NHCH$_3$, —C(O)N(CH$_3$)$_2$ or 3-hydroxyl-oxetan-3-yl, wherein the $C_{1-6}$ alkyl is optionally substituted with one or more halo;
U and V are each independently chosen from N or CH;
$R_5$ is hydrogen, $C_{1-6}$ alkyl, —C(O)—($C_{1-6}$ alkyl), —C(O)—($C_{3-6}$ cycloalkyl), —C(O)-phenyl, —C(O)NH—($C_{1-6}$ alkyl), —C(O)NH—($C_{3-6}$ cycloalkyl), —C(O)N($C_{1-6}$ alkyl)$_2$, phenyl, 5-6 membered monocyclic heteroaryl or 8-10 membered bicyclic heteroaryl, wherein the $C_{1-6}$ alkyl, $C_{3-6}$ cycloalkyl, phenyl, 5-6 membered monocyclic heteroaryl or 8-10 membered bicyclic heteroaryl is each optionally substituted with one or more groups chosen from:
1) halogen;
2) oxo;
3) —CN;
4) $C_{1-6}$ alkyl;
5) $C_{2-6}$ alkenyl;
6) $C_{2-6}$ alkynyl;
7) $C_{1-6}$ alkoxy;
8) $C_{1-6}$ haloalkyl;
9) —($C_{1-6}$ alkyl)-OH;
10) —($C_{1-6}$ alkyl)-O—($C_{1-6}$ alkyl);
11) $C_{3-6}$ cycloalkyl;

12) 3-12 membered heterocyclyl optionally substituted with one or more substituents chosen from halogen, hydroxyl, oxo, —CN, $C_{1-6}$ alkyl, $C_{1-6}$ haloalkyl, $C_{3-6}$ cycloalkyl, $C_{2-6}$ alkynyl, $C_{1-6}$ alkoxy, —($C_{1-6}$ alkyl)-CN, —($C_{1-6}$ alkyl)-O—($C_{1-6}$ alkyl), —($C_{1-6}$ alkyl)-OH, 4-6 membered heterocyclyl, 4-6 membered fluoroheterocyclyl and deuterated 4-6 membered heterocyclyl, wherein the $C_{1-6}$ alkyl is optionally substituted with one or more —OH;

13) 5-6 membered monocyclic heteroaryl optionally substituted with one or more substituents chosen from halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O—($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and 4-6 membered heterocyclyl;

14) phenyl optionally substituted with one or more substituents chosen from halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and 4-6 membered heterocyclyl;

15) —NR$_a$'R$_a$'', wherein R$_a$' and R$_a$'' are each independently chosen from hydrogen, $C_{1-6}$ alkyl, $C_{3-6}$ cycloalkyl, —($C_{1-6}$ alkyl)-O—($C_{1-6}$ alkyl) and 4-6 membered heterocyclyl, wherein the 4-6 membered heterocyclyl is optionally substituted with one or more substituents of —($C_{1-6}$ alkyl)-OH, the $C_{1-6}$ alkyl is optionally substituted with one or more —NR$_e$'R$_e$'', and R$_e$' and R$_e$'' are each independently chosen from hydrogen, $C_{1-6}$ alkyl, —($C_{1-6}$ alkyl)-OH and 4-6 membered heterocyclyl;

16) —C(O)NR$_b$'R$_b$'', wherein R$_b$' and R$_b$'' together with the N atoms to which they are attached form 4-6 membered heterocyclyl, wherein the 4-6 membered heterocyclyl is optionally substituted with one or more substituents chosen from halogen, —OH, $C_{1-6}$ alkyl, —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and —($C_{1-6}$ alkyl)-OH; and 17) —C(O)R$_c$, wherein R$_c$ is chosen from hydrogen, $C_{1-6}$ alkyl, $C_{2-6}$ alkenyl, $C_{2-6}$ alkynyl and —($C_{1-6}$ alkyl)-O—($C_{1-6}$ alkyl);

R$_6$ is halogen, $C_{1-6}$ alkyl or hydroxyl;

m is 0, 1, 2 or 3; and

R$_{11}$ is hydrogen, $C_{1-6}$ alkyl or $C_{1-6}$ deuteroalkyl;

provided that the 3-12 membered heterocyclyl, when substituted, is not piperazin-1-yl substituted with $C_{1-6}$ alkyl at both 2- and 6-positions;

preferably, U is CH, and V is N or CH; more preferably, both U and V are CH;

preferably, R$_{11}$ is $C_{1-3}$ alkyl, preferably methyl or ethyl, and more preferably methyl;

preferably, 5-6 membered monocyclic heteroaryl is 6 membered monocyclic heteroaryl, more preferably pyridyl, pyrazinyl and pyrimidyl;

preferably, 5-6 membered monocyclic heteroaryl is 5 membered monocyclic heteroaryl, more preferably triazolyl;

preferably, 8-10 membered bicyclic heteroaryl is 9 membered bicyclic heteroaryl, more preferably 4,5,6,7-tetrahydropyrazolo[1,5-a]pyrazinyl; and/or preferably, 3-12 membered heterocyclyl is 4-8 membered heterocyclyl, more preferably 4-6 membered heterocyclyl; provided that the 3-12 membered heterocyclyl, when substituted, is not piperazin-1-yl substituted with $C_{1-6}$ alkyl at both 2- and 6-positions;

more preferably, 3-12 membered heterocyclyl is oxetanyl, azetidinyl, tetrahydropyranyl, morpholinyl, piperazinyl or tetrahydropyridyl; provided that the 3-12 membered heterocyclyl, when substituted, is not piperazin-1-yl substituted with $C_{1-6}$ alkyl at both 2- and 6-positions.

Embodiment 5. The compound of any one of embodiments 1-4, or a pharmaceutically acceptable salt thereof, or a solvate, a racemic mixture, an enantiomer, a diastereomer or a tautomer thereof, wherein both X$_1$ and X$_2$ are CH, or one of X$_1$ and X$_2$ is N, and the other is CH;

and preferably, both X$_1$ and X$_2$ are CH.

Embodiment 6. The compound of any one of embodiments 1-4, or a pharmaceutically acceptable salt thereof, or a solvate, a racemic mixture, an enantiomer, a diastereomer or a tautomer thereof, wherein X$_1$ is N, X$_2$ is CR$_{14}$, wherein R$_{14}$ is chosen from $C_{1-6}$ alkyl.

Embodiment 7. The compound of any one of embodiments 1-6, or a pharmaceutically acceptable salt thereof, or a solvate, a racemic mixture, an enantiomer, a diastereomer or a tautomer thereof, wherein Y$_2$ is CH.

Embodiment 8. The compound of any one of embodiments 1-7, or a pharmaceutically acceptable salt thereof, or a solvate, a racemic mixture, an enantiomer, a diastereomer or a tautomer thereof, wherein R$_3$ is hydrogen or halogen.

Embodiment 9. The compound of any one of embodiments 1-8, or a pharmaceutically acceptable salt thereof, or a solvate, a racemic mixture, an enantiomer, a diastereomer or a tautomer thereof, wherein R$_4$ is $C_{1-6}$ alkyl, —($C_{1-3}$ alkyl)-OH, —($C_{1-3}$ deuteroalkyl)-OH, —($C_{1-3}$ alkyl)-O—($C_{1-3}$ alkyl) or —CHO, wherein the $C_{1-6}$ alkyl is optionally substituted with one or more halo;

preferably, R$_4$ is $C_{1-6}$ alkyl or —($C_{1-3}$ alkyl)-O—($C_{1-3}$ alkyl), wherein the $C_{1-6}$ alkyl is substituted with one or more halo;

preferably, R$_4$ is hydroxymethyl, hydroxy deuteromethyl, hydroxyethyl, methoxymethyl or fluoromethyl;

more preferably, R$_4$ is hydroxymethyl or hydroxy deuteromethyl;

and more preferably, R$_4$ is hydroxymethyl.

Embodiment 10. The compound of any one of embodiments 1-9, or a pharmaceutically acceptable salt thereof, or a solvate, a racemic mixture, an enantiomer, a diastereomer or a tautomer thereof, wherein R$_3$ is hydrogen, and R$_4$ is —($C_{1-3}$ alkyl)-OH.

Embodiment 11. The compound of any one of embodiments 1-10, or a pharmaceutically acceptable salt thereof, or a solvate, a racemic mixture, an enantiomer, a diastereomer or a tautomer thereof, wherein R$_5$ is hydrogen, —C(O)—($C_{1-6}$ alkyl), —C(O)—($C_{3-6}$ cycloalkyl), —C(O)— phenyl, —C(O)NH—($C_{1-6}$ alkyl), —C(O)NH—($C_{3-6}$ cycloalkyl) or —C(O)N($C_{1-6}$ alkyl)$_2$.

Embodiment 12. The compound of any one of embodiments 1-10, or a pharmaceutically acceptable salt thereof, or a solvate, a racemic mixture, an enantiomer, a diastereomer or a tautomer thereof, wherein R$_5$ is 5-6 membered monocyclic heteroaryl or 8-10 membered bicyclic heteroaryl, wherein the 5-6 membered monocyclic heteroaryl or 8-10 membered bicyclic heteroaryl is each optionally substituted with one or more groups chosen from:

$C_{3-6}$ cycloalkyl;

3-12 membered heterocyclyl optionally substituted with one or more $C_{1-6}$ alkyl, wherein the $C_{1-6}$ alkyl is substituted with one or more —OH; and —NR$_a$'R$_a$'', wherein R$_a$' and R$_a$'' are each independently chosen from hydrogen and $C_{1-6}$ alkyl, wherein the $C_{1-6}$ alkyl is optionally substituted with —NR$_e$'R$_e$", and R$_e$' and R$_e$" are each independently chosen from C$_{1-6}$ alkyl, —(C$_{1-6}$ alkyl)-OH and 4-6 membered heterocyclyl;

provided that if R$_1$ and R$_2$ together with the carbon atoms to which they are attached form the following structures:

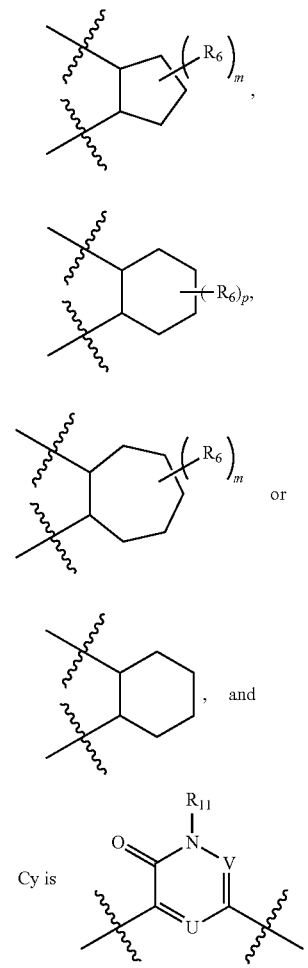

(I-1)

(I-3)

(I-4)

(I-6)

Cy is then the 3-12 membered heterocyclyl, when substituted, is not piperazin-1-yl substituted with C$_{1-6}$ alkyl at both 2- and 6-positions.

Embodiment 13. The compound of any one of embodiments 1-10, or a pharmaceutically acceptable salt thereof, or a solvate, a racemic mixture, an enantiomer, a diastereomer or a tautomer thereof, wherein R$_5$ is chosen from

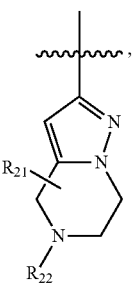, 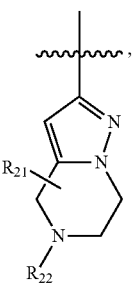, ,

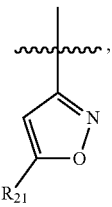, 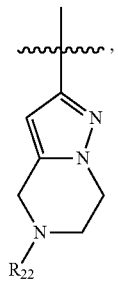, 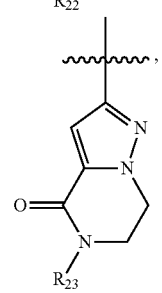,

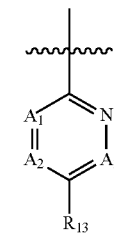, 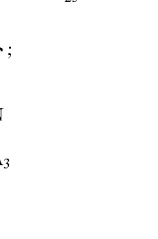, and

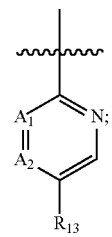;

wherein
R$_{21}$ is chosen from C$_{1-6}$ alkyl, C$_{1-6}$ haloalkyl and —(C$_{1-6}$ alkyl)-O—(C$_{1-6}$ alkyl);
n is 0, 1 or 2;
R$_{22}$ and R$_{23}$ are each independently chosen from hydrogen, —CN, C$_{1-6}$ alkyl, C$_{1-6}$ haloalkyl, —(C$_{1-6}$ alkyl)-O—(C$_{1-6}$ alkyl), 4-6 membered heterocyclyl or —C(O)R$_c$, and R$_c$ is chosen from hydrogen, C$_{1-6}$ alkyl or —(C$_{1-6}$ alkyl)-O—(C$_{1-6}$ alkyl);
R$_{24}$ is chosen from hydrogen, C$_{1-6}$ alkyl, —(C$_{1-6}$ alkyl)-O—(C$_{1-6}$ alkyl), or —C(O)NR$_b$'R$_b$", wherein R$_b$' and R$_b$" together with the N atoms to which they are attached form 4-6 membered heterocyclyl; preferably, R$_5$ is A$_1$, A$_2$ and A$_3$ are each independently CH or N; and R$_{13}$ is chosen from:
1) hydrogen;
2) C$_{1-6}$ alkyl;
3) C$_{1-6}$ alkoxy;
4) halogen;
5) C$_{3-6}$ cycloalkyl;
6) 3-12 membered heterocyclyl optionally substituted with one or more substituents chosen from oxo, —CN, $C_{1-6}$ alkyl, $C_{1-6}$ alkoxy, —($C_{1-6}$ alkyl)-CN, —($C_{1-6}$ alkyl)-O—($C_{1-6}$ alkyl), 4-6 membered heterocyclyl and deuterated 4-6 membered heterocyclyl, wherein the $C_{1-6}$ alkyl is optionally substituted with one or more —OH;
7) phenyl optionally substituted with one or more substituents chosen from 4-6 membered heterocyclyl;
8) —$NR_a'R_a''$, wherein $R_a'$ and $R_a''$ are each independently chosen from hydrogen, $C_{1-6}$ alkyl, —($C_{1-6}$ alkyl)-O—($C_{1-6}$ alkyl) and 4-6 membered heterocyclyl, wherein the 4-6 membered heterocyclyl is optionally substituted with —($C_{1-6}$ alkyl)-OH, the $C_{1-6}$ alkyl is optionally substituted with one or more —$NR_e'R_e''$, and $R_e'$ and $R_e''$ are each independently chosen from hydrogen, $C_{1-6}$ alkyl, —($C_{1-6}$ alkyl)-OH and 4-6 membered heterocyclyl; and
9) —$C(O)NR_b'R_b''$, wherein $R_b'$ and $R_b''$ together with the N atoms to which they are attached form 4-6 membered heterocyclyl, wherein the 4-6 membered heterocyclyl is optionally substituted with one or more $C_{1-6}$ alkyl; provided that if $R_1$ and $R_2$ together with the carbon atoms to which they are attached form the following structures:

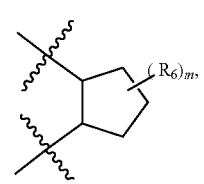
(I-1)

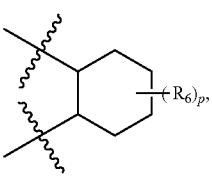
(I-3)

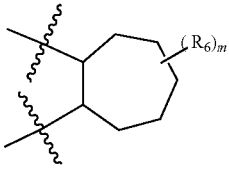
(I-4)

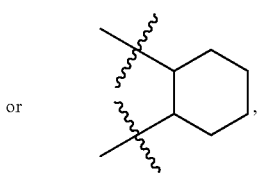
(I-6)

or 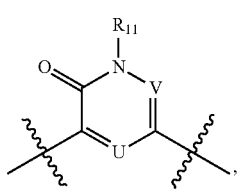, and Cy is

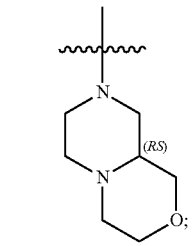 [SMILES: *N1CCN2CCOCC2C1], then the 3-12 membered heterocyclyl, when substituted, is not piperazin-1-yl substituted with $C_{1-6}$ alkyl at both 2- and 6-positions.

Embodiment 14. The compound of embodiment 13, or a pharmaceutically acceptable salt thereof, or a solvate, a racemic mixture, an enantiomer, a diastereomer or a tautomer thereof, wherein $R_{13}$ is 3-12 membered heterocyclyl, preferably

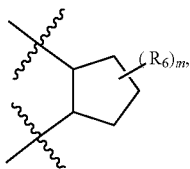

provided that if $R_1$ and $R_2$ together with the carbon atoms to which they are attached form the following structures:

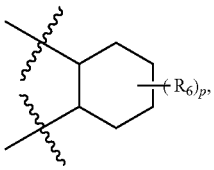
(I-1)

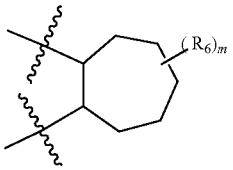
(I-3)

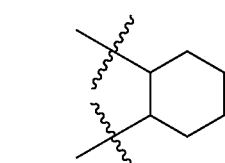
(I-4)

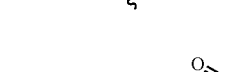
(I-6)

or 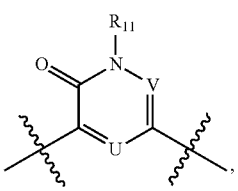, and Cy is

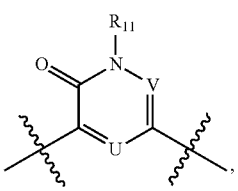, then the 3-12 membered heterocyclyl, when substituted, is not piperazin-1-yl substituted with $C_{1-6}$ alkyl at both 2- and 6-positions.

Embodiment 15. The compound of embodiment 13, or a pharmaceutically acceptable salt thereof, or a solvate, a racemic mixture, an enantiomer, a diastereomer or a tautomer thereof, wherein $R_{13}$ is piperazinyl optionally substituted with one or more substituents chosen from $C_{1-6}$ alkyl and 4-5 membered heterocyclyl;

provided that if R₁ and R₂ together with the carbon atoms to which they are attached form the following structures:

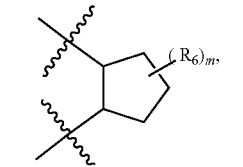 (I-1)

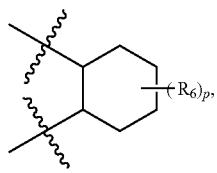 (I-3)

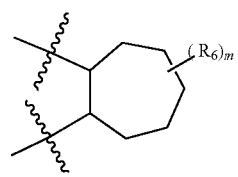 (I-4)

or 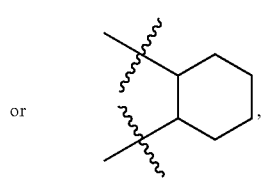 (I-6)

and Cy is 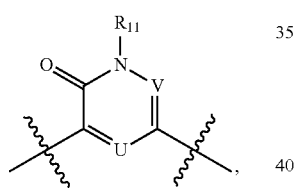

then the piperazinyl, when substituted, is not piperazin-1-yl substituted with $C_{1-6}$ alkyl at both 2- and 6-positions.

Embodiment 16. The compound of any one of embodiments 1-13, or a pharmaceutically acceptable salt thereof, or a solvate, a racemic mixture, an enantiomer, a diastereomer or a tautomer thereof, wherein R₅ is chosen from

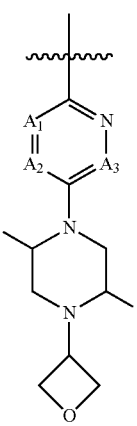 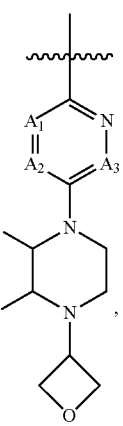

-continued

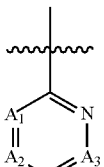 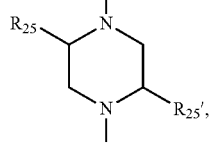

 

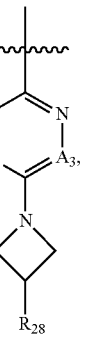 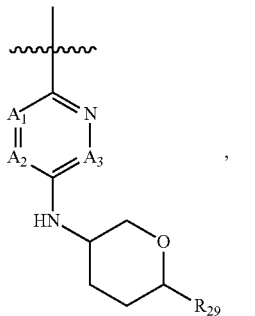

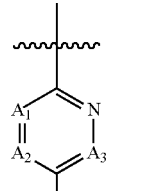 and

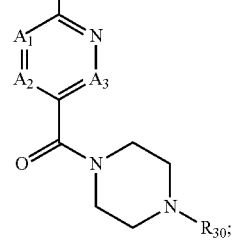

wherein $R_{24}$, $R_{24}'$, $R_{25}$, $R_{25}'$, $R_{27}$ and $R_{27}'$ are each independently chosen from hydrogen, oxo and $C_{1-6}$ alkyl;

$R_{26}$ is $C_{1-6}$ alkyl, —($C_{1-6}$ alkyl)-O—($C_{1-6}$ alkyl) or tetrahydrofuranyl;

$R_{28}$ is $C_{1-6}$ alkoxy; $R_{29}$ is hydrogen or —($C_{1-6}$ alkyl)-OH;

$R_{30}$ is $C_{1-6}$ alkyl;

$A_1$, $A_2$ and $A_3$ are each independently CH or N; preferably, both $A_1$ and $A_2$ are CH, or one of $A_1$ and $A_2$ is N, and the other is CH; and more preferably, both $A_1$ and $A_2$ are CH.

Embodiment 17. The compound of any one of embodiments 1-16, or a pharmaceutically acceptable salt thereof, or a solvate, a racemic mixture, an enantiomer, a diastereomer or a tautomer thereof, wherein $R_5$ is

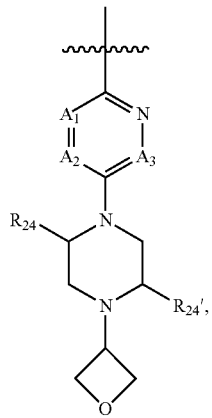

wherein $A_1$, $A_2$ and $A_3$ are each independently CH or N, and $R_{24}$ and $R_{24}'$ are each independently chosen from hydrogen, oxo and $C_{1-6}$ alkyl;

and preferably, when $R_{24}$ is $C_{1-6}$ alkyl (such as $C_{1-3}$ alkyl, more preferably methyl), $R_5$ is preferably

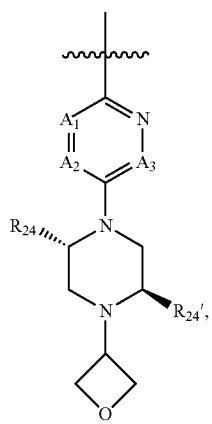

wherein $A_1$, $A_2$ and $A_3$ are each independently CH or N, and $R_{24}'$ is $C_{1-6}$ alkyl (such as $C_{1-3}$ alkyl, more preferably methyl), and more preferably

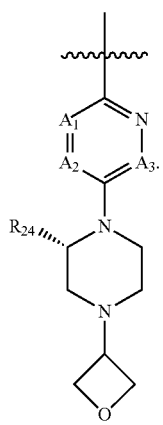

Embodiment 18. The compound of embodiments 16 or 17, or a pharmaceutically acceptable salt thereof, or a solvate, a racemic mixture, an enantiomer, a diastereomer or a tautomer thereof, wherein $R_{24}$ and $R_{24}'$ are each independently chosen from hydrogen and $C_{1-6}$ alkyl.

Embodiment 19. The compound of any one of embodiments 13-18, or a pharmaceutically acceptable salt thereof, or a solvate, a racemic mixture, an enantiomer, a diastereomer or a tautomer thereof, wherein $A_1$, $A_2$ and $A_3$ are all CH, or $A_1$ is N and both $A_2$ and $A_3$ are CH, or $A_3$ is N and both $A_1$ and $A_2$ are CH.

Embodiment 20. The compound of any one of embodiments 1-13, or a pharmaceutically acceptable salt thereof, or a solvate, a racemic mixture, an enantiomer, a diastereomer or a tautomer thereof, wherein $R_5$ is chosen from:

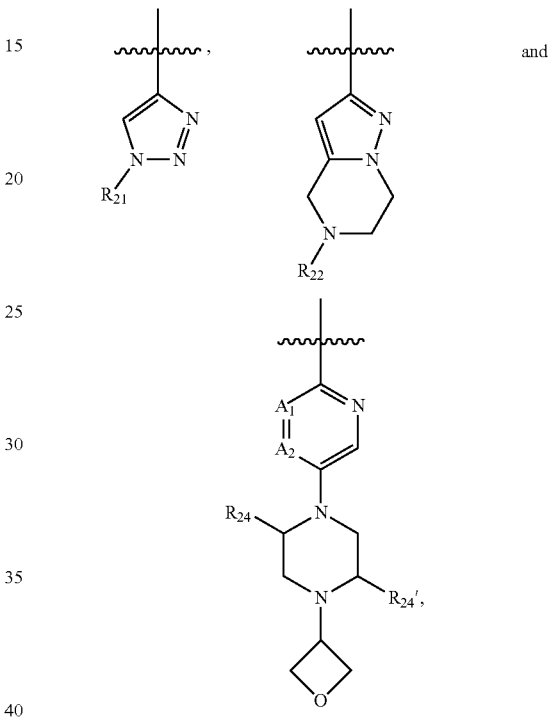

wherein $R_{21}$ is $C_{1-6}$ alkyl; $R_{22}$ is chosen from hydrogen, $C_{1-6}$ alkyl and 4 membered heterocyclyl; $A_1$ and $A_2$ are respectively CH; and $R_{24}$ and $R_{24}'$ are each independently chosen from hydrogen and $C_{1-6}$ alkyl.

Embodiment 21. The compound of any one of embodiments 4-20, or a pharmaceutically acceptable salt thereof, or a solvate, a racemic mixture, an enantiomer, a diastereomer or a tautomer thereof, wherein

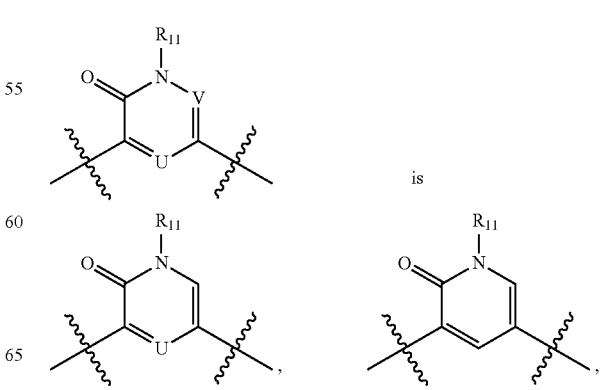

is

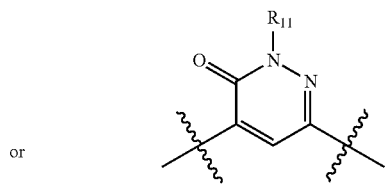

or

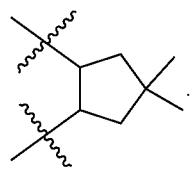

wherein R₁₁ is $C_{1-6}$ alkyl or $C_{1-6}$ deuteroalkyl;
preferably, R₁₁ is $C_{1-3}$ alkyl, preferably methyl or ethyl, and more preferably methyl; and preferably, R₁₁ is $C_{1-3}$ deuteroalkyl, preferably trideuteromethyl.

Embodiment 22. The compound of any one of embodiments 4-21, or a pharmaceutically acceptable salt thereof, or a solvate, a racemic mixture, an enantiomer, a diastereomer or a tautomer thereof, wherein both X₁ and X₂ are CH, or one of X₁ and X₂ is N, and the other is CH; Y₂ is CH; R₃ is hydrogen; R₄ is —($C_{1-3}$ alkyl)-OH; U is CH, V is N or CH, and R₁₁ is $C_{1-3}$ alkyl; R₅ is chosen from

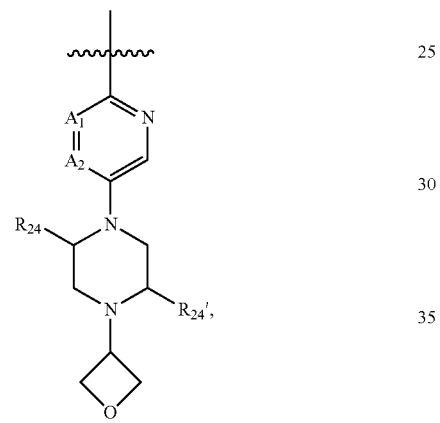

wherein R₂₄ and R₂₄' are each independently chosen from hydrogen, oxo and $C_{1-6}$ alkyl, both A₁ and A₂ are CH, or A₁ is N and A₂ is CH; R₆ is $C_{1-6}$ alkyl; and m is 0 or 2.

Embodiment 23. The compound of any one of embodiments 4-22, or a pharmaceutically acceptable salt thereof, or a solvate, a racemic mixture, an enantiomer, a diastereomer or a tautomer thereof, wherein both U and V are CH, and R₁₁ is methyl.

Embodiment 24. The compound of any one of embodiments 1-23, or a pharmaceutically acceptable salt thereof, or a solvate, a racemic mixture, an enantiomer, a diastereomer or a tautomer thereof, wherein R₆ is $C_{1-3}$ alkyl; and m is 2.

Embodiment 25. The compound of any one of embodiments 1-24, or a pharmaceutically acceptable salt thereof, or a solvate, a racemic mixture, an enantiomer, a diastereomer or a tautomer thereof, wherein R₆ is $C_{1-3}$ alkyl; and m is 1.

Embodiment 26. The compound of any one of embodiments 1-24, or a pharmaceutically acceptable salt thereof, or a solvate, a racemic mixture, an enantiomer, a diastereomer or a tautomer thereof, wherein R₆ is $C_{1-6}$ alkyl or hydroxyl; and m is 3.

Embodiment 27. The compound of any one of embodiments 1-26, or a pharmaceutically acceptable salt thereof, or a solvate, a racemic mixture, an enantiomer, a diastereomer or a tautomer thereof, wherein R₆ together with the five-membered ring to which they are attached forms

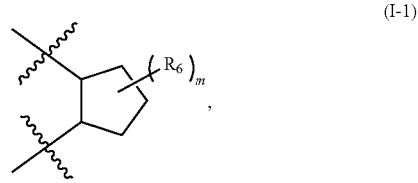

Embodiment 28. The compound of any one of embodiments 1-27, or a pharmaceutically acceptable salt thereof, or a solvate, a racemic mixture, an enantiomer, a diastereomer or a tautomer thereof, wherein 3-12 membered heterocyclyl is chosen from oxetanyl, azetidinyl, tetrahydropyranyl, morpholinyl, piperazinyl, tetrahydropyridyl, azaoxaspiro[5.3]nonyl, diazabicyclo[2.2.1]heptyl, diazaspiro[5.2]octyl, diazaoxabicyclo[4.4.0]decyl, azaoxaspiro[5.4]decyl and diazabicyclo[3.1.1]heptyl, provided that if R₁ and R₂ together with the carbon atoms to which they are attached form the following structures:

(I-1)

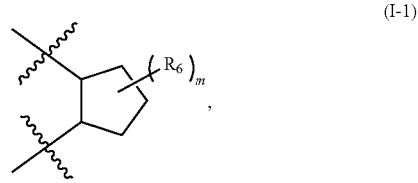

(I-3)

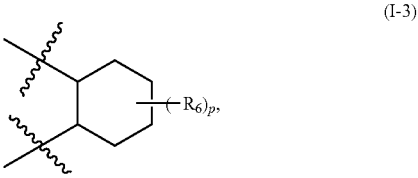

(I-4)

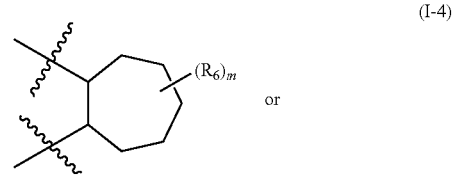

or (I-6)

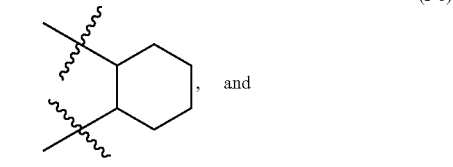

and

Cy is 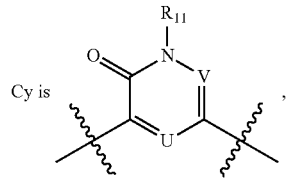, then 3-12 membered heterocyclyl, when substituted, is not piperazin-1-yl substituted with $C_{1-6}$ alkyl at both 2- and 6-positions;

preferably, 3-12 membered heterocyclyl is chosen from:

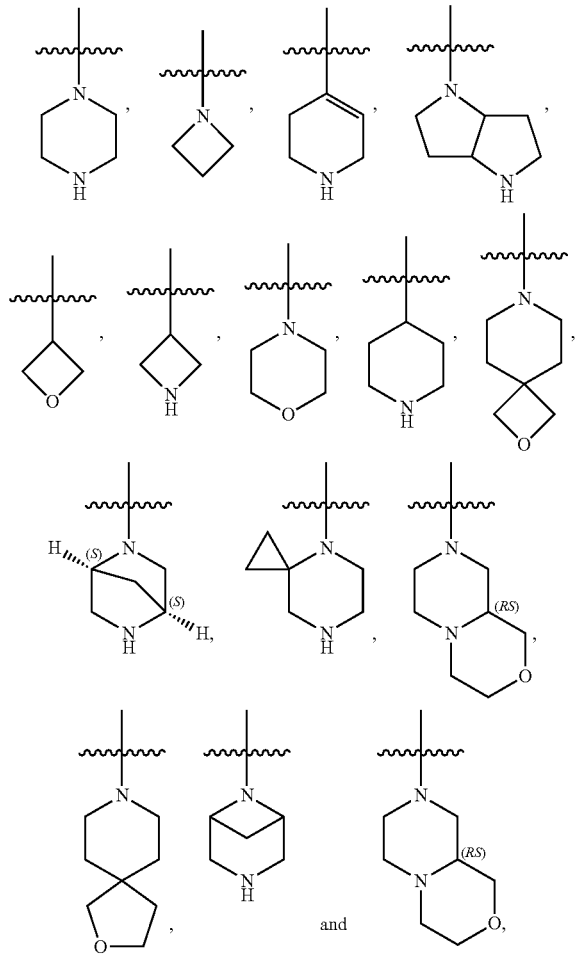

provided that if $R_1$ and $R_2$ together with the carbon atoms to which they are attached form the following structures:

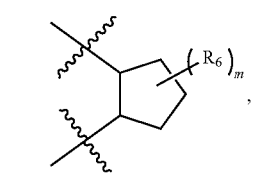
(I-1)

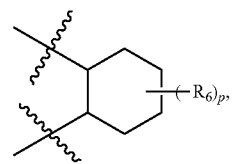
(I-3)

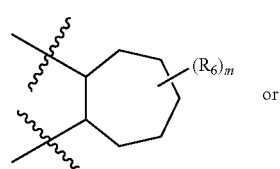
(I-4)

or

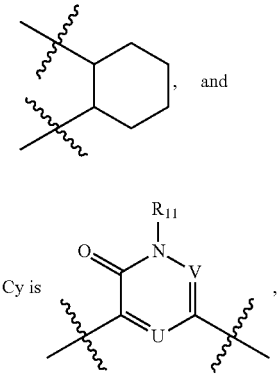
(I-6)

Cy is then the 3-12 membered heterocyclyl, when substituted, is not piperazin-1-yl substituted with $C_{1-6}$ alkyl at both 2- and 6-positions.

Embodiment 29. The compound of embodiment 4, or a pharmaceutically acceptable salt thereof, or a solvate, a racemic mixture, an enantiomer, a diastereomer or a tautomer thereof, wherein both $X_1$ and $X_2$ are CH; $Y_2$ is CH; $R_3$ is hydrogen; $R_4$ is —($C_{1-3}$ alkyl)-OH; both U and V are CH, and $R_{11}$ is methyl; $R_5$ is chosen from

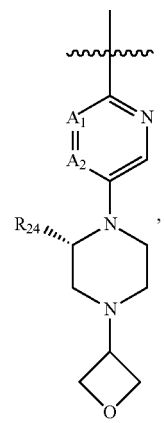

wherein $R_{24}$ is $C_{1-3}$ alkyl, and both $A_1$ and $A_2$ are CH; and $R_6$ together with the five-membered ring to which they are attached forms

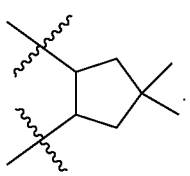 [SMILES: *C1CC(C)(C)CC1*]

Embodiment 30. The compound of embodiment 1, or a pharmaceutically acceptable salt thereof, or a solvate, a racemic mixture, an enantiomer, a diastereomer or a tautomer thereof, wherein the compound is a compound of formula (IB)

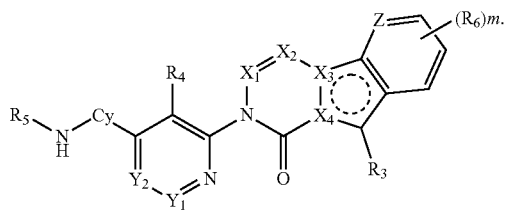

(IB)

Embodiment 31. The compound of embodiment 30, or a pharmaceutically acceptable salt thereof, or a solvate, a racemic mixture, an enantiomer, a diastereomer or a tautomer thereof, wherein the compound is a compound of formula (IV):

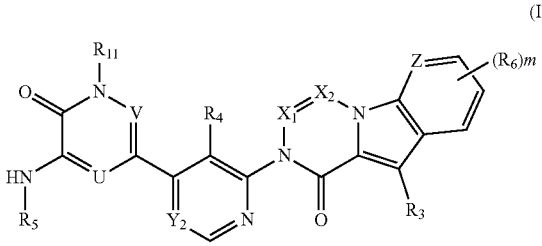

(IV)

wherein
$X_1$ and $X_2$ are each independently CH or N; or, $X_1$ is N, $X_2$ is $CR_{14}$, wherein $R_{14}$ is chosen from $C_{1-6}$ alkyl;
$Y_2$ is CH or N;
$R_3$ is hydrogen, deuterium, halogen or $C_{1-6}$ haloalkyl;
$R_4$ is hydrogen, halogen, —CN, $C_{1-6}$ alkyl, —($C_{1-3}$ alkyl)-OH, —($C_{1-3}$ deuteroalkyl)-OH, —($C_{1-3}$ alkyl)-O—($C_{1-3}$ alkyl), —O—($C_{1-3}$ alkyl), —CHO, —C(O)NH$_2$, —C(O)NHCH$_3$, —C(O)N(CH$_3$)$_2$ or 3-hydroxyl-oxetan-3-yl, wherein the $C_{1-6}$ alkyl is optionally substituted with one or more halo;
U and V are each independently chosen from N or CH;
Z is N or CH;
$R_5$ is hydrogen, $C_{1-6}$ alkyl, —C(O)—($C_{1-6}$ alkyl), —C(O)—($C_{3-6}$ cycloalkyl), —C(O)-phenyl, —C(O)NH—($C_{1-6}$ alkyl), —C(O)NH—($C_{3-6}$ cycloalkyl), —C(O)N($C_{1-6}$ alkyl)$_2$, phenyl, 5-6 membered monocyclic heteroaryl or 8-10 membered bicyclic heteroaryl, wherein the $C_{1-6}$ alkyl, $C_{3-6}$ cycloalkyl, phenyl, 5-6 membered monocyclic heteroaryl or 8-10 membered bicyclic heteroaryl is each optionally substituted with one or more groups chosen from:
1) halogen;
2) oxo;
3) —CN;
4) $C_{1-6}$ alkyl;
5) $C_{2-6}$ alkenyl;
6) $C_{2-6}$ alkynyl;
7) $C_{1-6}$ alkoxy;
8) $C_{1-6}$ haloalkyl;
9) —($C_{1-6}$ alkyl)-OH;
10) —($C_{1-6}$ alkyl)-O—($C_{1-6}$ alkyl);
11) $C_{3-6}$ cycloalkyl;
12) 3-12 membered heterocyclyl optionally substituted with one or more substituents chosen from halogen, hydroxyl, oxo, —CN, $C_{1-6}$ alkyl, $C_{1-6}$ haloalkyl, $C_{3-6}$ cycloalkyl, $C_{2-6}$ alkynyl, $C_{1-6}$ alkoxy, —($C_{1-6}$ alkyl)-CN, —($C_{1-6}$ alkyl)-O—($C_{1-6}$ alkyl), —($C_{1-6}$ alkyl)-OH, 4-6 membered heterocyclyl, 4-6 membered fluoroheterocyclyl and deuterated 4-6 membered heterocyclyl, wherein the $C_{1-6}$ alkyl is optionally substituted with one or more —OH;
13) 5-6 membered monocyclic heteroaryl optionally substituted with one or more substituents chosen from halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O—($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and 4-6 membered heterocyclyl;
14) phenyl optionally substituted with one or more substituents chosen from halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and 4-6 membered heterocyclyl;
15) —NR$_a$'R$_a$", wherein R$_a$' and R$_a$" are each independently chosen from hydrogen, $C_{1-6}$ alkyl, $C_{3-6}$ cycloalkyl, —($C_{1-6}$ alkyl)-O—($C_{1-6}$ alkyl) and 4-6 membered heterocyclyl, wherein the 4-6 membered heterocyclyl is optionally substituted with one or more substituents of —($C_{1-6}$ alkyl)-OH, the $C_{1-6}$ alkyl is optionally substituted with one or more —NR$_e$'R$_e$", and R$_e$' and R$_e$" are each independently chosen from hydrogen, $C_{1-6}$ alkyl, —($C_{1-6}$ alkyl)-OH and 4-6 membered heterocyclyl;
16) —C(O)NR$_b$'R$_b$", wherein R$_b$' and R$_b$" together with the N atoms to which they are attached form 4-6 membered heterocyclyl, wherein the 4-6 membered heterocyclyl is optionally substituted with one or more substituents chosen from halogen, —OH, $C_{1-6}$ alkyl, —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and —($C_{1-6}$ alkyl)-OH; and
17) —C(O)R$_c$, wherein R$_c$ is chosen from hydrogen, $C_{1-6}$ alkyl, $C_{2-6}$ alkenyl, $C_{2-6}$ alkynyl and —($C_{1-6}$ alkyl)-O—($C_{1-6}$ alkyl);

$R_6$ is halogen, $C_{1-6}$ alkyl or hydroxyl;
m is 0, 1, 2 or 3; and
$R_1$ is hydrogen, $C_{1-6}$ alkyl or $C_{1-6}$ deuteroalkyl;
preferably, both $X_1$ and $X_2$ are CH, or one of $X_1$ and $X_2$ is N, and the other is CH;
preferably, both $X_1$ and $X_2$ are CH;
preferably, $Y_2$ is CH;
preferably, $R_3$ is hydrogen or halogen;
preferably, $R_4$ is $C_{1-6}$ alkyl, —($C_{1-3}$ alkyl)-OH, —($C_{1-3}$ deuteroalkyl)-OH, —($C_{1-3}$ alkyl)-O—($C_{1-3}$ alkyl) or —CHO, wherein the $C_{1-6}$ alkyl is optionally substituted with one or more halogen; more preferably $R_4$ is —($C_{1-3}$ alkyl)-OH;
preferably, $R_4$ is $C_{1-6}$ alkyl or —($C_{1-3}$ alkyl)-O—($C_{1-3}$ alkyl), wherein the $C_{1-6}$ alkyl is substituted with one or more halo;
preferably, $R_4$ is hydroxymethyl, hydroxy deuteromethyl, hydroxyethyl, methoxymethyl or fluoromethyl; more preferably, $R_4$ is hydroxymethyl;
preferably, $R_3$ is hydrogen, and $R_4$ is —($C_{1-3}$ alkyl)-OH;

preferably

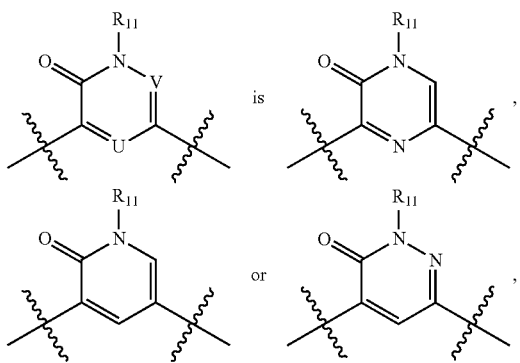

is or wherein $R_{11}$ is $C_{1-6}$ alkyl or $C_{1-6}$ deuteroalkyl;
preferably, Z is CH;
preferably, U is CH, and V is N or CH; more preferably, both U and V are CH;
preferably, both U and V are CH, and $R_{11}$ is methyl;
preferably, $R_{11}$ is $C_{1-3}$ alkyl, preferably methyl or ethyl, and more preferably methyl;
preferably, $R_{11}$ is $C_{1-3}$ deuteroalkyl, preferably trideuteromethyl;
preferably, $R_6$ is halogen;
preferably, $R_6$ is $C_{1-3}$ alkyl;
preferably, m is 0 or 1;
preferably, 5-6 membered monocyclic heteroaryl is 6 membered monocyclic heteroaryl, more preferably pyridyl, pyrazinyl and pyrimidyl;
preferably, 5-6 membered monocyclic heteroaryl is 5 membered monocyclic heteroaryl, more preferably triazolyl;
preferably, 8-10 membered bicyclic heteroaryl is 9 membered bicyclic heteroaryl, more preferably 4,5,6,7-tetrahydropyrazolo[1,5-a]pyrazinyl; and/or
and preferably, 3-12 membered heterocyclyl is 4-6 membered heterocyclyl, more preferably oxetanyl, azetidinyl, tetrahydropyranyl, morpholinyl, piperazinyl or tetrahydropyridyl.

Embodiment 32. The compound of any one of embodiments 30-31, or a pharmaceutically acceptable salt thereof, or a solvate, a racemic mixture, an enantiomer, a diastereomer or a tautomer thereof, wherein $Y_2$ is CH.

Embodiment 33. The compound of any one of embodiments 30-32, or a pharmaceutically acceptable salt thereof, or a solvate, a racemic mixture, an enantiomer, a diastereomer or a tautomer thereof, wherein $R_5$ is hydrogen, —C(O)—($C_{1-6}$ alkyl), —C(O)—($C_{3-6}$ cycloalkyl), —C(O)— phenyl, —C(O)NH—($C_{1-6}$ alkyl), —C(O)NH—($C_{3-6}$ cycloalkyl) or —C(O)N($C_{1-6}$ alkyl)$_2$.

Embodiment 34. The compound of any one of embodiments 30-32, or a pharmaceutically acceptable salt thereof, or a solvate, a racemic mixture, an enantiomer, a diastereomer or a tautomer thereof, wherein $R_5$ is 5-6 membered monocyclic heteroaryl or 8-10 membered bicyclic heteroaryl, wherein the 5-6 membered monocyclic heteroaryl or 8-10 membered bicyclic heteroaryl is each optionally substituted with one or more groups chosen from:
$C_{3-6}$ cycloalkyl;
3-12 membered heterocyclyl optionally substituted with one or more $C_{1-6}$ alkyl, wherein the $C_{1-6}$ alkyl is substituted with one or more —OH; and
—$NR_a'R_a''$, wherein $R_a'$ and $R_a''$ are each independently chosen from hydrogen and $C_{1-6}$ alkyl, wherein the $C_{1-6}$ alkyl is optionally substituted with —$NR_e'R_e''$, and $R_e'$ and $R_e''$ are each independently chosen from $C_{1-6}$ alkyl, —($C_{1-6}$ alkyl)-OH and 4-6 membered heterocyclyl.

Embodiment 35. The compound of any one of embodiments 30-34, or a pharmaceutically acceptable salt thereof, or a solvate, a racemic mixture, an enantiomer, a diastereomer or a tautomer thereof, wherein $R_5$ is chosen from:

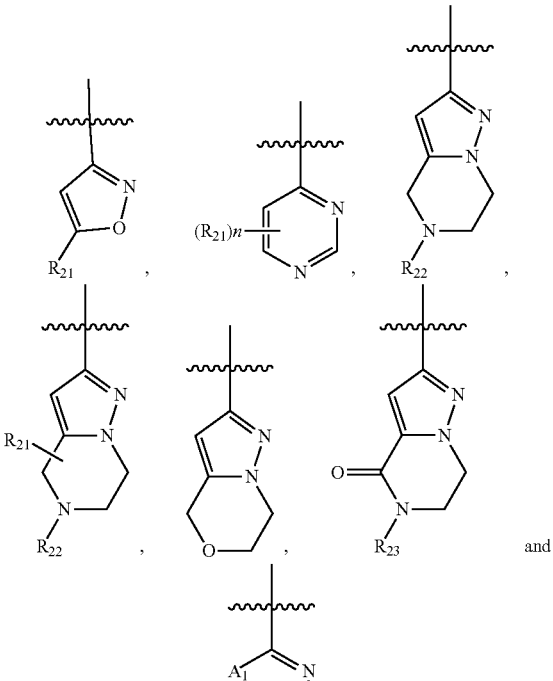

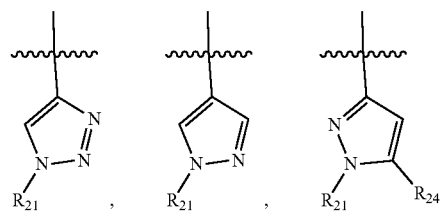

and wherein
$R_{21}$ is chosen from $C_{1-6}$ alkyl, $C_{1-6}$ haloalkyl and —($C_{1-6}$ alkyl)-O—($C_{1-6}$ alkyl);
n is 0, 1 or 2;
$R_{22}$ and $R_{23}$ are each independently chosen from hydrogen, —CN, $C_{1-6}$ alkyl, $C_{1-6}$ haloalkyl, —($C_{1-6}$ alkyl)-O—($C_{1-6}$ alkyl), 4-6 membered heterocyclyl or —C(O)$R_c$, and $R_c$ is chosen from hydrogen, $C_{1-6}$ alkyl or —($C_{1-6}$ alkyl)-O—($C_{1-6}$ alkyl);
$R_{24}$ is chosen from hydrogen, $C_{1-6}$ alkyl, —($C_{1-6}$ alkyl)-O—($C_{1-6}$ alkyl), or —C(O)$NR_b'R_b''$, wherein $R_b'$ and $R_b''$ together with the N atoms to which they are attached form 4-6 membered heterocyclyl;
$A_1$, $A_2$ and $A_3$ are each independently CH or N; and
$R_{13}$ is chosen from:
1) hydrogen;
2) $C_{1-6}$ alkyl;

3) $C_{1-6}$ alkoxy;
4) halogen;
5) $C_{3-6}$ cycloalkyl;
6) 4-8 membered heterocyclyl optionally substituted with one or more substituents chosen from oxo, —CN, $C_{1-6}$ alkyl, $C_{1-6}$ alkoxy, —($C_{1-6}$ alkyl)-CN, —($C_{1-6}$ alkyl)-O—($C_{1-6}$ alkyl), 4-6 membered heterocyclyl and deuterated 4-6 membered heterocyclyl, wherein the $C_{1-6}$ alkyl is optionally substituted with one or more —OH;
7) phenyl optionally substituted with one or more substituents chosen from 4-6 membered heterocyclyl;
8) —$NR_a'R_a''$, wherein $R_a'$ and $R_a''$ are each independently chosen from hydrogen, $C_{1-6}$ alkyl, —($C_{1-6}$ alkyl)-O—($C_{1-6}$ alkyl) and 4-6 membered heterocyclyl, wherein the 4-6 membered heterocyclyl is optionally substituted with one or more —($C_{1-6}$ alkyl)-OH, the $C_{1-6}$ alkyl is optionally substituted with one or more —$NR_e'R_e''$, and $R_e'$ and $R_e''$ are each independently chosen from hydrogen, $C_{1-6}$ alkyl, —($C_{1-6}$ alkyl)-OH and 4-6 membered heterocyclyl; and
9) —$C(O)NR_b'R_b''$, wherein $R_b'$ and $R_b''$ together with the N atoms to which they are attached form 4-6 membered heterocyclyl, wherein the 4-6 membered heterocyclyl is optionally substituted with one or more $C_{1-6}$ alkyl;

preferably, $R_5$ is

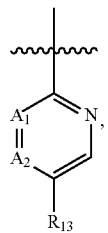

wherein $A_1$ and $A_2$ are each independently CH or N, and $R_{13}$ is 4-6 membered heterocyclyl optionally substituted with one or more substituents chosen from oxo, $C_{1-6}$ alkyl, $C_{1-6}$ alkoxy, —($C_{1-6}$ alkyl)-O—($C_{1-6}$ alkyl) and 4-6 membered heterocyclyl;

preferably, $R_5$ is

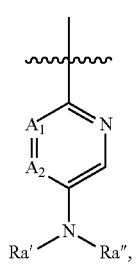

wherein $A_1$ and $A_2$ are each independently CH or N; $R_a'$ and $R_a''$ together with the N atoms to which they are attached form 4-6 membered heterocyclyl, wherein the 4-6 membered heterocyclyl is optionally substituted with one or more substituents chosen from oxo, $C_{1-6}$ alkyl, $C_{1-6}$ alkoxy and 4-6 membered heterocyclyl;

preferably, $R_5$ is

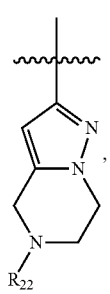

wherein $R_{22}$ is chosen from hydrogen, —CN, $C_{1-6}$ alkyl, $C_{1-6}$ haloalkyl, —($C_{1-6}$ alkyl)-O—($C_{1-6}$ alkyl), 4-6 membered heterocyclyl or —$C(O)R_c$, and $R_c$ is chosen from hydrogen, $C_{1-6}$ alkyl or —($C_{1-6}$ alkyl)-O—($C_{1-6}$ alkyl);

preferably, $R_{13}$ is piperazinyl optionally substituted with one or more substituents chosen from $C_{1-6}$ alkyl and 4-5 membered heterocyclyl;

preferably, $R_5$ is chosen from:

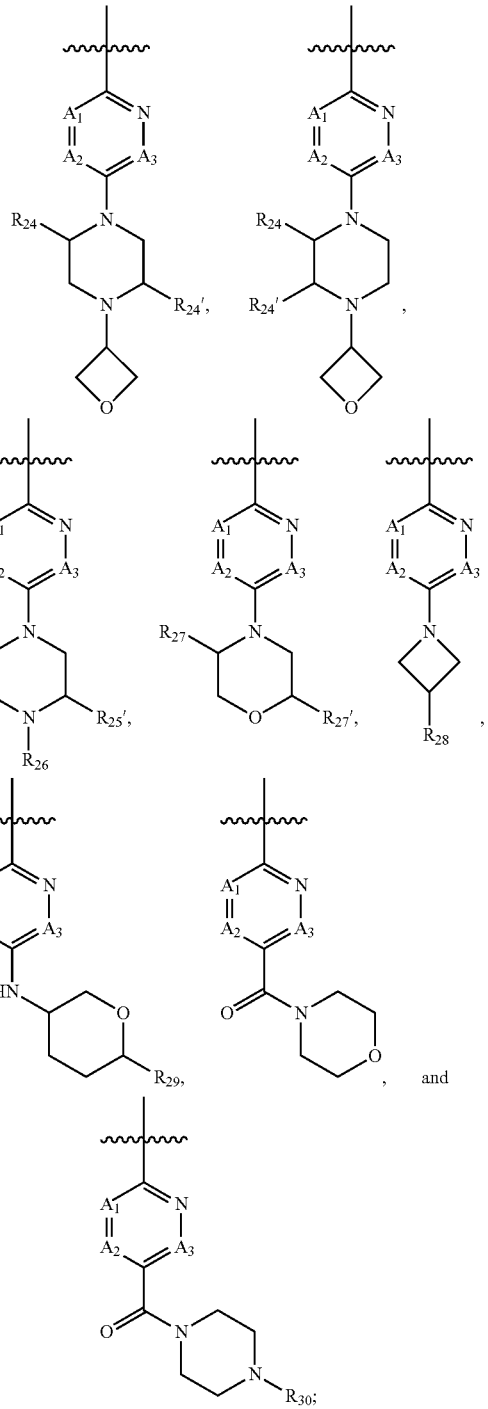

wherein $R_{24}$, $R_{24}'$, $R_{25}$, $R_{25}'$, $R_{27}$ and $R_{27}'$ are each independently chosen from hydrogen, oxo and $C_{1-6}$ alkyl;

$R_{26}$ is $C_{1-6}$ alkyl, —($C_{1-6}$ alkyl)-O—($C_{1-6}$ alkyl) or tetrahydrofuranyl;

R$_{28}$ is C$_{1-6}$ alkoxy; R$_{29}$ is hydrogen or —(C$_{1-6}$ alkyl)-OH;

R$_{30}$ is C$_{1-6}$ alkyl; and

A$_1$, A$_2$ and A$_3$ are each independently CH or N;
preferably, R$_5$ is

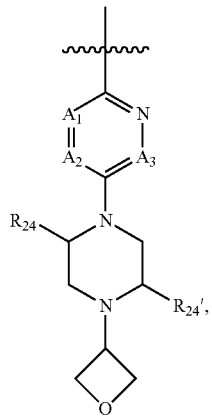

wherein A$_1$, A$_2$ and A$_3$ are each independently CH or N, and R$_{24}$ and R$_{24}'$ are each independently chosen from hydrogen, oxo and C$_{1-6}$ alkyl;

preferably, when R$_{24}$ is C$_{1-6}$ alkyl (such as C$_{1-3}$ alkyl, more preferably methyl), R$_5$ is preferably

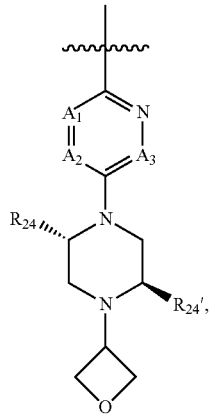

wherein A$_1$, A$_2$ and A$_3$ are each independently CH or N, and R$_{24}'$ is C$_{1-6}$ alkyl (such as C$_{1-3}$ alkyl, more preferably methyl), and more preferably

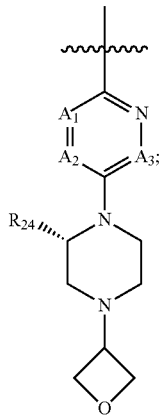

preferably, R$_{24}$ and R$_{24}'$ are each independently chosen from hydrogen and C$_{1-6}$ alkyl;

preferably, A$_1$, A$_2$ and A$_3$ are all CH, or A$_1$ is N and both A$_2$ and A$_3$ are CH, or A$_3$ is N and both A$_1$ and A$_2$ are CH;

and preferably, A$_1$, A$_2$ and A$_3$ are all CH.

Embodiment 36. The compound of any one of embodiments 30-35, or a pharmaceutically acceptable salt thereof, or a solvate, a racemic mixture, an enantiomer, a diastereomer or a tautomer thereof, wherein both X$_1$ and X$_2$ are CH, or one of X$_1$ and X$_2$ is N, and the other is CH;

Y$_2$ is CH;

R$_3$ is hydrogen;

R$_4$ is —(C$_{1-3}$ alkyl)-OH;

Z is CH;

U is CH, and V is N or CH;

R$_5$ is

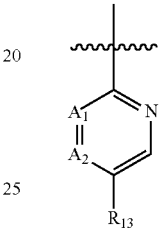 or 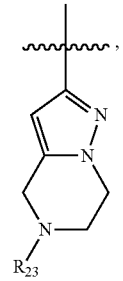, wherein A$_1$ and A$_2$ are each independently CH or N, and R$_{13}$ is 4-6 membered heterocyclyl optionally substituted with one or more substituents chosen from oxo, C$_{1-6}$ alkyl, C$_{1-6}$ alkoxy, —(C$_{1-6}$ alkyl)-O—(C$_{1-6}$ alkyl) and 4-6 membered heterocyclyl; R$_{22}$ is chosen from hydrogen, —CN, C$_{1-6}$ alkyl, C$_{1-6}$ haloalkyl, —(C$_{1-6}$ alkyl)-O—(C$_{1-6}$ alkyl), 4-6 membered heterocyclyl or —C(O)R$_c$, and R$_c$ is chosen from hydrogen, C$_{1-6}$ alkyl or —(C$_{1-6}$ alkyl)-O—(C$_{1-6}$ alkyl);

R$_6$ is hydrogen or halogen;

m is 0, 1 or 2; and

R$_{11}$ is C$_{1-3}$ alkyl;

preferably, R$_5$ is chosen from

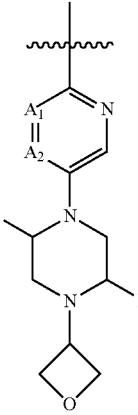

wherein R$_{24}$ and R$_{24}'$ are each independently chosen from hydrogen, oxo and C$_{1-6}$ alkyl, both A$_1$ and A$_2$ are CH, or A$_1$ is N and A$_2$ is CH;

and more preferably, both A$_1$ and A$_2$ are CH.

Embodiment 37. The compound of embodiment 1, or a pharmaceutically acceptable salt thereof, or a solvate, a racemic mixture, an enantiomer, a diastereomer or a tautomer thereof, which is chosen from.

| No. | Structural formula |
|---|---|
| 1 | 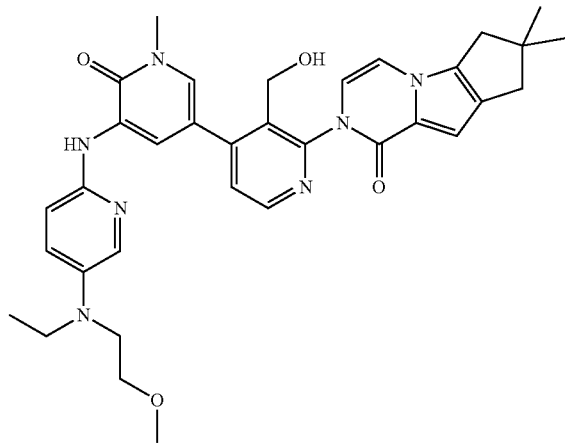 [SMILES: CCN(CCOC)c1ccc(Nc2cc(-c3ccnc(-n4ccn5c6c(cc5c4=O)CC(C)(C)C6)c3CO)cn(C)c2=O)nc1] |
| 2 | 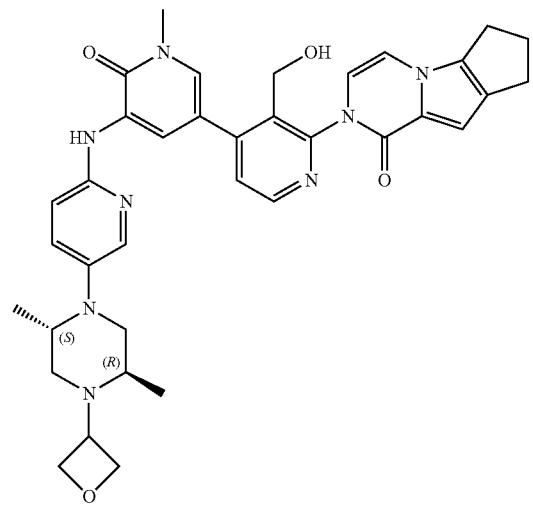 |
| 3 | 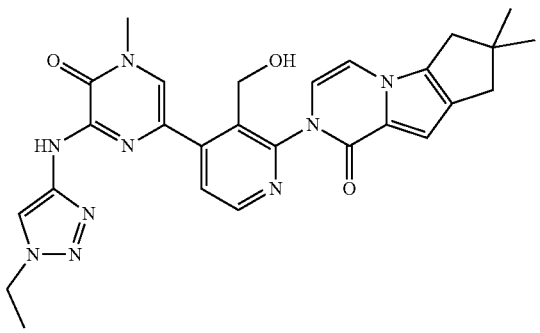 [SMILES: CCn1cc(Nc2nc(-c3ccnc(-n4ccn5c6c(cc5c4=O)CC(C)(C)C6)c3CO)cn(C)c2=O)nn1] |
| 4 | 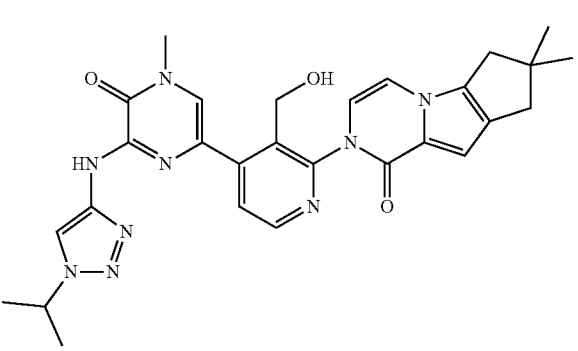 [SMILES: CC(C)n1cc(Nc2nc(-c3ccnc(-n4ccn5c6c(cc5c4=O)CC(C)(C)C6)c3CO)cn(C)c2=O)nn1] |

-continued
| No. | Structural formula |
|---|---|
| 5 | 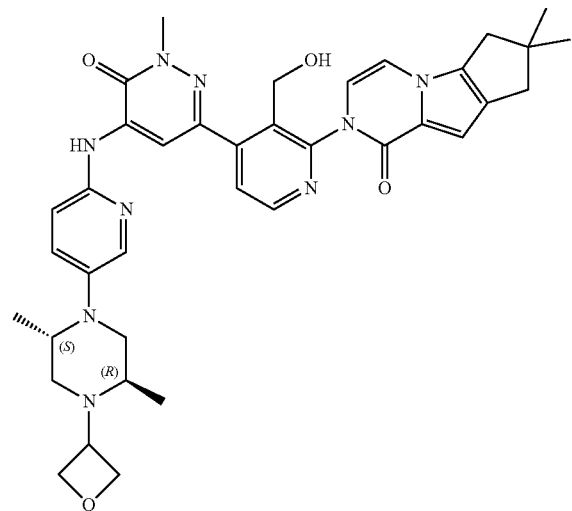 |
| 6 | 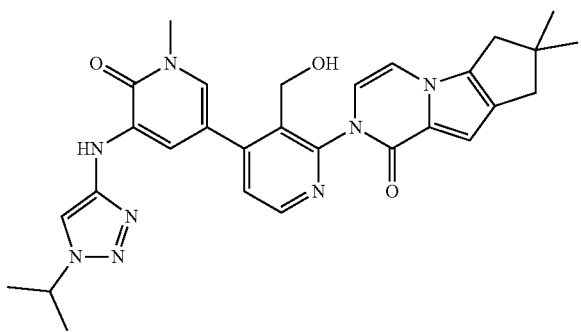 [SMILES: CC(C)n1cc(Nc2cc(-c3ccnc(-n4ccn5c6c(cc5c4=O)CC(C)(C)C6)c3CO)cn(C)c2=O)nn1] |
| 7 | 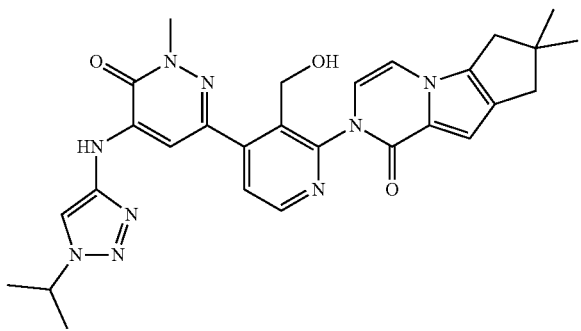 [SMILES: CC(C)n1cc(Nc2cc(-c3ccnc(-n4ccn5c6c(cc5c4=O)CC(C)(C)C6)c3CO)nn(C)c2=O)nn1] |

-continued
| No. | Structural formula |
|-----|--------------------|
| 8 | 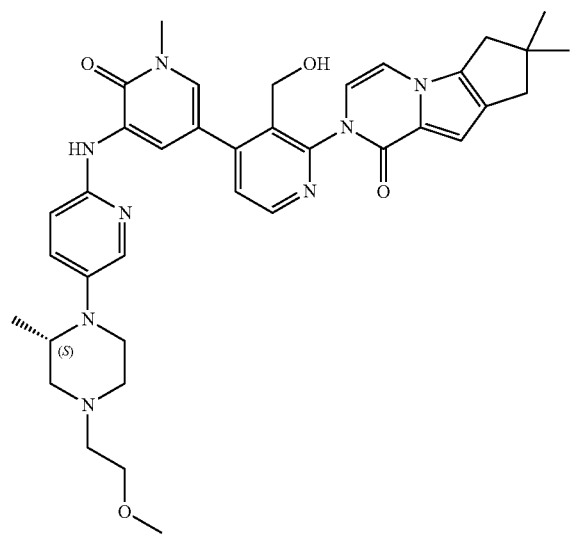 |
| 9 | 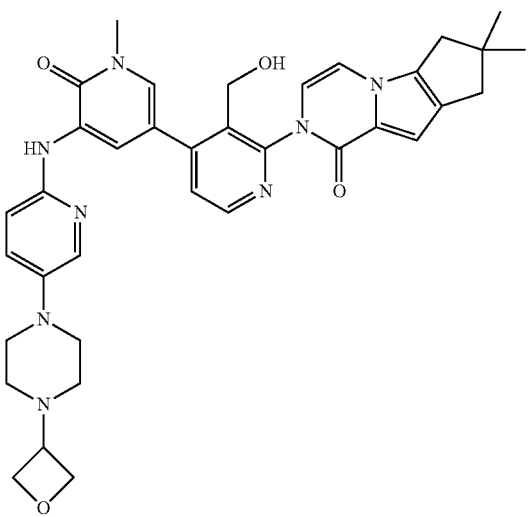 [SMILES: Cn1cc(-c2ccnc(-n3ccn4c5c(cc4c3=O)CC(C)(C)C5)c2CO)cc(Nc2ccc(N3CCN(C4COC4)CC3)cn2)c1=O] |
| 10 | 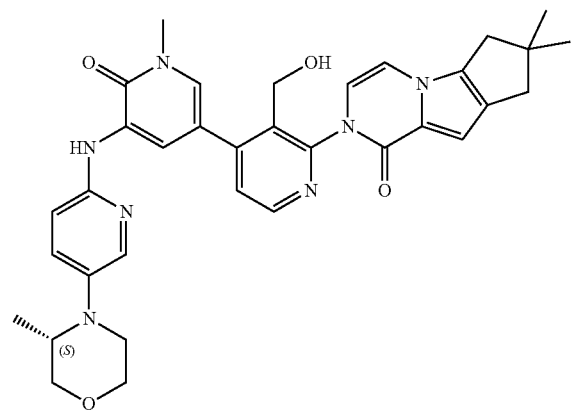 |

| No. | Structural formula |
|---|---|
| 11 | 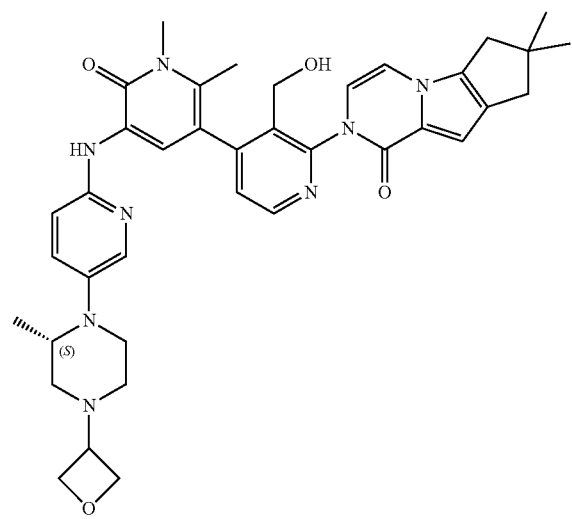 |
| 12 | 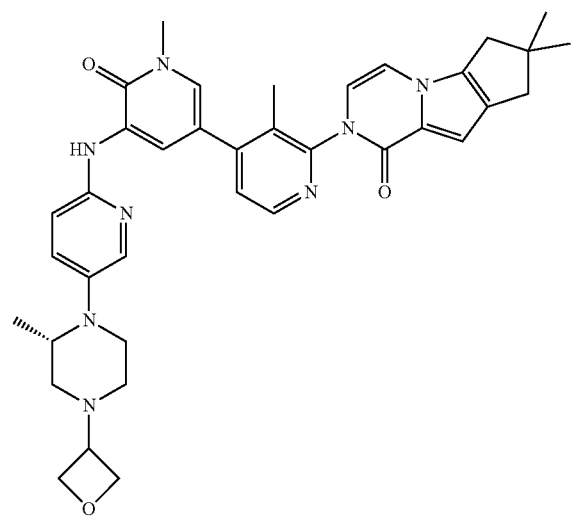 |
| 13 | 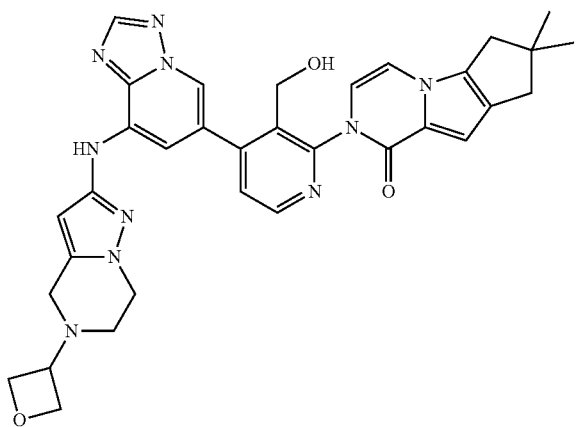 [SMILES: CC1(C)Cc2cc3c(=O)n(-c4nccc(-c5cc(Nc6cc7n(n6)CCN(C6COC6)C7)c6ncnn6c5)c4CO)ccn3c2C1] |

-continued

| No. | Structural formula |
|---|---|
| 14 | |
| 15 | |
| 16 | |
| 17 | |

-continued

| No. | Structural formula |
|---|---|
| 18 | |
| 19 | |
| 20 | |

| No. | Structural formula |
|---|---|
| 21 | |
| 22 | |
| 23 | |

| No. | Structural formula |
|---|---|
| 24 | 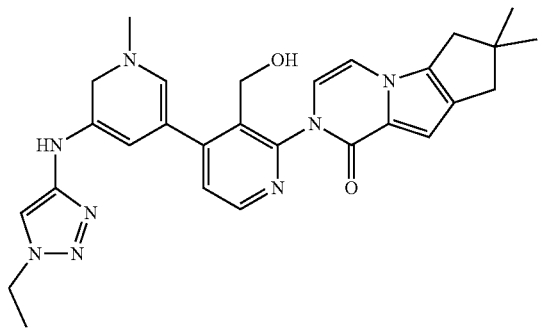 [SMILES: CCn1cc(NC2=CC(c3ccnc(-n4ccn5c6c(cc5c4=O)CC(C)(C)C6)c3CO)=CN(C)C2)nn1] |
| 25 | 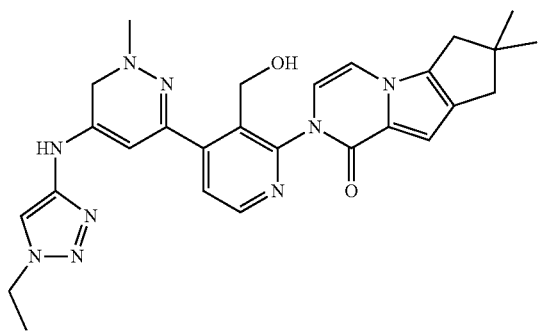 [SMILES: CCn1cc(NC2=CC(c3ccnc(-n4ccn5c6c(cc5c4=O)CC(C)(C)C6)c3CO)=NN(C)C2)nn1] |
| 26 | 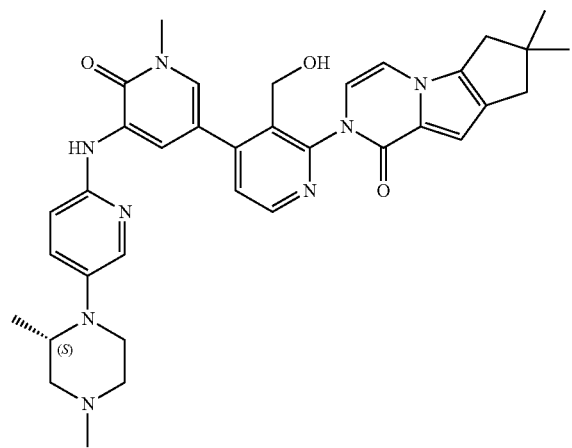 |

| No. | Structural formula |
|---|---|
| 27 | 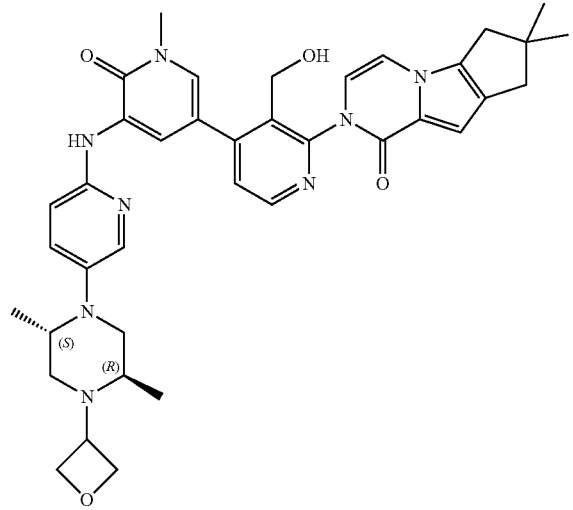 |
| 28 | 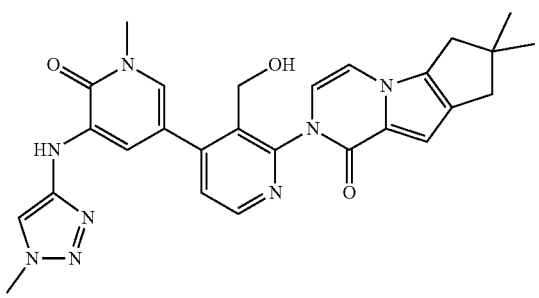 |
| 29 | 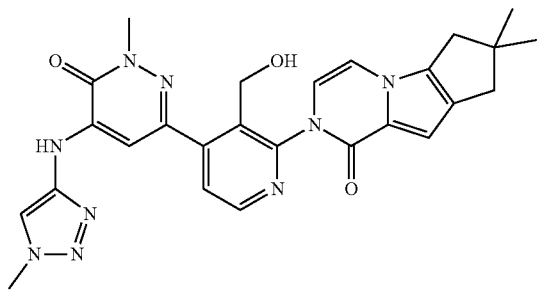 |
| 30 | 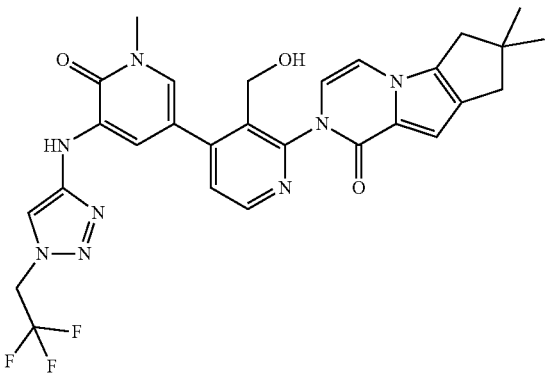 [SMILES: Cn1cc(-c2ccnc(-n3ccn4c5c(cc4c3=O)CC(C)(C)C5)c2CO)cc(Nc2cn(CC(F)(F)F)nn2)c1=O] |

| No. | Structural formula |
|---|---|
| 31 | 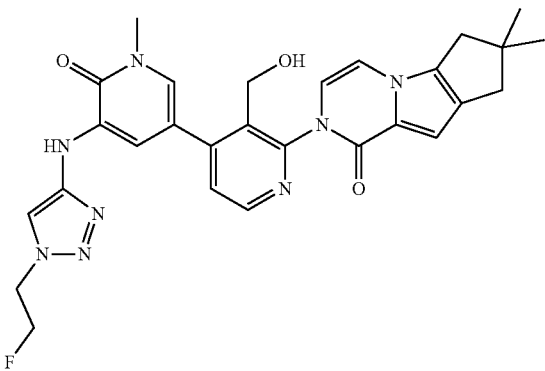 [SMILES: Cn1cc(-c2ccnc(-n3ccn4c5c(cc4c3=O)CC(C)(C)C5)c2CO)cc(Nc2cn(CCF)nn2)c1=O] |
| 32 | 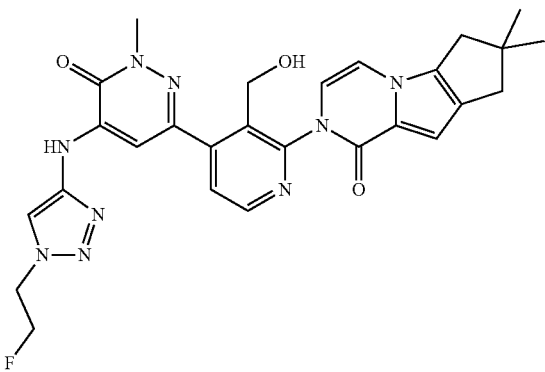 [SMILES: Cn1nc(-c2ccnc(-n3ccn4c5c(cc4c3=O)CC(C)(C)C5)c2CO)cc(Nc2cn(CCF)nn2)c1=O] |
| 33 | 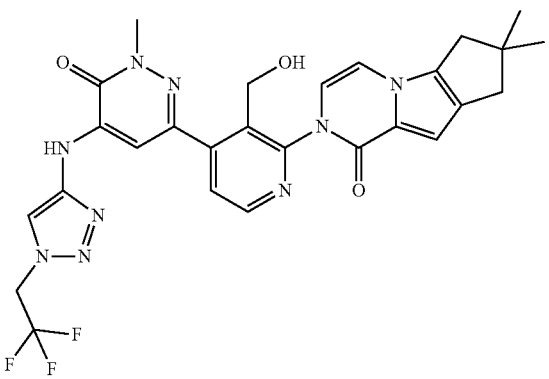 [SMILES: Cn1nc(-c2ccnc(-n3ccn4c5c(cc4c3=O)CC(C)(C)C5)c2CO)cc(Nc2cn(CC(F)(F)F)nn2)c1=O] |

| No. | Structural formula |
|---|---|
| 34 | 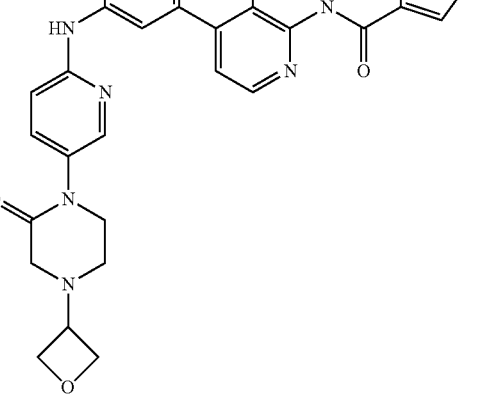 |
| 35 | 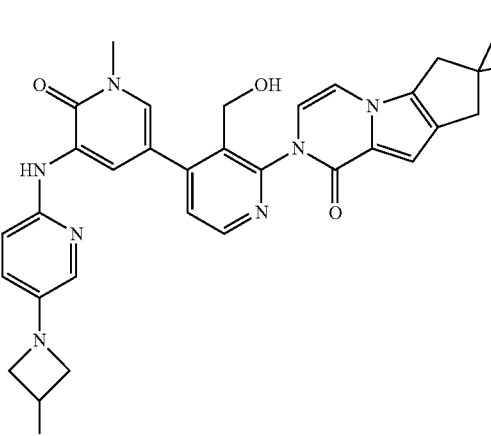 |
| 36 | 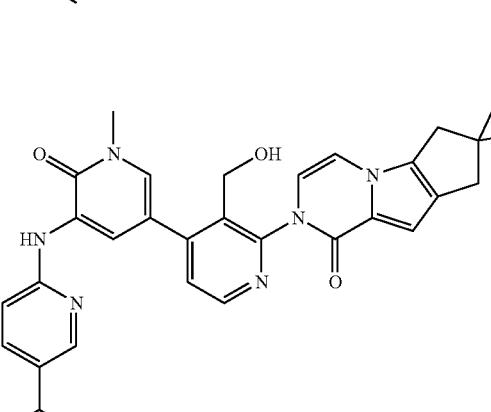 |

-continued

| No. | Structural formula |
|---|---|
| 37 | |
| 38 | |
| 39 | |

-continued

| No. | Structural formula |
|---|---|
| 40 | |
| 41 | |
| 42 | |
| 43 | |

| No. | Structural formula |
|---|---|
| 44 | 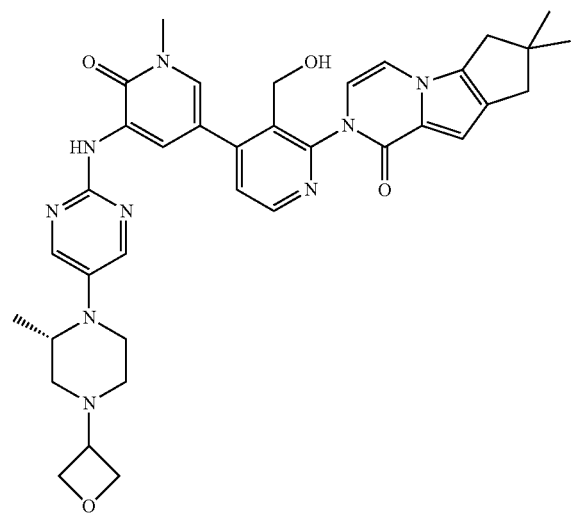 |
| 45 | 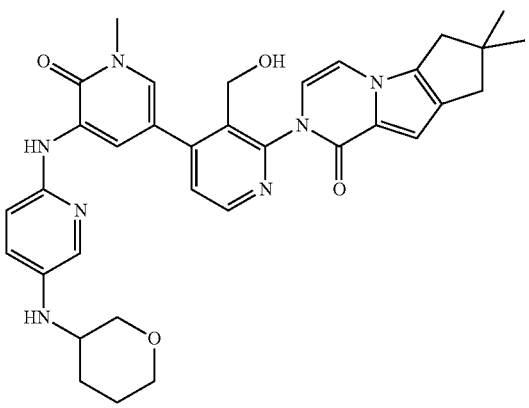 [SMILES: Cn1cc(-c2ccnc(-n3ccn4c5c(cc4c3=O)CC(C)(C)C5)c2CO)cc(Nc2ccc(NC3CCCOC3)cn2)c1=O] |
| 46 | 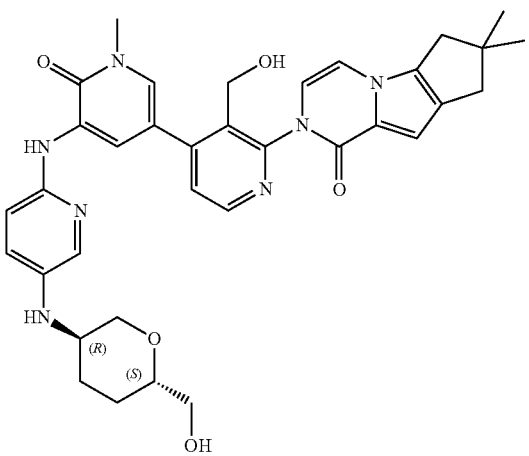 |

| No. | Structural formula |
|---|---|
| 47 | 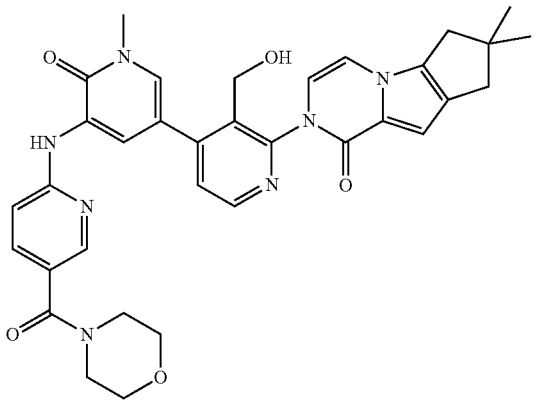 [SMILES: Cn1cc(-c2ccnc(-n3ccn4c5c(cc4c3=O)CC(C)(C)C5)c2CO)cc(Nc2ccc(C(=O)N3CCOCC3)cn2)c1=O] |
| 48 | 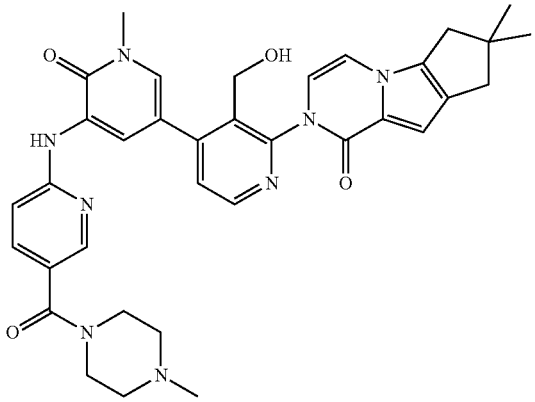 [SMILES: CN1CCN(C(=O)c2ccc(Nc3cc(-c4ccnc(-n5ccn6c7c(cc6c5=O)CC(C)(C)C7)c4CO)cn(C)c3=O)nc2)CC1] |
| 49 | 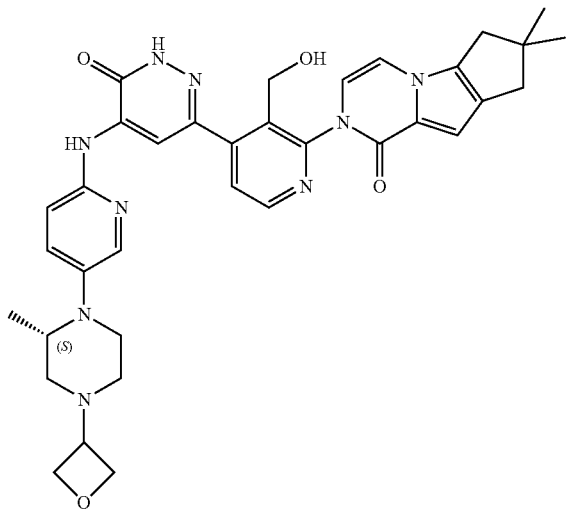 |

| No. | Structural formula |
|---|---|
| 50 | 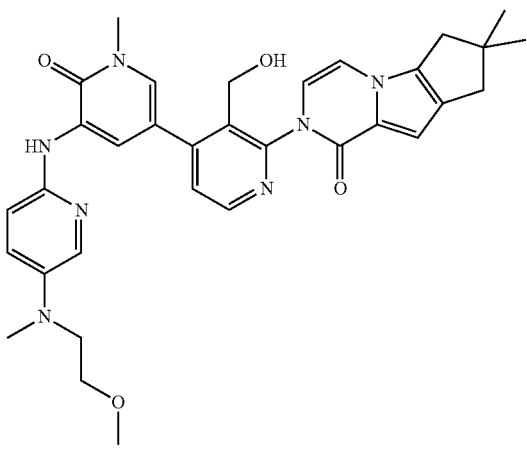 [SMILES: COCCN(C)c1ccc(Nc2cc(-c3ccnc(-n4ccn5c6c(cc5c4=O)CC(C)(C)C6)c3CO)cn(C)c2=O)nc1] |
| 51 | 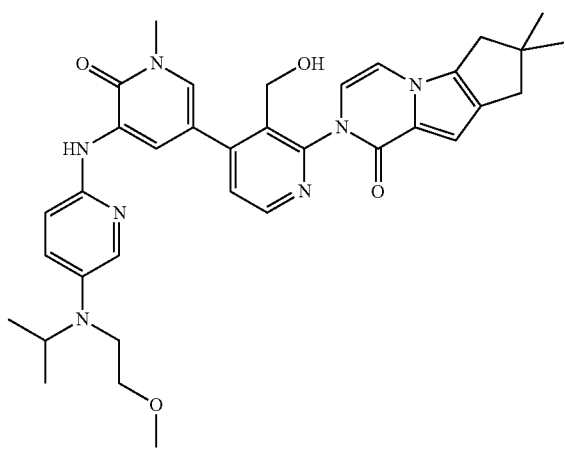 [SMILES: COCCN(c1ccc(Nc2cc(-c3ccnc(-n4ccn5c6c(cc5c4=O)CC(C)(C)C6)c3CO)cn(C)c2=O)nc1)C(C)C] |
| 52 | 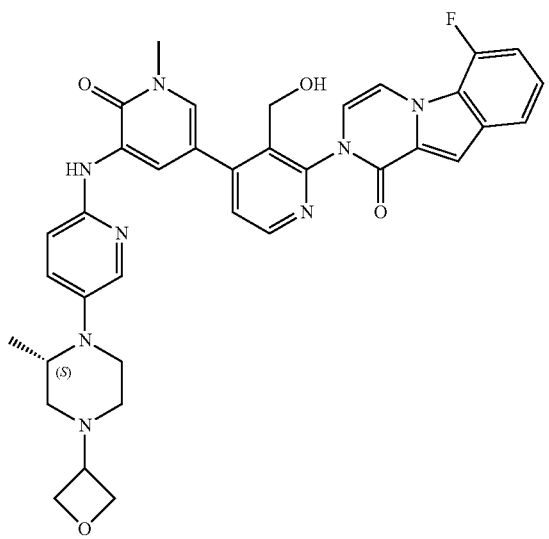 |

-continued

| No. | Structural formula |
|---|---|
| 53 | |
| 54 | |
| 55 | |
| 56 | |

-continued
| No. | Structural formula |
|---|---|
| 57 | 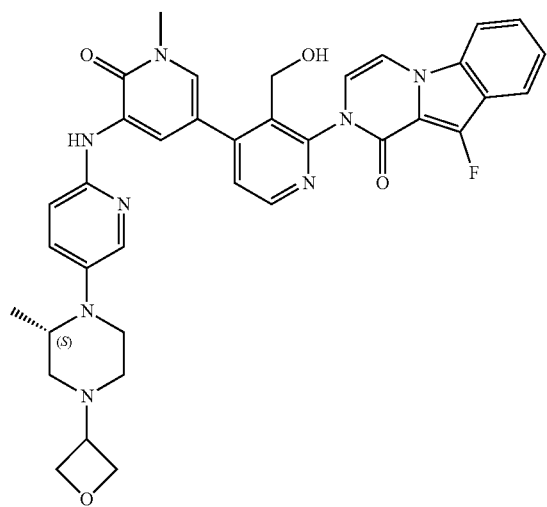 |
| 58 | 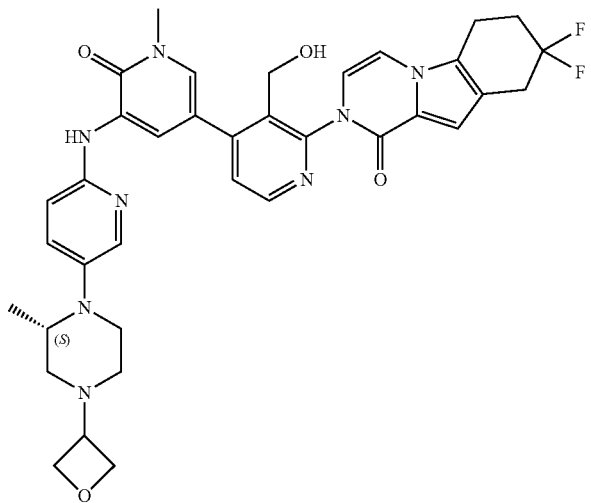 |
| 59 | 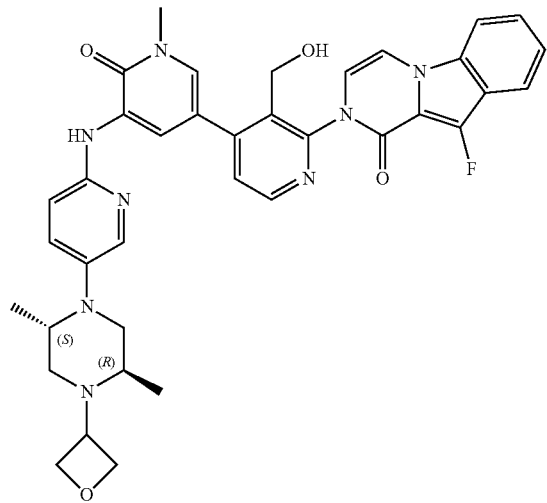 |

-continued

| No. | Structural formula |
|---|---|
| 60 | |
| 61 | |
| 62 | |

-continued
| No. | Structural formula |
|---|---|
| 63 | 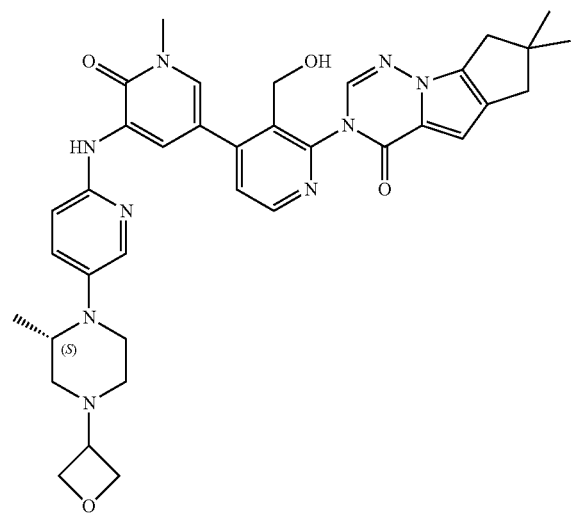 |
| 64 | 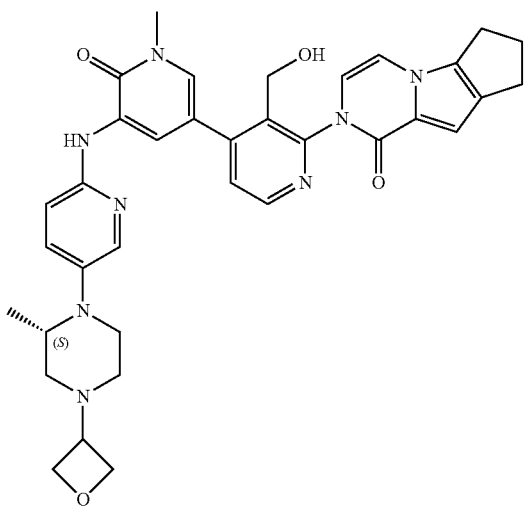 |
| 65 | 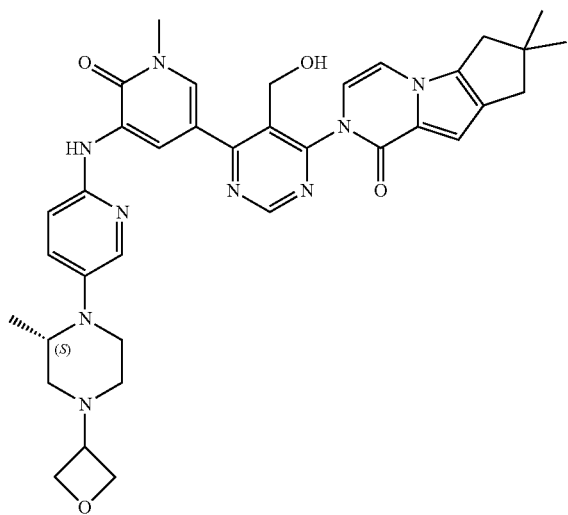 |

| No. | Structural formula |
|---|---|
| 66 | 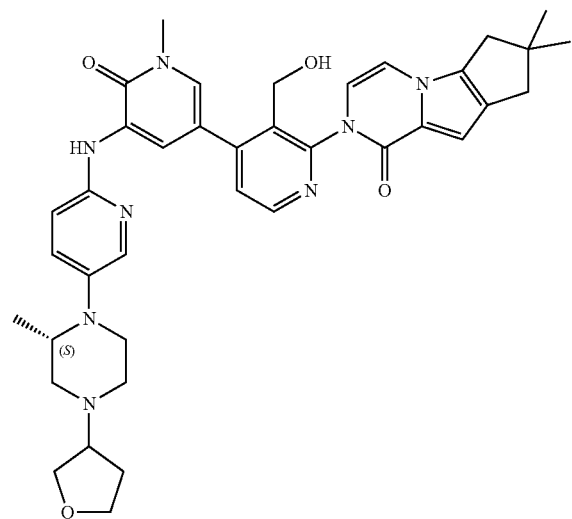 |
| 67 | 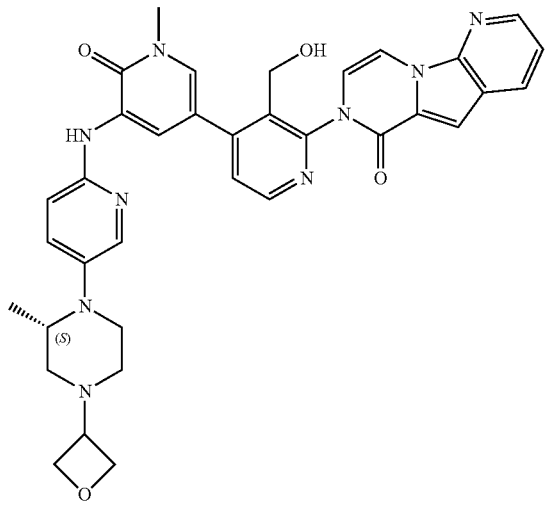 |
| 68 | 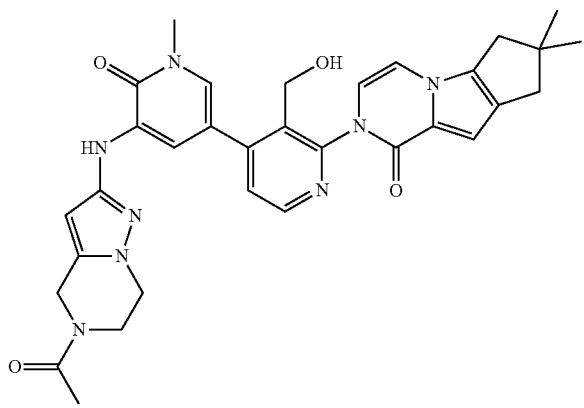 [SMILES: CC(=O)N1CCn2nc(Nc3cc(-c4ccnc(-n5ccn6c7c(cc6c5=O)CC(C)(C)C7)c4CO)cn(C)c3=O)cc2C1] |

| No. | Structural formula |
|---|---|
| 69 | 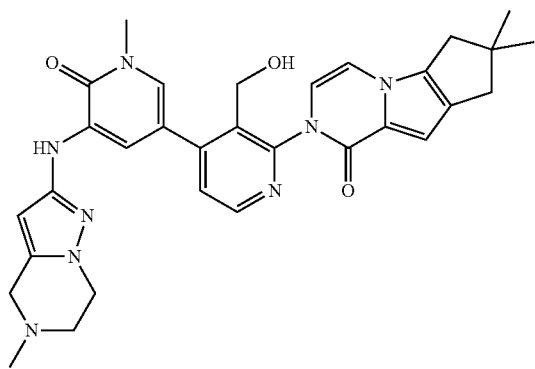 [SMILES: CN1CCn2nc(Nc3cc(-c4ccnc(-n5ccn6c7c(cc6c5=O)CC(C)(C)C7)c4CO)cn(C)c3=O)cc2C1] |
| 70 | 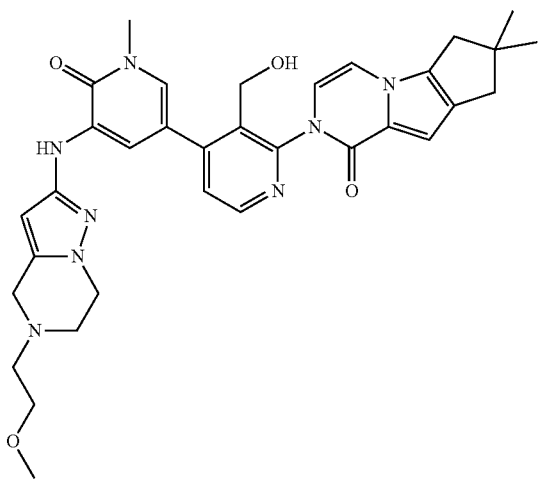 [SMILES: COCCN1CCn2nc(Nc3cc(-c4ccnc(-n5ccn6c7c(cc6c5=O)CC(C)(C)C7)c4CO)cn(C)c3=O)cc2C1] |
| 71 | 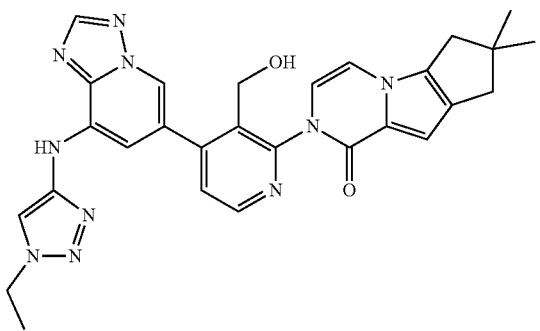 [SMILES: CCn1cc(Nc2cc(-c3ccnc(-n4ccn5c6c(cc5c4=O)CC(C)(C)C6)c3CO)cn3ncnc23)nn1] |

| No. | Structural formula |
|---|---|
| 72 | 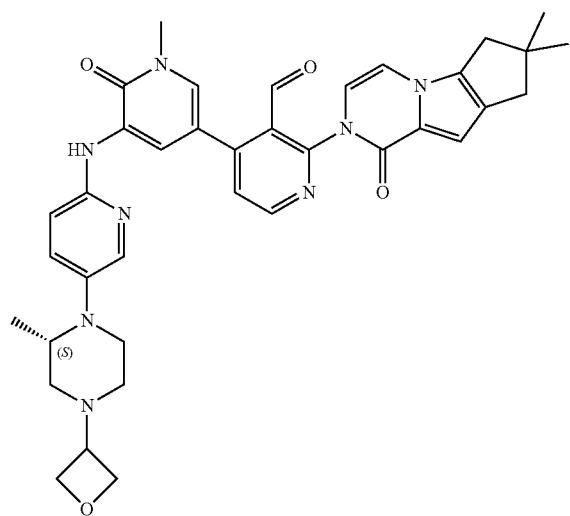 |
| 73 | 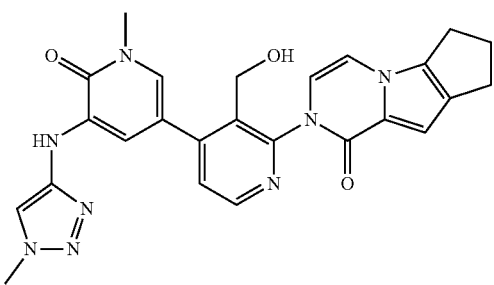 |
| 74 | 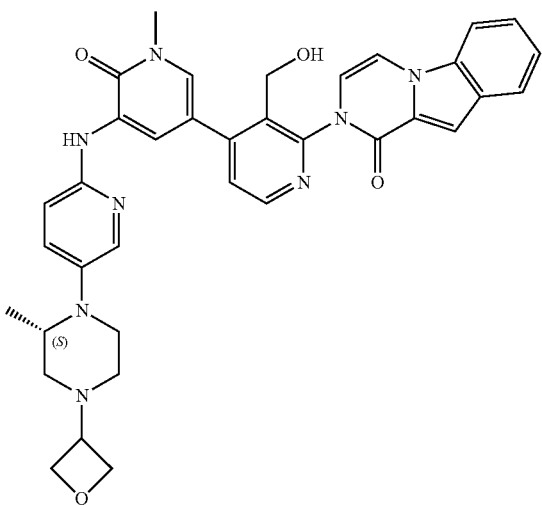 |

-continued

| No. | Structural formula |
|---|---|
| 75 | |
| 76 | |
| 77 | |

-continued
| No. | Structural formula |
|---|---|
| 78 | 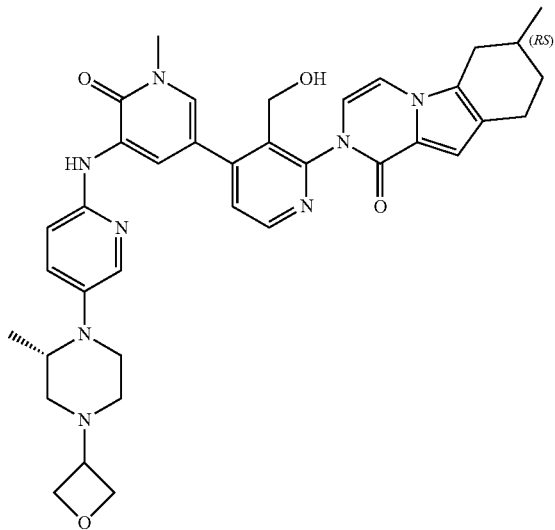 [SMILES: CC1CCc2cc3c(=O)n(-c4nccc(-c5cc(Nc6ccc(N7CCN(C8COC8)C[C@@H]7C)cn6)c(=O)n(C)c5)c4CO)ccn3c2C1] |
| 79 | 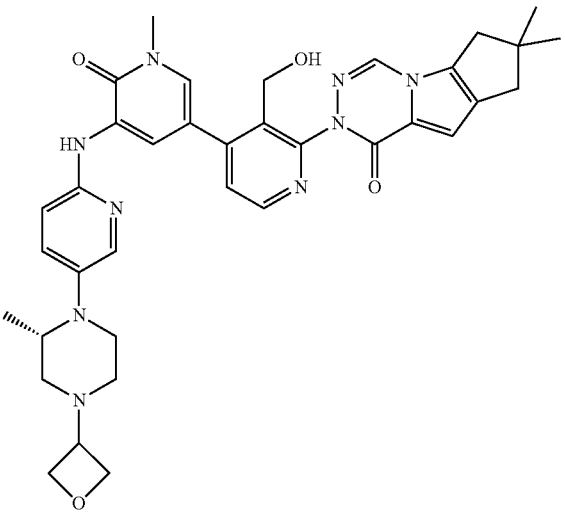 |
| 80 | 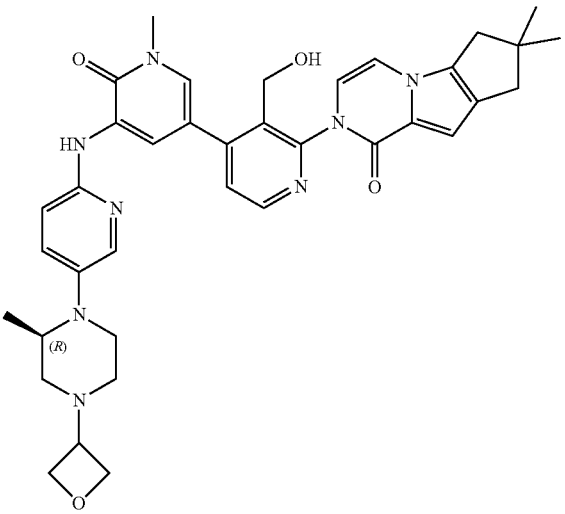 |

| No. | Structural formula |
|---|---|
| 81 | 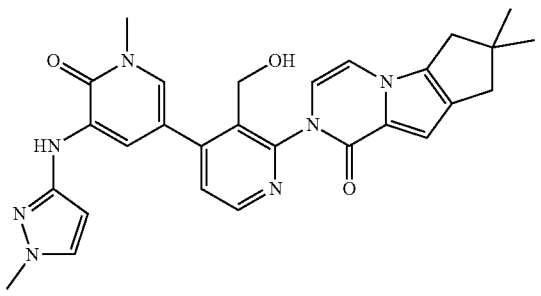 |
| 82 | 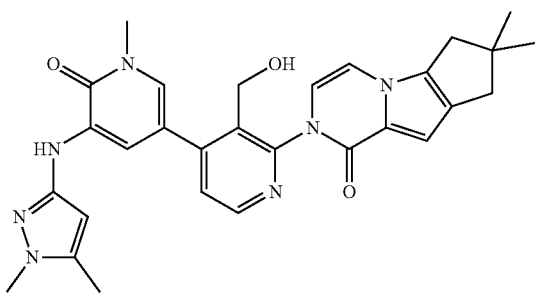 |
| 83 | 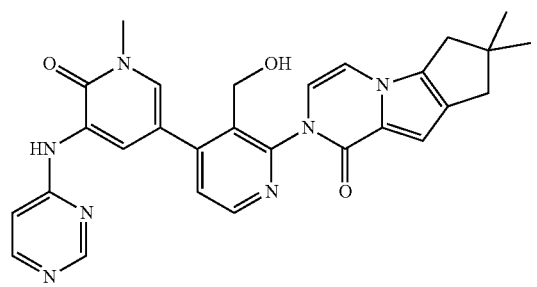 [SMILES: Cn1cc(-c2ccnc(-n3ccn4c5c(cc4c3=O)CC(C)(C)C5)c2CO)cc(Nc2ccncn2)c1=O] |
| 84 | 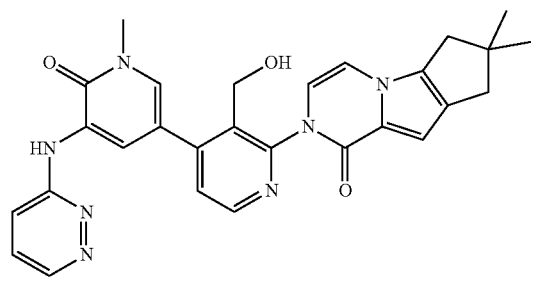 [SMILES: Cn1cc(-c2ccnc(-n3ccn4c5c(cc4c3=O)CC(C)(C)C5)c2CO)cc(Nc2cccnn2)c1=O] |
| 85 | 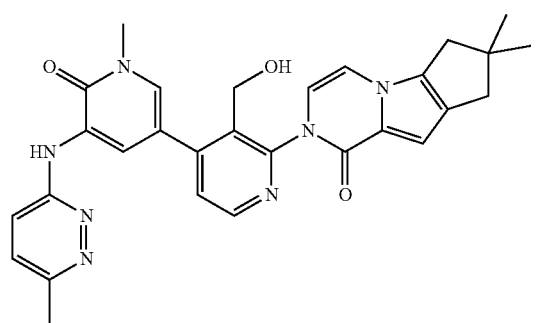 [SMILES: Cc1ccc(Nc2cc(-c3ccnc(-n4ccn5c6c(cc5c4=O)CC(C)(C)C6)c3CO)cn(C)c2=O)nn1] |

| No. | Structural formula |
|---|---|
| 86 | 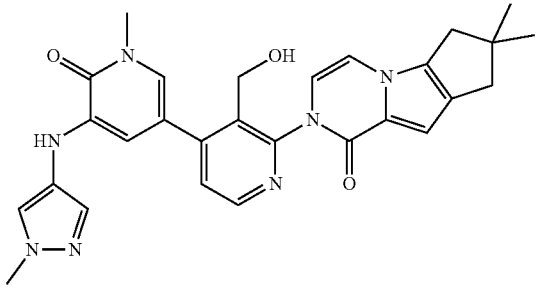 |
| 87 | 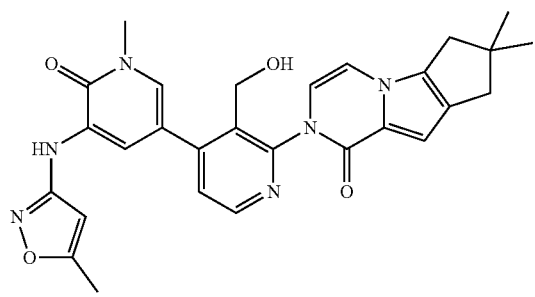 |
| 88 | 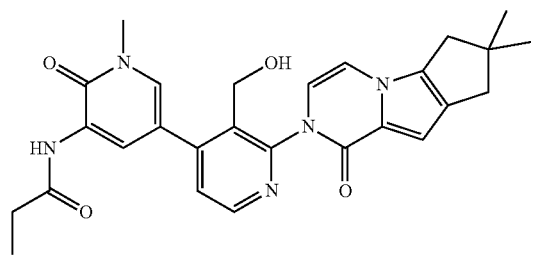 [SMILES: CCC(=O)Nc1cc(-c2ccnc(-n3ccn4c5c(cc4c3=O)CC(C)(C)C5)c2CO)cn(C)c1=O] |
| 89 | 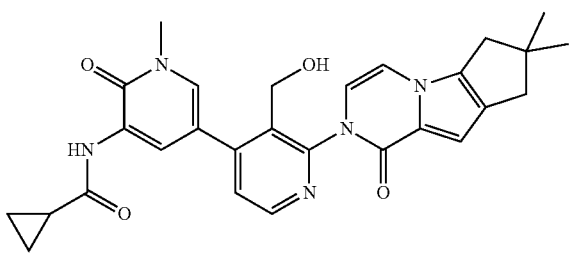 [SMILES: Cn1cc(-c2ccnc(-n3ccn4c5c(cc4c3=O)CC(C)(C)C5)c2CO)cc(NC(=O)C2CC2)c1=O] |
| 90 | 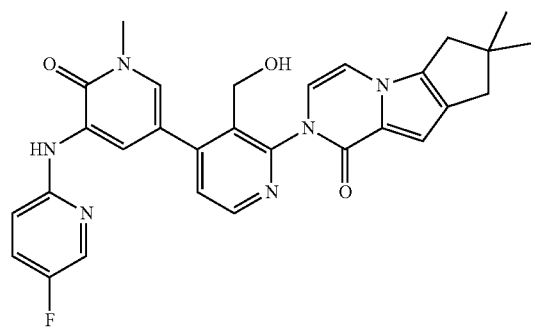 [SMILES: Cn1cc(-c2ccnc(-n3ccn4c5c(cc4c3=O)CC(C)(C)C5)c2CO)cc(Nc2ccc(F)cn2)c1=O] |

-continued

| No. | Structural formula |
|---|---|
| 91 | |
| 92 | |
| 93 | |

| No. | Structural formula |
|---|---|
| 94 | 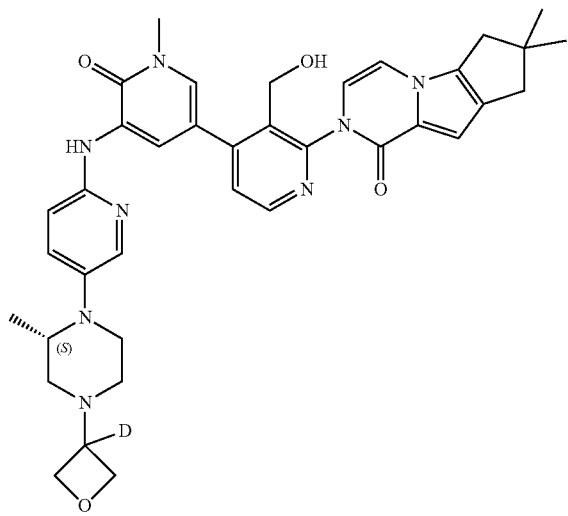 |
| 95 | 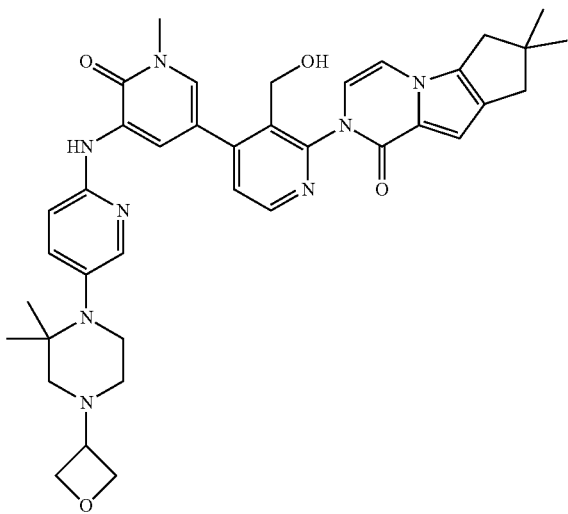 |
| 96 | 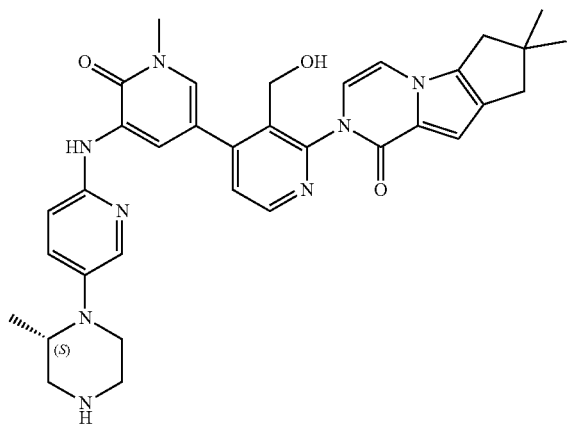 |

| No. | Structural formula |
|---|---|
| 97 | 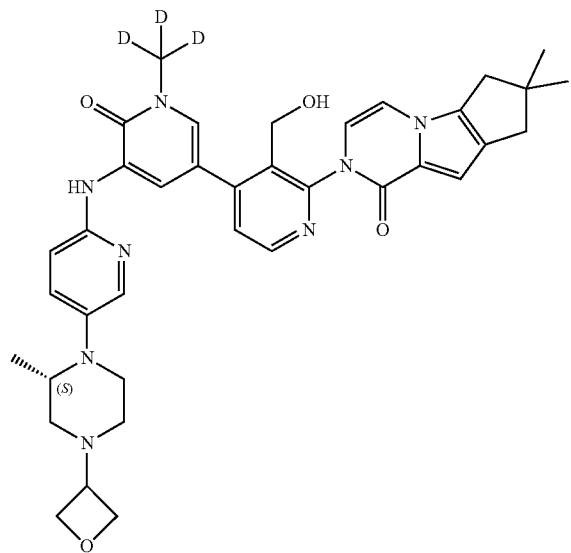 |
| 98 | 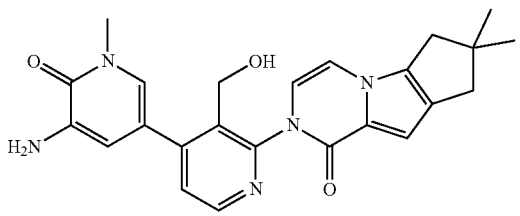 [SMILES: Cn1cc(-c2ccnc(-n3ccn4c5c(cc4c3=O)CC(C)(C)C5)c2CO)cc(N)c1=O] |
| 99 | 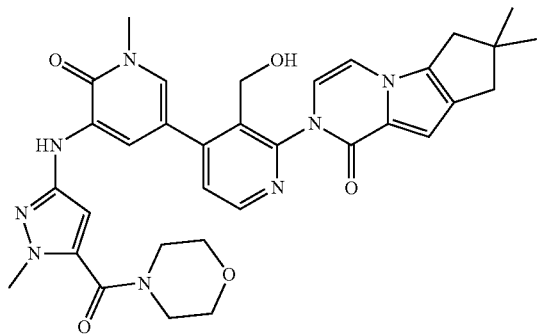 |

-continued
| No. | Structural formula |
|---|---|
| 100 | 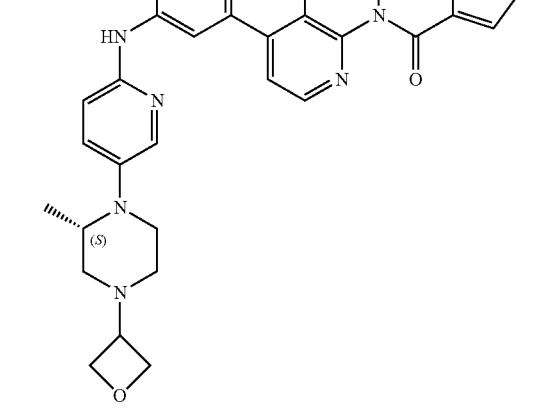 |
| 101 | 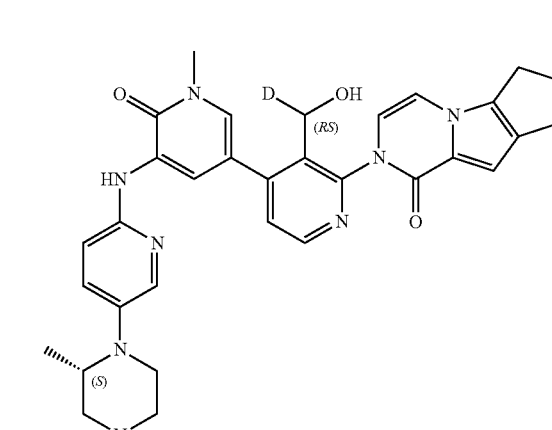 |
| 102 | 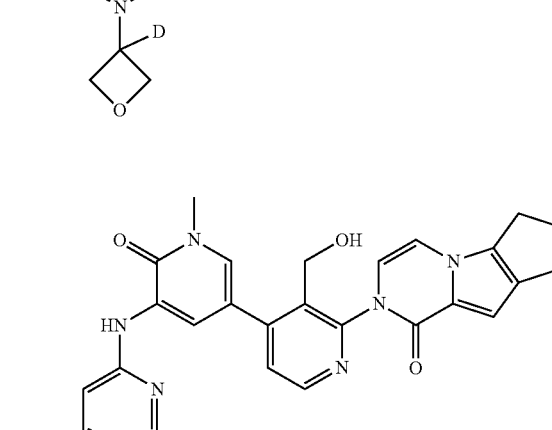 |

| No. | Structural formula |
|---|---|
| 103 | 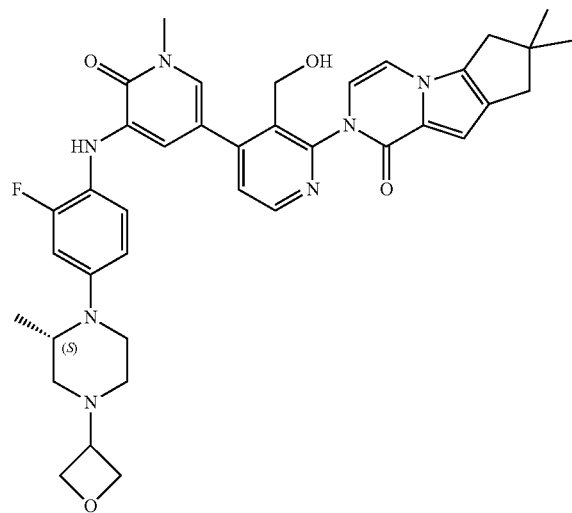 |
| 104 | 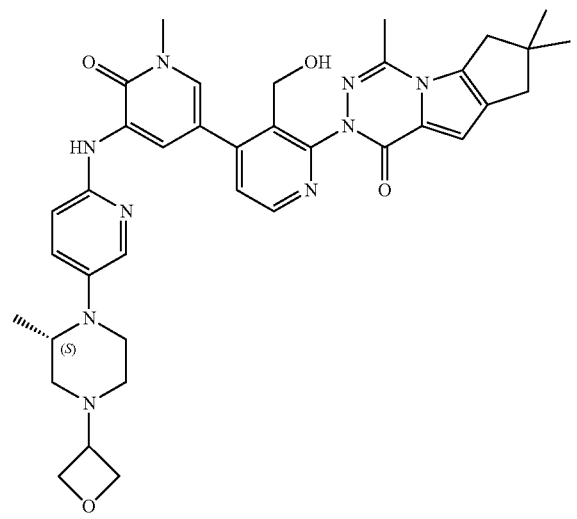 |
| 105 | 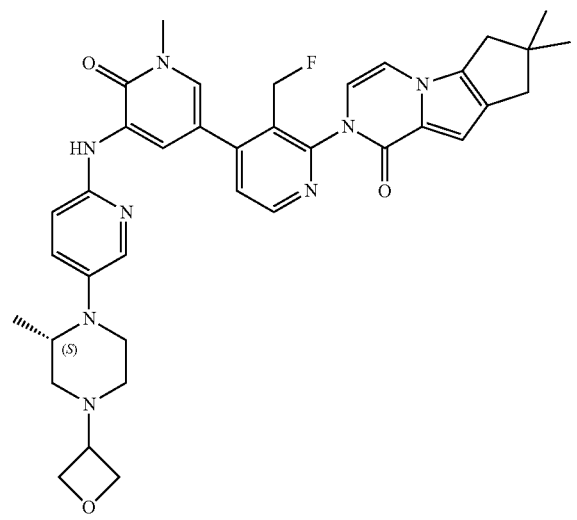 |

-continued
| No. | Structural formula |
|---|---|
| 106 | 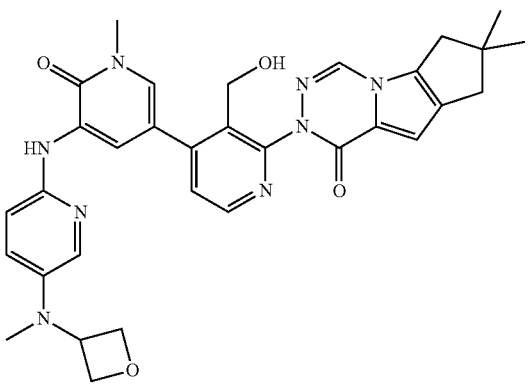 [SMILES: CN(c1ccc(Nc2cc(-c3ccnc(-n4ncn5c6c(cc5c4=O)CC(C)(C)C6)c3CO)cn(C)c2=O)nc1)C1COC1] |
| 107 | 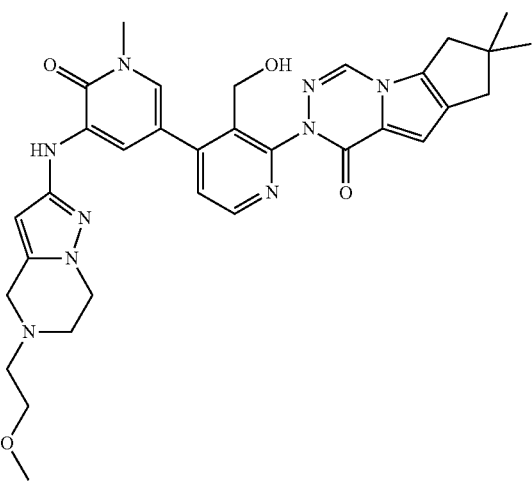 [SMILES: COCCN1CCn2nc(Nc3cc(-c4ccnc(-n5ncn6c7c(cc6c5=O)CC(C)(C)C7)c4CO)cn(C)c3=O)cc2C1] |
| 108 | 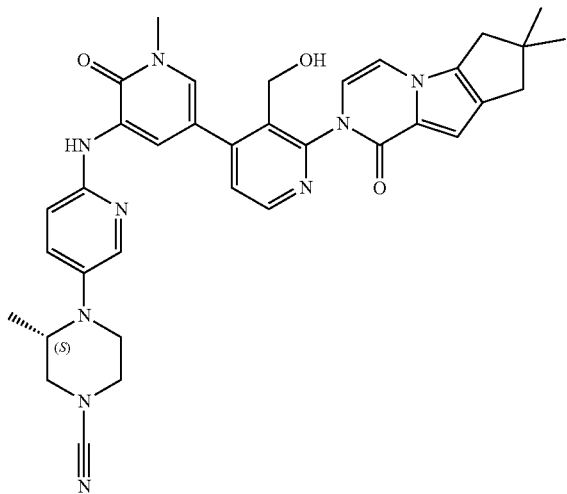 |

-continued
| No. | Structural formula |
|---|---|
| 109 | 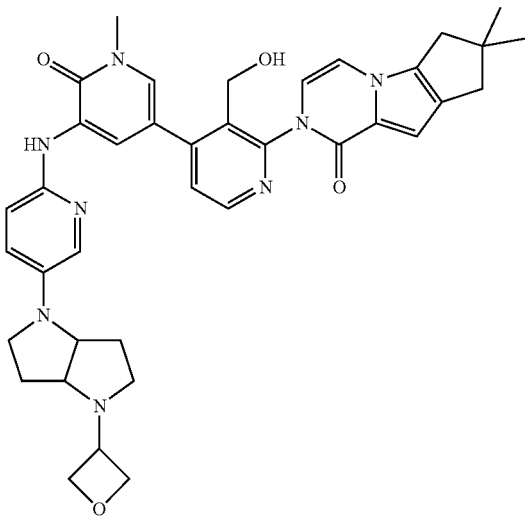 [SMILES: Cn1cc(-c2ccnc(-n3ccn4c5c(cc4c3=O)CC(C)(C)C5)c2CO)cc(Nc2ccc(N3CCC4C3CCN4C3COC3)cn2)c1=O] |
| 110 | 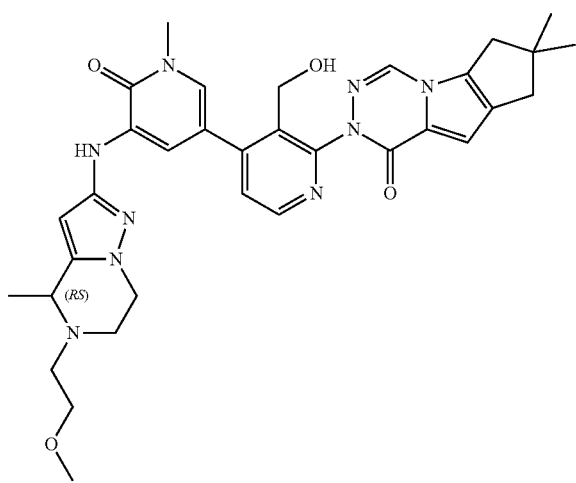 |
| 111 | 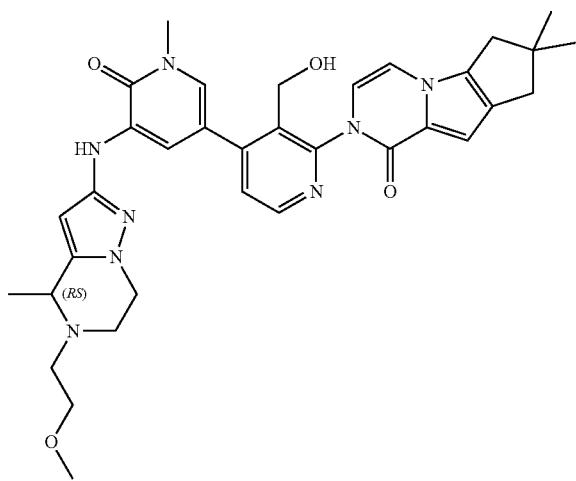 |

| No. | Structural formula |
|---|---|
| 112 | 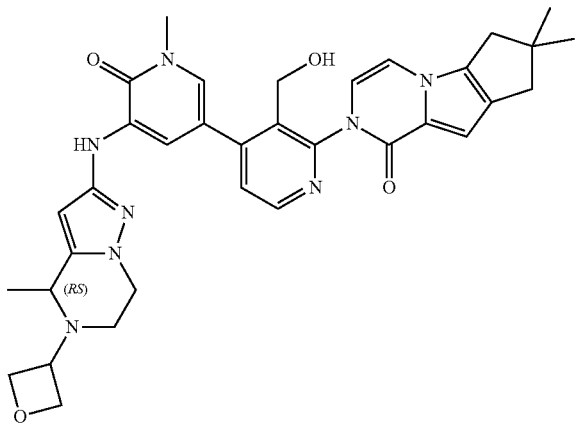 |
| 114 | 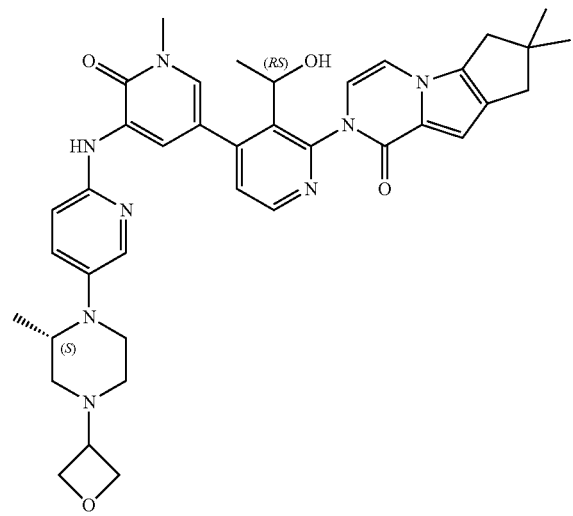 |
| 115 | 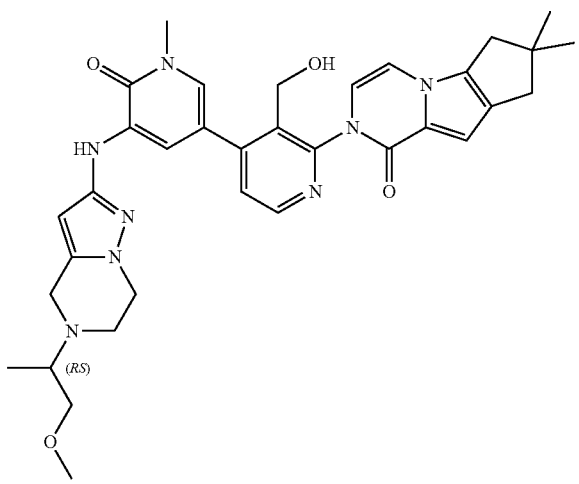 [SMILES: COCC(C)N1CCn2nc(Nc3cc(-c4ccnc(-n5ccn6c7c(cc6c5=O)CC(C)(C)C7)c4CO)cn(C)c3=O)cc2C1] |

| No. | Structural formula |
|---|---|
| 116 & 117 | 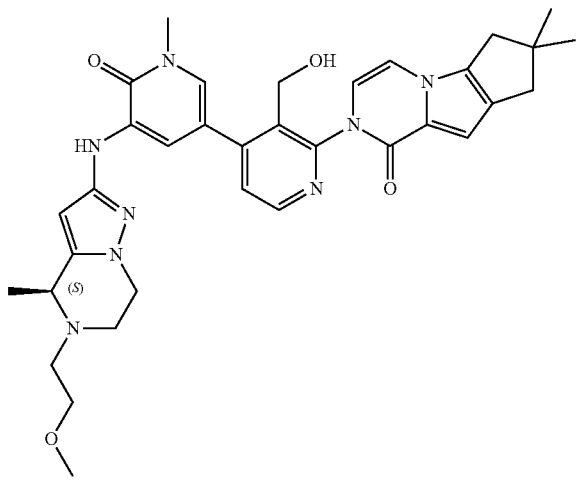 |
| | 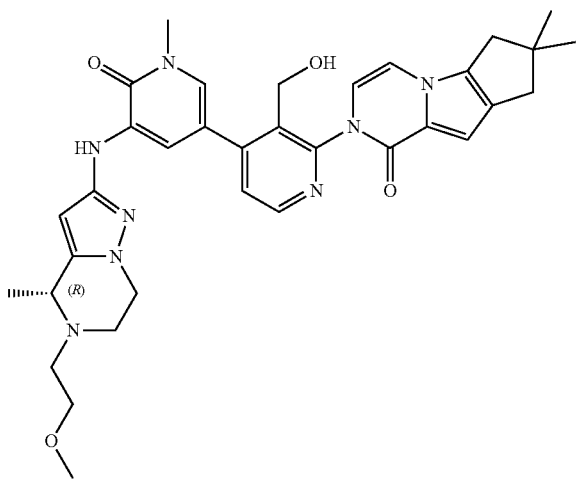 |
| 118 | 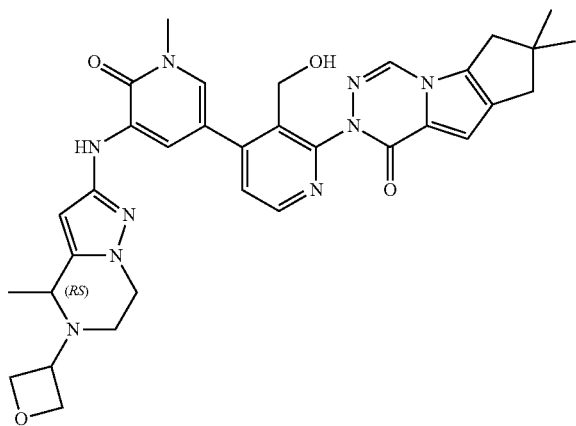 |

| No. | Structural formula |
|---|---|
| 119 & 120 | 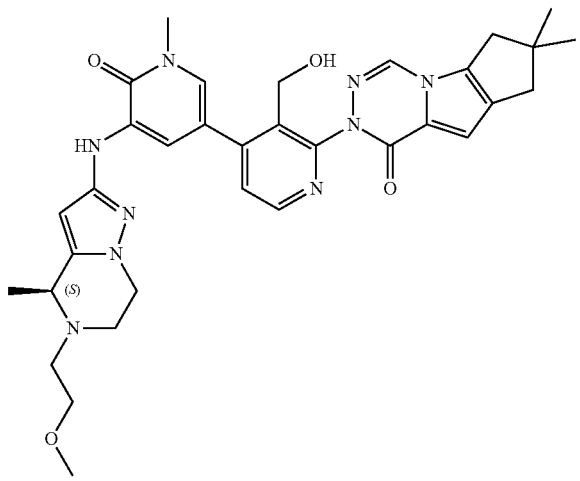 |
| | 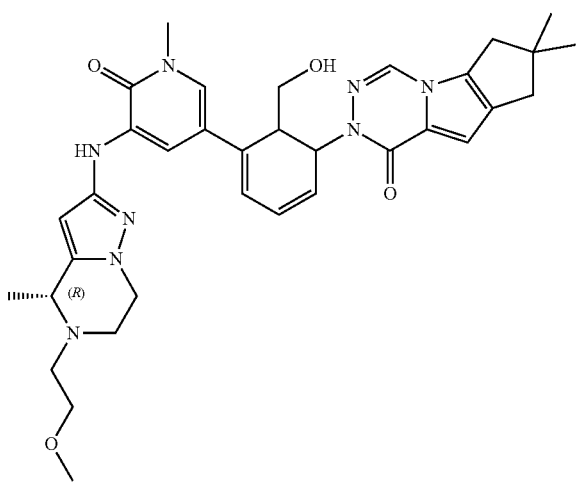 |
| 121 | 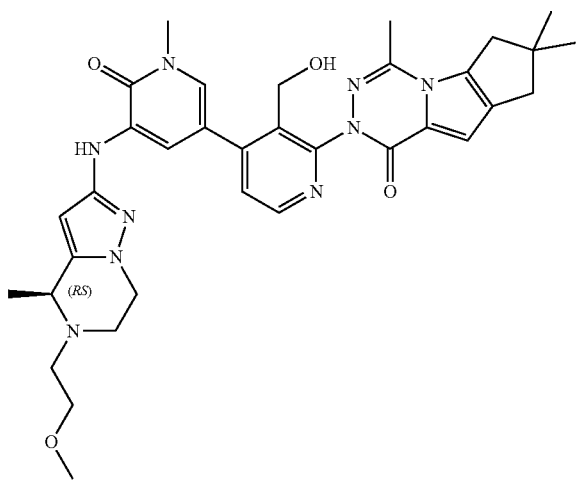 |

| No. | Structural formula |
|---|---|
| 122 | 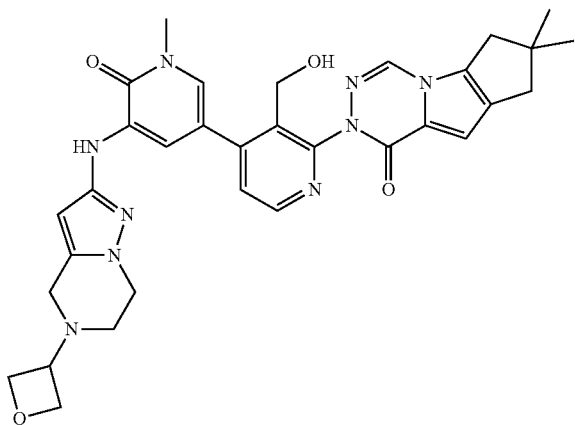 |
| 123 | 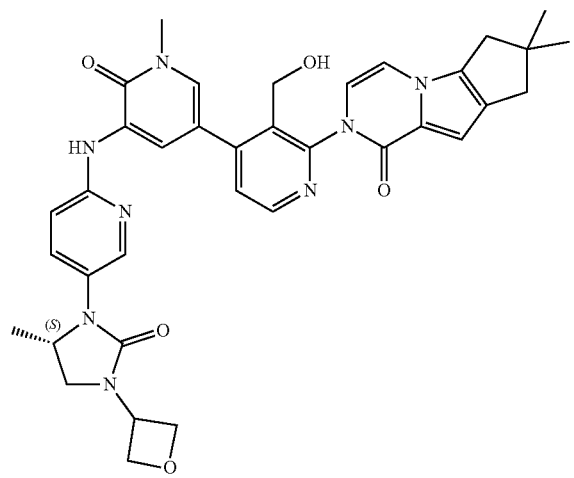 |
| 124 | 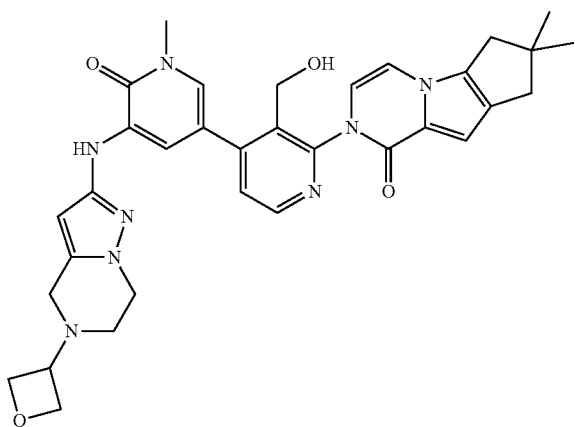 |

| No. | Structural formula |
|---|---|
| 125 | 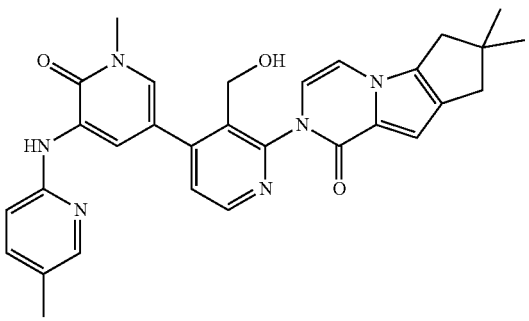 [SMILES: Cc1ccc(Nc2cc(-c3ccnc(-n4ccn5c6c(cc5c4=O)CC(C)(C)C6)c3CO)cn(C)c2=O)nc1] |
| 126 | 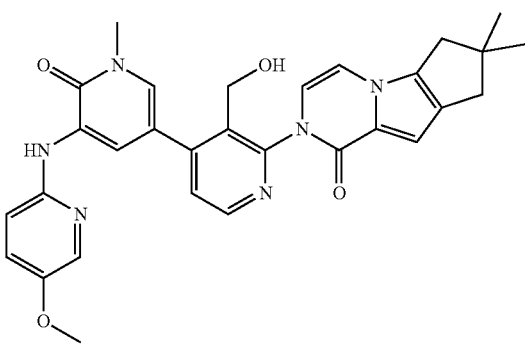 [SMILES: COc1ccc(Nc2cc(-c3ccnc(-n4ccn5c6c(cc5c4=O)CC(C)(C)C6)c3CO)cn(C)c2=O)nc1] |
| 127 | 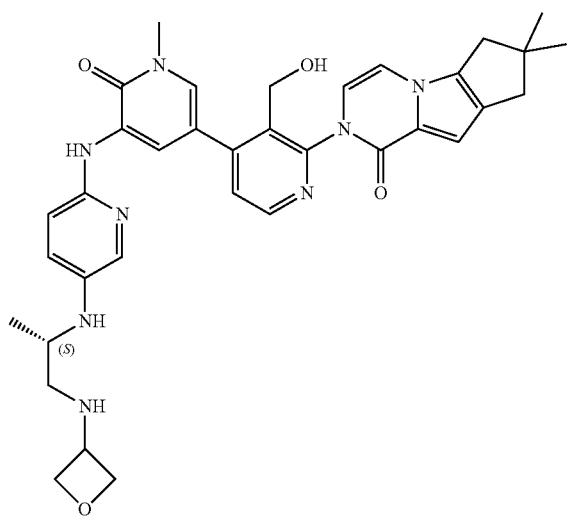 |
| 130 | 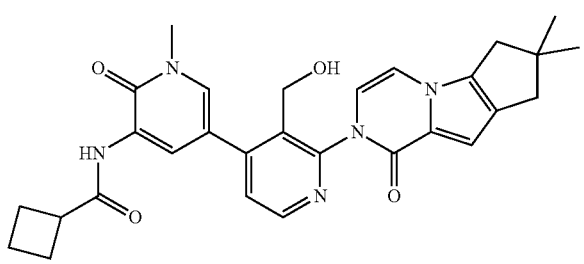 [SMILES: Cn1cc(-c2ccnc(-n3ccn4c5c(cc4c3=O)CC(C)(C)C5)c2CO)cc(NC(=O)C2CCC2)c1=O] |

| No. | Structural formula |
|---|---|
| 131 | 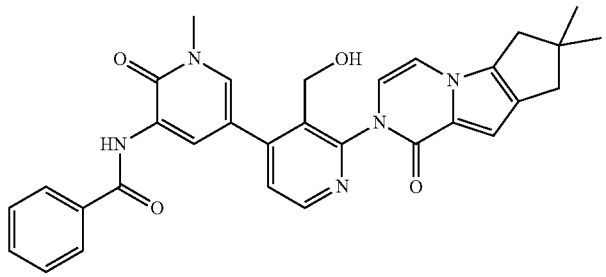 [SMILES: Cn1cc(-c2ccnc(-n3ccn4c5c(cc4c3=O)CC(C)(C)C5)c2CO)cc(NC(=O)c2ccccc2)c1=O] |
| 132 | 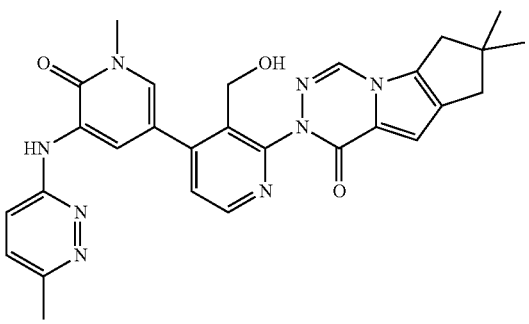 [SMILES: Cc1ccc(Nc2cc(-c3ccnc(-n4ncn5c6c(cc5c4=O)CC(C)(C)C6)c3CO)cn(C)c2=O)nn1] |
| 133 | 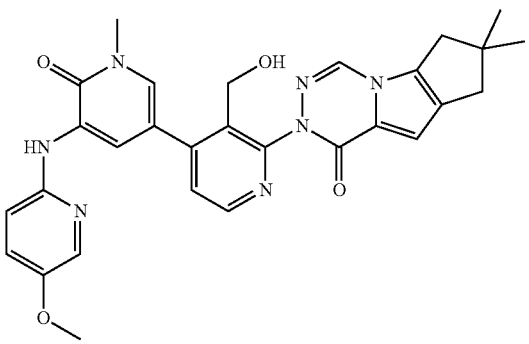 [SMILES: COc1ccc(Nc2cc(-c3ccnc(-n4ncn5c6c(cc5c4=O)CC(C)(C)C6)c3CO)cn(C)c2=O)nc1] |
| 134 | 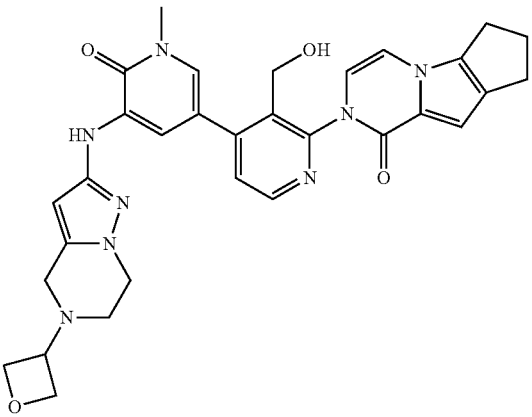 [SMILES: Cn1cc(-c2ccnc(-n3ccn4c5c(cc4c3=O)CCC5)c2CO)cc(Nc2cc3n(n2)CCN(C2COC2)C3)c1=O] |

| No. | Structural formula |
|---|---|
| 135 | 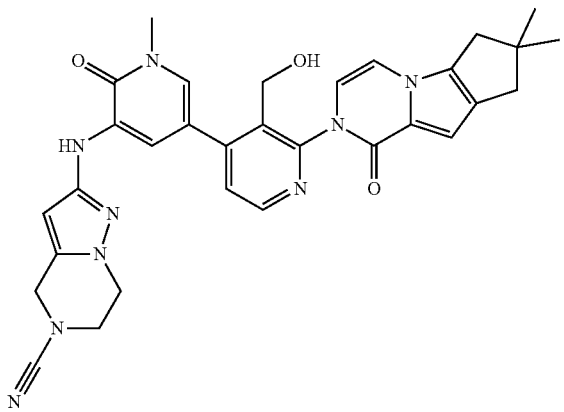 [SMILES: Cn1cc(-c2ccnc(-n3ccn4c5c(cc4c3=O)CC(C)(C)C5)c2CO)cc(Nc2cc3n(n2)CCN(C#N)C3)c1=O] |
| 136 & 137 | 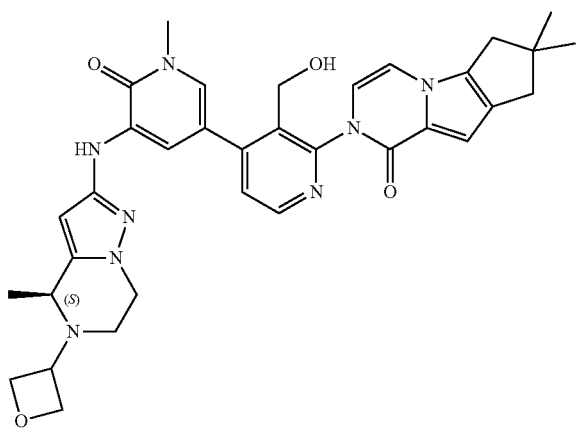 |
| | 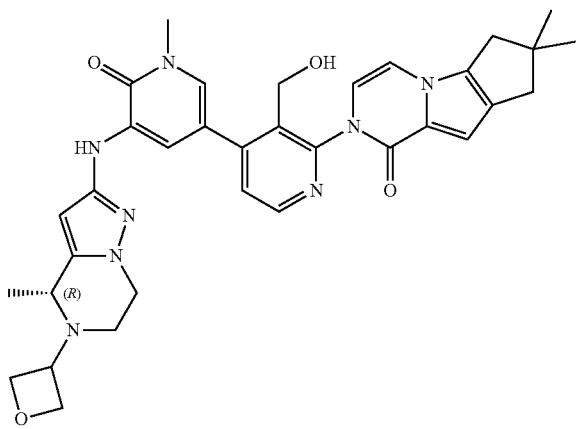 |
| 138 | 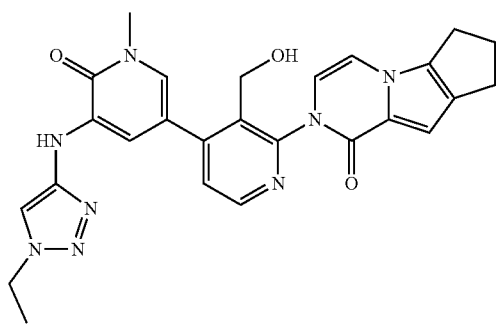 [SMILES: CCn1cc(Nc2cc(-c3ccnc(-n4ccn5c6c(cc5c4=O)CCC6)c3CO)cn(C)c2=O)nn1] |

| No. | Structural formula |
|-----|--------------------|
| 139 | 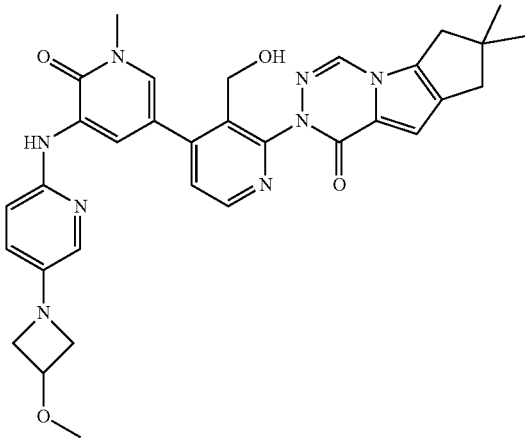 |
| 140 | 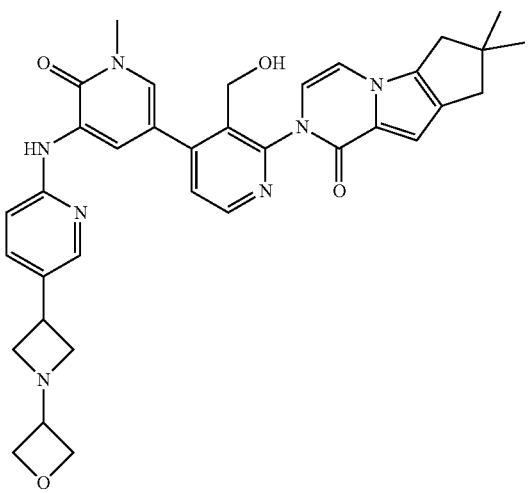 [SMILES: Cn1cc(-c2ccnc(-n3ccn4c5c(cc4c3=O)CC(C)(C)C5)c2CO)cc(Nc2ccc(C3CN(C4COC4)C3)cn2)c1=O] |
| 141 | 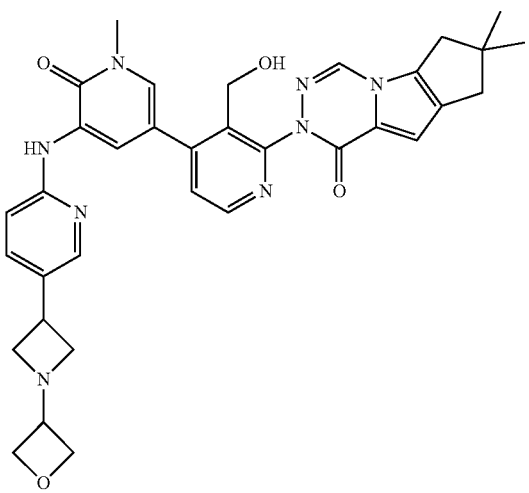 [SMILES: Cn1cc(-c2ccnc(-n3ncn4c5c(cc4c3=O)CC(C)(C)C5)c2CO)cc(Nc2ccc(C3CN(C4COC4)C3)cn2)c1=O] |

| No. | Structural formula |
|---|---|
| 142 | 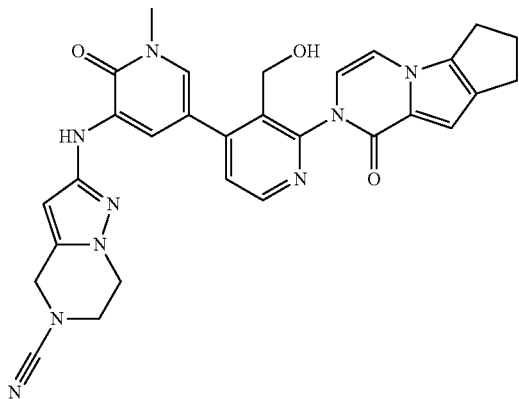 [SMILES: Cn1cc(-c2ccnc(-n3ccn4c5c(cc4c3=O)CCC5)c2CO)cc(Nc2cc3n(n2)CCN(C#N)C3)c1=O] |
| 143 | 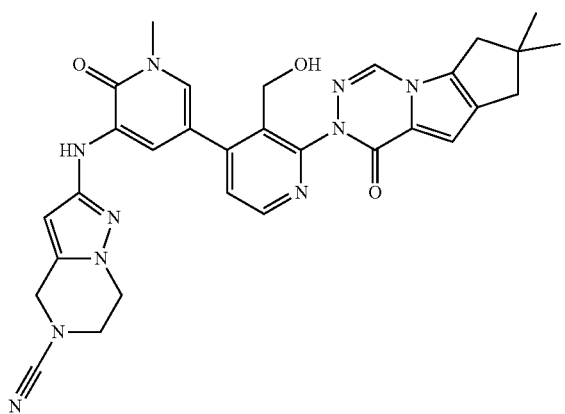 [SMILES: Cn1cc(-c2ccnc(-n3ncn4c5c(cc4c3=O)CC(C)(C)C5)c2CO)cc(Nc2cc3n(n2)CCN(C#N)C3)c1=O] |
| 144 | 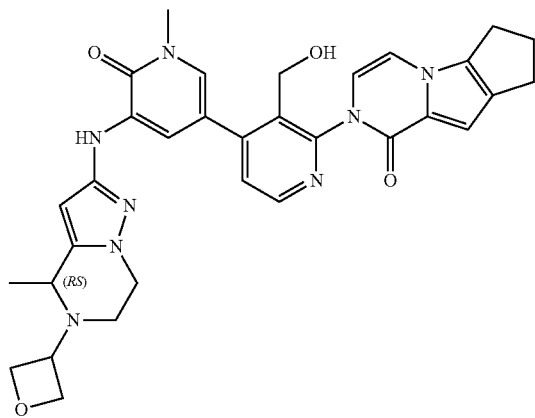 [SMILES: CC1c2cc(Nc3cc(-c4ccnc(-n5ccn6c7c(cc6c5=O)CCC7)c4CO)cn(C)c3=O)nn2CCN1C1COC1] |

| No. | Structural formula |
|---|---|
| 145 | |
| 146 | |
| 147 | |
| 148 | |

-continued
| No. | Structural formula |
|---|---|
| 149 | 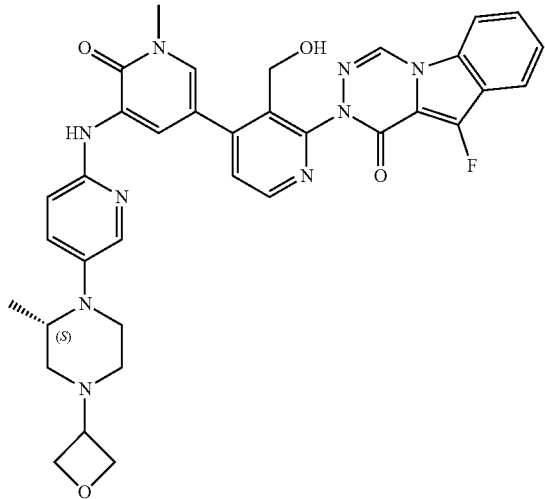 |
| 150 | 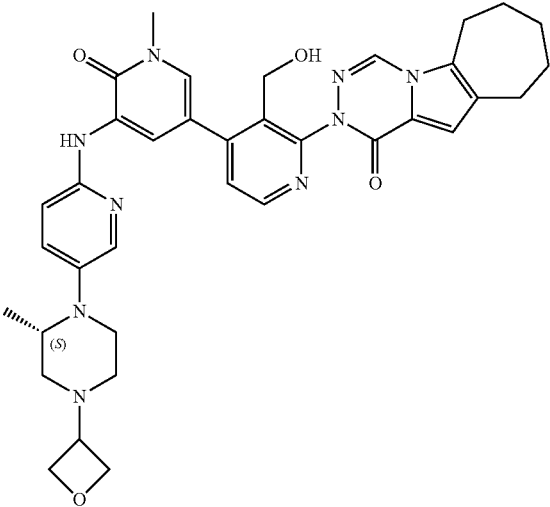 |
| 151 | 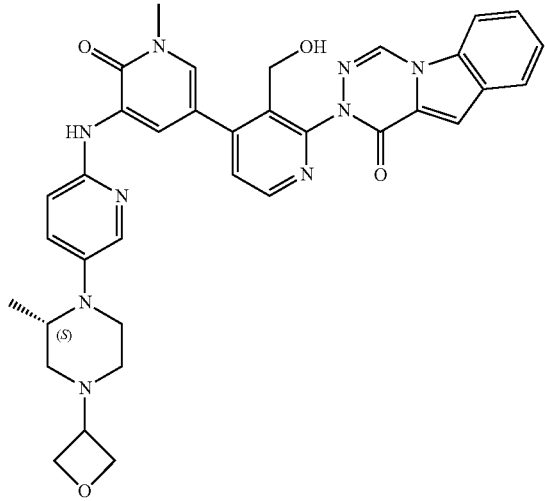 |

| No. | Structural formula |
|---|---|
| 152 | 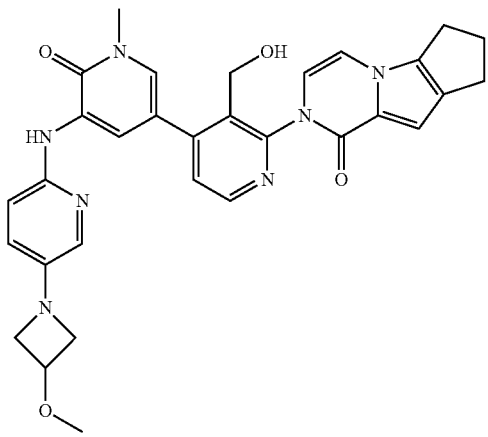 [SMILES: COC1CN(c2ccc(Nc3cc(-c4ccnc(-n5ccn6c7c(cc6c5=O)CCC7)c4CO)cn(C)c3=O)nc2)C1] |
| 153 | 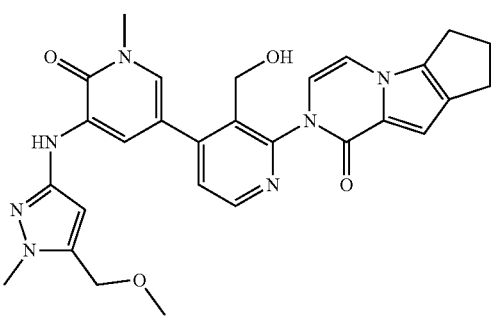 [SMILES: COCc1cc(Nc2cc(-c3ccnc(-n4ccn5c6c(cc5c4=O)CCC6)c3CO)cn(C)c2=O)nn1C] |
| 154 | 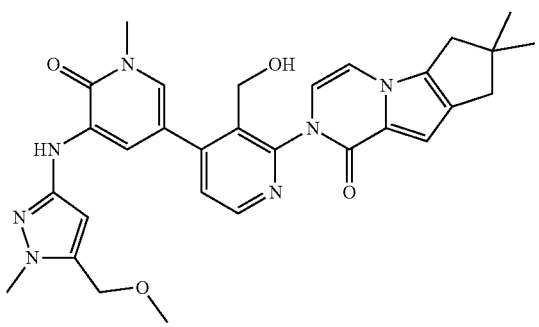 |
| 155 | 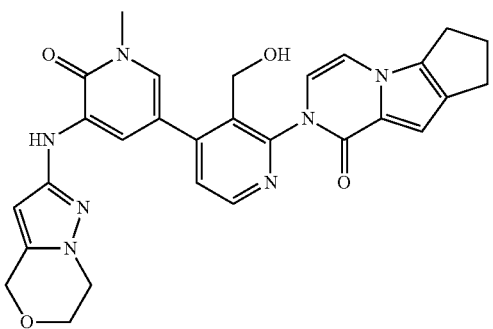 [SMILES: Cn1cc(-c2ccnc(-n3ccn4c5c(cc4c3=O)CCC5)c2CO)cc(Nc2cc3n(n2)CCOC3)c1=O] |

-continued
| No. | Structural formula |
|---|---|
| 156 | 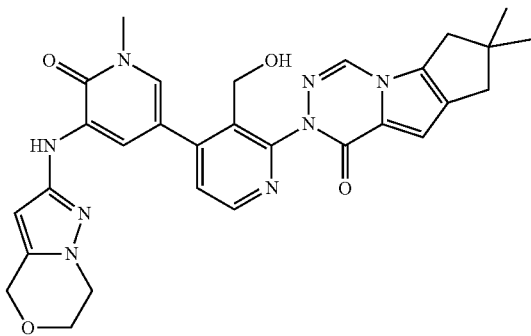 [SMILES: Cn1cc(-c2ccnc(-n3ncn4c5c(cc4c3=O)CC(C)(C)C5)c2CO)cc(Nc2cc3n(n2)CCOC3)c1=O] |
| 157 | 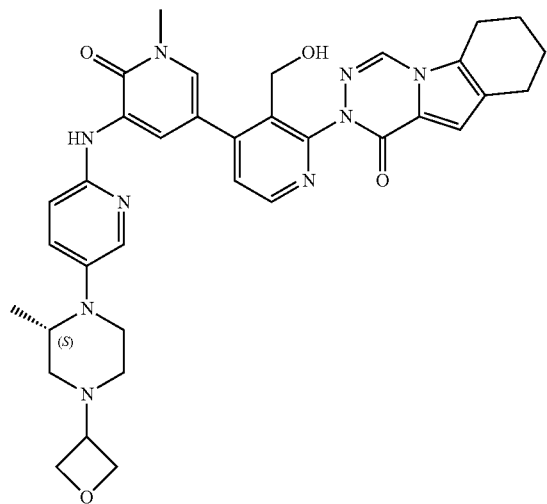 |
| 158 | 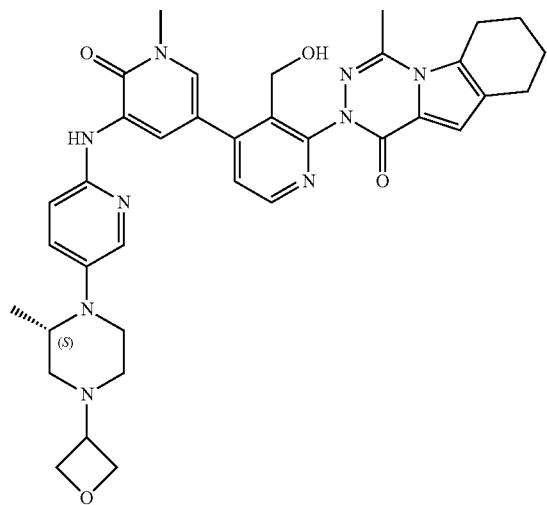 |

| No. | Structural formula |
|---|---|
| 159 | 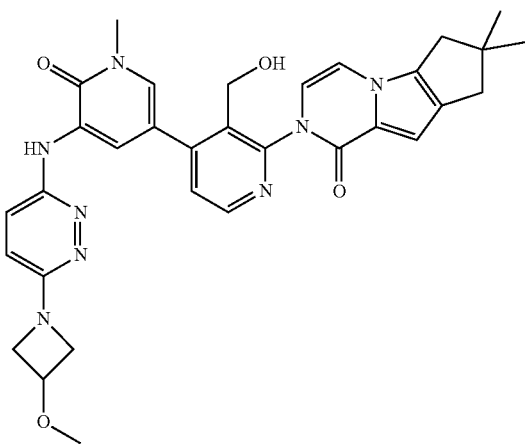 [SMILES: COC1CN(c2ccc(Nc3cc(-c4ccnc(-n5ccn6c7c(cc6c5=O)CC(C)(C)C7)c4CO)cn(C)c3=O)nn2)C1] |
| 160 | 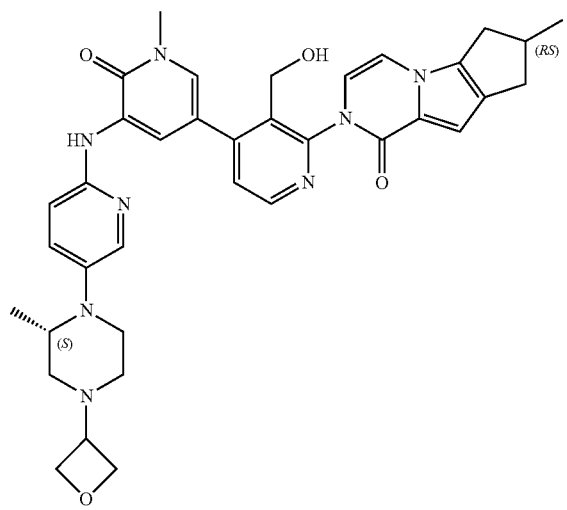 |
| 161 | 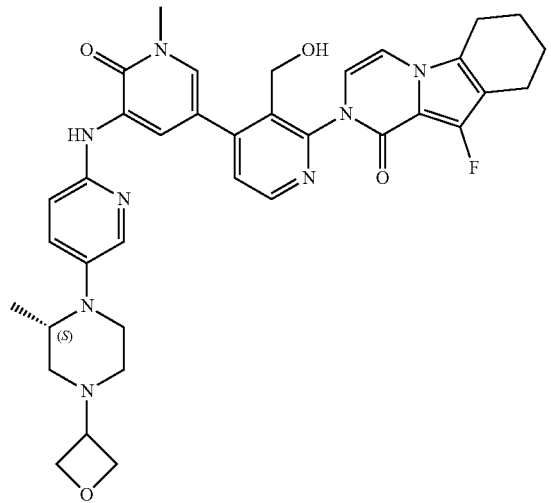 |

-continued
| No. | Structural formula |
|---|---|
| 162 | 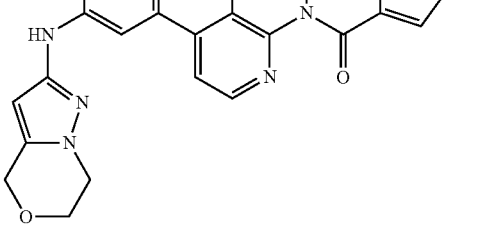 |
| 163 | 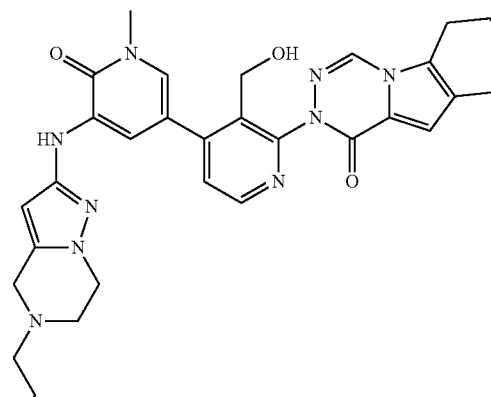 |
| 164 | 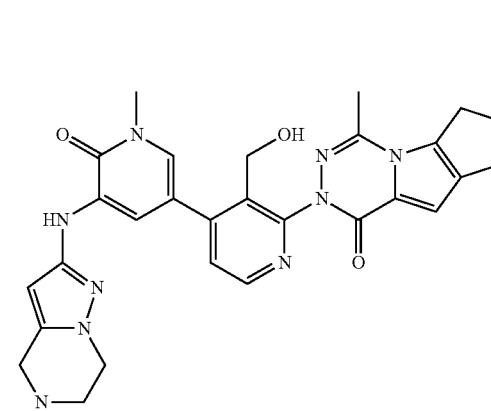 |

| No. | Structural formula |
|---|---|
| 165 | 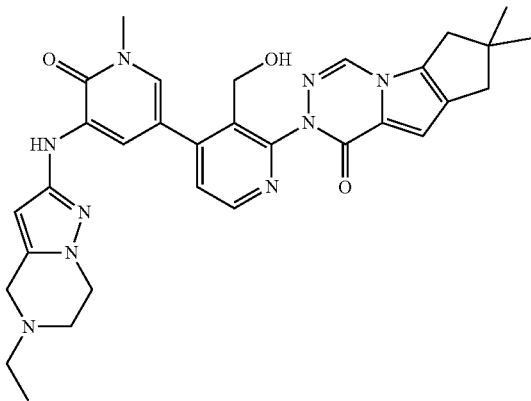 [SMILES: CCN1CCn2nc(Nc3cc(-c4ccnc(-n5ncn6c7c(cc6c5=O)CC(C)(C)C7)c4CO)cn(C)c3=O)cc2C1] |
| 166 | 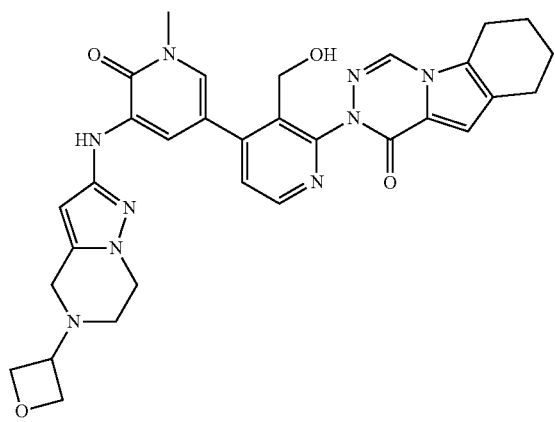 [SMILES: Cn1cc(-c2ccnc(-n3ncn4c5c(cc4c3=O)CCCC5)c2CO)cc(Nc2cc3n(n2)CCN(C2COC2)C3)c1=O] |
| 167 | 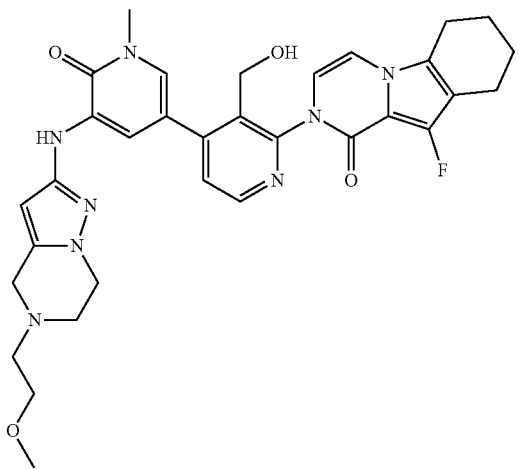 |

| No. | Structural formula |
|---|---|
| 168 | 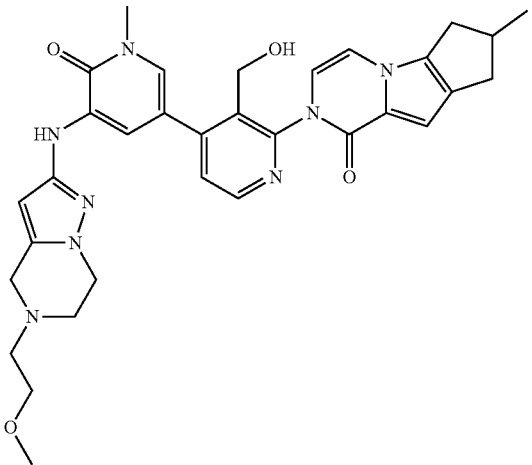 [SMILES: COCCN1CCn2nc(Nc3cc(-c4ccnc(-n5ccn6c7c(cc6c5=O)CC(C)C7)c4CO)cn(C)c3=O)cc2C1] |
| 169 | 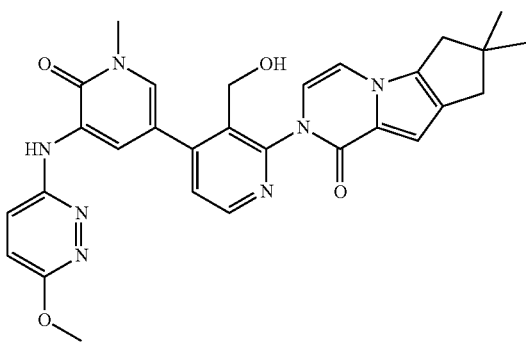 [SMILES: COc1ccc(Nc2cc(-c3ccnc(-n4ccn5c6c(cc5c4=O)CC(C)(C)C6)c3CO)cn(C)c2=O)nn1] |
| 170 | 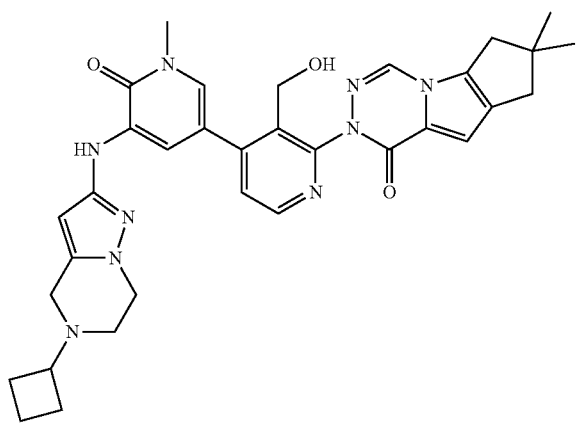 [SMILES: Cn1cc(-c2ccnc(-n3ncn4c5c(cc4c3=O)CC(C)(C)C5)c2CO)cc(Nc2cc3n(n2)CCN(C2CCC2)C3)c1=O] |

-continued
| No. | Structural formula |
|---|---|
| 171 | 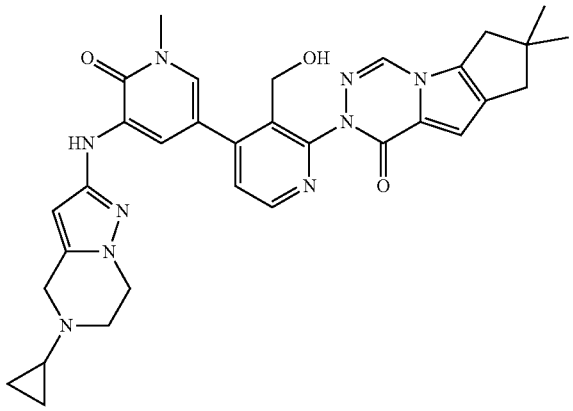 [SMILES: Cn1cc(-c2ccnc(-n3ncn4c5c(cc4c3=O)CC(C)(C)C5)c2CO)cc(Nc2cc3n(n2)CCN(C2CC2)C3)c1=O] |
| 172 | 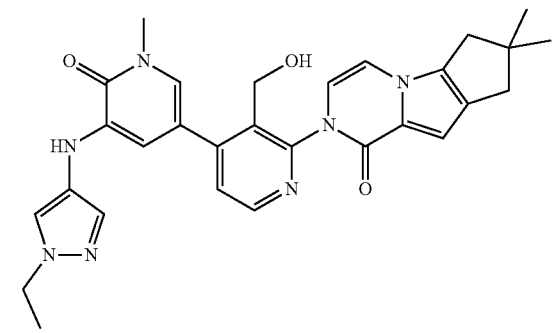 |
| 173 | 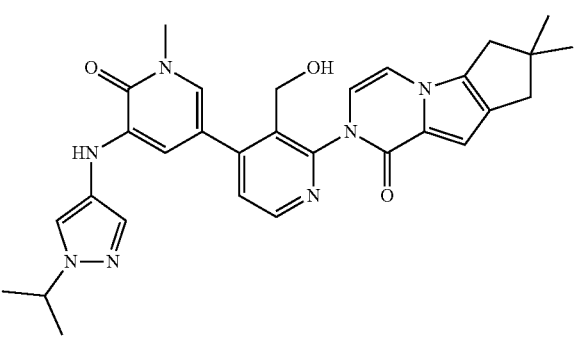 |
| 174 | 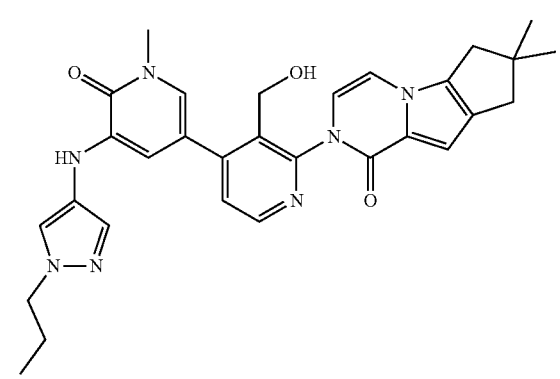 [SMILES: CCCn1cc(Nc2cc(-c3ccnc(-n4ccn5c6c(cc5c4=O)CC(C)(C)C6)c3CO)cn(C)c2=O)cn1] |

US 11,478,474 B2
149
-continued
| No. | Structural formula |
|---|---|
| 175 | 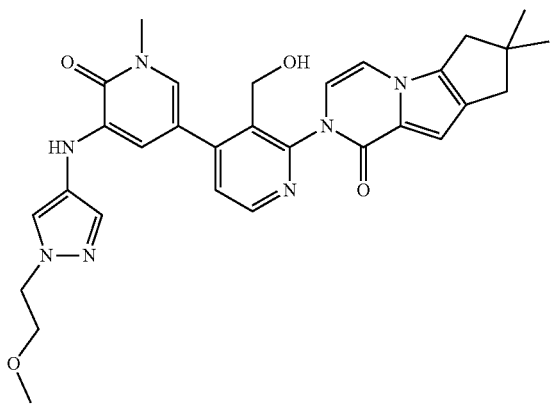 [SMILES: COCCn1cc(Nc2cc(-c3ccnc(-n4ccn5c6c(cc5c4=O)CC(C)(C)C6)c3CO)cn(C)c2=O)cn1] |
| 176 | 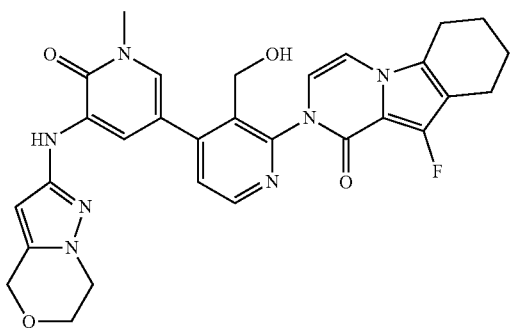 [SMILES: Cn1cc(-c2ccnc(-n3ccn4c5c(c(F)c4c3=O)CCCC5)c2CO)cc(Nc2cc3n(n2)CCOC3)c1=O] |
| 177 | 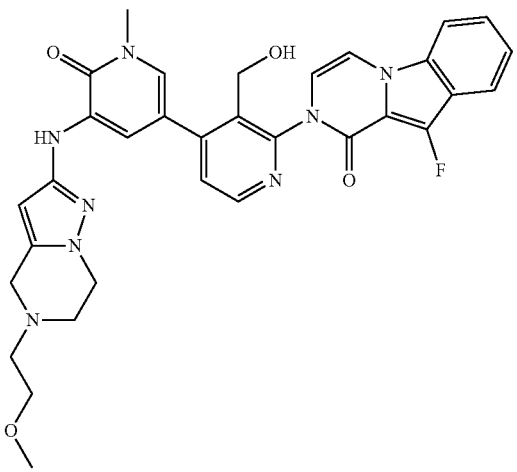 [SMILES: COCCN1CCn2nc(Nc3cc(-c4ccnc(-n5ccn6c(c(F)c7ccccc76)c5=O)c4CO)cn(C)c3=O)cc2C1] |
150

| No. | Structural formula |
|---|---|
| 178 | 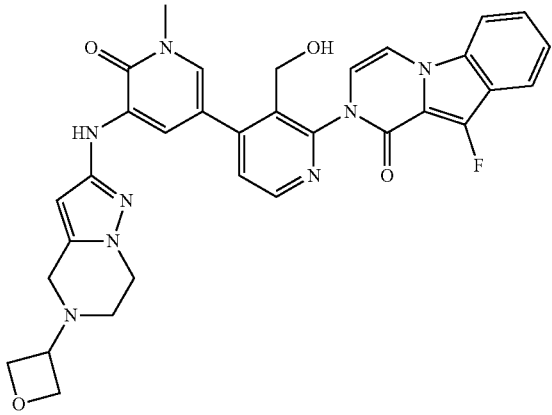 [SMILES: Cn1cc(-c2ccnc(-n3ccn4c(c(F)c5ccccc54)c3=O)c2CO)cc(Nc2cc3n(n2)CCN(C2COC2)C3)c1=O] |
| 179 | 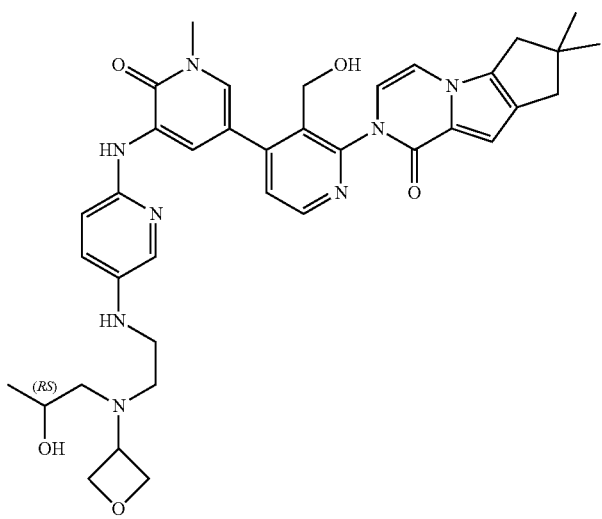 [SMILES: CC(O)CN(CCNc1ccc(Nc2cc(-c3ccnc(-n4ccn5c6c(cc5c4=O)CC(C)(C)C6)c3CO)cn(C)c2=O)nc1)C1COC1] |
| 180 | 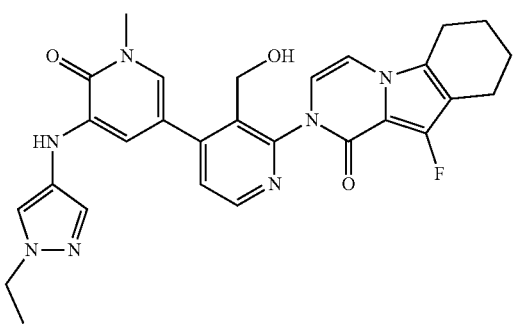 [SMILES: CCn1cc(Nc2cc(-c3ccnc(-n4ccn5c6c(c(F)c5c4=O)CCCC6)c3CO)cn(C)c2=O)cn1] |
| 181 | 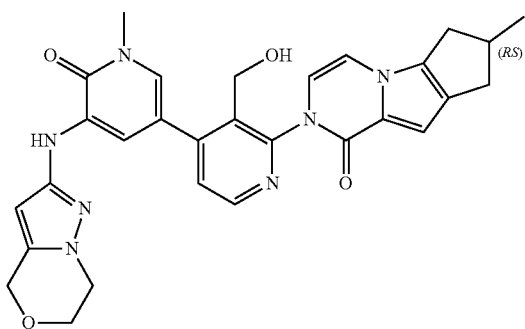 [SMILES: CC1Cc2cc3c(=O)n(-c4nccc(-c5cc(Nc6cc7n(n6)CCOC7)c(=O)n(C)c5)c4CO)ccn3c2C1] |

| No. | Structural formula |
|---|---|
| 182 | 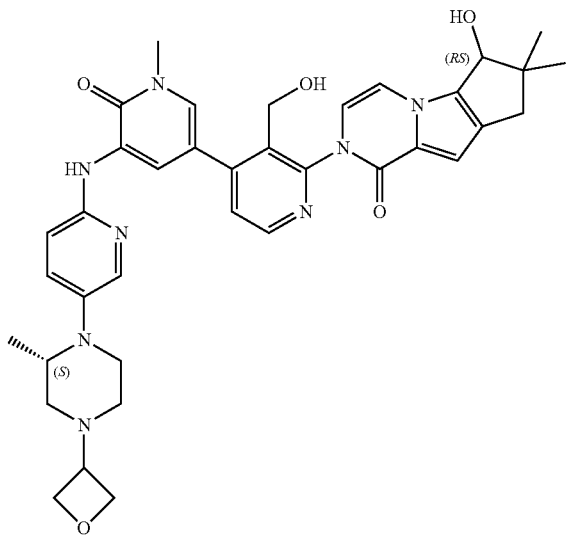 |
| 183 | 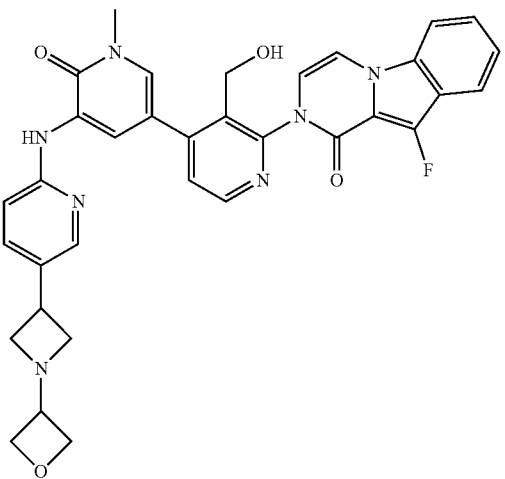 [SMILES: Cn1cc(-c2ccnc(-n3ccn4c(c(F)c5ccccc54)c3=O)c2CO)cc(Nc2ccc(C3CN(C4COC4)C3)cn2)c1=O] |
| 184 | 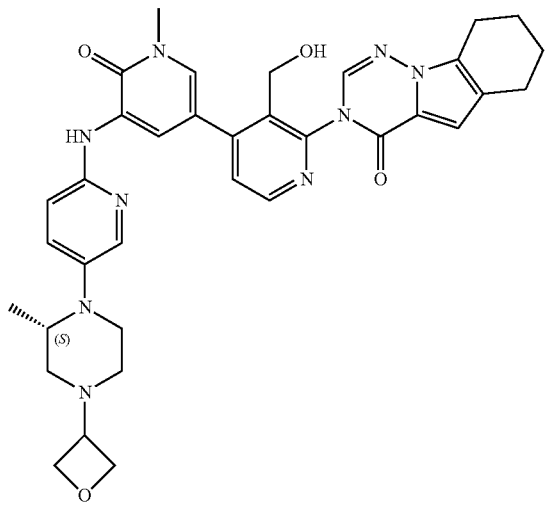 |

| No. | Structural formula |
|---|---|
| 185 | 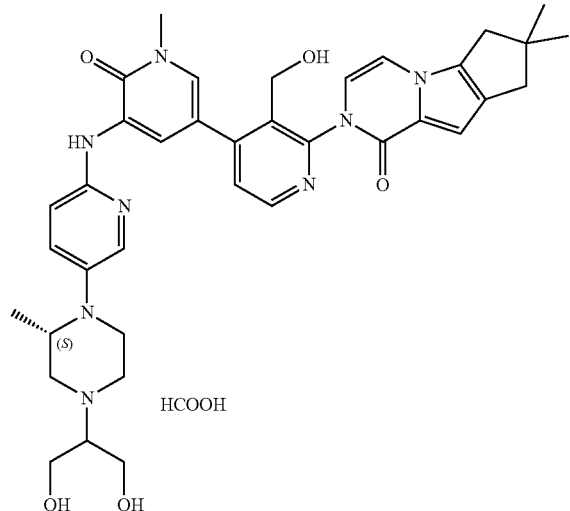 HCOOH |
| 186 | 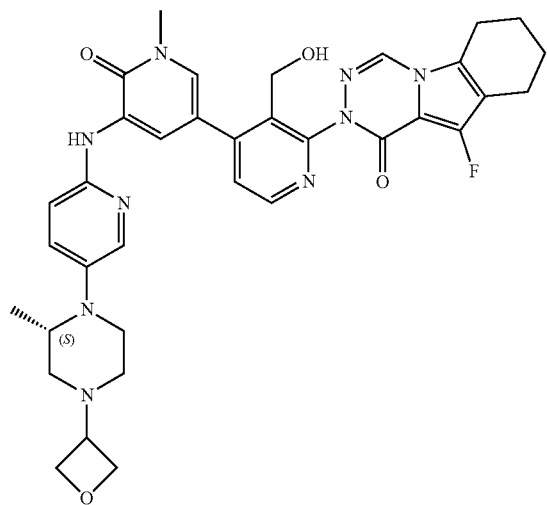 |
| 187 | 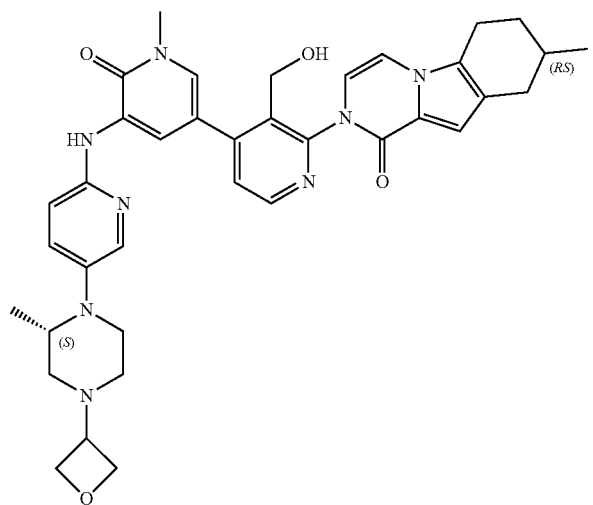 |

-continued
| No. | Structural formula |
|---|---|
| 188 | 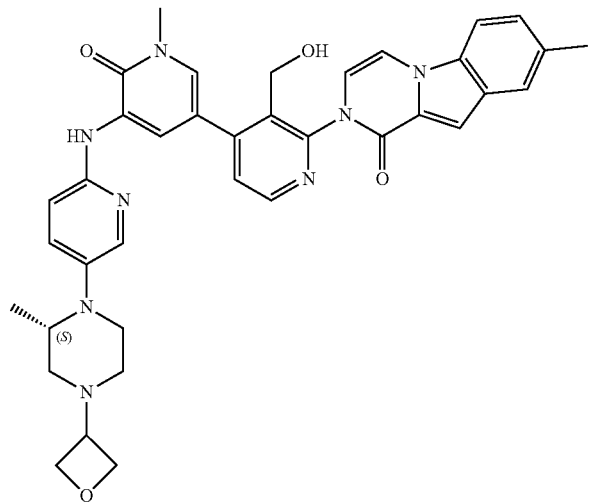 |
| 189 | 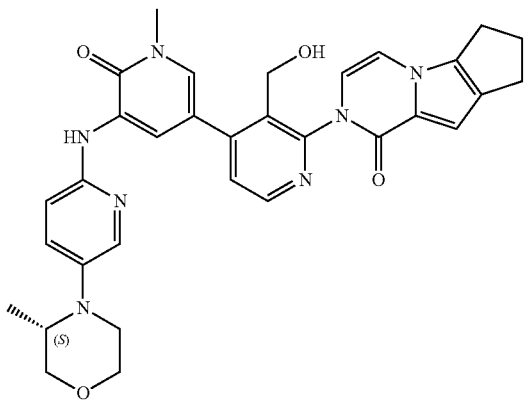 |
| 190 | 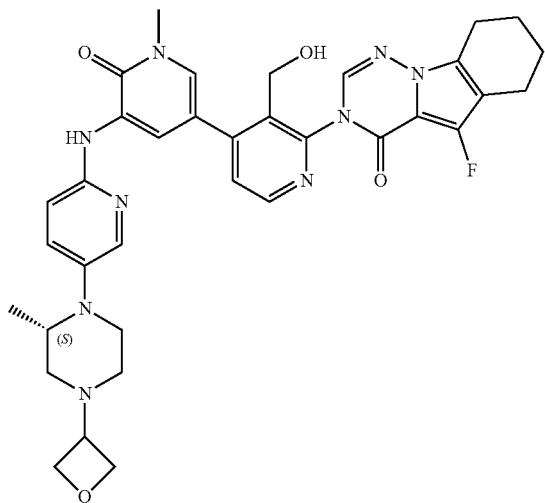 |

| No. | Structural formula |
|---|---|
| 191 | 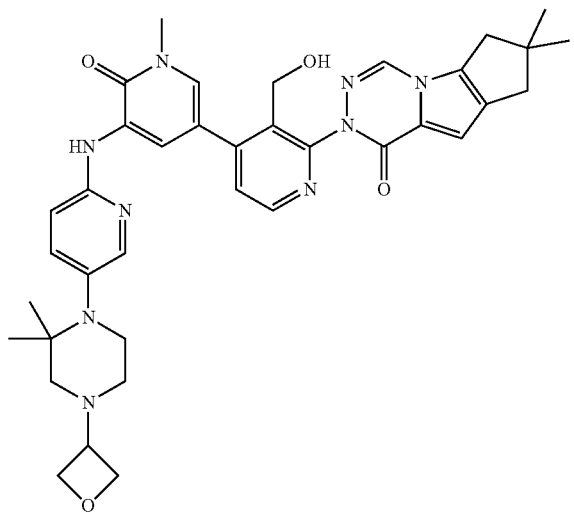 |
| 192 | 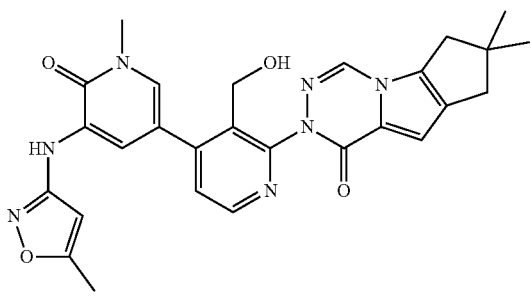 |
| 193 | 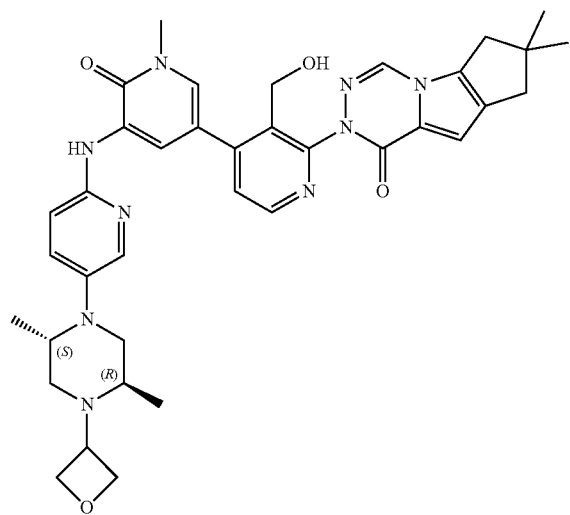 |

| No. | Structural formula |
|---|---|
| 194 | |
| 195 | |
| 196 | |

| No. | Structural formula |
|---|---|
| 197 | 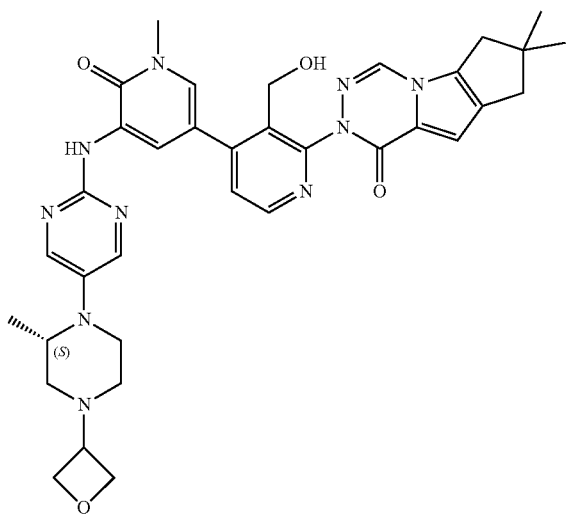 |
| 198 & 199 | 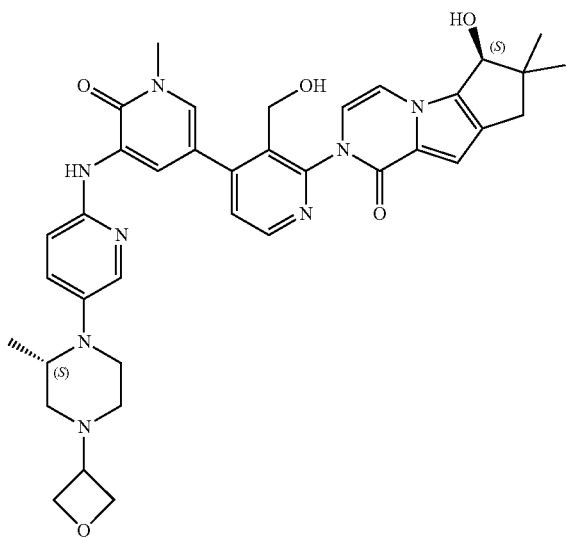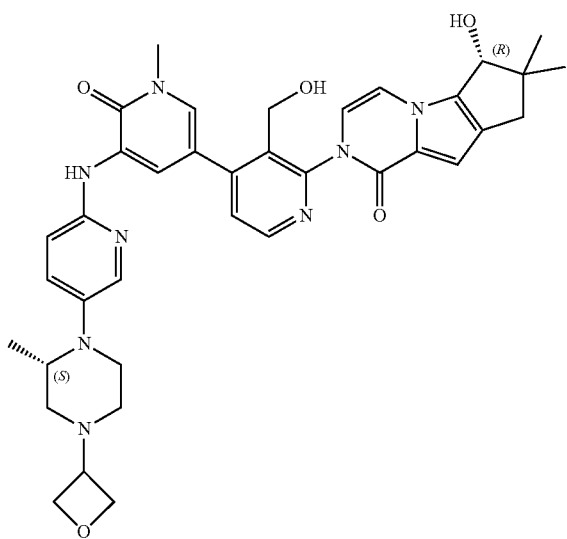 |

| No. | Structural formula |
|---|---|
| 200 | (chemical structure) |
| 201 | (chemical structure) |
| 202 | (chemical structure) |

| No. | Structural formula |
|---|---|
| 203 | 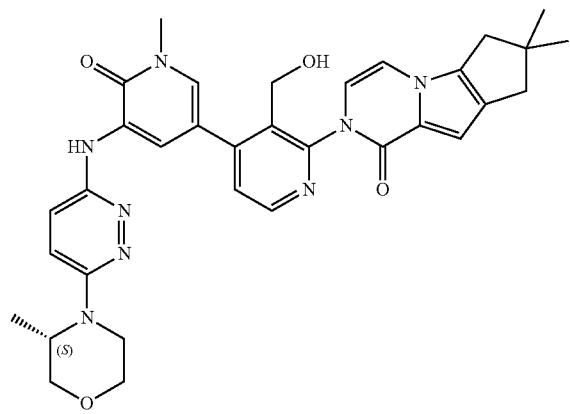 |
| 204 | 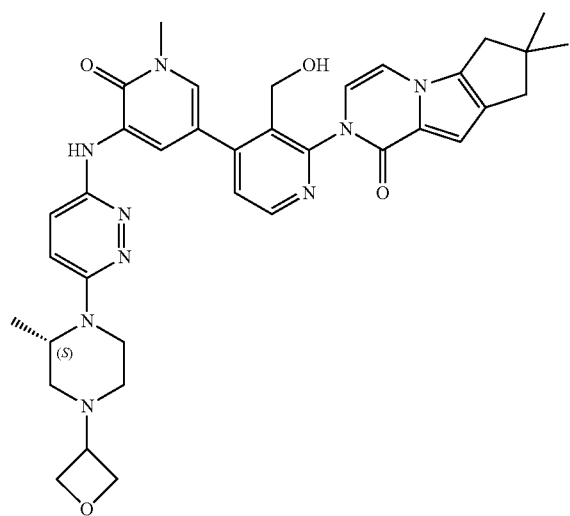 |
| 205 | 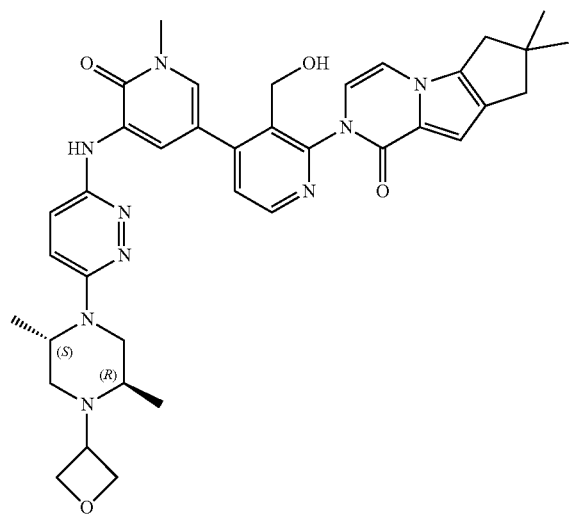 |

| No. | Structural formula |
|---|---|
| 206 | 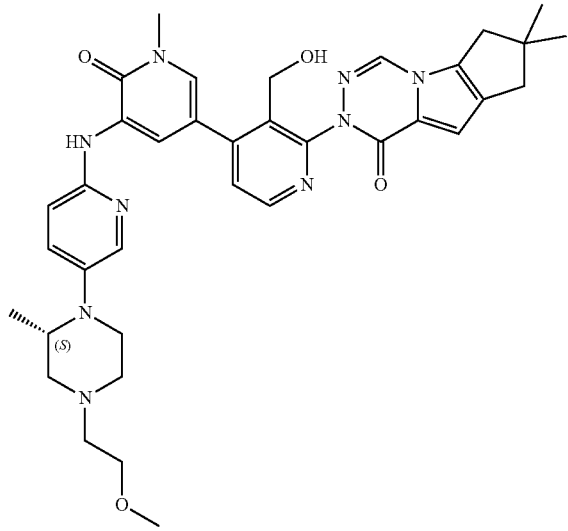 |
| 207 | 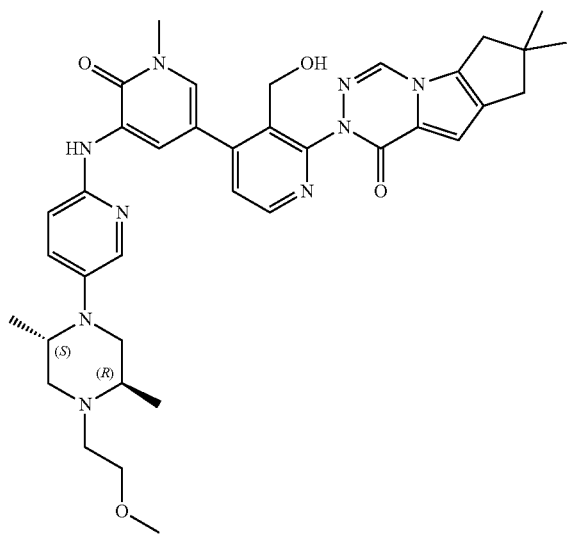 |
| 208 | 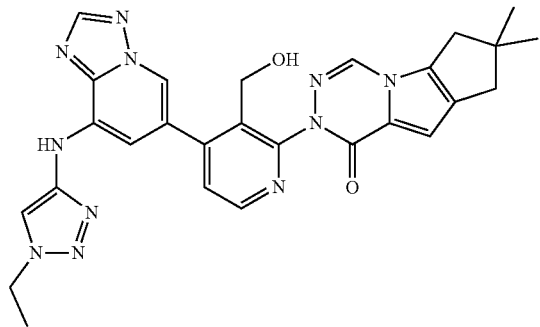 [SMILES: CCn1cc(Nc2cc(-c3ccnc(-n4ncn5c6c(cc5c4=O)CC(C)(C)C6)c3CO)cn3ncnc23)nn1] |

| No. | Structural formula |
|---|---|
| 209 | |
| 210 | |
| 211 | |

| No. | Structural formula |
|---|---|
| 212 | 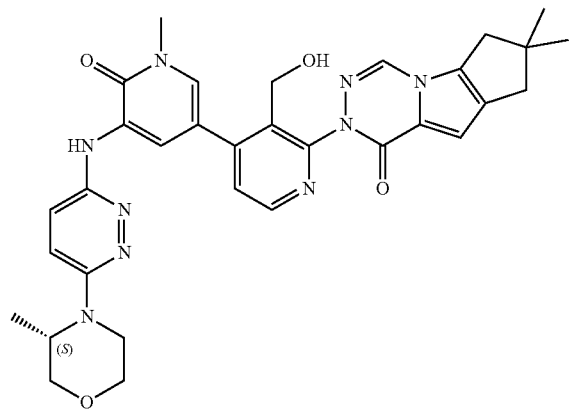 |
| 213 | 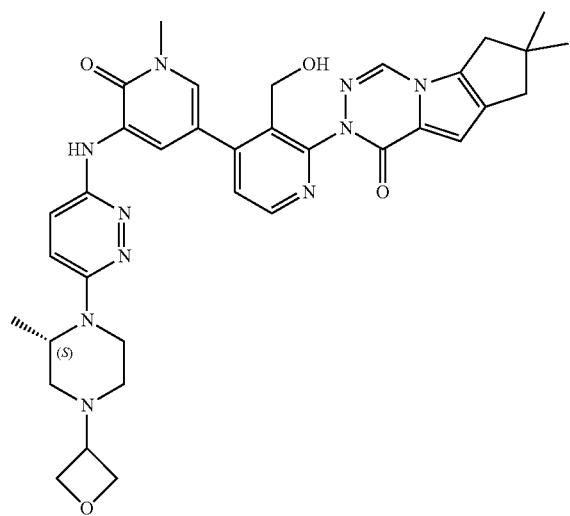 |
| 214 | 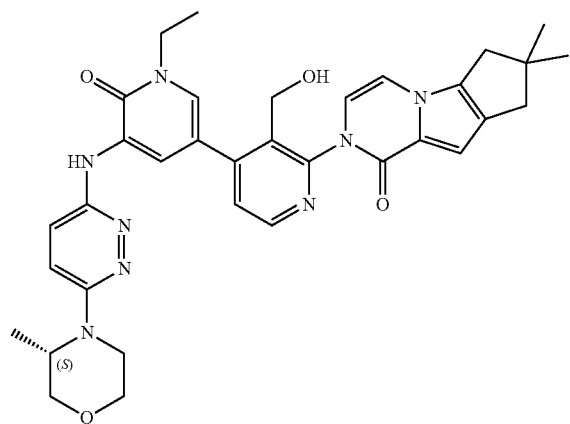 |

| No. | Structural formula |
|---|---|
| 215 | 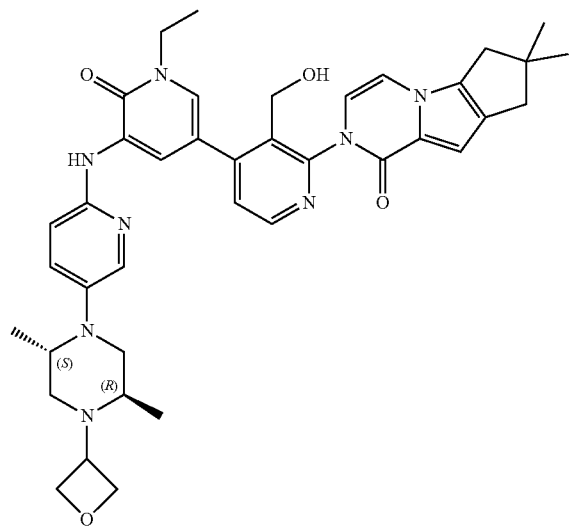 |
| 216 | 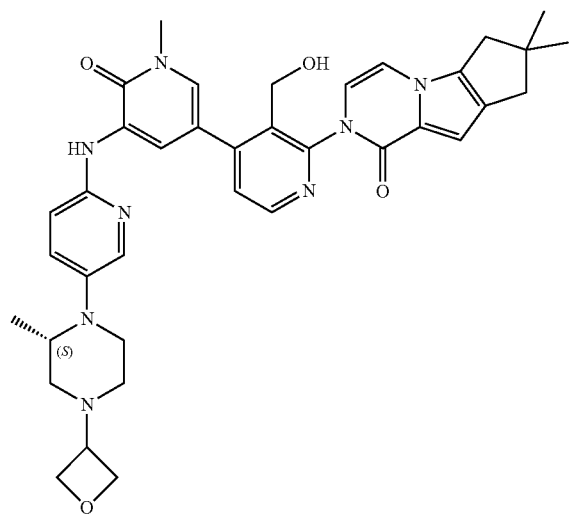 |
| 217 | 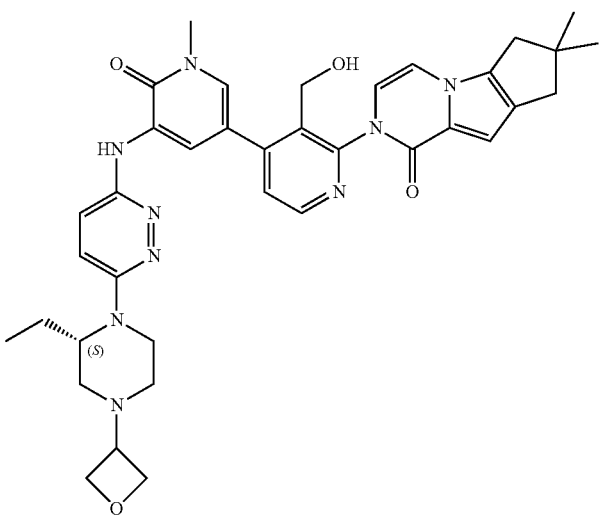 |

| No. | Structural formula |
|---|---|
| 218 | 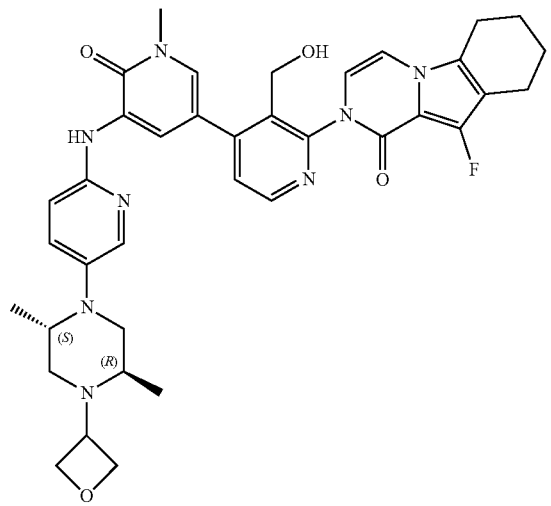 |
| 219 | 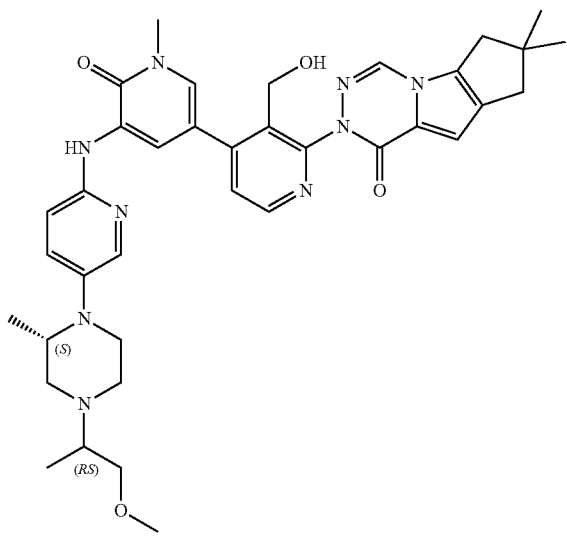 |
| 220 | 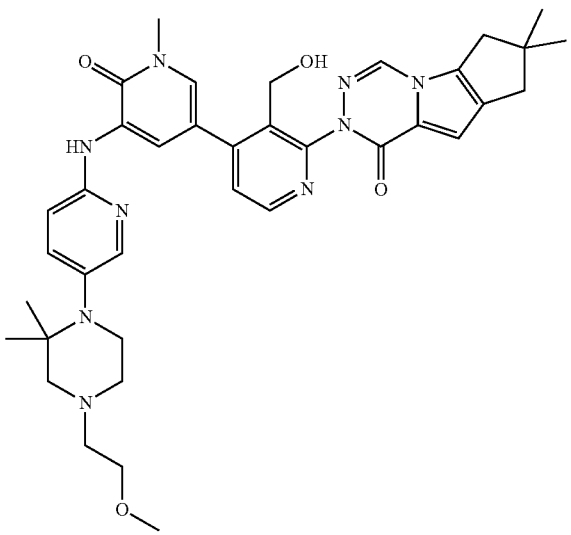 |

| No. | Structural formula |
|---|---|
| 221 | 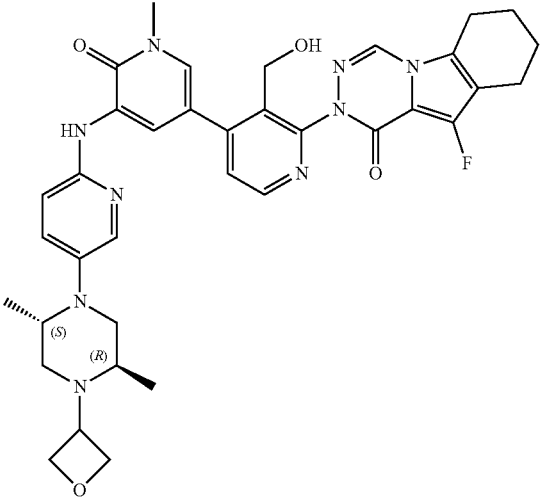 |
| 222 | 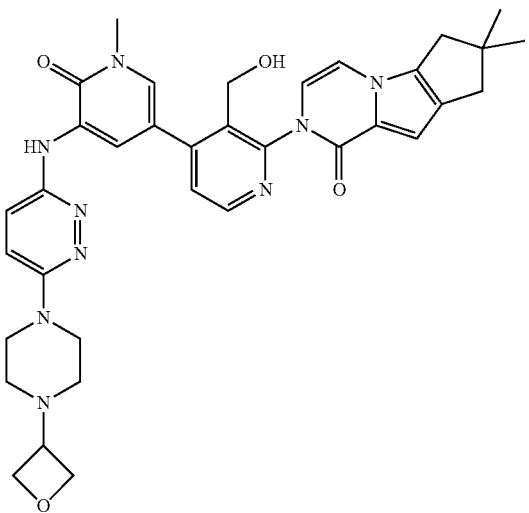 [SMILES: Cn1cc(-c2ccnc(-n3ccn4c5c(cc4c3=O)CC(C)(C)C5)c2CO)cc(Nc2ccc(N3CCN(C4COC4)CC3)nn2)c1=O] |
| 223 | 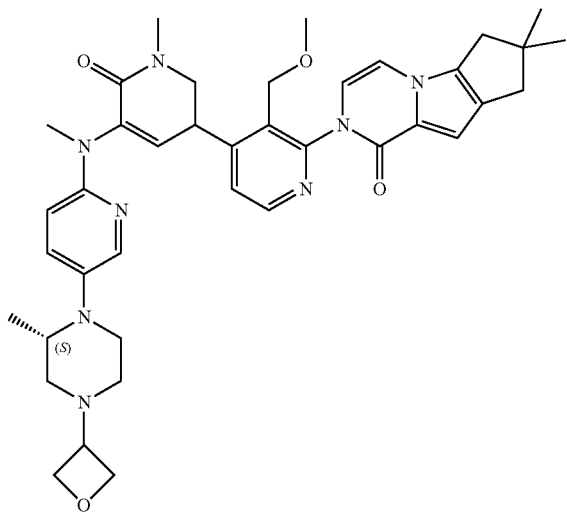 |

US 11,478,474 B2
181                                                 182
-continued
| No. | Structural formula |
|---|---|
| 224 | 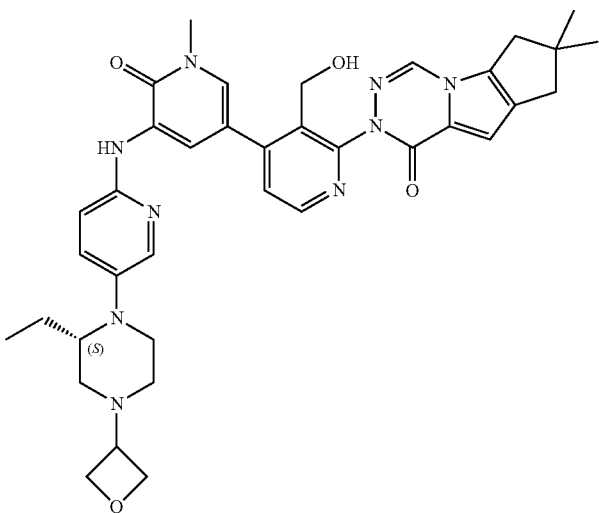 |
| 225 | 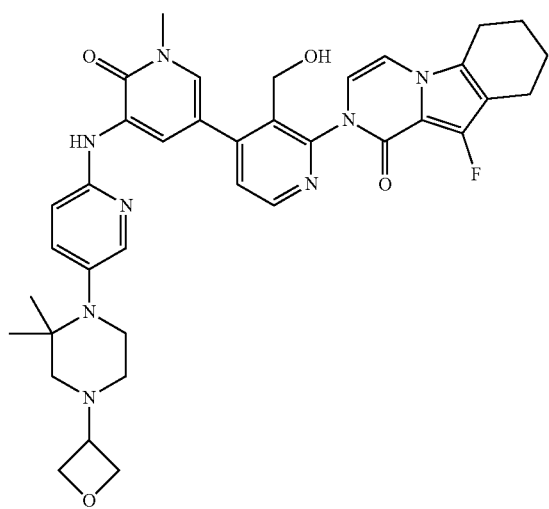 [SMILES: Cn1cc(-c2ccnc(-n3ccn4c5c(c(F)c4c3=O)CCCC5)c2CO)cc(Nc2ccc(N3CCN(C4COC4)CC3(C)C)cn2)c1=O] |
| 226 | 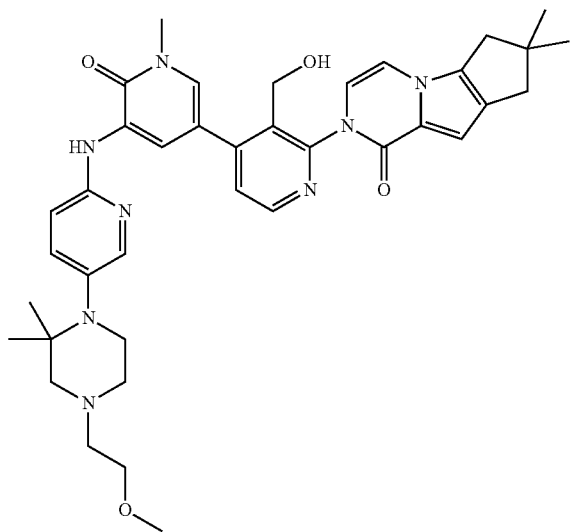 |

| No. | Structural formula |
|---|---|
| 227 | 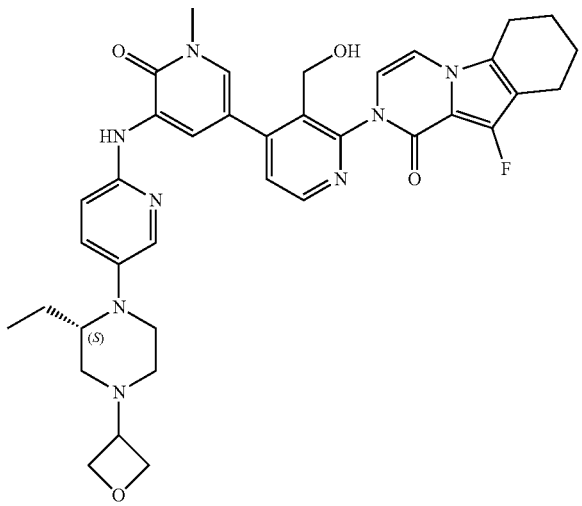 |
| 228 | 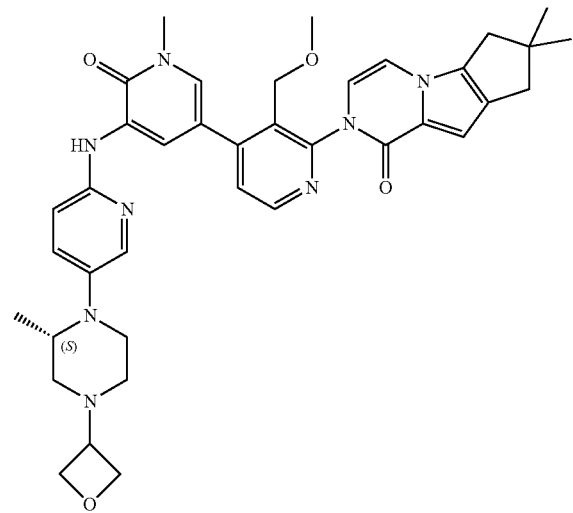 |
| 229 | 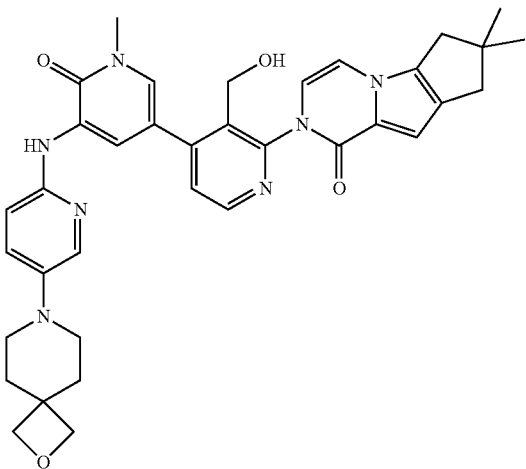 [SMILES: Cn1cc(-c2ccnc(-n3ccn4c5c(cc4c3=O)CC(C)(C)C5)c2CO)cc(Nc2ccc(N3CCC4(CC3)COC4)cn2)c1=O] |

| No. | Structural formula |
|---|---|
| 230 | 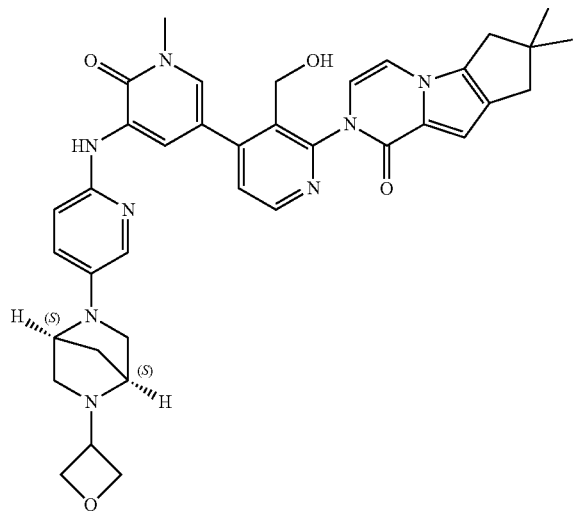 |
| 231 | 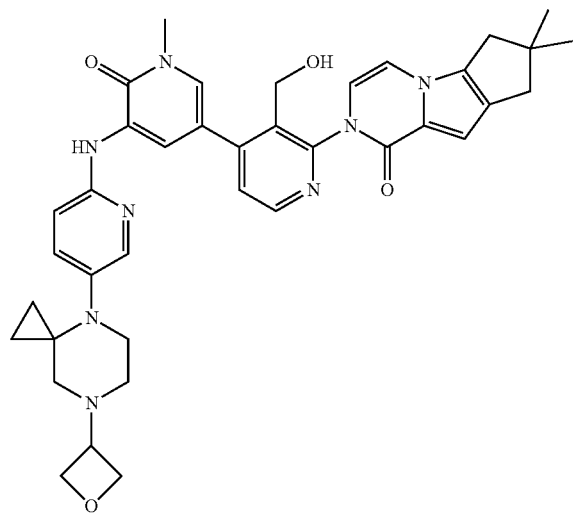 [SMILES: Cn1cc(-c2ccnc(-n3ccn4c5c(cc4c3=O)CC(C)(C)C5)c2CO)cc(Nc2ccc(N3CCN(C4COC4)CC34CC4)cn2)c1=O] |
| 232 | 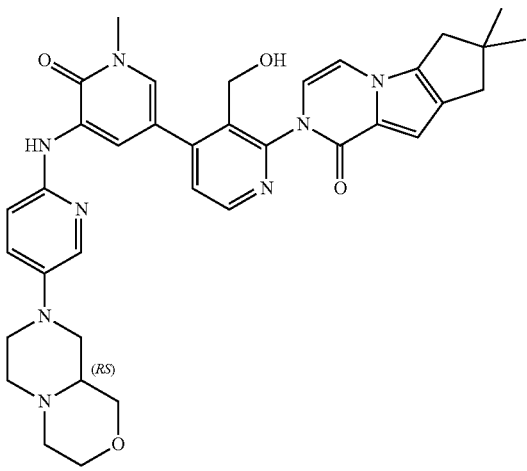 [SMILES: Cn1cc(-c2ccnc(-n3ccn4c5c(cc4c3=O)CC(C)(C)C5)c2CO)cc(Nc2ccc(N3CCN4CCOCC4C3)cn2)c1=O] |

| No. | Structural formula |
|---|---|
| 233 | 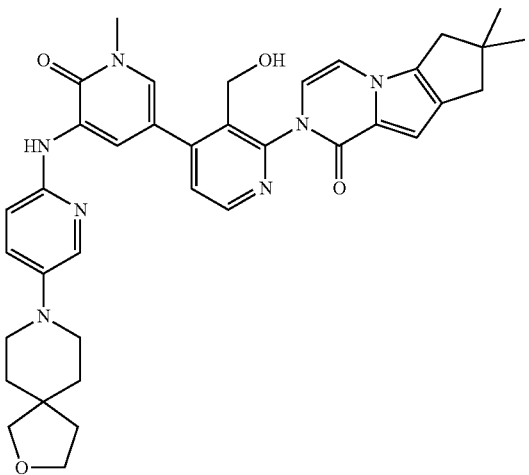 [SMILES: Cn1cc(-c2ccnc(-n3ccn4c5c(cc4c3=O)CC(C)(C)C5)c2CO)cc(Nc2ccc(N3CCC4(CCOC4)CC3)cn2)c1=O] |
| 234 | 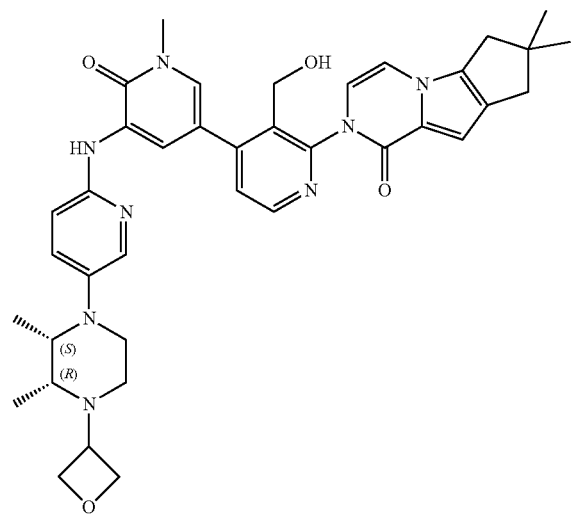 |
| 235 | 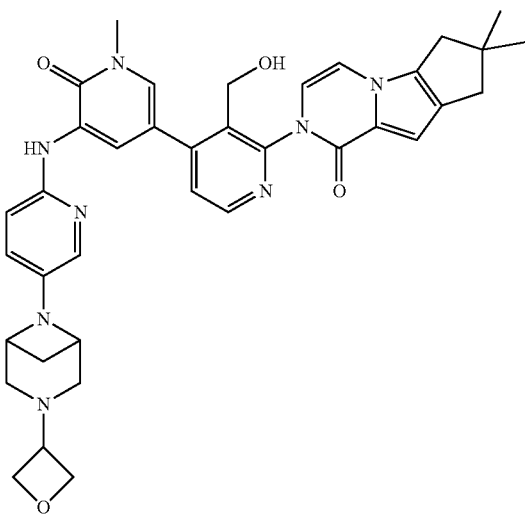 [SMILES: Cn1cc(-c2ccnc(-n3ccn4c5c(cc4c3=O)CC(C)(C)C5)c2CO)cc(Nc2ccc(N3C4CC3CN(C3COC3)C4)cn2)c1=O] |

| No. | Structural formula |
|---|---|
| 236 | 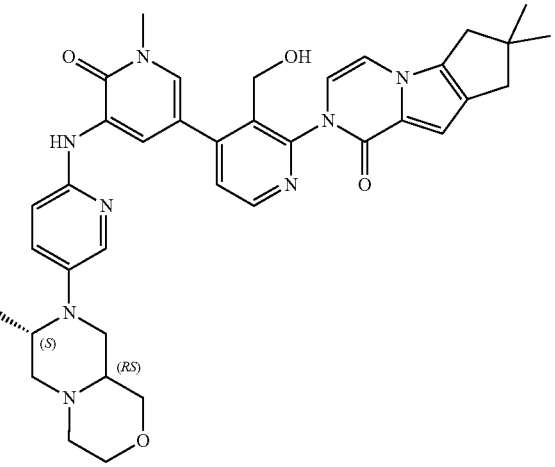 |

Embodiment 38. A pharmaceutical composition, comprising the compound of any one of embodiments 1-37 and/or a pharmaceutically acceptable salt thereof, and optionally comprising a pharmaceutically acceptable excipient.

Embodiment 39. A method of in vivo or in vitro inhibiting the activity of BTK, comprising contacting BTK with an effective amount of the compound of any one of embodiments 1-37, and/or a pharmaceutically acceptable salt thereof.

Embodiment 40. Use of the compound of any one of embodiments 1-37 and/or a pharmaceutically acceptable salt thereof in the manufacture of a medicament for treating or preventing a disease mediated by BTK or at least in part by BTK, preferably for treating or preventing cancer, an inflammatory disease or autoimmune disease, wherein the cancer is preferably solid tumor or hematologic malignancy, including lymphoma, leukemia and myeloma; the cancer is more preferably chosen from B cell malignancy, diffuse large B-cell lymphoma (DLBCL), large B-cell lymphoma (LBCL), B-cell lymphoma, mantle cell lymphoma, follicular lymphoma, non-Hodgkin's lymphoma, Hodgkin's lymphoma, Waldenstrom macroglobulinemia, marginal zone lymphoma, Burkitt's lymphoma, non-Burkitt's highly degree B cell malignant lymphoma, extranodal marginal-zone B-cell lymphoma, small lymphotic lymphoma (SLL), lymphoblastic lymphoma, lymphocytic leukemia, myelogenous leukemia, acute myelogenous leukemia (AML), chronic myelogenous leukemia (CML), human acute monocytic leukemia, acute lymphocytic leukemia (ALL), B cell acute lymphocytic leukemia (B-ALL), hairy cell leukemia, chronic lymphocytic leukemia (CLL) (such as high risk CLL), myelodysplastic syndrome, acute lymphoblastic leukemia, myeloma (such as multiple myeloma) or graft versus host disease; and the inflammatory disease or autoimmune disease is preferably chosen from: systemic inflammation and local inflammation, arthritis, rheumatoid arthritis, inflammation associated with immunosuppression, organ-graft refection, allergic disease, ulcerative colitis, Crohn's disease, dermatitis, asthma, lupus erythematosus, Sjogren syndrome, multiple sclerosis, scleroderma (also referred to as systemic sclerosis), multiple sclerosis osteoporosis, idiopathic thrombocytopenic purpura, autoimmune hemolytic anemia, antineutrophil cytoplasmatic antibody vasculitis, chronic obstructive pulmonary disease, psoriasis, sicca syndrome, pemphigus valgaris, diseases associated with kidney transplantation.

Embodiment 41. A method of treating or preventing a disease in a subject, comprising administering to the subject in need thereof an effective amount of the compound of any one of embodiments 1-37, and/or a pharmaceutically acceptable salt thereof, wherein the disease is a disease mediated by BTK or at least in part by BTK; the disease is preferably cancer, an inflammatory disease or autoimmune disease; the cancer is preferably solid tumor or hematologic malignancy, including lymphoma, leukemia and myeloma; the cancer is more preferably chosen from B cell malignancy, diffuse large B-cell lymphoma (DLBCL), large B-cell lymphoma (LBCL), B-cell lymphoma, mantle cell lymphoma, follicular lymphoma, non-Hodgkin's lymphoma, Hodgkin's lymphoma, Waldenstrom macroglobulinemia, marginal zone lymphoma, Burkitt's lymphoma, non-Burkitt's highly degree B cell malignant lymphoma, extranodal marginal-zone B-cell lymphoma, small lymphotic lymphoma (SLL), lymphoblastic lymphoma, lymphocytic leukemia, myelogenous leukemia, acute myelogenous leukemia (AML), chronic myelogenous leukemia (CML), human acute monocytic leukemia, acute lymphocytic leukemia (ALL), B cell acute lymphocytic leukemia (B-ALL), hairy cell leukemia, chronic lymphocytic leukemia (CLL) (such as high risk CLL), myelodysplastic syndrome, acute lymphoblastic leukemia, myeloma (such as multiple myeloma) or graft versus host disease; and the inflammatory disease or autoimmune disease is preferably chosen from: systemic inflammation and local inflammation, arthritis, rheumatoid arthritis, inflammation associated with immunosuppression, organ-graft refection, allergic disease, ulcerative colitis, Crohn's disease, dermatitis, asthma, lupus erythematosus, Sjogren syndrome, multiple sclerosis, scleroderma, multiple sclerosis osteoporosis, idiopathic thrombocytopenic purpura, autoimmune hemolytic anemia, antineutrophil cytoplasmatic antibody vasculitis, chronic obstructive pulmonary disease, psoriasis, sicca syndrome, pemphigus valgaris, and diseases associated with kidney transplantation.

Embodiment 42. The compound of any one of embodiments 1-37 and/or a pharmaceutically acceptable salt thereof, for use as a medicament.

Embodiment 43. The compound of any one of embodiments 1-37 and/or a pharmaceutically acceptable salt thereof, for use in treating or preventing a disease mediated by BTK or at least in part by BTK, and preferably for use in treating or preventing cancer, an inflammatory disease or autoimmune disease, wherein the cancer is preferably solid tumor or hematologic malignancy, including lymphoma, leukemia and myeloma; the cancer is more preferably chosen from B cell malignancy, diffuse large B-cell lymphoma (DLBCL), large B-cell lymphoma (LBCL), B-cell lymphoma, mantle cell lymphoma, follicular lymphoma, non-Hodgkin's lymphoma, Hodgkin's lymphoma, Waldenstrom macroglobulinemia, marginal zone lymphoma, Burkitt's lymphoma, non-Burkitt's highly degree B cell malignant lymphoma, extranodal marginal-zone B-cell lymphoma, small lymphotic lymphoma (SLL), lymphoblastic lymphoma, lymphocytic leukemia, myelogenous leukemia, acute myelogenous leukemia (AML), chronic myelogenous leukemia (CML), human acute monocytic leukemia, acute lymphocytic leukemia (ALL), B cell acute lymphocytic leukemia (B-ALL), hairy cell leukemia, chronic lymphocytic leukemia (CLL) (such as high risk CLL), myelodysplastic syndrome, acute lymphoblastic leukemia, myeloma (such as multiple myeloma) or graft versus host disease; and the inflammatory disease or autoimmune disease is preferably chosen from: systemic inflammation and local inflammation, arthritis, rheumatoid arthritis, inflammation associated with immunosuppression, organ-graft refection, allergic disease, ulcerative colitis, Crohn's disease, dermatitis, asthma, lupus erythematosus, Sjogren syndrome, multiple sclerosis, scleroderma, multiple sclerosis osteoporosis, idiopathic thrombocytopenic purpura, autoimmune hemolytic anemia, antineutrophil cytoplasmatic antibody vasculitis, chronic obstructive pulmonary disease, psoriasis, sicca syndrome, pemphigus valgaris, and diseases associated with kidney transplantation.

Embodiment 44. A pharmaceutical combination, comprising the compound of any one of embodiments 1-37 and/or a pharmaceutically acceptable salt thereof, and at least one additional therapeutic agent, wherein the therapeutic agent is preferably chosen from: an anti-inflammatory agent, an immunomodulator or an anti-tumor active agent, wherein the anti-tumor active agent includes a chemotherapeutic agent, an immune checkpoint inhibitor or agonist, and a targeted therapeutic agent.

Embodiment 45. A compound of formula (VI):

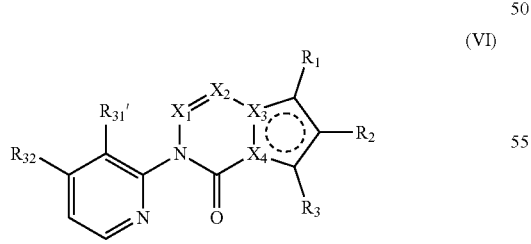

(VI)

or a solvate, a racemic mixture, an enantiomer, a diastereomer and a tautomer thereof, wherein
$X_1$, $X_2$, $X_3$, $X_4$, $R_1$, $R_2$ and $R_3$ are as defined in any one of embodiments 1-34;
$R_{31'}$ is —CHO, —$C_{1-3}$ alkyl-OH, —$C_{1-3}$ alkyl-OAc, $C_{1-3}$ alkyl, —C(O)—$C_{1-3}$ alkyl or $C_{1-3}$ haloalkyl, and
$R_{32}$ is halogen, —B(OH)$_2$, —B(O$C_{1-6}$ alkyl)$_2$,

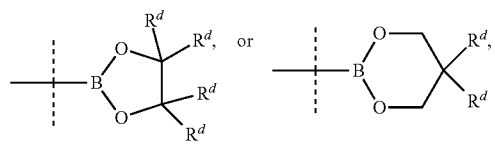

and $R_d$ is hydrogen or $C_{1-6}$ alkyl.

Embodiment 46. The compound of embodiment 45, which is

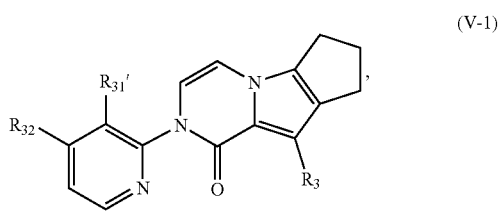

(V-1)

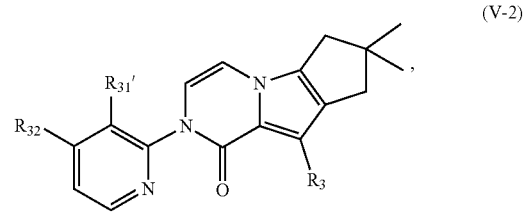

(V-2)

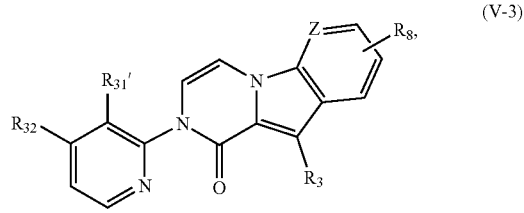

(V-3)

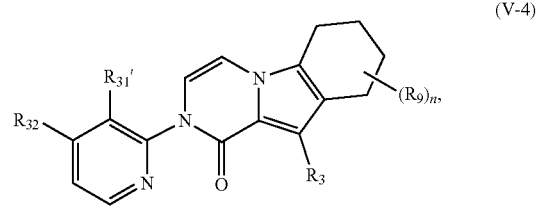

(V-4)

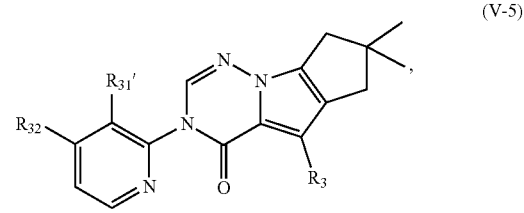

(V-5)

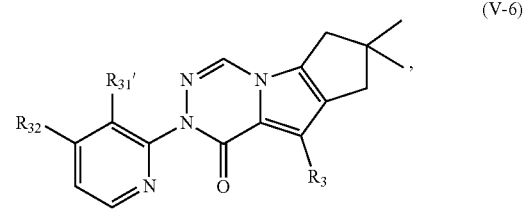

(V-6)

-continued
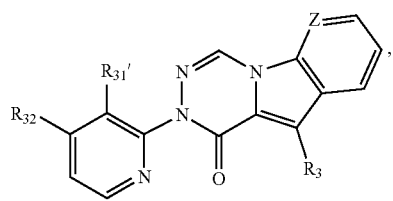
(V-7)
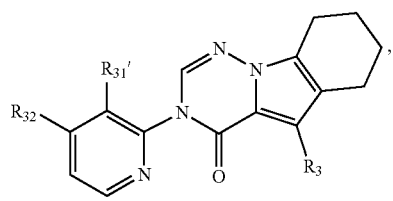
(V-8)
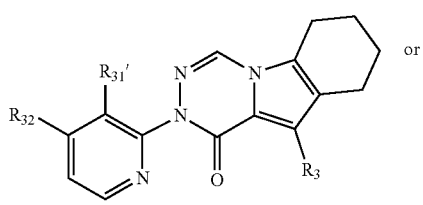
(V-9) or
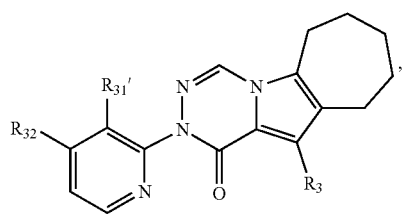
(V-10)
wherein Z is N or CR$_7$; R$_7$ and R$_8$ are each independently hydrogen or halogen; R$_9$ is halogen or C$_{1-6}$ alkyl; and n is 1 or 2.
Embodiment 47. The compound of embodiment 45, which is chosen from:
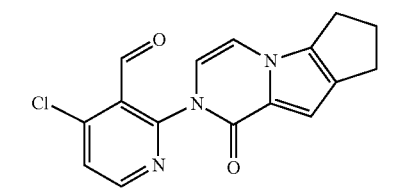
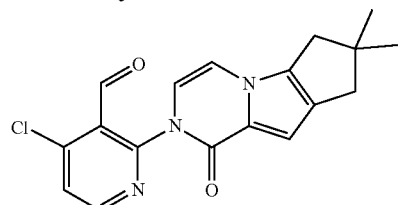
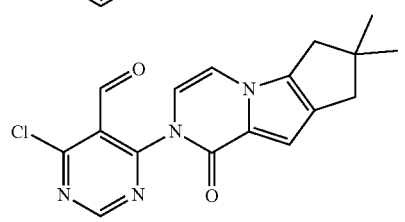
-continued
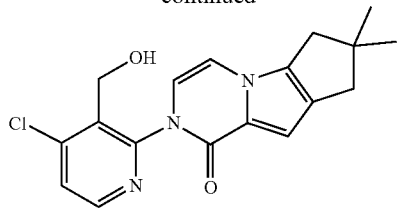
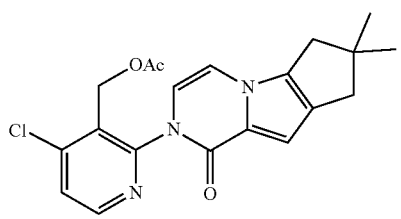
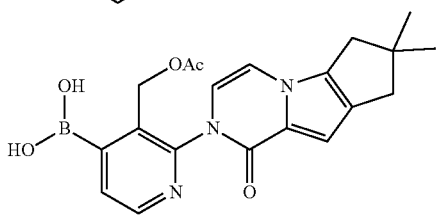
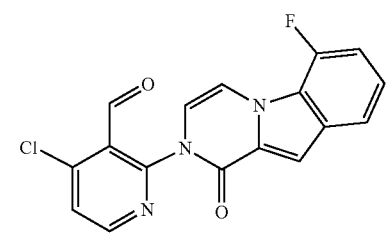
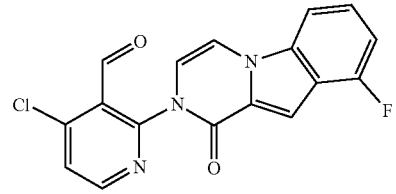
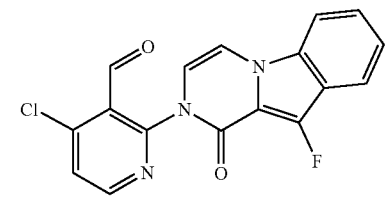
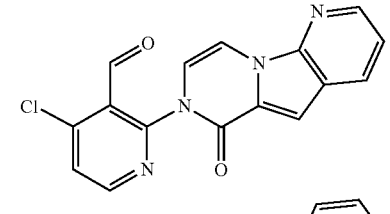
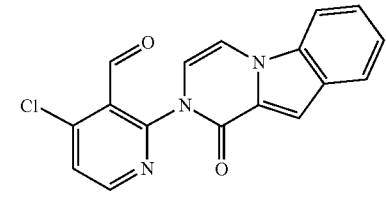

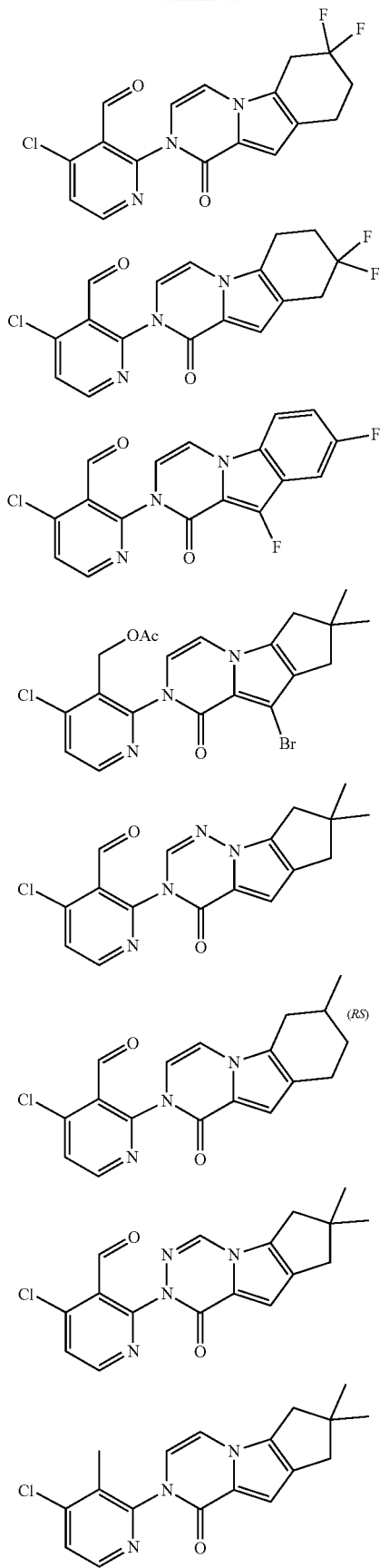
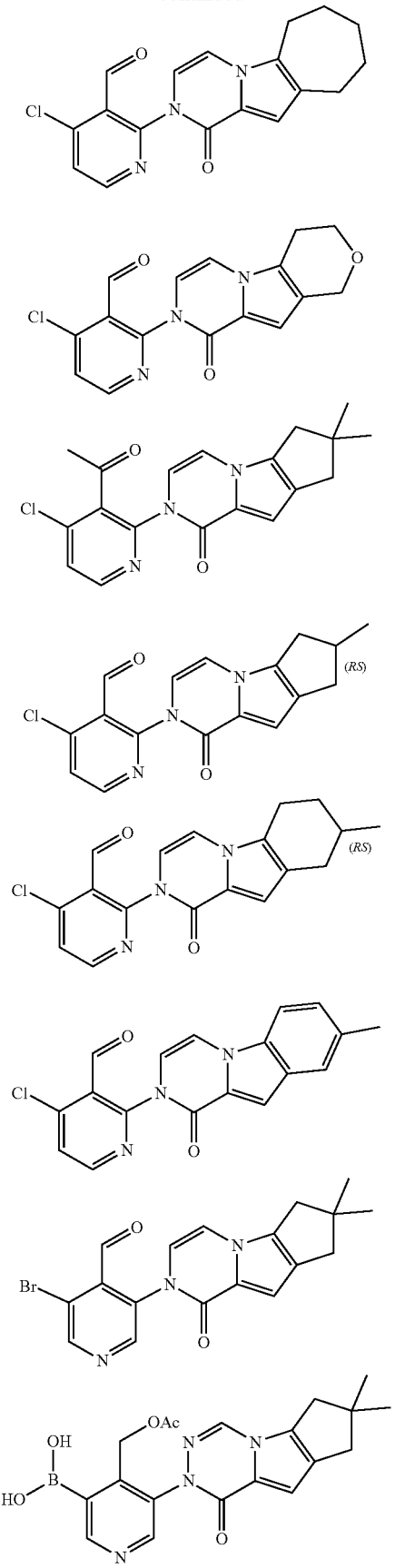

197
-continued
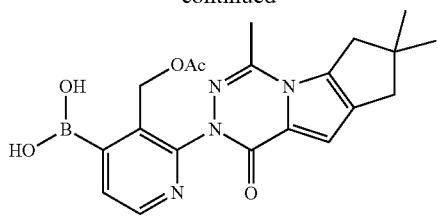
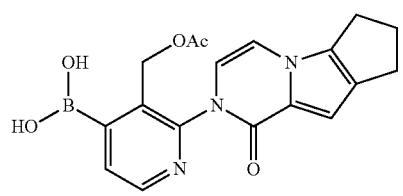
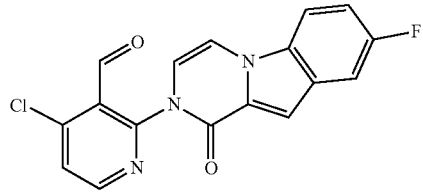
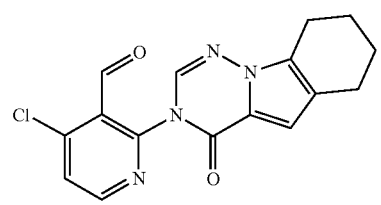
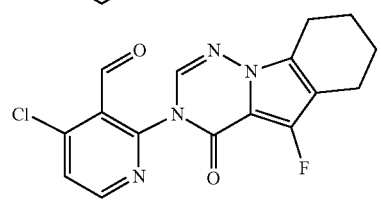
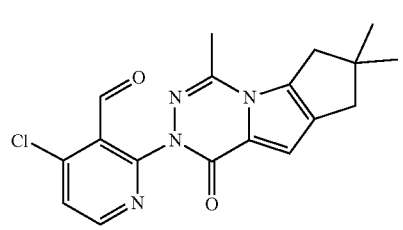
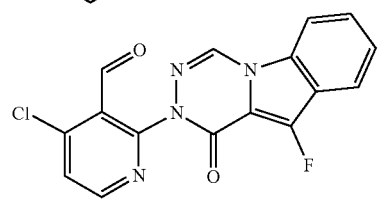
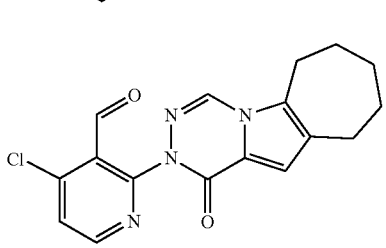
198
-continued
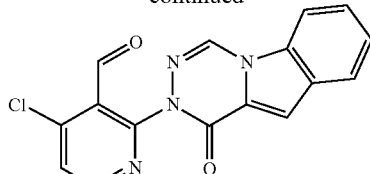
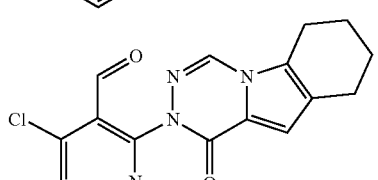
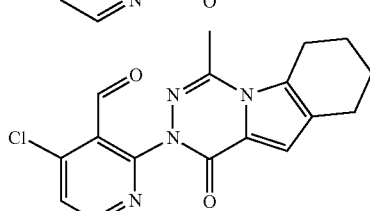
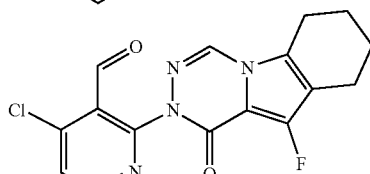
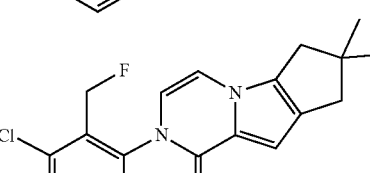
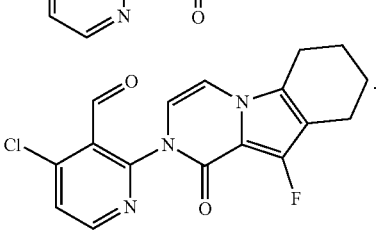
DETAILED DESCRIPTION OF EMBODIMENTS
(II)
Embodiment 1. A compound of formula (I):
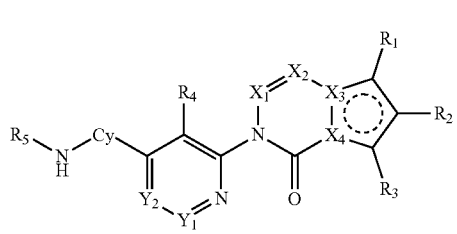
(I)
or a pharmaceutically acceptable salt thereof, or a solvate, a racemic mixture, an enantiomer, a diastereomer or a tautomer thereof, wherein $X_1$ and $X_2$ are each independently CH or N; $X_3$ and $X_4$ are each independently C or N;

$Y_1$ and $Y_2$ are each independently $CR_{10}$ or N;

$R_1$ and $R_2$ are each independently chosen from hydrogen, deuterium, halogen, $C_{1-6}$ alkyl, $C_{2-6}$ alkynyl, $C_{1-6}$ haloalkyl, $C_{3-6}$ cycloalkyl and phenyl; or $R_1$ and $R_2$ together with the carbon atoms to which they are attached form the following structures:

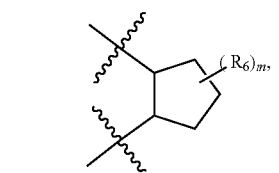
(I-1)

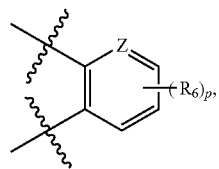
(I-2)

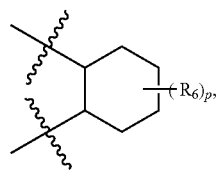
(I-3)

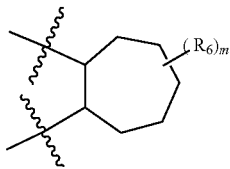
(I-4)

or

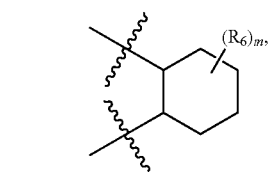
(I-5)

wherein $R_6$ is independently chosen from deuterium, halogen, $C_{1-6}$ alkyl, $C_{2-6}$ alkynyl, $C_{1-6}$ deuteroalkyl and $C_{1-6}$ haloalkyl; or two $R_6$ together with the carbon atoms to which they are attached form 3-6 membered cycloalkyl; m is 0, 1, 2, 3 or 4; p is 1, 2, 3 or 4; Z is N or $CR_7$;

$R_7$ is chosen from hydrogen, deuterium, $C_{1-6}$ alkyl, halogen and $C_{1-6}$ haloalkyl;

$R_3$ is hydrogen, deuterium, halogen or $C_{1-6}$ haloalkyl;

$R_4$ is hydrogen, halogen, —CN, $C_{1-6}$ alkyl, $C_{2-6}$ alkynyl, —($C_{1-3}$ alkyl)-OH, —($C_{1-3}$ alkyl)-O—($C_{1-3}$ alkyl), —O—($C_{1-3}$ alkyl), —CHO, —C(O)NH$_2$, —C(O)NHCH$_3$, —C(O)N(CH$_3$)$_2$ or 3-hydroxyl-oxetan-3-yl, wherein the $C_{1-6}$ alkyl or $C_{1-3}$ alkyl is each optionally substituted with one or more deuterium or halo;

Cy is

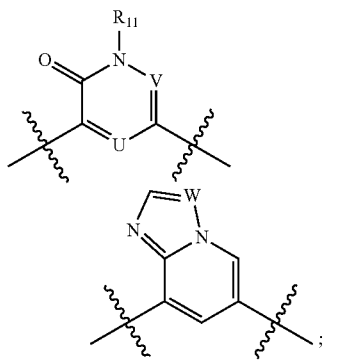

or wherein $R_{11}$ is chosen from hydrogen, $C_{1-6}$ alkyl and $C_{3-6}$ cycloalkyl, wherein the $C_{1-6}$ alkyl is optionally substituted with one or more deuterium or halo;

U, V and W are each independently N or $CR_{12}$; $R_{12}$ is hydrogen, deuterium or halogen;

$R_5$ is hydrogen, $C_{1-6}$ alkyl, —C(O)—($C_{1-6}$ alkyl), —C(O)—($C_{3-6}$ cycloalkyl), —C(O)NH—($C_{1-6}$ alkyl), —C(O)NH—($C_{3-6}$ cycloalkyl), —C(O)N($C_{1-6}$ alkyl)$_2$, phenyl, 5-6 membered monocyclic heteroaryl or 8-10 membered bicyclic heteroaryl, wherein the $C_{1-6}$ alkyl, $C_{3-6}$ cycloalkyl, phenyl, 5-6 membered monocyclic heteroaryl or 8-10 membered bicyclic heteroaryl is each optionally substituted with one or more groups chosen from:

1) halogen;
2) oxo;
3) —CN;
4) $C_{1-6}$ alkyl;
5) $C_{2-6}$ alkenyl;
6) $C_{2-6}$ alkynyl;
7) $C_{1-6}$ alkoxy;
8) $C_{1-6}$ haloalkyl;
9) —($C_{1-6}$ alkyl)-OH;
10) —($C_{1-6}$ alkyl)-O—($C_{1-6}$ alkyl);
11) 4-8 membered heterocyclyl optionally substituted with one or more groups chosen from: deuterium, halogen, hydroxyl, oxo, —CN, $C_{1-6}$ alkyl, $C_{1-6}$ haloalkyl, $C_{3-6}$ cycloalkyl, $C_{2-6}$ alkynyl, $C_{1-6}$ alkoxy, —($C_{1-6}$ alkyl)-CN, —($C_{1-6}$ alkyl)-O—($C_{1-6}$ alkyl), —($C_{1-6}$ alkyl)-OH and 4-6 membered heterocyclyl, wherein the $C_{1-6}$ alkyl, $C_{3-6}$ cycloalkyl or 4-6 membered heterocyclyl is each optionally substituted with one or more groups chosen from: deuterium, halogen, —NH$_2$, —NH($C_{1-6}$ alkyl), —N($C_{1-6}$ alkyl)$_2$ and —NH($C_{3-6}$ cycloalkyl);
12) 5-6 membered monocyclic heteroaryl optionally substituted with one or more groups chosen from: halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O—($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and 4-6 membered heterocyclyl;
13) phenyl optionally substituted with one or more groups chosen from: halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O—($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N—($C_{1-6}$ alkyl)$_2$, —($C_{1-6}$ alkyl)-NH($C_{3-6}$ cycloalkyl) and 4-6 membered heterocyclyl;

14) —NR$_a$'R$_a$", wherein R$_a$' and R$_a$" are each independently chosen from hydrogen, $C_{1-6}$ alkyl, $C_{3-6}$ cycloalkyl, —($C_{1-6}$ alkyl)-O—($C_{1-6}$ alkyl) and 4-6 membered heterocyclyl, wherein the 4-6 membered heterocyclyl is optionally substituted with one or more substituents of —($C_{1-6}$ alkyl)-OH;

15) —C(O)NR$_b$'R$_b$", wherein R$_b$' and R$_b$" together with the N atoms to which they are attached form 4-6 membered heterocyclyl optionally substituted with one or more groups chosen from: deuterium, halogen, —OH, $C_{1-6}$ alkyl, —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl), —NH$_2$, —NH($C_{1-6}$ alkyl), —N($C_{1-6}$ alkyl)$_2$, —NH($C_{3-6}$ cycloalkyl) and —($C_{1-6}$ alkyl)-OH; and 16) —C(O)R$_c$, wherein R$_c$ is chosen from hydrogen, $C_{1-6}$ alkyl, $C_{2-6}$ alkenyl, $C_{2-6}$ alkynyl, —($C_{1-6}$ alkyl)-OH and —($C_{1-6}$ alkyl)-O—($C_{1-6}$ alkyl);

$R_{10}$ is hydrogen, deuterium, halogen, CN, $C_{1-6}$ alkyl or $C_{1-6}$ haloalkyl Embodiment 2. The compound of embodiment 1, or a pharmaceutically acceptable salt thereof, or a solvate, a racemic mixture, an enantiomer, a diastereomer or a tautomer thereof, wherein the compound is a compound of formula (IA):

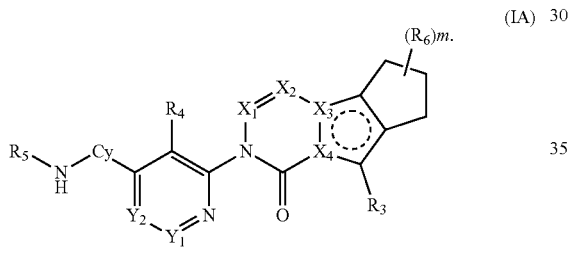

(IA)

Embodiment 3. The compound of embodiment 2, or a pharmaceutically acceptable salt thereof, or a solvate, a racemic mixture, an enantiomer, a diastereomer or a tautomer thereof, wherein the compound is a compound of formula (II):

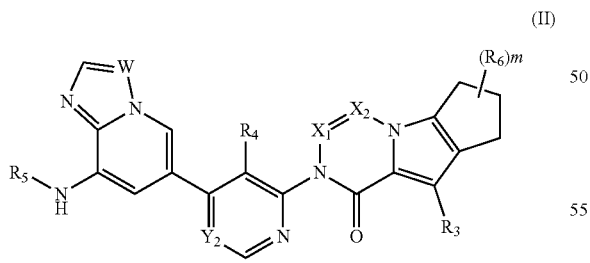

(II)

wherein
$X_1$ and $X_2$ are each independently CH or N;
$Y_2$ is CH or N;
$R_3$ is hydrogen, deuterium, halogen or $C_{1-6}$ haloalkyl;
$R_4$ is hydrogen, halogen, —CN, $C_{1-6}$ alkyl, —($C_{1-3}$ alkyl)-OH, —($C_{1-3}$ deuteroalkyl)-OH, —($C_{1-3}$ alkyl)-O—($C_{1-3}$ alkyl), —O—($C_{1-3}$ alkyl), —CHO, —C(O)NH$_2$, —C(O)NHCH$_3$, —C(O)N(CH$_3$)$_2$ or 3-hydroxy-oxetan-3-yl;

W is N or CR$_{12}$, and R$_{12}$ is hydrogen or halogen;
$R_5$ is $C_{1-6}$ alkyl, phenyl, 5-6 membered monocyclic heteroaryl or 8-10 membered bicyclic heteroaryl, each of which is optionally substituted with one or more groups chosen from:
1) halogen;
2) oxo;
3) —CN;
4) $C_{1-6}$ alkyl;
5) $C_{2-6}$ alkenyl;
6) $C_{2-6}$ alkynyl;
7) $C_{1-6}$ alkoxy;
8) $C_{1-6}$ haloalkyl;
9) —($C_{1-6}$ alkyl)-OH;
10) —($C_{1-6}$ alkyl)-O—($C_{1-6}$ alkyl);
11) 4-8 membered heterocyclyl optionally substituted with one or more substituents chosen from halogen, hydroxyl, oxo, —CN, $C_{1-6}$ alkyl, $C_{1-6}$ haloalkyl, $C_{3-6}$ cycloalkyl, $C_{2-6}$ alkynyl, $C_{1-6}$ alkoxy, —($C_{1-6}$ alkyl)-CN, —($C_{1-6}$ alkyl)-O—($C_{1-6}$ alkyl), —($C_{1-6}$ alkyl)-OH, 4-6 membered heterocyclyl and 4-6 membered fluoroheterocyclyl;
12) 5-6 membered monocyclic heteroaryl optionally substituted with one or more substituents chosen from halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O—($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and 4-6 membered heterocyclyl;
13) phenyl optionally substituted with one or more substituents chosen from halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and 4-6 membered heterocyclyl;
14) —NR$_a$'R$_a$", wherein R$_a$' and R$_a$" are each independently chosen from hydrogen, $C_{1-6}$ alkyl, $C_{3-6}$ cycloalkyl, —($C_{1-6}$ alkyl)-O—($C_{1-6}$ alkyl) and 4-6 membered heterocyclyl, wherein the 4-6 membered heterocyclyl is optionally substituted with one or more substituents of —($C_{1-6}$ alkyl)-OH;
15) —C(O)NR$_b$'R$_b$", wherein R$_b$' and R$_b$" together with the N atoms to which they are attached form 4-6 membered heterocyclyl, wherein the 4-6 membered heterocyclyl is optionally substituted with one or more substituents chosen from halogen, —OH, $C_{1-6}$ alkyl, —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and —($C_{1-6}$ alkyl)-OH; and
16) —C(O)R$_c$, wherein R$_c$ is chosen from hydrogen, $C_{1-6}$ alkyl, $C_{2-6}$ alkenyl, $C_{2-6}$ alkynyl and —($C_{1-6}$ alkyl)-O—($C_{1-6}$ alkyl);

$R_6$ is halogen or $C_{1-6}$ alkyl; and
m is 0, 1 or 2;
preferably, W is N or CR$_{12}$, and R$_{12}$ is halogen;
preferably, R$_5$ is 5-6 membered monocyclic heteroaryl or 8-10 membered bicyclic heteroaryl optionally substituted with one or more groups chosen from:
1) $C_{1-6}$ alkyl; and
2) 4-6 membered heterocycloalkyl, which is optionally substituted with $C_{1-6}$ alkyl and 4-6 membered heterocyclyl;
preferably, 5-6 membered monocyclic heteroaryl is 5 membered monocyclic heteroaryl, more preferably triazolyl;

preferably, 8-10 membered bicyclic heteroaryl is 8 membered bicyclic heteroaryl, more preferably 4,5,6,7-tetrahydropyrazolo[1,5-a]pyrazinyl.

Embodiment 4. The compound of embodiment 2, or a pharmaceutically acceptable salt thereof, or a solvate, a racemic mixture, an enantiomer, a diastereomer or a tautomer thereof, wherein the compound is a compound of formula (III):

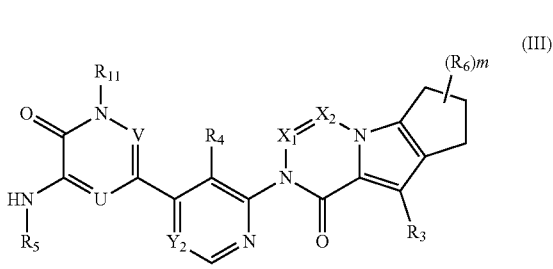

(III)

wherein $X_1$ and $X_2$ are each independently CH or N;

$Y_2$ is CH or N;

$R_3$ is hydrogen, deuterium, halogen or $C_{1-6}$ haloalkyl;

$R_4$ is hydrogen, halogen, —CN, $C_{1-6}$ alkyl, —($C_{1-3}$ alkyl)-OH, —($C_{1-3}$ deuteroalkyl)-OH, —($C_{1-3}$ alkyl)-O—($C_{1-3}$ alkyl), —O—($C_{1-3}$ alkyl), —CHO, —C(O)NH$_2$, —C(O)NHCH$_3$, —C(O)N(CH$_3$)$_2$ or 3-hydroxyl-oxetan-3-yl;

U and V are each independently chosen from N or CH;

$R_5$ is $C_{1-6}$ alkyl, phenyl, 5-6 membered monocyclic heteroaryl or 8-10 membered bicyclic heteroaryl, each of which is optionally substituted with one or more groups chosen from:

1) halogen;
2) oxo;
3) —CN;
4) $C_{1-6}$ alkyl;
5) $C_{2-6}$ alkenyl;
6) $C_{2-6}$ alkynyl;
7) $C_{1-6}$ alkoxy;
8) $C_{1-6}$ haloalkyl;
9) —($C_{1-6}$ alkyl)-OH;
10) —($C_{1-6}$ alkyl)-O—($C_{1-6}$ alkyl);
11) 4-8 membered heterocyclyl optionally substituted with one or more substituents chosen from halogen, hydroxyl, oxo, —CN, $C_{1-6}$ alkyl, $C_{1-6}$ haloalkyl, $C_{3-6}$ cycloalkyl, $C_{2-6}$ alkynyl, $C_{1-6}$ alkoxy, —($C_{1-6}$ alkyl)-CN, —($C_{1-6}$ alkyl)-O—($C_{1-6}$ alkyl), —($C_{1-6}$ alkyl)-OH, 4-6 membered heterocyclyl and 4-6 membered fluoroheterocyclyl;
12) 5-6 membered monocyclic heteroaryl optionally substituted with one or more substituents chosen from halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O—($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and 4-6 membered heterocyclyl;
13) phenyl optionally substituted with one or more substituents chosen from halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and 4-6 membered heterocyclyl;
14) —NR$_a$'R$_a$'', wherein R$_a$' and R$_a$'' are each independently chosen from hydrogen, $C_{1-6}$ alkyl, $C_{3-6}$ cycloalkyl, —($C_{1-6}$ alkyl)-O—($C_{1-6}$ alkyl) and 4-6 membered heterocyclyl, wherein the 4-6 membered heterocyclyl is optionally substituted with one or more substituents of —($C_{1-6}$ alkyl)-OH;
15) —C(O)NR$_b$'R$_b$'', wherein R$_b$' and R$_b$'' together with the N atoms to which they are attached form 4-6 membered heterocyclyl, wherein the 4-6 membered heterocyclyl is optionally substituted with one or more substituents chosen from halogen, —OH, $C_{1-6}$ alkyl, —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and —($C_{1-6}$ alkyl)-OH; and
16) —C(O)R$_c$, wherein R$_c$ is chosen from hydrogen, $C_{1-6}$ alkyl, $C_{2-6}$ alkenyl, $C_{2-6}$ alkynyl and —($C_{1-6}$ alkyl)-O—($C_{1-6}$ alkyl);

$R_6$ is halogen or $C_{1-6}$ alkyl;

m is 0, 1 or 2; and $R_{11}$ is hydrogen, $C_{1-6}$ alkyl or $C_{1-6}$ deuteroalkyl;

preferably, U is CH, and V is N or CH; more preferably, both U and V are CH;

preferably, $R_{11}$ is $C_{1-3}$ alkyl, preferably methyl or ethyl, and more preferably methyl;

preferably, 5-6 membered monocyclic heteroaryl is 6 membered monocyclic heteroaryl, more preferably pyridyl, pyrazinyl and pyrimidyl;

preferably, 5-6 membered monocyclic heteroaryl is 5 membered monocyclic heteroaryl, more preferably triazolyl;

preferably, 8-10 membered bicyclic heteroaryl is 9 membered bicyclic heteroaryl, more preferably 4,5,6,7-tetrahydropyrazolo[1,5-a]pyrazinyl;

and preferably, 4-8 membered heterocyclyl is 4-6 membered heterocyclyl, more preferably oxetanyl, azetidinyl, tetrahydropyranyl, morpholinyl, piperazinyl or tetrahydropyridyl.

Embodiment 5. The compound of any one of embodiments 1-4, or a pharmaceutically acceptable salt thereof, or a solvate, a racemic mixture, an enantiomer, a diastereomer or a tautomer thereof, wherein both $X_1$ and $X_2$ are CH, or one of $X_1$ and $X_2$ is N, and the other is CH;

and preferably, both $X_1$ and $X_2$ are CH.

Embodiment 6. The compound of any one of embodiments 1-5, or a pharmaceutically acceptable salt thereof, or a solvate, a racemic mixture, an enantiomer, a diastereomer or a tautomer thereof, wherein $Y_2$ is CH.

Embodiment 7. The compound of any one of embodiments 1-6, or a pharmaceutically acceptable salt thereof, or a solvate, a racemic mixture, an enantiomer, a diastereomer or a tautomer thereof, wherein $R_3$ is hydrogen or halogen.

Embodiment 8. The compound of any one of embodiments 1-7, or a pharmaceutically acceptable salt thereof, or a solvate, a racemic mixture, an enantiomer, a diastereomer or a tautomer thereof, wherein $R_4$ is $C_{1-6}$ alkyl, —($C_{1-3}$ alkyl)-OH, —($C_{1-3}$ deuteroalkyl)-OH or —CHO;

and preferably, $R_4$ is hydroxymethyl or hydroxy deuteromethyl.

Embodiment 9. The compound of any one of embodiments 1-8, or a pharmaceutically acceptable salt thereof, or a solvate, a racemic mixture, an enantiomer, a diastereomer or a tautomer thereof, wherein $R_3$ is hydrogen, and $R_4$ is —($C_{1-3}$ alkyl)-OH.

Embodiment 10. The compound of any one of embodiments 1-9, or a pharmaceutically acceptable salt thereof, or a solvate, a racemic mixture, an enantiomer, a diastereomer or a tautomer thereof, wherein $R_5$ is chosen from

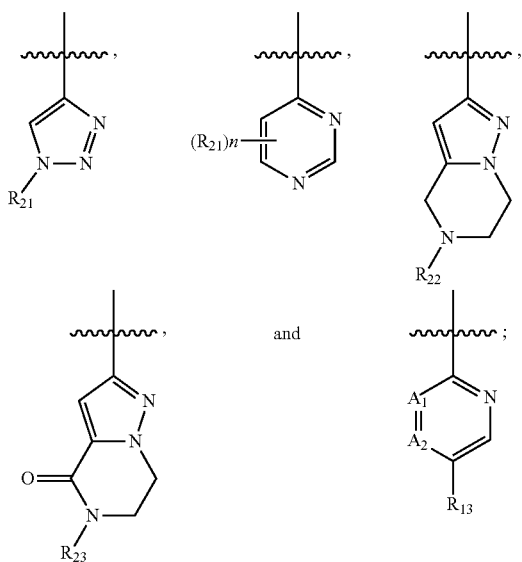

wherein
R$_{21}$ is chosen from C$_{1-6}$ alkyl, C$_{1-6}$ haloalkyl and —(C$_{1-6}$ alkyl)-O—(C$_{1-6}$ alkyl);
n is 0, 1 or 2;
R$_{22}$ and R$_{23}$ are each independently chosen from hydrogen, C$_{1-6}$ alkyl, C$_{1-6}$ haloalkyl, —(C$_{1-6}$ alkyl)-O—(C$_{1-6}$ alkyl), 4-6 membered heterocyclyl or —C(O)R$_c$, and R$_c$ is chosen from hydrogen, C$_{1-6}$ alkyl or —(C$_{1-6}$ alkyl)-O—(C$_{1-6}$ alkyl);
A$_1$ and A$_2$ are each independently CH or N; and R$_{13}$ is chosen from:
1) hydrogen;
2) C$_{1-6}$ alkyl;
3) 4-6 membered heterocyclyl optionally substituted with one or more substituents chosen from oxo, C$_{1-6}$ alkyl, C$_{1-6}$ alkoxy, —(C$_{1-6}$ alkyl)-O—(C$_{1-6}$ alkyl) and 4-6 membered heterocyclyl;
4) phenyl optionally substituted with one or more substituents chosen from 4-6 membered heterocyclyl;
5) —NR$_a$'R$_a$", wherein R$_a$' and R$_a$" are each independently chosen from hydrogen, C$_{1-6}$ alkyl, —(C$_{1-6}$ alkyl)-O—(C$_{1-6}$ alkyl) and 4-6 membered heterocyclyl, wherein the 4-6 membered heterocyclyl is optionally substituted with —(C$_{1-6}$ alkyl)-OH; and
6) —C(O)NR$_b$'R$_b$", wherein R$_b$' and R$_b$" together with the N atoms to which they are attached form 4-6 membered heterocyclyl, wherein the 4-6 membered heterocyclyl is optionally substituted with one or more C$_{1-6}$ alkyl;
preferably, R$_5$ is

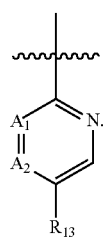

Embodiment 11. The compound of embodiment 10, or a pharmaceutically acceptable salt thereof, or a solvate, a racemic mixture, an enantiomer, a diastereomer or a tautomer thereof, wherein R$_{13}$ is piperazinyl optionally substituted with one or more substituents chosen from C$_{1-6}$ alkyl and 4-5 membered heterocyclyl.

Embodiment 12. The compound of any one of embodiments 1-10, or a pharmaceutically acceptable salt thereof, or a solvate, a racemic mixture, an enantiomer, a diastereomer or a tautomer thereof, wherein R$_5$ is chosen from

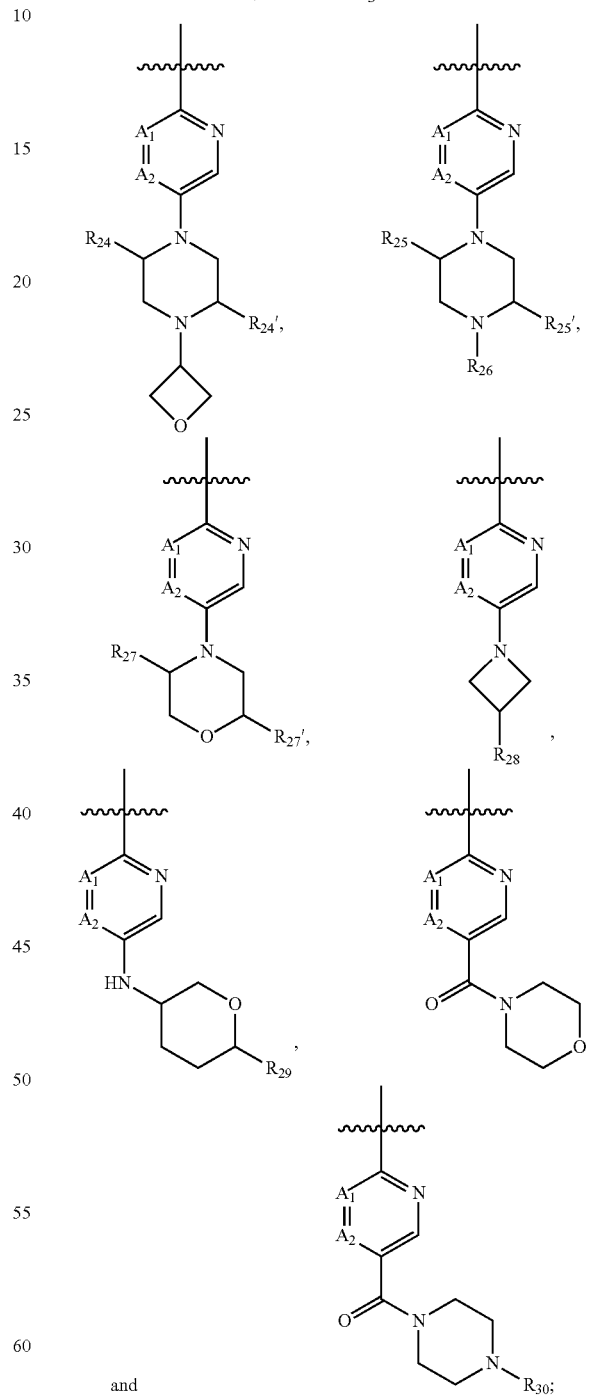

wherein R$_{24}$, R$_{24}$', R$_{25}$, R$_{25}$', R$_{27}$ and R$_{27}$' are each independently chosen from hydrogen, oxo and C$_{1-6}$ alkyl;
R$_{26}$ is C$_{1-6}$ alkyl, —(C$_{1-6}$ alkyl)-O—(C$_{1-6}$ alkyl) or tetrahydrofuranyl;

$R_{28}$ is $C_{1-6}$ alkoxy; $R_{29}$ is hydrogen or —($C_{1-6}$ alkyl)-OH; $R_{30}$ is $C_{1-6}$ alkyl;

$A_1$ and $A_2$ are each independently CH or N;

preferably, both $A_1$ and $A_2$ are CH, or one of $A_1$ and $A_2$ is N, and the other is CH; and more preferably, both $A_1$ and $A_2$ are CH.

Embodiment 13. The compound of any one of embodiments 1-12, or a pharmaceutically acceptable salt thereof, or a solvate, a racemic mixture, an enantiomer, a diastereomer or a tautomer thereof, wherein $R_5$ is chosen from

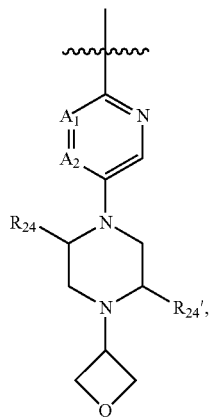

wherein $R_{24}$ and $R_{24}'$ are each independently chosen from hydrogen, oxo and $C_{1-6}$ alkyl;

preferably, when $R_{24}$ is $C_{1-6}$ alkyl (such as $C_{1-3}$ alkyl, more preferably methyl),

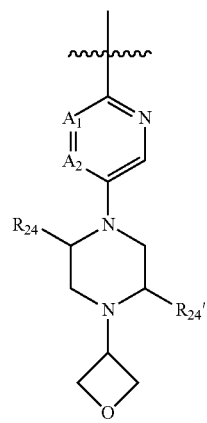

is preferably

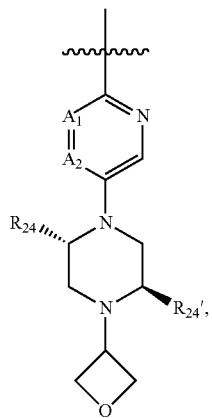

wherein $R_{24}'$ is $C_{1-6}$ alkyl (such as $C_{1-3}$ alkyl, more preferably methyl), and more preferably

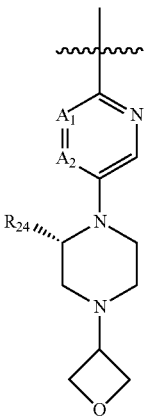

Embodiment 14. The compound of embodiments 12 or 13, or a pharmaceutically acceptable salt thereof, or a solvate, a racemic mixture, an enantiomer, a diastereomer or a tautomer thereof, wherein $R_{24}$ and $R_{24}'$ are each independently chosen from hydrogen and $C_{1-6}$ alkyl.

Embodiment 15. The compound of any one of embodiments 10-14, or a pharmaceutically acceptable salt thereof, or a solvate, a racemic mixture, an enantiomer, a diastereomer or a tautomer thereof, wherein both $A_1$ and $A_2$ are CH, or $A_1$ is N and $A_2$ is CH.

Embodiment 16. The compound of any one of embodiments 1-10, or a pharmaceutically acceptable salt thereof, or a solvate, a racemic mixture, an enantiomer, a diastereomer or a tautomer thereof, wherein $R_5$ is chosen from:

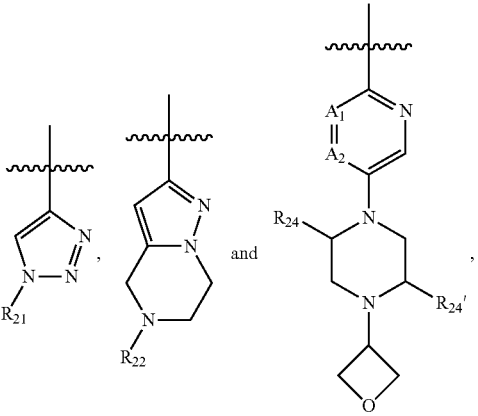

wherein $R_{21}$ is $C_{1-6}$ alkyl; $R_{22}$ is chosen from hydrogen, $C_{1-6}$ alkyl and 4 membered heterocyclyl; $A_1$ and $A_2$ are respectively CH; and $R_{24}$ and $R_{24}'$ are each independently chosen from hydrogen and $C_{1-6}$ alkyl.

Embodiment 17. The compound of any one of embodiments 4-16, or a pharmaceutically acceptable salt thereof, or a solvate, a racemic mixture, an enantiomer, a diastereomer or a tautomer thereof,

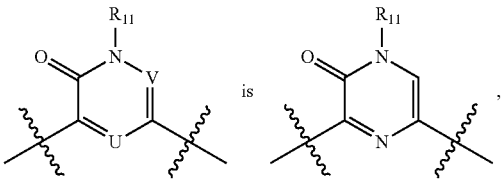

-continued

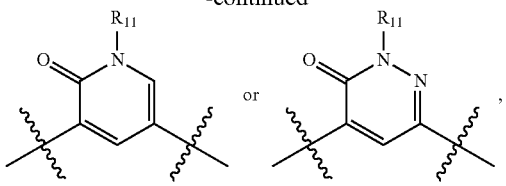

wherein R$_{11}$ is C$_{1-6}$ alkyl or C$_{1-6}$ deuteroalkyl;
preferably, R$_{11}$ is C$_{1-3}$ alkyl, preferably methyl or ethyl, and more preferably methyl; and preferably, R$_{11}$ is C$_{1-3}$ deuteroalkyl, preferably trideuteromethyl.

Embodiment 18. The compound of any one of embodiments 4-17, or a pharmaceutically acceptable salt thereof, or a solvate, a racemic mixture, an enantiomer, a diastereomer or a tautomer thereof, wherein both X$_1$ and X$_2$ are CH, or one of X$_1$ and X$_2$ is N, and the other is CH; Y$_2$ is CH; R$_3$ is hydrogen; R$_4$ is —(C$_{1-3}$ alkyl)-OH; U is CH, V is N or CH, and R$_{11}$ is C$_{1-3}$ alkyl; R$_5$ is chosen from

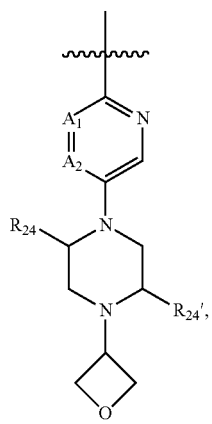

wherein R$_{24}$ and R$_{24}$' are each independently chosen from hydrogen, oxo and C$_{1-6}$ alkyl, both A$_1$ and A$_2$ are CH, or A$_1$ is N and A$_2$ is CH; R$_6$ is C$_{1-6}$ alkyl; and m is 0 or 2.

Embodiment 19. The compound of any one of embodiments 4-18, or a pharmaceutically acceptable salt thereof, or a solvate, a racemic mixture, an enantiomer, a diastereomer or a tautomer thereof, wherein both U and V are CH, and R$_{11}$ is methyl.

Embodiment 20. The compound of any one of embodiments 1-19, or a pharmaceutically acceptable salt thereof, or a solvate, a racemic mixture, an enantiomer, a diastereomer or a tautomer thereof, wherein R$_6$ is C$_{1-3}$ alkyl; and m is 2.

Embodiment 21. The compound of any one of embodiments 1-20, or a pharmaceutically acceptable salt thereof, or a solvate, a racemic mixture, an enantiomer, a diastereomer or a tautomer thereof, wherein R$_6$ together with the five-membered ring to which they are attached forms

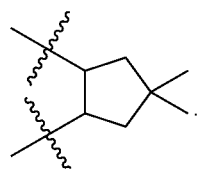 [SMILES: *C1CC(C)(C)CC1*]

Embodiment 22. The compound of embodiment 1, or a pharmaceutically acceptable salt thereof, or a solvate, a racemic mixture, an enantiomer, a diastereomer or a tautomer thereof, wherein the compound is a compound of formula (IB)

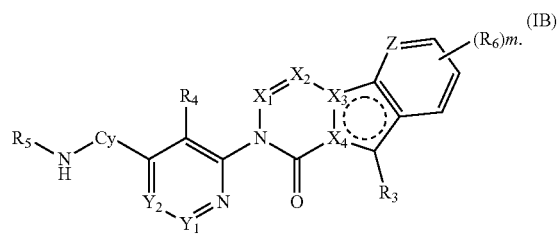

Embodiment 23. The compound of embodiment 22, or a pharmaceutically acceptable salt thereof, or a solvate, a racemic mixture, an enantiomer, a diastereomer or a tautomer thereof, wherein the compound is a compound of formula (IV):

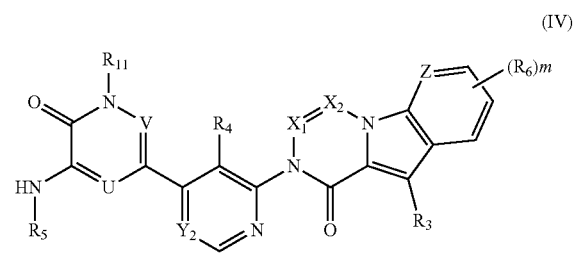

wherein
X$_1$ and X$_2$ are each independently CH or N;
Y$_2$ is CH or N;
R$_3$ is hydrogen, deuterium, halogen or C$_{1-6}$ haloalkyl;
R$_4$ is hydrogen, halogen, —CN, C$_{1-6}$ alkyl, —(C$_{1-3}$ alkyl)-OH, —(C$_{1-3}$ deuteroalkyl)-OH, —(C$_{1-3}$ alkyl)-O—(C$_{1-3}$ alkyl), —O—(C$_{1-3}$ alkyl), —CHO, —C(O)NH$_2$, —C(O)NHCH$_3$, —C(O)N(CH$_3$)$_2$ or 3-hydroxyl-oxetan-3-yl;
U and V are each independently chosen from N or CH;
Z is N or CH;
R$_5$ is C$_{1-6}$ alkyl, phenyl, 5-6 membered monocyclic heteroaryl or 8-10 membered bicyclic heteroaryl, each of which is optionally substituted with one or more groups chosen from:
1) halogen;
2) oxo;
3) —CN;
4) C$_{1-6}$ alkyl;
5) C$_{2-6}$ alkenyl;
6) C$_{2-6}$ alkynyl;
7) C$_{1-6}$ alkoxy;
8) C$_{1-6}$ haloalkyl;
9) —(C$_{1-6}$ alkyl)-OH;
10) —(C$_{1-6}$ alkyl)-O—(C$_{1-6}$ alkyl);
11) 4-8 membered heterocyclyl optionally substituted with one or more substituents chosen from halogen, hydroxyl, oxo, —CN, C$_{1-6}$ alkyl, C$_{1-6}$ haloalkyl, C$_{3-6}$ cycloalkyl, C$_{2-6}$ alkynyl, C$_{1-6}$ alkoxy, —(C$_{1-6}$ alkyl)-CN, —(C$_{1-6}$ alkyl)-O—(C$_{1-6}$ alkyl), —(C$_{1-6}$ alkyl)-OH, 4-6 membered heterocyclyl and 4-6 membered fluoroheterocyclyl;
12) 5-6 membered monocyclic heteroaryl optionally substituted with one or more substituents chosen from halogen, —CN, —(C$_{1-6}$ alkyl)-CN, —(C$_{1-6}$ alkyl)-OH, $C_{1-6}$ alkyl, $C_{3-6}$ cycloalkyl, $C_{1-6}$ alkoxy, —($C_{1-6}$ alkyl)-O—($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and 4-6 membered heterocyclyl;
13) phenyl optionally substituted with one or more substituents chosen from halogen, —CN, —($C_{1-6}$ alkyl)-CN, —($C_{1-6}$ alkyl)-OH, $C_{1-6}$ alkyl, $C_{3-6}$ cycloalkyl, $C_{1-6}$ alkoxy, —($C_{1-6}$ alkyl)-O($C_{1-6}$ alkyl), —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and 4-6 membered heterocyclyl;
14) —NR$_a$'R$_a$", wherein R$_a$' and R$_a$" are each independently chosen from hydrogen, $C_{1-6}$ alkyl, $C_{3-6}$ cycloalkyl, —($C_{1-6}$ alkyl)-O—($C_{1-6}$ alkyl) and 4-6 membered heterocyclyl, wherein the 4-6 membered heterocyclyl is optionally substituted with one or more substituents of —($C_{1-6}$ alkyl)-OH;
15) —C(O)NR$_b$'R$_b$", wherein R$_b$' and R$_b$" together with the N atoms to which they are attached form 4-6 membered heterocyclyl, wherein the 4-6 membered heterocyclyl is optionally substituted with one or more substituents chosen from halogen, —OH, $C_{1-6}$ alkyl, —($C_{1-6}$ alkyl)-NH$_2$, —($C_{1-6}$ alkyl)-NH($C_{1-6}$ alkyl), —($C_{1-6}$ alkyl)-N($C_{1-6}$ alkyl)$_2$, —($C_{1-6}$ alkyl)-NH($C_{3-6}$ cycloalkyl) and —($C_{1-6}$ alkyl)-OH; and
16) —C(O)R$_c$, wherein R$_c$ is chosen from hydrogen, $C_{1-6}$ alkyl, $C_{2-6}$ alkenyl, $C_{2-6}$ alkynyl and —($C_{1-6}$ alkyl)-O—($C_{1-6}$ alkyl);
$R_6$ is halogen or $C_{1-6}$ alkyl;
m is 0, 1 or 2; and
$R_{11}$ is hydrogen, $C_{1-6}$ alkyl or $C_{1-6}$ deuteroalkyl;
preferably, both $X_1$ and $X_2$ are CH, or one of $X_1$ and $X_2$ is N, and the other is CH;
preferably, both $X_1$ and $X_2$ are CH;
preferably, $Y_2$ is CH;
preferably, $R_3$ is hydrogen or halogen;
preferably, $R_4$ is $C_{1-6}$ alkyl, —($C_{1-3}$ alkyl)-OH, —($C_{1-3}$ deuteroalkyl)-OH or —CHO; more preferably $R_4$ is —($C_{1-3}$ alkyl)-OH;
preferably, $R_4$ is hydroxymethyl or hydroxy deuteromethyl;
preferably, $R_3$ is hydrogen, and $R_4$ is —($C_{1-3}$ alkyl)-OH;
preferably,

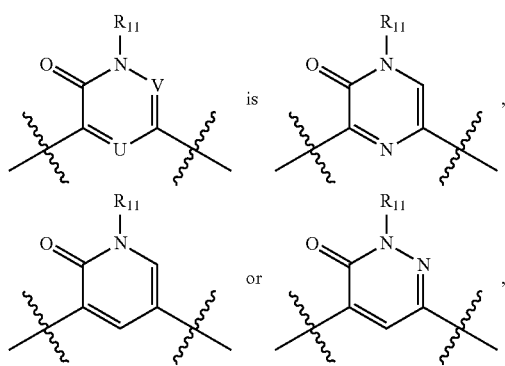

is wherein $R_{11}$ is $C_{1-6}$ alkyl or $C_{1-6}$ deuteroalkyl;
preferably, Z is CH;
preferably, U is CH, and V is N or CH; more preferably, both U and V are CH;
preferably, both U and V are CH, and $R_{11}$ is methyl;

preferably, $R_{11}$ is $C_{1-3}$ alkyl, preferably methyl or ethyl, and more preferably methyl;
preferably, $R_{11}$ is $C_{1-3}$ deuteroalkyl, preferably trideuteromethyl;
preferably, $R_6$ is halogen;
preferably, m is 0 or 1;
preferably, 5-6 membered monocyclic heteroaryl is 6 membered monocyclic heteroaryl, more preferably pyridyl, pyrazinyl and pyrimidyl;
preferably, 5-6 membered monocyclic heteroaryl is 5 membered monocyclic heteroaryl, more preferably triazolyl;
preferably, 8-10 membered bicyclic heteroaryl is 9 membered bicyclic heteroaryl, more preferably 4,5,6,7-tetrahydropyrazolo[1,5-a]pyrazinyl;
and preferably, 4-8 membered heterocyclyl is 4-6 membered heterocyclyl, more preferably oxetanyl, azetidinyl, tetrahydropyranyl, morpholinyl, piperazinyl or tetrahydropyridyl.

Embodiment 24. The compound of any one of embodiments 22-23, or a pharmaceutically acceptable salt thereof, or a solvate, a racemic mixture, an enantiomer, a diastereomer or a tautomer thereof, wherein $Y_2$ is CH.

Embodiment 25. The compound of any one of embodiments 22-24, or a pharmaceutically acceptable salt thereof, or a solvate, a racemic mixture, an enantiomer, a diastereomer or a tautomer thereof, wherein $R_5$ is chosen from:

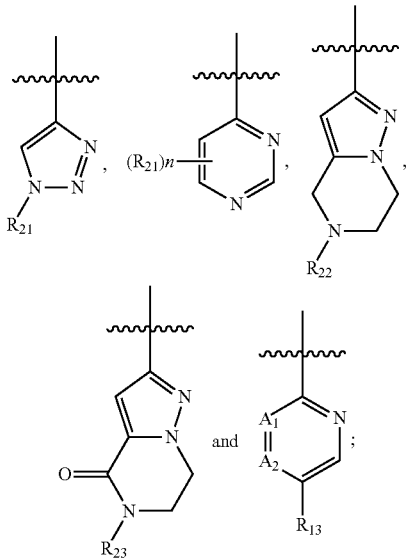

wherein
$R_{21}$ is chosen from $C_{1-6}$ alkyl, $C_{1-6}$ haloalkyl and —($C_{1-6}$ alkyl)-O—($C_{1-6}$ alkyl);
n is 0, 1 or 2;
$R_{22}$ and $R_{23}$ are each independently chosen from hydrogen, $C_{1-6}$ alkyl, $C_{1-6}$ haloalkyl, —($C_{1-6}$ alkyl)-O—($C_{1-6}$ alkyl), 4-6 membered heterocyclyl or —C(O)R$_c$, and R$_c$ is chosen from hydrogen, $C_{1-6}$ alkyl or —($C_{1-6}$ alkyl)-O—($C_{1-6}$ alkyl);
$A_1$ and $A_2$ are each independently CH or N; and
$R_{13}$ is chosen from:
1) hydrogen;
2) $C_{1-6}$ alkyl;
3) 4-6 membered heterocyclyl optionally substituted with one or more substituents chosen from oxo, $C_{1-6}$ alkyl, $C_{1-6}$ alkoxy, —($C_{1-6}$ alkyl)-O—($C_{1-6}$ alkyl) and 4-6 membered heterocyclyl;

4) phenyl optionally substituted with one or more substituents chosen from 4-6 membered heterocyclyl;
5) —NR$_a$'R$_a$", wherein R$_a$' and R$_a$" are each independently chosen from hydrogen, C$_{1-6}$ alkyl, —(C$_{1-6}$ alkyl)-O—(C$_{1-6}$ alkyl) and 4-6 membered heterocyclyl, wherein the 4-6 membered heterocyclyl is optionally substituted with one or more —(C$_{1-6}$ alkyl)-OH; and
6) —C(O)NR$_b$'R$_b$", wherein R$_b$' and R$_b$" together with the N atoms to which they are attached form 4-6 membered heterocyclyl, wherein the 4-6 membered heterocyclyl is optionally substituted with one or more C$_{1-6}$ alkyl;
preferably, R$_5$ is

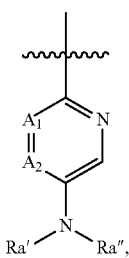

wherein A$_1$ and A$_2$ are each independently CH or N; R$_a$' and R$_a$" together with the N atoms to which they are attached form 4-6 membered heterocyclyl, wherein the 4-6 membered heterocyclyl is optionally substituted with one or more substituents chosen from oxo, C$_{1-6}$ alkyl, C$_{1-6}$ alkoxy and 4-6 membered heterocyclyl;
preferably, R$_{13}$ is piperazinyl optionally substituted with one or more substituents chosen from C$_{1-6}$ alkyl and 4-5 membered heterocyclyl;
preferably, R$_5$ is chosen from:

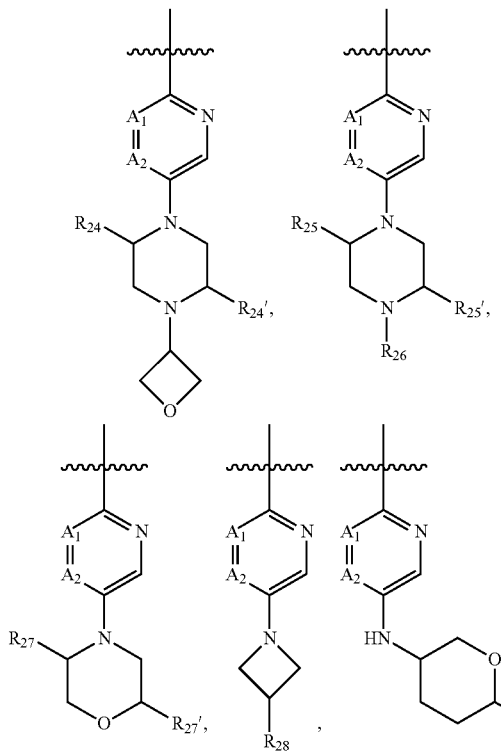

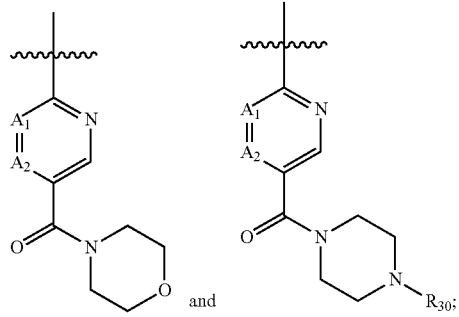

wherein R$_{24}$, R$_{24}$', R$_{25}$, R$_{25}$', R$_{27}$ and R$_{27}$' are each independently chosen from hydrogen, oxo and C$_{1-6}$ alkyl;
R$_{26}$ is C$_{1-6}$ alkyl, —(C$_{1-6}$ alkyl)-O—(C$_{1-6}$ alkyl) or tetrahydrofuranyl;
R$_{28}$ is C$_{1-6}$ alkoxy; R$_{29}$ is hydrogen or —(C$_{1-6}$ alkyl)-OH;
R$_{30}$ is C$_{1-6}$ alkyl; and
A$_1$ and A$_2$ are each independently CH or N;
preferably, R$_5$ is chosen from

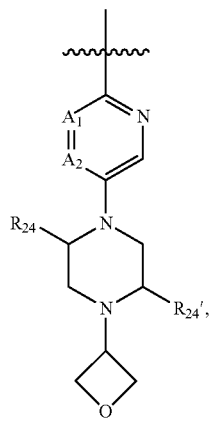

wherein R$_{24}$ and R$_{24}$' are each independently chosen from hydrogen, oxo and C$_{1-6}$ alkyl;
more preferably, when R$_{24}$ is C$_{1-6}$ alkyl (such as C$_{1-3}$ alkyl, more preferably methyl),

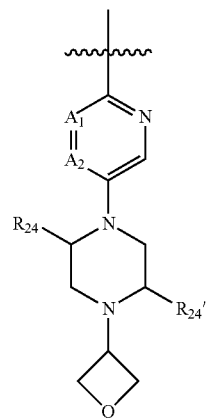

is preferably

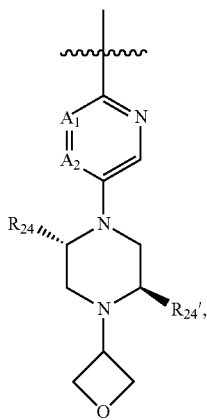

wherein R$_{24}$' is C$_{1-6}$ alkyl (such as C$_{1-3}$ alkyl, more preferably methyl), and more preferably

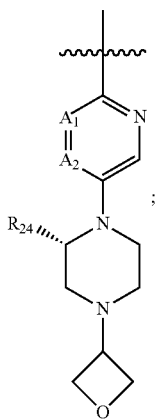

preferably, R$_{24}$ and R$_{24}$' are each independently chosen from hydrogen and C$_{1-6}$ alkyl;
preferably, one of A$_1$ and A$_2$ is N, and the other is CH;
preferably, A$_1$ is N and A$_2$ is CH;
and preferably, both A$_1$ and A$_2$ are CH.

Embodiment 26. The compound of any one of embodiments 22-25, or a pharmaceutically acceptable salt thereof, or a solvate, a racemic mixture, an enantiomer, a diastereomer or a tautomer thereof, wherein
  both X$_1$ and X$_2$ are CH, or one of X$_1$ and X$_2$ is N, and the other is CH;
  Y$_2$ is CH;
  R$_3$ is hydrogen;
  R$_4$ is —(C$_{1-3}$ alkyl)-OH;
  Z is CH;
  U is CH, and V is N or CH;
  R$_5$ is chosen from

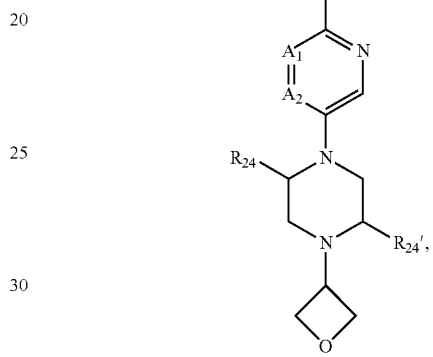

wherein R$_{24}$ and R$_{24}$' are each independently chosen from hydrogen, oxo and C$_{1-6}$ alkyl, both A$_1$ and A$_2$ are CH, or A$_1$ is N and A$_2$ is CH;
  R$_6$ is hydrogen or halogen;
  m is 0, 1 or 2; and
  R$_{11}$ is C$_{1-3}$ alkyl;
  and preferably, both A$_1$ and A$_2$ are CH.

Embodiment 27. The compound of embodiment 1, or a pharmaceutically acceptable salt thereof, or a solvate, a racemic mixture, an enantiomer, a diastereomer or a tautomer thereof, which is chosen from:

| No. | Structural formula |
|---|---|
| 1 | |

| No. | Structural formula |
|---|---|
| 2 | 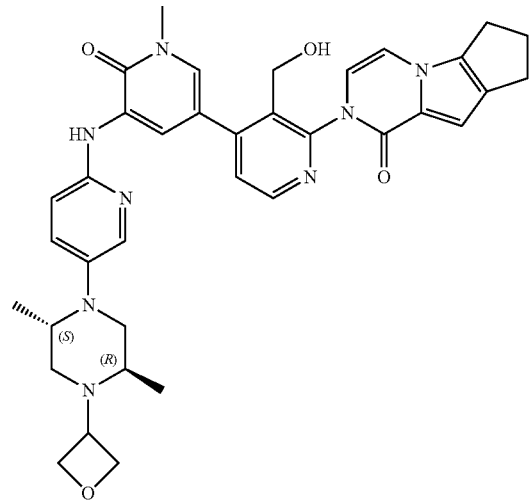 |
| 3 | 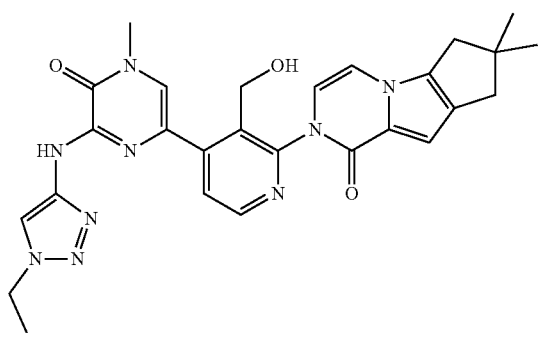 [SMILES: CCn1cc(Nc2nc(-c3ccnc(-n4ccn5c6c(cc5c4=O)CC(C)(C)C6)c3CO)cn(C)c2=O)nn1] |
| 4 | 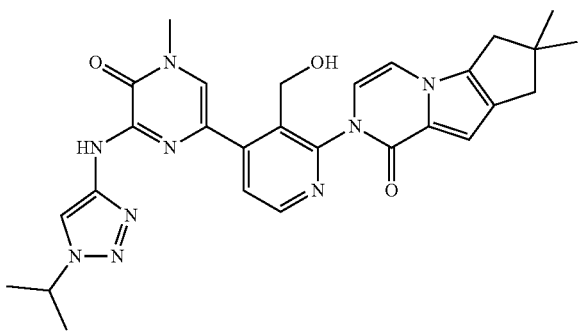 [SMILES: CC(C)n1cc(Nc2nc(-c3ccnc(-n4ccn5c6c(cc5c4=O)CC(C)(C)C6)c3CO)cn(C)c2=O)nn1] |

| No. | Structural formula |
|---|---|
| 5 | 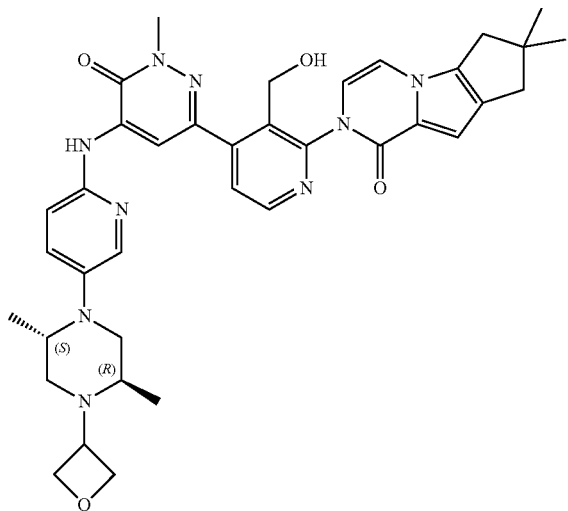 |
| 6 | 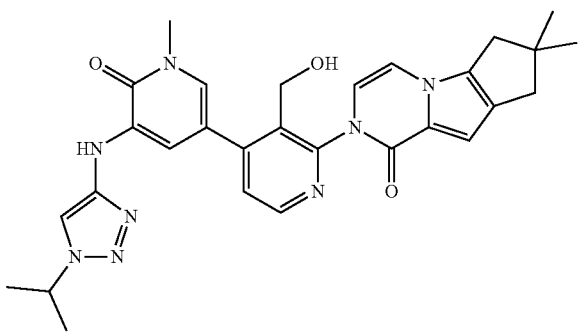 [SMILES: CC(C)n1cc(Nc2cc(-c3ccnc(-n4ccn5c6c(cc5c4=O)CC(C)(C)C6)c3CO)cn(C)c2=O)nn1] |
| 7 | 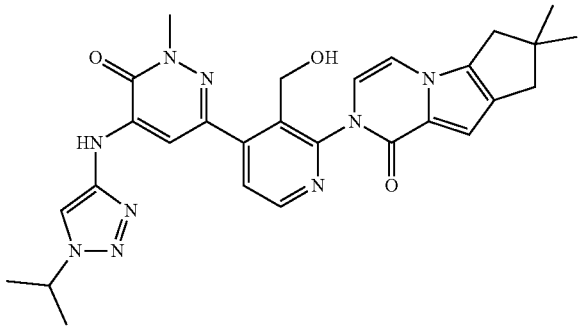 [SMILES: CC(C)n1cc(Nc2cc(-c3ccnc(-n4ccn5c6c(cc5c4=O)CC(C)(C)C6)c3CO)nn(C)c2=O)nn1] |

-continued
| No. | Structural formula |
|---|---|
| 8 | 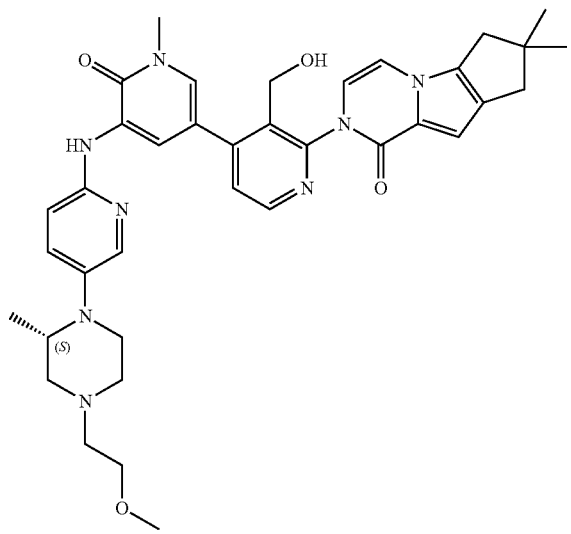 |
| 9 | 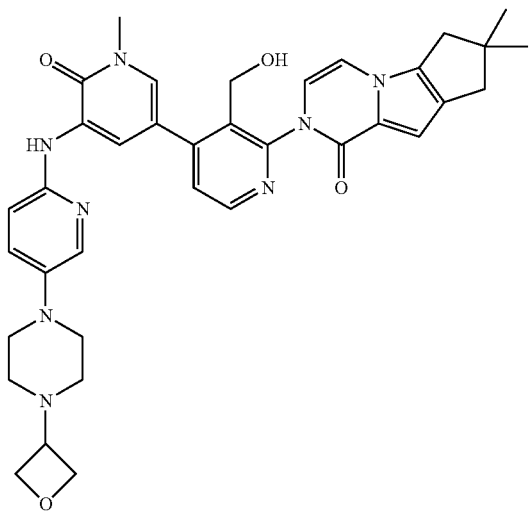 [SMILES: Cn1cc(-c2ccnc(-n3ccn4c5c(cc4c3=O)CC(C)(C)C5)c2CO)cc(Nc2ccc(N3CCN(C4COC4)CC3)cn2)c1=O] |
| 10 | 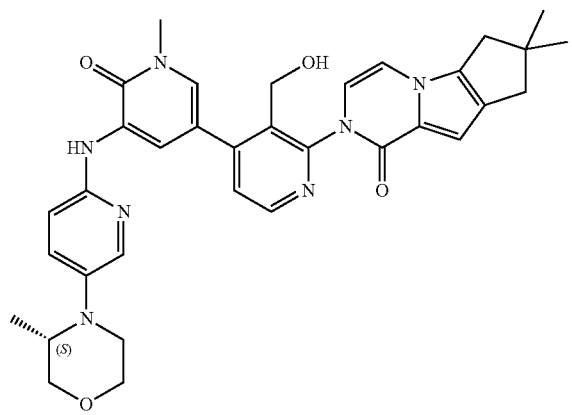 |

| No. | Structural formula |
|---|---|
| 11 | 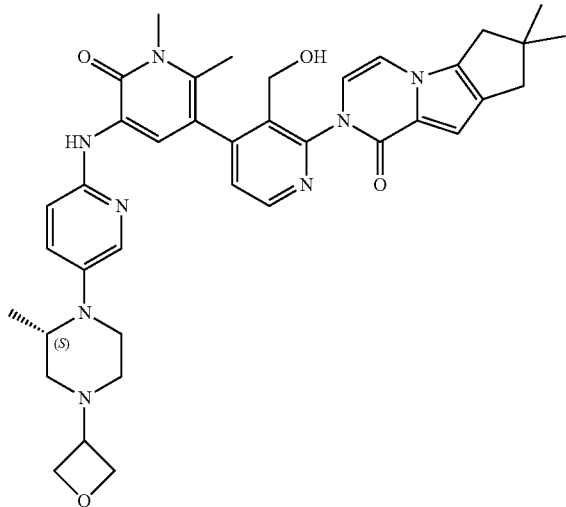 |
| 12 | 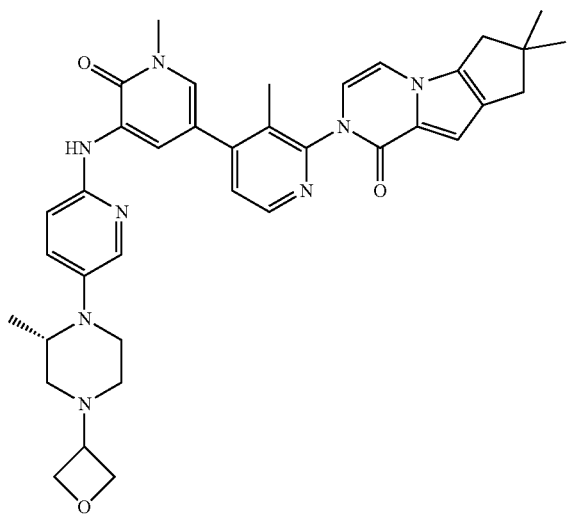 |
| 13 | 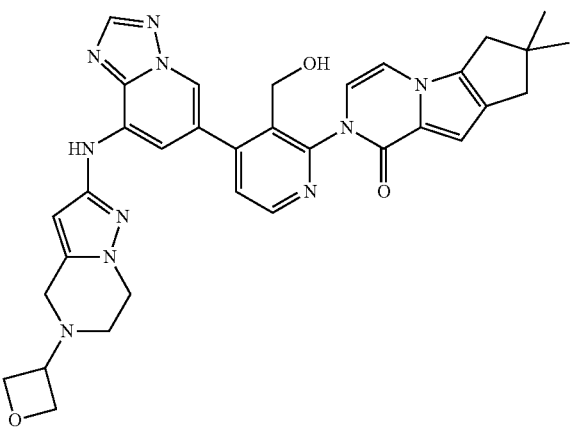 [SMILES: CC1(C)Cc2cc3c(=O)n(-c4nccc(-c5cc(Nc6cc7n(n6)CCN(C6COC6)C7)c6ncnn6c5)c4CO)ccn3c2C1] |

-continued
| No. | Structural formula |
|---|---|
| 14 | 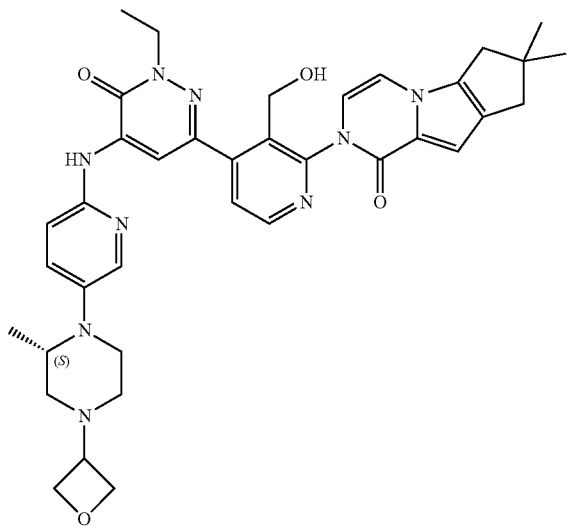 |
| 15 | 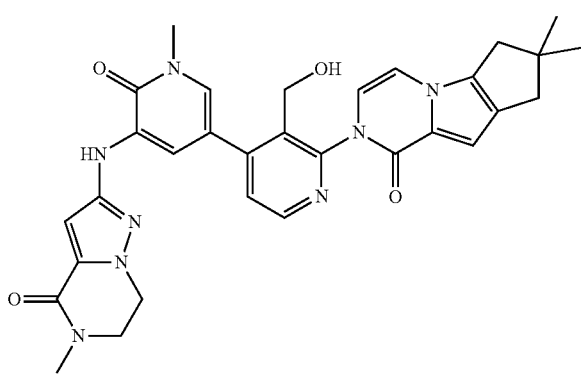 [SMILES: CN1CCn2nc(Nc3cc(-c4ccnc(-n5ccn6c7c(cc6c5=O)CC(C)(C)C7)c4CO)cn(C)c3=O)cc2C1=O] |
| 16 | 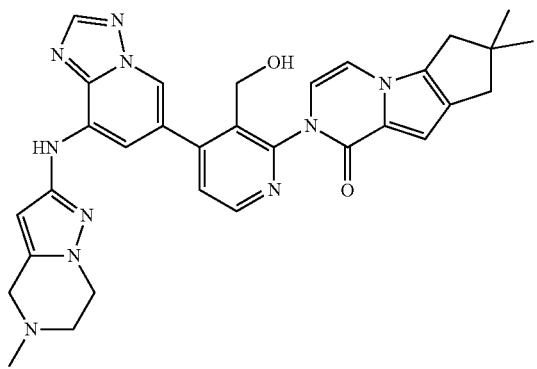 [SMILES: CN1CCn2nc(Nc3cc(-c4ccnc(-n5ccn6c7c(cc6c5=O)CC(C)(C)C7)c4CO)cn4ncnc34)cc2C1] |
| 17 | 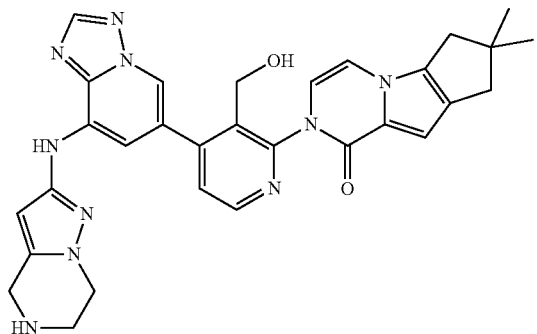 [SMILES: CC1(C)Cc2cc3c(=O)n(-c4nccc(-c5cc(Nc6cc7n(n6)CCNC7)c6ncnn6c5)c4CO)ccn3c2C1] |

-continued
| No. | Structural formula |
|---|---|
| 18 | 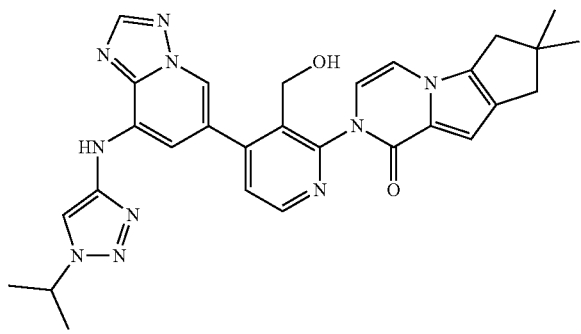 [SMILES: CC(C)n1cc(Nc2cc(-c3ccnc(-n4ccn5c6c(cc5c4=O)CC(C)(C)C6)c3CO)cn3ncnc23)nn1] |
| 19 | 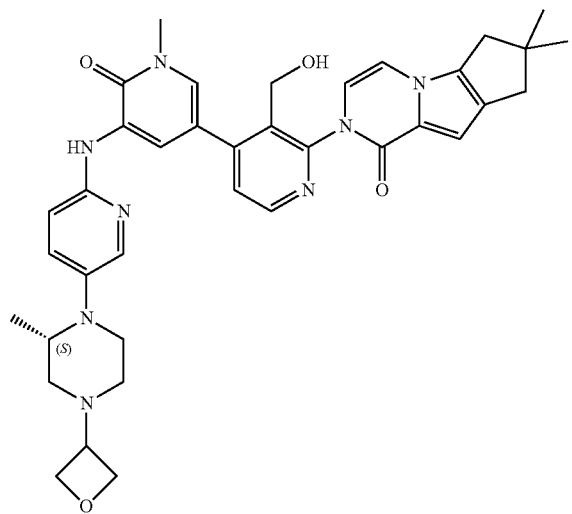 |
| 20 | 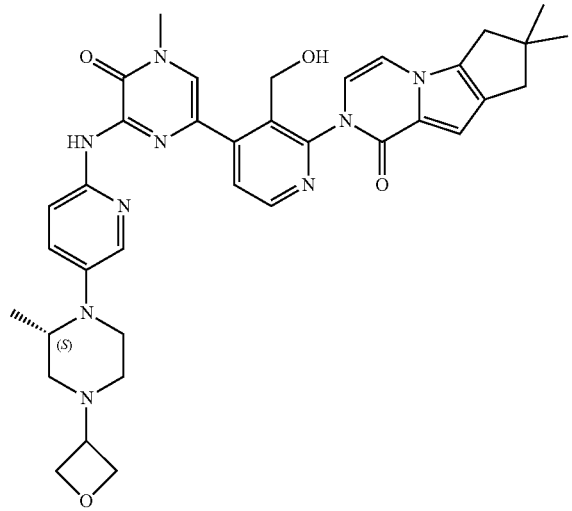 |

| No. | Structural formula |
|---|---|
| 21 | 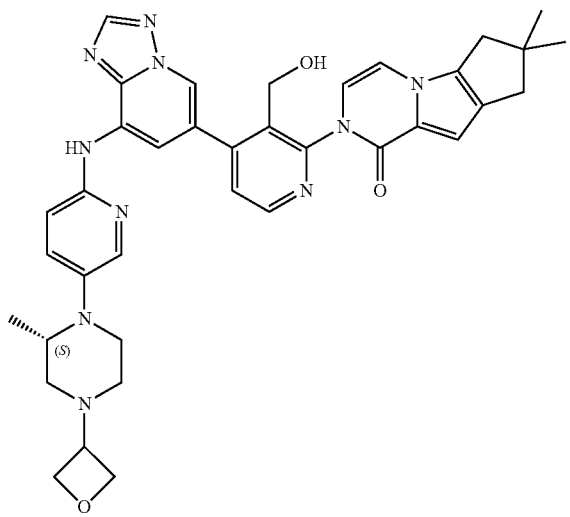 |
| 22 | 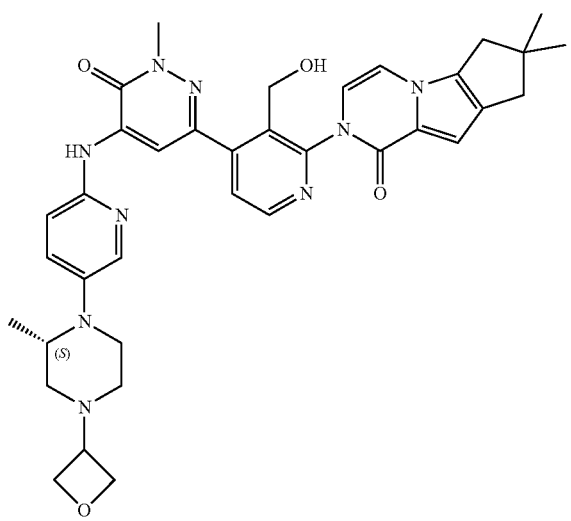 |
| 23 | 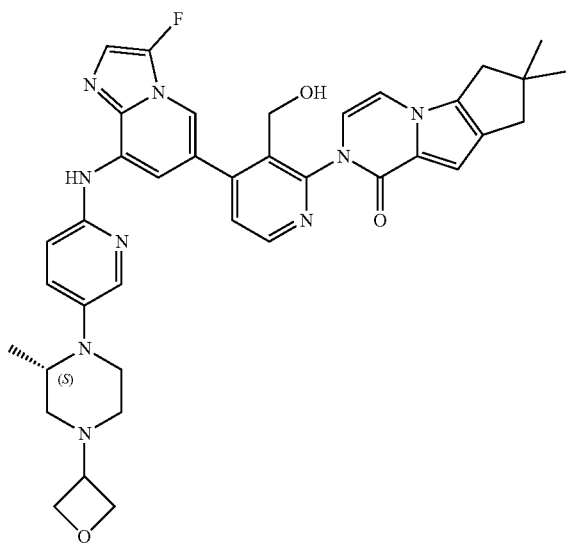 |

-continued
| No. | Structural formula |
|---|---|
| 24 | 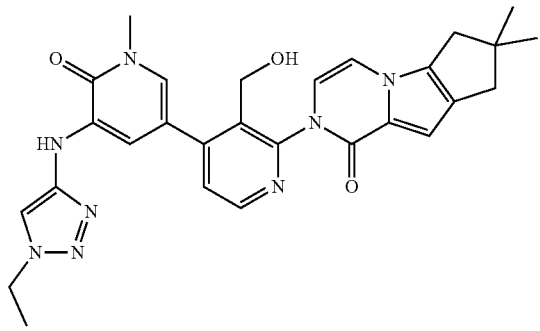 [SMILES: CCn1cc(Nc2cc(-c3ccnc(-n4ccn5c6c(cc5c4=O)CC(C)(C)C6)c3CO)cn(C)c2=O)nn1] |
| 25 | 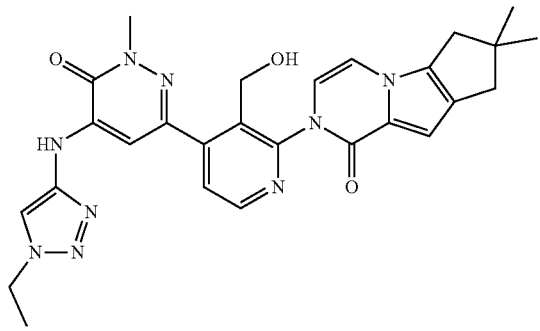 |
| 26 | 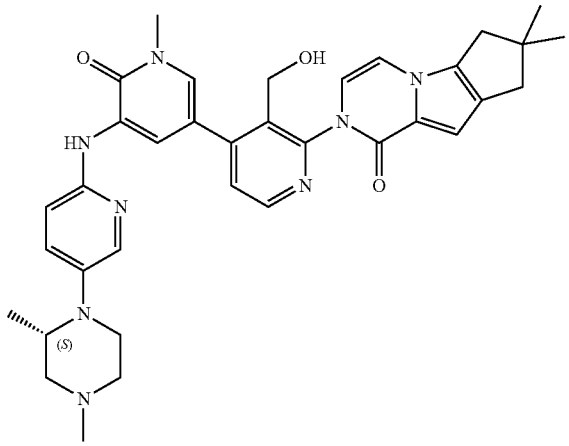 |

| No. | Structural formula |
| --- | --- |
| 27 | |
| 28 | |
| 29 | |
| 30 | |

| No. | Structural formula |
|---|---|
| 31 | 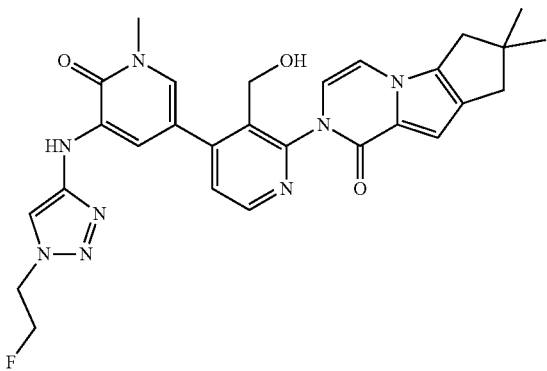 [SMILES: Cn1cc(-c2ccnc(-n3ccn4c5c(cc4c3=O)CC(C)(C)C5)c2CO)cc(Nc2cn(CCF)nn2)c1=O] |
| 32 | 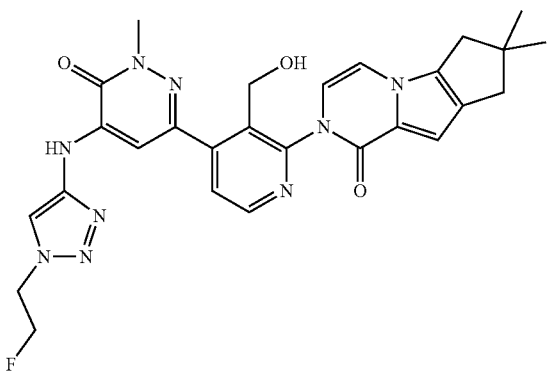 |
| 33 | 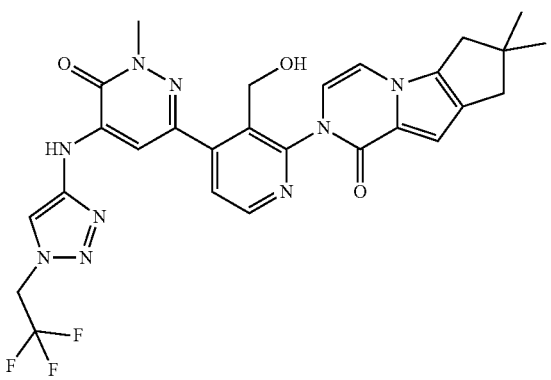 [SMILES: Cn1nc(-c2ccnc(-n3ccn4c5c(cc4c3=O)CC(C)(C)C5)c2CO)cc(Nc2cn(CC(F)(F)F)nn2)c1=O] |

-continued
| No. | Structural formula |
| --- | --- |
| 34 | 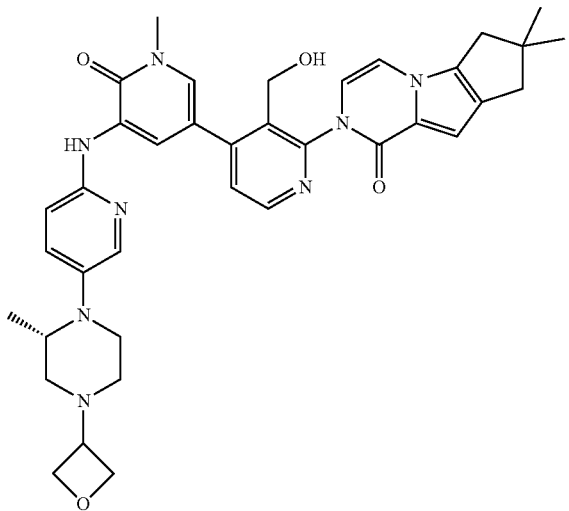 |
| 35 | 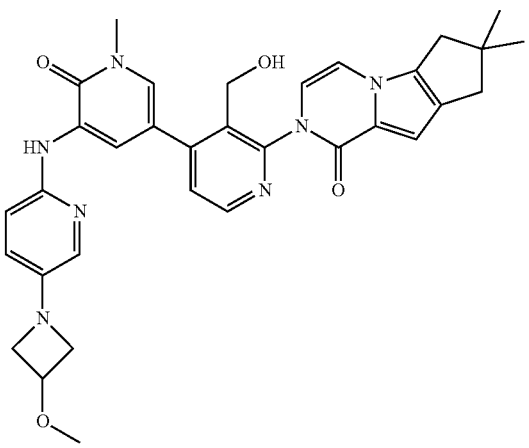 [SMILES: COC1CN(c2ccc(Nc3cc(-c4ccnc(-n5ccn6c7c(cc6c5=O)CC(C)(C)C7)c4CO)cn(C)c3=O)nc2)C1] |
| 36 | 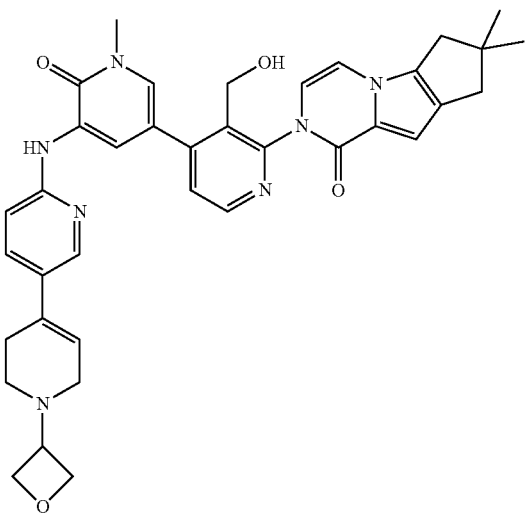 [SMILES: Cn1cc(-c2ccnc(-n3ccn4c5c(cc4c3=O)CC(C)(C)C5)c2CO)cc(Nc2ccc(C3=CCN(C4COC4)CC3)cn2)c1=O] |

| No. | Structural formula |
|---|---|
| 37 | 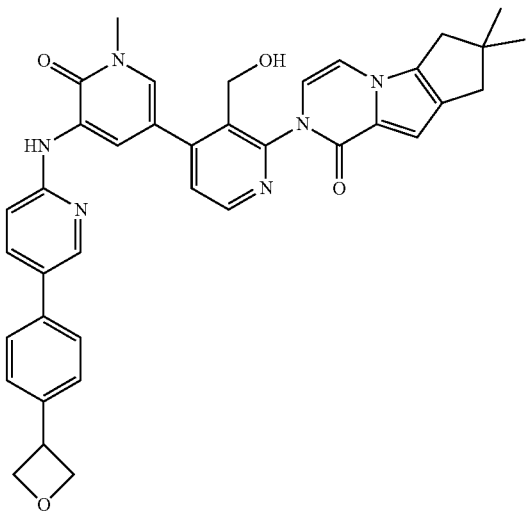 [SMILES: Cn1cc(-c2ccnc(-n3ccn4c5c(cc4c3=O)CC(C)(C)C5)c2CO)cc(Nc2ccc(-c3ccc(C4COC4)cc3)cn2)c1=O] |
| 38 | 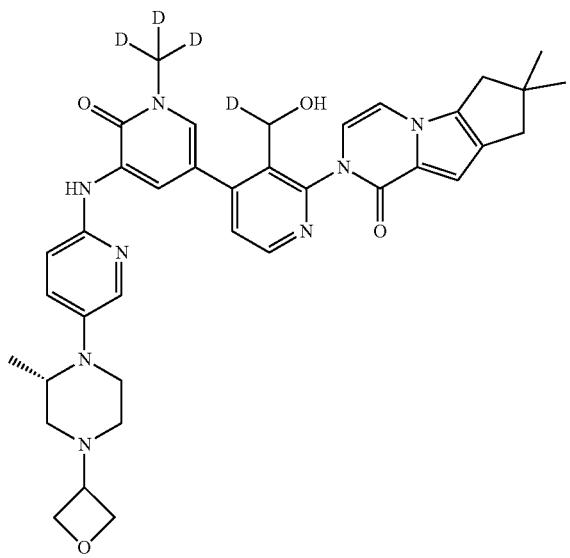 |
| 39 | 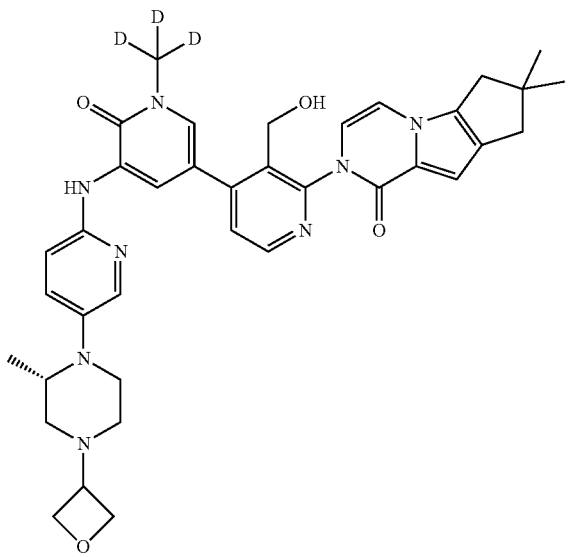 |

| No. | Structural formula |
|---|---|
| 40 | 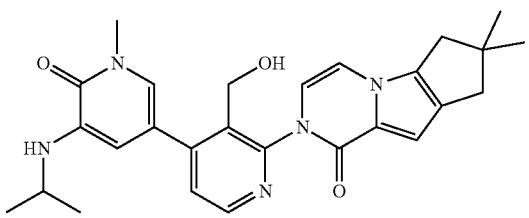 [SMILES: CC(C)Nc1cc(-c2ccnc(-n3ccn4c5c(cc4c3=O)CC(C)(C)C5)c2CO)cn(C)c1=O] |
| 41 | 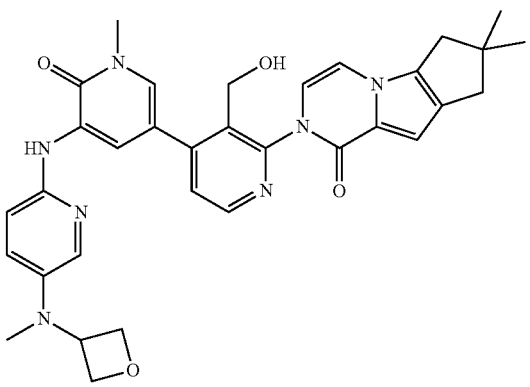 [SMILES: CN(c1ccc(Nc2cc(-c3ccnc(-n4ccn5c6c(cc5c4=O)CC(C)(C)C6)c3CO)cn(C)c2=O)nc1)C1COC1] |
| 42 | 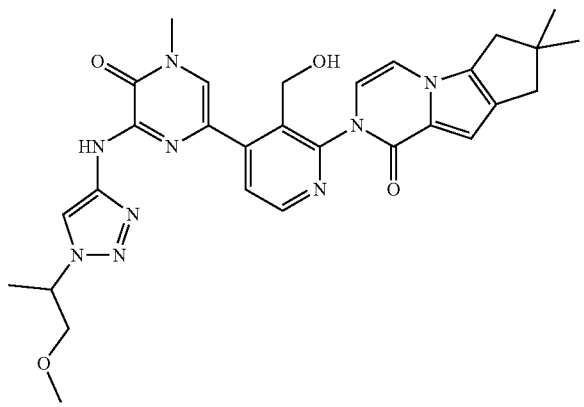 [SMILES: COCC(C)n1cc(Nc2nc(-c3ccnc(-n4ccn5c6c(cc5c4=O)CC(C)(C)C6)c3CO)cn(C)c2=O)nn1] |
| 43 | 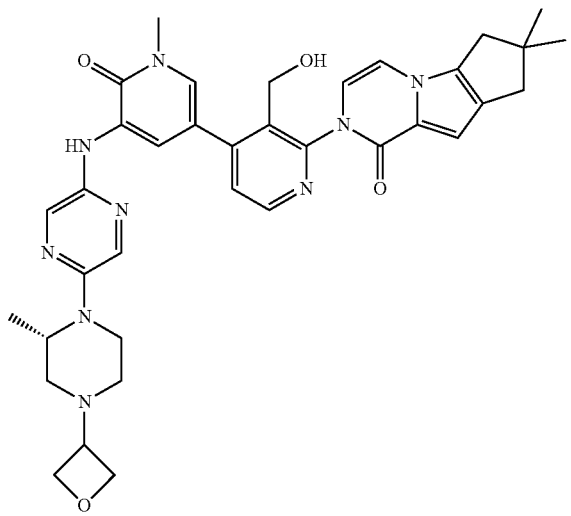 |

-continued
| No. | Structural formula |
|---|---|
| 44 | 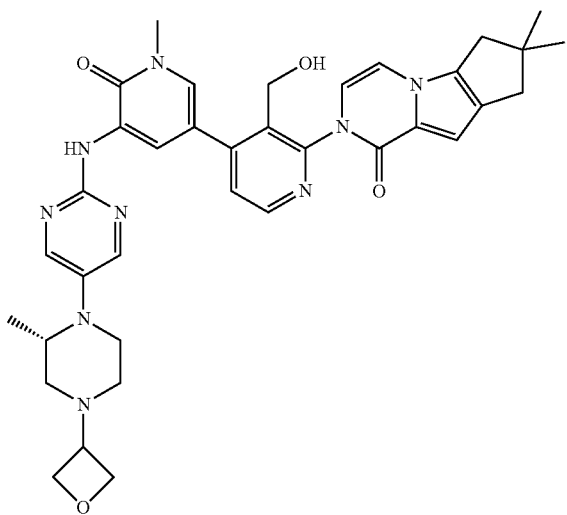 |
| 45 | 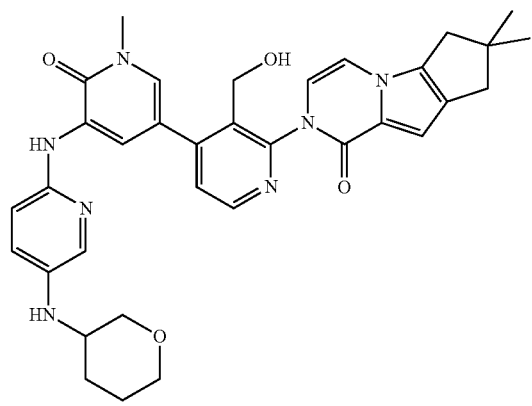 [SMILES: Cn1cc(-c2ccnc(-n3ccn4c5c(cc4c3=O)CC(C)(C)C5)c2CO)cc(Nc2ccc(NC3CCCOC3)cn2)c1=O] |
| 46 | 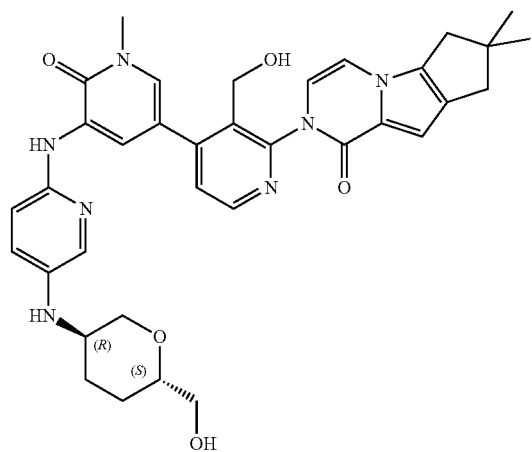 |

| No. | Structural formula |
|---|---|
| 47 | 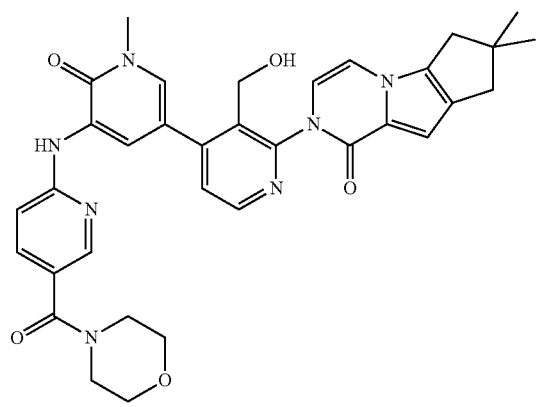 [SMILES: Cn1cc(-c2ccnc(-n3ccn4c5c(cc4c3=O)CC(C)(C)C5)c2CO)cc(Nc2ccc(C(=O)N3CCOCC3)cn2)c1=O] |
| 48 | 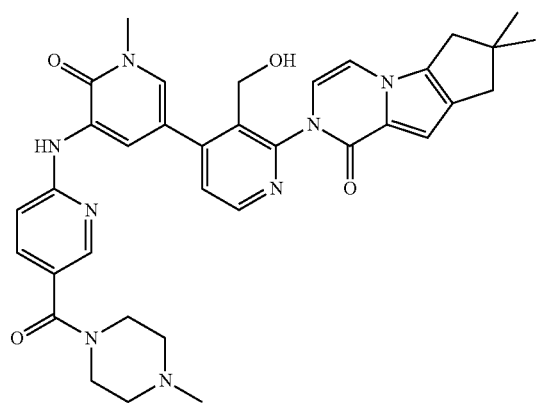 [SMILES: CN1CCN(C(=O)c2ccc(Nc3cc(-c4ccnc(-n5ccn6c7c(cc6c5=O)CC(C)(C)C7)c4CO)cn(C)c3=O)nc2)CC1] |
| 49 | 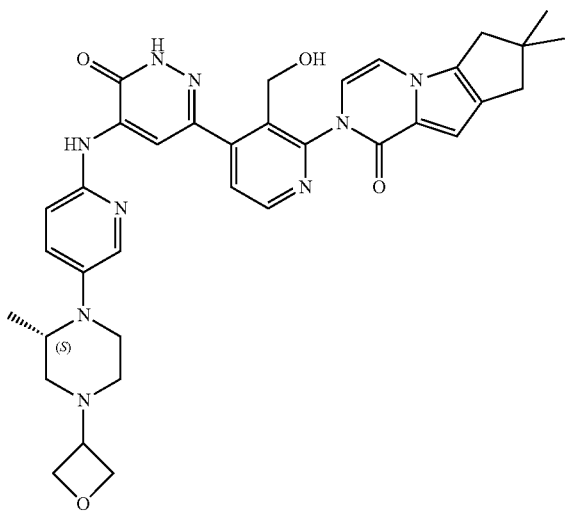 |

-continued
| No. | Structural formula |
|---|---|
| 50 | 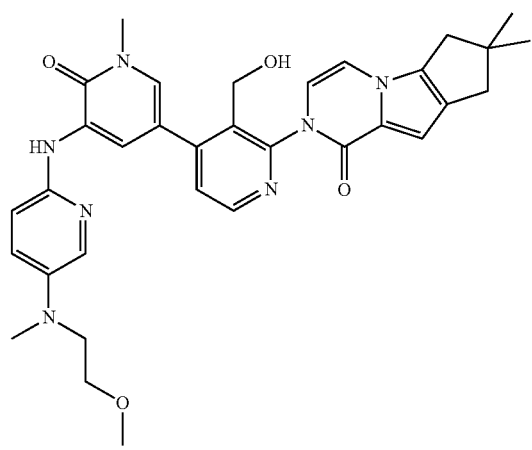 [SMILES: COCCN(C)c1ccc(Nc2cc(-c3ccnc(-n4ccn5c6c(cc5c4=O)CC(C)(C)C6)c3CO)cn(C)c2=O)nc1] |
| 51 | 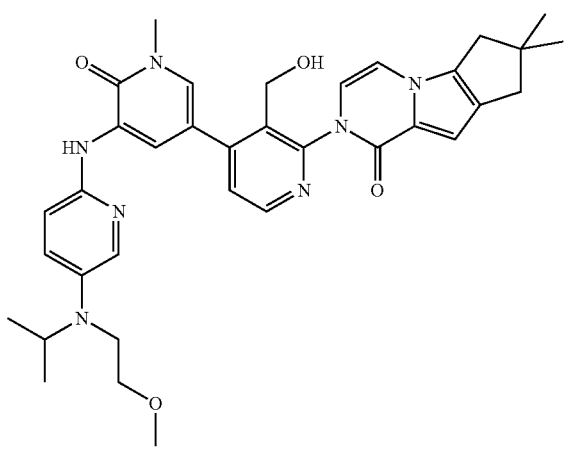 [SMILES: COCCN(c1ccc(Nc2cc(-c3ccnc(-n4ccn5c6c(cc5c4=O)CC(C)(C)C6)c3CO)cn(C)c2=O)nc1)C(C)C] |
| 52 | 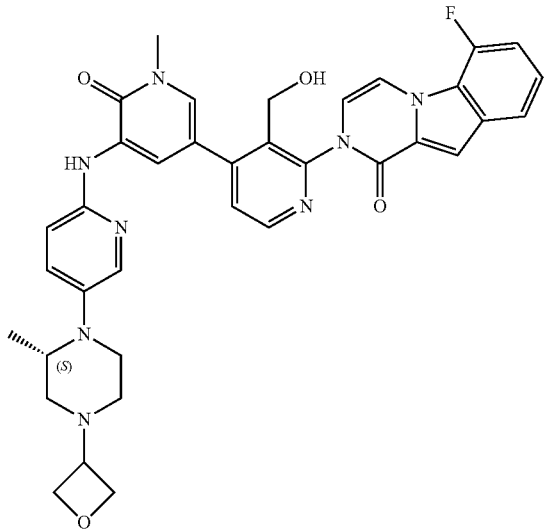 |

| No. | Structural formula |
|---|---|
| 53 | 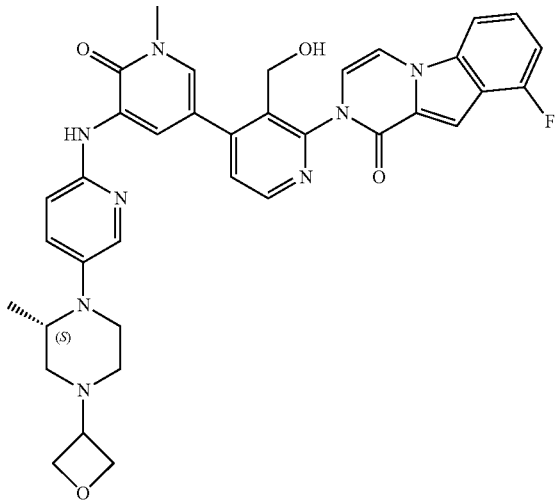 |
| 54 | 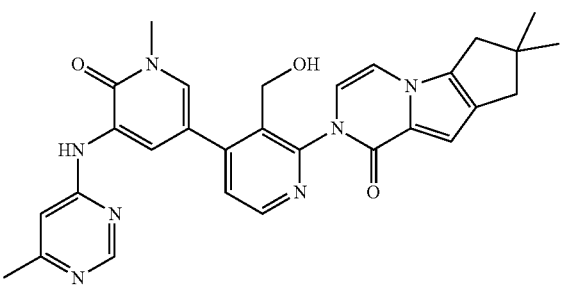 |
| 55 | 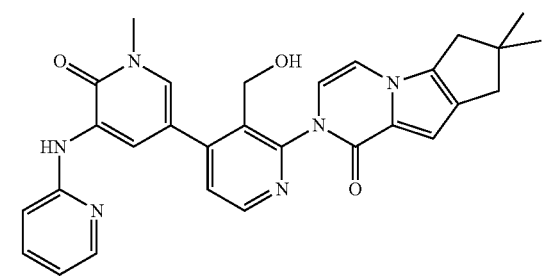 [SMILES: Cn1cc(-c2ccnc(-n3ccn4c5c(cc4c3=O)CC(C)(C)C5)c2CO)cc(Nc2ccccn2)c1=O] |
| 56 | 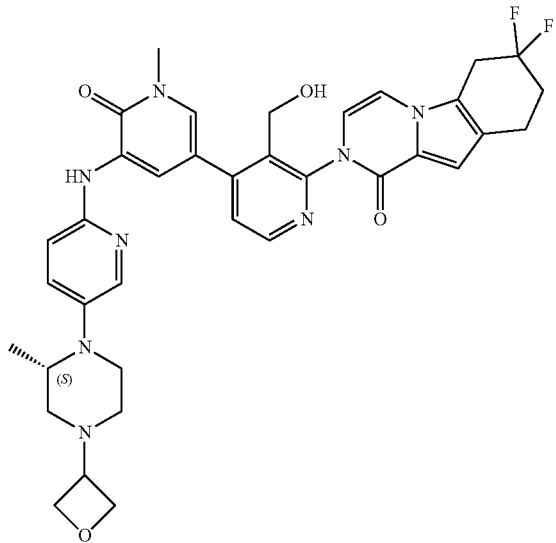 |

| No. | Structural formula |
|---|---|
| 57 | 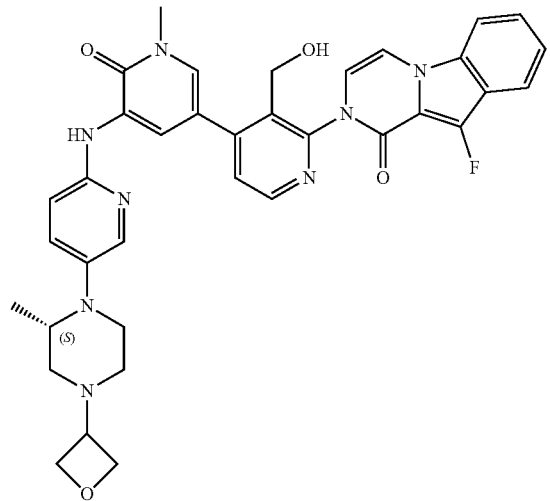 |
| 58 | 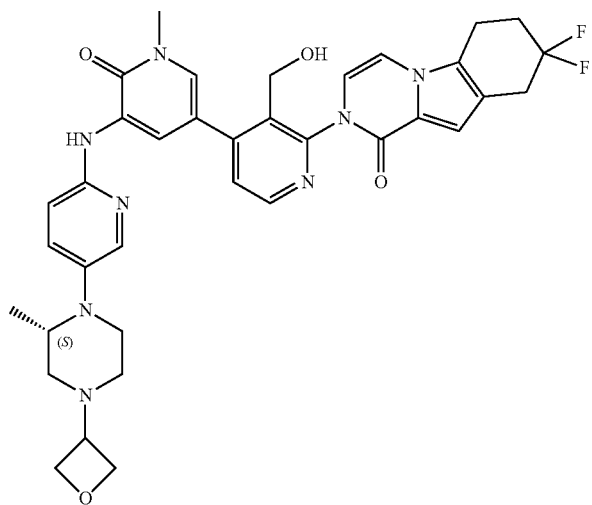 |
| 59 | 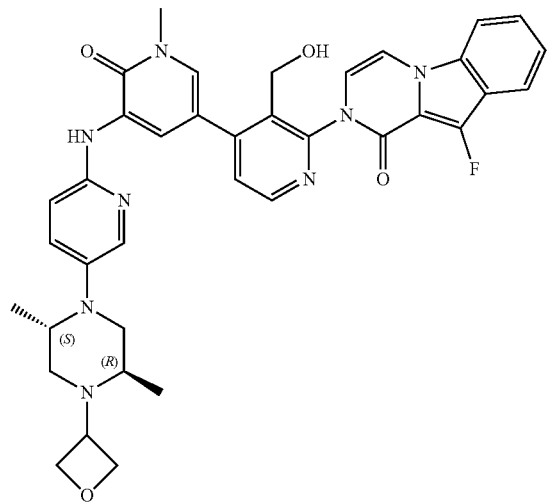 |

-continued

| No. | Structural formula |
|---|---|
| 60 | |
| 61 | |
| 62 | |

| No. | Structural formula |
|---|---|
| 63 | 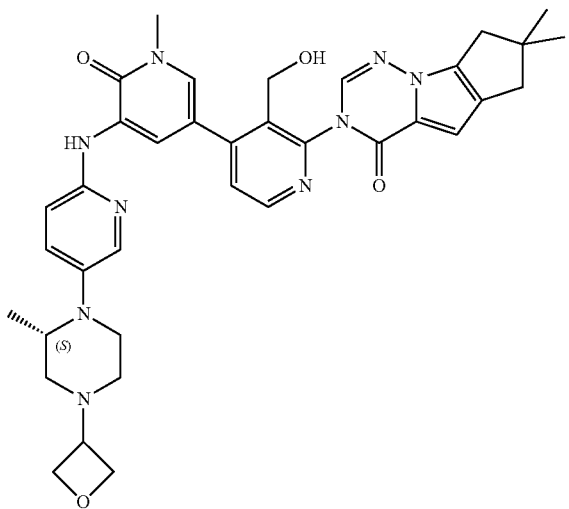 |
| 64 | 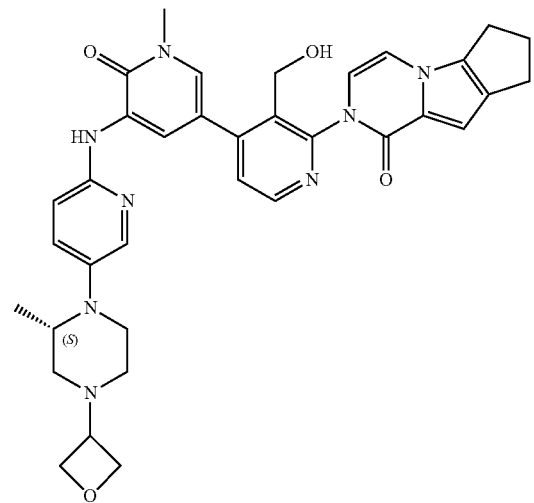 |
| 65 | 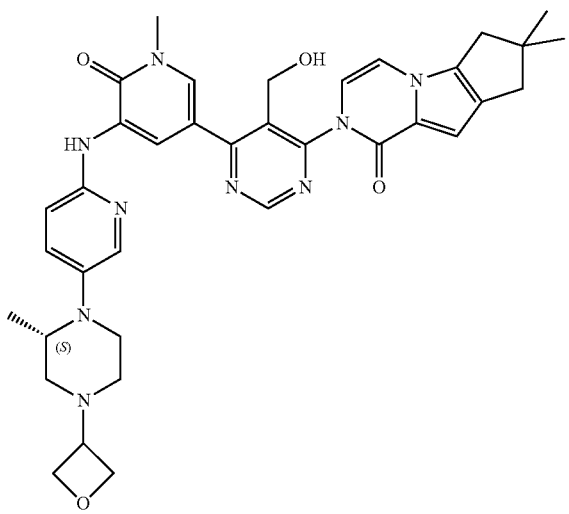 |

| No. | Structural formula |
|---|---|
| 66 | 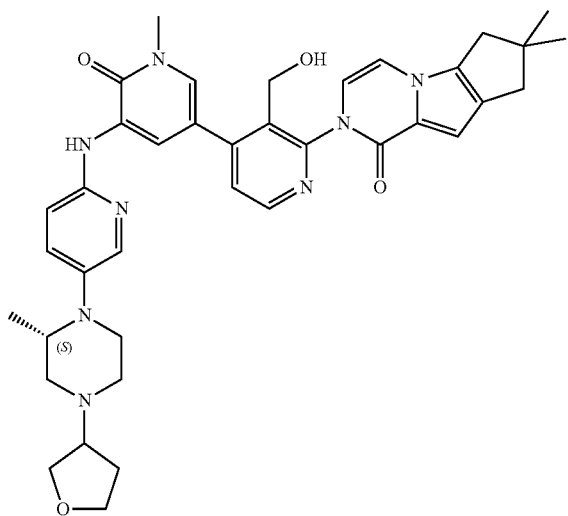 |
| 67 | 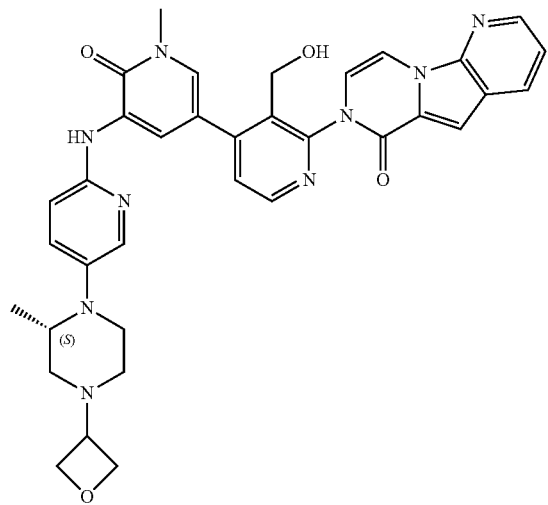 |
| 68 | 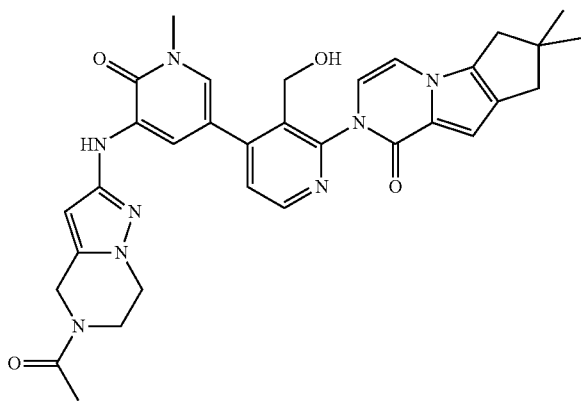 [SMILES: CC(=O)N1CCn2nc(Nc3cc(-c4ccnc(-n5ccn6c7c(cc6c5=O)CC(C)(C)C7)c4CO)cn(C)c3=O)cc2C1] |

-continued
| No. | Structural formula |
|---|---|
| 69 | 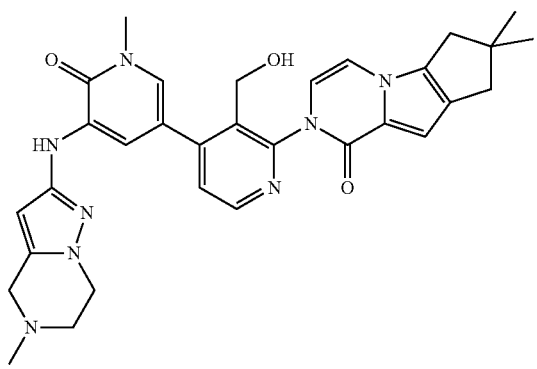 [SMILES: CN1CCn2nc(Nc3cc(-c4ccnc(-n5ccn6c7c(cc6c5=O)CC(C)(C)C7)c4CO)cn(C)c3=O)cc2C1] |
| 70 | 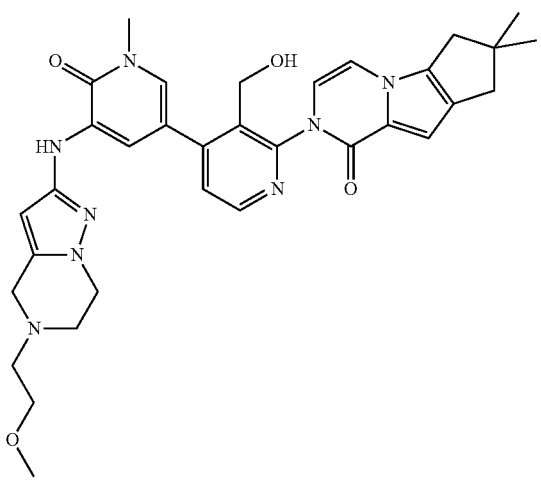 [SMILES: COCCN1CCn2nc(Nc3cc(-c4ccnc(-n5ccn6c7c(cc6c5=O)CC(C)(C)C7)c4CO)cn(C)c3=O)cc2C1] |
| 71 | 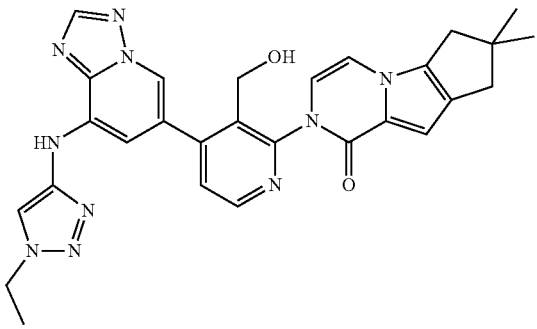 [SMILES: CCn1cc(Nc2cc(-c3ccnc(-n4ccn5c6c(cc5c4=O)CC(C)(C)C6)c3CO)cn3ncnc23)nn1] |

| No. | Structural formula |
|---|---|
| 72 | 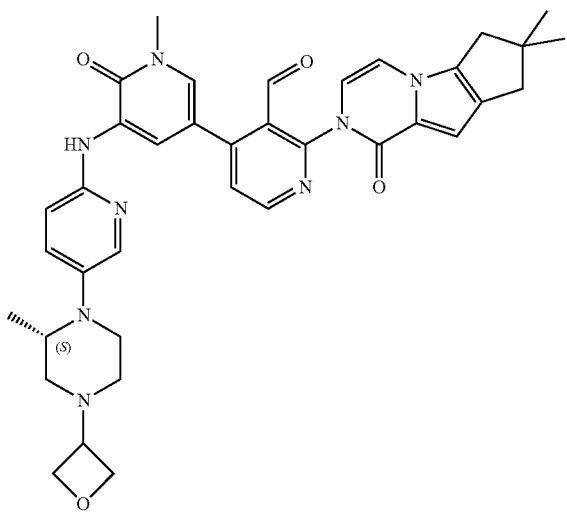 |
| 73 | 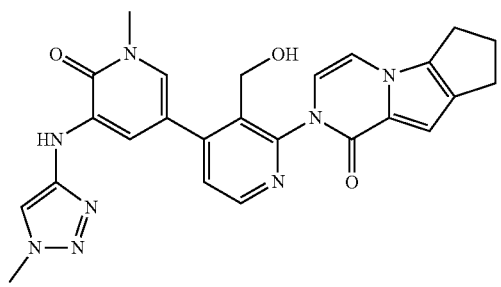 [SMILES: Cn1cc(Nc2cc(-c3ccnc(-n4ccn5c6c(cc5c4=O)CCC6)c3CO)cn(C)c2=O)nn1] |
| 74 | 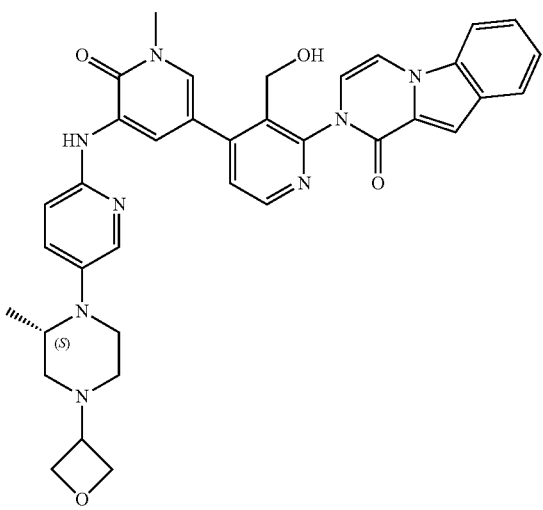 |

-continued
| No. | Structural formula |
|---|---|
| 75 | 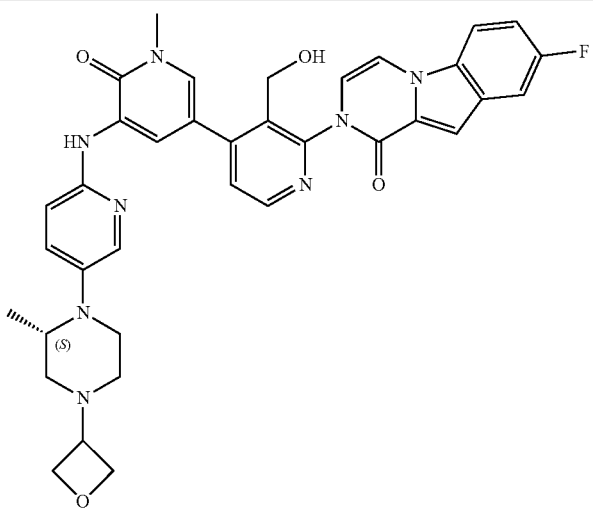 |
| 76 | 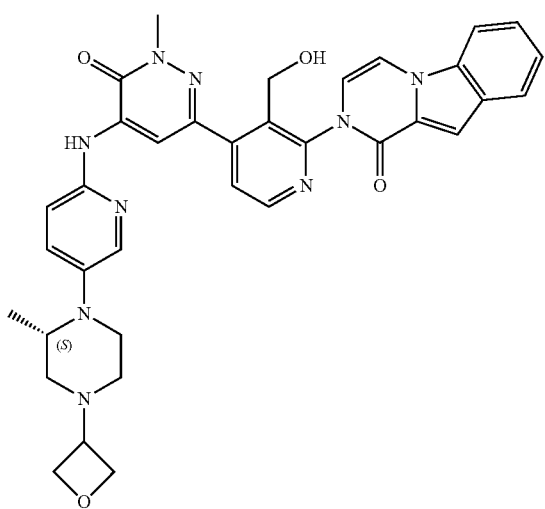 |
| 77 | 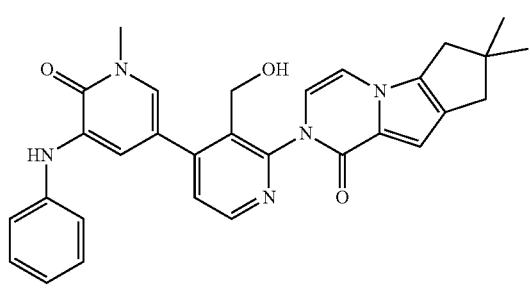 [SMILES: Cn1cc(-c2ccnc(-n3ccn4c5c(cc4c3=O)CC(C)(C)C5)c2CO)cc(Nc2ccccc2)c1=O] |

-continued
| No. | Structural formula |
|---|---|
| 78 | 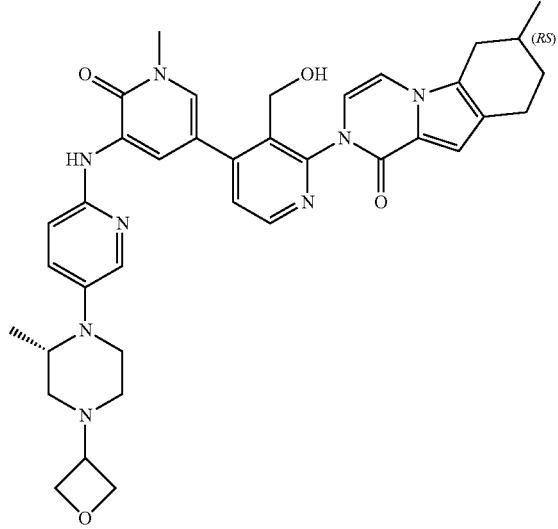 [SMILES: CC1CCc2cc3c(=O)n(-c4nccc(-c5cc(Nc6ccc(N7CCN(C8COC8)C[C@@H]7C)cn6)c(=O)n(C)c5)c4CO)ccn3c2C1] |
| 79 | 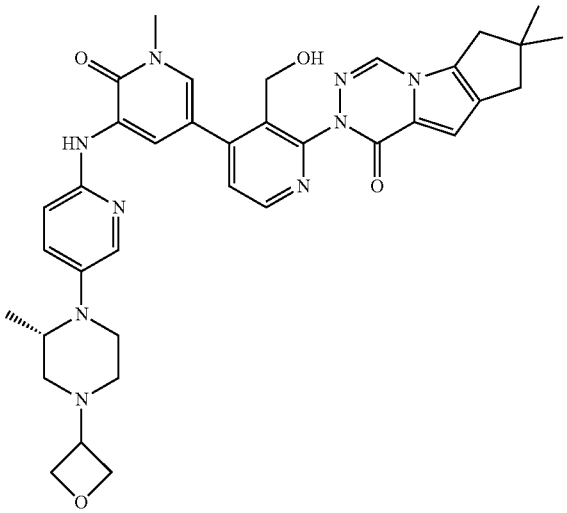 |
| 80 | 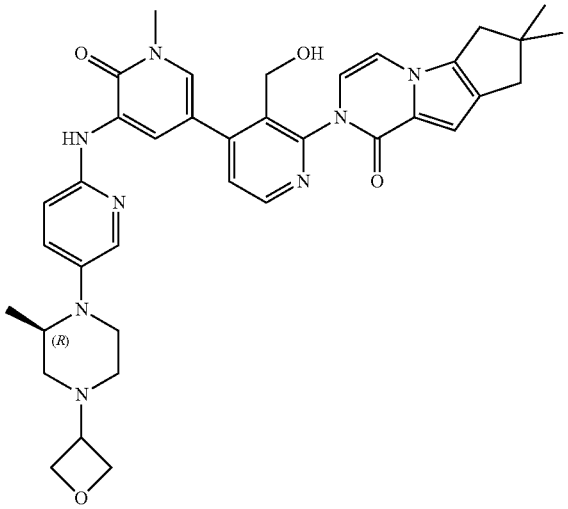 |

Embodiment 28. A pharmaceutical composition, comprising the compound of any one of embodiments 1-27 and/or a pharmaceutically acceptable salt thereof, and optionally comprising a pharmaceutically acceptable excipient.

Embodiment 29. A method of in vivo or in vitro inhibiting the activity of BTK, comprising contacting BTK with an effective amount of the compound of any one of embodiments 1-27, and/or a pharmaceutically acceptable salt thereof.

Embodiment 30. Use of the compound of any one of embodiments 1-27 and/or a pharmaceutically acceptable salt thereof in the manufacture of a medicament for treating or preventing a disease mediated by BTK or at least in part by BTK, preferably for treating or preventing cancer, an inflammatory disease or autoimmune disease, wherein the cancer is preferably solid tumor or hematologic malignancy, including lymphoma, leukemia and myeloma; the cancer is more preferably chosen from B cell malignancy, diffuse large B-cell lymphoma (DLBCL), large B-cell lymphoma (LBCL), B-cell lymphoma, mantle cell lymphoma, follicular lymphoma, non-Hodgkin's lymphoma, Hodgkin's lymphoma, Waldenstrom macroglobulinemia, marginal zone lymphoma, Burkitt's lymphoma, non-Burkitt's highly degree B cell malignant lymphoma, extranodal marginal-zone B-cell lymphoma, small lymphotic lymphoma (SLL), lymphoblastic lymphoma, lymphocytic leukemia, myelogenous leukemia, acute myelogenous leukemia (AML), chronic myelogenous leukemia (CML), human acute monocytic leukemia, acute lymphocytic leukemia (ALL), B cell acute lymphocytic leukemia (B-ALL), hairy cell leukemia, chronic lymphocytic leukemia (CLL) (such as high risk CLL), myelodysplastic syndrome, acute lymphoblastic leukemia, myeloma (such as multiple myeloma) or graft versus host disease; and the inflammatory disease or autoimmune disease is preferably chosen from: systemic inflammation and local inflammation, arthritis, rheumatoid arthritis, inflammation associated with immunosuppression, organ-graft refection, allergic disease, ulcerative colitis, Crohn's disease, dermatitis, asthma, lupus erythematosus, Sjogren syndrome, multiple sclerosis, scleroderma (also referred to as systemic sclerosis), multiple sclerosis osteoporosis, idiopathic thrombocytopenic purpura, autoimmune hemolytic anemia, antineutrophil cytoplasmatic antibody vasculitis, chronic obstructive pulmonary disease, psoriasis, sicca syndrome, pemphigus valgaris, diseases associated with kidney transplantation.

Embodiment 31. A method of treating or preventing a disease in a subject, comprising administering to the subject in need thereof an effective amount of the compound of any one of embodiments 1-27, and/or a pharmaceutically acceptable salt thereof, wherein the disease is a disease mediated by BTK or at least in part by BTK; the disease is preferably cancer, an inflammatory disease or autoimmune disease; the cancer is preferably solid tumor or hematologic malignancy, including lymphoma, leukemia and myeloma; the cancer is more preferably chosen from B cell malignancy, diffuse large B-cell lymphoma (DLBCL), large B-cell lymphoma (LBCL), B-cell lymphoma, mantle cell lymphoma, follicular lymphoma, non-Hodgkin's lymphoma, Hodgkin's lymphoma, Waldenstrom macroglobulinemia, marginal zone lymphoma, Burkitt's lymphoma, non-Burkitt's highly degree B cell malignant lymphoma, extranodal marginal-zone B-cell lymphoma, small lymphotic lymphoma (SLL), lymphoblastic lymphoma, lymphocytic leukemia, myelogenous leukemia, acute myelogenous leukemia (AML), chronic myelogenous leukemia (CML), human acute monocytic leukemia, acute lymphocytic leukemia (ALL), B cell acute lymphocytic leukemia (B-ALL), hairy cell leukemia, chronic lymphocytic leukemia (CLL) (such as high risk CLL), myelodysplastic syndrome, acute lymphoblastic leukemia, myeloma (such as multiple myeloma) or graft versus host disease; and the inflammatory disease or autoimmune disease is preferably chosen from: systemic inflammation and local inflammation, arthritis, rheumatoid arthritis, inflammation associated with immunosuppression, organ-graft refection, allergic disease, ulcerative colitis, Crohn's disease, dermatitis, asthma, lupus erythematosus, Sjogren syndrome, multiple sclerosis, scleroderma, multiple sclerosis osteoporosis, idiopathic thrombocytopenic purpura, autoimmune hemolytic anemia, antineutrophil cytoplasmatic antibody vasculitis, chronic obstructive pulmonary disease, psoriasis, sicca syndrome, pemphigus valgaris, and diseases associated with kidney transplantation.

Embodiment 32. The compound of any one of embodiments 1-27 and/or a pharmaceutically acceptable salt thereof, for use as a medicament.

Embodiment 33. The compound of any one of embodiments 1-27 and/or a pharmaceutically acceptable salt thereof, for use in treating or preventing a disease mediated by BTK or at least in part by BTK, and preferably for use in treating or preventing cancer, an inflammatory disease or autoimmune disease, wherein the cancer is preferably solid tumor or hematologic malignancy, including lymphoma, leukemia and myeloma; the cancer is more preferably chosen from B cell malignancy, diffuse large B-cell lymphoma (DLBCL), large B-cell lymphoma (LBCL), B-cell lymphoma, mantle cell lymphoma, follicular lymphoma, non-Hodgkin's lymphoma, Hodgkin's lymphoma, Waldenstrom macroglobulinemia, marginal zone lymphoma, Burkitt's lymphoma, non-Burkitt's highly degree B cell malignant lymphoma, extranodal marginal-zone B-cell lymphoma, small lymphotic lymphoma (SLL), lymphoblastic lymphoma, lymphocytic leukemia, myelogenous leukemia, acute myelogenous leukemia (AML), chronic myelogenous leukemia (CML), human acute monocytic leukemia, acute lymphocytic leukemia (ALL), B cell acute lymphocytic leukemia (B-ALL), hairy cell leukemia, chronic lymphocytic leukemia (CLL) (such as high risk CLL), myelodysplastic syndrome, acute lymphoblastic leukemia, myeloma (such as multiple myeloma) or graft versus host disease; and the inflammatory disease or autoimmune disease is preferably chosen from: systemic inflammation and local inflammation, arthritis, rheumatoid arthritis, inflammation associated with immunosuppression, organ-graft refection, allergic disease, ulcerative colitis, Crohn's disease, dermatitis, asthma, lupus erythematosus, Sjogren syndrome, multiple sclerosis, scleroderma, multiple sclerosis osteoporosis, idiopathic thrombocytopenic purpura, autoimmune hemolytic anemia, antineutrophil cytoplasmatic antibody vasculitis, chronic obstructive pulmonary disease, psoriasis, sicca syndrome, pemphigus valgaris, and diseases associated with kidney transplantation.

Embodiment 34. A pharmaceutical combination, comprising the compound of any one of embodiments 1-27 and/or a pharmaceutically acceptable salt thereof, and at least one additional therapeutic agent, wherein the therapeutic agent is preferably chosen from: an anti-inflammatory agent, an immunomodulator or an anti-tumor active agent, wherein the anti-tumor active agent includes a chemotherapeutic agent, an immune checkpoint inhibitor or agonist, and a targeted therapeutic agent.

Embodiment 35. A compound of formula (V):

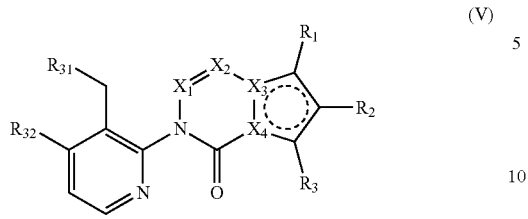

or a solvate, a racemic mixture, an enantiomer, a diastereomer and a tautomer thereof,
wherein
$X_1$, $X_2$, $X_3$, $X_4$, $R_1$, $R_2$ and $R_3$ are as defined in any one of embodiments 1-27;
$R_{31}$ is —OH, oxo (=O), or —O—($C_{1-6}$ alkyl), and
$R_{32}$ is halogen, —B(OH)$_2$, —B(O$C_{1-6}$ alkyl)$_2$,

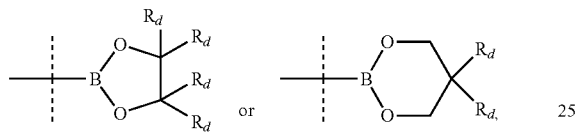

and $R_d$ is hydrogen or $C_{1-6}$ alkyl.

Embodiment 36. The compound of embodiment 35, which is

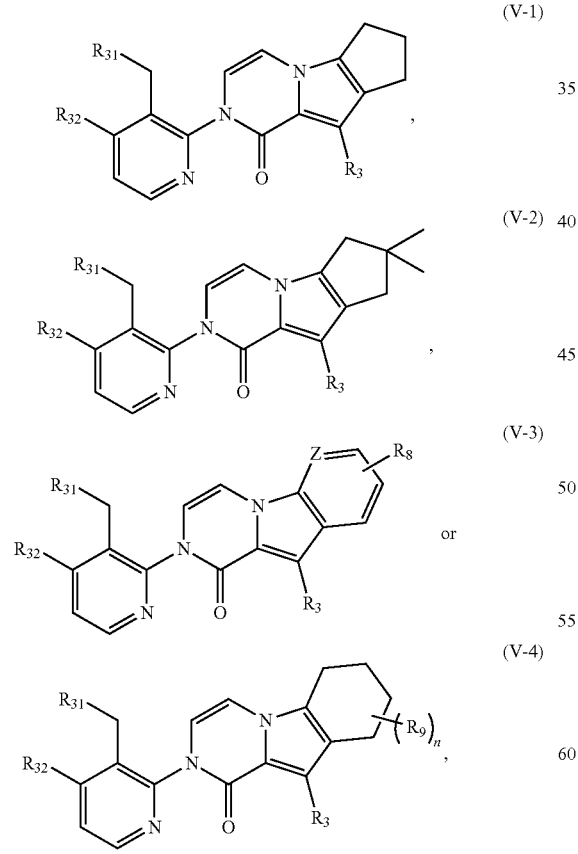

and Z is N or CR$_7$; R$_7$ and R$_8$ are each independently hydrogen or halogen; R$_9$ is halogen or $C_{1-6}$ alkyl; and n is 1 or 2.

Embodiment 37. A compound, which is chosen from:

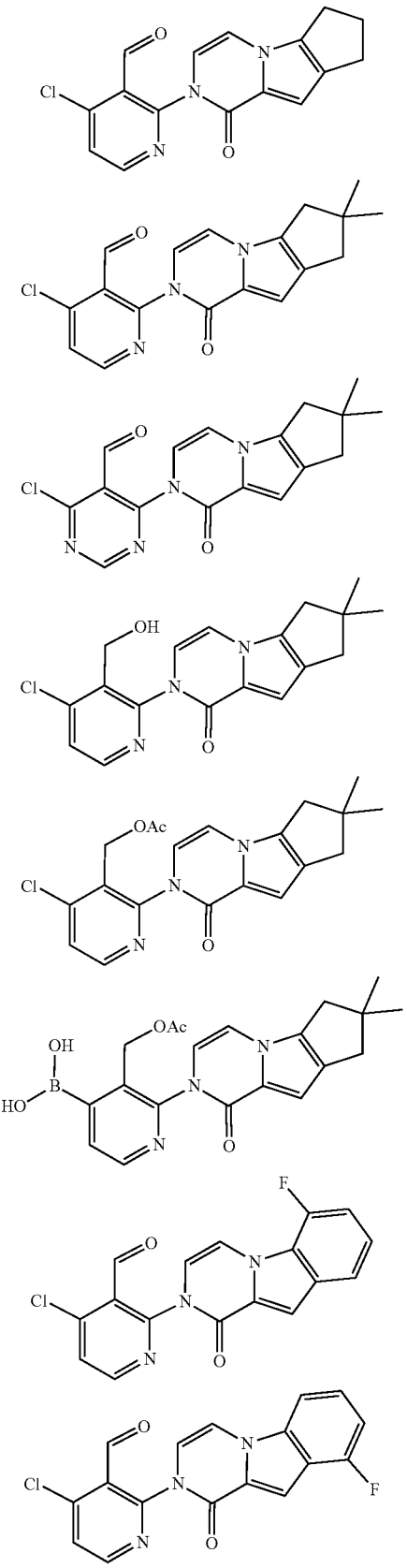

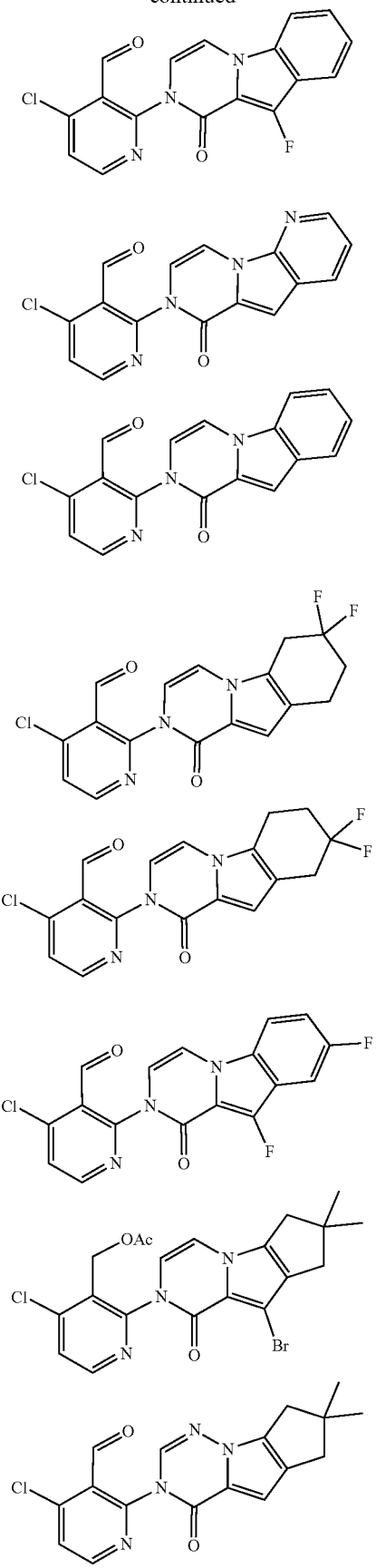

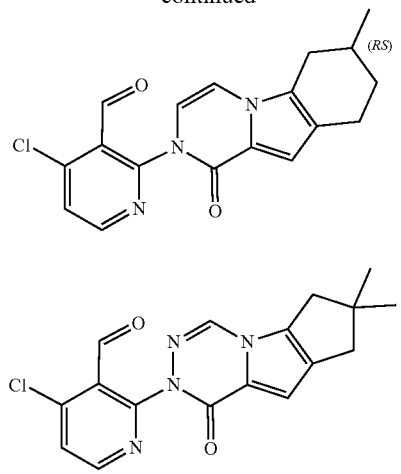

The various embodiments of the present invention (including the following examples) and the features of the various embodiments should be interpreted as being arbitrarily combined with each other, and the various solutions obtained by these mutual combinations are all included in the scope of the present invention, just like the solutions obtained by listing these mutual combinations specifically and individually herein, unless clearly stated otherwise in the context.

General Synthetic Methods

The compound of formula (I) and/or a pharmaceutically acceptable salt thereof described herein can be synthesized using commercially available starting materials, by methods known in the art, or methods disclosed in the patent application. The synthetic routes shown in Scheme 1 to Scheme 2 illustrate the general synthetic methods for preparing the compounds of the present invention, and the synthetic routes shown in Scheme 3 to Scheme 6 illustrate the general synthetic methods for preparing the material 1-1 used in Scheme 1 to Scheme 2.

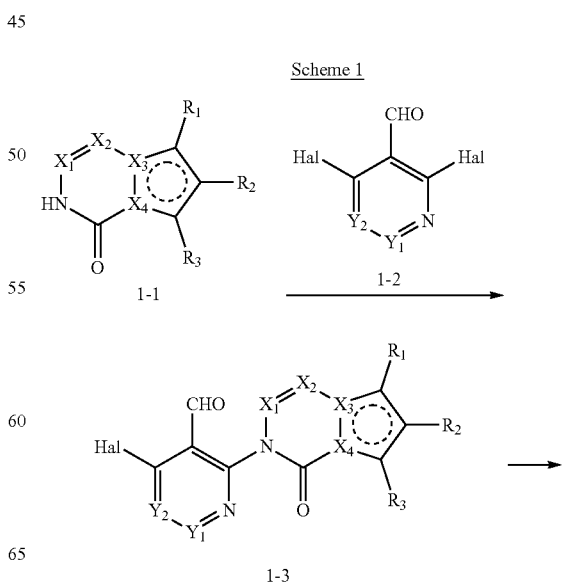

Scheme 1

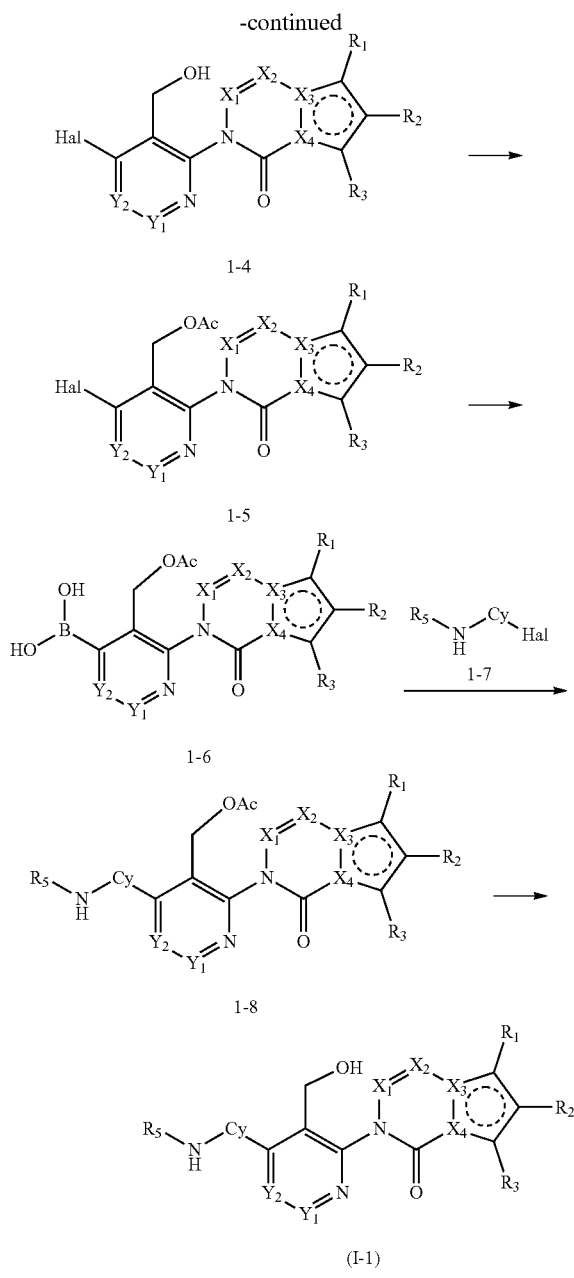

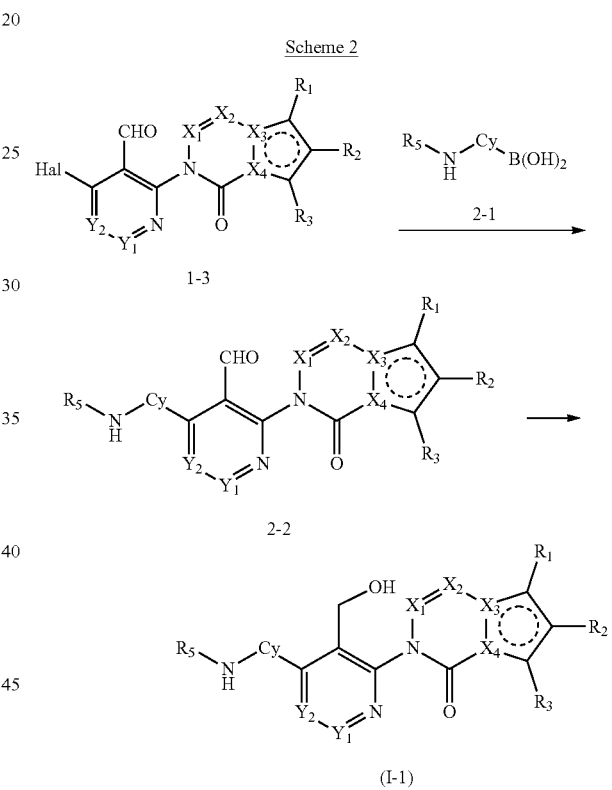

to)diboron under suitable conditions to obtain a boracic acid or boronic acid ester compound of formula 1-6. The compound of formula 1-6 is reacted with a halide of formula 1-7 by Suzuki coupling reaction under the catalysis of appropriate palladium reagent to obtain a compound of formula 1-8. Palladium catalyzed Suzuki coupling reaction is carried out under suitable conditions. The solvent used can be chosen from polar solvents such as 1,4-dioxane, DMF, THF or mixed solvent of 1,4-dioxane and water. The base used can be chosen from $Cs_2CO_3$, $Na_2CO_3$, $K_3PO_4$, etc., and the catalyst used can be chosen from $Pd(dppf)Cl_2 \cdot CH_2Cl_2$, $Pd(PPh_3)_4$, $Pd(OAc)_2$, etc. A compound of formula (I-1) of the present invention is obtained by deacetylating the compound of formula 1-8 under appropriate alkaline conditions. The base used can be chosen from potassium carbonate, sodium carbonate, lithium hydroxide, etc., and the solvent used can be chosen from polar solvents, such as methanol, ethanol or mixed solvent of methanol and water.

As shown in Scheme 1, a compound of formula 1-1 is reacted with a dihaloarylaldehyde compound of formula 1-2 under the catalysis of cuprous iodide to obtain a compound of formula 1-3. The carbon-nitrogen coupling reaction catalyzed by cuprous iodide is carried out under suitable conditions. The solvent used can be chosen from polar solvents such as 1,4-dioxane, DMF, etc., and the base used can be chosen from $Cs_2CO_3$, $Na_2CO_3$, $K_3PO_4$, etc. Under suitable conditions, a compound of formula 1-4 is obtained by reducing the compound of formula 1-3.

The reducing agent used can be chosen from sodium borohydride, potassium borohydride, lithium borohydride, etc., and the solvent used can be chosen from polar solvents, such as methanol, ethanol or mixed solvent of methanol and dichloromethane. A compound of formula 1-5 is obtained by acetylating the hydroxyl on the compound of formula 1-4. The compound of formula 1-5 is reacted with bis(pinacola- As shown in Scheme 2, the compound of formula 1-3 is reacted with a boracic acid or boric acid ester of formula 2-1 by Suzuki coupling reaction under the catalysis of appropriate palladium reagent to obtain a compound of formula 2-2. Palladium catalyzed Suzuki coupling reaction is carried out under suitable conditions. The solvent used can be chosen from polar solvents such as 1,4-dioxane, DMF, THF or mixed solvent of 1,4-dioxane and water, the base used can be chosen from $Cs_2CO_3$, $Na_2CO_3$, $K_3PO_4$, etc., and the catalyst used can be chosen from $Pd(dppf)Cl_2 \cdot CH_2Cl_2$, $Pd(PPh_3)_4$, $Pd(OAc)_2$, etc. Under suitable conditions, the compound of formula (I-1) is obtained by reducing the compound of formula 2-2. The reducing agent used can be chosen from sodium borohydride, potassium borohydride, lithium borohydride, etc., and the solvent used can be chosen from polar solvents, such as methanol, ethanol or mixed solvent of methanol and dichloromethane.

Scheme 3

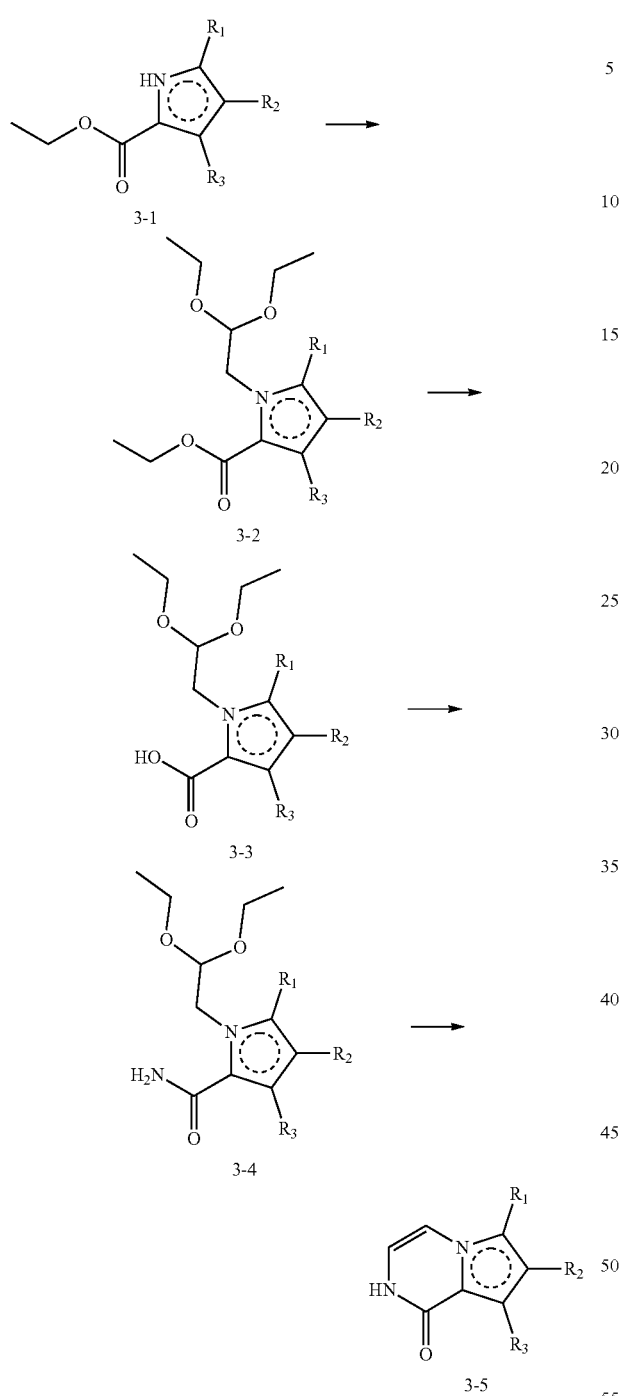

solvent of methanol and water. The compound of formula 3-3 is subjected to a condensation reaction with HATU and aqueous ammonia to obtain a compound of formula 3-4. The compound of formula 3-4 is subjected to ring closure in acetic acid to obtain a compound of formula 3-5.

Scheme 4

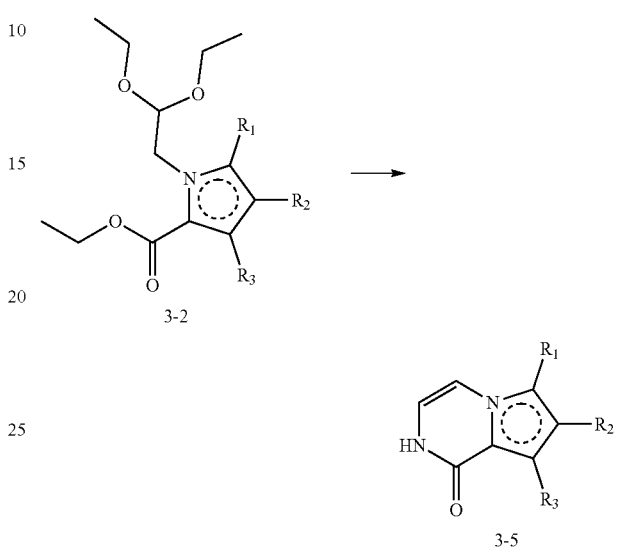

As shown in Scheme 4, the compound of formula 3-2 can be subjected to a ring closure reaction with ammonium acetate in acetic acid to obtain a compound of formula 3-5.

Scheme 5

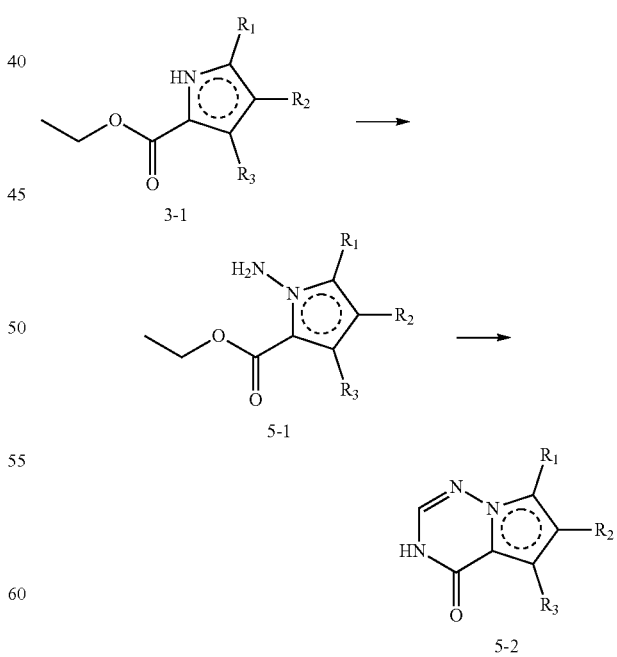

As shown in Scheme 3, the compound of formula 3-1 is subjected to a substitution reaction with bromoacetaldehyde diethyl acetal under suitable conditions to obtain a compound of formula 3-2. The base used can be chosen from cesium carbonate, etc., and the solvent used can be chosen from polar solvents such as DMF or 1,4-dioxane. The compound of formula 3-2 is hydrolyzed in an alkaline solution to obtain a compound of formula 3-3. The base used can be chosen from lithium hydroxide, potassium carbonate, sodium carbonate, etc., and the solvent used can be chosen from polar solvents, such as methanol, ethanol or mixed As shown in Scheme 5, the compound of formula 3-1 is reacted with O-(2,4-dinitrophenyl)hydroxylamine to obtain a compound of formula 5-1. The compound of formula 5-1 is subjected to a ring closure reaction with ammonium acetate in formamide solution to obtain a compound of formula 5-2.

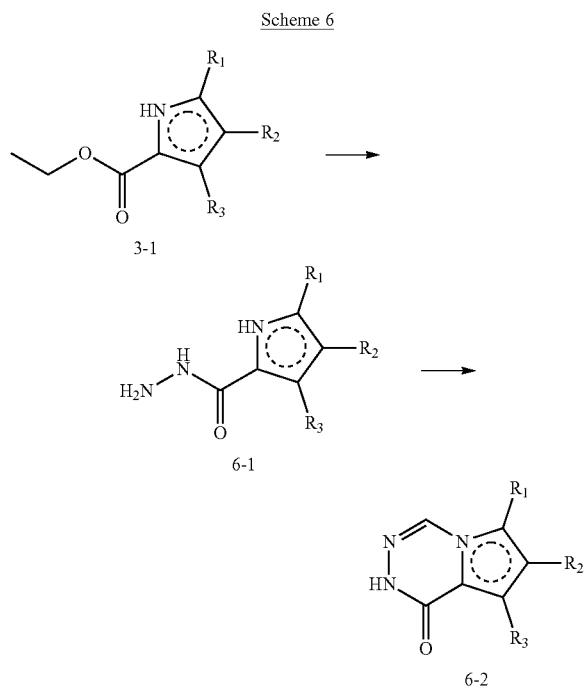

Scheme 6

As shown in Scheme, the compound of formula 3-1 is subjected to a substitution reaction with hydrazine hydrate to obtain a compound of formula 6-1. The compound of formula 6-1 is subjected to a ring closure reaction with triethyl orthoformate in DMF solution to obtain a compound of formula 6-2.

The substituents of the compounds thus obtained can be further modified to provide other desired compounds. Synthetic chemistry transformations are described, for example, in R. Larock, *Comprehensive Organic Transformations*, VCH Publishers (1989); L. Fieser and M. Fieser, *Fieser and Fieser's Reagents for Organic Synthesis*, John Wiley and Sons (1994); L. Paquette, ed., *Encyclopedia of Reagents for Organic Synthesis*, John Wiley and Sons (1995) and subsequent editions thereof.

Before use, the compound(s) of the present invention can be purified by column chromatography, high performance liquid chromatography, crystallization or other suitable methods.

Pharmaceutical Compositions and Utility

The compound of the present invention herein (e.g., a compound of any of the embodiments as described herein) is used, alone or in combination with one or more additional therapeutic agents, to formulate pharmaceutical compositions. A pharmaceutical composition comprises: (a) an effective amount of the compounds of the present invention; (b) a pharmaceutically acceptable excipient (e.g., one or more pharmaceutically acceptable carriers); and optionally (c) at least one additional therapeutic agent.

A pharmaceutically acceptable excipient refers to an excipient that is compatible with active ingredients of the composition (and in some embodiments, capable of stabilizing the active ingredients) and not deleterious to the subject to be treated. For example, solubilizing agents, such as cyclodextrins (which form specific, more soluble complexes with the compounds of the present invention), can be utilized as pharmaceutical excipients for delivery of the active ingredients. Examples of other excipients or carries include colloidal silicon dioxide, magnesium stearate, cellulose, sodium lauryl sulfate, and pigments such as D&C Yellow #10. Suitable pharmaceutically acceptable excipients are disclosed in Remington's Pharmaceutical Sciences, A. Osol, a standard reference text in the art.

A pharmaceutical composition comprising a compound of the present invention herein can be administered in various known manners, such as orally, topically, rectally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A pharmaceutical composition described herein can be prepared in the form of tablet, capsule, sachet, dragee, powder, granule, lozenge, powder for reconstitution, liquid preparation, or suppository. In some embodiments, a pharmaceutical composition comprising a compound of the present invention herein is formulated for intravenous infusion, topical administration, or oral administration.

An oral composition can be any orally acceptable dosage form including, but not limited to, tablets, capsules, emulsions, and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

In some embodiments, the compound of the present invention can be present in an amount of 1, 5, 10, 15, 20, 25, 50, 75, 80, 85, 90, 95, 100, 125, 150, 200, 250, 300, 400 and 500 mg in a tablet. In some embodiments, the compound of the present invention can be present in an amount of 1, 5, 10, 15, 20, 25, 50, 75, 80, 85, 90, 95, 100, 125, 150, 200, 250, 300, 400 and 500 mg in a capsule.

A sterile injectable composition (e.g., aqueous or oleaginous suspension) can be formulated according to techniques known in the art using suitable dispersing or wetting agents (for example, Tween 80) and suspending agents. The sterile injectable composition can also be a sterile injectable solution or suspension in a non-toxic parenterally acceptable diluent or solvent, for example, as a solution in 1,3-butanediol. Among the pharmaceutically acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives, and natural pharmaceutically acceptable oils, such as olive oil or castor oil, especially in their polyoxyethylated versions, can be used as sterile injectable medium. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment, and the like. Suitable carriers for the composition include vegetable or mineral oils, white petrolatum (white soft paraffin), branched chain fats or oils, animal fats and high molecular weight alcohols (greater than C12). In some embodiments, the pharmaceutically acceptable carrier is one in which the active ingredient is soluble. Emulsifiers, stabilizers, humectants and antioxidants may also be included as well as agents imparting color or fragrance, if desired. Additionally, transdermal penetration enhancers may be employed in those topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient, dissolved in a small amount of an oil, such as almond oil, is admixed. An example of such a cream is one which includes, by weight, about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond oil and about 70% by weight white soft paraffin.

Suitable in vitro assays can be used to evaluate the effect of the compounds of the present invention in inhibiting the activity of BTK. The compounds of the present invention can further be examined for additional effects in preventing or treating cancer by in vivo assays. For example, the compound of the present invention can be administered to an animal (e.g., a mouse model) having cancer and its therapeutic effects can be accessed. If the pre-clinical results are successful, the dosage range and administration route for animals, such as humans, can be projected.

The compound of the present invention can be shown to have sufficient pre-clinical practical utility to merit clinical trials hoped to demonstrate a beneficial therapeutic or prophylactic effect, for example, in subjects with cancer.

As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and hematologic malignancies, such as leukemia, lymphoma or myeloma. The term "cancer" encompasses diseases of skin, tissues, organs, bone, cartilage, blood, and vessels. The term "cancer" further encompasses primary cancer, and metastatic cancer, recurrent cancer and refractory cancer.

Non-limiting examples of solid tumors include pancreatic cancer; bladder cancer; colorectal cancer; breast cancer, including metastatic breast cancer; prostate cancer, including androgen-dependent and androgen-independent prostate cancer; testicular cancer; renal cancer, including, e.g., metastatic renal cell carcinoma; urothelial carcinoma; liver cancer; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; endometrial cancer; gastric cancer; esophageal cancer; head and neck cancer, including, e.g., squamous cell carcinoma of the head and neck; skin cancer, including, e.g., melanoma and basal carcinoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; sarcoma, including, e.g., Kaposi's sarcoma; adrenal carcinoma; mesothelial carcinoma; choriocarcinoma; muscle carcinoma; connective tissue carcinoma; and thyroid carcinoma.

Non-limiting examples of hematologic malignancies include acute myelogenous leukemia (AML); chronic myelogenous leukemia (CML), including accelerated phase CML and CML blastic phase (CML-BP); acute lymphocytic leukemia (ALL); chronic lymphocytic leukemia (CLL), including high risk CLL; human acute monocytic leukemia (M(5)); hairy cell leukemia; lymphocytic leukemia; chronic lymphoid leukemia; myelogenous leukemia; myelodysplastic syndrome or acute lymphoblastic leukemia; small lymphotic lymphoma (SLL), lymphoblastic lymphoma, and Hodgkin's lymphoma; non-Hodgkin's lymphoma (NHL); follicular lymphoma; mantle cell lymphoma (MCL); B-cell lymphoma; T cell lymphoma; diffuse large B-cell lymphoma (DLBCL); large B-cell lymphoma (LBCL); follicular lymphoma, marginal zone lymphoma, Burkitt's lymphoma, non-Burkitt's highly degree B cell malignant lymphoma, extranodal marginal-zone B-cell lymphoma; multiple myeloma (MM); Waldenstrom macroglobulinemia; myelodysplastic syndrome (MDS), including refractory anemia (RA), refractory anemia with ring sideroblasts (RARS), refractory anemia with excess of blast (RAEB) and refractory anemia with excess blasts in transformation (RAEB-T); and myeloproliferative syndrome.

In some embodiments, hematologic malignancy is recurrent or refractory diffuse large B-cell lymphoma (DLBCL), recurrent or refractory mantle cell lymphoma, recurrent or refractory follicular lymphoma, recurrent or refractory CLL, recurrent or refractory SLL, and recurrent or refractory multiple myeloma.

The compound of the present invention can be used to achieve a beneficial therapeutic or prophylactic effect, for example, in subjects with cancer.

The compound of the present invention can be used to achieve a beneficial therapeutic or prophylactic effect, for example, in subjects with an autoimmune disease, or in subjects with inflammatory diseases.

The term "autoimmune disease" refers to a disease or disorder arising from and/or directed against an individual's own tissues or organs, or a co-segregate or manifestation thereof, or resulting condition therefrom. Examples of autoimmune diseases include, but are not limited to: chronic obstructive pulmonary disease (COPD), allergic rhinitis, lupus erythematosus, myasthenia gravis, Sjogren syndrome, multiple sclerosis (MS), scleroderma (also referred to as systemic sclerosis), multiple sclerosis osteoporosis, arthritis (such as rheumatoid arthritis (RA), and collagen-induced arthritis), psoriasis, inflammatory bowel disease, asthma, idiopathic thrombocytopenic purpura, autoimmune hemolytic anemia, antineutrophil cytoplasmatic antibody vasculitis, chronic obstructive pulmonary disease, sicca syndrome, pemphigus valgaris, and diseases associated with kidney transplantation and myeloproliferative disease, such as myelofibrosis, and post-polycythemia vera/essential thrombocytosis myelofibrosis (post-PV/ET myelofibrosis). In some embodiment, autoimmune disease is chosen from arthritis, such as, rheumatoid arthritis (RA), collagen induced arthritis, and the like.

The term "inflammatory disease" or "inflammatory condition" refers to a pathological state that leads to inflammation, especially due to neutrophil chemotaxis. Non-limiting examples of inflammatory diseases include systemic inflammation and local inflammation, inflammation associated with immunosuppression, organ-graft refection, allergic disease, inflammatory skin disease (including psoriasis and atopic dermatitis); systemic scleroderma and sclerosis; reactions associated with inflammatory bowel diseases (IBD, such as Crohn's disease and ulcerative colitis); ischemia reperfusion injury, including reperfusion injury of tissue caused by surgery, myocardial ischemia, such as myocardial infarction, cardiac arrest, reperfusion after heart operation and abnormal contractile response of coronary vessel after percutaneous transluminal coronary angioplasty, surgical tissue reperfusion injury of stroke and abdominal aortic aneurysm; cerebral edema secondary to stroke; cranial injury, and hemorrhagic shock; suffocation; adult respiratory distress syndrome; acute lung injury; Behcet's disease; dermatomyositis; polymyositis; multiple sclerosis (MS); dermatitis; meningitis; encephalitis; uveitis; osteoarthritis; lupus nephritis; autoimmune disease such as rheumatoid arthritis (RA), Sjorgen's syndrome, and vasculitis; diseases involving leukopedesis; septicemia or central nervous system (CNS) inflammatory disease secondary to trauma, and multiple organ injury syndrome; alcoholic hepatitis; bacterial pneumonia; antigen-antibody complex mediated disease, including glomerulonephritis; pyaemia; sarcoidosis; immunopathologic responses to tissue/organ transplantation; lung inflammation, including pleurisy, alveolitis, vasculitis, pneumonia, chronic bronchitis, bronchiectasia, diffuse panbronchiolitis, hypersensitivity pneumonitis, idiopathic pulmonary fibrosis (IPF), cystic fibrosis, etc. Preferably indications include, but are not limited to, chronic inflammation, autoimmune diabetes, rheumatoid arthritis (RA), rheumatoid spondylitis, gouty arthritis and other arthrosis conditions, multiple sclerosis (MS), asthma, systemic lupus erythematosus, adult respiratory distress syndrome, Behcet's disease, psoriasis, chronic pulmonary inflammatory disease, graft versus host reaction, Crohn's disease, ulcerative colitis, inflammatory bowel disease (IBD), Alzheimer's disease and pyresis, and any diseases associated with inflammation and related conditions.

In addition, the compounds of the present invention (e.g., a compound of any of the embodiments as described herein) can be administered in combination with additional therapeutic agents for the treatment of diseases or disorders described herein, such as cancer, an inflammatory disease or autoimmune disease. The additional active ingredients may be administered separately with the compound of the present invention or included with such an ingredient in a pharmaceutical composition according to the disclosure, such as a fixed-dose combination drug product. In some embodiments, additional active ingredients are those that are known or discovered to be effective in the treatment of diseases mediated by BTK or at least in part by BTK, such as another BTK inhibitor or a compound active against another target associated with the particular disease. The combination may serve to increase efficacy (e.g., by including in the combination a compound potentiating the potency or effectiveness of the compound of the present invention), decrease one or more side effects, or decrease the required dose of the compound of the present invention.

In some embodiments, the compounds of the present invention (such as any compound herein) can be administered in combination with additional therapeutic agents, such as anti-inflammatory agents, immunomodulators or anti-tumor active agents, wherein the anti-tumor active agents include chemotherapeutic agents, immune checkpoint inhibitors or agonists, and targeted therapeutic agents.

The term "anti-tumor active agent" as used herein refers to any agent that is administered to a subject suffering from cancer for the purposes of treating the cancer, such as a chemotherapeutic agent, an immune checkpoint inhibitor or agonist, and a targeted therapeutic agent.

Non-limiting examples of chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, mitoxantrone, idarubicin, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); and free radical generators such as bleomycin; nucleoside mimetics (e.g., 5-fluorouracil, capecitabine, gemcitabine, fludarabine, cytarabine, azacitidine, mercaptopurine, thioguanine, pentostatin, and hydroxyurea); paclitaxel, docetaxel, and related analogs; vincristine, vinblastin, and related analogs; thalidomide and related analogs (e.g., CC-5013 and CC-4047).

Non-limiting examples of immune checkpoint inhibitors or agonists include PD-1 inhibitors, for example, anti-PD-1 antibodies, such as pembrolizumab and nivolumab; PD-L1 inhibitors, for example, anti-PD-L1 antibodies, such as atezolizumab, durvalumab, and avelumab; CTLA-4 inhibitors, such as anti-CTLA-4 antibody, for example ipilimumab; and BTLA inhibitors, LAG-3 inhibitors, TIM3 inhibitors, TIGIT inhibitors, VISTA inhibitors, OX-40 agonists, and the like.

Targeted therapeutic agents include various small molecule or macromolecular targeted therapeutic agents, and non-limiting examples thereof include: protein tyrosine kinase inhibitors (such as imatinib mesylate and gefitinib); proteasome inhibitors (such as bortezomib); NF-κB inhibitors, including IκB kinase inhibitors; PI3Kδ inhibitors; SYK inhibitors; Bcl2 inhibitors; antibodies that bind to proteins overexpressed in cancer to down-regulate cell replication, such as anti-CD20 antibody (such as rituximab, ibritumomab tiuxetan, and tositumomab), anti-Her2 monoclonal antibody (trastuzumab), anti-EGFR antibody (cetuximab) and anti-VEGFR antibody (bevacizumab); anti-angiogenic drugs, such as lenalidomide; and other protein or enzyme inhibitors, these proteins or enzymes are known to be upregulated, overexpressed or activated in cancers, and the inhibiting on them can down-regulate cell replication.

EXAMPLES

The examples below are intended to be purely exemplary and should not be considered to be limiting in any way. Efforts have been made to ensure the accuracy with respect to numbers used (for example, amounts, temperature, etc.), but those skilled in the art should understand that some experimental errors and deviations should be accounted for. Unless indicated otherwise, parts are parts by weight, temperature is in degrees Centigrade, and pressure is at or near atmospheric. All MS data were determined by Agilent 6120 or Agilent 1100. All NMR data were generated using a Varian 400 MR machine. All reagents and materials, except synthesized intermediates, used in the present invention are commercially available. The reference GDC-0853 (fenebrutinib) was purchased from Shanghai Linkchem Medical Technology Co., Ltd. All compound names except the reagents are generated by Chemdraw 16.0.

If there is any atom with empty valence(s) in any one of the structures disclosed herein, the empty balance(s) is (are) the hydrogen atom(s) which is (are) omitted for convenience purpose.

In the present application, in the case of inconsistency of the name and structure of a compound, when the two of which are both given for the compound, it is subject to the structure of the compound, unless the context shows that the structure of the compound is incorrect and the name is correct.

In the following examples, the abbreviations are used:
Ac Acetyl
AcOK Potassium acetate
BINAP Bis-(diphenylphosphino)-1,1'-binaphthyl
CDI N,N'-carbonyldiimidazole
CD$_3$OD Deuterated methanol
DCM Dichloromethane
DIAD Diisopropyl azodicarboxylate
DIEA N,N-diisopropylethylamine
DMF N,N-dimethylformamide
DMSO Dimethyl sulfoxide
DMSO-d$_6$ Deuterated dimethyl sulfoxide
EA/EtOAc Ethyl acetate
Et$_3$N Triethylamine
EtOH Ethanol
g Gram
HATU 2-(7-azabenzotriazole)-N,N,N',N'-tetramethyluronium hexafluorophosphate
HMDSLi Lithium hexamethyldisilazide
L Liter
M Mole/liter
MeOH Methanol
mg Milligram
mL Milliliter
mmol Millimole
mol Mole
NBS N-bromosuccinimide
Pd$_2$(dba)$_3$ Tris(dibenzylidene acetone)dipalladium
Pd(dppf)Cl$_2$ CH$_2$Cl$_2$ [1,1'-bis(diphenylphosphino) ferrocene]palladium dichloride dichloromethane complex
PE Petroleum ether
TFA Trifluoroacetic acid
THF Tetrahydrofuran
Xphos 2-dicyclohexylphosphine-2',4',6'-triisopropyl biphenyl
Xant-phos 4,5-bis(diphenylphosphino)-9,9-dimethylxanthene Example 1 Synthesis of Compounds Intermediate I-1

4-chloro-2-(1-oxo-1,6,7,8-tetrahydro-2H-cyclopenta[4,5]pyrrolo[1,2-a]pyrazin-2-yl)nicotinaldehyde

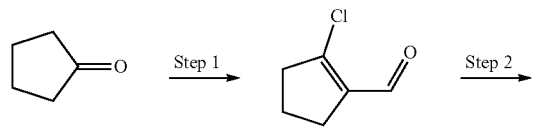

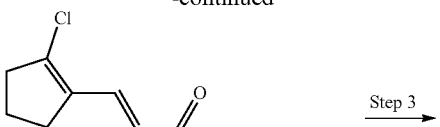

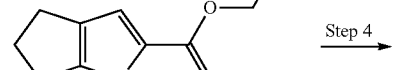

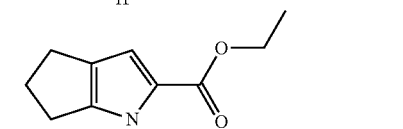

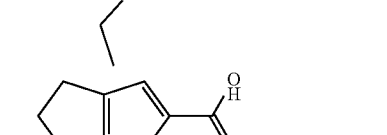

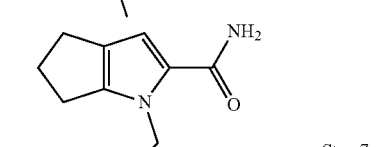

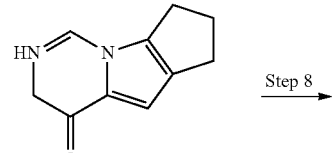

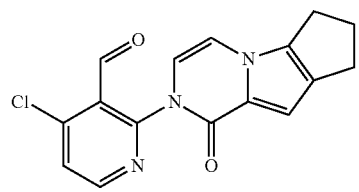

I-1

Step 1: 2-chlorocyclopentan-1-ene-1-carbaldehyde

At 0-5° C., phosphorus oxychloride (4.45 mL, 47.7 mmol) was dropwise added to DMF (4.6 mL, 59.6 mmol)

under nitrogen. The reaction solution was stirred at 0-5° C. for 10 minutes, and then further stirred at room temperature for 15 minutes. Cyclopentanone (2.5 g, 29.8 mmol) was dropwise added to the above-mentioned reaction solution at 0-5° C., which was reacted at room temperature for 1 hour, and then poured into ice water (the pH value was adjusted to 5 with an aqueous sodium carbonate solution), and 100 mL of water was added. The reaction solution was extracted with petroleum ether/ethyl acetate=10/1 (100 mL×2), and the organic phase was collected and combined, washed with saturated brine (100 mL), dried with anhydrous sodium sulfate, and concentrated to give the target product (2.4 g, yield 62%), which was directly used in the next step.

Step 2: (E)-3-(2-chlorocyclopenta-1-ene-1-yl)ethyl acrylate

Under nitrogen, 2-chlorocyclopentan-1-ene-1-carbaldehyde (2.4 g, 18.4 mmol) and ethoxy(formylmethylene)triphenylphosphorane (6.4 g, 18.4 mmol) were placed in dichloromethane (30 mL), which was reacted at the reflux temperature for 6 hours. The reaction solution was concentrated in vacuum under reduced pressure, and the resulting residue was purified with silica gel column chromatography (petroleum ether/ethyl acetate) to give the target product (3.3 g, yield 89%). [M+H]$^+$ 201.1

Step 3: Ethyl 1,4,5,6-tetrahydrocyclopentadieno[b]pyrrole-2-carboxylate

Under nitrogen, to a solution of (E)-3-(2-chlorocyclopenta-1-ene-1-yl)ethyl acrylate (3.3 g, 16.5 mmol) in DMSO (20 mL) was added sodium azide (1.6 g, 24 mmol), which was reacted at 65° C. for 16 hours. Water (200 mL) was added to the reaction solution, and the mixture was extracted with ethyl acetate (50 mL×2). The organic phase was collected and combined, and concentrated in vacuum under reduced pressure, and the resulting residue was purified with silica gel column chromatography (petroleum ether/ethyl acetate) to give the target product (700 mg, yield 24%). [M+H]$^+$ 180.1. $^1$H NMR (400 MHz, CDCl$_3$): δ 8.81 (s, 1H), 6.65 (s, 1H), 4.30-4.26 (m, 2H), 2.75-2.55 (m, 4H), 2.42-2.40 (m, 2H), 1.35-1.31 (m, 3H).

Step 4: Ethyl 1-(2,2-diethoxyethyl)-1,4,5,6-tetrahydrocyclopentadieno[b]pyrrole-2-carboxylate To a solution of ethyl 1,4,5,6-tetrahydrocyclopentadieno[b]pyrrole-2-carboxylate (700 mg, 3.9 mmol) in DMF(5 mL) was added cesium carbonate (3.2 g, 9.7 mmol) and bromoacetaldehyde diethyl acetal (1.55 g, 7.8 mmol), which was reacted at 100° C. for 16 hours. Water (50 mL) was added to the reaction solution, and the mixture was extracted with ethyl acetate (20 mL×2). The organic phase was collected and combined, and concentrated in vacuum under reduced pressure, and the resulting residue was purified with silica gel column chromatography (petroleum ether/ethyl acetate) to give the target product (1.0 g, yield 92%). [M+Na]$^+$318.1

Step 5: 1-(2,2-diethoxyethyl)-1,4,5,6-tetrahydrocyclopentadieno[b]pyrrole-2-carboxylic Acid To a solution of ethyl 1-(2,2-diethoxyethyl)-1,4,5,6-tetrahydrocyclopentadieno[b]pyrrole-2-carboxylate (1.0 g, 3.6 mmol) in ethanol (10 mL) and water (10 mL) was added lithium hydroxide monohydrate (650 mg, 14.4 mmol), which was reacted at 80° C. for 12 hours. Ethanol was removed in vacuum under reduced pressure, and the pH was adjusted to 5-6 with concentrated hydrochloric acid, and water (20 mL) was added. The reaction solution was extracted with ethyl acetate (20 mL×2), the organic phase was collected and combined, dried with anhydrous sodium sulfate, and concentrated to give the target product (800 mg, yield 83%). [M−H]$^−$ 266.1

Step 6: 1-(2,2-diethoxyethyl)-1,4,5,6-tetrahydrocyclopentadieno[b]pyrrole-2-carboxamide At 0-5° C., under nitrogen, to a solution of 1-(2,2-diethoxyethyl)-1,4,5,6-tetrahydrocyclopentadieno[b]pyrrole-2-carboxylic acid (800 mg, 3 mmol) in DMF(5 mL) was added triethylamine (0.84 mL, 6 mmol) and HATU (1.7 g, 4.5 mmol). After reacting at room temperature for 30 minutes, the reaction solution was poured into concentrated aqueous ammonia (20 mL) and stirred for 10 minutes. Water (20 mL) was added, the reaction solution was extracted with dichloromethane (20 mL×2), and the organic phase was collected and combined, and concentrated to give the target product (1.0 g, yield 125%), which was directly used in the next step.

Step 7: 7,8-dihydro-2H-cyclopenta[4,5]pyrrolo[1,2-a]pyrazin-1(6H)-one 1-(2,2-diethoxyethyl)-1,4,5,6-tetrahydrocyclopentadieno[b]pyrrole-2-carboxamide (1.0 g, 3.75 mmol) was dissolved in acetic acid (10 mL), which was reacted at 100° C. for 4 hours (acetic acid was removed in vacuum under reduced pressure, the pH value was adjusted to 8 with aqueous ammonia), water (20 mL) was added, and the mixture was extracted with dichloromethane (20 mL×2). The organic phase was collected and combined, and concentrated in vacuum under reduced pressure, and the resulting residue was purified with silica gel column chromatography (dichloromethane/methanol) to give the target product (600 mg, yield 92%). [M+H]$^+$ 175.1

Step 8: 4-chloro-2-(1-oxo-1,6,7,8-tetrahydro-2H-cyclopenta[4,5]pyrrolo[1,2-a]pyrazin-2-yl)nicotinaldehyde Under nitrogen, to a solution of 7,8-dihydro-2H-cyclopenta[4,5]pyrrolo[1,2-a]pyrazin-1(6H)-one (600 mg, 3.5 mmol) and 2-bromo-4-chloronicotinaldehyde (1.1 g, 5.1 mmol) in 1,4-dioxane (30 mL) was added cuprous iodide (665 mg, 3.5 mmol), 4,7-dimethoxy-1,10-phenanthroline (580 mg, 2.45 mmol) and cesium carbonate (2.2 g, 7.0 mmol). The mixture was reacted at 90° C. for 12 hours, and then cooled to room temperature. The mixture was concentrated in vacuum under reduced pressure, and the resulting residue was purified with silica gel column chromatography (petroleum ether/ethyl acetate) to give the target product (400 mg, yield 37%). [M+H]$^+$ 314.0

The intermediates in the following table were prepared with corresponding materials and reagents according to the preparation steps of intermediate I-1:

| Intermediate | Structural formula | LC-MS [M + H]+ |
| --- | --- | --- |
| I-55 | | 342.0 |
| I-64 | | 343.0 |
| I-77 | | 328.0 |
| I-79 | | 342.0 |
| I-80 | | 330.0 |
| I-84 | | 356.1 |
| I-90 | | 328.1 |

| Intermediate | Structural formula | LC-MS [M + H]+ |
|---|---|---|
| I-95 | | 341.8 |
| I-96 | | 338.0 |
| I-98 | | 386.0, 388.0 |
Intermediate I-2
(5-((5-((2S,5R)-2,5-dimethyl-4-(oxetan-3-yl)piperazin-1-yl)pyridin-2-yl)amino)-1-methyl-6-oxo-1,6-dihydropyridin-3-yl)boracic Acid
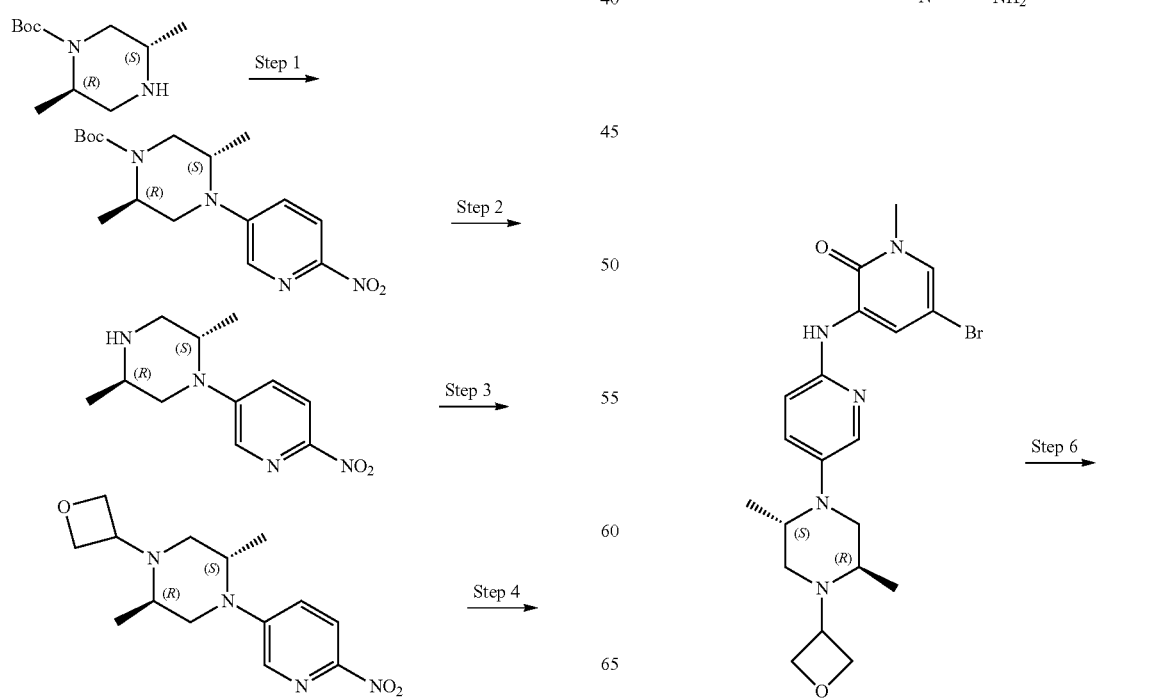

-continued

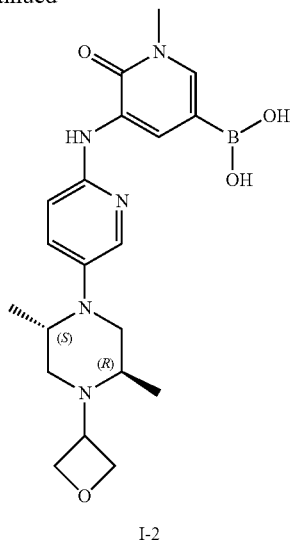

I-2

Step 1: t-butyl (2R,5S)-2,5-dimethyl-4-(6-nitropyridin-3-yl)piperazin-1-carboxylate Under nitrogen, to a solution of 5-bromo-2-nitropyridine (7.0 g, 32.7 mmol) and t-butyl (2R,5S)-2,5-dimethylpiperazin-1-carboxylate (10.0 g, 49.0 mmol) in 1,4-dioxane (150 mL) was added Xant-phos (3.8 g, 0.64 mmol), Pd$_2$(dba)$_3$ (3.0 g, 0.32 mmol) and cesium carbonate (21.3 g, 65.3 mmol). The mixture was reacted at 100° C. for 16 hours, and then cooled to room temperature. The reaction solution was concentrated in vacuum under reduced pressure, and the resulting residue was purified with silica gel column chromatography (petroleum ether/ethyl acetate) to give the target product. [M+H]$^+$ 337.1

Step 2: (2R,5S)-2,5-dimethyl-1-(6-nitropyridin-3-yl)piperazine

Under nitrogen, to a solution of t-butyl (2R,5S)-2,5-dimethyl-4-(6-nitropyridin-3-yl)piperazin-1-carboxylate obtained from step 1 in methanol (10 mL) was added concentrated hydrochloric acid (3 mL). The reaction was stirred at room temperature for 30 minutes, and concentrated in vacuum under reduced pressure, and the resulting residue was purified with silica gel column chromatography (methanol/water) to give the target product (3.3 g, two-step yield 43%). [M+H]$^+$ 237.1

Step 3: (2S,5R)-2,5-dimethyl-1-(6-nitropyridin-3-yl)-4-(oxetan-3-yl)piperazine

Under nitrogen, to a solution of (2R,5S)-2,5-dimethyl-1-(6-nitropyridin-3-yl) piperazine (3.3 g, 14.0 mmol) and oxetan-3-one (3.1 g, 42.0 mmol) in methanol (20 mL) was added zinc chloride (5.7 g, 42.0 mmol) and sodium cyanoborohydride (2.6 g, 42.0 mmol). The reaction was stirred at 50° C. for 5 hours, and concentrated in vacuum under reduced pressure, and the resulting residue was purified with silica gel column chromatography (methanol/water) to give the target product (3.3 g, yield 80%). [M+H]$^+$ 293.1

Step 4: 5-((2S,5R)-2,5-dimethyl-4-(oxetan-3-yl)piperazin-1-yl)pyridin-2-amine

At room temperature, to a mixture of (2S,5R)-2,5-dimethyl-1-(6-nitropyridin-3-yl)-4-(oxetan-3-yl)piperazine (3.3 g, 11.3 mmol) and 10% palladium-carbon (with 50% water, 400 mg) in methanol (50 mL) was introduced with hydrogen, which was reacted at room temperature for 12 hours. The reaction solution was filtered, and the filtrate was collected, and concentrated in vacuum under reduced pressure to give the target product (2.94 g, yield 99%), which was directly used in the next step. [M+H]$^+$ 263.1

Step 5: 5-bromo-3-((5-((2S,5R)-2,5-dimethyl-4-(oxetan-3-yl)piperazin-1-yl)pyridin-2-yl)amino)-1-methylpyridin-2(1H)-one Under nitrogen, to a solution of 5-((2S,5R)-2,5-dimethyl-4-(oxetan-3-yl)piperazin-1-yl)pyridin-2-amine (2.94 g, 11.2 mmol), 3,5-dibromo-1-methylpyridin-2(1H)-one (3.0 g, 11.2 mmol) in 1,4-dioxane (150 mL) was added Xant-phos (325 mg, 0.56 mmol), Pd$_2$(dba)$_3$ (515 mg, 0.56 mmol) and cesium carbonate (7.3 g, 22.5 mmol). The mixture was reacted at 100° C. for 16 hours, and then cooled to room temperature. The reaction solution was concentrated in vacuum under reduced pressure, and the resulting residue was purified with silica gel column chromatography (methanol/dichloromethane) to give (4.7 g, yield 93%). [M+H]$^+$ 448.1, 450.0

Step 6: (5-((5-((2S,5R)-2,5-dimethyl-4-(oxetan-3-yl)piperazin-1-yl)pyridin-2-yl)amino)-1-methyl-6-oxo-1,6-dihydropyridin-3-yl)boracic Acid Under nitrogen, to a solution of 5-bromo-3-((5-((2S,5R)-2,5-dimethyl-4-(oxetan-3-yl)piperazin-1-yl)pyridin-2-yl)amino)-1-methylpyridin-2(1H)-one (4.7 g, 10.5 mmol), bis (pinacolato)diboron (13.3 g, 52.4 mmol) in 1,4-dioxane (200 mL) was added Xphos (500 mg, 1.05 mmol), Pd$_2$(dba)$_3$ (480 mg, 0.52 mmol) and potassium acetate (3.0 g, 31.4 mmol). The mixture was reacted at 60° C. for 16 hours, and then cooled to room temperature. The reaction solution was filtered, and the filtrate was collected and concentrated in vacuum under reduced pressure, and the resulting residue was purified with silica gel column chromatography (methanol/water) to give the target compound (2.3 g, yield 53%). [M+H]$^+$ 414.2

The intermediates in the following table were prepared with corresponding materials and reagents according to the preparation steps of intermediate I-2:

| Intermediate | Structural formula | LC-MS [M + H]$^+$ |
|---|---|---|
| I-7 |  | 405.1 |

-continued
| Intermediate | Structural formula | LC-MS [M + H]+ |
|---|---|---|
| I-11 | 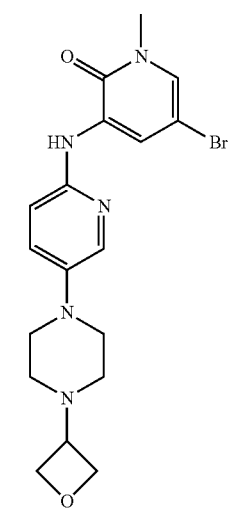 [SMILES: Cn1cc(Br)cc(Nc2ccc(N3CCN(C4COC4)CC3)cn2)c1=O] | 420.1, 422.1 |
| I-14 | 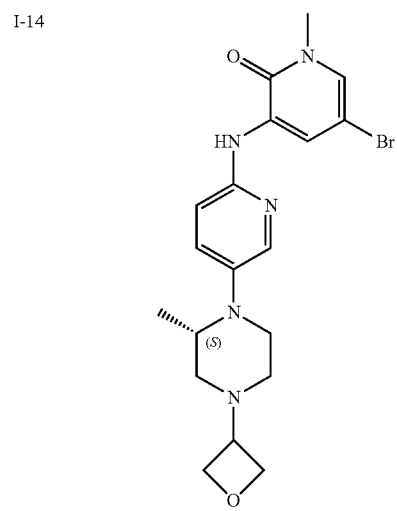 | 434.1, 436.1 |
| I-15 | 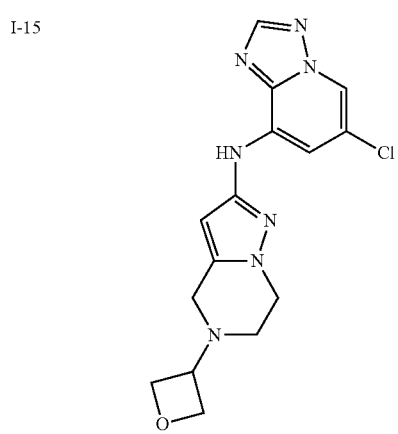 | 346.0 |
-continued
| Intermediate | Structural formula | LC-MS [M + H]+ |
|---|---|---|
| I-18 | 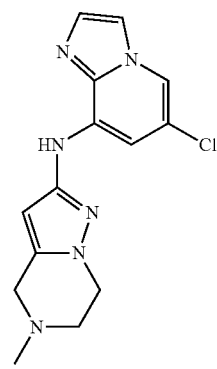 [SMILES: CN1CCn2nc(Nc3cc(Cl)cn4ccnc34)cc2C1] | 304.1 |
| I-35 | 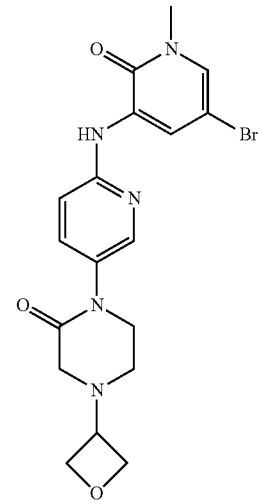 [SMILES: Cn1cc(Br)cc(Nc2ccc(N3CCN(C4COC4)CC3=O)cn2)c1=O] | 434.0, 436.0 |
| I-54 | 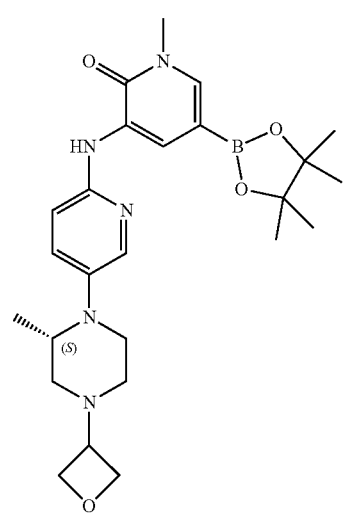 | 482.3 |

-continued
| Intermediate | Structural formula | LC-MS [M + H]+ |
|---|---|---|
| I-56 | 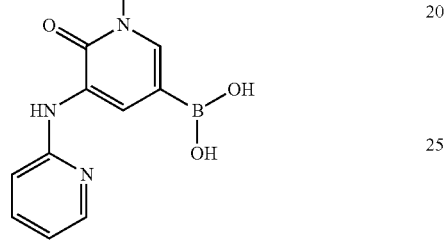 | 261.1 |
| I-57 | | 246.0 |
| I-65 | 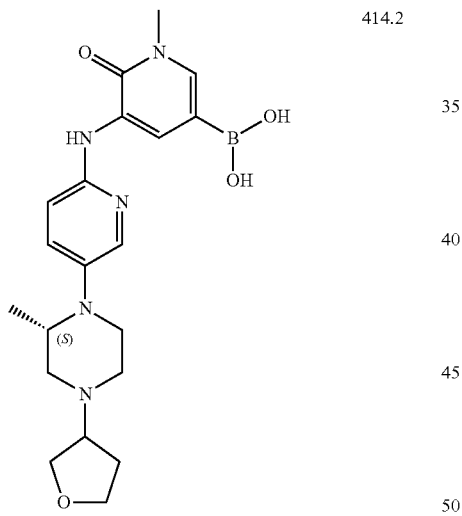 | 414.2 |
| I-67 | 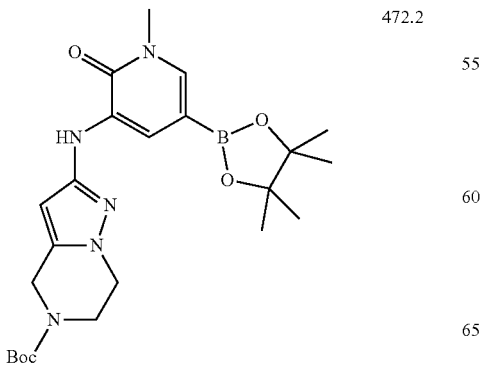 | 472.2 |
-continued
| Intermediate | Structural formula | LC-MS [M + H]+ |
|---|---|---|
| I-69 | 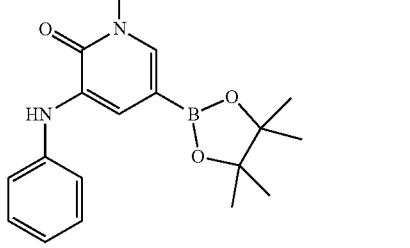 | 332.1 |
| I-73 | | 327.1 |
| I-76 | 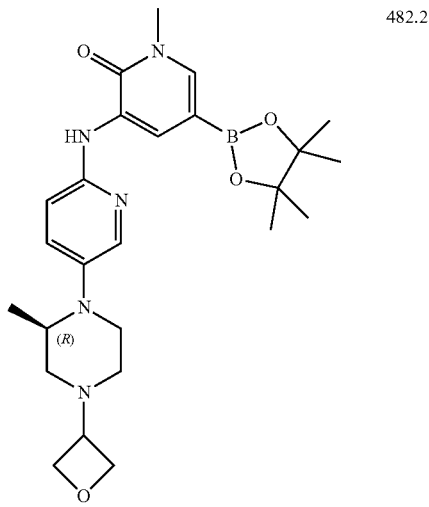 | 482.2 |

| Intermediate | Structural formula | LC-MS [M + H]+ |
|---|---|---|
| I-78 | 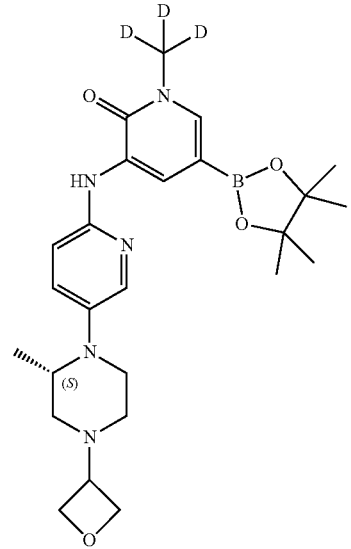 | 485.3 |
| I-134 | 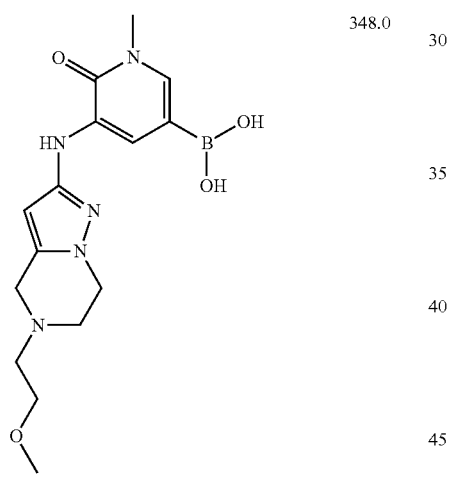 | 348.0 |
| I-136 | 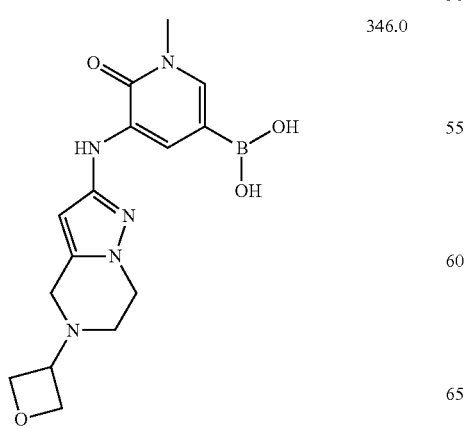 | 346.0 |
| Intermediate | Structural formula | LC-MS [M + H]+ |
|---|---|---|
| I-144 | 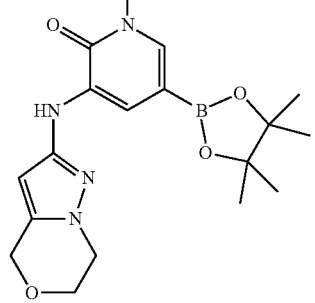 | 373.0 |
| I-145 | 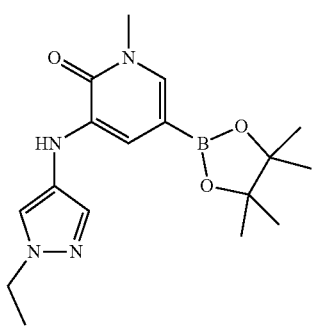 [SMILES: CCn1cc(Nc2cc(B3OC(C)(C)C(C)(C)O3)cn(C)c2=O)cn1] | 345.0 |
| I-146 | 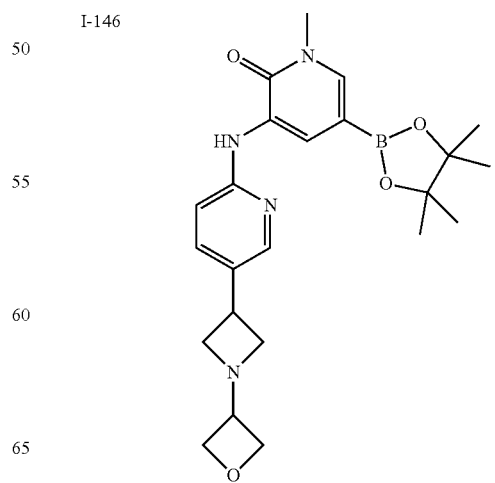 | 439.0 |

299
-continued
| Intermediate | Structural formula | LC-MS [M + H]+ |
|---|---|---|
| I-162 | | 414.0 |
| I-166 | | 496.2 |
| I-167 | | 496.2 |
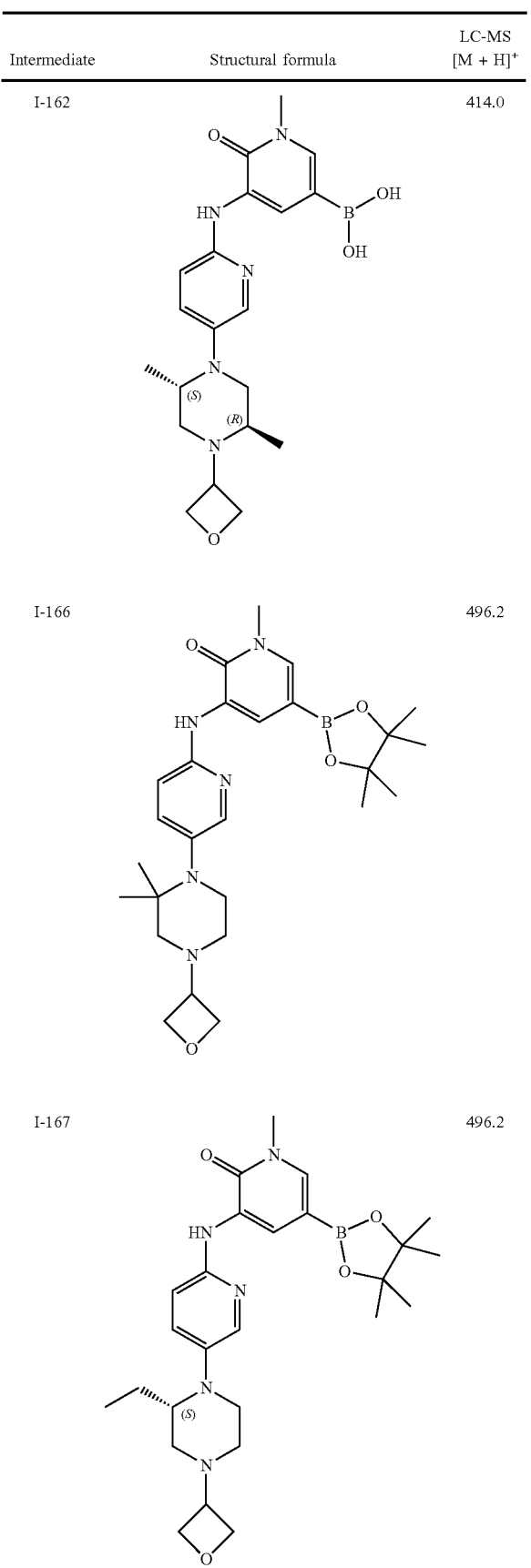
300
-continued
| Intermediate | Structural formula | LC-MS [M + H]+ |
|---|---|---|
| I-168 | | 293.1 |
| I-169 | | 266.1 |
| I-170 | | 249.1 |
| I-171 | | 223.1 |
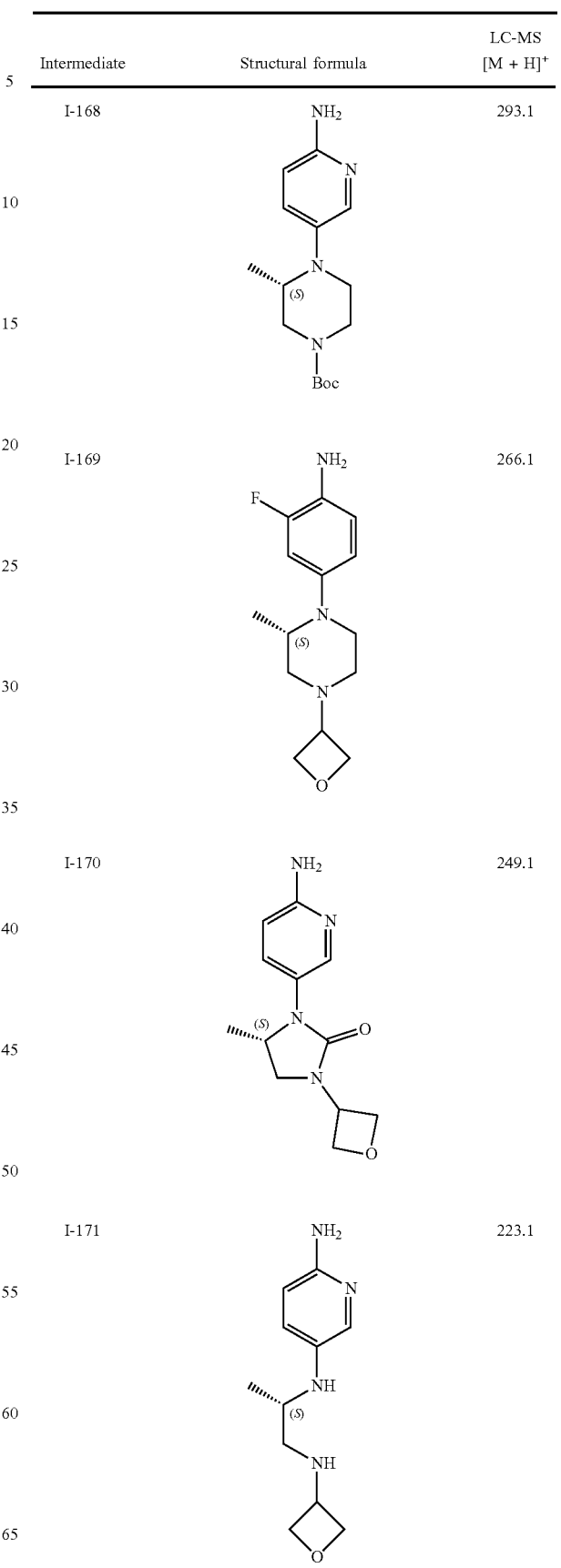

| Intermediate | Structural formula | LC-MS [M + H]+ |
|---|---|---|
| I-172 | 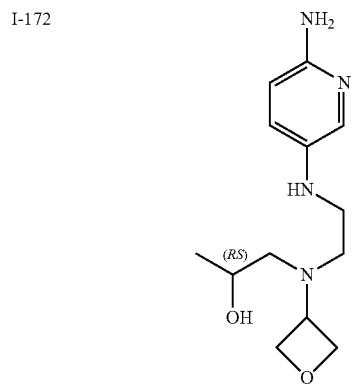 | 267.0 |
| I-173 | 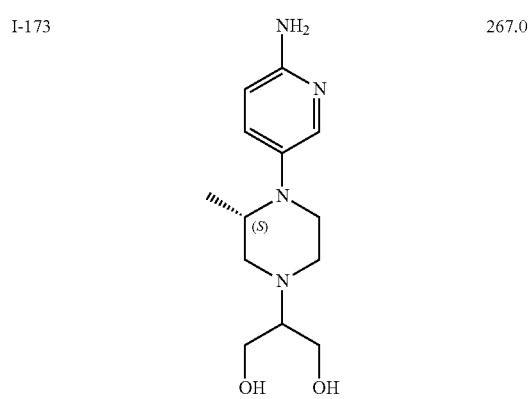 | 267.0 |
| I-174 | 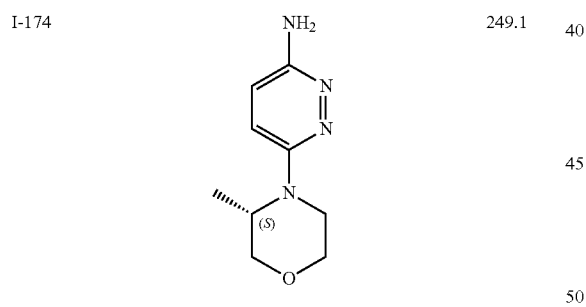 | 249.1 |
| I-175 | 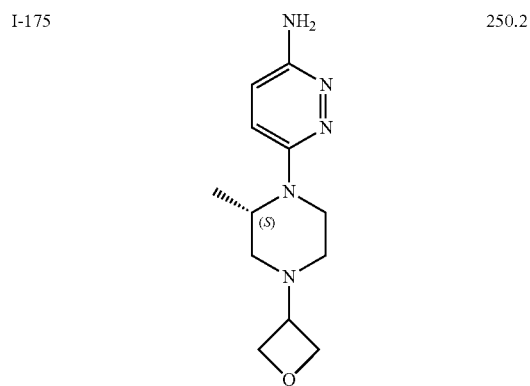 | 250.2 |
| Intermediate | Structural formula | LC-MS [M + H]+ |
|---|---|---|
| I-176 | 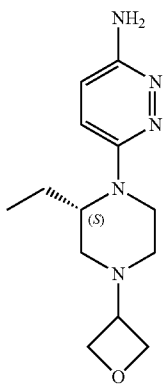 | 264.2 |
| I-177 | 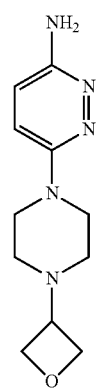 | 236.0 |
| I-178 | 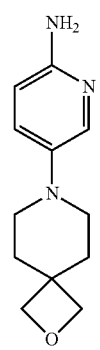 | 220.1 |
| I-179 | 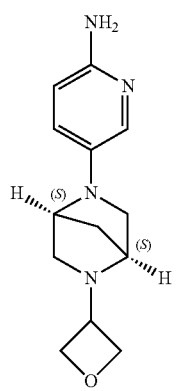 | 247.0 |

-continued

| Intermediate | Structural formula | LC-MS [M + H]+ |
|---|---|---|
| I-180 | | 261.1 |
| I-181 | | 235.1 |
| I-182 | | 234.1 |
| I-183 | | 263.1 |

-continued

| Intermediate | Structural formula | LC-MS [M + H]+ |
|---|---|---|
| I-184 | | 247.1 |
| I-185 | | 249.1 |
| I-186 | | 483.3 |

Intermediate I-3

5-bromo-3-((5-ethyl(2-methoxyethyl)amino)pyridin-2-yl)amino)-1-methylpyridin-2(1H)-one

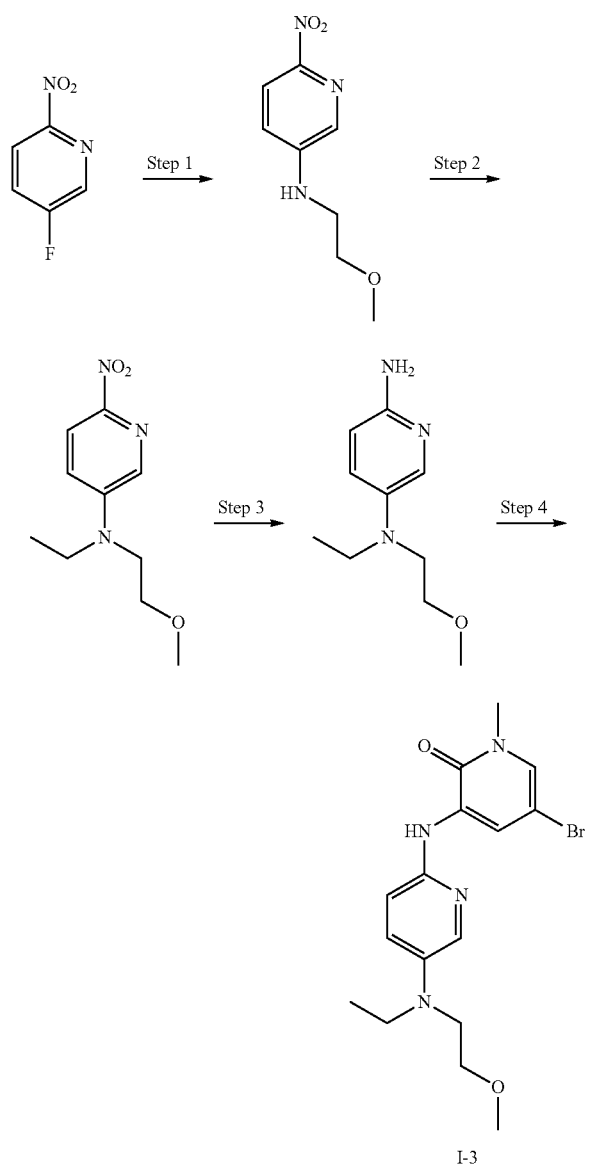

I-3

Step 1: N-(2-methoxyethyl)-6-nitropyridin-3-amine

To a solution of 5-fluoro-2-nitropyridine (4.26 g, 30 mmol) and 2-methoxyethylamine (2.48 g, 33 mmol) in DMSO (30 mL) was added triethylamine (21.2 g, 210 mmol). The mixture was reacted at 100° C. for 4 hours, and then cooled to room temperature. The reaction solution was poured into water (200 mL), and extracted with ethyl acetate (200 mL×2). The organic phase was collected and combined, and concentrated in vacuum under reduced pressure, and the resulting residue was purified with silica gel column chromatography (methanol/dichloromethane) to give the target product (5.92 g, yield 100%). [M+H]$^+$ 198.1

Step 2: N-ethyl-N-(2-methoxyethyl)-6-nitropyridin-3-amine

At 0-5° C., under nitrogen, to a solution of N-(2-methoxyethyl)-6-nitropyridin-3-amine (986 mg, 5.0 mmol) in DMF (10 mL) was added 60% sodium hydride (mineral oil dispersion) (240 mg, 6.0 mmol), and stirred at this temperature for 1 hour. Bromoethane was added to the mixture, and the mixture was reacted at 60° C. for 2 hours, and cooled to room temperature. The reaction solution was concentrated in vacuum under reduced pressure, and the resulting residue was dissolved in dichloromethane (100 mL), and washed with water (50 mL). The organic phase was collected, and concentrated in vacuum under reduced pressure to give the target product (1.13 g, yield 100%), which was directly used in the next step. [M+H]$^+$ 226.1

Step 3: N-ethyl-N-(2-methoxyethyl)pyridin-2,5-diamine

At room temperature, to a mixture of N-ethyl-N-(2-methoxyethyl)-6-nitropyridin-3-amine (1.13 g, 5.0 mmol) and 10% palladium-carbon (with 50% water, 200 mg) in methanol (20 mL) was introduced with hydrogen, which was reacted at room temperature for 16 hours. The reaction solution was filtered, and the filtrate was collected and concentrated in vacuum under reduced pressure, and the resulting residue was purified with silica gel column chromatography (methanol/water) to give the target product (875 mg, yield 90%). [M+H]$^+$ 196.1

Step 4: 5-bromo-3-((5-ethyl(2-methoxyethyl)amino)pyridin-2-yl)amino)-1-methylpyridin-2(1H)-one Under nitrogen, to a solution of N-ethyl-N-(2-methoxyethyl)pyridin-2,5-diamine (195 mg, 1.0 mmol), 3,5-dibromo-1-methylpyridin-2(1H)-one (267 mg, 1.0 mmol) in 1,4-dioxane (5 mL) was added Xant-phos (58 mg, 0.1 mmol), Pd$_2$(dba)$_3$ (92 mg, 0.1 mmol) and cesium carbonate (652 mg, 2.0 mmol). The mixture was reacted at 100° C. for 16 hours, and then cooled to room temperature. The reaction solution was concentrated in vacuum under reduced pressure, and the resulting residue was purified with silica gel column chromatography (methanol/dichloromethane) to give the target product (257 mg, yield 67%). [M+H]$^+$ 381.1, 383.1

The intermediates in the following table were prepared with corresponding materials and reagents according to the preparation steps of intermediate I-3:

| Intermediate | Structural formula | LC-MS [M + H]$^+$ |
|---|---|---|
| I-8 | | 312.0, 313.9 |

-continued
| Intermediate | Structural formula | LC-MS [M + H]+ |
|---|---|---|
| I-9 | 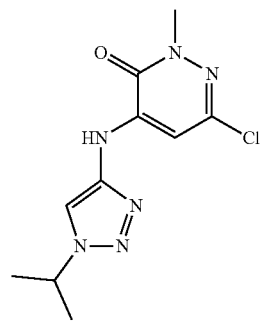 [SMILES: CC(C)n1cc(Nc2cc(Cl)nn(C)c2=O)nn1] | 269.0 |
| I-10 | 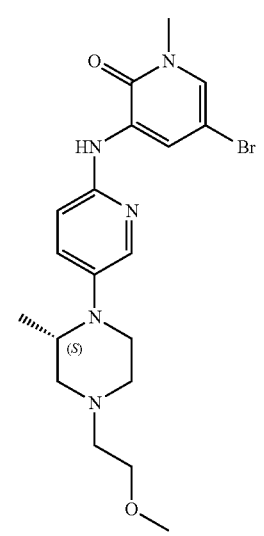 | 436.1, 438.1 |
-continued
| Intermediate | Structural formula | LC-MS [M + H]+ |
|---|---|---|
| I-12 | 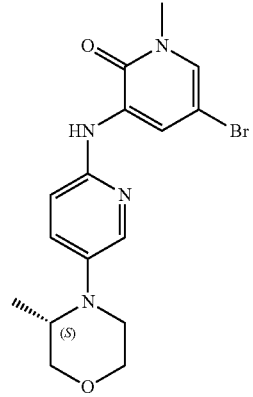 | 379.0, 381.0 |
|  |  | 381.0 |
| I-17 |  | 352.0, 354.0 |
| I-19 |  | 390.0 |
438.1

309
-continued
| Intermediate | Structural formula | LC-MS [M + H]+ |
|---|---|---|
| I-20 | 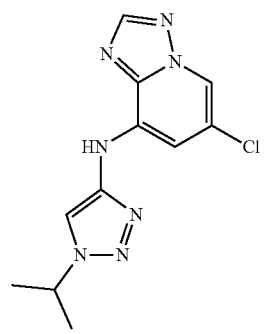 [SMILES: CC(C)n1cc(Nc2cc(Cl)cn3ncnc23)nn1] | 278.0 |
| I-21 | 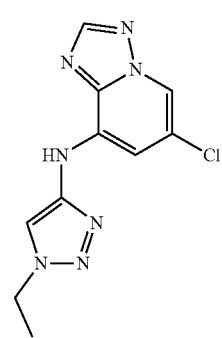 [SMILES: CCn1cc(Nc2cc(Cl)cn3ncnc23)nn1] | 264.0 |
| I-22 | 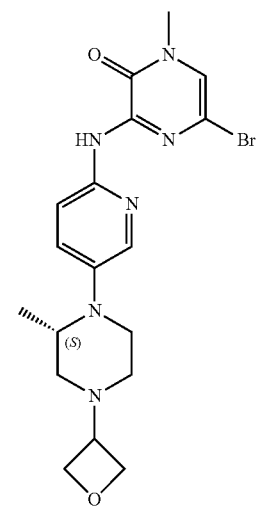 | 434.9, 436.9 |
310
-continued
| Intermediate | Structural formula | LC-MS [M + H]+ |
|---|---|---|
| I-23 | 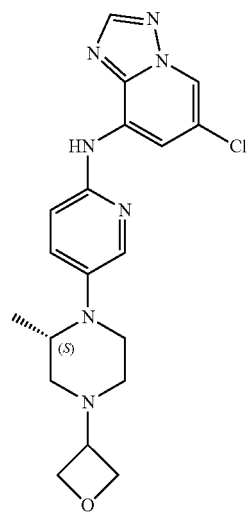 | 400.1 |
| I-24 | 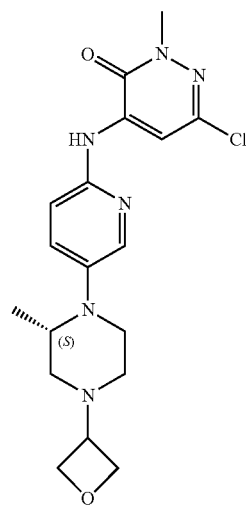 | 391.1 |
| I-25 | 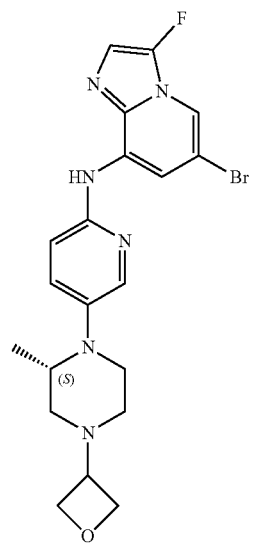 | 461.1, 463.1 |

-continued

| Intermediate | Structural formula | LC-MS [M + H]+ |
|---|---|---|
| I-26 | (1-methyl-2-oxo-pyridine with Br and NH-(1-ethyl-triazole)) | 298.0, 300.0 |
| I-27 | (1-methyl-3-oxo-pyridazine with Cl and NH-(1-ethyl-triazole)) | 255.0 |
| I-28 | (1-methyl-2-oxo-pyridine with Br and NH-pyridine-(S)-2-methyl-4-methylpiperazine) | 392.1, 394.1 |
| I-29 | (1-methyl-2-oxo-pyridine with Br and NH-(1-methyl-triazole)) | 284.0, 286.0 |

-continued

| Intermediate | Structural formula | LC-MS [M + H]+ |
|---|---|---|
| I-30 | (1-methyl-3-oxo-pyridazine with Cl and NH-(1-methyl-triazole)) | 241.0 |
| I-36 | (1-methyl-2-oxo-pyridine with Br and NH-pyridine-azetidine-OMe) | 365.0, 367.0 |
| I-40 | (1-methyl-2-oxo-pyridine with Br and NH-isopropyl) | 245.0 247.0 |
| I-41 | (1-methyl-2-oxo-pyridine with Br and NH-pyridine-N(Me)-oxetane) | 365.0, 367.0 |

| Intermediate | Structural formula | LC-MS [M + H]+ |
|---|---|---|
| I-49 | | 507.2 |
| I-50 | | 367.0, 369.0 |
| I-51 | | 395.1, 397.1 |

| Intermediate | Structural formula | LC-MS [M + H]+ |
|---|---|---|
| I-81 | | 437.1, 439.1 |
| I-100 | | 283.0, 285.0 |
| I-101 | | 297.0, 299.0 |
| I-102 | | 281.0, 283.0 |

-continued
| Intermediate | Structural formula | LC-MS [M + H]+ |
|---|---|---|
| I-103 | 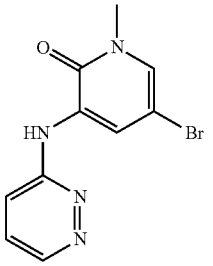 [SMILES: Cn1cc(Br)cc(Nc2cccnn2)c1=O] | 281.0, 283.0 |
| I-104 | 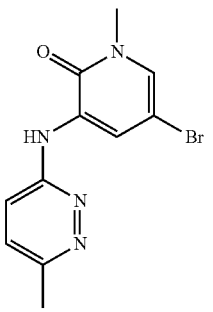 [SMILES: Cc1ccc(Nc2cc(Br)cn(C)c2=O)nn1] | 295.0, 297.0 |
| I-105 | 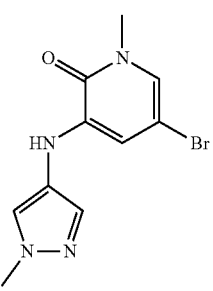 [SMILES: Cn1cc(Nc2cc(Br)cn(C)c2=O)cn1] | 283.0, 285.0 |
| I-106 | 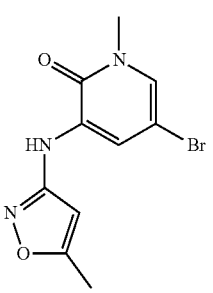 [SMILES: Cc1cc(Nc2cc(Br)cn(C)c2=O)no1] | 284.0, 286.0 |
| I-109 | 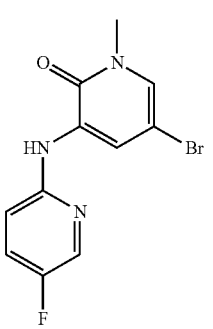 [SMILES: Cn1cc(Br)cc(Nc2ccc(F)cn2)c1=O] | 298.0, 300.0 |
-continued
| Intermediate | Structural formula | LC-MS [M + H]+ |
|---|---|---|
| I-110 | 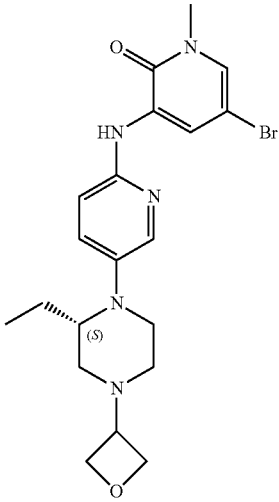 | 448.1, 450.1 |
| I-111 | 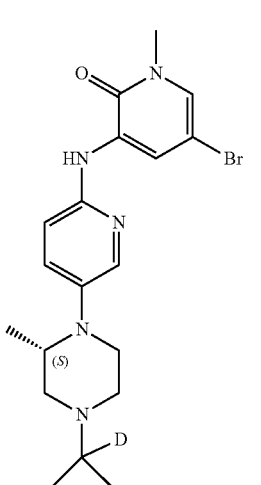 | 435.1, 437.1 |
| I-112 | 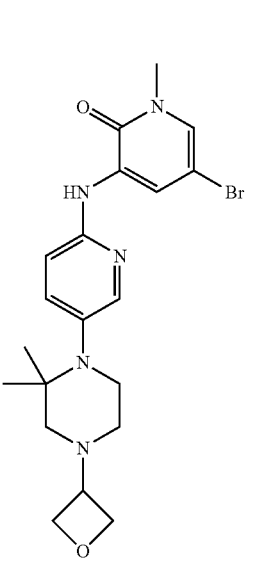 [SMILES: Cn1cc(Br)cc(Nc2ccc(N3CCN(C4COC4)CC3(C)C)cn2)c1=O] | 448.1, 450.1 |

317
-continued
| Intermediate | Structural formula | LC-MS [M + H]⁺ |
|---|---|---|
| I-113 | 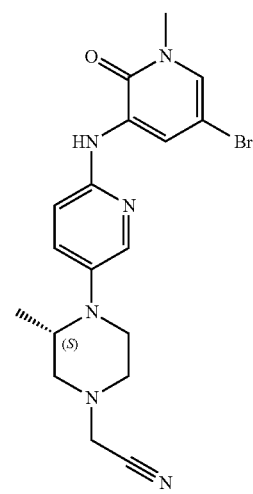 | 417.1, 419.1 |
| I-115 | 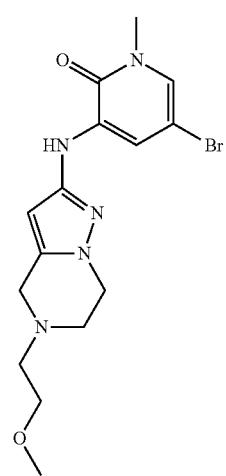 [SMILES: COCCN1CCn2nc(Nc3cc(Br)cn(C)c3=O)cc2C1] | 382.1, 384.1 |
| I-116 | 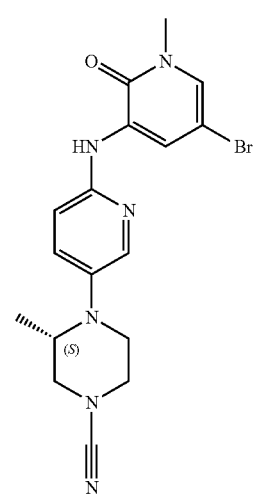 | 403.1, 405.1 |
318
-continued
| Intermediate | Structural formula | LC-MS [M + H]⁺ |
|---|---|---|
| I-117 | 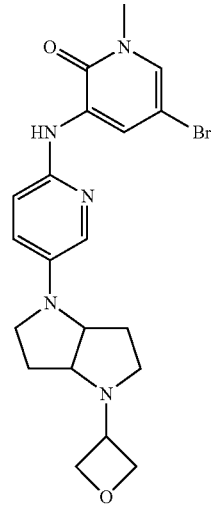 [SMILES: Cn1cc(Br)cc(Nc2ccc(N3CCC4C3CCN4C3COC3)cn2)c1=O] | 446.1, 448.1 |
| I-118 | 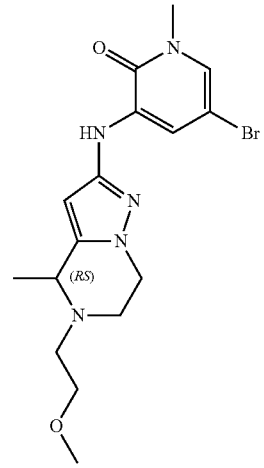 [SMILES: COCCN1CCn2nc(Nc3cc(Br)cn(C)c3=O)cc2C1C] | 396.1, 398.1 |
| I-119 | 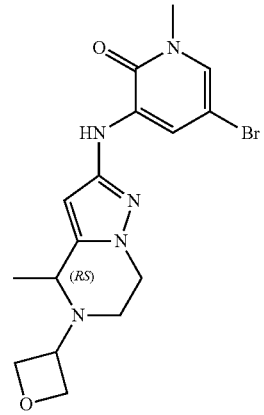 [SMILES: CC1c2cc(Nc3cc(Br)cn(C)c3=O)nn2CCN1C1COC1] | 394.1, 396.1 |

-continued
| Intermediate | Structural formula | LC-MS [M + H]+ |
|---|---|---|
| I-120 | 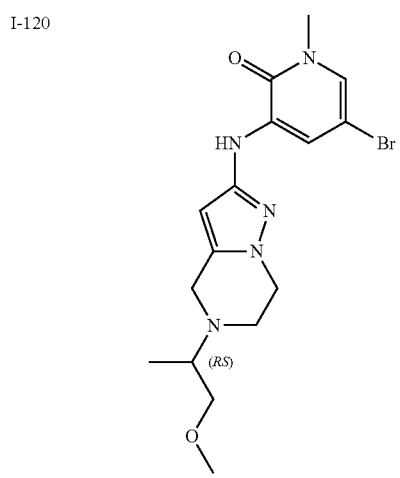 | 396.1, 398.1 |
| I-122 | 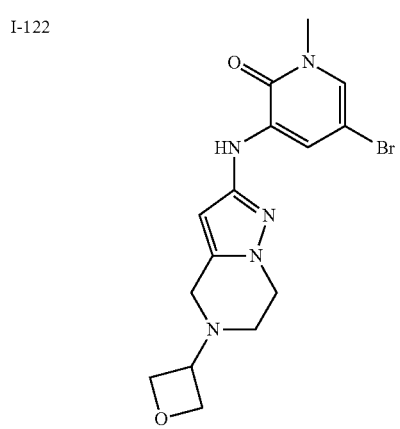 | 380.0, 382.0 |
| I-123 | 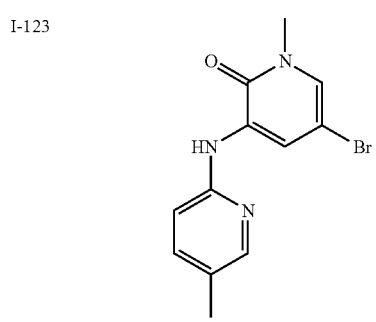 | 294.0, 296.0 |
| I-124 | 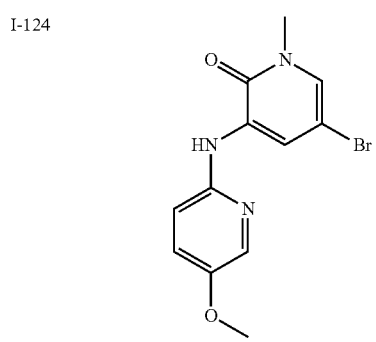 | 310.0, 312.0 |
-continued
| Intermediate | Structural formula | LC-MS [M + H]+ |
|---|---|---|
| I-130 | 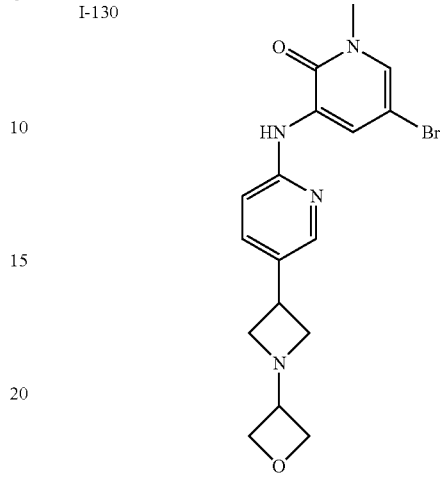 | 391.0, 393.0 |
| I-131 | 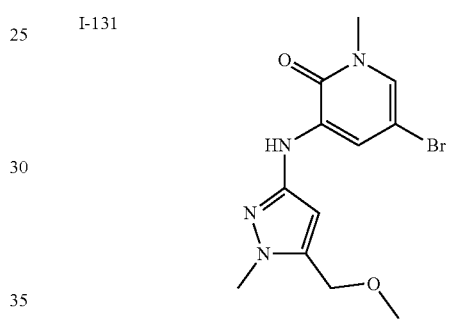 | 327.0, 329.0 |
| I-132 | 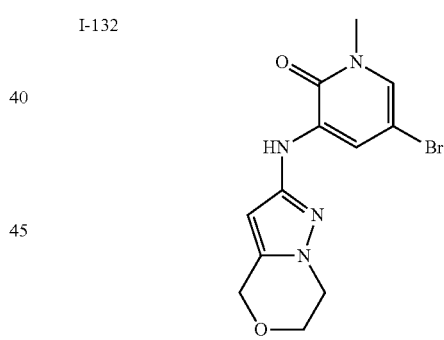 | 325.0, 327.0 |
| I-133 | 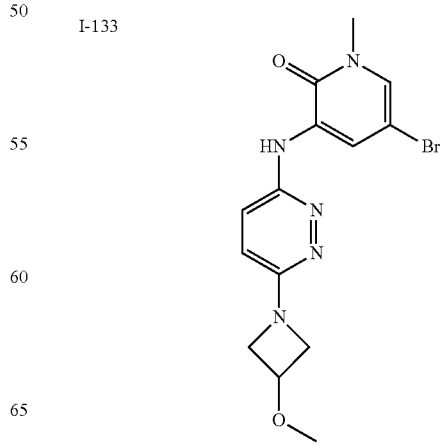 | 366.1, 368.0 |

-continued

| Intermediate | Structural formula | LC-MS [M + H]+ |
|---|---|---|
| I-135 | | 352.0, 354.0 |
| I-137 | | 311.0, 313.0 |
| I-138 | | 378.1, 380.01 |
| I-139 | | 364.0, 366.0 |

-continued

| Intermediate | Structural formula | LC-MS [M + H]+ |
|---|---|---|
| I-140 | | 297.0, 299.0 |
| I-141 | | 311.0, 313.0 |
| I-142 | | 311.0, 313.0 |
| I-143 | | 327.0, 329.0 |

323
-continued

| Intermediate | Structural formula | LC-MS [M + H]+ |
|---|---|---|
| I-147 | | 379.0, 381.0 |
| I-148 | | 367.0, 369.0 |
| I-149 | | 448.1, 450.1 |
| I-150 | | 380.0, 382.0 |

324
-continued

| Intermediate | Structural formula | LC-MS [M + H]+ |
|---|---|---|
| I-151 | | 435.1, 437.1 |
| I-152 | | 420.7, 422.7 |
| I-153 | | 405.1 |

-continued

| Intermediate | Structural formula | LC-MS [M + H]+ |
|---|---|---|
| I-154 | | 448.1, 450.1 |
| I-155 | | 449.1, 451.1 |
| I-156 | | 436.1, 438.1 |

-continued

| Intermediate | Structural formula | LC-MS [M + H]+ |
|---|---|---|
| I-157 | | 450.1, 452.1 |
| I-158 | | 462.1, 464.1 |
| I-159 | | 380.2, 382.2 |

| Intermediate | Structural formula | LC-MS [M + H]+ |
|---|---|---|
| I-160 | | 435.1, 437.1 |
| I-161 | | 393.8, 395.8 |
| I-163 | | 450.1, 452.1 |
| I-164 | | 450.1, 452.1 |
| I-187 | | 424.1, 426.1 |
Intermediate I-4
(3-(acetoxymethyl)-2-(7,7-dimethyl-1-oxo-1,6,7,8-tetrahydro-2H-cyclopenta[4,5]pyrrolo[1,2-a]pyrazin-2-yl)pyridin-4-yl)boracic Acid
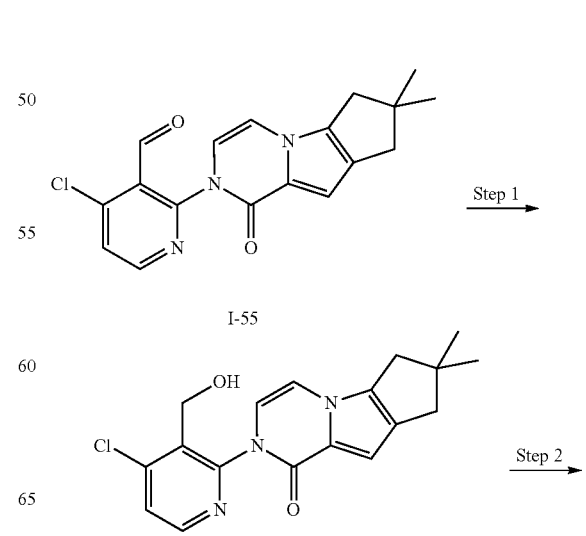

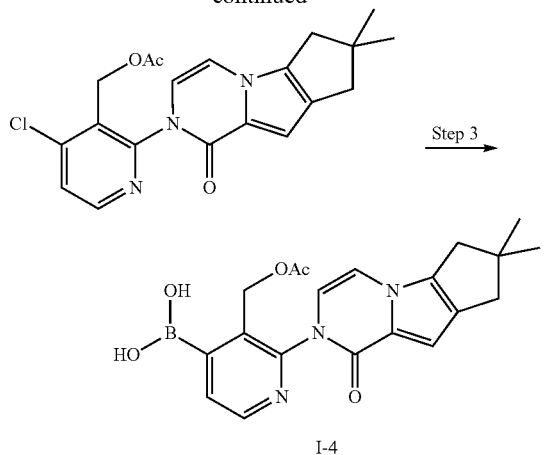

Step 1: 2-(4-chloro-3-(hydroxymethyl)pyridin-2-yl)-7,7-dimethyl-7,8-dihydro-2H-cyclopenta[4,5]pyrrolo[1,2-a]pyrazin-1(6H)-one At 0-5° C., under nitrogen, to a solution of 4-chloro-2-(7,7-dimethyl-1-oxo-1,6,7,8-tetrahydro-2H-cyclopenta[4,5]pyrrolo[1,2-a]pyrazin-2-yl) nicotinaldehyde (1.71 g, 5.0 mmol) (intermediate I-55) in methanol (5 mL) and dichloromethane (15 mL) was added sodium borohydride (0.13 g, 3.5 mmol), and the mixture was reacted at this temperature for 10 minutes. A saturated aqueous ammonium chloride solution (5 mL) was added to the reaction solution, and the mixture was extracted with dichloromethane (30 mL×2). The organic phase was collected and combined, and concentrated in vacuum under reduced pressure to give the target product (1.72 g, yield 100%), which was directly used in the next step. [M+H]$^+$ 344.1

Step 2: Acetic acid (4-chloro-2-(7,7-dimethyl-1-oxo-1,6,7,8-tetrahydro-2H-cyclopenta[4,5]pyrrolo[1,2-a]pyrazin-2-yl)pyridin-3-yl)methyl ester At 0-5° C., under nitrogen, to a solution of 2-(4-chloro-3-(hydroxymethyl)pyridin-2-yl)-7,7-dimethyl-7,8-dihydro-2H-cyclopenta[4,5]pyrrolo[1,2-a]pyrazin-1(6H)-one (1.72 g, 5.0 mmol) and triethylamine (2.53 g, 25 mmol) in dichloromethane (30 mL) was added acetylchloride (1.18 g, 15 mmol), and the mixture was reacted at this temperature for 1 hour. Water (20 mL) and dichloromethane (30 mL) were added to the reaction solution, the organic phase was collected and combined, and concentrated in vacuum under reduced pressure, and the resulting residue was purified with silica gel column chromatography (petroleum ether/ethyl acetate) to give the target product (1.65 g, yield 86%). [M+H]$^+$ 386.1

Step 3: (3-(acetoxymethyl)-2-(7,7-dimethyl-1-oxo-1,6,7,8-tetrahydro-2H-cyclopenta[4,5]pyrrolo[1,2-a]pyrazin-2-yl)pyridin-4-yl)boracic Acid Under nitrogen, to a solution of acetic acid (4-chloro-2-(7,7-dimethyl-1-oxo-1,6,7,8-tetrahydro-2H-cyclopenta[4,5]pyrrolo[1,2-a]pyrazin-2-yl)pyridin-3-yl)methyl ester (3.0 g, 7.79 mmol), bis(pinacolato)diboron (5.9 g, 23.3 mmol) in 1,4-dioxane (120 mL) was added Xphos (333 mg, 0.7 mmol), Pd(dppf)Cl$_2$ CH$_2$Cl$_2$ (570 mg, 0.7 mmol) and potassium acetate (2.3 g, 23.3 mmol). The mixture was reacted at 90° C. for 16 hours, and then cooled to room temperature. The reaction solution was concentrated in vacuum under reduced pressure, and the resulting residue was purified with silica gel column chromatography (methanol/water) to give the target product (2.9 g, yield 94%). [M+H]$^+$ 396.1

The intermediates in the following table were prepared with corresponding materials and reagents according to the preparation steps of intermediate T-4:

| Intermediate | Structural formula | LC-MS [M + H]$^+$ |
|---|---|---|
| I-114 | | 397.1 |
| I-121 | | 411.1 |
| I-129 | | 368.1 |

331

Intermediate I-5

5-bromo-3-((1-ethyl-1H-1,2,3-triazole-4-yl)amino)-1-methylpyrazin-2(1H)-one

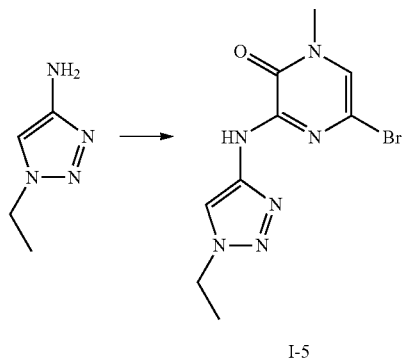

I-5

Under nitrogen, 3,5-dibromo-1-methylpyrazin-2(1H)-one (5.0 g, 18.7 mmol) and 1-ethyl-1H-1,2,3-triazole-4-amine (2.1 g, 18.7 mmol) were dissolved in N-methylpyrrolidone (7 mL). The mixture was reacted at 120° C. for 3 hours, and cooled to room temperature. The mixture was filtered, and the filter cake was washed with methanol (5 mL), to give the target product (3.9 g, yield 50%). [M+H]$^+$ 299.0, 301.0

The intermediate in the following table was prepared with corresponding materials and reagents according to the preparation steps of intermediate I-5:

| Intermediate | Structural formula | LC-MS [M + H]$^+$ |
|---|---|---|
| I-6 | | 313.0, 315.0 |

Intermediate I-13

(S)-5-bromo-1,6-dimethyl-3-((5-(2-methyl-4-(oxetan-3-yl)piperazin-1-yl)pyridin-2-yl)amino)pyridin-2(1H)-one

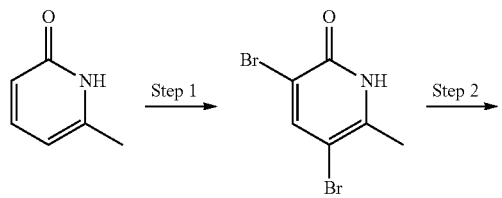

332

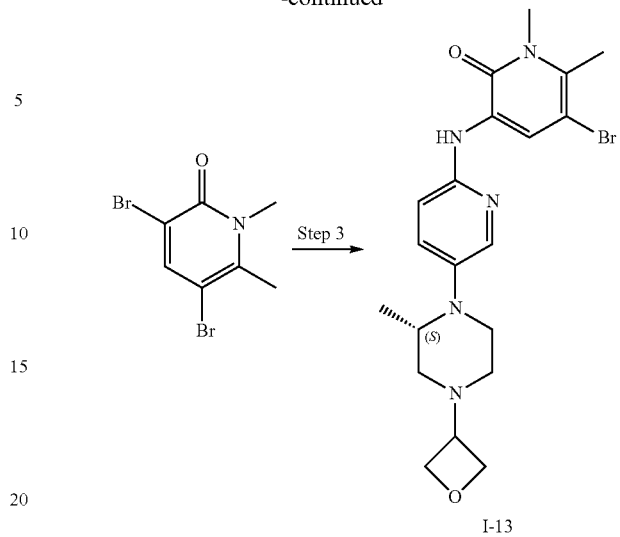

I-13

Step 1: 3,5-dibromo-6-methylpyridin-2(1H)-one

Under nitrogen, to a solution of 6-methylpyridin-2(1H)-one (949 mg, 8.7 mmol) in DMF(30 mL) was added NBS (3.1 g, 17.4 mmol). The mixture was reacted at room temperature for 4 hours. The reaction solution was poured into water (50 mL), and the precipitated solid was collected, and then washed with methanol to give the target product, which was directly used in the next step.

Step 2: 3,5-dibromo-1,6-dimethylpyridin-2(1H)-one

Under nitrogen, to a solution of 3,5-dibromo-6-methylpyridin-2(1H)-one (2.3 g, 8.7 mmol) in DMF(30 mL) was added iodomethane (1.3 g, 8.7 mmol) and cesium carbonate (1.6 g, 11.3 mmol). The mixture was reacted at room temperature for 2 hours. The reaction solution was poured into water (50 mL), the precipitated solid was collected, and then the solid was washed with methanol to give the target product (2.2 g, two-step yield 92%). [M+H]$^+$ 281.8

Step 3: (S)-5-bromo-1,6-dimethyl-3-((5-(2-methyl-4-(oxetan-3-yl)piperazin-1-yl)pyridin-2-yl)amino)pyridin-2(1H)-one The intermediate I-13 was prepared with 3,5-dibromo-1,6-dimethylpyridin-2(1H)-one and corresponding reagents according to the corresponding steps of intermediate I-2. [M+H]$^+$ 448.1, 450.1

Intermediate I-16

(S)-6-chloro-2-ethyl-4-((5-(2-methyl-4-(oxetan-3-yl)piperazin-1-yl)pyridin-2-yl)amino) pyridazine-3(2H)-one

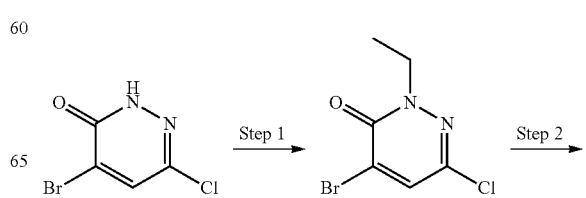

333

-continued

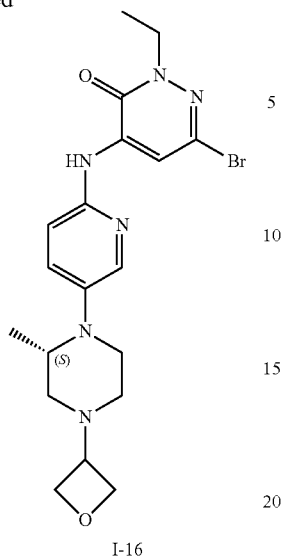

I-16

Step 1: 4-bromo-6-chloro-2-ethylpyridazine-3(2H)-one

At 0-5° C., under nitrogen, to a solution of 4-bromo-6-chloro-3(2H)-one (1.0 g, 4.8 mmol) in DMF(20 mL) was added 60% sodium hydride (mineral oil dispersion) (0.46 g, 11.5 mmol). The mixture was reacted at 0-5° C. for 30 minutes, then iodoethene (1.5 g, 9.6 mmol) was added, and the reaction was continued at room temperature for 5 minutes. The reaction solution was poured into water, extracted with ethyl acetate, the organic phase was collected and combined, and concentrated in vacuum under reduced pressure, and the resulting residue was purified with silica gel column chromatography (methanol/water) to give the target product (0.91 g, yield 80%). [M+H]$^+$ 238.9

Step 2: (S)-6-chloro-2-ethyl-4-((5-(2-methyl-4-(oxetan-3-yl)piperazin-1-yl)pyridin-2-yl)amino)pyridazine-3(2H)-one The intermediate I-16 was prepared with 4-bromo-6-chloro-2-ethylpyridazine-3(2H)-one and corresponding reagents according to the corresponding steps of intermediate I-2. [M+H]$^+$ 405.1

Intermediate I-31

5-bromo-1-methyl-3-((1-(2,2,2-trifluoroethyl)-1H-1,2,3-triazole-4-yl)amino)pyridin-2(1H)-one

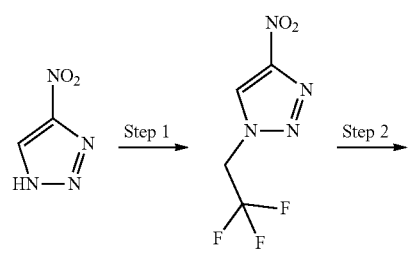

334

-continued

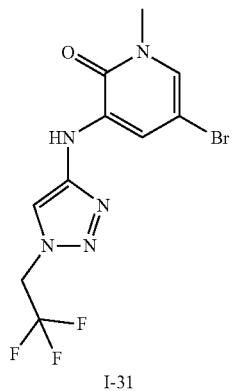

I-31

Step 1: 4-nitro-1-(2,2,2-trifluoroethyl)-1H-1,2,3-triazole

At 0-5° C., under nitrogen, to a solution of 4-nitro-1H-1,2,3-triazole (4.0 g, 35.1 mmol), 2-trifluoroethanol (5.12 mL, 43.8 mmol) and triphenylphosphine (18.4 g, 43.8 mmol) in tetrahydrofuran (180 ml) was added DIAD (13.9 g, 43.8 mmol). The mixture was reacted at 60° C. for 16 hours, and then cooled to room temperature, concentrated in vacuum under reduced pressure, and the resulting residue was purified with silica gel column chromatography (petroleum ether/ethyl acetate) to give the target product (4.61 g, yield 68%). [M+H]$^+$ 197.0

Step 2: 5-bromo-1-methyl-3-((1-(2,2,2-trifluoroethyl)-1H-1,2,3-triazole-4-yl)amino)pyridin-2(1H)-one The intermediate I-31 was prepared with 4-nitro-1-(2,2,2-trifluoroethyl)-1H-1,2,3-triazole and corresponding reagents according to the corresponding steps of intermediate I-3. [M+H]$^+$ 352.0, 353.9

The intermediates in the following table were prepared with corresponding materials and reagents according to the preparation steps of intermediates I-31, I-3 and I-5:

| Intermediate | Structural formula | LC-MS [M + H]$^+$ |
|---|---|---|
| I-32 |  | 316.0, 318.0 |

335
-continued

| Intermediate | Structural formula | LC-MS [M + H]+ |
|---|---|---|
| I-133 | | 317.0, 319.0 |
| I-134 | | 353.0, 354.9 |
| I-142 | | 343.0, 345.0 |

336

Intermediate I-37

5-bromo-1-methyl-3-((1'-(oxetan-3-yl)-1',2',3',6'-tetrahydro-[3,4'-bispyridin]-6-yl)amino)pyridin-2 (1H)-one

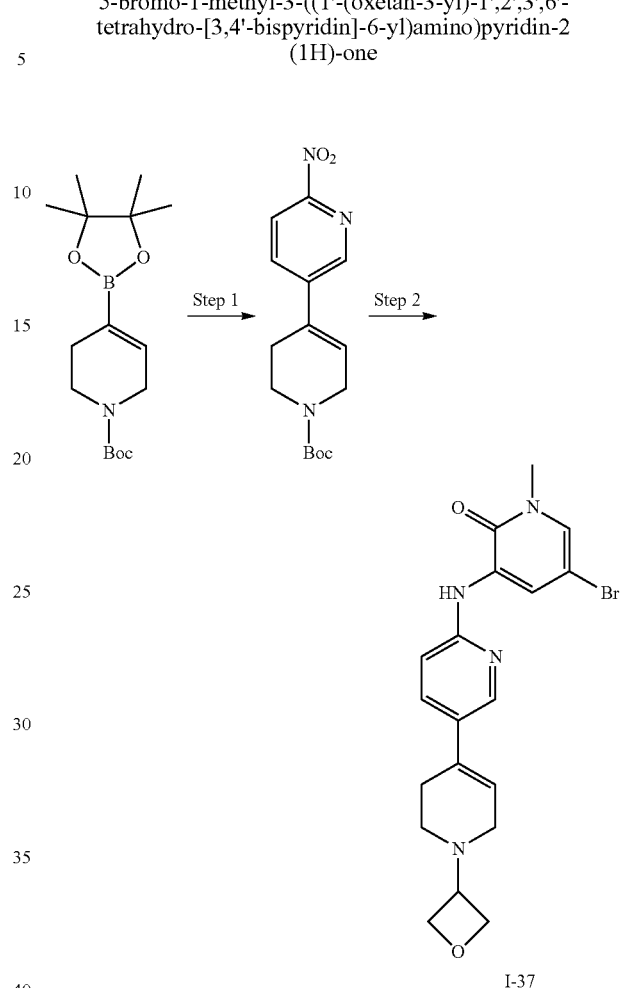

I-37

Step 1: t-butyl 6-nitro-3',6'-dihydro-[3,4'-bispyridin]-1'(2'H)carboxylate

Under nitrogen, to a solution of 1-nitrogen-tert-butyl-4,5-cyclohexene-4-borate (4.41 g, 15 mmol), 5-fluoro-2-nitropyridine (3.03 g, 15 mmol) in 1,4-dioxane (20 mL) and water (2 mL) was added Pd(dppf)Cl$_2$ CH$_2$Cl$_2$ (612 mg, 0.75 mmol) and sodium carbonate (3.18 g, 30 mmol). The mixture was reacted at 100° C. for 3 hours, and then cooled to room temperature, concentrated in vacuum under reduced pressure, and the resulting residue was purified with silica gel column chromatography (petroleum ether/ethyl acetate) to give the target product (4.58 g, yield 100%). [M+H]$^+$ 306.1

Step 2: 5-bromo-1-methyl-3-((1'-(oxetan-3-yl)-1',2',3',6'-tetrahydro-[3,4'-bispyridin]-6-yl)amino)pyridin-2(1H)-one The intermediate I-37 was prepared with t-butyl 6-nitro-3',6'-dihydro-[3,4'-bispyridin]-1'(2'H) carboxylate and corresponding reagents according to the corresponding steps of intermediate I-2. [M+H]$^+$ 417.0, 419.0

The intermediate in the following table was prepared with corresponding materials and reagents according to the preparation steps of intermediate I-37:

| Intermediate | Structural formula | LC-MS [M + H]+ |
|---|---|---|
| I-38 | 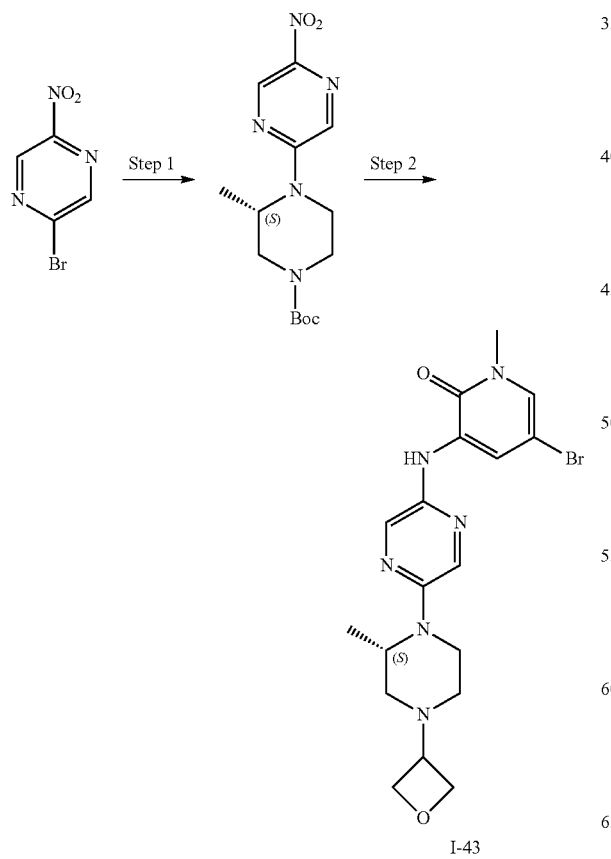 | 412.0, 414.0 |

Intermediate I-43

(S)-5-bromo-1-methyl-3-((5-(2-methyl-4-(oxetan-3-yl)piperazin-1-yl)pyrazin-2-yl)aminopyridin-2(1H)-one

Step 1: t-butyl (S)-3-methyl-4-(5-nitropyrazin-2-yl)piperazin-1-carboxylate

To a solution of 2-bromo-5-nitropyrazine (1.22 g, 6.0 mmol), t-butyl (S)-3-methylpiperazin-1-carboxylate (1.00 g, 5.0 mmol) in DMF(10 mL) was added potassium carbonate (1.38 g, 10 mmol). The mixture was reacted at 80° C. for 4 hours, and then cooled to room temperature, concentrated in vacuum under reduced pressure, and the resulting residue was purified with silica gel column chromatography (petroleum ether/ethyl acetate) to give the target product (1.50 g, yield 93%). [M+H−56]+268.1

Step 2: (S)-5-bromo-1-methyl-3-((5-(2-methyl-4-(oxetan-3-yl)piperazin-1-yl)pyrazin-2-yl)amino)pyridin-2(1H)-one The intermediate I-43 was prepared with t-butyl (S)-3-methyl-4-(5-nitropyrazin-2-yl) piperazin-1-carboxylate and corresponding reagents according to the corresponding steps of intermediate I-2. [M+H]+ 435.1, 437.1

Intermediate I-44

(S)-5-bromo-1-methyl-3-((5-(2-methyl-4-(oxetan-3-yl)piperazin-1-yl)pyrimidin-2-yl)amino)pyridin-2(1H)-one

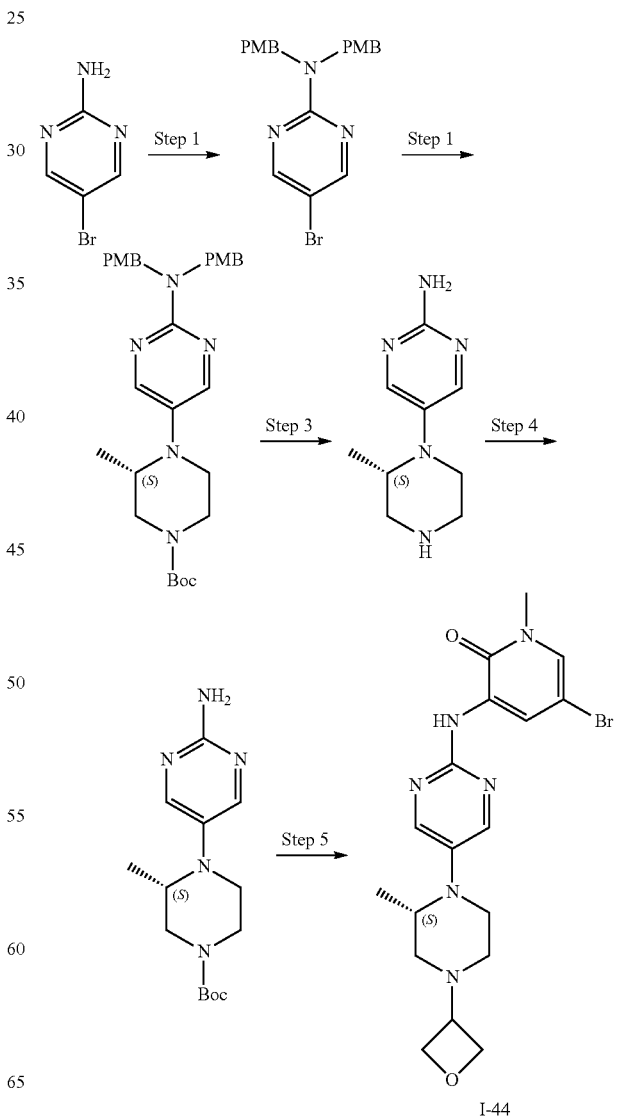

Step 1: 5-bromo-N,N-bis(4-methoxy benzyl)pyrimidin-2-amine

At 0-5° C., under nitrogen, to a solution of 5-bromopyrimidin-2-amine (3.48 g, 20 mmol) in tetrahydrofuran (60 mL) was added 60% sodium hydride (mineral oil dispersion) (1.72 g, 43 mmol). The mixture was reacted at 0-5° C. for 30 minutes, then p-methoxybenzyl chloride (7.83 g, 50 mmol) was added, and the reaction was continued at 75° C. for 8 hours. The reaction solution was poured into water, extracted with ethyl acetate, the organic phase was collected and combined, and concentrated in vacuum under reduced pressure, and the resulting residue was purified with silica gel column chromatography (petroleum ether/ethyl acetate) to give the target product (2.07 g, yield 25%). [M+H]$^+$ 414.1, 416.1

Step 2: t-butyl (S)-4-(2-(bis(4-methoxy benzyl)amino)pyrimidin-5-yl)-3-methylpiperazin-1-carboxylate Under nitrogen, to a solution of 5-bromo-N,N-bis(4-methoxy benzyl)pyrimidin-2-amine (2.07 g, 5.0 mmol) and t-butyl (S)-3-methylpiperazin-1-carboxylate (10.0 g, 49.0 mmol) in toluene (30 mL) was added BINAP (311 mg, 0.50 mmol), Pd$_2$(dba)$_3$ (229 mg, 0.25 mmol) and tert-butoxysodium (960 mg, 10 mmol). The mixture was reacted at 80° C. for 8 hours, and then cooled to room temperature. The reaction solution was concentrated in vacuum under reduced pressure, and the resulting residue was purified with silica gel column chromatography (petroleum ether/ethyl acetate) to give the target product (1.60 g, yield 30%). [M+H]$^+$ 534.3

Step 3: (S)-5-(2-methylpiperazin-1-yl)pyrimidin-2-amine

Under nitrogen, a solution of t-butyl (S)-4-(2-(bis(4-methoxy benzyl)amino)pyrimidin-5-yl)-3-methylpiperazin-1-carboxylate (1.60 g, 3.0 mmol) in trifluoroacetic acid (10 mL) was stirred at room temperature for 30 minutes, concentrated in vacuum under reduced pressure, to give the target product, which was directly used in the next step. [M+H]$^+$ 194.1

Step 4: t-butyl (S)-4-(2-aminopyrimidin-5-yl)-3-methylpiperazin-1-carboxylate To a solution of (S)-5-(2-methylpiperazin-1-yl)pyrimidin-2-amine obtained from the previous step and di-tert-butyl dicarbonate (720 mg, 3.3 mmol) in dichloromethane (10 mL) was added triethylamine (455 mg, 4.5 mmol). The mixture was reacted at room temperature for 1 hours. The mixture was concentrated in vacuum under reduced pressure, and the resulting residue was purified with silica gel column chromatography (dichloromethane/methanol) to give the target product (880 mg, two-step yield 100%). [M+H]$^+$ 294.1

Step 5: (S)-5-bromo-1-methyl-3-((5-(2-methyl-4-(oxetan-3-yl)piperazin-1-yl)pyrimidin-2-yl)amino)pyridin-2(1H)-one The intermediate I-44 was prepared with t-butyl (S)-4-(2-aminopyrimidin-5-yl)-3-methylpiperazin-1-carboxylate and corresponding reagents according to the corresponding steps of intermediate I-2. [M+H]$^+$ 435.0, 437.0

Intermediate I-45

5-bromo-1-methyl-3-((5-((tetrahydro-2H-pyran-3-yl)amino)pyridin-2-yl)amino)pyridin-2(1H)-one

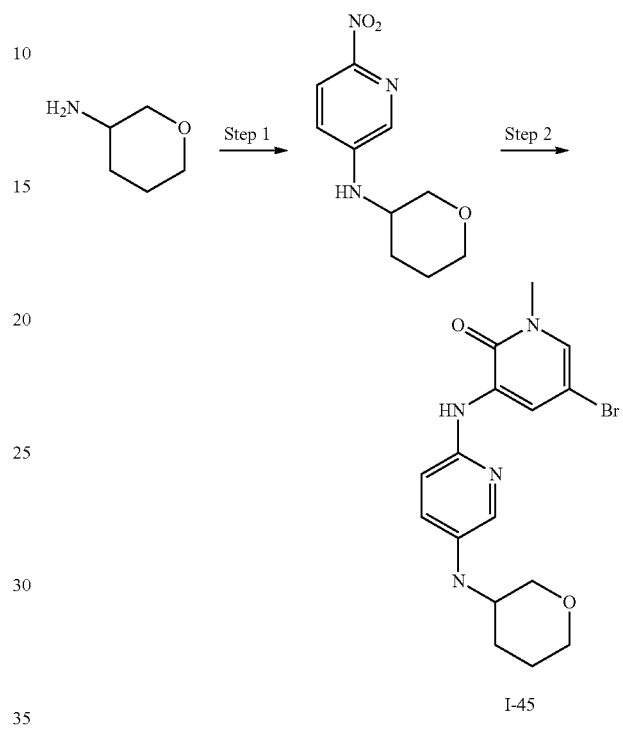

I-45

Step 1: 6-nitro-N-(tetrahydro-2H-pyran-3-yl)pyridin-3-amine

Under nitrogen, to a solution of tetrahydro-2H-pyran-3-amine (0.61 g, 6.0 mmol) and 5-bromo-2-nitropyridine (1.46 g, 7.2 mmol) in 1,4-dioxane (50 mL) was added BINAP (0.37 g, 0.60 mmol), Pd$_2$(dba)$_3$ (0.55 g, 0.60 mmol) and cesium carbonate (3.91 g, 12 mmol). The mixture was reacted at 100° C. for 16 hours, and then cooled to room temperature. The reaction solution was concentrated in vacuum under reduced pressure, and the resulting residue was purified with silica gel column chromatography (dichloromethane/methanol) to give the target product (0.72 g, yield 54%). [M+H]$^+$ 224.1

Step 2: 5-bromo-1-methyl-3-((5-((tetrahydro-2H-pyran-3-yl)amino)pyridin-2-yl)amino)pyridin-2(1H)-one The intermediate I-45 was prepared with 6-nitro-N-(tetrahydro-2H-pyran-3-yl) pyridin-3-amine and corresponding reagents according to the corresponding steps of intermediate I-3. [M+H]$^+$ 379.0, 381.0

The intermediate in the following table was prepared with corresponding materials and reagents according to the preparation steps of intermediate I-45:

| Intermediate | Structural formula | LC-MS [M + H]+ |
|---|---|---|
| I-46 | | 409.0, 411.0 |

Intermediate I-47

5-bromo-1-methyl-3-((5-(morpholin-4-carbonyl)pyridin-2-yl)amino)pyridin-2(1H)-one

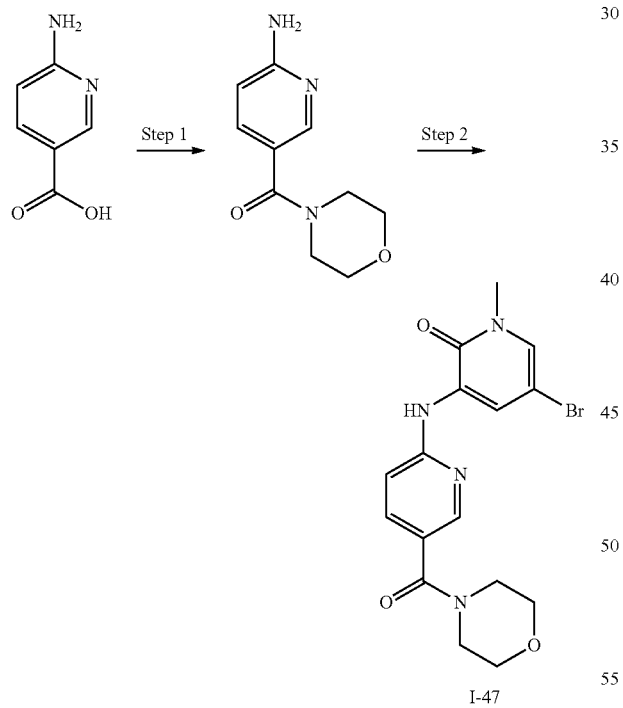

I-47

Step 1: (6-aminopyridin-3-yl)(morpholino)ketone

Under nitrogen, a solution of 6-aminonicotinic acid (1.38 g, 10 mmol), CDI(1.95 g, 12 mmol) in DMF (12 mL) was reacted at 70° C. for 1 hour, and then stirred at room temperature for 1 hour. Morpholine (1.74 g, 20 mmol) was added to the mixture, and the mixture was reacted at room temperature for 16 hours. The reaction solution was concentrated in vacuum under reduced pressure, and the result-ing residue was purified with silica gel column chromatography (dichloromethane/methanol) to give the target product (1.05 g, yield 51%). [M+H]+ 208.1

Step 2: 5-bromo-1-methyl-3-((5-(morpholin-4-carbonyl)pyridin-2-yl)amino)pyridin-2(1H)-one The intermediate I-47 was prepared with (6-aminopyridin-3-yl)(morpholino)ketone and corresponding reagents according to the corresponding steps of intermediate I-3. [M+H]+ 393.0, 395.0

The intermediates in the following table were prepared with corresponding materials and reagents according to the preparation steps of intermediate I-47:

| Intermediate | Structural formula | LC-MS [M + H]+ |
|---|---|---|
| I-48 | | 406.0, 408.0 |
| I-165 | | 396.0, 398.0 |

Intermediate I-52

4-chloro-2-(6-fluoro-1-oxopyrazino[1,2-a]indol-2(1H)-yl)nicotinaldehyde

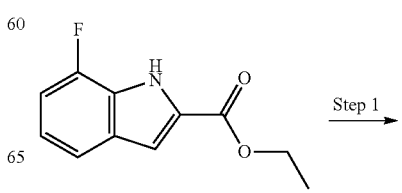

Step 1

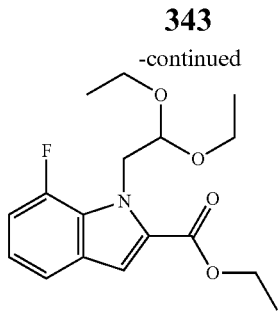

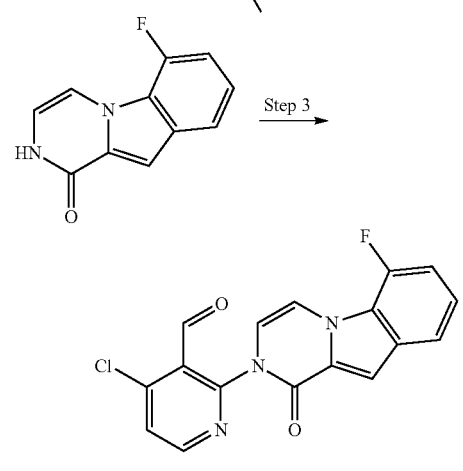

I-52

Step 1: Ethyl 1-(2,2-diethoxyethyl)-7-fluoro-1H-indol-2-carboxylate

To a solution of ethyl 7-fluoro-1H-indol-2-carboxylate (2.07 g, 10 mmol) in DMF(15 mL) was added 2-bromo-1,1-diethoxyethane (4.0 g, 20 mmol) and cesium carbonate (8.2 g, 25 mmol). The mixture was reacted at 110° C. for 16 hours, and then cooled to room temperature, poured into water, and extracted with ethyl acetate. The organic phase was collected and combined, and concentrated in vacuum under reduced pressure, and the resulting residue was purified with silica gel column chromatography (petroleum ether/ethyl acetate) to give the target product (2.5 g, yield 77%). [M+H–EtOH]+ 278.1

Step 2: 6-fluoropyrazino[1,2-a]indol-1(2H)-one

To a solution of ethyl 1-(2,2-diethoxyethyl)-7-fluoro-1H-indol-2-carboxylate (2.5 g, 7.7 mmol) in acetic acid (50 mL) was added ammonium acetate (12 g, 154 mmol). The mixture was reacted at 110° C. for 16 hours, and then cooled to room temperature, concentrated in vacuum under reduced pressure, and the resulting residue was purified with silica gel column chromatography (petroleum ether/ethyl acetate) to give the target product (2.5 g, yield 77%). [M+H]+ 203.0

Step 3: 4-chloro-2-(6-fluoro-1-oxopyrazino[1,2-a]indol-2(1H)-yl)nicotinaldehyde

The intermediate I-52 was prepared with 6-fluoropyrazino[1,2-a]indol-1(2H)-one and corresponding reagents according to the corresponding steps of intermediate I-1. [M+H]+ 342.0

The intermediates in the following table were prepared with corresponding materials and reagents according to the preparation steps of intermediates I-52 and I-1:

| Intermediate | Structural formula | LC-MS [M + H]+ |
|---|---|---|
| I-53 | | 342.0 |
| I-59 | | 342.0 |
| I-66 | | 325.0 |
| I-70 | | 324.0 |
| I-71 | | 342.0 |

Intermediate I-58

4-chloro-2-(7,7-difluoro-1-oxo-6,7,8,9-tetrahydropyrazino[1,2-a]indol-2(1H)-yl)nicotinaldehyde

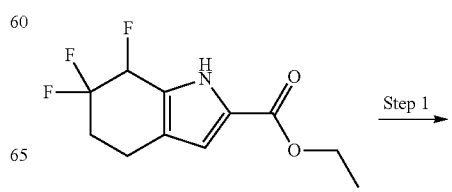

Step 1

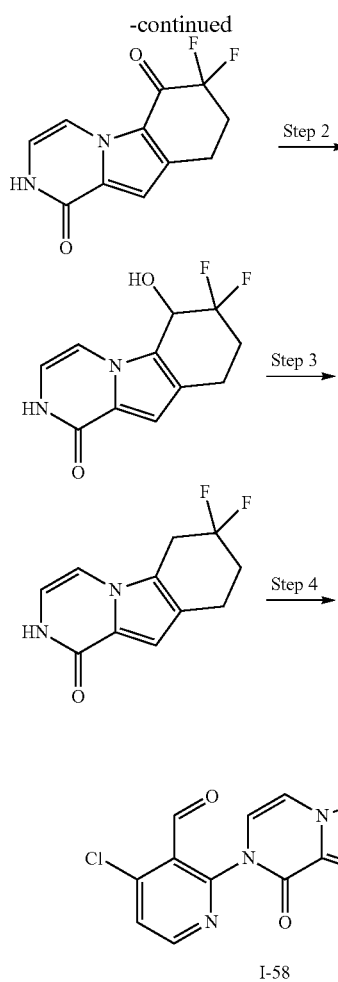

from the previous step in trifluoroacetic acid (5 mL) was added triethylsilane (771 mg, 6.3 mmol). The mixture was reacted at room temperature for 1 hour, and concentrated in vacuum under reduced pressure, a saturated aqueous sodium bicarbonate solution (10 mL) was added to the resulting residue, and the mixture was extracted with dichloromethane (10 mL×2). The organic phase was collected and combined, and concentrated in vacuum under reduced pressure, and the resulting residue was purified with silica gel column chromatography (methanol/water) to give the target product (120 mg, two-step yield 26%). [M+H]$^+$ 225.0

Step 4: 4-chloro-2-(7,7-difluoro-1-oxo-6,7,8,9-tetrahydropyrazino[1,2-a]indol-2(1H)-yl)nicotinaldehyde The intermediate I-58 was prepared with 7,7-difluoro-6,7,8,9-tetrahydropyrazino[1,2-a]indol-1(2H)-one and corresponding reagents according to the corresponding steps of intermediate I-1. [M+H]$^+$ 364.0

The intermediate in the following table was prepared with corresponding materials and reagents according to the preparation steps of intermediate I-58:

| Intermediate | Structural formula | LC-MS [M + H]$^+$ |
|---|---|---|
| I-60 | 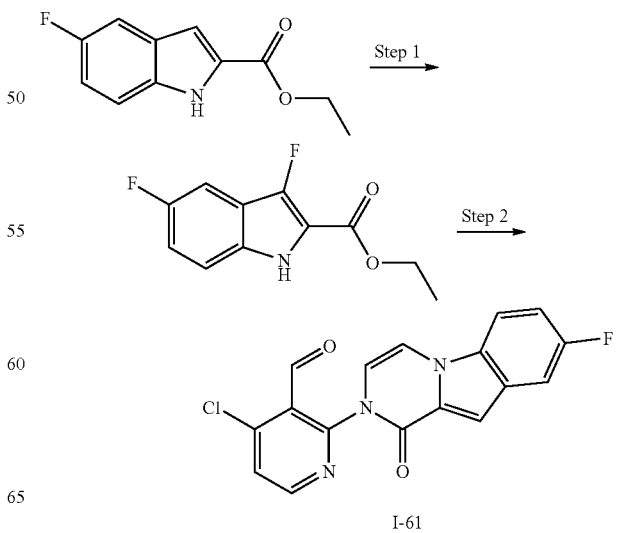 | 364.0 |

Intermediate I-61

4-chloro-2-(8,10-difluoro-1-oxopyrazino[1,2-a]indol-2(1H)-yl)nicotinaldehyde

Step 1: 7,7-difluoro-8,9-dihydropyrazino[1,2-a]indol-1,6(2H,7H)-dione

The target compound was prepared with ethyl 6,6-fluoro-7-oxo-4,5,6,7-tetrahydro-1H-indol-2-carboxylate according to the corresponding steps of intermediate I-1. [M+H]$^+$ 239.0

Step 2: 7,7-difluoro-6-hydroxyl-6,7,8,9-tetrahydropyrazino[1,2-a]indol-1(2H)-one At 0-5° C., under nitrogen, to a solution of 7,7-difluoro-8,9-dihydropyrazino[1,2-a]indol-1,6(2H,7H)-dione (500 mg, 2.1 mmol) in methanol (10 mL) was added sodium borohydride (239 mg, 6.3 mmol), and the mixture was reacted at this temperature for 10 minutes. A saturated aqueous ammonium chloride solution (5 mL) was added to the reaction solution, and the mixture was extracted with dichloromethane (10 mL×2). The organic phase was collected and combined, and concentrated in vacuum under reduced pressure to give the target product, which was directly used in the next step.

Step 3: 7,7-difluoro-6,7,8,9-tetrahydropyrazino[1,2-a]indol-1(2H)-one

Under nitrogen, to a solution of 7,7-difluoro-6-hydroxyl-6,7,8,9-tetrahydropyrazino[1,2-a]indol-1(2H)-one obtained

Step 1: Ethyl 3,5-difluoro-1H-indol-2-carboxylate

At 0-5° C., under nitrogen, to a solution of ethyl 5-fluoro-1H-indol-2-carboxylate (4.14 g, 20 mmol) in acetonitrile (100 mL) was added Selectfluor (7.08 g, 20 mmol), and the mixture was reacted at this temperature for 16 hours. A saturated aqueous ammonium chloride solution (20 mL) and water (100 mL) were added to the reaction solution, and the mixture was extracted with ethyl acetate (50 mL×2). The organic phase was collected and combined, and concentrated in vacuum under reduced pressure, and the resulting residue was purified with silica gel column chromatography (ethyl acetate/petroleum ether) to give the target product (2.4 g, yield 53%). [M+H]$^+$ 226.0.

Step 2: 4-chloro-2-(8,10-difluoro-1-oxopyrazino[1,2-a]indol-2(1H)-yl)nicotinaldehyde The intermediate I-61 was prepared with ethyl 3,5-difluoro-1H-indol-2-carboxylate and corresponding reagents according to the corresponding steps of intermediate I-52. [M+H]$^+$ 360.0

Intermediate I-62

Acetic acid (2-(9-bromo-7,7-dimethyl-1-oxo-1,6,7,8-tetrahydro-2H-cyclopenta[4,5]pyrrolo[1,2-a]pyrazin-2-yl)-4-chloropyridin-3-yl)methyl ester

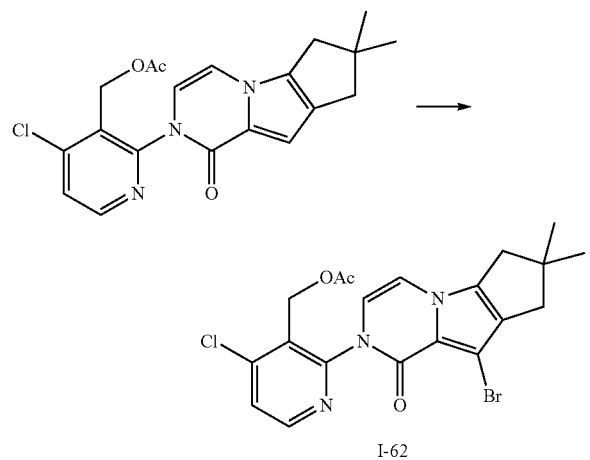

At 0° C., to a solution of acetic acid (4-chloro-2-(7,7-dimethyl-1-oxo-1,6,7,8-tetrahydro-2H-cyclopenta[4,5]pyrrolo[1,2-a]pyrazin-2-yl)pyridin-3-yl)methyl ester (800 mg, 2.07 mmol) in dichloromethane (30 mL) was added NBS (367 mg, 2.07 mmol). The mixture was reacted at room temperature for 16 hours, quenched with a saturated aqueous ammonium chloride solution, and extracted with ethyl acetate. The organic phase was collected and combined, dried with anhydrous sodium sulfate, and concentrated in vacuum under reduced pressure, and the resulting residue was purified with silica gel column chromatography (petroleum ether/ethyl acetate) to give the target product (800 mg, yield 83%). [M+H]$^+$ 464.0, 466.0

Intermediate I-63

4-chloro-2-(7,7-dimethyl-4-oxo-4,6,7,8-tetrahydro-3H-cyclopenta[4,5]pyrrolo[2,1-f][1,2,4]triazin-3-yl)nicotinaldehyde

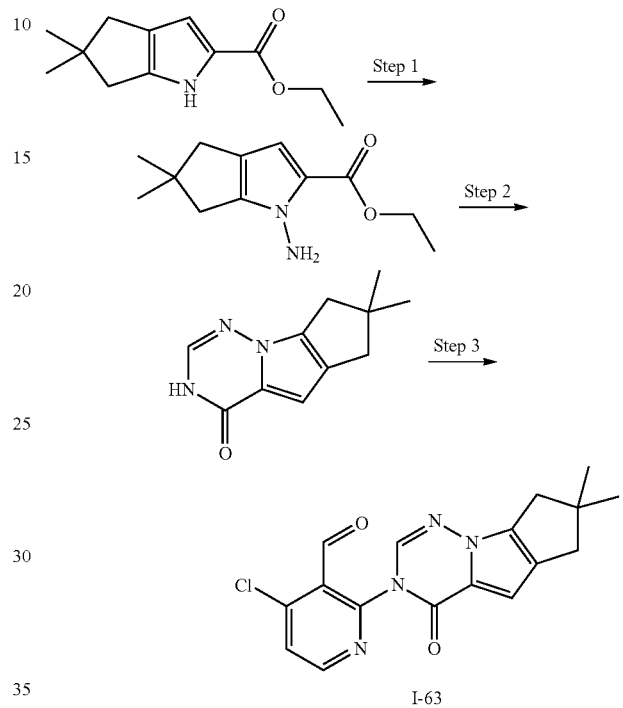

Step 1: Ethyl 1-amino-5,5-dimethyl-1,4,5,6-tetrahydrocyclopentadieno[b]pyrrole-2-carboxylate At 0-5° C., under nitrogen, to a solution of ethyl 5,5-dimethyl-1,4,5,6-tetrahydrocyclopentadieno[b]pyrrole-2-carboxylate (5.0 g, 24.1 mmol) in DMF (30 mL) was added 60% sodium hydride (mineral oil dispersion) (1.06 g, 26.5 mmol). The mixture was reacted at 0-5° C. for 30 minutes, then O-(2,4-dinitrophenyl) hydroxylamine (5.3 g, 26.5 mmol) was added to the reaction solution, and the mixture was reacted at room temperature for 3 hours. The mixture was concentrated in vacuum under reduced pressure, and the resulting residue was purified with silica gel column chromatography (petroleum ether/ethyl acetate) to give the target product (4.3 g, yield 75%). [M+H]$^+$ 223.0

Step 2: 7,7-dimethyl-7,8-dihydro-3H-cyclopenta[4,5]pyrrolo[2,1-f][1,2,4]triazin-4(6H)-one Under nitrogen, to a mixture of ethyl 1-amino-5,5-dimethyl-1,4,5,6-tetrahydrocyclopentadieno[b]pyrrole-2-carboxylate (4.3 g, 19.3 mmol) and formamide (30 mL) was added ammonium acetate (7.4 g, 96.5 mmol). The mixture was reacted at 140° C. for 16 hours, and then cooled to room temperature. The mixture was filtered, and the filter cake was collected and washed with methanol to give the target product (3.1 g, yield 80%). [M+H]$^+$ 204.0

Step 3: 4-chloro-2-(7,7-dimethyl-4-oxo-4,6,7,8-tetrahydro-3H-cyclopenta[4,5]pyrrolo[2,1-f][1,2,4]triazin-3-yl)nicotinaldehyde The intermediate I-63 was prepared with 7,7-dimethyl-7,8-dihydro-3H-cyclopenta[4,5]pyrrolo[2,1-f][1,2,4]triazin-4(6H)-one and corresponding reagents according to the corresponding steps of intermediate I-1. [M+H]+ 343.1

The intermediates in the following table were prepared with corresponding materials and reagents according to the preparation steps of intermediate I-63:

| Intermediate | Structural formula | LC-MS [M + H]+ |
|---|---|---|
| I-93 | | 329.0 |
| I-97 | | 347.0 |

Intermediate I-68

(8-((tert-butoxycarbonyl) (1-ethyl-1H-1,2,3-triazole-4-yl)amino)-[1,2,4]triazolo[1,5-a]pyridin-6-yl)boracic Acid

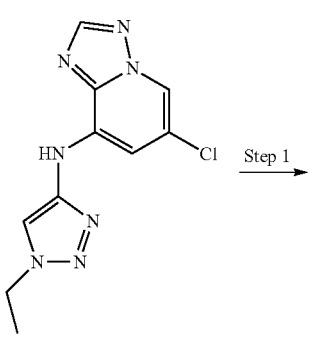

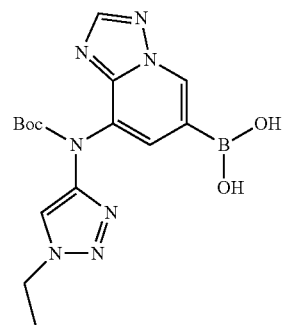

I-68

The intermediate I-68 was prepared with intermediate I-21 and corresponding reagents according to step 1 of intermediate I-74 and step 6 of intermediate I-2. [M+H]+ 374.1

The intermediate in the following table was prepared with corresponding materials and reagents according to the preparation steps of intermediate I-68:

| Intermediate | Structural formula | LC-MS [M + H]+ |
|---|---|---|
| I-72 | | 501.2 |

Intermediate I-74

4-chloro-2-(7-methyl-1-oxo-6,7,8,9-tetrahydropyrazino[1,2-a]indol-2(1H)-yl)nicotinaldehyde

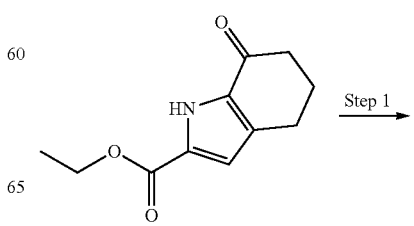

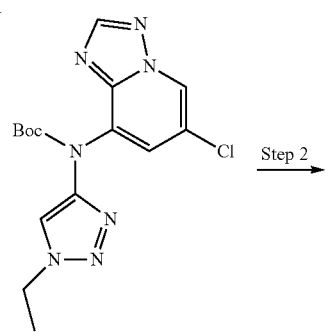

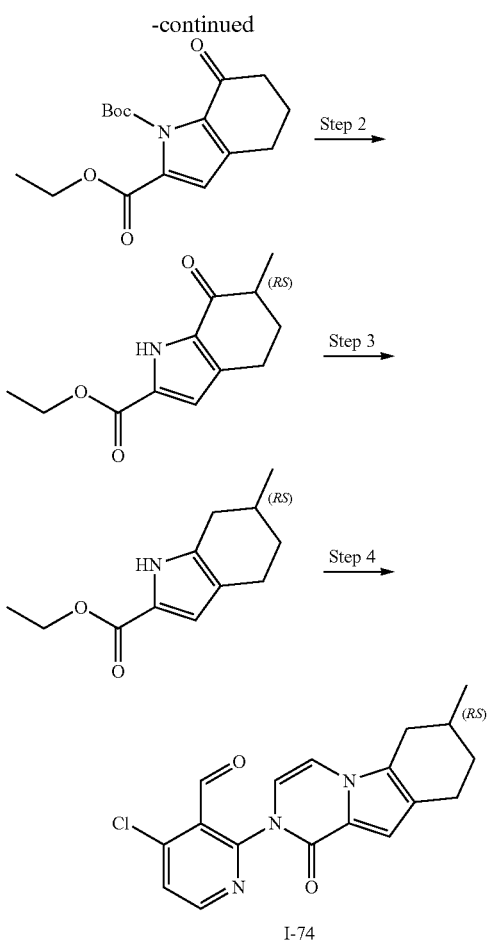

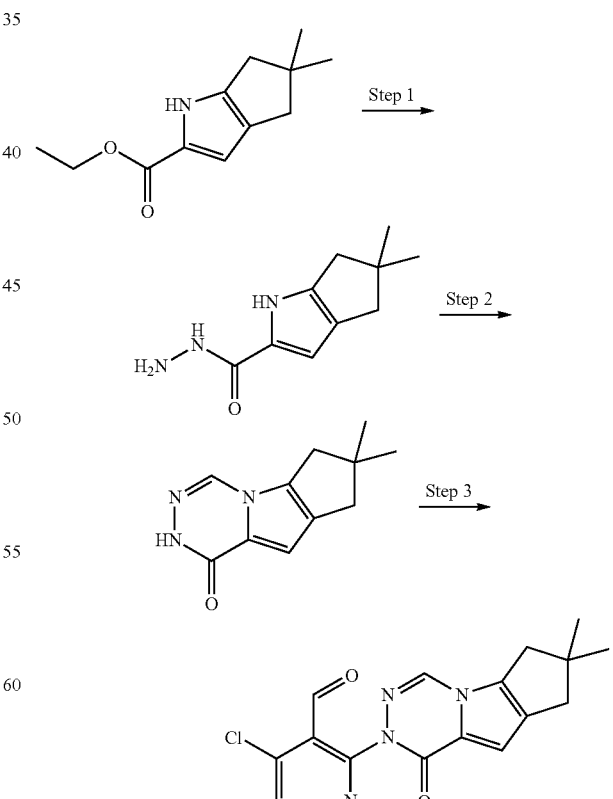

Step 1: 7-oxo-4,5,6,7-tetrahydro-1H-indol-1,2-dicarboxylic acid 1-(tert-butyl)ester 2-ethyl ester To a solution of ethyl 7-oxo-4,5,6,7-tetrahydro-1H-indol-2-carboxylate (2.07 g, 10 mmol) and di-tert-butyl dicarbonate (7.51 g, 30 mmol) in tetrahydrofuran (30 mL) was added 4-dimethylaminopyridine (0.12 g, 1.0 mmol). The mixture was reacted at room temperature for 16 hours. The mixture was concentrated in vacuum under reduced pressure, and the resulting residue was purified with silica gel column chromatography (petroleum ether/ethyl acetate) to give the target product (3.07 g, yield 100%). [M+Na]+330.3

Step 2: Ethyl 6-methyl-7-oxo-4,5,6,7-tetrahydro-1H-indol-2-carboxylate

At −78° C., under nitrogen, to a solution of 7-oxo-4,5,6,7-tetrahydro-1H-indol-1,2-dicarboxylic acid 1-(tert-butyl)ester 2-ethyl ester (3.07 g, 10 mmol) in tetrahydrofuran (50 mL) was dropwise added 1M HMDSLi/tetrahydrofuran solution (24 mL, 24 mmol), the mixture was naturally warmed to 0° C., and the reaction was continued for 30 minutes. At −78° C., iodomethane (3.41 g, 24 mmol) was dropwise added to the reaction solution, the mixture was naturally warmed to room temperature, and the reaction was continued for 4 hours. The reaction solution was cooled to 0° C., and quenched by adding a saturated aqueous ammonium chloride solution, extracted with ethyl acetate (50 mL×2). The organic phase was collected and combined, dried with anhydrous sodium sulfate, and concentrated in vacuum under reduced pressure. Under nitrogen, the resulting residue trifluoroacetic acid (10 mL) solution was stirred at room temperature for 30 minutes, and concentrated in vacuum under reduced pressure, and the resulting residue was purified with silica gel column chromatography (water/methanol) to give the target product (1.19 g, yield 54%). [M+H]+ 221.1

Step 3: Ethyl 6-methyl-4,5,6,7-tetrahydro-1H-indol-2-carboxylate

Under nitrogen, to a solution of ethyl 6-methyl-7-oxo-4,5,6,7-tetrahydro-1H-indol-2-carboxylate (1.19 g, 5.38 mmol) in trifluoroacetic acid (10 mL) was added triethylsilane (2.5 mL). The mixture was reacted at room temperature for 16 hours, and concentrated in vacuum under reduced pressure, and the resulting residue was purified with silica gel column chromatography (methanol/water) to give the target product (980 mg, yield 88%). [M+H]+ 208.1

Step 4: 4-chloro-2-(7-methyl-1-oxo-6,7,8,9-tetrahydropyrazino[1,2-a]indol-2(1H)-yl)nicotinaldehyde The intermediate I-74 was prepared with ethyl 6-methyl-4,5,6,7-tetrahydro-1H-indol-2-carboxylate and corresponding reagents according to the corresponding steps of intermediate I-1. [M+H]+ 342.0

Intermediate I-75

4-chloro-2-(7,7-dimethyl-1-oxo-1,6,7,8-tetrahydro-2H-cyclopenta[4,5]pyrrolo[1,2-d][1,2,4]triazin-2-yl)nicotinaldehyde

Step 1: 5,5-dimethyl-1,4,5,6-tetrahydrocyclopentadieno[b]pyrrole-2-carbohydrazide A solution of ethyl 5,5-dimethyl-1,4,5,6-tetrahydrocyclopentadieno[b]pyrrole-2-carboxylate (2.49 g, 12 mmol), an aqueous hydrazine hydrate solution (20 mL, 36 mmol) in ethanol (8 mL) was reacted in microwave reactor at 150° C. for 2 hours, and then cooled to room temperature. The reaction was filtered and washed with water, and the filter cake was collected, and dried in vacuum under reduced pressure to give the target product (2.09 g, yield 90%). [M+H]$^+$ 194.1

Step 2: 7,7-dimethyl-7,8-dihydro-2H-cyclopenta[4,5]pyrrolo[1,2-d][1,2,4]triazin-1(6H)-one Under nitrogen, a solution of 5,5-dimethyl-1,4,5,6-tetrahydrocyclopentadieno[b]pyrrole-2-carbohydrazide (2.09 g, 10.5 mmol), triethyl orthoformate (3.11 g, 21.0 mmol) in DMF(8 mL) was reacted at 160° C. for 16 hours. The reaction was cooled to room temperature, filtered, and washed with methanol, and the filter cake was collected, and dried in vacuum under reduced pressure to give the target product (1.65 g, yield 77%). [M+H]$^+$ 204.1

Step 3: 4-chloro-2-(7,7-dimethyl-1-oxo-1,6,7,8-tetrahydro-2H-cyclopenta[4,5]pyrrolo[1,2-d][1,2,4]triazin-2-yl)nicotinaldehyde The intermediate I-75 was prepared with 7,7-dimethyl-7,8-dihydro-2H-cyclopenta[4,5]pyrrolo[1,2-d][1,2,4]triazin-1(6H)-one and corresponding reagents according to the corresponding steps of intermediate I-1. [M+H]$^+$ 343.1

The intermediates in the following table were prepared with corresponding materials and reagents according to the preparation steps of intermediate I-75:

| Intermediate | Structural formula | LC-MS [M + H]$^+$ |
|---|---|---|
| I-82 | | 357.1 |
| I-85 | 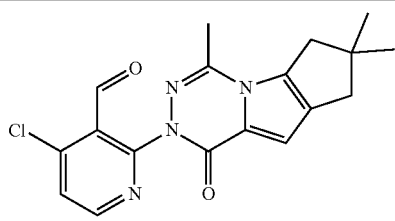 [SMILES: Cc1nn(-c2nccc(Cl)c2C=O)c(=O)c2cc3c(n12)CC(C)(C)C3] | 342.8 |
| I-86 | 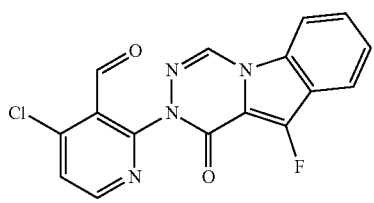 [SMILES: O=Cc1c(Cl)ccnc1-n1ncn2c(c(F)c3ccccc32)c1=O] | 343.0 |
| I-87 | 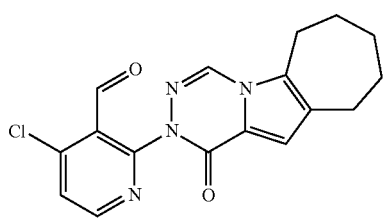 [SMILES: O=Cc1c(Cl)ccnc1-n1ncn2c3c(cc2c1=O)CCCCC3] | 325.0 |
| I-88 | | 328.8 |
| I-89 | | 343.0 |
| I-94 | | 347.0 |

Intermediate I-83

2-(4-chloro-3-(fluoromethyl)pyridin-2-yl)-7,7-dimethyl-7,8-dihydro-2H-cyclopenta[4,5]pyrrolo[1,2-a]pyrazin-1(6H)-one

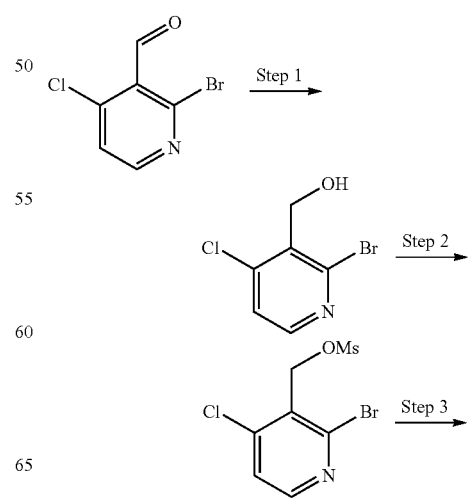

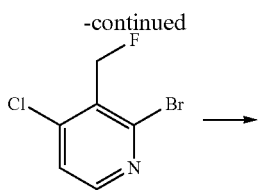

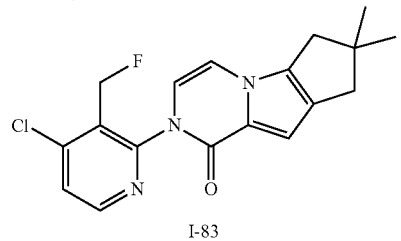

I-83

Step 1: (2-bromo-4-chloropyridin-3-yl)methanol

At 0-5° C., to a solution of 2-bromo-4-chloronicotinaldehyde (2.7 g, 12.2 mmol) in dichloromethane (30 mL) and methanol (10 mL) was added sodium borohydride (325 mg, 8.6 mmol), and stirred at this temperature for 30 minutes. The reaction was quenched by adding water to the reaction solution, and extracted with dichloromethane, the organic phase was collected, and concentrated in vacuum under reduced pressure, and the resulting residue was purified with silica gel column chromatography (petroleum ether/ethyl acetate) to give the target product (2.5 g, yield 92%).

Step 2: (2-bromo-4-chloropyridin-3-yl)methyl methanesulfonate

At 0-5° C., to a solution of (2-bromo-4-chloropyridin-3-yl) methanol (1.0 g, 4.5 mmol) in dichloromethane (30 mL) was added methanesulfonyl chloride (573 mg, 5.0 mmol), and stirred at this temperature for 30 minutes. The reaction was quenched by adding water to the reaction solution, and extracted with dichloromethane, the organic phase was collected, and dried with anhydrous sodium sulfate. The reaction solution was filtered, and the filtrate was collected, concentrated in vacuum under reduced pressure to give the target product (1.35 g, yield 100%), which was directly used in the next step. [M+H]$^+$ 299.9, 301.9

Step 3: 2-bromo-4-chloro-3-(fluoromethyl)pyridine

To a solution of (2-bromo-4-chloropyridin-3-yl) methyl methanesulfonate (1.35 g, 5.0 mmol) in dried tetrahydrofuran (20 mL) was added 1M tetrabutylammonium fluoride/tetrahydrofuran (5.0 mL, 5.0 mmol), and stirred at 65° C. for 2 hours. The reaction was quenched by adding water to the reaction solution, and extracted with ethyl acetate, the organic phase was collected, and concentrated in vacuum under reduced pressure, and the resulting residue was treated with silica gel column chromatography (petroleum ether/ethyl acetate) to give the target product (700 mg, yield 62%). [M+H]$^+$ 223.9, 225.9

2-(4-chloro-3-(fluoromethyl) pyridin-2-yl)-7,7-dimethyl-7,8-dihydro-2H-cyclopenta[4,5]pyrrolo[1,2-a]pyrazin-1 (6H)-one was prepared with corresponding materials and reagents according to preparation step 8 of intermediate I-1. [M+H]$^+$ 346.1

Intermediate I-91

4-chloro-2-(10-fluoro-1-oxo-6,7,8,9-tetrahydropyrazino[1,2-a]indol-2(1H)-yl)nicotinaldehyde

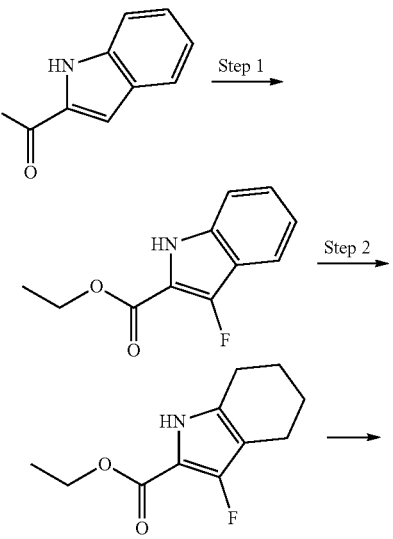

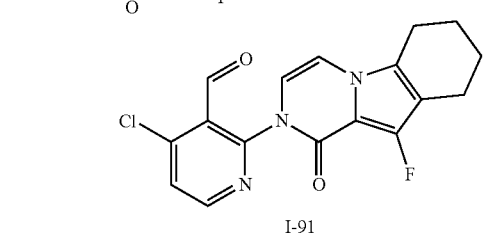

I-91

Step 1: Ethyl 3-fluoro-1H-indol-2-carboxylate

To a solution of ethyl 1H-indol-2-carboxylate (35.0 g, 185 mmol) in acetonitrile (1.75 L) was added 1-chloromethyl-4-fluoro-1,4-diazobicyclo[2.2.2]octanedi (tetrafluoroboric acid)salt (65.5 g, 1185 mmol), and stirred at room temperature for 45 minutes. The reaction was quenched by adding saturated brine, the organic phase was collected, and concentrated in vacuum under reduced pressure, and the resulting residue was purified with silica gel column chromatography (petroleum ether/ethyl acetate) to give the target product (18.0 g, yield 47%).

Step 2: Ethyl 3-fluoro-4,5,6,7-tetrahydro-1H-indol-2-carboxylate

To a solution of ethyl 3-fluoro-1H-indol-2-carboxylate (10.5 g, 50.7 mmol) in acetic acid (210 mL) was added platinum dioxide (1.57 g, 1185 mmol). Under stirring at room temperature, the reaction solution was introduced with hydrogen, and reacted for 8 hours. The reaction solution was filtered, the filtrate was collected, and concentrated in vacuum under reduced pressure, and the resulting residue was diluted by adding water, and neutralized to pH=8 with aqueous ammonia. The reaction solution was extracted with ethyl acetate, and the organic phase was collected, and concentrated in vacuum under reduced pressure, to give the target product (10.5 g, yield 98%). [M+H]$^+$ 212.0

4-chloro-2-(10-fluoro-1-oxo-6,7,8,9-tetrahydropyrazino[1,2-a]indol-2(1H)-yl) nicotinaldehyde was prepared with corresponding materials and reagents according to preparation steps 5-8 of intermediate I-1. [M+H]+ 346.0

Intermediate I-92

(RS)-2-(4-chloro-3-pyridine carboxaldehyde-2-yl)-7,7-dimethyl-1-oxo-1,6,7,8-tetrahydro-2H-cyclopenta[4,5]pyrrolo[1,2-a]pyrazin-6-yl acetate

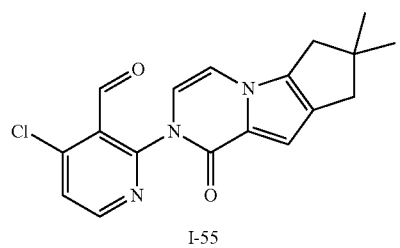

I-55

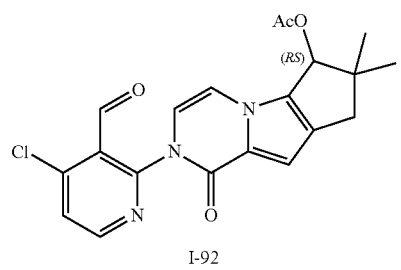

I-92

To a solution of intermediate I-55 (1.0 g, 3.0 mmol) in 1,4-dioxane (15 mL) was added lead acetate (2.0 g, 4.5 mmol), and the reaction was stirred at room temperature for 3 hours. The reaction solution was concentrated in vacuum under reduced pressure, and the resulting residue was diluted by adding water, and neutralized to pH=8 with aqueous ammonia. The reaction solution was extracted with ethyl acetate, the organic phase was collected, and concentrated in vacuum under reduced pressure, and the resulting residue was purified with silica gel column chromatography (methanol/water) to give the target product (600 mg, yield 50%). [M+H]+ 400.0

Intermediate I-99

(5-bromo-2'-(7,7-dimethyl-1-oxo-1,6,7,8-tetrahydro-2H-cyclopenta[4,5]pyrrolo[1,2-a]pyrazin-2-yl)-1-methyl-6-oxo-1,6-dihydro-[3,4'-bispyridin]-3'-yl) methyl acetate

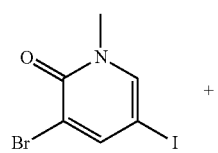

-continued

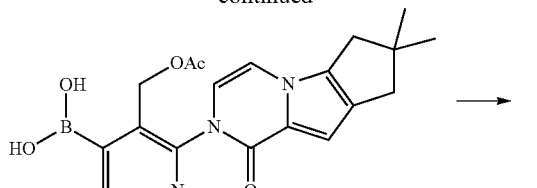

I-4

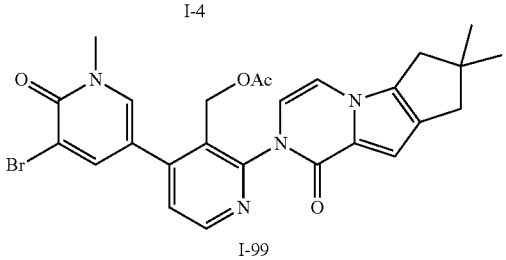

I-99

Under nitrogen, a solution of 3-bromo-5-iodo-1-methylpyridin-2(1H)-one (626 mg, 2.0 10 mmol), intermediate I-4 (790 mg, 2.0 mmol), Pd(dppf)Cl$_2$ CH$_2$Cl$_2$ (162 mg, 0.20 mmol), Xphos (94 mg, 0.20 mmol) and potassium phosphate (848 mg, 4.0 mmol) in acetonitrile (40 mL) and water (2 mL) was reacted at 30° C. for 3 hours. The reaction solution was concentrated in vacuum under reduced pressure, and the resulting residue was purified with silica gel column chromatography (methanol/water) to give the target product. [M+H]+ 537.1, 539.1

Intermediate I-107

N-(5-bromo-1-methyl-2-oxo-1,2-dihydropyridin-3-yl)propanamide

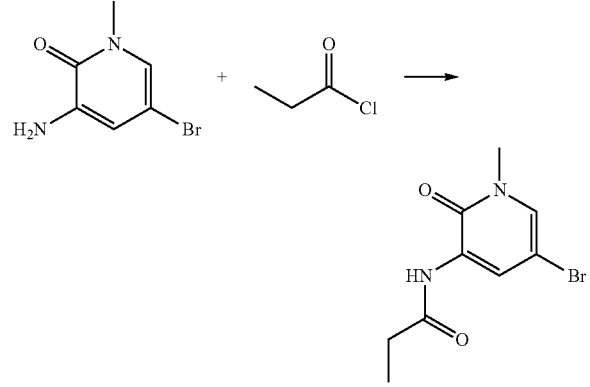

I-107

Under nitrogen, to a solution of 3-amino-5-bromo-1-methylpyridin-2(1H)-one (609 mg, 3.0 mmol), propionyl chloride (416 mg, 4.5 mmol) in dichloromethane (20 mL) was dropwise added triethylamine (455 mg, 4.5 mmol), and reacted at room temperature for 1 hour. The reaction solution was concentrated in vacuum under reduced pressure, and the resulting residue was purified with silica gel column chromatography (methanol/dichloromethane) to give the target product. [M+H]+ 259.0, 261.0

The intermediates in the following table were prepared with corresponding materials and reagents according to the preparation steps of intermediate I-107:

| Intermediate | Structural formula | LC-MS [M + H]+ |
|---|---|---|
| I-108 | | 259.0, 261.0 |
| I-127 | | 285.0, 287.0 |
| I-128 | | 307.0, 309.0 |

Compound 1

2-(5-(((5-(ethyl (2-methoxyethyl)amino)pyridin-2-yl)amino)-3'-(hydroxymethyl)-1-methyl-6-oxo-1,6-dihydro-[3,4'-bispyridin]-2'-yl)-7,7-dimethyl-7,8-dihydro-2H-cyclopenta[4,5]pyrrolo[1,2-a]pyrazin-1(6H)-one

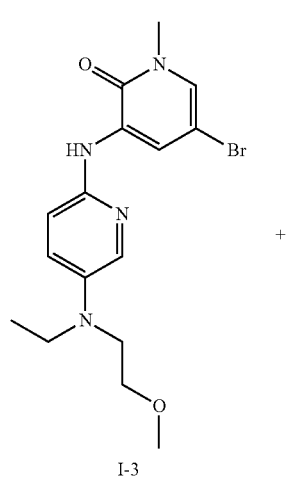

+

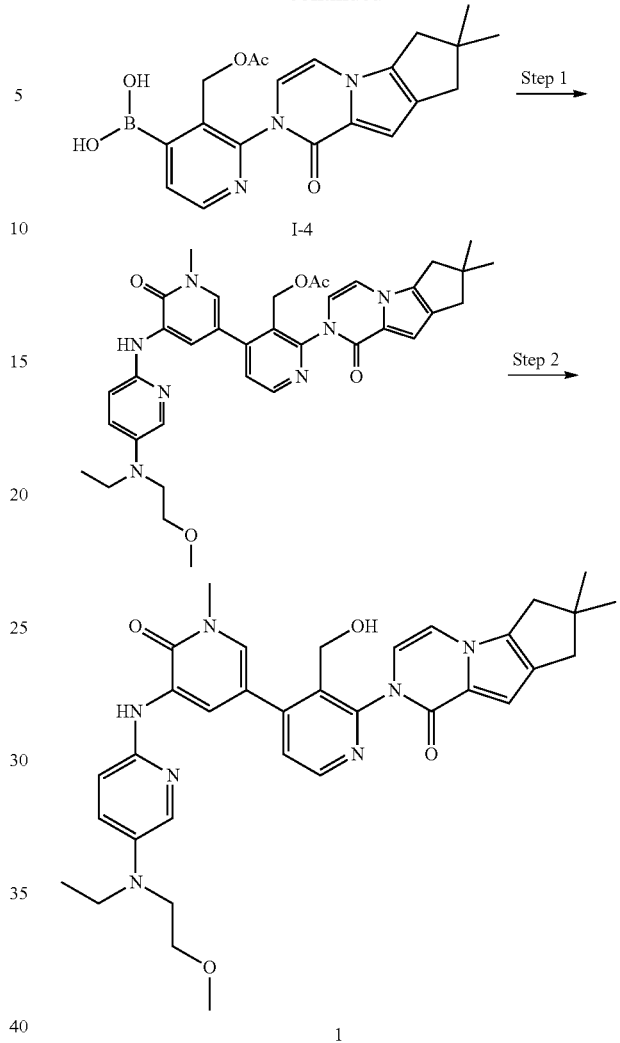

Step 1: Acetic acid (2'-(7,7-dimethyl-1-oxo-1,6,7,8-tetrahydro-2H-cyclopenta[4,5]pyrrolo[1,2-a]pyrazin-2-yl)-5-((5-(ethyl (2-methoxyethyl)amino)pyridin-2-yl)amino)-1-methyl-6-oxo-1,6-dihydro-[3,4'-bispyridin]-3'-yl)methyl ester Under nitrogen, to a solution of intermediate I-3 (126 mg, 0.33 mmol) and intermediate I-4 (134 mg, 0.33 mmol) in 1,4-dioxane (5.0 mL) and water (0.5 mL) was added Xphos (31 mg, 0.066 mmol), Pd(dppf)Cl$_2$ CH$_2$Cl$_2$ (27 mg, 0.033 mmol) and potassium phosphate trihydrate (264 mg, 0.99 mmol). The mixture was reacted at 100° C. for 4 hours, and then cooled to room temperature. The reaction solution was concentrated in vacuum under reduced pressure, and the resulting residue was purified with silica gel column chromatography (methanol/water) to give the target product. [M+H]+ 652.3

Step 2: 2-(5-((5-(ethyl (2-methoxyethyl)amino)pyridin-2-yl)amino)-3'-(hydroxymethyl)-1-methyl-6-oxo-1,6-dihydro-[3,4'-bispyridin]-2'-yl)-7,7-dimethyl-7,8-dihydro-2H-cyclopenta[4,5]pyrrolo[1,2-a]pyrazin-1(6H)-one To a solution of acetic acid (2'-(7,7-dimethyl-1-oxo-1,6,7,8-tetrahydro-2H-cyclopenta[4,5]pyrrolo[1,2-a]pyrazin-2- yl)-5-((5-(ethyl (2-methoxyethyl)amino)pyridin-2-yl) amino)-1-methyl-6-oxo-1,6-dihydro-[3,4'-bispyridin]-3'-yl) methyl ester obtained from step 1 in methanol (5 mL) was added potassium carbonate (137 mg, 0.99 mmol), which was reacted at room temperature for 2 hours. The reaction solution was concentrated in vacuum under reduced pressure, and the resulting residue was purified with thin layer chromatography (methanol/dichloromethane=1/20) to give the target product (100 mg, two-step yield 50%). [M+H]+ 610.3. ¹H NMR (400 MHz, CD₃OD): δ 8.57-8.51 (m, 1H), 8.42-8.37 (m, 1H), 7.77-7.74 (m, 1H), 7.60-7.57 (m, 1H), 7.48-7.45 (m, 1H), 7.23-7.19 (m, 2H), 7.01-6.97 (m, 1H), 6.95-6.91 (m, 1H), 6.80-6.76 (m, 1H), 4.61-4.57 (m, 1H), 4.50-4.45 (m, 1H), 3.69 (s, 3H), 3.53-3.50 (m, 2H), 3.44-3.40 (m, 2H), 3.39-3.34 (m, 2H), 3.32 (s, 3H), 2.78-2.69 (m, 2H), 2.66-2.57 (m, 2H), 1.30-1.27 (m, 6H), 1.13-1.08 (m, 3H).

The compounds in the following table were prepared with corresponding intermediates and reagents according to the preparation steps of compound 1:

| Compound | Structural formula | LC-MS [M + H]+ | 1HNMR | Intermediate |
|---|---|---|---|---|
| 3 | | 528.2 | ¹H NMR (400 MHz, CD₃OD): δ 8.55 (d, J = 5.1 Hz, 1H), 8.39 (s, 1H), 7.73 (d, J = 5.1 Hz, 1H), 7.59 (s, 1H), 7.22 (d, J = 5.9 Hz, 1H), 6.92 (s, 1H), 6.81 (d, J = 6.0 Hz, 1H), 4.84-4.78 (m, 1H), 4.54-4.49 (m, 1H), 4.46-4.40 (m, 2H), 3.64 (s, 3H), 2.80-2.70 (m, 2H), 2.62 (s, 2H), 1.57-1.49 (m, 3H), 1.31-1.27 (m, 6H). | I-5 and I-4 |
| 4 | | 542.2 | ¹H NMR (400 MHz, CD₃OD): δ 8.53 (d, J = 5.1 Hz, 1H), 8.39 (s, 1H), 7.71 (d, J = 5.1 Hz, 1H), 7.57 (s, 1H), 7.20 (d, J = 5.9 Hz, 1H), 6.91 (s, 1H), 6.80 (d, J = 5.9 Hz, 1H), 4.85-4.78 (m, 2H), 4.53-4.46 (m, 1H), 3.63 (s, 3H), 2.79-2.69 (m, 2H), 2.61 (s, 2H), 1.61-1.53 (m, 6H), 1.31-1.26 (m, 6H). | I-6 and I-4 |
| 5 | | 678.3 | ¹H NMR (400 MHz, CD₃OD): δ 8.66-8.60 (m, 2H), 8.10 (d, J = 2.7 Hz, 1H), 7.69 (d, J = 5.1 Hz, 1H), 7.57-7.51 (m, 1H), 7.25-7.15 (m, 2H), 6.93 (s, 1H), 6.82 (d, J = 5.9 Hz, 1H), 4.83-4.78 (m, 1H), 4.76-4.62 (m, 5H), 4.57-4.50 (m, 1H), 3.89 (s, 3H), 3.85-3.75 (m, 1H), 3.38-3.33 (m, 1H), 3.04-2.97 (m, 1H), 2.83-2.73 (m, 4H), 2.65-2.56 (m, 3H), 2.09-1.95 (m, 1H), 1.31-1.28 (m, 6H), 0.95-0.89 (m, 6H). | I-7 and I-4 |

| Compound | Structural formula | LC-MS [M + H]+ | 1HNMR | Intermediate |
|---|---|---|---|---|
| 6 | | 541.2 | 1H NMR (400 MHz, CD3OD/CDCl3): δ 8.52 (d, J = 5.1 Hz, 1H), 7.89 (s, 1H), 7.72-7.66 (m, 1H), 7.51 (d, J = 5.1 Hz, 1H), 7.43-7.38 (m, 1H), 7.07 (d, J = 6.0 Hz, 1H), 6.99 (s, 1H), 6.65 (d, J = 5.9 Hz, 1H), 4.79-4.71 (m, 1H), 4.52-4.43 (m, 2H), 3.70 (s, 3H), 2.78-2.69 (m, 2H), 2.61 (s, 2H), 1.59-1.54 (m, 6H), 1.29-1.26 (m, 6H). | I-8 and I-4 |
| 7 | | 542.2 | 1H NMR (400 MHz, CD3OD/CDCl3): δ 8.60 (d, J = 5.1 Hz, 1H), 7.97 (s, 1H), 7.71-7.67 (m, 2H), 7.10-7.04 (m, 1H), 6.97 (s, 1H), 6.68 (d, J = 5.9 Hz, 1H), 4.84-4.74 (m, 1H), 4.59-4.54 (m, 2H), 3.89 (s, 3H), 2.78-2.68 (m, 2H), 2.61 (s, 2H), 1.60-1.55 (m, 6H), 1.29-1.27 (m, 6H). | I-9 and I-4 |
| 8 | | 665.3 | 1H NMR (400 MHz, CD3OD): δ 8.68 (d, J = 2.2 Hz, 1H), 8.53 (d, J = 5.1 Hz, 1H), 7.95 (d, J = 2.8 Hz, 1H), 7.57 (d, J = 5.1 Hz, 1H), 7.52 (d, J = 2.2 Hz, 1H), 7.46-7.41 (m, 1H), 7.21 (d, J = 5.9 Hz, 1H), 7.02 (d, J = 8.9 Hz, 1H), 6.93 (s, 1H), 6.80-6.76 (m, 1H), 4.63-4.41 (m, 2H), 3.68 (s, 3H), 3.60-3.50 (m, 2H), 3.44-3.39 (m, 1H), 3.37-3.33 (m, 3H), 3.09-2.96 (m, 2H), 2.80-2.72 (m, 3H), 2.71-2.65 (m, 1H), 2.64-2.54 (m, 5H), 2.38-2.27 (m, 1H), 1.31-1.25 (m, 6H), 0.92 (d, J = 6.3 Hz, 3H). | I-10 and I-4 |

-continued

| Compound | Structural formula | LC-MS [M + H]+ | 1HNMR | Intermediate |
|---|---|---|---|---|
| 9 | | 649.3 | ¹H NMR (400 MHz, CD₃OD): δ 7.85-7.79 (m, 1H), 7.72 (d, J = 5.1 Hz, 1H), 7.09 (d, J = 2.8 Hz, 1H), 6.76 (d, J = 5.1 Hz, 1H), 6.68 (d, J = 2.0 Hz, 1H), 6.60-6.53 (m, 1H), 6.43-6.36 (m, 1H), 6.21-6.16 (m, 1H), 6.11 (s, 1H), 6.01-5.94 (m, 1H), 3.94-3.86 (m, 2H), 3.84-3.75 (m, 3H), 3.71-3.63 (m, 1H), 2.87 (s, 3H), 2.78-2.66 (m, 1H), 2.36-2.30 (m, 4H), 2.00-1.87 (m, 2H), 1.85-1.78 (m, 2H), 1.73-1.66 (m, 4H), 0.50-0.44 (m, 6H). | I-11 and I-4 |
| 10 | | 608.3 | ¹H NMR (400 MHz, CD₃OD): δ 8.66 (s, 1H), 8.54 (s, 1H), 7.92 (s, 1H), 7.62-7.48 (m, 2H), 7.41 (d, J = 7.3 Hz, 1H), 7.22 (d, J = 5.8 Hz, 1H), 7.03 (d, J = 8.8 Hz, 1H), 6.94 (s, 1H), 6.78 (d, J = 5.8 Hz, 1H), 4.60 (d, J = 12.0 Hz, 1H), 4.49 (d, J = 12.1 Hz, 1H), 3.91-3.62 (m, 6H), 3.58-3.45 (m, 2H), 3.3.11-2.96 (m, 2H), 2.80-2.68 (m, 2H), 2.65-2.58 (s, 2H), 1.33-1.26 (m, 6H), 0.95 (d, J = 6.3 Hz, 3H). | I-12 and I-4 |
| 11 | | 677.3 | ¹H NMR (400 MHz, CD₃OD): δ 8.55 (d, J = 5.0 Hz, 1H), 8.37-8.30 (m, 1H), 7.93-7.80 (m, 1H), 7.45-7.36 (m, 2H), 7.24-7.17 (m, 1H), 6.97 (d, J = 8.8 Hz, 1H), 6.93-6.88 (m, 1H), 6.85-6.81 (m, 1H), 4.72-4.38 (m, 6H), 3.75-3.65 (m, 3H), 3.53-3.37 (m, 2H), 3.09-2.95 (m, 2H), 2.78-2.66 (m, 2H), 2.62-2.51 (m, 3H), 2.50-2.39 (m, 2H), 2.22-2.10 (m, 4H), 1.27 (d, J = 7.9 Hz, 6H), 0.98-0.88 (m, 3H). | I-13 and I-4 |

| Compound | Structural formula | LC-MS [M + H]+ | 1HNMR | Intermediate |
|---|---|---|---|---|
| 13 | | 619.1 | ¹H NMR (400 MHz, CD₃OD): δ 8.56 (m, 1H), 8.49 (m, 1H), 8.34 (s, 1H), 8.03 (m, 1H), 7.61 (m, 1H), 7.17 (m, 1H), 6.91 (s, 1H), 6.79 (m, 1H), 5.86 (s, 1H), 4.72 (m, 2H), 4.62 (m, 2H), 4.50 (m, 2H), 4.04 (m, 2H), 3.73 (m, 1H), 3.56 (m, 2H), 2.83 (m, 2H), 2.71 (m, 2H), 2.59 (m, 2H), 1.26 (m, 6H). | I-15 and I-4 |
| 14 | | 678.3 | ¹H NMR (400 MHz, CD₃OD): δ 8.64-8.59 (m, 1H), 8.55 (s, 1H), 8.07-7.99 (m, 1H), 7.72-7.67 (m, 1H), 7.48-7.42 (m, 1H), 7.23-7.19 (m, 1H), 7.18-7.12 (m, 1H), 6.92 (s, 1H), 6.84-6.78 (m, 1H), 4.79-4.74 (m, 1H), 4.73-4.68 (m, 2H), 4.66-4.62 (m, 1H), 4.61-4.57 (m, 1H), 4.56-4.49 (m, 1H), 4.36-4.27 (m, 2H), 3.77-3.62 (m, 1H), 3.55-3.47 (m, 1H), 3.22-3.06 (m, 2H), 2.79-2.67 (m, 2H), 2.66-2.56 (m, 3H), 2.53-2.45 (m, 1H), 2.39-2.33 (m, 2H), 1.45-1.39 (m, 3H), 1.31-1.25 (m, 6H), 1.08-0.99 (m, 3H). | I-16 and I-4 |
| 15 | | 581.2 | ¹H NMR (400 MHz, CD₃OD): δ 8.56-8.48 (m, 1H), 8.17-8.11 (m, 1H), 7.60-7.51 (m, 1H), 7.48-7.41 (m, 1H), 7.25-7.18 (m, 1H), 6.92 (s, 1H), 6.80-6.75 (m, 1H), 6.51 (s, 1H), 4.61-4.43 (m, 2H), 4.29-4.22 (m, 2H), 3.84-3.74 (m, 2H), 3.67 (s, 3H), 3.09 (s, 3H), 2.78-2.68 (m, 2H), 2.66-2.57 (m, 2H), 1.30-1.27 (m, 6H). | I-17 and I-4 |

-continued

| Compound | Structural formula | LC-MS [M + H]⁺ | 1HNMR | Intermediate |
|---|---|---|---|---|
| 16 | | 577.1 | ¹H NMR (400 MHz, CD₃OD): δ 8.59 (d, J = 5.0 Hz, 1H), 8.51 (s, 1H), 8.36 (s, 1H), 8.06 (s, 1H), 7.64 (d, J = 5.1 Hz, 1H), 7.21 (d, J = 5.9 Hz, 1H), 6.92 (s, 1H), 6.80 (d, J = 5.6 Hz, 1H), 5.89 (s, 1H), 4.52-4.48 (m, 2H), 4.07-4.05 (m, 2H), 3.64-3.62 (m, 2H), 2.94-2.92 (m, 2H), 2.78-2.66 (m, 2H), 2.65-2.55 (m, 2H), 2.47 (s, 3H), 1.28-1.26 (m, 6H). | I-18 and I-4 |
| 17 | | 563.1 | ¹H NMR (400 MHz, CD₃OD): δ 8.60 (d, J = 5.0 Hz, 1H), 8.51 (d, J = 1.3 Hz, 1H), 8.37 (s, 1H), 8.02 (d, J = 1.3 Hz, 1H), 7.64 (d, J = 5.1 Hz, 1H), 7.21 (d, J = 6.0 Hz, 1H), 6.92 (s, 1H), 6.80 (d, J = 5.9 Hz, 1H), 5.89 (s, 1H), 4.57-4.46 (m, 2H), 4.05-3.93 (m, 4H), 3.23 (t, J = 5.6 Hz, 2H), 2.79-2.55 (m, 4H), 1.30-1.26 (m, 6H). | I-19 and I-4 |
| 18 | | 551.2 | ¹H NMR (400 MHz, CD₃OD): δ 8.53 (d, J = 5.1 Hz, 1H), 8.47 (d, J = 1.2 Hz, 1H), 8.32 (s, 1H), 7.92 (s, 1H), 7.58 (d, J = 5.1 Hz, 1H), 7.53 (d, J = 1.2 Hz, 1H), 7.15 (d, J = 5.9 Hz, 1H), 6.85 (s, 1H), 6.72 (d, J = 5.9 Hz, 1H), 4.54-4.33 (m, 3H), 2.72-2.60 (m, 2H), 2.59-2.48 (m, 2H), 1.55-1.42 (m, 6H), 1.25-1.15 (m, 6H). | I-20 and I-4 |
| 19 | | 663.3 | ¹H NMR (400 MHz, CD₃OD): δ 8.70-8.68 (m, 1H), 8.57 (d, J = 5.1 Hz, 1H), 7.98-7.96 (m, 1H), 7.61 (d, J = 5.1 Hz, 1H), 7.56-7.54 (m, 1H), 7.48-7.44 (m, 1H), 7.24 (d, J = 5.9 Hz, 1H), 7.06-7.04 (m, 1H), 6.96 (s, 1H), 6.81 (d, J = 5.9 Hz, 1H), 4.76-4.60 (m, 5H), 4.53-4.50 (m, 1H), 3.70 (s, 3H), 3.55-3.51 (m, 2H), 3.15-3.03 (m, 2H), 2.82-2.70 (m, 2H), 2.65-2.63 (m, 2H), 2.62-2.55 (m, 1H), 2.50-2.48 (m, 2H), 2.25-2.21 (m, 1H), 1.33-1.29 (m, 6H), 0.99 (d, J = 6.4 Hz, 3H). | I-14 and I-4 |

-continued

| Compound | Structural formula | LC-MS [M + H]+ | 1HNMR | Intermediate |
|---|---|---|---|---|
| 20 | | 664.3 | ¹H NMR (400 MHz, CD₃OD): δ 8.45 (d, J = 5.1 Hz, 1H), 8.02-7.98 (m, 1H), 7.85-7.83 (m, 1H), 7.67-7.65 (m, 1H), 7.55 (s, 1H), 7.42-7.37 (m, 1H), 7.12 (d, J = 5.9 Hz, 1H), 6.84 (s, 1H), 6.70 (d, J = 5.9 Hz, 1H), 4.64-4.45 (m, 5H), 4.40-4.36 (m, 1H), 3.66-3.64 (m, 1H), 3.55 (s, 3H), 3.44-3.34 (m, 1H), 3.09-3.01 (m, 2H), 2.70-2.59 (m, 2H), 2.52-2.50 (m, 3H), 2.38-2.25 (m, 2H), 2.21-2.19 (m, 1H), 1.21-1.19 (m, 6H), 0.95 (d, J = 6.3 Hz, 3H). | I-22 and I-4 |
| 21 | | 673.3 | ¹H NMR (400 MHz, CD₃OD): δ 8.73-8.71 (m, 1H), 8.64-8.60 (m, 2H), 8.40 (s, 1H), 7.99 (d, J = 2.6 Hz, 1H), 7.67 (d, J = 5.0 Hz, 1H), 7.49-7.45 (m, 1H), 7.22 (d, J = 5.9 Hz, 1H), 7.08 (d, J = 8.9 Hz, 1H), 6.95 (s, 1H), 6.83 (d, J = 5.9 Hz, 1H), 4.74-4.70 (m, 2H), 4.66-4.48 (m, 4H), 3.63-3.46 (m, 2H), 3.17-3.03 (m, 2H), 2.81-2.69 (m, 2H), 2.63-2.59 (m, 2H), 2.56-2.54 (m, 2H), 2.44-2.42 (m, 1H), 2.28-2.26 (m, 1H), 1.32-1.28 (m, 6H), 1.01 (d, J = 6.3 Hz, 3H). | I-23 and I-4 |
| 22 | | 664.3 | ¹H NMR (400 MHz, CD₃OD): δ 8.53 (d, J = 5.0 Hz, 1H), 8.46 (s, 1H), 7.94 (d, J = 2.7 Hz, 1H), 7.59 (d, J = 5.1 Hz, 1H), 7.39-7.35 (m, 1H), 7.12-7.08 (m, 2H), 6.84 (s, 1H), 6.72 (d, J = 5.9 Hz, 1H), 4.65-4.45 (m, 6H), 3.66-3.55 (m, 1H), 3.45-3.36 (m, 1H), 3.07-3.03 (m, 2H), 2.71-2.59 (m, 2H), 2.53-2.50 (m, 3H), 2.41-2.39 (m, 1H), 2.29-2.25 (m, 2H), 1.22-1.18 (m, 6H), 0.95 (d, J = 6.4 Hz, 3H). | I-24 and I-4 |

| Compound | Structural formula | LC-MS [M + H]+ | 1HNMR | Intermediate |
|---|---|---|---|---|
| 23 | | 690.3 | 1H NMR (400 MHz, CD3OD): δ 8.59 (d, J = 5.1 Hz, 1H), 8.33 (s, 1H), 8.04 (s, 1H), 7.97 (d, J = 2.7 Hz, 1H), 7.66 (d, J = 5.0 Hz, 1H), 7.48-7.46 (m, 1H), 7.28-7.18 (m, 2H), 7.06 (d, J = 8.9 Hz, 1H), 6.93 (s, 1H), 6.80 (d, J = 5.4 Hz, 1H), 4.72-4.68 (m, 2H), 4.64-4.56 (m, 3H), 4.50-4.48 (m, 1H), 3.59-3.45 (m, 2H), 3.16-3.02 (m, 2H), 2.78-2.42 (m, 7H), 2.26-2.24 (m, 1H), 1.29-1.27 (m, 6H), 0.99 (d, J = 6.3 Hz, 3H). | I-25 and I-4 |
| 24 | | 527.2 | 1H NMR (400 MHz, CD3OD): δ 8.54 (d, J = 5.1 Hz, 1H), 7.91 (s, 1H), 7.62-7.57 (m, 2H), 7.48-7.46 (m, 1H), 7.23 (d, J = 5.9 Hz, 1H), 6.94 (s, 1H), 6.77 (d, J = 5.9 Hz, 1H), 4.56-4.47 (m, 2H), 4.38 (q, J = 7.3 Hz, 2H), 3.70 (s, 3H), 2.76-2.72 (m, 2H), 2.62-2.58 (m, 2H), 1.51 (t, J = 7.4 Hz, 3H), 1.30-1.27 (m, 6H). | I-26 and I-4 |
| 25 | | 528.2 | 1H NMR (400 MHz, CD3OD): δ 8.60 (d, J = 5.1 Hz, 1H), 7.92 (s, 1H), 7.69 (d, J = 5.1 Hz, 1H), 7.61 (s, 1H), 7.21 (d, J = 5.9 Hz, 1H), 6.92 (s, 1H), 6.79 (d, J = 5.9 Hz, 1H), 4.72-4.70 (m, 1H), 4.51-4.49 (m, 1H), 4.41 (q, J = 7.3 Hz, 2H), 3.87 (s, 3H), 2.80-2.68 (m, 2H), 2.66-2.55 (m, 2H), 1.52 (t, J = 7.3 Hz, 3H), 1.30-1.27 (m, 6H). | I-27 and I-4 |

| Compound | Structural formula | LC-MS [M + H]⁺ | 1HNMR | Intermediate |
|---|---|---|---|---|
| 26 | | 621.3 | ¹H NMR (400 MHz, CD₃OD): δ 8.69 (d, J = 2.3 Hz, 1H), 8.55 (d, J = 5.1 Hz, 1H), 7.96 (d, J = 2.7 Hz, 1H), 7.59 (d, J = 5.1 Hz, 1H), 7.53 (d, J = 2.3 Hz, 1H), 7.46-7.44 (m, 1H), 7.22 (d, J = 5.9 Hz, 1H), 7.03 (d, J = 8.9 Hz, 1H), 6.94 (s, 1H), 6.79 (d, J = 5.9 Hz, 1H), 4.63-4.42 (m, 2H), 3.70 (s, 3H), 3.44-3.40 (m, 1H), 3.10-3.01 (m, 2H), 2.79-2.70 (m, 3H), 2.65-2.52 (m, 4H), 2.36-2.27 (m, 4H), 1.31-1.27 (m, 6H), 0.94 (d, J = 6.4 Hz, 3H). | I-28 and I-4 |
| 27 | | 677.3 | ¹H NMR (400 MHz, CD₃OD): δ 8.73 (d, J = 2.2 Hz, 1H), 8.55 (d, J = 5.1 Hz, 1H), 8.00 (d, J = 2.6 Hz, 1H), 7.62-7.53 (m, 2H), 7.51-7.47 (m, 1H), 7.22 (d, J = 5.9 Hz, 1H), 7.04 (d, J = 8.9 Hz, 1H), 6.94 (s, 1H), 6.79 (d, J = 5.9 Hz, 1H), 4.75-4.71 (m, 1H), 4.70-4.57 (m, 4H), 4.50-4.48 (m, 1H), 3.79-3.77 (m, 1H), 3.70 (s, 3H), 3.26-3.14 (m, 1H), 2.92-2.89 (m, 1H), 2.80-2.57 (m, 6H), 2.55-2.45 (m, 1H), 1.96-1.92 (m, 1H), 1.31-1.27 (m, 6H), 0.90-0.87 (m, 6H). | I-2 and I-4, Steps 5 |
| 28 | | 513.2 | ¹H NMR (400 MHz, CD₃OD): δ 8.52 (d, J = 5.1 Hz, 1H), 7.83 (s, 1H), 7.59-7.55 (m, 2H), 7.47-7.45 (m, 1H), 7.24-7.20 (m, 1H), 6.93-6.91 (m, 1H), 6.78-6.74 (m, 1H), 4.52-4.46 (m, 2H), 4.04 (s, 3H), 3.69 (s, 3H), 2.79-2.67 (m, 2H), 2.66-2.56 (m, 2H), 1.29-1.26 (m, 6H). | I-29 and I-4 |
| 29 | | 514.2 | ¹H NMR (400 MHz, CD₃OD): δ 8.59 (d, J = 5.0 Hz, 1H), 7.86 (s, 1H), 7.68 (d, J = 5.1 Hz, 1H), 7.61-7.59 (m, 1H), 7.22-7.20 (m, 1H), 6.91-6.59 (m, 1H), 6.81-6.76 (m, 1H), 4.74-4.46 (m, 2H), 4.07 (s, 3H), 3.86 (s, 3H), 2.78-2.68 (m, 2H), 2.66-2.56 (m, 2H), 1.30-1.28 (m, 6H). | I-30 and I-4 |

-continued

| Compound | Structural formula | LC-MS [M + H]+ | 1HNMR | Intermediate |
|---|---|---|---|---|
| 30 | | 581.2 | ¹H NMR (400 MHz, CD₃OD): δ 8.55 (d, J = 5.2 Hz, 1H), 8.01 (s, 1H), 7.71 (d, J = 2.0 Hz, 1H), 7.59 (d, J = 5.2 Hz, 1H), 7.50 (d, J = 2.0 Hz, 1H), 7.24 (d, J = 6.0 Hz, 1H), 6.94 (s, 1H), 6.78 (d, J = 6.0 Hz, 1H), 5.28-5.21 (m, 2H), 4.58-4.46 (m, 2H), 3.71 (s, 3H), 2.75 (d, J = 2.8 Hz, 2H), 2.63 (s, 2H), 1.29 (d, J = 5.6 Hz, 6H). | I-31 and I-4 |
| 31 | | 545.2 | ¹H NMR (400 MHz, CD₃OD): δ 8.56 (d, J = 5.2 Hz, 1H), 8.16 (d, J = 2.4 Hz, 1H), 7.58 (d, J = 5.2 Hz, 1H), 7.50 (d, J = 2.0 Hz, 1H), 7.48 (m, 1H), 7.23 (d, J = 6.0 Hz, 1H), 6.94 (s, 1H), 6.8.0 (d, J = 6.0 Hz, 1H), 4.79-4.76 (m, 1H), 4.65-4.47 (m, 5H), 3.71 (s, 3H), 2.75 (d, J = 3.2 Hz, 2H), 2.63 (s, 2H), 1.29 (d, J = 6.4 Hz, 6H). | I-32 and I-4 |
| 32 | | 546.2 | ¹H NMR (400 MHz, CD₃OD-d₄): δ 8.63 (d, J = 4.8 Hz, 1H), 8.04 (s, 1H), 7.68 (d, J = 4.8 Hz, 1H), 7.57 (s, 1H), 7.23 (d, J = 6.0 Hz, 1H), 6.93 (s, 1H), 6.82 (d, J = 6.0 Hz, 1H), 4.82-4.73 (m, 3H), 4.70-4.66 (m, 1H), 4.64-4.60 (m, 1H), 4.52 (d, J = 12.4 Hz, 1H), 3.89 (s, 3H), 2.75 (d, J = 2.4 Hz, 2H), 2.63 (s, 2H), 1.30 (d, J = 5.2 Hz, 6H). | I-33 and I-4 |
| 33 | | 582.1 | ¹H NMR (400 MHz, CD₃OD-d₄): δ 8.62 (d, J = 5.2 Hz, 1H), 8.04 (s, 1H), 7.75 (s, 1H), 7.70 (d, J = 5.2 Hz, 1H), 7.22 (d, J = 6.0 Hz, 1H), 6.93 (s, 1H), 6.81 (d, J = 6.0 Hz, 1H), 5.33-5.27 (m, 2H), 4.74 (d, J = 12.4 Hz, 1H), 4.51 (d, J = 12.8 Hz, 1H), 3.89 (s, 3H), 2.74 (s, 2H), 2.62 (s, 2H), 1.29 (d, J = 4.8 Hz, 6H). | I-34 and I-4 |

| Compound | Structural formula | LC-MS [M + H]+ | 1HNMR | Intermediate |
|---|---|---|---|---|
| 34 | | 663.3 | 1H NMR (400 MHz, CD3OD): δ 8.87 (d, J = 2.4 Hz, 1H), 8.56 (d, J = 5.2 Hz, 1H), 8.18 (d, J = 2.4 Hz, 1H), 7.62-7.56 (m, 3H), 7.23 (d, J = 6.0 Hz, 1H), 7.12 (d, J = 8.8 Hz, 1H), 6.94 (s, 1H), 6.79 (d, J = 6.0 Hz, 1H), 4.76-4.73 (m, 3H), 4.66-4.59 (m, 3H), 4.49 (d, J = 12.4 Hz, 1H), 3.74 (d, J = 5.2 Hz, 1H), 3.72 (s, 3H), 3.71-3.67 (m, 1H), 3.21 (s, 2H), 2.83-2.78 (m, 2H), 2.75 (d, J = 3.2 Hz, 2H), 2.63 (s, 2H), 1.29 (d, J = 6.4 Hz, 6H). | I-35 and I-4 |
| 35 | | 594.2 | 1H NMR (400 MHz, CD3OD): δ 8.55 (d, J = 5.2 Hz, 1H), 8.51 (d, J = 2.0 Hz, 1H), 7.58 (d, J = 5.2 Hz, 1H), 7.53 (d, J = 2.4 Hz, 1H), 7.48 (d, J = 2.0 Hz, 1H), 7.23 (d, J = 5.6 Hz, 1H), 7.02-6.90 (m, 3H), 6.79 (d, J = 5.6 Hz, 1H), 4.60 (d, J = 12.0 Hz, 1H), 4.48 (d, J = 12.0 Hz, 1H), 4.36-4.31 (m, 1H), 4.14-4.04 (m, 2H), 3.70 (s, 3H), 3.63-3.60 (m, 2H), 3.34 (s, 3H), 2.74 (d, J = 3.6 Hz, 2H), 2.62 (s, 2H), 1.29 (d, J = 6.4 Hz, 6H). | I-36 and I-4 |
| 36 | | 646.3 | 1H NMR (400 MHz, CD3OD): δ 8.83 (d, J = 2.0 Hz, 1H), 8.56 (d, J = 5.2 Hz, 1H), 8.29 (s, 1H), 7.73-7.71(m, 1H), 7.61 (d, J = 5.2 Hz, 1H), 7.57 (d, J = 2.0 Hz, 1H), 7.23 (d, J = 6.0 Hz, 1H), 7.04 (d, J = 8.4 Hz, 1H), 6.94 (s, 1H), 6.80 (d, J = 6.0 Hz, 1H), 6.10 (s, 1H), 4.75-4.72 (m, 2H), 4.68-4.60 (m, 3H), 4.50 (d, J = 12.4 Hz, 1H), 3.71 (s, 3H), 3.68-3.62 (m, 1H), 3.07 (s, 2H), 2.74 (d, J = 3.2 Hz, 2H), 2.65-2.56 (m, 6H), 1.29 (d, J = 6.4 Hz, 6H). | I-37 and I-4 |

| Compound | Structural formula | LC-MS [M + H]+ | 1HNMR | Intermediate |
|---|---|---|---|---|
| 37 | | 641.3 | 1H NMR (400 MHz, CD3OD): δ 8.89 (d, J = 2.4 Hz, 1H), 8.57 (d, J = 5.2 Hz, 1H), 8.50 (d, J = 2.4 Hz, 1H), 7.91-7.88 (m, 1H), 7.62-7.58 (m, 4H), 7.50 (d, J = 8.4 Hz, 2H), 7.24 (d, J = 6.0 Hz, 1H), 7.13 (d, J = 8.4 Hz, 1H), 6.94 (s, 1H), 6.81 (d, J = 6.0 Hz, 1H), 5.12-5.09 (m, 2H), 4.79-4.75 (m, 2H), 4.63 (d, J = 12.0 Hz, 1H), 4.51 (d, J = 12.0 Hz, 1H), 4.34-4.27 (m, 1H), 3.72 (s, 3H), 2.74 (d, J = 3.6 Hz, 2H), 2.62 (s, 2H), 1.29 (d, J = 6.8 Hz, 6H). | I-38 and I-4 |
| 40 | | 474.2 | 1H NMR (400 MHz, CD3OD): δ 8.52 (d, J = 4.8 Hz, 1H), 7.53 (d, J = 5.2 Hz, 1H), 7.23-7.21 (m, 2H), 6.93 (s, 1H), 6.76 (d, J = 6.0 Hz, 1H), 6.66 (d, J = 2.0 Hz, 1H), 4.54 (d, J = 11.6 Hz, 1H), 4.46 (d, J = 12.0 Hz, 1H), 3.64 (s, 3H), 3.61-3.56 (m, 1H), 2.74 (d, J = 3.6 Hz, 2H), 2.62 (s, 2H), 1.29 (d, J = 6.4 Hz, 6H), 1.23 (m, 6H). | I-40 and I-4 |
| 41 | | 594.3 | 1H NMR (400 MHz, CD3OD): δ 8.62 (d, J = 2.0 Hz, 1H), 8.54 (d, J = 5.2 Hz, 1H), 7.64 (d, J = 2.4 Hz, 1H), 7.57 (d, J = 4.8 Hz, 1H), 7.50 (d, J = 1.6 Hz, 1H), 7.25-7.16 (m, 2H), 6.99 (d, J = 8.8 Hz, 1H), 6.93(s, 1H), 6.78 (d, J = 5.6 Hz, 1H), 4.84-4.81 (m, 2H), 4.64-4.57 (m, 3H), 4.52-4.40 (m, 2H), 3.69 (s, 3H), 2.78 (s, 3H), 2.74 (d, J = 3.2 Hz, 2H), 2.62 (s, 2H), 1.29 (d, J = 6.0 Hz, 6H). | I-41 and I-4 |

-continued

| Compound | Structural formula | LC-MS [M + H]+ | 1HNMR | Intermediate |
|---|---|---|---|---|
| 42 | | 572.4 | 1H NMR (400 MHz, CD3OD): δ 8.58-8.53 (m, 1H), 8.43-8.38 (m, 1H), 7.76-7.73 (m, 1H), 7.62-7.59 (m, 1H), 7.24-7.20 (m, 1H), 6.95-6.90 (m, 1H), 6.84-6.79 (m, 1H), 4.86-4.81 (m, 2H), 4.54-4.49 (m, 1H), 3.82-3.74 (m, 1H), 3.72-3.68 (m, 1H), 3.65 (s, 3H), 3.29-3.27 (m, 3H), 2.79-2.70 (m, 2H), 2.67-2.58 (m, 2H), 1.59-1.54 (m, 3H), 1.31-1.28 (m, 6H). | I-42 and I-4 |
| 43 | | 664.3 | 1H NMR (400 MHz, CD3OD): δ 8.57-8.53 (m, 1H), 8.53-8.50 (m, 1H), 8.11-8.06 (m, 1H), 7.85-7.81 (m, 1H), 7.58-7.55 (m, 1H), 7.52-7.49 (m, 1H), 7.24-7.20 (m, 1H), 6.95-6.92 (m, 1H), 6.81-6.76 (m, 1H), 4.72-4.68 (m, 2H), 4.67-4.64 (m, 1H), 4.62-4.57 (m, 2H), 4.51-4.46 (m, 1H), 4.41-4.34 (m, 1H), 3.82-3.75 (m, 1H), 3.70 (s, 3H), 3.50-3.43 (m, 1H), 3.18-3.11 (m, 1H), 2.84-2.79 (m, 1H), 2.78-2.69 (m, 2H), 2.67-2.58 (m, 3H), 2.26-2.18 (m, 1H), 2.09-2.00 (m, 1H), 1.31-1.28 (m, 6H), 1.23-1.19 (m, 3H). | I-43 and I-4 |
| 44 | | 664.3 | 1H NMR (400 MHz, CD3OD): δ 8.81-8.75 (m, 1H), 8.58-8.54 (m, 1H), 8.33-8.28 (m, 2H), 7.62-7.60 (m, 1H), 7.59-7.57 (m, 1H), 7.25-7.20 (m, 1H), 6.96-6.92 (m, 1H), 6.82-6.77 (m, 1H), 4.73-4.68 (m, 2H), 4.66-4.57 (m, 3H), 4.52-4.46 (m, 1H), 3.71 (s, 3H), 3.65-3.58 (m, 1H), 3.55-3.46 (m, 1H), 3.19-3.07 (m, 2H), 2.80-2.69 (m, 2H), 2.67-2.58 (m, 2H), 2.58-2.50 (m, 2H), 2.46-2.38 (m, 1H), 2.33-2.24 (m, 1H), 1.31-1.28 (m, 6H), 1.07-1.01 (m, 3H). | I-44 and I-4 |

-continued

| Compound | Structural formula | LC-MS [M + H]+ | 1HNMR | Intermediate |
|---|---|---|---|---|
| 45 | | 608.3 | 1H NMR (400 MHz, CD3OD): δ 8.57-8.51 (m, 1H), 8.40-8.34 (m, 1H), 7.73-7.69 (m, 1H), 7.60-7.57 (m, 1H), 7.48-7.44 (m, 1H), 7.25-7.20 (m, 1H), 7.13-7.08 (m, 1H), 6.98-6.89 (m, 2H), 6.81-6.75 (m, 1H), 4.60-4.57 (m, 1H), 4.50-4.45 (m, 1H), 3.95-3.90 (m, 1H), 3.81-3.75 (m, 1H), 3.70 (s, 3H), 3.50-3.44 (m, 1H), 3.41-3.35 (m, 1H), 3.26-3.20 (m, 1H), 2.96-2.69 (m, 2H), 2.67-2.34 (m, 2H), 2.07-2.00 (m, 1H), 1.81-1.71 (m, 1H), 1.69-1.59 (m, 1H), 1.56-1.46 (m, 1H), 1.31-1.28 (m, 6H). | I-45 and I-4 |
| 46 | | 638.3 | 1H NMR (400 MHz, CD3OD): δ 8.56-8.51 (m, 1H), 8.38-8.34 (m, 1H), 7.72-7.68 (m, 1H), 7.59-7.56 (m, 1H), 7.47-7.43 (m, 1H), 7.24-7.20 (m, 1H), 7.12-7.07 (m, 1H), 6.97-6.88 (m, 2H), 6.81-6.75 (m, 1H), 4.61-4.57 (m, 1H), 4.50-4.45 (m, 1H), 4.12-4.06 (m, 1H), 3.69 (s, 3H), 3.52-3.49 (m, 2H), 3.40-3.35 (m, 1H), 3.34-3.32 (m, 1H), 3.11-3.03 (m, 1H), 2.96-2.69 (m, 2H), 2.67-2.34 (m, 2H), 2.20-2.12 (m, 1H), 1.76-1.67 (m, 1H), 1.48-1.38 (m, 2H), 1.32-1.28 (m, 6H). | I-46 and I-4 |
| 47 | | 622.3 | 1H NMR (400 MHz, CD3OD): δ 8.96-8.92 (m, 1H), 8.57-8.55 (m, 1H), 8.34-8.32 (m, 1H), 7.71-7.67 (m, 1H), 7.63-7.61 (m, 1H), 7.60-7.57 (m, 1H), 7.24-7.22 (m, 1H), 7.12-7.09 (m, 1H), 6.95-6.92 (m, 1H), 6.80-6.78 (m, 1H), 4.62-4.58 (m, 1H), 4.51-4.47 (m, 1H), 3.75-3.58 (m, 11H), 2.80-2.69 (m, 2H), 2.67-2.58 (m, 2H), 1.30-1.28 (m, 6H). | I-47 and I-4 |

| Compound | Structural formula | LC-MS [M + H]+ | 1HNMR | Intermediate |
|---|---|---|---|---|
| 48 | | 635.3 | 1H NMR (400 MHz, CD3OD): δ 8.95-8.92 (m, 1H), 8.57-8.54 (m, 1H), 8.33-8.30 (m, 1H), 7.69 7.66 (m, 1H), 7.63 7.61 (m, 1H), 7.59 7.57 (m, 1H), 7.24-7.21 (m, 1H), 7.11-7.08 (m, 1H), 6.94-6.92 (m, 1H), 6.80-6.77 (m, 1H), 4.62-4.57 (m, 1H), 4.51-4.46 (m, 1H), 3.76-3.56 (m, 7H), 2.79-2.69 (m, 2H), 2.66-2.58 (m, 2H), 2.54-2.40 (m, 4H), 2.31 (s, 3H), 1.30-1.27 (m, 6H). | I-48 and I-4 |
| 49 | | 650.3 | 1H NMR (400 MHz, CD3OD): δ 8.64-8.60 (m, 1H), 8.60-8.58 (m, 1H), 8.06-8.01 (m, 1H), 7.72-7.68 (m, 1H), 7.48-7.43 (m, 1H), 7.23-7.19 (m, 1H), 7.18-7.14 (m, 1H), 6.94-6.91 (m, 1H), 6.82-6.79 (m, 1H), 4.74-4.68 (m, 3H), 4.66-4.57 (m, 2H), 4.53-4.47 (m, 1H), 3.76-3.65 (m, 1H), 3.53-3.45 (m, 1H), 3.21-3.06 (m, 2H), 2.79-2.67 (m, 2H), 2.66-2.61 (m, 2H), 2.61-2.55 (m, 1H), 2.51-2.45 (m, 1H), 2.38-2.31 (m, 2H), 1.29-1.28 (m, 6H), 1.06-1.01 (m, 3H). | I-49 and I-4 |
| 50 | | 596.3 | 1H NMR (400 MHz, CD3OD): δ 8.56-8.51 (m, 1H), 8.45-8.40 (m, 1H), 7.78-7.74 (m, 1H), 7.60-7.56 (m, 1H), 7.49-7.45 (m, 1H), 7.25-7.20 (m, 2H), 7.01-6.96 (m, 1H), 6.95-6.91 (m, 1H), 6.80-6.75 (m, 1H), 4.62-4.56 (m, 1H), 4.50-4.44 (m, 1H), 3.69 (s, 3H), 3.56-3.52 (m, 2H), 3.47-3.42 (m, 2H), 3.32 (s, 3H), 2.92 (s, 3H), 2.78-2.69 (m, 2H), 2.66-2.57 (m, 2H), 1.30-1.26 (m, 6H). | I-50 and I-4 |

-continued

| Compound | Structural formula | LC-MS [M + H]+ | 1HNMR | Intermediate |
|---|---|---|---|---|
| 51 | | 624.3 | 1H NMR (400 MHz, CD3OD): δ 8.57-8.52 (m, 1H), 8.51-8.45 (m, 1H), 7.89-7.81 (m, 1H), 7.61-7.57 (m, 1H), 7.50-7.46 (m, 1H), 7.34-7.29 (m, 1H), 7.24-7.20 (m, 1H), 7.02-6.97 (m, 1H), 6.96-6.90 (m, 1H), 6.81-6.75 (m, 1H), 4.62-4.56 (m, 1H), 4.51-4.45 (m, 1H), 3.89-3.79 (m, 1H), 3.70 (s, 3H), 3.46-3.40 (m, 2H), 3.35-3.31 (m, 5H), 2.79-2.69 (m, 2H), 2.66-2.57 (m, 2H), 1.30-1.27 (m, 6H), 1.17-1.11 (m, 6H). | I-51 and I-4 |
| 80 | | 663.3 | 1H NMR (400 MHz, CD3OD): δ 8.68 (d, J = 2.1 Hz, 1H), 8.55 (d, J = 5.1 Hz, 1H), 7.95 (d, J = 2.7 Hz, 1H), 7.59 (d, J = 5.1 Hz, 1H), 7.53 (d, J = 2.2 Hz, 1H), 7.46-7.42 (m, 1H), 7.22 (d, J = 5.9 Hz, 1H), 7.03 (d, J = 8.9 Hz, 1H), 6.93 (s, 1H), 6.78 (d, J = 5.9 Hz, 1H), 4.75-4.41 (m, 6H), 3.70 (s, 3H), 3.53-2.49 (m, 2H), 3.14-2.96 (m, 2H), 2.80-2.68 (m, 2H), 2.65-2.40 (m, 5H), 2.22-2.18 (m, 1H), 1.30-1.28 (m, 6H), 0.97 (d, J = 6.3 Hz, 3H). | I-76 and I-4 |
| 81 | | 512.2 | 1H NMR (400 MHz, CD3OD/CDCl3 = 1/1) δ 8.55-8.50 (m, 1H), 7.91-7.87 (m, 1H), 7.54-7.52 (m, 1H), 7.48-7.45 (m, 1H), 7.34-7.31 (m, 1H), 7.11-7.07 (m, 1H), 6.97-6.93 (m, 1H), 6.71-6.66 (m, 1H), 6.02-5.97 (m, 1H), 4.56-4.50 (m, 1H), 4.46-4.39 (m, 1H), 3.77 (s, 3H), 3.68 (s, 3H), 2.76-2.66 (m, 2H), 2.65-2.55 (m, 2H), 1.29-1.25 (m, 6H). | I-100 and I-4 |
| 82 | | 526.2 | 1H NMR (400 MHz, CD3OD) δ 8.55-8.48 (m, 1H), 7.92-7.85 (m, 1H), 7.58-7.53 (m, 1H), 7.43-7.38 (m, 1H), 7.23-7.18 (m, 1H), 6.96-6.88 (m, 1H), 6.80-6.73 (m, 1H), 5.89-5.82 (m, 1H), 4.59-4.53 (m, 1H), 4.49-4.42 (m, 1H), 3.67 (s, 3H), 3.64 (s, 3H), 2.79-2.67 (m, 2H), 2.66-2.55 (m, 2H), 2.22 (s, 3H), 1.30-1.26 (m, 6H). | I-101 and I-4 |

| Compound | Structural formula | LC-MS [M + H]+ | 1HNMR | Intermediate |
|---|---|---|---|---|
| 83 | | 510.2 | ¹H NMR (400 MHz, CD₃OD) δ 8.93 (d, J = 2.4 Hz, 1H), 8.66 (s, 1H), 8.56 (d, J = 5.2 Hz, 1H), 8.26 (d, J = 6.0 Hz, 1H), 7.72 (d, J = 2.4 Hz, 1H), 7.58 (d, J = 4.8 Hz, 1H), 7.22 (d, J = 6.0 Hz, 1H), 7.07 (d, J = 6.0 Hz, 1H), 6.93 (s, 1H), 6.79 (d, J = 6.0 Hz, 1H), 4.59 (d, J = 12.0 Hz, 1H), 4.48 (d, J = 12.0 Hz, 1H), 3.70 (s, 3H), 2.73 (d, J = 3.2 Hz, 2H), 2.62 (s, 2H), 1.28 (d, J = 6.4 Hz, 6H). | I-102 and I-4 |
| 84 | | 510.2 | ¹H NMR (400 MHz, CD₃OD) δ 8.95 (d, J = 1.9 Hz, 1H), 8.64 (d, J = 4.4 Hz, 1H), 8.55 (d, J = 5.2 Hz, 1H), 7.77 (d, J = 2.0 Hz, 1H), 7.60 (d, J = 4.8 Hz, 1H), 7.48-7.45 (m, 1H), 7.39 (d, J = 8.4 Hz, 1H), 7.14 (d, J = 6.4 Hz, 1H), 6.95 (s, 1H), 6.73 (d, J = 6.0 Hz, 1H), 4.56 (d, J = 12.0 Hz, 1H), 4.45 (d, J = 12.4 Hz, 1H), 3.73 (s, 3H), 2.72 (s, 2H), 2.61 (s, 2H), 1.28 (d, J = 3.6 Hz, 6H). | I-103 and I-4 |
| 85 | | 524.2 | ¹H NMR (400 MHz, CD₃OD) δ 8.93 (d, J = 2.4 Hz, 1H), 8.56 (d, J = 5.2 Hz, 1H), 7.71 (d, J = 2.4 Hz, 1H), 7.62 (d, J = 5.2 Hz, 1H), 7.40 (d, J = 4.0 Hz, 2H), 7.22 (d, J = 6.0 Hz, 1H), 6.93 (s, 1H), 6.78 (d, J = 5.6 Hz, 1H), 4.59 (d, J = 12.0 Hz, 1H), 4.49 (d, J = 12.1 Hz, 1H), 3.72 (s, 3H), 2.74 (d, J = 2.6 Hz, 2H), 2.62 (s, 2H), 2.53 (s, 3H), 1.29 (d, J = 5.6 Hz, 6H). | I-104 and I-4 |
| 86 | | 512.2 | ¹H NMR (400 MHz, CD₃OD) δ 8.53-8.48 (m, 1H), 7.76-7.70 (m, 1H), 7.53-7.46 (m, 2H), 7.32-7.28 (m, 1H), 7.24-7.20 (m, 1H), 7.06-7.01 (m, 1H), 6.95-6.90 (m, 1H), 6.77-6.72 (m, 1H), 4.55-4.42 (m, 2H), 3.83 (s, 3H), 3.68 (s, 3H), 2.79-2.68 (m, 2H), 2.67-2.56 (m, 2H), 1.30-1.27 (m, 6H). | I-105 and I-4 |

| Compound | Structural formula | LC-MS [M + H]⁺ | 1HNMR | Intermediate |
|---|---|---|---|---|
| 87 | | 513.2 | ¹H NMR (400 MHz, CD₃OD) δ 8.58-8.53 (m, 1H), 8.16-8.11 (m, 1H), 7.63-7.57 (m, 2H), 7.24-7.20 (m, 1H), 6.95-6.91 (m, 1H), 6.80-6.77 (m, 1H), 6.06-6.01 (m, 1H), 4.60-4.44 (m, 2H), 3.69 (s, 3H), 2.81-2.68 (m, 2H), 2.67-2.56 (m, 2H), 2.33 (s, 3H), 1.30-1.27 (m, 6H). | I-106 and I-4 |
| 88 | | 488.2 | ¹H NMR (400 MHz, CD₃OD) δ 8.62-8.57 (m, 1H), 8.57-8.52 (m, 1H), 7.82-7.77 (m, 1H), 7.55-7.52 (m, 1H), 7.24-7.19 (m, 1H), 6.95-6.90 (m, 1H), 6.80-6.75 (m, 1H), 4.56-4.41 (m, 2H), 3.67 (s, 3H), 2.78-2.68 (m, 2H), 2.66-2.56 (m, 2H), 2.52-2.45 (m, 2H), 1.30-1.26 (m, 6H), 1.21-1.15 (m, 3H). | I-107 and I-4 |
| 89 | | 500.2 | ¹H NMR (400 MHz, CD₃OD) δ 8.59-8.50 (m, 2H), 7.82-7.75 (m, 1H), 7.55-7.50 (m, 1H), 7.24-7.17 (m, 1H), 6.95-6.88 (m, 1H), 6.80-6.73 (m, 1H), 4.57-4.39 (m, 2H), 3.68 (s, 3H), 2.78-2.68 (m, 2H), 2.66-2.56 (m, 2H), 2.01-1.88 (m, 1H), 1.31-1.25 (m, 6H), 0.97-0.85 (m, 4H). | I-108 and I-4 |
| 90 | | 527.2 | ¹H NMR (400 MHz, CD₃OD/CDCl₃ = 1.1) δ 8.74-8.69 (m, 1H), 8.57-8.52 (m, 1H), 8.07-8.03 (m, 1H), 7.62-7.61 (m, 1H), 7.55-7.53 (m, 1H), 7.40-7.34 (m, 1H), 7.11-7.07 (m, 1H), 7.00-6.94 (m, 2H), 6.71-6.68 (m, 1H), 4.56-4.41 (m, 2H), 3.70 (s, 3H), 2.77-2.65 (m, 2H), 2.65-2.56 (m, 2H), 1.29-1.25 (m, 6H). | I-109 and I-4 |

| Compound | Structural formula | LC-MS [M + H]+ | 1HNMR | Intermediate |
|---|---|---|---|---|
| 91 | | 677.3 | 1H NMR (400 MHz, CD3OD) δ 8.64-8.60 (m, 1H), 8.56-8.52 (m, 1H), 7.92-7.87 (m, 1H), 7.60-7.56 (m, 1H), 7.52-7.49 (m, 1H), 7.42-7.37 (m, 1H), 7.23-7.20 (m, 1H), 7.04-6.98 (m, 1H), 6.94-6.91 (m, 1H), 6.80-6.75 (m, 1H), 4.73-4.67 (m, 2H), 4.65-4.59 (m, 2H), 4.58-4.56 (m, 1H), 4.51-4.44 (m, 1H), 3.69 (s, 3H), 3.52-3.45 (m, 1H), 3.41-3.34 (m, 1H), 3.16-3.05 (m, 2H), 2.78-2.68 (m, 2H), 2.66-2.54 (m, 3H), 2.50-2.38 (m, 2H), 2.35-2.26 (m, 1H), 1.70-1.58 (m, 1H), 1.42-1.33 (m, 1H), 1.30-1.26 (m, 6H), 0.86-0.079 (m, 3H). | I-110 and I-4 |
| 94 | | 664.3 | 1H NMR (400 MHz, CD3OD): δ 8.67 (d, J = 2.1 Hz, 1H), 8.55 (d, J = 5.1 Hz, 1H), 7.94 (d, J = 2.7 Hz, 1H), 7.58 (d, J = 5.1 Hz, 1H), 7.52 (d, J = 2.3 Hz, 1H), 7.44 (dd, J = 9.0, 2.8 Hz, 1H), 7.22 (d, J = 5.9 Hz, 1H), 7.02 (d, J = 8.9 Hz, 1H), 6.93 (s, 1H), 6.78 (d, J = 5.9 Hz, 1H), 4.72-4.46 (m, 6H), 3.70 (s, 3H), 3.53-3.45 (m, 1H), 3.12-2.99 (m, 2H), 2.79-2.68 (m, 2H), 2.65-2.60 (m, 2H), 2.60-2.54 (m, 1H), 2.51-2.43 (m, 1H), 2.26-2.16 (m, 1H), 1.28 (d, J = 6.3 Hz, 6H), 0.96 (d, J = 6.3 Hz, 3H). | I-111 and I-4 |
| 95 | | 677.4 | 1H NMR (400 MHz, CD3OD) δ 8.75 (d, J = 2.3 Hz, 1H), 8.56 (d, J = 5.1 Hz, 1H), 8.02 (d, J = 2.6 Hz, 1H), 7.60 (d, J = 5.1 Hz, 1H), 7.55 (d, J = 2.2 Hz, 1H), 7.50-7.48 (m, 1H), 7.23 (d, J = 5.9 Hz, 1H), 7.00 (d, J = 8.8 Hz, 1H), 6.94 (s, 1H), 6.79 (d, J = 5.9 Hz, 1H), 4.70-4.50 (m, 6H), 3.71 (s, 3H), 3.45-3.43 (m, 1H), 3.15-3.13 (m, 2H), 2.79-2.68 (m, 2H), 2.67-2.57 (m, 2H), 2.44-2.42 (m, 2H), 2.25-2.15 (m, 2H), 1.29-1.27 (m, 6H), 1.07-1.05 (m, 6H). | I-112 and I-4 |

-continued

| Compound | Structural formula | LC-MS [M + H]+ | 1HNMR | Intermediate |
|---|---|---|---|---|
| 97 | | 666.3 | 1H NMR (400 MHz, CD3OD) δ 8.68 (d, J = 2.1 Hz, 1H), 8.55 (d, J = 5.0 Hz, 1H), 7.95 (d, J = 2.7 Hz, 1H), 7.59 (d, J = 5.2 Hz, 1H), 7.52 (d, J = 2.3 Hz, 1H), 7.44 (dd, J = 8.9, 2.8 Hz, 1H), 7.22 (d, J = 5.9 Hz, 1H), 7.03 (d, J = 8.9 Hz, 1H), 6.93 (s, 1H), 6.78 (d, J = 5.9 Hz, 1H), 4.72-4.47 (m, 6H), 3.56-3.44 (m, 2H), 3.14-3.01 (m, 2H), 2.79-2.69 (m, 2H), 2.66-2.59 (m, 2H), 2.59-2.54 (m, 1H), 2.50-2.4.3 (m, 2H), 2.26-2.14 (m, 1H), 1.29 (d, J = 6.4 Hz, 6H), 0.97 (d, J = 6.3 Hz, 3H). | I-81 and I-4 |
| 99 | | 625.3 | 1H NMR (400 MHz, CD3OD) δ 8.57-8.52 (m, 1H), 8.12-8.07 (m, 1H), 7.58-7.55 (m, 1H), 7.46-7.42 (m, 1H), 7.25-7.20 (m, 1H), 6.95-6.90 (m, 1H), 6.81-6.75 (m, 1H), 6.27-6.21(m, 1H), 4.60-4.54 (m, 1H), 4.50-4.44 (m, 1H), 3.79 (s, 3H), 3.75-3.61 (m, 11H), 2.78-2.68 (m, 2H), 2.66-2.56 (m, 2H), 1.30-1.27 (m, 6H). | I-165 and I-4 |
| 102 | | 646.3 | 1H NMR (400 MHz, CD3OD): δ 8.68 (d, J = 2.0 Hz, 1H), 8.55 (d, J = 5.1 Hz, 1H), 7.94 (d, J = 2.5 Hz, 1H), 7.59 (d, J = 5.1 Hz, 1H), 7.52 (d, J = 2.0 Hz, 1H), 7.43 (dd, J = 8.9, 2.8 Hz, 1H), 7.22 (d, J = 5.9 Hz, 1H), 7.02 (d, J = 8.9 Hz, 1H), 6.93 (s, 1H), 6.78 (dd, J = 5.9, 0.6 Hz, 1H), 4.66-4.43 (m, 2H), 3.75-3.63 (m, 5H), 3.62-3.50 (m, 1H), 3.14-3.03 (m, 2H), 2.83-2.58 (m, 7H), 2.54-2.46 (m, 1H), 1.28 (d, J = 6.5 Hz, 6H), 0.97 (d, J = 6.4 Hz, 3H). | I-113 and I-4 |

| Compound | Structural formula | LC-MS [M + H]+ | 1HNMR | Intermediate |
|---|---|---|---|---|
| 106 | | 595.3 | ¹H NMR (400 MHz, CD₃OD/CDCl₃ = 2/1) δ 8.57-8.52 (m, 2H), 8.31-8.27 (m, 1H), 7.62-7.59 (m, 1H), 7.57-7.53 (m, 1H), 7.50-7.46 (m, 1H), 7.20-7.16 (m, 1H), 7.07-7.04 (m, 1H), 6.96-6.92 (m, 1H), 4.85-4.81 (m, 2H), 4.66-4.62 (m, 2H), 4.56-4.43 (m, 3H), 3.69 (s, 3H), 2.84-2.79 (m, 2H), 2.78 (s, 3H), 2.66-2.60 (m, 2H), 1.30 (s, 6H). | I-41 and I-114 |
| 107 | | 612.3 | ¹H NMR (400 MHz, CD₃OD) δ 8.55-8.49 (m, 1H), 8.41-8.36 (m, 1H), 7.97-7.90 (m, 1H), 7.58-7.55 (m, 1H), 7.41-7.36 (m, 1H), 7.70-6.99 (m, 1H), 5.90-5.78 (m, 1H), 4.59-4.49 (m, 2H), 4.04-3.97 (m, 2H), 3.72-3.68 (m, 2H), 3.66 (s, 3H), 3.59-3.55 (m, 2H), 3.33 (s, 3H), 3.04-2.97 (m, 2H), 2.85-2.80 (m, 2H), 2.78-2.72 (m, 2H), 2.63 (s, 2H), 1.29 (s, 6H). | I-115 and I-114 |
| 108 | | 632.3 | ¹H NMR (400 MHz, CD₃OD): δ 8.71 (d, J = 1.8 Hz, 1H), 8.55 (d, J = 5.1 Hz, 1H), 7.94 (d, J = 2.5 Hz, 1H), 7.58 (d, J = 5.2 Hz, 1H), 7.53 (d, J = 1.8 Hz, 1H), 7.43 (dd, J = 8.8, 2.7 Hz, 1H), 7.22 (d, J = 5.9 Hz, 1H), 7.03 (d, J = 8.9 Hz, 1H), 6.93 (s, 1H), 6.78 (d, J = 6.0 Hz, 1H), 4.64-4.45 (m, 2H), 3.70 (s, 3H), 3.58-3.33 (m, 4H), 3.15-3.09 (m, 3H), 2.79-2.69 (m, 2H), 2.66-2.55 (m, 2H), 1.28 (d, J = 6.5 Hz, 6H), 0.98 (d, J = 6.4 Hz, 3H). | I-116 and I-4 |

-continued

| Compound | Structural formula | LC-MS [M + H]+ | 1HNMR | Intermediate |
|---|---|---|---|---|
| 109 | | 675.3 | ¹H NMR (400 MHz, CD₃OD): δ 8.52 (d, J = 5.0 Hz, 1H), 8.43 (s, 1H), 7.63 (s, 1H), 7.56 (d, J = 5.1 Hz, 1H), 7.45 (d, J = 2.1 Hz, 1H), 7.20 (d, J = 5.9 Hz, 1H), 7.08 (dd, J = 9.0, 2.8 Hz, 1H), 6.99 (d, J = 8.7 Hz, 1H), 6.92 (s, 1H), 6.76 (d, J = 5.9 Hz, 1H), 4.77-4.67 (m, 4H), 4.60-4.44 (m, 2H), 4.24-4.14 (m, 1H), 4.08-3.97 (m, 1H), 3.68 (s, 3H), 3.54-3.40 (m, 2H), 3.24-3.15 (m, 1H), 3.02-2.92 (m, 1H), 2.77-2.69 (m, 2H), 2.68-2.57 (m, 3H), 2.29-2.16 (m, 1H), 2.00-1.90 (m, 2H), 1.66-1.55 (m, 1H), 1.27 (d, J = 6.4 Hz, 6H). | I-117 and I-4 |
| 110 | | 626.3 | ¹H NMR (400 MHz, CD₃OD) δ 8.58-8.47 (m, 1H), 8.45-8.34 (m, 1H), 7.99-7.88 (m, 1H), 7.61-7.51 (m, 1H), 7.43-7.33 (m, 1H), 7.08-6.98 (m, 1H), 5.95-5.85 (m, 1H), 4.62-4.47 (m, 2H), 4.03-3.91 (m, 2H), 3.81-3.74 (m, 1H), 3.67 (s, 3H), 3.59-3.51 (m, 2H), 3.38-3.31 (m, 4H), 2.98-2.86 (m, 2H), 2.86-2.78 (m, 2H), 2.73-2.65 (m, 1H), 2.65-2.58 (m, 2H), 1.43-1.36 (m, 3H), 1.29 (s, 6H). | I-118 and I-114 |
| 111 | | 625.3 | ¹H NMR (400 MHz, CD₃OD) δ 8.55 (s, 1H), 8.02-7.91 (m, 1H), 7.56 (s, 1H), 7.41 (d, J = 1.9 Hz, 1H), 7.20 (d, J = 5.8 Hz, 1H), 6.92 (s, 1H), 6.76 (d, J = 5.8 Hz, 1H), 5.86 (s, 1H), 4.52-4.48 (m, 2H), 3.99-3.95 (m, 2H), 3.84-3.72 (m, 1H), 3.67 (s, 3H), 3.59-3.46 (m, 2H), 3.37-3.35 (m, 1H), 3.33 (s, 3H), 2.97-2.83 (m, 2H), 2.78-2.56 (m, 5H), 1.40 (d, J = 6.5 Hz, 3H), 1.29-1.26 (m, 6H). | I-118 and I-4 |

| Compound | Structural formula | LC-MS [M + H]⁺ | 1HNMR | Intermediate |
|---|---|---|---|---|
| 112 | | 623.3 | ¹H NMR (400 MHz, CD₃OD) δ 8.49 (d, J = 4.6 Hz, 1H), 7.97 (d, J = 0.7 Hz, 1H), 7.53 (d, J = 5.0 Hz, 1H), 7.40 (d, J = 1.3 Hz, 1H), 7.18 (d, J = 5.9 Hz, 1H), 6.91 (s, 1H), 6.75 (d, J = 5.9 Hz, 1H), 5.87 (s, 1H), 4.72-4.64 (m, 4H), 4.56-4.43 (m, 2H), 4.05-3.89 (m, 3H), 3.78-3.76 (m, 1H), 3.63 (s, 3H), 3.19-3.09 (m, 1H), 2.82-2.54 (m, 5H), 1.27-1.23 (m, 9H). | I-119 and I-4 |
| 115 | | 625.2 | ¹H NMR (400 MHz, CD₃OD) δ 8.52 (d, J = 5.1 Hz, 1H), 7.95 (d, J = 2.2 Hz, 1H), 7.56 (d, J = 5.1 Hz, 1H), 7.42 (d, J = 2.2 Hz, 1H), 7.21 (d, J = 5.9 Hz, 1H), 6.92 (s, 1H), 6.76 (d, J = 5.9 Hz, 1H), 5.84 (s, 1H), 4.58-4.42 (m, 2H), 3.98 (t, J = 5.5 Hz, 2H), 3.86-3.74 (m, 2H), 3.67 (s, 3H), 3.53-3.51 (m, 1H), 3.41-3.39 (m, 1H), 3.32 (s, 3H), 3.11-2.91 (m, 3H), 2.79-2.67 (m, 2H), 2.67-2.55 (m, 2H), 1.30-1.26 (m, 6H), 1.10 (d, J = 6.8 Hz, 3H). | I-120 and I-4 |
| 118 | | 624.3 | ¹H NMR (400 MHz, CD₃OD) δ 8.56-8.52 (m, 1H), 8.42-8.38 (m, 1H), 7.98-7.93 (m, 1H), 7.60-7.57 (m, 1H), 7.41-7.38 (m, 1H), 7.06-7.02 (m, 1H), 5.92-5.89 (m, 1H), 4.72-4.68 (m, 3H), 4.65-4.62 (m, 1H), 4.59-4.51 (m, 2H), 4.06-4.00 (m, 1H), 3.99-3.94 (m, 2H), 3.84-3.78 (m, 1H), 3.68 (s, 3H), 3.21-3.15 (m, 1H), 2.86-2.79 (m, 3H), 2.66-2.62 (m, 2H), 1.30 (s, 6H), 1.29-1.27 (m, 3H). | I-119 and I-114 |

| Compound | Structural formula | LC-MS [M + H]+ | 1HNMR | Intermediate |
|---|---|---|---|---|
| 121 | | 640.3 | 1H NMR (400 MHz, CD3OD) δ 8.56-8.51 (m, 1H), 7.96-7.92 (m, 1H), 7.59-7.57 (m, 1H), 7.42-7.38 (m, 1H), 7.06-7.02 (m, 1H), 5.93-5.89 (m, 1H), 4.59-4.50 (m, 2H), 4.02-3.94 (m, 2H), 3.83-3.75 (m, 1H), 3.68 (s, 3H), 3.59-3.53 (m, 2H), 3.40-3.35 (m, 1H), 3.07-3.02 (m, 2H), 3.00-2.86 (m, 2H), 2.73-2.65 (m, 1H), 2.63-2.60 (m, 5H), 1.43-1.38 (m, 3H), 1.31 (s, 6H). | I-118 and I-121 |
| 122 | | 610.3 | 1H NMR (400 MHz, CD3OD) δ 8.56-8.51 (m, 1H), 8.42-8.38 (m, 1H), 7.98-7.94 (m, 1H), 7.60-7.56 (m, 1H), 7.42-7.38 (m, 1H), 7.06-7.02 (m, 1H), 5.88-5.85 (m, 1H), 4.75-4.72 (m, 2H), 4.64-4.61 (m, 2H), 4.58-4.52 (m, 2H), 4.06-4.01 (m, 2H), 3.78-3.71 (m, 1H), 3.68 (s, 3H), 3.58-3.54 (m, 2H), 2.86-2.81 (m, 4H), 2.65-2.62 (m, 2H), 1.30 (s, 6H). | I-122 and I-114 |
| 124 | | 609.3 | 1H NMR (400 MHz, CD3OD) δ 8.56-8.50 (m, 1H), 7.99 (d, J = 2.2 Hz, 1H), 7.57 (d, J = 5.1 Hz, 1H), 7.43 (d, J = 2.2 Hz, 1H), 7.21 (d, J = 5.9 Hz, 1H), 6.92 (s, 1H), 6.77 (d, J = 6.0 Hz, 1H), 5.91-5.84 (m, 1H), 4.75-4.46 (m, 6H), 4.03 (t, J = 5.6 Hz, 2H), 3.78-3.71 (m, 1H), 3.68 (s, 3H), 3.56 (s, 2H), 2.86-2.55 (m, 6H), 1.30-1.26 (m, 6H). | I-122 and I-4 |

-continued

| Compound | Structural formula | LC-MS [M + H]+ | 1HNMR | Intermediate |
|---|---|---|---|---|
| 125 | | 523.2 | ¹H NMR (400 MHz, CD₃OD) δ 8.72-8.66 (m, 1H), 8.58-8.52 (m, 1H), 8.05-8.00 (m, 1H), 7.60-7.57 (m, 1H), 7.55-7.52 (m, 1H), 7.48-7.43 (m, 1H), 7.25-7.20 (m, 1H), 7.00-6.90 (m, 2H), 6.81-6.76 (m, 1H), 4.62-4.57 (m, 1H), 4.51-4.45 (m, 1H), 3.70 (s, 3H), 2.80-2.67 (m, 2H), 2.67-2.56 (m, 2H), 2.22 (s, 3H), 1.30-1.27 (m, 6H). | I-123 and I-4 |
| 126 | | 539.2 | ¹H NMR (400 MHz, CD₃OD) δ 8.67-8.62 (m, 1H), 8.57-8.52 (m, 1H), 7.93-7.88 (m, 1H), 7.59-7.56 (m, 1H), 7.52-7.49 (m, 1H), 7.31-7.27 (m, 1H), 7.24-7.20 (m, 1H), 7.04-6.99 (m, 1H), 6.95-6.91 (m, 1H), 6.80-6.76 (m, 1H), 4.62-4.57 (m, 1H), 4.51-4.44 (m, 1H), 3.79 (s, 3H), 3.69 (s, 3H), 2.79-2.68 (m, 2H), 2.66-2.57 (m, 2H), 1.30-1.26 (m, 6H). | I-124 and I-4 |
| 130 | | 514.0 | ¹H NMR (400 MHz, CD₃OD) δ 8.64-8.59 (m, 1H), 8.58-8.53 (m, 1H), 7.82-7.76 (m, 1H), 7.58-7.51 (m, 1H), 7.27-7.18 (m, 1H), 6.96-6.90 (m, 1H), 6.81-6.75 (m, 1H), 4.59-4.49 (m, 1H), 4.49-4.39 (m, 1H), 3.67 (s, 3H), 3.43-3.37 (m, 1H), 2.79-2.69 (m, 2H), 2.67-2.56 (m, 2H), 2.39-2.27 (m, 2H), 2.26-2.17 (m, 2H), 2.10-1.97 (m, 1H), 1.96-1.81 (m, 1H), 1.30-1.26 (m, 6H). | I-127 and I-4 |
| 131 | | 536.0 | ¹H NMR (400 MHz, CD₃OD) δ 8.79-8.72 (m, 1H), 8.61-8.54 (m, 1H), 7.98-7.92 (m, 2H), 7.89-7.82 (m, 1H), 7.64-7.57 (m, 2H), 7.57-7.49 (m, 2H), 7.26-7.20 (m, 1H), 6.93 (s, 1H), 6.83-6.76 (m, 1H), 4.61-4.55 (m, 1H), 4.52-4.43 (m, 1H), 3.73 (s, 3H), 2.80-2.67 (m, 2H), 2.67-2.56 (m, 2H), 1.30-1.27 (m, 6H). | I-128 and I-4 |

| Compound | Structural formula | LC-MS [M + H]+ | 1HNMR | Intermediate |
|---|---|---|---|---|
| 132 | | 525.2 | ¹H NMR (400 MHz, CD₃OD/CDCl₃ = 2/1) δ 8.98-8.94 (m, 1H), 8.61-8.56 (m, 1H), 8.37-8.33 (m, 1H), 7.73-7.70 (m, 1H), 7.65-7.62 (m, 1H), 7.41-7.33 (m, 2H), 7.11-7.05 (m, 1H), 4.62-4.55 (m, 2H), 3.71 (s, 3H), 2.87-2.83 (m, 2H), 2.69-2.64 (m, 2H), 2.53 (s, 3H), 1.30 (s, 6H). | I-104 and I-114 |
| 133 | | 540.2 | ¹H NMR (400 MHz, CD₃OD) δ 8.62-8.59 (m, 1H), 8.54-8.51 (m, 1H), 8.41-8.38 (m, 1H), 7.92-7.89 (m, 1H), 7.59-7.56 (m, 1H), 7.48-7.45 (m, 1H), 7.29-7.25 (m, 1H), 7.05-7.02 (m, 1H), 7.02-6.98 (m, 1H), 4.60-4.52 (m, 2H), 3.79 (s, 3H), 3.68 (s, 3H), 2.86-2.79 (m, 2H), 2.65-2.60 (m, 2H), 1.30 (s, 6H). | I-124 and I-114 |
| 134 | | 581.2 | ¹H NMR (400 MHz, CD₃OD/CDCl₃ = 2/1) δ 8.59-8.54 (m, 1H), 7.99-7.94 (m, 1H), 7.59-7.56 (m, 1H), 7.50-7.47 (m, 1H), 7.21-7.17 (m, 1H), 7.01-6.97 (m, 1H), 6.78-6.72 (m, 1H), 5.90-5.86 (m, 1H), 4.80-4.76 (m, 2H), 4.69-4.65 (m, 2H), 4.60-4.55 (m, 1H), 4.50-4.45 (m, 1H), 4.12-4.05 (m, 2H), 3.82-3.75 (m, 1H), 3.72 (s, 3H), 3.62-3.57 (m, 2H), 2.96-2.90 (m, 2H), 2.89-2.85 (m, 2H), 2.84-2.79 (m, 2H), 2.63-2.54 (m, 2H). | I-122 and I-129 |
| 138 | | 499.0 | ¹H NMR (400 MHz, CDCl₃) δ 8.52 (d, J = 3.6 Hz, 1H), 7.79 (d, J = 2.2 Hz, 1H), 7.70 (s, 1H), 7.57 (s, 1H), 7.43-7.38 (m, 2H), 7.04 (s, 1H), 6.95-6.92 (m, 1H), 6.61 (d, J = 3.9 Hz, 1H), 5.28-5.24 (m, 1H), 4.50-4.33 (m, 4H), 3.70 (s, 3H), 2.86-2.82 (m, 4H), 2.61-2.50 (m, 2H), 1.55 (t, J = 7.4 Hz, 3H). | I-26 and I-129 |

-continued

| Compound | Structural formula | LC-MS [M + H]+ | 1HNMR | Intermediate |
|---|---|---|---|---|
| 139 | | 595.2 | ¹H NMR (400 MHz, CD₃OD) δ 8.56-8.52 (m, 1H), 8.49-8.46 (m, 1H), 8.42-8.39 (m, 1H), 7.60-7.58 (m, 1H), 7.54-7.52 (m, 1H), 7.47-7.43 (m, 1H), 7.04 (s, 1H), 6.99-6.93 (m, 2H), 4.62-4.51 (m, 2H), 4.36-4.29 (m, 1H), 4.10-4.04 (m, 2H), 3.69 (s, 3H), 3.63-3.59 (m, 2H), 3.31 (s, 3H), 2.85-2.82 (m, 2H), 2.65-2.62 (m, 2H), 1.30 (s, 6H). | I-36 and I-114 |
| 140 | | 620.2 | ¹H NMR (400 MHz, CD₃OD) δ 8.81-8.76 (m, 1H), 8.58-8.52 (m, 1H), 8.16-8.11 (m, 1H), 7.71-7.67 (m, 1H), 7.60-7.55 (m, 2H), 7.25-7.19 (m, 1H), 7.08-7.02 (m, 1H), 6.93 (s, 1H), 6.81-6.75 (m, 1H), 4.76-4.71 (m, 2H), 4.62-4.58 (m, 1H), 4.52-4.46 (m, 3H), 3.88-3.80 (m, 1H), 3.78-3.71 (m, 3H), 3.70 (s, 3H), 3.28-3.24 (m, 2H), 2.79-2.68 (m, 2H), 2.66-2.56 (m, 2H), 1.29-1.26 (m, 6H). | I-130 and I-4 |
| 141 | | 621.2 | ¹H NMR (400 MHz, CD₃OD) δ 8.77-8.73 (m, 1H), 8.57-8.53 (m, 1H), 8.43-8.39 (m, 1H), 8.16-8.11 (m, 1H), 7.70-7.67 (m, 1H), 7.61-7.58 (m, 1H), 7.55-7.51 (m, 1H), 7.07-7.02 (m, 2H), 4.75-4.72 (m, 2H), 4.61-4.54 (m, 2H), 4.52-4.48 (m, 2H), 3.87-3.81 (m, 1H), 3.78-3.71 (m, 3H), 3.70 (s, 3H), 3.28-3.26 (m, 2H), 2.87-2.80 (m, 2H), 2.66-2.61 (m, 2H), 1.31-1.29 (m, 6H). | I-130 and I-114 |

-continued

| Compound | Structural formula | LC-MS [M + H]+ | 1HNMR | Intermediate |
|---|---|---|---|---|
| 144 | | 595.3 | 1H NMR (400 MHz, CD3OD) δ 8.55-8.51 (m, 1H), 8.00-7.97 (m, 1H), 7.58-7.56 (m, 1H), 7.43-7.41 (m, 1H), 7.26-7.23 (m, 1H), 6.95-6.91 (m, 1H), 6.79-6.75 (m, 1H), 5.92-5.88 (m, 1H), 4.72-4.68 (m, 3H), 4.65-4.61 (m, 1H), 4.58-4.54 (m, 1H), 4.48-4.43 (m, 1H), 4.06-4.00 (m, 1H), 3.98-3.94 (m, 2H), 3.83-3.78 (m, 1H), 3.68 (s, 3H), 3.21-3.14 (m, 1H), 2.93-2.87 (m, 2H), 2.85-2.76 (m, 3H), 2.59-2.52 (m, 2H), 1.28-1.26 (m, 3H). | I-119 and I-129 |
| 145 | | 597.3 | 1H NMR (400 MHz, CD3OD) δ 8.55-8.51 (m, 1H), 7.99-7.95 (m, 1H), 7.58-7.56 (m, 1H), 7.43-7.40 (m, 1H), 7.25-7.22 (m, 1H), 6.95-6.91 (m, 1H), 6.79-6.75 (m, 1H), 5.92-5.88 (m, 1H), 4.59-4.53 (m, 1H), 4.50-4.42 (m, 1H), 4.02-3.94 (m, 2H), 3.81-3.76 (m, 1H), 3.68 (s, 3H), 3.58-3.53 (m, 2H), 3.38-3.34 (m, 1H), 3.33 (s, 3H), 2.98-2.88 (m, 4H), 2.81-2.76 (m, 2H), 2.72-2.65 (m, 1H), 2.59-2.51 (m, 2H), 1.42-1.38 (m, 3H). | I-118 and I-129 |
| 146 | | 511.2 | 1H NMR (400 MHz, CD3OD/CDCl3 = 1/2) δ 8.63-8.61 (m, 1H), 8.60-8.57 (m, 1H), 7.97-7.91 (m, 1H), 7.71-7.67 (m, 1H), 7.60-7.56 (m, 1H), 7.30-7.25 (m, 1H), 7.12-7.08 (m, 1H), 7.08-7.02 (m, 1H), 6.97-6.92 (m, 1H), 6.72-6.66 (m, 1H), 4.57-4.53 (m, 1H), 4.45-4.40 (m, 1H), 3.84 (s, 3H), 3.75 (s, 3H), 2.96-2.89 (m, 2H), 2.86-2.80 (m, 2H), 2.64-2.56 (m, 2H). | I-124 and I-129 |
| 147 | | 496.2 | 1H NMR (400 MHz, CD3OD/CDCl3 = 1/2) δ 8.99-8.95 (m, 1H), 8.59-8.55 (m, 1H), 7.93-7.89 (m, 1H), 7.61-7.58 (m, 1H), 7.34-7.30 (m, 1H), 7.22-7.18 (m, 1H), 7.10-7.07 (m, 1H), 7.07-7.03 (m, 1H), 6.73-6.67 (m, 1H), 4.58-4.52 (m, 1H), 4.43-4.38 (m, 1H), 3.77 (s, 3H), 2.95-2.90 (m, 2H), 2.86-2.81 (m, 2H), 2.63-2.57 (m, 5H). | I-104 and I-129 |

| Compound | Structural formula | LC-MS [M + H]+ | 1HNMR | Intermediate |
|---|---|---|---|---|
| 148 | | 583.2 | 1H NMR (400 MHz, CD3OD) δ 8.58-8.54 (m, 1H), 7.97-7.92 (m, 1H), 7.60-7.57 (m, 1H), 7.50-7.46 (m, 1H), 7.23-7.19 (m, 1H), 7.00-6.95 (m, 1H), 6.78-6.73 (m, 1H), 5.89-5.84 (m, 1H), 4.56-4.54 (m, 1H), 4.50-4.45 (m, 1H), 4.09-4.03 (m, 2H), 3.76-3.73 (m, 2H), 3.71 (s, 3H), 3.63-3.59 (m, 2H), 3.37 (s, 3H), 3.08-3.02 (m, 2H), 2.95-2.90 (m, 2H), 2.84-2.78 (m, 4H), 2.62-2.54 (m, 2H). | I-115 and I-129 |
| 152 | | 566.0 | 1H NMR (400 MHz, CD3OD/CDCl3 = 3/1) δ 8.53 (d, J = 5.1 Hz, 1H), 8.45 (d, J = 2.2 Hz, 1H), 7.56-7.52 (m, 3H), 7.15 (d, J = 5.9 Hz, 1H), 6.99-6.86 (m, 3H), 6.71 (d, J = 5.9 Hz, 1H), 4.57-4.45 (m, 2H), 4.37-4.28 (m, 1H), 4.09-4.07 (m, 2H), 3.73-3.60 (m, 5H), 3.31 (s, 3H), 2.90-2.88 (m, 2H), 2.80-2.78 (m, 2H), 2.57-2.55 (m, 2H). | I-36 and I-129 |
| 153 | | 528.2 | 1H NMR (400 MHz, CDCl3) δ 8.53 (d, J = 5.0 Hz, 1H), 7.97-7.95 (m, 1H), 7.73-7.71 (m, 1H), 7.51-7.35 (m, 2H), 7.02 (s, 1H), 6.92 (d, J = 5.8 Hz, 1H), 6.63 (d, J = 5.9 Hz, 1H), 5.88 (s, 1H), 5.05 (d, J = 11.0 Hz, 1H), 4.50-4.38 (m, 4H), 3.80-3.64 (m, 6H), 3.32 (s, 3H), 2.92-2.72 (m, 4H), 2.62-2.47 (m, 2H). | I-131 and I-129 |
| 154 | | 556.3 | 1H NMR (400 MHz, CD3OD) δ 8.53 (d, J = 5.1 Hz, 1H), 7.98 (d, J = 2.2 Hz, 1H), 7.56 (d, J = 5.1 Hz, 1H), 7.42 (d, J = 2.2 Hz, 1H), 7.21 (d, J = 5.9 Hz, 1H), 6.92 (s, 1H), 6.77 (d, J = 5.9 Hz, 1H), 6.06 (s, 1H), 4.63-4.37 (m, 4H), 3.74-3.66 (m, 6H), 3.31 (s, 3H), 2.80-2.53 (m, 4H), 1.30-1.26 (m, 6H). | I-131 and I-4 |

| Compound | Structural formula | LC-MS [M + H]+ | 1HNMR | Intermediate |
|---|---|---|---|---|
| 155 | | 526.0 | ¹H NMR (400 MHz, CDCl₃) δ 8.53 (d, J = 5.1 Hz, 1H), 7.99 (d, J = 2.2 Hz, 1H), 7.73 (d, J = 2.2 Hz, 1H), 7.49-7.41 (m, 2H), 7.00 (s, 1H), 6.92 (d, J = 5.9 Hz, 1H), 6.63 (d, J = 5.9 Hz, 1H), 5.69 (s, 1H), 5.06 (d, J = 9.9 Hz, 1H), 4.77 (s, 2H), 4.57-4.26 (m, 2H), 4.14-3.98 (m, 4H), 3.67 (s, 3H), 2.88-2.75 (m, 4H), 2.59-2.50 (m, 2H). | I-132 and I-129 |
| 156 | | 555.0 | ¹H NMR (400 MHz, CD₃OD) δ 8.57-8.50 (m, 1H), 8.39 (s, 1H), 8.01-7.92 (m, 1H), 7.59-7.54 (m, 1H), 7.43-7.36 (m, 1H), 7.03 (s, 1H), 5.84 (s, 1H), 4.76-4.71 (m, 2H), 4.59-4.48 (m, 2H), 4.09-4.04 (m, 2H), 4.01-3.94 (m, 2H), 3.67 (s, 3H), 2.85-2.79 (m, 2H), 2.66-2.60 (m, 2H), 1.30 (s, 6H). | I-132 and I-114 |
| 159 | | 595.0 | ¹H NMR (400 MHz, CD₃OD) δ 8.80-8.78 (m, 1H), 8.52 (d, J = 5.1 Hz, 1H), 7.65-7.49 (m, 2H), 7.32-7.12 (m, 2H), 6.96-6.64 (m, 3H), 4.65-4.29 (m, 4H), 4.28-4.15 (m, 2H), 3.85-3.83 (m, 2H), 3.68 (s, 3H), 3.31 (s, 3H), 2.80-2.52 (m, 4H), 1.29-1.25 (m, 6H). | I-133 and I-4 |
| 162 | | 554.0 | ¹H NMR (400 MHz, CD₃OD) δ 8.57-8.50 (m, 1H), 8.05-7.97 (m, 1H), 7.62-7.53 (m, 1H), 7.44 (s, 1H), 7.26-7.16 (m, 1H), 6.92 (s, 1H), 6.82-6.73 (m, 1H), 5.85 (s, 1H), 4.80-4.69 (m, 2H), 4.61-4.53 (m, 1H), 4.51-4.41 (m, 1H), 4.10-4.05 (m, 2H), 4.03-3.93 (m, 2H), 3.68 (s, 3H), 2.77-2.70 (m, 2H), 2.63-2.58 (m, 2H), 1.29-1.25 (m, 6H). | I-132 and I-4 |

| Compound | Structural formula | LC-MS [M + H]+ | 1HNMR | Intermediate |
|---|---|---|---|---|
| 164 | | 624.3 | 1H NMR (400 MHz, CD3OD) δ 8.55-8.49 (m, 1H), 7.98-7.92 (m, 1H), 7.58-7.54 (m, 1H), 7.42-7.37 (m, 1H), 7.06-7.01 (m, 1H), 5.89-5.82 (m, 1H), 4.74-4.70 (m, 2H), 4.64-4.59 (m, 2H), 4.56-4.49 (m, 2H), 4.05-3.98 (m, 2H), 3.76-3.70 (m, 1H), 3.67 (s, 3H), 3.60-3.48 (m, 2H), 3.06-3.01 (m, 2H), 2.86-2.79 (m, 2H), 2.62-2.58 (m, 5H), 1.30 (s, 6H). | I-122 and I-121 |
| 165 | | 582.3 | 1H NMR (400 MHz, CD3OD) δ 8.54-8.48 (m, 1H), 8.41-8.35 (m, 1H), 7.96-7.92 (m, 1H), 7.57-7.53 (m, 1H), 7.40-7.36 (m, 1H), 7.06-6.99 (m, 1H), 5.88-5.83 (m, 1H), 4.58-4.48 (m, 2H), 4.04-3.99 (m, 2H), 3.65 (s, 3H), 3.64-3.62 (m, 2H), 2.95-2.91 (m, 2H), 2.84-2.79 (m, 2H), 2.63-2.57 (m, 4H), 1.29 (s, 6H), 1.17-1.13 (m, 3H). | I-135 and I-114 |
| 169 | | 540.2 | 1H NMR (400 MHz, CD3OD/CDCl3 = 1/1) δ 8.94-8.85 (m, 1H), 8.63-8.55 (m, 1H), 7.84-7.78 (m, 1H), 7.66-7.61 (m, 1H), 7.34-7.28 (m, 1H), 7.13-7.08 (m, 1H), 7.07-6.99 (m, 2H), 6.76-6.67 (m, 1H), 4.58-4.55 (m, 2H), 4.47-4.41 (m, 1H), 4.05 (s, 3H), 3.77 (s, 3H), 2.80-2.72 (m, 2H), 2.70-2.62 (m, 2H), 1.33 (s, 6H). | I-137 and I-4 |

-continued

| Compound | Structural formula | LC-MS [M + H]⁺ | 1HNMR | Intermediate |
|---|---|---|---|---|
| 170 | | 608.3 | ¹H NMR (400 MHz, CD₃OD/CDCl₃ = 1/1) δ 8.62-8.56 (m, 1H), 8.26-8.21 (m, 1H), 7.94-7.90 (m, 1H), 7.58-7.56 (m, 1H), 7.49-7.45 (m, 1H), 7.14-7.09 (m, 1H), 5.87-5.83 (m, 1H), 4.58-4.49 (m, 2H), 4.10-4.05 (m, 2H), 3.72 (s, 3H), 3.60-3.55 (m, 2H), 3.07-2.98 (m, 1H), 2.88-2.83 (m, 4H), 2.70-2.65 (m, 2H), 2.20-2.12 (m, 2H), 2.01-1.90 (m, 2H), 1.84-1.72 (m, 2H), 1.34 (s, 6H). | I-138 and I-114 |
| 171 | | 594.3 | ¹H NMR (400 MHz, CD₃OD/CDCl₃ = 1/1) δ 8.62-8.55 (m, 1H), 8.28-8.23 (m, 1H), 7.93-7.88 (m, 1H), 7.58-7.55 (m, 1H), 7.48-7.45 (m, 1H), 7.14-7.09 (m, 1H), 5.87-5.82 (m, 1H), 4.57-4.52 (m, 2H), 4.08-4.03 (m, 2H), 3.86-3.82 (m, 2H), 3.72 (s, 3H), 3.19-3.14 (m, 2H), 2.87-2.82 (m, 2H), 2.77-2.65 (m, 2H), 1.98-1.90 (m, 1H), 1.34 (s, 6H), 0.64-0.57 (m, 2H), 0.56-0.51 (m, 2H). | I-139 and I-114 |
| 172 | | 526.2 | ¹H NMR (400 MHz, CD₃OD) δ 8.52-8.48 (m, 1H), 7.81-7.77 (m, 1H), 7.53-7.48 (m, 2H), 7.30-7.28 (m, 1H), 7.23-7.20 (m, 1H), 7.07-7.04 (m, 1H), 6.94-6.90 (m, 1H), 6.77-6.72 (m, 1H), 4.53-4.42 (m, 2H), 4.14-4.07 (m, 2H), 3.67 (s, 3H), 2.77-2.68 (m, 2H), 2.65-2.56 (m, 2H), 1.43-1.38 (m, 3H), 1.29-1.26 (m, 6H). | I-140 and I-4 |
| 173 | | 540.2 | ¹H NMR (400 MHz, CD₃OD) δ 8.53-8.49 (m, 1H), 7.84-7.81 (m, 1H), 7.54-7.49 (m, 2H), 7.30-7.27 (m, 1H), 7.24-7.21 (m, 1H), 7.10-7.07 (m, 1H), 6.94-6.90 (m, 1H), 6.77-6.73 (m, 1H), 4.53-4.45 (m, 2H), 4.45-4.40 (m, 1H), 3.68 (s, 3H), 2.76-2.70 (m, 2H), 2.63-2.59 (m, 2H), 1.46-1.43 (m, 6H), 1.29-1.27 (m, 6H). | I-141 and I-4 |

-continued

| Compound | Structural formula | LC-MS [M + H]+ | 1HNMR | Intermediate |
|---|---|---|---|---|
| 174 | | 540.3 | ¹H NMR (400 MHz, CD₃OD) δ 8.53-8.48 (m, 1H), 7.81-7.77 (m, 1H), 7.54-2.48 (m, 2H), 7.31-7.28 (m, 1H), 7.23-7.20 (m, 1H), 7.07-7.05 (m, 1H), 6.94-6.90 (m, 1H), 6.76-6.73 (m, 1H), 4.53-4.42 (m, 2H), 4.05-4.00 (m, 2H), 3.68 (s, 3H), 2.78-2.68 (m, 2H), 2.66-2.56 (m, 2H), 1.87-1.77 (m, 2H), 1.29-1.27 (m, 6H), 0.89-0.85 (m, 3H). | I-142 and I-4 |
| 175 | | 556.2 | ¹H NMR (400 MHz, CD₃OD) δ 8.52-8.49 (m, 1H), 7.79-7.77 (m, 1H), 7.53-7.50 (m, 2H), 7.32-7.29 (m, 1H), 7.23-7.20 (m, 1H), 7.06-7.04 (m, 1H), 6.93-6.90 (m, 1H), 6.76-6.72 (m, 1H), 4.54-4.42 (m, 2H), 4.24-4.20 (m, 2H), 3.71-3.67 (m, 5H), 2.78-2.68 (m, 2H), 2.65-2.57 (m, 2H), 1.29-1.27 (m, 6H). | I-143 and I-4 |
| 189 | | 580.2 | ¹H NMR (400 MHz, CDCl₃) δ 8.67 (d, J = 2.1 Hz, 1H), 8.56 (d, J = 5.0 Hz, 1H), 7.93 (t, J = 2.4 Hz, 1H), 7.89-7.78 (m, 2H), 7.51-7.47 (m, 1H), 7.29-7.25 (m, 1H), 7.03 (s, 1H), 6.93 (d, J = 5.9 Hz, 1H), 6.81 (d, J = 8.9 Hz, 1H), 6.64 (d, J = 5.9 Hz, 1H), 5.09 (d, J = 11.5 Hz, 1H), 4.56-4.27 (m, 2H), 3.93-3.69 (m, 6H), 3.59-3.52 (m, 1H), 3.42-3.40 (m, 1H), 3.07-2.95 (m, 2H), 2.85-2.81 (m, 4H), 2.63-2.47 (m, 2H), 0.96-0.94 (m, 3H). | I-147 and I-129 |

-continued

| Compound | Structural formula | LC-MS [M + H]⁺ | 1HNMR | Intermediate |
|---|---|---|---|---|
| 191 | | 678.4 | ¹H NMR (400 MHz, CD₃OD/Cl₃ = 1/1) δ 8.67-8.61 (m, 1H), 8.58-8.54 (m, 1H), 8.22-8.17 (m, 1H), 8.03-7.99 (m, 1H), 7.57-7.54 (m, 2H), 7.42-7.39 (m, 1H), 7.09-7.05 (m, 1H), 6.91-6.86 (m, 1H), 4.70-4.64 (m, 3H), 4.56-4.48 (m, 3H), 3.69 (s, 3H), 3.50-3.43 (m, 1H), 3.20-3.03 (m, 2H), 2.82-2.77 (m, 2H), 2.64-2.60 (m, 2H), 2.46-2.37 (m, 2H), 2.21-2.15 (m, 2H), 1.29 (s, 6H), 1.04 (s, 6H). | I-112 and I-114 |
| 192 | | 514.2 | ¹H NMR (400 MHz, CD₃OD/CDCl₃ = 1/1) δ 8.56-8.54 (m, 1H), 8.22-8.18 (m, 1H), 8.08-8.06 (m, 1H), 7.64-7.62 (m, 1H), 7.56-7.54 (m, 1H), 7.08-7.05 (m, 1H), 5.95-5.92 (m, 1H), 4.52-4.46 (m, 2H), 3.69 (s, 3H), 2.81-2.78 (m, 2H), 2.63-2.61 (m, 2H), 2.33 (s, 3H), 1.29 (s, 6H). | I-106 and I-114 |
| 193 | | 678.3 | ¹H NMR (400 MHz, CDCl₃) δ 8.72-8.67 (m, 1H), 8.64-8.60 (m, 1H), 8.04-8.01 (m, 1H), 8.00-7.96 (m, 1H), 7.89-7.85 (m, 1H), 7.72-7.69 (m, 1H), 7.51-7.49 (m, 1H), 7.38-7.33 (m, 1H), 7.12-7.09 (m, 1H), 6.83-6.78 (m, 1H), 4.77-4.70 (m, 2H), 4.66-4.58 (m, 2H), 4.54-4.41 (m, 2H), 3.79-3.69 (m, 4H), 3.24-3.12 (m, 1H), 2.94-2.86 (m, 1H), 2.78-2.76 (m, 2H), 2.75-2.66 (m, 2H), 2.66-2.63 (m, 2H), 2.52-2.45 (m, 1H), 1.97-1.94 (m, 1H), 1.31 (s, 6H), 0.91-0.87 (m, 6H). | I-149 and I-114 |

-continued

| Compound | Structural formula | LC-MS [M + H]+ | 1HNMR | Intermediate |
|---|---|---|---|---|
| 195 | | 610.3 | ¹H NMR (400 MHz, CD₃OD/CDCl₃ = 1/1) δ 8.74-8.65 (m, 1H), 8.61-8.52 (m, 1H), 8.27-8.15 (m, 3H), 7.63-7.58 (m, 1H), 7.54-7.51 (m, 1H), 7.10-7.03 (m, 1H), 4.53-4.48 (m, 2H), 3.91-3.82 (m, 2H), 3.78-3.73 (m, 1H), 3.70 (s, 3H), 3.59-3.54 (m, 1H), 3.51-3.45 (m, 1H), 3.11-3.01 (m, 2H), 2.83-2.77 (m, 2H), 2.66-2.59 (m, 2H), 1.29 (s, 6H), 1.02-0.96 (m, 3H). | I-150 and I-114 |
| 196 | | 609.3 | ¹H NMR (400 MHz, CD₃OD/CDCl₃ = 1/1) δ 8.59-8.57 (m, 1H), 8.57-8.54 (m, 1H), 8.21-8.17 (m, 1H), 7.92-7.88 (m, 1H), 7.56-7.53 (m, 1H), 7.53-7.51 (m, 1H), 7.35-7.31 (m, 1H), 7.08-7.05 (m, 1H), 6.95-6.91 (m, 1H), 4.53-4.45 (m, 2H), 3.90-3.82 (m, 2H), 3.78-3.72 (m, 1H), 3.69 (s, 3H), 3.57-3.52 (m, 1H), 3.47-3.40 (m, 1H), 3.08-2.95 (m, 2H), 2.87-2.71 (m, 2H), 2.68-2.55 (m, 2H), 1.29 (s, 6H), 0.95-0.92 (m, 3H). | I-147 and I-114 |
| 197 | | 665.3 | ¹H NMR (400 MHz, CD₃OD/CDCl₃ = 1/1) δ 8.72-8.68 (m, 1H), 8.59-8.55 (m, 1H), 8.25-8.23 (m, 2H), 8.22-8.19 (m, 1H), 7.63-7.60 (m, 1H), 7.55-7.52 (m, 1H), 7.09-7.05 (m, 1H), 4.72-4.68 (m, 2H), 4.66-4.64 (m, 1H), 4.60-4.56 (m, 1H), 4.54-4.47 (m, 2H), 3.70 (s, 3H), 3.55-3.48 (m, 2H), 3.15-3.05 (m, 2H), 2.83-2.76 (m, 2H), 2.65-2.60 (m, 2H), 2.57-2.52 (m, 1H), 2.51-2.43 (m, 2H), 2.24-2.18 (m, 1H), 1.29 (s, 6H), 1.03-0.99 (m, 3H). | I-151 and I-114 |

-continued

| Compound | Structural formula | LC-MS [M + H]+ | 1HNMR | Intermediate |
|---|---|---|---|---|
| 200 | | 649.3 | 1H NMR (400 MHz, CD3OD): δ 8.94 (d, J = 2.3 Hz, 1H), 8.56 (d, J = 5.1 Hz, 1H), 7.71 (d, J = 2.3 Hz, 1H), 7.63 (d, J = 5.1 Hz, 1H), 7.49 (d, J = 9.3 Hz, 1H), 7.42 (d, J = 9.2 Hz, 1H), 7.22 (dd, J = 5.9, 0.6 Hz, 1H), 6.93 (s, 1H), 6.78 (d, J = 5.9 Hz, 1H), 4.71-4.46 (m, 6H), 3.72 (s, 3H), 3.58-3.49 (m, 1H), 2.94-2.82 (m, 3H), 2.79-2.69 (m, 2H), 2.66-2.58 (m, 2H), 2.05-1.81 (m, 6H), 1.29 (d, J = 5.4 Hz, 6H). | I-152 and I-4 |
| 201 | | 678.2 | 1H NMR (400 MHz, CDCl3) δ 8.64-8.60 (m, 2H), 8.25 (s, 1H), 8.09 (d, J = 2.6 Hz, 1H), 7.55 (d, J = 5.0 Hz, 1H), 7.39-7.35 (m, 1H), 7.02-6.91 (m, 2H), 6.87 (d, J = 5.9 Hz, 1H), 6.65 (d, J = 5.9 Hz, 1H), 4.76-4.54 (m, 5H), 4.50-4.46 (m, 2H), 3.90 (s, 3H), 3.77-3.75 (m, 1H), 3.32-3.30 (m, 1H), 3.00-2.98 (m, 1H), 2.80-2.53 (m, 7H), 2.02-2.00 (m, 1H), 1.30-1.26 (m, 6H), 0.95-0.89 (m, 6H). | I-153 and I-4 |
| 202 | | 677.2 | 1H NMR (400 MHz, CD3OD) δ 8.67-8.65 (m, 1H), 8.57-8.55 (m, 1H), 7.96-7.95 (m, 1H), 7.63-7.59 (m, 1H), 7.59-7.55 (m, 1H), 7.49-7.42 (m, 1H), 7.26-7.20 (m, 1H), 7.07-7.00 (m, 1H), 6.94 (s, 1H), 6.82-6.76 (m, 1H), 4.72-4.68 (m, 2H), 4.65-4.58 (m, 4H), 4.20-4.14 (m, 2H), 3.52-3.47 (m, 2H), 3.13-3.02 (m, 2H), 2.80-2.69 (m, 2H), 2.66-2.61 (m, 2H), 2.60-2.54 (m, 1H), 2.51-2.45 (m, 2H), 2.22-2.18 (m, 1H), 1.44-1.40 (m, 3H), 1.28-1.27 (m, 6H), 0.98-0.96 (m, 3H). | I-154 and I-4 |

-continued

| Compound | Structural formula | LC-MS [M + H]+ | 1HNMR | Intermediate |
|---|---|---|---|---|
| 205 | | 678.2 | ¹H NMR (400 MHz, CD₃OD/CDCl₃ = 1/1): δ 8.78 (d, J = 2.2 Hz, 1H), 8.54 (d, J = 5.1 Hz, 1H), 7.67 (d, J = 2.2 Hz, 1H), 7.60 (dd, J = 5.1, 3.3 Hz, 1H), 7.19 (q, J = 9.7 Hz, 2H), 7.11 (d, J = 6.0 Hz, 1H), 6.95 (s, 1H), 6.69 (d, J = 5.9 Hz, 1H), 4.69-4.41 (m, 6H), 4.33-4.23 (m, 1H), 3.93-3.83 (m, 1H), 3.76-3.63 (m, 4H), 3.44-3.34 (m, 1H), 3.06-2.95 (m, 1H), 2.91-2.81 (m, 1H), 2.78-2.65 (m, 2H), 2.64-2.55 (m, 2H), 2.41-2.28 (m, 1H), 1.30-1.22 (m, 9H), 0.98-0.89 (m, 3H). | I-155 and I-4 |
| 206 | | 666.3 | ¹H NMR (400 MHz, CDCl₃) δ 8.74-8.55 (m, 2H), 8.02-7.90 (m, 2H), 7.84-7.77 (m, 1H), 7.72-7.64 (m, 1H), 7.55-7.46 (m, 1H), 7.33-7.27 (m, 1H), 7.14-7.04 (m, 1H), 6.82-6.75 (m, 1H), 4.59-4.33 (m, 3H), 3.70 (s, 3H), 3.56-3.49 (m, 2H), 3.44-3.38 (m, 1H), 3.36 (s, 3H), 3.1-2.99 (m, 2H), 2.80-2.70 (m, 3H), 2.67-2.55 (m, 6H), 2.36-2.28 (m, 1H), 1.31 (s, 6H), 0.95 (s, 3H). | I-156 and I-114 |
| 207 | | 680.4 | ¹H NMR (400 MHz, CDCl₃) δ 8.77-8.66 (m, 1H), 8.66-8.57 (m, 1H), 8.06-8.01 (m, 1H), 8.01-7.94 (m, 1H), 7.90-7.81 (m, 1H), 7.76-7.66 (m, 1H), 7.56-7.46 (m, 1H), 7.40-7.33 (m, 1H), 7.14-7.06 (m, 1H), 6.82-6.75 (m, 1H), 4.60-4.34 (m, 3H), 3.70 (s, 3H), 3.59-3.46 (m, 2H), 3.35 (s, 3H), 3.16-3.07 (s, 1H), 3.06-2.95 (m, 2H), 2.94-2.87 (m, 1H), 2.82-2.66 (m, 3H), 2.66-2.53 (m, 3H), 2.49-2.43 (m, 1H), 2.24-2.17 (m, 1H), 1.30 (s, 6H), 1.08-1.00 (m, 3H), 0.90-0.83 (m, 3H). | I-157 and I-114 |

-continued

| Compound | Structural formula | LC-MS [M + H]+ | 1HNMR | Intermediate |
|---|---|---|---|---|
| 208 | | 538.2 | ¹H NMR (400 MHz, CDCl₃) δ 8.72-8.68 (m, 1H), 8.41-8.37 (m, 1H), 8.37-8.33 (m, 1H), 8.04-8.00 (m, 2H), 7.81-7.77 (m, 1H), 7.73-7.71 (m, 1H), 7.54-7.52 (m, 1H), 7.17-7.13 (m, 1H), 4.75-4.70 (m, 1H), 4.57-4.49 (m, 2H), 4.44-4.38 (m, 2H), 2.81-2.78 (m, 2H), 2.68-2.65 (m, 2H), 1.61-1.56 (m, 3H), 1.33 (s, 6H). | I-21 and I-114 |
| 209 | | 679.3 | ¹H NMR (400 MHz, CDCl₃) δ 8.76-8.72 (m, 1H), 8.62-8.59 (m, 1H), 8.02-7.97 (m, 1H), 7.78-7.75 (m, 1H), 7.75-7.73 (m, 1H), 7.55-7.52 (m, 1H), 7.12-7.08 (m, 1H), 6.99-6.94 (m, 2H), 4.69-4.66 (m, 2H), 4.65-4.60 (m, 2H), 4.53-4.37 (m, 3H), 4.33-4.29 (m, 1H), 3.91-3.84 (m, 1H), 3.80-3.75 (m, 1H), 3.73 (s, 3H), 3.44-3.38 (m, 1H), 3.06-2.99 (m, 1H), 2.91-2.85 (m, 1H), 2.81-2.74 (m, 2H), 2.67-2.61 (m, 2H), 2.36-2.32 (m, 1H), 1.32 (s, 6H), 1.25 (s, 3H), 0.94-0.92 (m, 3H). | I-155 and I-114 |
| 210 | | 692.3 | ¹H NMR (400 MHz, CDCl₃) δ 8.70-8.66 (m, 1H), 8.65-8.60 (m, 1H), 8.05-8.01 (m, 1H), 8.00-7.96 (m, 1H), 7.90-7.86 (m, 1H), 7.77-7.74 (m, 1H), 7.54-7.50 (m, 1H), 7.37-7.33 (m, 1H), 7.12-7.08 (m, 1H), 6.82-6.77 (m, 1H), 4.77-4.68 (m, 2H), 4.66-4.58 (m, 2H), 4.56-4.40 (m, 3H), 4.21-4.11 (m, 2H), 3.79-3.69 (m, 1H), 3.23-3.12 (m, 1H), 2.94-2.87 (m, 1H), 2.80-2.76 (m, 2H), 2.76-2.67 (m, 2H), 2.66-2.62 (m, 2H), 2.52-2.41 (m, 1H), 1.98-1.91 (m, 1H), 1.46-1.41 (m, 3H), 1.31 (s, 6H), 0.91-0.86 (m, 6H). | I-158 and I-114 |

| Compound | Structural formula | LC-MS [M + H]+ | 1HNMR | Intermediate |
|---|---|---|---|---|
| 211 | | 678.4 | 1H NMR (400 MHz, CDCl3) δ 8.68-8.64 (m, 1H), 8.64-8.59 (m, 1H), 8.01-7.93 (m, 2H), 7.86-7.81 (m, 1H), 7.76-7.72 (m, 1H), 7.54-7.50 (m, 1H), 7.32-7.28 (m, 1H), 7.13-7.07 (m, 1H), 6.82-6.77 (m, 1H), 4.72-4.59 (m, 4H), 4.55-4.38 (m, 3H), 4.20-4.11 (m, 2H), 3.57-3.38 (m, 2H), 3.11-3.01 (m, 2H), 2.81-2.72 (m, 2H), 2.68-2.60 (m, 2H), 2.58-2.51 (m, 1H), 2.49-2.40 (m, 2H), 2.23-2.16 (m, 1H), 1.47-1.40 (m, 3H), 1.31 (s, 6H), 1.00-0.96 (m, 3H). | I-154 and I-114 |
| 212 | | 610.3 | 1H NMR (400 MHz, CDCl3) δ 8.76-8.72 (m, 1H), 8.63-8.58 (m, 1H), 8.01-7.96 (m, 1H), 7.81-7.74 (m, 2H), 7.56-7.50 (m, 1H), 7.12-7.08 (m, 1H), 7.01-6.92 (m, 2H), 4.56-4.36 (m, 2H), 4.16-4.09 (m, 1H), 4.05-3.97 (m, 1H), 3.84-3.76 (m, 3H), 3.72 (s, 3H), 3.67-3.60 (m, 1H), 3.37-3.25 (m, 1H), 2.81-2.73 (m, 2H), 2.67-2.61 (m, 2H), 1.31 (s, 6H), 1.25-1.22 (m, 3H). | I-159 and I-114 |
| 213 | | 665.3 | 1H NMR (400 MHz, CDCl3) δ 8.77-8.72 (m, 1H), 8.62-8.58 (m, 1H), 8.00-7.96 (m, 1H), 7.82-7.70 (m, 2H), 7.55-7.51 (m, 1H), 7.11-7.07 (m, 1H), 6.98-6.95 (m, 2H), 4.70-4.64 (m, 3H), 4.61-4.57 (m, 1H), 4.54-4.36 (m, 2H), 4.34-4.28 (m, 1H), 4.02 3.93 (m, 1H), 3.72 (s, 3H), 3.51-3.44 (m, 1H), 3.32-3.30 (m, 1H), 2.82-2.75 (m, 3H), 2.66-2.62 (m, 2H), 2.62-2.57 (m, 1H), 2.27-2.22 (m, 1H), 2.08-1.97 (m, 2H), 1.31 (s, 6H), 1.28-1.25 (m, 3H). | I-160 and I-114 |

-continued

| Compound | Structural formula | LC-MS [M + H]+ | 1HNMR | Intermediate |
|---|---|---|---|---|
| 214 | | 623.2 | 1H NMR (400 MHz, CD3OD/CDCl3 = 1/1) δ 8.81-8.74 (m, 1H), 8.57-8.50 (m, 1H), 7.76-7.69 (m, 1H), 7.64-7.59 (m, 1H), 7.27-7.21 (m, 1H), 7.19-7.13 (m, 1H), 7.14-7.09 (m, 1H), 6.95 (s, 1H), 6.73-6.66 (m, 1H), 4.57-4.48 (m, 1H), 4.44-4.39 (m, 1H), 4.23-4.10 (m, 3H), 4.02-3.96 (m, 1H), 3.84-3.74 (m, 2H), 3.74-3.68 (m, 1H), 3.66-3.59 (m, 1H), 3.29-3.22 (m, 1H), 2.78-2.66 (m, 2H), 2.66-2.55 (m, 2H), 1.46-1.39 (m, 3H), 1.30-1.25 (m, 6H), 1.22-1.18 (m, 3H). | I-161 and I-4 |
| 215 | | 691.4 | 1H NMR (400 MHz, CD3OD) δ 8.75-8.69 (m, 1H), 8.58-8.53 (m, 1H), 8.03-7.97 (m, 1H), 7.62-7.58 (m, 2H), 7.51-7.47 (m, 1H), 7.24-7.19 (m, 1H), 7.06-7.00 (m, 1H), 6.93 (s, 1H), 6.81-6.75 (m, 1H), 4.75-4.71 (m, 1H), 4.69-4.65 (m, 2H), 4.64-4.57 (m, 2H), 4.50-4.46 (m, 1H), 4.20-4.12 (m, 2H), 3.81-3.73 (m, 1H), 3.24-3.16 (m, 1H), 2.94-2.88 (m, 1H), 2.78-2.69 (m, 4H), 2.66-2.58 (m, 2H), 2.54-2.46 (m, 1H), 2.00-1.88 (m, 1H), 1.44-1.39 (m, 3H), 1.30-1.27 (m, 6H), 0.90-0.86 (m, 6H). | I-158 and I-4 |
| 219 | | 680.4 | 1H NMR (400 MHz, CDCl3) δ 8.69-8.64 (m, 1H), 8.64-8.60 (m, 1H), 8.01-7.97 (m, 1H), 7.97-7.94 (m, 1H), 7.83-7.77 (m, 1H), 7.72-7.67 (m, 1H), 7.55-7.48 (m, 1H), 7.32-7.28 (m, 1H), 7.12-7.08 (m, 1H), 6.82-6.77 (m, 1H), 4.63-4.33 (m, 3H), 3.71 (s, 3H), 3.52-3.46 (m, 1H), 3.45-3.38 (m, 1H), 3.35 (s, 3H), 3.33-3.28 (m, 1H), 3.07-3.00 (m, 2H), 2.85-2.75 (m, 4H), 2.75-2.60 (m, 4H), 2.47-2.42 (m, 1H), 1.31 (s, 6H), 1.08-1.03 (m, 3H), 0.98-0.92 (m, 3H). | I-163 and I-114 |

-continued

| Compound | Structural formula | LC-MS [M + H]+ | 1HNMR | Intermediate |
|---|---|---|---|---|
| 220 | | 680.4 | ¹H NMR (400 MHz, CDCl₃) δ 8.73-8.67 (m, 1H), 8.66-8.60 (m, 1H), 8.06-8.02 (m, 1H), 8.00-7.96 (m, 1H), 7.88-7.84 (m, 1H), 7.73-7.69 (m, 1H), 7.53-7.50 (m, 1H), 7.37-7.33 (m, 1H), 7.12-7.08 (m, 1H), 6.77-6.73 (m, 1H), 4.57-4.36 (m, 3H), 3.71 (s, 3H), 3.54-3.50 (m, 2H), 3.36 (s, 3H), 3.20-3.00 (m, 2H), 2.81-2.73 (m, 2H), 2.68-2.61 (m, 2H), 2.60-2.53 (m, 4H), 2.39-2.32 (m, 2H), 1.31 (s, 6H), 1.03 (s, 6H). | I-164 and I-114 |
| 224 | | 678.4 | ¹H NMR (400 MHz, CDCl₃) δ 8.69-8.58 (m, 2H), 8.01-7.95 (m, 1H), 7.94-7.88 (m, 1H), 7.82-7.75 (m, 1H), 7.69-7.66 (m, 1H), 7.52-7.49 (m, 1H), 7.14-7.07 (m, 1H), 6.84-6.75 (m, 1H), 4.71-4.58 (m, 4H), 4.57-4.35 (m, 3H), 3.71 (s, 3H), 3.54-3.46 (m, 1H), 3.32 (s, 1H), 3.16-3.07 (m, 2H), 2.81-2.74 (m, 2H), 2.68-2.61 (m, 2H), 2.59-2.52 (m, 1H), 2.47-2.37 (m, 2H), 2.36-2.27 (m, 1H), 1.44-1.34 (m, 2H), 1.31 (s, 6H), 0.85-0.77 (m, 3H). | I-110 and I-114 |
| 226 | | 679.4 | ¹H NMR (400 MHz, CD₃OD) δ 8.73 (d, J = 2.1 Hz, 1H), 8.55 (d, J = 5.1 Hz, 1H), 8.01 (d, J = 2.5 Hz, 1H), 7.59 (d, J = 5.1 Hz, 1H), 7.54 (d, J = 2.2 Hz, 1H), 7.48-7.46 (m, 1H), 7.22 (d, J = 5.9 Hz, 1H), 6.99 (d, J = 8.8 Hz, 1H), 6.93 (s, 1H), 6.78 (d, J = 5.9 Hz, 1H), 4.59-4.46 (m, 2H), 3.70 (s, 3H), 3.57-3.51 (m, 2H), 3.34 (s, 3H), 3.13-3.09 (m, 2H), 2.74-2.70 (m, 2H), 2.64-2.51 (m, 6H), 2.41-2.39 (m, 2H), 1.30-1.26 (m, 6H), 1.05-1.01 (m, 6H). | I-164 and I-4 |

441

Compound 2

2-(5-((5-((2S,5R)-2,5-dimethyl-4-(oxetan-3-yl)piperazin-1-yl)pyridin-2-yl)amino)-3'-(hydroxymethyl)-1-methyl-6-oxo-1,6-dihydro-[3,4'-bispyridin]-2'-yl)-7,8-dihydro-2H-cyclopenta[4,5]pyrrolo[1,2-a]pyrazin-1(6H)-one

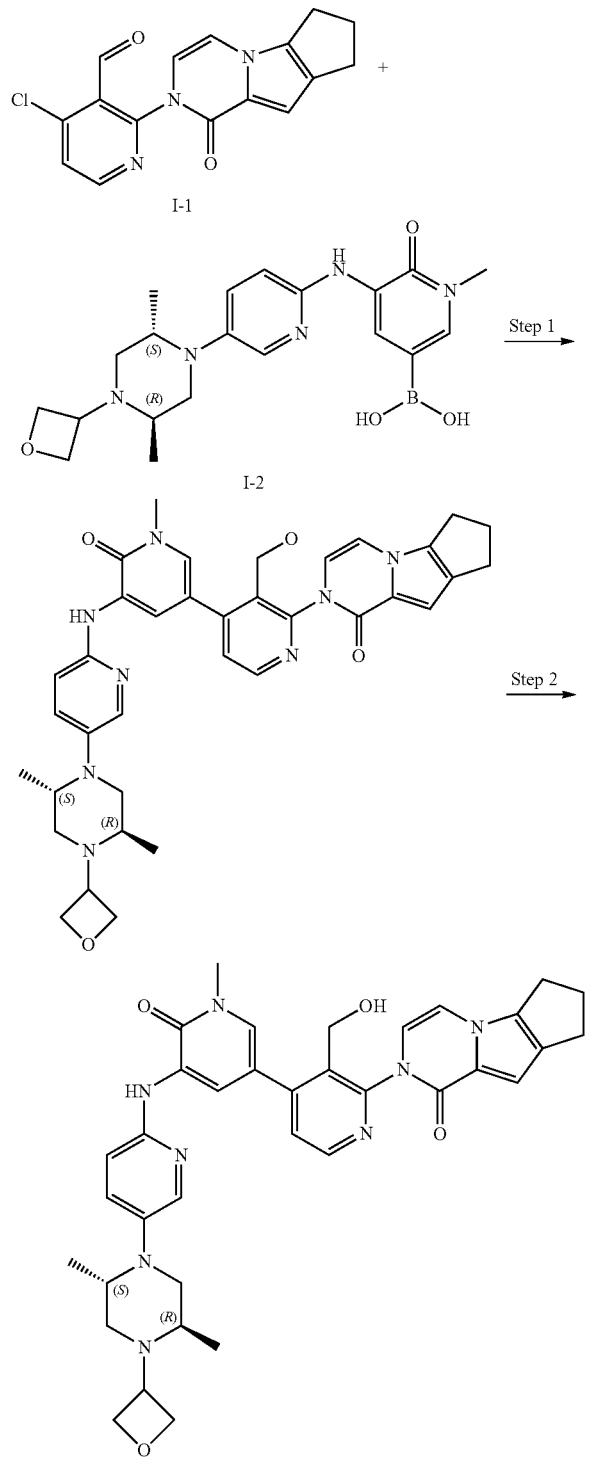

442

Step 1: 5-((5-((2S,5R)-2,5-dimethyl-4-(oxetan-3-yl)piperazin-1-yl)pyridin-2-yl)amino)-1-methyl-6-oxo-2'-(1-oxo-1,6,7,8-tetrahydro-2H-cyclopenta[4,5]pyrrolo[1,2-a]pyrazin-2-yl)-1,6-dihydro-[3,4'-bispyridin]-3'-carbaldehyde Under nitrogen, to a solution of (5-((5-((2S,5R)-2,5-dimethyl-4-(oxetan-3-yl)piperazin-1-yl)pyridin-2-yl)amino)-1-methyl-6-oxo-1,6-dihydropyridin-3-yl)boracic acid (171 mg, 0.41 mmol) and 4-chloro-2-(1-oxo-1,6,7,8-tetrahydro-2H-cyclopenta[4,5]pyrrolo[1,2-a]pyrazin-2-yl)nicotinaldehyde (100 mg, 0.32 mmol) in 1,4-dioxane (10 mL) and water (2 mL) was added Xphos (20 mg, 0.03 mmol), Pd(dppf)Cl$_2$CH$_2$Cl$_2$ (25 mg, 0.03 mmol) and cesium carbonate (260 mg, 0.8 mmol). The mixture was reacted at 90° C. for 4 hours, and then cooled to room temperature. Water (30 mL) was added to the reaction solution, and the mixture was extracted with ethyl acetate (30 mL×2). The organic phase was collected and combined, and concentrated in vacuum under reduced pressure to give the target product (180 mg, yield 68%), which was directly used in the next step. [M+H]$^+$ 647.3

Step 2: 2-(5-((5-((2S,5R)-2,5-dimethyl-4-(oxetan-3-yl)piperazin-1-yl)pyridin-2-yl)amino)-3'-(hydroxymethyl)-1-methyl-6-oxo-1,6-dihydro-[3,4'-bispyridin]-2'-yl)-7,8-dihydro-2H-cyclopenta[4,5]pyrrolo[1,2-a]pyrazin-1(6H)-one At 0-5° C., under nitrogen, to a solution of 5-((5-((2S,5R)-2,5-dimethyl-4-(oxetan-3-yl)piperazin-1-yl)pyridin-2-yl)amino)-1-methyl-6-oxo-2'-(1-oxo-1,6,7,8-tetrahydro-2H-cyclopenta[4,5]pyrrolo[1,2-a]pyrazin-2-yl)-1,6-dihydro-[3,4'-bispyridin]-3'-carbaldehyde (180 mg, 0.28 mmol) in methanol (4 mL) and dichloromethane (10 mL) was added sodium borohydride (16 mg, 0.42 mmol), and reacted at room temperature for 15 minutes. The reaction was quenched by adding water (0.5 mL) to the reaction solution, and concentrated in vacuum under reduced pressure, and the resulting residue was purified with silica gel column chromatography (methanol/water) and purified with thin layer chromatography (methanol/dichloromethane=1/20) to give the target product (80 mg, yield 44%). [M+H]$^+$ 649.3. $^1$H NMR (400 MHz, CD$_3$OD): δ 8.73 (d, J=2.2 Hz, 1H), 8.54 (d, J=5.1 Hz, 1H), 8.00 (d, J=2.6 Hz, 1H), 7.59-7.46 (m, 3H), 7.24 (d, J=5.9 Hz, 1H), 7.03 (d, J=8.8 Hz, 1H), 6.94 (s, 1H), 6.79 (d, J=5.9 Hz, 1H), 4.77-4.55 (m, 5H), 4.49-4.47 (m, 1H), 3.81-3.64 (m, 4H), 3.20-3.18 (m, 1H), 2.91-2.87 (m, 3H), 2.77-2.73 (m, 4H), 2.62-2.42 (m, 3H), 1.94-1.92 (m, 1H), 0.89-0.86 (m, 6H).

The compounds in the following table were prepared with corresponding intermediates and reagents according to the preparation steps of compound 2:

| Compound | Structural formula | LC-MS [M+H]+ | 1HNMR | Intermediate |
|---|---|---|---|---|
| 12 | | 647.3 | ¹H NMR (400 MHz, CD₃OD): δ 8.62-8.54 (m, 1H), 8.44-8.37 (m, 1H), 7.99-7.90 (m, 1H), 7.46-7.33 (m, 2H), 7.21-7.14 (m, 1H), 7.13-7.05 (m, 1H), 6.98-6.88 (m, 2H), 6.69-6.61 (m, 1H), 4.73-4.68 (m, 2H), 4.66-4.58 (m, 2H), 3.70 (s, 3H), 3.55-3.39 (m, 2H), 3.11-3.00 (m, 2H), 2.76-2.67 (m, 2H), 2.62-2.54 (m, 3H), 2.51-2.42 (m, 2H), 2.23 (s, 3H), 2.20-2.15 (m, 1H), 1.29-1.26 (m, 6H), 0.98-0.93 (m, 3H). | I-54 and I-77 |
| 38 | | 667.4 | ¹H NMR (400 MHz, CD₃OD): δ 8.67 (d, J = 2.3 Hz, 1H), 8.52 (d, J = 5.1 Hz, 1H), 7.93 (d, J = 2.7 Hz, 1H), 7.56 (d, J = 5.1 Hz, 1H), 7.53-7.48 (m, 1H), 7.41 (dd, J = 8.9, 2.8 Hz, 1H), 7.20 (d, J = 5.9 Hz, 1H), 7.01 (d, J = 8.9 Hz, 1H), 6.92 (s, 1H), 6.77 (d, J = 5.9 Hz, 1H), 4.72-4.44 (m, 5H), 3.54-3.42 (m, 2H), 3.12-2.95 (m, 2H), 2.77-2.66 (m, 2H), 2.65-2.58 (m, 2H), 2.57-2.51 (m, 1H), 2.49-2.39 (m, 2H), 2.23-2.14 (m, 1H), 1.27 (d, J = 6.2 Hz, 6H), 0.95 (d, J = 6.3 Hz, 3H). | I-78 and I-55, NaBD₄ |

| Compound | Structural formula | LC-MS [M + H]+ | 1HNMR | Intermediate |
|---|---|---|---|---|
| 39 | 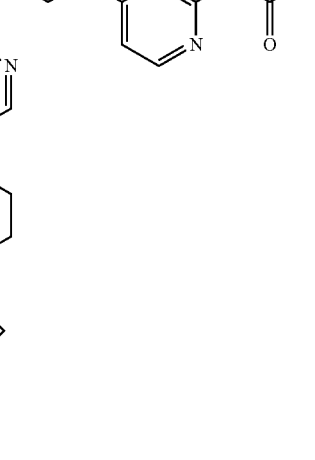 | 666.3 | ¹H NMR (400 MHz, CD₃OD): δ 8.68 (d, J = 2.1 Hz, 1H), 8.55 (d, J = 5.0 Hz, 1H), 7.95 (d, J = 2.7 Hz, 1H), 7.59 (d, J = 5.2 Hz, 1H), 7.52 (d, J = 2.3 Hz, 1H), 7.44 (dd, J = 8.9, 2.8 Hz, 1H), 7.22 (d, J = 5.9 Hz, 1H), 7.03 (d, J = 8.9 Hz, 1H), 6.93 (s, 1H), 6.78 (d, J = 5.9 Hz, 1H), 4.72-4.47 (m, 6H), 3.56-3.44 (m, 2H), 3.14-3.01 (m, 2H), 2.79-2.69 (m, 2H), 2.66-2.59 (m, 2H), 2.59-2.54 (m, 1H), 2.50-2.43 (m, 2H), 2.26-2.14 (m, 1H), 1.29 (d, J = 6.4 Hz, 6H), 0.97 (d, J = 6.3 Hz, 3H). | I-78 and I-55 |
| 52 | 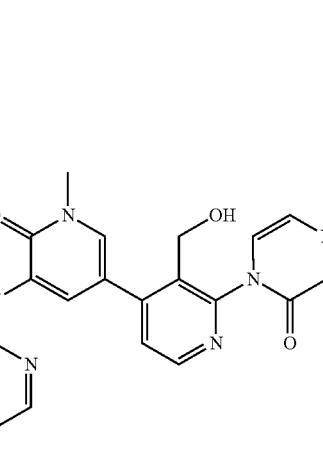 | 663.3 | ¹H NMR (400 MHz, CD₃OD): δ 8.68 (d, J = 2.0 Hz, 1H), 8.59 (d, J = 5.1 Hz, 1H), 7.96 (d, J = 2.5 Hz, 1H), 7.89 (d, J = 6.0 Hz, 1H), 7.66 (d, J = 8.2 Hz, 1H), 7.62 (d, J = 5.1 Hz, 1H), 7.56-7.52 (m, 1H), 7.50 (d, J = 2.0 Hz, 1H), 7.48-7.42 (m, 1H), 7.34-7.25 (m, 1H), 7.24-7.16 (m, 1H), 7.06-7.00 (m, 1H), 6.93-6.88 (m, 1H), 4.73-4.58 (m, 6H), 3.70 (s, 3H), 3.56-3.45 (m, 2H), 3.16-3.02 (m, 2H), 2.62-2.55 (m, 1H), 2.52-2.45 (m, 2H), 2.26-2.16 (m, 1H), 1.01-0.95 (m, 3H). | I-52 and I-54 |

| Compound | Structural formula | LC-MS [M + H]+ | 1HNMR | Intermediate |
|---|---|---|---|---|
| 53 | 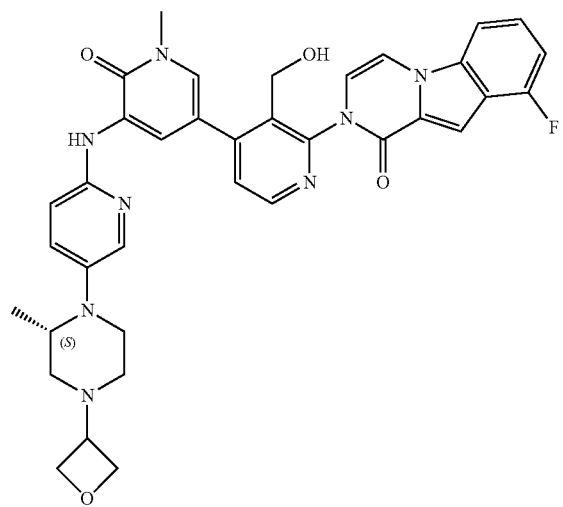 | 663.3 | ¹H NMR (400 MHz, CD₃OD): δ 8.68 (d, J = 1.9 Hz, 1H), 8.59 (d, J = 5.1 Hz, 1H), 7.99-7.95 (m, 1H), 7.91-7.86 (m, 1H), 7.80-7.75 (m, 1H), 7.62 (d, J = 5.1 Hz, 1H), 7.53-7.50 (m, 2H), 7.48-7.41 (m, 2H), 7.08-7.01 (m, 2H), 6.94 (d, J = 6.0 Hz, 1H), 4.72-4.59 (m, 6H), 3.71 (s, 3H), 3.55-3.47 (m, 2H), 3.12-3.05 (m, 2H), 2.64-2.54 (m, 1H), 2.52-2.44 (m, 2H), 2.25-2.15 (m, 1H), 1.02-0.95 (m, 3H). | I-53 and I-54 |
| 54 | 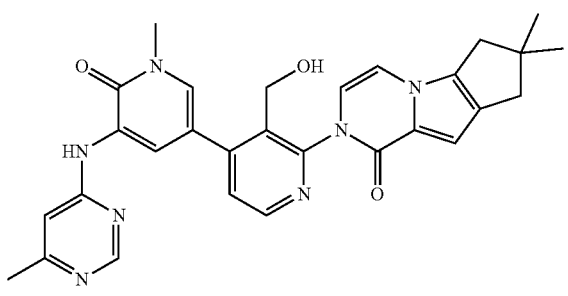 | 524.2 | ¹H NMR (400 MHz, CD₃OD): δ 8.93-8.86 (m, 1H), 8.60-8.50 (m, 2H), 7.74-7.66 (m, 1H), 7.57 (d, J = 5.1 Hz, 1H), 7.22 (d, J = 5.9 Hz, 1H), 6.93 (s, 2H), 6.79 (d, J = 5.9 Hz, 1H), 4.66-4.56 (m, 1H), 4.54-4.46 (m, 1H), 3.70 (s, 3H), 2.84-2.70 (m, 2H), 2.66-2.56 (m, 2H), 2.37 (s, 3H), 1.33-1.24 (m, 6H). | I-55 and I-56 |
| 55 | 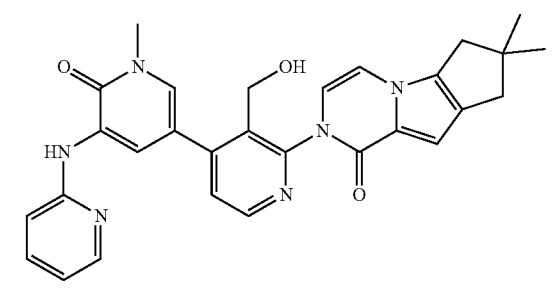 [SMILES: Cn1cc(-c2ccnc(-n3ccn4c5c(cc4c3=O)CC(C)(C)C5)c2CO)cc(Nc2ccccn2)c1=O] | 509.2 | ¹H NMR (400 MHz, CD₃OD): δ 8.81-8.76 (m, 1H), 8.59-8.53 (m, 1H), 8.22-8.16 (m, 1H), 7.63-7.56 (m, 3H), 7.25-7.21 (m, 1H), 7.06-7.01 (m, 1H), 6.96-6.92 (m, 1H), 6.85-6.78 (m, 2H), 4.63-4.58 (m, 1H), 4.52-4.45 (m, 1H), 3.71 (s, 3H), 2.80-2.69 (m, 2H), 2.67-2.57 (m, 2H), 1.30-1.27 (m, 6H). | I-55 and I-57 |

| Compound | Structural formula | LC-MS [M + H]+ | 1HNMR | Intermediate |
|---|---|---|---|---|
| 56 | | 685.3 | ¹H NMR (400 MHz, CD₃OD): δ 8.67 (d, J = 2.3 Hz, 1H), 8.54 (d, J = 5.1 Hz, 1H), 7.94 (d, J = 2.7 Hz, 1H), 7.58 (d, J = 5.1 Hz, 1H), 7.50 (d, J = 2.3 Hz, 1H), 7.44 (dd, J = 8.9, 2.9 Hz, 1H), 7.28 (d, J = 6.0 Hz, 1H), 7.07-6.97 (m, 2H), 6.84 (d, J = 6.0 Hz, 1H), 4.73-4.46 (m, 6H), 3.69 (s, 3H), 3.53-3.46 (m, 2H), 3.42-3.33 (m, 2H), 3.14-3.00 (m, 2H), 2.95-2.82 (m, 2H), 2.59-2.40 (m, 3H), 2.36-2.18 (m, 3H), 0.97 (d, J = 6.3 Hz, 3H). | I-58 and I-54 |
| 57 | | 663.3 | ¹H NMR (400 MHz, CD₃OD): δ 8.68 (d, J = 2.3 Hz, 1H), 8.59 (d, J = 5.1 Hz, 1H), 7.97 (d, J = 2.8 Hz, 1H), 7.92 (d, J = 8.4 Hz, 1H), 7.83 (d, J = 8.3 Hz, 1H), 7.78 (dd, J = 6.1, 1.5 Hz, 1H), 7.61 (d, J = 5.1 Hz, 1H), 7.57-7.49 (m, 2H), 7.45 (dd, J = 8.9, 2.8 Hz, 1H), 7.42-7.35 (m, 1H), 7.03 (d, J = 8.9 Hz, 1H), 6.78 (d, J = 6.1 Hz, 1H), 4.74-4.57 (m, 6H), 3.71 (s, 3H), 3.55-3.46 (m, 2H), 3.15-3.01 (m, 2H), 2.61-2.53 (m, 1H), 2.52-2.43 (m, 2H), 2.26-2.15 (m, 1H), 0.98 (d, J = 6.3 Hz, 3H). | I-59 and I-54 |
| 58 | | 685.3 | ¹H NMR (400 MHz, CD₃OD): δ 8.67 (d, J = 2.3 Hz, 1H), 8.54 (t, J = 4.9 Hz, 1H), 7.94 (d, J = 2.7 Hz, 1H), 7.59 (d, J = 5.1 Hz, 1H), 7.51 (d, J = 2.3 Hz, 1H), 7.44 (dd, J = 9.0, 2.9 Hz, 1H), 7.29 (dd, J = 6.0, 0.5 Hz, 1H), 7.10-6.97 (m, 2H), 6.85 (d, J = 6.0 Hz, 1H), 4.72-4.45 (m, 6H), 3.69 (s, 3H), 3.55-3.45 (m, 2H), 3.21-3.16 (m, 2H), 3.12-2.97 (m, 4H), 2.61-2.52 (m, 1H), 2.49-2.32 (m, 4H), 2.24-2.15 (m, 1H), 0.96 (d, J = 6.3 Hz, 3H). | I-60 and I-54 |

-continued

| Compound | Structural formula | LC-MS [M + H]⁺ | 1HNMR | Intermediate |
|---|---|---|---|---|
| 59 | | 677.3 | ¹H NMR (400 MHz, CD₃OD): δ 8.73 (d, J = 2.3 Hz, 1H), 8.65-8.53 (m, 1H), 8.10-7.97 (m, 1H), 7.92 (d, J = 8.4 Hz, 1H), 7.83 (d, J = 8.2 Hz, 1H), 7.78 (d, J = 4.7 Hz, 1H), 7.60 (d, J = 5.1 Hz, 1H), 7.58-7.44 (m, 3H), 7.43-7.34 (m, 1H), 7.08-6.96 (m, 1H), 6.77 (d, J = 6.1 Hz, 1H), 4.75-4.52 (m, 6H), 3.89-3.56 (m, 5H), 3.21 (d, J = 6.3 Hz, 1H), 2.98-2.86 (m, 1H), 2.80-2.65 (m, 2H), 2.58-2.41 (m, 1H), 2.02-1.86 (m, 1H), 0.89 (d, J = 6.3 Hz, 6H). | I-59 and I-2 |
| 60 | | 681.2 | ¹H NMR (400 MHz, CD₃OD): δ 8.66 (d, J = 2.3 Hz, 1H), 8.57 (d, J = 5.1 Hz, 1H), 7.99-7.91 (m, 2H), 7.76 (d, J = 4.9 Hz, 1H), 7.59 (d, J = 5.1 Hz, 1H), 7.51-7.40 (m, 3H), 7.36-7.25 (m, 1H), 7.01 (d, J = 8.9 Hz, 1H), 6.79 (d, J = 6.1 Hz, 1H), 4.71-4.55 (m, 6H), 3.69 (s, 3H), 3.58-3.46 (m, 2H), 3.14-3.00 (m, 2H), 2.60-2.52 (m, 1H), 2.49-2.41 (m, 2H), 2.25-2.15 (m, 1H), 0.96 (d, J = 6.3 Hz, 3H). | I-61 and I-54 |
| 61 | | 695.3 | ¹H NMR (400 MHz, CD₃OD): δ 8.73 (d, J = 2.2 Hz, 1H), 8.59 (d, J = 5.1 Hz, 1H), 8.04-7.95 (m, 2H), 7.79 (d, J = 6.1 Hz, 1H), 7.61 (d, J = 5.1 Hz, 1H), 7.55-7.45 (m, 3H), 7.37-7.29 (m, 1H), 7.04 (d, J = 8.8 Hz, 1H), 6.81 (d, J = 6.0 Hz, 1H), 4.75-4.57 (m, 6H), 3.83-3.74 (m, 1H), 3.72 (s, 3H), 3.26-3.16 (m, 1H), 2.97-2.88 (m, 1H), 2.81-2.68 (m, 2H), 2.57-2.45 (m, 1H), 2.0-1.90 (m, 1H), 0.89 (d, J = 6.3 Hz, 6H). | I-61 and I-2 |

-continued

| Compound | Structural formula | LC-MS [M+H]+ | 1HNMR | Intermediate |
|---|---|---|---|---|
| 62 | | 741.2 | ¹H NMR (400 MHz, CD₃OD): δ 8.67 (d, J = 2.2 Hz, 1H), 8.55 (d, J = 5.1 Hz, 1H), 7.96 (s, 1H), 7.59 (d, J = 5.1 Hz, 1H), 7.52 (d, J = 2.2 Hz, 1H), 7.45 (dd, J = 8.9, 2.8 Hz, 1H), 7.17 (d, J = 6.1 Hz, 1H), 7.03 (d, J = 8.9 Hz, 1H), 6.79 (d, J = 5.9 Hz, 1H), 4.72-4.49 (m, 6H), 3.56-3.43 (m, 2H), 3.14-3.01 (m, 2H), 2.83-2.73 (m, 2H), 2.62-2.53 (m, 3H), 2.51-2.44 (m, 2H), 2.25-2.16 (m, 1H), 1.30 (d, J = 6.1 Hz, 6H), 0.97 (d, J = 6.3 Hz, 3H). | I-62 and I-54 |
| 63 | | 664.3 | ¹H NMR (400 MHz, CD₃OD): δ 8.66 (d, J = 2.3 Hz, 1H), 8.58 (d, J = 5.1 Hz, 1H), 7.95 (d, J = 2.8 Hz, 1H), 7.90 (s, 1H), 7.62 (d, J = 5.1 Hz, 1H), 7.49-7.42 (m, 2H), 7.03 (d, J = 8.9 Hz, 1H), 6.88 (s, 1H), 4.77-4.47 (m, 6H), 3.70 (s, 1H), 3.55-3.46 (m, 2H), 3.16-2.99 (mz, 2H), 2.87-2.74 (m, 2H), 2.68-2.60 (m, 2H), 2.60-2.54(m, 1H) 2.52-2.43 (m, 2H), 2.24-2.18 (m, 1H), 1.29 (d, J = 8.0 Hz, 6H), 0.97 (d, J = 6.4 Hz, 3H). | I-63 and I-54 |
| 64 | | 635.3 | ¹H NMR (400 MHz, CD₃OD): δ 8.68 (d, J = 2.0 Hz, 1H), 8.56 (d, J = 5.1 Hz, 1H), 7.95 (d, J = 2.8 Hz, 1H), 7.60 (d, J = 5.1 Hz, 1H), 7.53 (d, J = 2.1 Hz, 1H), 7.45 (dd, J = 8.9, 2.8 Hz, 1H), 7.26 (d, J = 5.9 Hz, 1H), 7.04 (d, J = 8.9 Hz, 1H), 6.95 (s, 1H), 6.82-6.77 (m, 1H), 4.74-4.46 (m, 6H), 3.71 (s, 3H), 3.56-3.45 (m, 2H), 3.13-3.02 (m, 2H), 2.96-2.88 (m, 2H), 2.83-2.76 (m, 2H), 2.61-2.53 (m, 3H), 2.50-2.45 (m, 2H), 2.24-2.17 (m, 1H), 0.97 (d, J = 6.4 Hz, 3H). | I-1 and I-54 |

-continued

| Compound | Structural formula | LC-MS [M+H]+ | 1HNMR | Intermediate |
|---|---|---|---|---|
| 65 | | 664.3 | ¹H NMR (400 MHz, CD₃OD): δ 9.11 (s, 1H), 8.94 (d, J = 2.3 Hz, 1H), 8.01-7.92 (m, 2H), 7.44 (dd, J = 8.9, 2.8 Hz, 1H), 7.23 (d, J = 6.0 Hz, 1H), 7.02 (d, J = 8.9 Hz, 1H), 6.97 (s, 1H), 6.91 (d, J = 6.0 Hz, 1H), 4.73-4.56 (m, 6H), 3.71 (s, 3H), 3.55-3.44 (m, 2H), 3.12-3.01 (m, 2H), 2.77-2.69 (m, 2H), 2.64-2.60 (m, 2H), 2.60-2.54 (m, 1H), 2.50-2.43 (m, 2H), 2.25-2.16 (m, 1H), 1.30-1.26 (m, 6H), 0.97 (d, J = 6.3 Hz, 3H). | I-64 and I-54 |
| 66 | | 677.3 | ¹H NMR (400 MHz, CD₃OD): δ 8.69 (d, J = 2.2 Hz, 1H), 8.55 (d, J = 5.1 Hz, 1H), 7.95 (d, J = 2.8 Hz, 1H), 7.59 (d, J = 5.1 Hz, 1H), 7.53 (d, J = 2.3 Hz, 1H), 7.44 (dd, J = 8.9, 2.8 Hz, 1H), 7.22 (d, J = 6.0 Hz, 1H), 7.03 (d, J = 8.9 Hz, 1H), 6.94 (s, 1H), 6.79 (d, J = 5.9 Hz, 1H), 4.65-4.43 (m, 2H), 4.00-3.83 (m, 2H), 3.78-3.60 (m, 5H), 3.49-3.36 (m, 1H), 3.09-2.95 (m, 3H), 2.81-2.54 (m, 7H), 2.42-2.26 (m, 1H), 2.16-2.03 (m, 1H), 1.94-1.79 (m, 1H), 1.31-1.27 (m, 6H), 0.97-0.92 (m, 3H). | I-55 and I-65 |
| 67 | | 646.3 | ¹H NMR (400 MHz, CD₃OD): δ 8.68 (s, 1H), 8.62-8.56 (m, 2H), 8.38-8.30 (m, 1H), 8.00-7.93 (m, 2H), 7.64-7.60 (m, 1H), 7.51-7.49 (m, 1H), 7.48 (s, 1H), 7.47-7.40 (m, 2H), 7.07-7.00 (m, 1H), 7.00-6.94 (m, 1H), 4.73-4.55 (m, 6H), 3.71 (s, 3H), 3.54-3.47 (m, 2H), 3.16-3.00 (m, 2H), 2.62-2.54 (m, 1H), 2.53-2.40 (m, 2H), 2.26-2.16 (m, 1H), 1.00-0.95 (m, 3H). | I-66 and I-54 |

| Compound | Structural formula | LC-MS [M + H]+ | 1HNMR | Intermediate |
|---|---|---|---|---|
| 71 | | 537.2 | ¹H NMR (400 MHz, CD₃OD): δ 8.71-8.53 (m, 2H), 8.43 (s, 1H), 8.00 (s, 1H), 7.76-7.57 (m, 2H), 7.26 (d, J = 5.1 Hz, 1H), 6.96 (s, 1H), 6.83 (d, J = 5.2 Hz, 1H), 4.61-4.40 (m, 4H), 2.83-2.60 (m, 4H), 1.57 (t, J = 6.7 Hz, 3H), 1.33-1.27 (m, 6H). | I-55 and I-68 |
| 72 | | 661.3 | ¹H NMR (400 MHz, CD₃OD): δ 9.97 (s, 1H), 8.68-8.64 (m, 2H), 7.94 (d, J = 2.6 Hz, 1H), 7.63 (d, J = 5.2 Hz, 1H), 7.45-7.41 (m, 1H), 7.34 (d, J = 2.3 Hz, 1H), 7.26-7.23 (m, 1H), 7.03-6.99 (m, 2H), 6.87-6.85 (m, 1H), 4.72-4.58 (m, 4H), 3.69 (s, 3H), 3.54-3.44 (m, 2H), 3.07-3.03 (m, 2H), 2.94-2.71 (m, 2H), 2.67-2.32 (m, 5H), 2.22-2.18 (m, 1H), 1.31-1.29 (m, 6H), 0.96 (d, J = 6.3 Hz, 3H). | I-55 and I-54 |
| 73 | | 485.1 | ¹H NMR (400 MHz, DMSO-d₆): δ 8.53 (d, J = 5.1 Hz, 1H), 8.33 (s, 1H), 7.80 (d, J = 2.2 Hz, 1H), 7.75 (s, 1H), 7.46-7.44 (m, 2H), 7.25 (d, J = 5.9 Hz, 1H), 6.83-6.74 (m, 2H), 5.02-4.97 (m, 1H), 4.42-4.38 (m, 1H), 4.34-4.30 (m, 1H), 3.97 (s, 3H), 3.58 (s, 3H), 2.88-2.82 (m, 2H), 2.71-2.67 (m, 2H), 2.46-2.42 (m, 2H). | I-1 and I-69 |

-continued

| Compound | Structural formula | LC-MS [M + H]+ | 1HNMR | Intermediate |
|---|---|---|---|---|
| 74 | | 645.3 | ¹H NMR (400 MHz, CD₃OD): δ 8.69 (d, J = 2.0 Hz, 1H), 8.60 (d, J = 5.2 Hz, 1H), 8.00-7.83 (m, 4H), 7.62 (d, J = 5.2 Hz, 1H), 7.55-7.42 (m, 4H), 7.37-7.33 (m, 1H), 7.04 (d, J = 8.8 Hz, 1H), 6.89 (d, J = 6.0 Hz, 1H), 4.75-4.53 (m, 7H), 3.72 (s, 3H), 3.59-3.44 (m, 2H), 3.13-3.05 (m, 2H), 2.63-2.54 (m, 1H), 2.50-2.47 (m, 2H), 2.27-2.13 (m, 1H), 0.98 (d, J = 6.4 Hz, 3H). | I-70 and I-54 |
| 75 | | 663.2 | ¹H NMR (400 MHz, CD₃OD): δ 8.68 (d, J = 2.2 Hz, 1H), 8.59 (d, J = 5.0 Hz, 1H), 8.00-7.94 (m, 2H), 7.89 (d, J = 5.8 Hz, 1H), 7.62 (d, J = 5.1 Hz, 1H), 7.55-7.50 (m, 2H), 7.48-7.43 (m, 2H), 7.28 (td, J = 9.4, 2.5 Hz, 1H), 7.04 (d, J = 9.0 Hz, 1H), 6.91 (d, J = 5.9 Hz, 1H), 4.72-4.54 (m, 7H), 3.72 (s, 3H), 3.50 (dd, J = 19.0, 5.7 Hz, 2H), 3.12-3.04 (m, 2H), 2.58 (d, J = 8.1 Hz, 1H), 2.48 (s, 2H), 2.28-2.15 (m, 1H), 0.98 (d, J = 6.2 Hz, 3H). | I-71 and I-54 |
| 76 | | 646.2 | ¹H NMR (400 MHz, CD₃OD): δ 8.66 (d, J = 4.8 Hz, 1H), 8.58 (s, 1H), 8.05 (d, J = 3.2 Hz, 1H), 7.94 (d, J = 8.8 Hz, 1H), 7.89-7.85 (m, 2H), 7.72 (d, J = 5.2 Hz, 1H), 7.52-7.44 (m, 3H), 7.37-7.33 (m, 1H), 7.18 (d, J = 8.8 Hz, 1H), 6.92 (d, J = 6.4 Hz, 1H), 4.74-4.55 (m, 5H), 3.89 (s, 3H), 3.52-3.48 (mHz, 1H), 3.22-3.07 (m, 2H), 2.55-2.44 (m, 1H), 2.40-2.33 (m, 2H), 2.03-1.98 (m, 1H), 1.88 (s, 2H), 1.04 (d, J = 6.0 Hz, 3H). | I-70 and I-72 |

-continued

| Compound | Structural formula | LC-MS [M+H]+ | 1HNMR | Intermediate |
|---|---|---|---|---|
| 77 | | 508.2 | $^1$H NMR (400 MHz, CD$_3$OD): δ 8.52 (d, J = 4.8 Hz, 1H), 7.52 (d, J = 5.2 Hz, 1H), 7.44 (d, J = 2.0 Hz, 1H), 7.41 (d, J = 2.0 Hz, 1H), 7.34-7.26 (m, 4H), 7.22 (d, J = 6.0 Hz, 1H), 7.02-6.95 (m, 1H), 6.93 (s, 1H), 6.77 (d, J = 6.0 Hz, 1H), 4.56 (d, J = 11.6 Hz, 1H), 4.48 (d, J = 12.0 Hz, 1H), 3.70 (s, 3H), 2.74 (d, J = 3.2 Hz, 2H), 2.62 (s, 2H), 1.29 (d, J = 5.6 Hz, 6H). | I-55 and I-73 |
| 78 | | 663.3 | $^1$H NMR (400 MHz, CD$_3$OD): δ 8.70-8.64 (m, 1H), 8.57-8.51 (m, 1H), 7.97-7.91 (m, 1H), 7.60-7.56 (m, 1H), 7.54-7.50 (m, 1H), 7.46-7.42 (m, 1H), 7.28-7.23 (m, 1H), 7.05-7.00 (m, 1H), 6.97-6.93 (m, 1H), 6.82-6.76 (m, 1H), 4.72-4.67 (m, 2H), 4.65-4.60 (m, 2H), 4.59-4.57 (m, 1H), 4.50-4.44 (m, 1H), 3.69 (s, 3H), 3.53-3.44 (m, 2H), 3.12-3.01 (m, 2H), 2.98-2.87 (m, 1H), 2.81-2.62 (m, 2H), 2.60-2.53 (m, 1H), 2.51-2.42 (m, 2H), 2.37-2.25 (m, 1H), 2.23-2.16 (m, 1H), 2.08-1.89 (m, 2H), 1.53-1.39 (m, 1H), 1.21-1.13 (m, 3H), 0.98-0.94 (m, 3H). | I-74 and I-54 |
| 79 | | 664.3 | $^1$H NMR (400 MHz, CD$_3$OD/CDCl$_3$ = 1/1): δ 8.68-8.62 (m, 1H), 8.62-8.55 (m, 1H), 8.34-8.28 (m, 1H), 8.03-7.95 (m, 1H), 7.70-7.65 (m, 1H), 7.62-7.59 (m, 1H), 7.46-7.41 (m, 1H), 7.13-7.07 (m, 1H), 7.05-6.96 (m, 1H), 4.75-4.72 (m, 2H), 4.70-4.63 (m, 2H), 4.61-4.53 (m, 2H), 3.74 (s, 3H), 3.59-3.52 (m, 1H), 3.51-3.43 (m, 1H), 3.15-3.05 (m, 2H), 2.90-2.81 (m, 2H), 2.71-2.64 (m, 2H), 2.64-2.58 (m, 1H), 2.56-2.45 (m, 2H), 2.27-2.16 (m, 1H), 1.34 (s, 6H), 1.05-0.95 (m, 3H). | I-75 and I-54 |

| Compound | Structural formula | LC-MS [M + H]+ | 1HNMR | Intermediate |
|---|---|---|---|---|
| 68a | | 551.2 | | I-55 and I-67 Concentrated hydrochloric acid, methanol, stirring at room temperature to remove Boc |
| 92 | | 663.3 | ¹H NMR (400 MHz, CD₃OD) δ 8.67 (d, J = 2.2 Hz, 1H), 8.53 (d, J = 5.1 Hz, 1H), 7.94 (d, J = 2.6 Hz, 1H), 7.57 (d, J = 5.1 Hz, 1H), 7.52 (d, J = 2.3 Hz, 1H), 7.43 (dd, J = 9.0, 2.7 Hz, 1H), 7.38 (d, J = 6.2 Hz, 1H), 7.02 (d, J = 8.9 Hz, 1H), 6.96 (s, 1H), 6.78 (d, J = 6.1 Hz, 1H), 4.73-4.44 (m, 6H), 3.69 (s, 3H), 3.57-3.45 (m, 2H), 3.14-3.00 (m, 2H), 2.97-2.88 (m, 2H), 2.79-2.71 (m, 2H), 2.63-2.55 (m, 1H), 2.52-2.43 (m, 2H), 2.27-2.16 (m, 1H), 1.97-1.87 (m, 2H), 1.83-1.66 (m, 4H), 0.96 (d, J = 6.3 Hz, 3H). | I-54 and I-79 |
| 93 | | 651.3 | ¹H NMR (400 MHz, CD₃OD) δ 8.67 (d, J = 2.3 Hz, 1H), 8.55 (d, J = 5.1 Hz, 1H), 7.95 (d, J = 2.8 Hz, 1H), 7.59 (d, J = 5.1 Hz, 1H), 7.51 (d, J = 2.3 Hz, 1H), 7.44 (dd, J = 8.9, 2.8 Hz, 1H), 7.32 (d, J = 6.0 Hz, 1H), 7.03 (d, J = 8.9 Hz, 1H), 6.96 (s, 1H), 6.85 (d, J = 6.0 Hz, 1H), 4.80-4.76 (m, 2H), 4.72-4.47 (m, 6H), 4.10-4.01 (m, 2H), 3.70 (s, 3H), 3.56-3.46 (m, 2H), 3.13-3.00 (m, 2H), 2.95-2.85 (m, 2H), 2.61-2.54 (m, 1H), 2.52-2.43 (m, 2H), 2.26-2.17 (m, 1H), 0.97 (d, J = 6.3 Hz, 3H). | I-54 and I-80 |

| Compound | Structural formula | LC-MS [M + H]+ | 1HNMR | Intermediate |
|---|---|---|---|---|
| 100 | | 664.3 | ¹H NMR (400 MHz, CD₃OD): δ 8.68 (d, J = 2.0 Hz, 1H), 8.54 (d, J = 5.1 Hz, 1H), 7.94 (d, J = 2.7 Hz, 1H), 7.58 (d, J = 5.1 Hz, 1H), 7.52 (d, J = 2.2 Hz, 1H), 7.44 (dd, J = 8.9, 2.6 Hz, 1H), 7.22 (d, J = 5.9 Hz, 1H), 7.02 (d, J = 8.9 Hz, 1H), 6.93 (s, 1H), 6.78 (d, J = 5.9 Hz, 1H), 4.74-4.43 (m, 5H), 3.69 (s, 3H), 3.55-3.44 (m, 2H), 3.13-2.98 (m, 2H), 2.82-2.68 (m, 2H), 2.63-2.53 (m, 3H), 2.46 (m, 2H), 2.20 (m, 1H), 1.28 (d, J = 6.4 Hz, 6H), 0.96 (d, J = 6.3 Hz, 3H). | I-54 and I-55, NaBD₄ |
| 101 | | 665.4 | ¹H NMR (400 MHz, CD₃OD): δ 8.68 (d, J = 2.2 Hz, 1H), 8.53 (d, J = 5.1 Hz, 1H), 7.94 (d, J = 2.7 Hz, 1H), 7.58 (d, J = 5.1 Hz, 1H), 7.52 (d, J = 2.1 Hz, 1H), 7.43 (dd, J = 8.9, 2.7 Hz, 1H), 7.21 (d, J = 5.9 Hz, 1H), 7.02 (d, J = 8.9 Hz, 1H), 6.92 (s, 1H), 6.78 (d, J = 5.9 Hz, 1H), 4.73-4.43 (m, 5H), 3.68 (s, 3H), 3.53-3.43 (m, 1H), 3.11-2.98 (m, 2H), 2.80-2.68 (m, 2H), 2.66-2.52 (m, 3H), 2.50-2.39 (m, 2H), 2.24-2.14 (m, 1H), 1.28 (d, J = 6.4 Hz, 6H), 0.96 (d, J = 6.3 Hz, 3H). | I-186 and I-55, NaBD₄ |
| 104 | | 678.3 | ¹H NMR (400 MHz, CD₃OD) δ 8.66-8.62 (m, 1H), 8.55-8.51 (m, 1H), 7.96-7.92 (m, 1H), 7.59-7.57 (m, 1H), 7.50-7.49 (m, 1H), 7.45-7.41 (m, 1H), 7.07-6.98 (m, 2H), 4.71-4.66 (m, 2H), 4.64-4.54 (m, 4H), 3.68 (s, 3H), 3.53-3.45 (m, 2H), 3.11-3.00 (m, 4H), 2.63-2.52 (m, 6H), 2.50-2.41 (m, 2H), 2.24-2.16 (m, 1H), 1.30 (s, 6H), 0.99-0.94 (m, 3H). | I-54 and I-82 |

| Compound | Structural formula | LC-MS [M+H]+ | 1HNMR | Intermediate |
|---|---|---|---|---|
| 105 | | 665.3 | ¹H NMR (400 MHz, CD₃OD) δ 8.70-8.51 (m, 2H), 7.92-7.90 (m, 1H), 7.55-7.53 (m, 1H), 7.38 (d, J = 6.9 Hz, 1H), 7.27 (s, 1H), 7.21-7.11 (m, 1H), 6.97-6.95 (m, 1H), 6.90-6.88 (m, 1H), 6.79-6.77 (m, 1H), 5.51-5.20 (m, 2H), 4.69-4.51 (m, 4H), 3.64 (s, 3H), 3.52-3.39 (m, 2H), 3.00-2.97 (m, 2H), 2.88-2.85 (m, 1H), 2.72-2.28 (m, 6H), 2.18-2.16 (m, 1H), 1.28-1.24 (m, 6H), 0.93 (d, J = 6.2 Hz, 3H). | I-54 and I-83 |
| 114 | | 677.4 | ¹H NMR (400 MHz, CD₃OD) δ 8.63-8.59 (m, 1H), 8.53-8.47 (m, 1H), 7.93-7.89 (m, 1H), 7.50-7.47 (m, 1H), 7.46-7.42 (m, 1H), 7.35-7.27 (m, 1H), 7.25-7.15 (m, 1H), 7.04-6.99 (m, 1H), 6.93-6.90 (m, 1H), 6.81-6.66 (m, 1H), 5.16-4.97 (m, 1H), 4.72-4.67 (m, 2H), 4.64-4.57 (m, 2H), 3.71-3.67 (m, 3H), 3.53-3.43 (m, 2H), 3.10-3.01 (m, 2H), 2.79-2.68 (m, 2H), 2.66-2.59 (m, 2H), 2.59-2.54 (m, 1H), 2.49-2.43 (m, 2H), 2.23-2.14 (m, 1H), 1.40-1.34 (m, 3H), 1.30-1.27 (m, 6H), 0.97-0.93 (m, 3H). | I-54 and I-84 |
| 149 | | 664.2 | ¹H NMR (400 MHz, CD₃OD/ CDCl₃ = 1/1): δ 8.91 (s, 1H), 8.60 (s, 1H), 8.56 (d, J = 4.9 Hz, 1H), 8.06 (s, 1H), 7.95 (s, 1H), 7.87 (d, J = 7.8 Hz, 1H), 7.72 (s, 1H), 7.64 (t, J = 7.9 Hz, 1H), 7.57 (s, 1H), 7.51 (t, J = 7.9 Hz, 1H), 7.41 (d, J = 8.7 Hz, 1H), 6.98 (d, J = 8.9 Hz, 1H), 4.71-4.58 (m, 6H), 3.70 (s, 3H), 3.54-3.42 (m, 2H), 3.11-2.99 (m, 2H), 2.61-2.52 (m, 1H), 2.52-2.40 (m, 2H), 2.22-2.12 (m, 1H), 0.96 (d, J = 6.0 Hz, 3H). | I-54 and I-85 |

-continued

| Compound | Structural formula | LC-MS [M + H]+ | 1HNMR | Intermediate |
|---|---|---|---|---|
| 150 | | 664.2 | ¹H NMR (400 MHz, CD₃OD): δ 8.64 (d, J = 2.3 Hz, 1H), 8.58-8.47 (m, 2H), 7.94 (d, J = 2.5 Hz, 1H), 7.58 (d, J = 5.1 Hz, 1H), 7.49 (d, J = 2.3 Hz, 1H), 7.43 (dd, J = 9.0, 2.8 Hz, 1H), 7.09-6.98 (m, 2H), 4.74-4.54 (m, 6H), 3.68 (s, 3H), 3.59-3.44 (m, 2H), 3.12-3.00 (m, 4H), 2.80-2.72 (m, 2H), 2.65-2.58 (m, 1H), 2.51 (t, J = 4.9 Hz, 2H), 2.28-2.19 (m, 1H), 1.98-1.88 (m, 2H), 1.83-1.70 (m, 4H), 0.96 (d, J = 6.4 Hz, 3H). | I-54 and I-86 |
| 151 | | 646.2 | ¹H NMR (400 MHz, DMSO-d₆): δ 9.29 (s, 1H), 8.61 (d, J = 2.3 Hz, 1H), 8.54 (d, J = 5.1 Hz, 1H), 8.46 (s, 1H), 8.28 (d, J = 8.4 Hz, 1H), 7.91 (d, J = 8.0 Hz, 1H), 7.82 (d, J = 2.8 Hz, 1H), 7.60-7.42 (m, 5H), 7.34 (dd, J = 9.0, 2.9 Hz, 1H), 7.22 (d, J = 9.1 Hz, 1H), 4.97 (t, J = 5.2 Hz, 1H), 4.54-4.35 (m, 6H), 3.69-3.62 (m, 1H), 3.57 (s, 3H), 3.46-3.40 (m, 1H), 3.09-3.03 (m, 1H), 2.95-2.87(m, 1H), 2.54-2.49 (m, 1H), 2.32-2.23 (m, 2H), 2.19-2.09 (m, 1H), 0.89 (d, J = 6.4 Hz, 3H). | I-54 and I-87 |
| 157 | | 650.2 | ¹H NMR (400 MHz, CD₃OD) δ 8.69-8.61 (m, 1H), 8.57-8.50 (m, 1H), 8.44 (s, 1H), 7.95 (s, 1H), 7.64-7.55 (m, 1H), 7.50 (s, 1H), 7.47-7.39 (m, 1H), 7.08-6.99 (m, 2H), 4.71-4.67 (m, 2H), 4.64-4.56 (m, 4H), 3.69 (s, 3H), 3.53-3.45 (m, 2H), 3.11-3.01 (m, 2H), 2.92-2.83 (m, 2H), 2.74-2.64 (m, 2H), 2.61-2.52 (m, 1H), 2.52-2.40 (m, 2H), 2.25-2.14 (m, 1H), 2.03-1.93 (m, 2H), 1.91-1.79 (m, 2H), 1.02-0.89 (m, 3H). | I-54 and I-88 |

-continued

| Compound | Structural formula | LC-MS [M + H]+ | 1HNMR | Intermediate |
|---|---|---|---|---|
| 158 | | 664.2 | ¹H NMR (400 MHz, CD₃OD) δ 8.66-8.60 (m, 1H), 8.55-8.49 (m, 1H), 7.97-7.88 (m, 1H), 7.60-7.53 (m, 1H), 7.52-7.46 (m, 1H), 7.45-7.38 (m, 1H), 7.05 (s, 1H), 7.03-6.96 (m, 1H), 4.71-4.65 (m, 2H), 4.64-4.52 (m, 4H), 3.67 (s, 3H), 3.53-3.43 (m, 2H), 3.19-3.11 (m, 2H), 3.10-2.99 (m, 2H), 2.74-2.64 (m, 5H), 2.57-2.51 (m, 1H), 2.50-2.39 (m, 2H), 2.23-2.14 (m, 1H), 1.98-1.88 (m, 2H), 1.84-1.74 (m, 2H), 1.00-0.89 (m, 3H). | I-54 and I-89 |
| 160 | | 649.2 | ¹H NMR (400 MHz, CD₃OD): δ 8.67 (d, J = 2.0 Hz, 1H), 8.53 (d, J = 5.0 Hz, 1H), 7.94 (s, 1H), 7.57 (d, J = 5.0 Hz, 1H), 7.52 (d, J = 2.1 Hz, 1H), 7.43 (dd, J = 8.9, 2.7 Hz, 1H), 7.22 (d, J = 5.8 Hz, 1H), 7.02 (d, J = 9.0 Hz, 1H), 6.91 (s, 1H), 6.77 (d, J = 5.8 Hz, 1H), 4.72-4.44 (m, 6H), 3.68 (s, 3H), 3.54-3.44 (m, 2H), 3.13-2.93 (m, 5H), 2.62-2.34 (m, 5H), 2.26-2.15 (m, 1H), 1.28-1.23 (m, 3H), 0.95 (d, J = 6.3 Hz, 3H). | I-54 and I-90 |
| 161 | | 667.2 | ¹H NMR (400 MHz, CD₃OD): δ 8.67 (d, J = 1.9 Hz, 1H), 8.53 (d, J = 5.1 Hz, 1H), 7.94 (d, J = 2.8 Hz, 1H), 7.57 (d, J = 5.1 Hz, 1H), 7.50 (d, J = 2.1 Hz, 1H), 7.44 (dd, J = 8.9, 2.7 Hz, 1H), 7.14 (d, J = 6.1 Hz, 1H), 7.02 (d, J = 8.9 Hz, 1H), 6.69 (d, J = 6.0 Hz, 1H), 4.71-4.47 (m, 6H), 3.69 (s, 3H), 3.53-3.45 (m, 2H), 3.12-3.00 (m, 2H), 2.78-2.67 (m, 2H), 2.65-2.54 (m, 3H), 2.49-2.41 (m, 2H), 2.24-2.14 (m, 1H), 1.98-1.87 (m, 2H), 1.87-1.76 (m, 2H), 0.96 (d, J = 6.3 Hz, 3H). | I-54 and I-91 |

-continued

| Compound | Structural formula | LC-MS [M + H]+ | 1HNMR | Intermediate |
|---|---|---|---|---|
| 163 | | 598.2 | ¹H NMR (400 MHz, CD₃OD) δ 8.57-8.46 (m, 1H), 8.40 (s, 1H), 7.93 (s, 1H), 7.62-7.48 (m, 1H), 7.38 (s, 1H), 7.02 (s, 1H), 5.83 (s, 1H), 4.59-4.44 (m, 2H), 4.04-3.93 (m, 2H), 3.73-3.61 (m, 5H), 3.59-3.52 (m, 2H), 3.32 (s, 3H), 3.03-2.94 (m, 2H), 2.89-2.80 (m, 2H), 2.78-2.71 (m, 2H), 2.71-2.63 (m, 2H), 2.00-1.90 (m, 2H), 1.89-1.79 (m, 2H). | I-134 and I-88 |
| 166 | | 596.2 | ¹H NMR (400 MHz, CD₃OD/ CDCl₃ = 1/1) δ 8.57-8.50 (m, 1H), 8.36 (s, 1H), 7.95-7.89 (m, 1H), 7.60-7.52 (m, 1H), 7.45-7.36 (m, 1H), 7.05 (s, 1H), 5.85 (s, 1H), 4.76-4.72 (m, 2H), 4.65-4.61 (m, 2H), 4.55-4.48 (m, 2H), 4.09-4.00 (m, 2H), 3.78-3.71 (m, 1H), 3.68 (s, 3H), 3.58-3.53 (m, 2H), 2.89-2.81 (m, 4H), 2.72-2.66 (m, 2H), 2.00-1.93 (m, 2H), 1.90-1.80 (m, 2H). | I-136 and I-88 |
| 167 | | 615.2 | ¹H NMR (400 MHz, CD₃OD): δ 8.52 (d, J = 5.1 Hz, 1H), 7.96 (d, J = 2.2 Hz, 1H), 7.55 (d, J = 5.1 Hz, 1H), 7.41 (d, J = 2.2 Hz, 1H), 7.14 (d, J = 6.0 Hz, 1H), 6.68 (d, J = 6.0 Hz, 1H), 5.85 (s, 1H), 4.61-4.45 (m, 2H), 4.05-3.98 (m, 2H), 3.74-3.70 (m, 2H), 3.67 (s, 3H), 3.60-3.55 (m, 2H), 3.33 (s, 3H), 3.05-2.98 (m, 2H), 2.79-2.70 (m, 4H), 2.64-2.57 (m, 2H), 1.96-1.79 (m, 4H). | I-134 and I-91 |

-continued

| Compound | Structural formula | LC-MS [M + H]+ | 1HNMR | Intermediate |
|---|---|---|---|---|
| 168 | | 597.2 | $^1$H NMR (400 MHz, CD$_3$OD): δ 8.52 (dd, J = 5.1, 0.5 Hz, 1H), 7.96 (d, J = 2.3 Hz, 1H), 7.55 (d, J = 5.1 Hz, 1H), 7.42 (d, J = 2.2 Hz, 1H), 7.21 (d, J = 5.9 Hz, 1H), 6.91 (s, 1H), 6.76 (d, J = 5.9 Hz, 1H), 5.84 (s, 1H), 4.58-4.41 (m, 2H), 4.00 (t, J = 5.6 Hz, 2H), 3.72-3.69 (m, 2H), 3.67 (s, 3H), 3.57 (t, J = 5.3 Hz, 2H), 3.33 (s, 3H), 3.13-2.93 (m, 5H), 2.75 (t, J = 5.3 Hz, 2H), 2.54-2.33 (m, 2H), 1.27-1.23 (m, 3H). | I-134 and I-90 |
| 176 | | 558.2 | $^1$H NMR (400 MHz, CD$_3$OD/ CDCl$_3$ = 3/1) δ 8.50 (d, J = 7.0 Hz, 1H), 7.93 (d, J = 5.8 Hz, 1H), 7.53 (d, J = 5.1 Hz, 1H), 7.43-7.41 (m, 1H), 7.10-7.00 (m, 1H), 6.63 (d, J = 6.0 Hz, 1H), 5.82 (s, 1H), 4.76-4.74 (m, 2H), 4.57-4.43 (m, 2H), 4.11-3.94 (m, 4H), 3.68 (s, 3H), 2.76-2.54 (m, 4H), 1.97-1.76 (m, 4H). | I-144 and I-91 |
| 177 | | 611.0 | $^1$H NMR (400 MHz, CD$_3$OD/ CDCl$_3$ = 1/1) δ 8.59-8.49 (m, 1H), 7.94-7.88 (m, 1H), 7.86-7.77 (m, 2H), 7.71-7.66 (m, 1H), 7.57-7.53 (m, 1H), 7.52-7.47 (m, 1H), 7.41-7.37 (m, 1H), 7.37-7.32 (m, 1H), 6.78-6.62 (m, 1H), 5.82 (s, 1H), 4.66-4.59 (m, 1H), 4.56-4.50 (m, 1H), 4.07-3.98 (m, 2H), 3.74-3.69 (m, 2H), 3.68 (s, 3H), 3.59-3.54 (m, 2H), 3.34 (s, 3H), 3.06-2.98 (m, 2H), 2.79-2.72 (m, 2H). | I-134 and I-59 |

-continued

| Compound | Structural formula | LC-MS [M + H]+ | 1HNMR | Intermediate |
|---|---|---|---|---|
| 178 | | 609.0 | ¹H NMR (400 MHz, CDCl₃) δ 8.60-8.52 (m, 1H), 8.01-7.96 (m, 1H), 7.88-7.85 (m, 1H), 7.67-7.63 (m, 2H), 7.52-7.48 (m, 2H), 7.38-7.34 (m, 2H), 6.65-6.57 (m, 1H), 5.71 (s, 1H), 4.75-4.71 (m, 2H), 4.67-4.64 (m, 2H), 4.62-4.57 (m, 2H), 4.45-4.36 (m, 1H), 4.13-4.03 (m, 2H), 3.79-3.71 (m, 1H), 3.70 (s, 3H), 3.56-3.52 (m, 2H), 3.48 (s, 1H), 2.82-2.78 (m, 2H). | I-136 and I-59 |
| 180 | | 530.2 | ¹H NMR (400 MHz, CD₃OD) δ 8.48 (d, J = 5.1 Hz, 1H), 7.79 (s, 1H), 7.53-7.45 (m, 2H), 7.27 (d, J = 5.5 Hz, 1H), 7.14-7.12 (m, 1H), 7.05-7.03 (m, 1H), 6.65 (d, J = 6.0 Hz, 1H), 4.56-4.39 (m, 2H), 4.10 (q, J = 7.3 Hz, 2H), 3.66 (s, 3H), 2.77-2.54 (m, 4H), 1.96-1.76 (m, 4H), 1.41 (t, J = 7.3 Hz, 3H). | I-145 and I-91 |
| 181 | | 540.0 | ¹H NMR (400 MHz, CDCl₃): δ 8.54 (d, J = 5.1 Hz, 1H), 7.99 (d, J = 2.3 Hz, 1H), 7.74 (d, J = 2.0 Hz, 1H), 7.50-7.40 (m, 2H), 7.01 (s, 1H), 6.91 (d, J = 5.9 Hz, 1H), 6.63 (d, J = 6.0 Hz, 1H), 5.70 (s, 1H), 5.11-5.02 (m, 1H), 4.78 (s, 2H), 4.53-4.45 (m, 1H), 4.39-4.28 (m, 1H), 4.11-4.02 (m, 4H), 3.70 (s, 3H), 3.10-2.94 (m, 3H), 2.51-2.35 (m, 2H), 1.27 (d, J = 6.2 Hz, 3H). | I-144 and I-90 |

-continued

| Compound | Structural formula | LC-MS [M + H]+ | 1HNMR | Intermediate |
|---|---|---|---|---|
| 182 | | 679.3 | $^1$H NMR (400 MHz, CD$_3$OD): δ 8.68 (t, J = 2.1 Hz, 1H), 8.54 (dd, J = 5.1, 1.6 Hz, 1H), 7.95 (d, J = 2.7 Hz, 1H), 7.58 (d, J = 5.1 Hz, 1H), 7.55-7.48 (m, 1H), 7.44 (dd, J = 8.9, 2.8 Hz, 1H), 7.39 (d, J = 5.9 Hz, 1H), 7.02 (d, J = 8.9 Hz, 1H), 6.91 (s, 1H), 6.83 (dd, J = 5.9, 1.9 Hz, 1H), 4.76-4.45 (m, 7H), 3.72-3.66 (m, 3H), 3.57-3.45 (m, 2H), 3.14-3.03 (m, 2H), 2.77-2.68 (m, 1H), 2.65-2.58 (m, 1H), 2.55-2.45 (m, 3H), 2.28-2.19 (m, 1H), 1.25-1.17 (m, 6H), 0.96 (d, J = 6.3 Hz, 3H). | I-54 and I-92, Removing Ac during the Suzuki reaction |
| 183 | | 620.4 | $^1$H NMR (400 MHz, CDCl$_3$) δ 8.80-8.75 (m, 1H), 8.63-8.57 (m, 1H), 8.24-8.12 (m, 1H), 7.91 (s, 1H), 7.89-7.86 (m, 1H), 7.86-7.84 (m, 1H), 7.68-7.64 (m, 1H), 7.62-7.58 (m, 1H), 7.53-7.49 (m, 2H), 7.39-7.35 (m, 2H), 6.86-6.81 (m, 1H), 6.66-6.60 (m, 1H), 4.73-4.70 (m, 2H), 4.67-4.58 (m, 2H), 4.58-4.55 (m, 2H), 4.46-4.37 (m, 1H), 3.83-3.77 (m, 1H), 3.76-3.72 (m, 5H), 3.69-3.64 (m, 1H), 3.27-3.22 (m, 2H). | I-146 and I-59 |
| 184 | | 650.3 | $^1$H NMR (400 MHz, CD$_3$OD) δ 8.61-8.57 (m, 1H), 8.57-8.52 (m, 1H), 7.96-7.90 (m, 1H), 7.78-7.70 (m, 1H), 7.58-7.55 (m, 1H), 7.50-7.46 (m, 1H), 7.40-7.34 (m, 1H), 6.97-6.86 (m, 2H), 4.72-4.68 (m, 2H), 4.62-4.53 (m, 3H), 4.47-4.41 (m, 2H), 3.69 (s, 3H), 3.54-3.48 (m, 1H), 3.46-3.38 (m, 1H), 3.09-3.01 (m, 2H), 2.88-2.79 (m, 2H), 2.69-2.62 (m, 2H), 2.59-2.53 (m, 1H), 2.50-2.41 (m, 2H), 2.21-2.13 (m, 1H), 1.94-1.78 (m, 4H), 0.98-0.92 (m, 3H). | I-54 and I-93 |

| Compound | Structural formula | LC-MS [M + H]+ | 1HNMR | Intermediate |
|---|---|---|---|---|
| 186 | | 668.2 | ¹H NMR (400 MHz, CD₃OD) δ 8.66-8.61 (m, 1H), 8.57-8.52 (m, 1H), 8.39-8.34 (m, 1H), 7.98-7.93 (m, 1H), 7.61-7.57 (m, 1H), 7.51-7.47 (m, 1H), 7.47-7.41 (m, 1H), 7.06-7.00 (m, 1H), 4.72-4.67 (m, 2H), 4.66-4.54 (m, 4H), 3.70 (s, 3H), 3.53-3.46 (m, 2H), 3.15-2.99 (m, 2H), 2.91-2.81 (m, 2H), 2.68-2.60 (m, 2H), 2.60-2.53 (m, 1H), 2.52-2.43 (m, 2H), 2.24-2.17 (m, 1H), 2.01-1.92 (m, 2H), 1.92-1.80 (m, 2H), 1.02-0.94 (m, 3H). | I-54 and I-94 |
| 187 | | 663.2 | ¹H NMR (400 MHz, CD₃OD): δ 8.67 (d, J = 2.3 Hz, 1H), 8.54 (d, J = 5.1 Hz, 1H), 7.94 (d, J = 2.8 Hz, 1H), 7.58 (d, J = 5.1 Hz, 1H), 7.52 (d, J = 2.3 Hz, 1H), 7.44 (dd, J = 9.0, 2.9 Hz, 1H), 7.24 (d, J = 5.9 Hz, 1H), 7.02 (d, J = 8.9 Hz, 1H), 6.93 (s, 1H), 6.79 (d, J = 6.0 Hz, 1H), 4.73-4.44 (m, 6H), 3.69 (s, 3H), 3.53-3.45 (m, 2H), 3.12-3.01 (m, 2H), 2.92-2.63 (m, 3H), 2.61-2.52 (m, 1H), 2.50-2.42 (m, 2H), 2.32-2.17 (m, 2H), 2.11-1.81 (m, 2H), 1.65-1.49 (m, 1H), 1.11 (dd, J = 6.6, 1.5 Hz, 3H), 0.96 (d, J = 6.3 Hz, 3H). | I-54 and I-95 |
| 188 | | 659.2 | ¹H NMR (400 MHz, CD₃OD/CDCl₃ = 1/1) δ 8.64 (d, J = 2.2 Hz, 1H), 8.57 (d, J = 5.1 Hz, 1H), 7.95 (d, J = 2.7 Hz, 1H), 7.73 (dd, J = 7.2, 4.2 Hz, 2H), 7.62-7.55 (m, 2H), 7.52 (d, J = 2.3 Hz, 1H), 7.40 (dd, J = 9.4, 3.3 Hz, 2H), 7.30 (dd, J = 8.7, 1.4 Hz, 1H), 6.97 (d, J = 8.9 Hz, 1H), 6.78 (d, J = 6.0 Hz, 1H), 4.72-4.49 (m, 6H), 3.70 (s, 3H), 3.55-3.42 (m, 2H), 3.09-3.01 (m, 2H), 2.60-2.54 (m, 1H), 2.50-2.43 (m, 5H), 2.22-2.13 (m, 1H), 0.96 (d, J = 6.3 Hz, 3H). | I-54 and I-96 |

-continued

| Compound | Structural formula | LC-MS [M + H]+ | 1HNMR | Intermediate |
|---|---|---|---|---|
| 190 | | 668.3 | ¹H NMR (400 MHz, CD₃OD/ CDCl₃ = 1/1) δ 8.61-8.56 (m, 1H), 8.56-8.52 (m, 1H), 7.96-7.91 (m, 1H), 7.68-7.63 (m, 1H), 7.58-7.55 (m, 1H), 7.48-7.43 (m, 1H), 7.41-7.36 (m, 1H), 6.97-6.89 (m, 1H), 4.74-4.69 (m, 2H), 4.64-4.56 (m, 3H), 4.50-4.44 (m, 1H), 3.69 (s, 3H), 3.54-3.48 (m, 1H), 3.47-3.38 (m, 1H), 3.10-3.00 (m, 2H), 2.87-2.76 (m, 2H), 2.63-2.53 (m, 3H), 2.51-2.41 (m, 2H), 2.21-2.12 (m, 1H), 1.92-1.84 (m, 2H), 1.84-1.76 (m, 2H), 0.99-0.91 (m, 3H). | I-54 and I-97 |
| 194 | | 598.3 | ¹H NMR (400 MHz, CD₃OD/ CDCl₃ = 1/1) δ 8.56-8.51 (m, 1H), 7.86-7.83 (m, 1H), 7.73-7.69 (m, 1H), 7.53-7.51 (m, 1H), 7.40-7.37 (m, 1H), 6.93-6.89 (m, 1H), 5.76-5.72 (m, 1H), 4.55-4.51 (m, 1H), 4.42-4.37 (m, 1H), 4.05-4.00 (m, 2H), 3.71-3.68 (m, 2H), 3.66 (s, 3H), 3.57-3.54 (m, 2H), 3.34 (s, 3H), 3.02-2.97 (m, 2H), 2.86-2.80 (m, 2H), 2.77-2.73 (m, 2H), 2.68-2.63 (m, 2H), 1.93-1.86 (m, 2H), 1.84-1.77 (m, 2H). | I-134 and I-93 |
| 216 | | 663.2 | ¹H NMR (400 MHz, CD₃OD) δ 8.64-8.58 (m, 2H), 8.48 (s, 1H), 7.93-7.84 (m, 1H), 7.42-7.35 (m, 1H), 7.35-7.30 (m, 1H), 7.18-7.14 (m, 1H), 7.01-6.95 (m, 1H), 6.88 (s, 1H), 6.74-6.69 (m, 1H), 4.69-4.63 (m, 2H), 4.62-4.52 (m, 3H), 4.49-4.40 (m, 1H), 3.65 (s, 3H), 3.50-3.40 (m, 2H), 3.07-2.93 (m, 2H), 2.73-2.64 (m, 2H), 2.62-2.54 (m, 2H), 2.53-2.47 (m, 1H), 2.47-2.35 (m, 2H), 2.21-2.13 (m, 1H), 1.28-1.20 (m, 6H), 0.96-0.88 (m, 3H). | I-54 and I-98 |

-continued

| Compound | Structural formula | LC-MS [M + H]⁺ | 1HNMR | Intermediate |
|---|---|---|---|---|
| 218 | 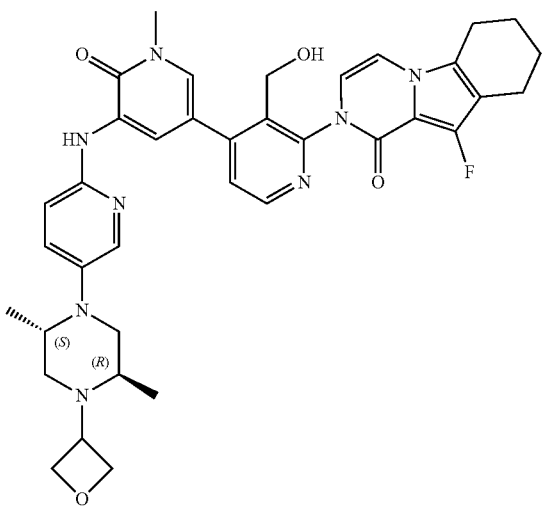 | 681.2 | ¹H NMR (400 MHz, CD₃OD): δ 8.72 (d, J = 2.2 Hz, 1H), 8.55 (d, J = 5.1 Hz, 1H), 8.01 (d, J = 2.6 Hz, 1H), 7.58 (d, J = 5.1 Hz, 1H), 7.56-7.47 (m, 2H), 7.15 (d, J = 4.6 Hz, 1H), 7.04 (d, J = 8.9 Hz, 1H), 6.70 (d, J = 6.1 Hz, 1H), 4.75-4.72 (m, 1H), 4.70-4.66 (m, 2H), 4.65-4.60 (m, 2H), 4.54-4.48 (m, 1H), 3.84-3.76 (m, 1H), 3.82-2.69 (s, 3H), 3.24-3.16 (m, 1H), 2.97-2.89 (m, 1H), 2.82-2.69 (m, 4H), 2.66-2.48 (m, 3H), 2.03-1.89 (m, 3H), 1.88-1.77 (m, 2H), 0.94-0.86 (m, 6H). | I-162 and I-91 |
| 221 | 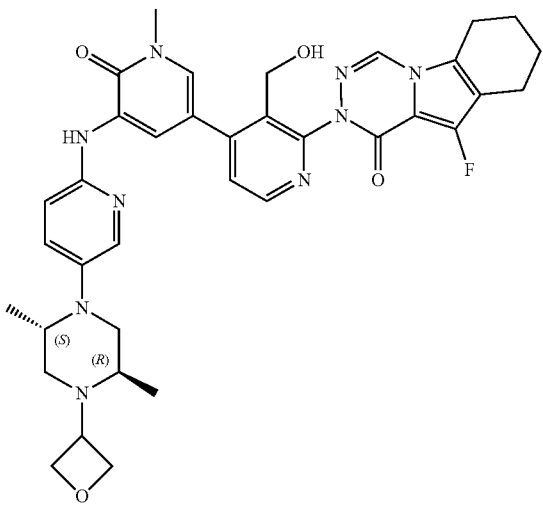 | 682.2 | ¹H NMR (400 MHz, CD₃OD/CDCl₃ = 1/1) δ 8.68-8.62 (m, 1H), 8.57-8.52 (m, 1H), 8.29-8.24 (m, 1H), 8.03-7.96 (m, 1H), 7.58-7.53 (m, 1H), 7.53-7.49 (m, 1H), 7.49-7.41 (m, 1H), 7.01-6.94 (m, 1H), 4.73-4.60 (m, 4H), 4.60-4.51 (m, 2H), 3.81-3.73 (m, 1H), 3.70 (s, 3H), 3.22-3.12 (m, 1H), 2.94-2.87 (m, 1H), 2.87-2.80 (m, 2H), 2.77-2.68 (m, 2H), 2.67-2.57 (m, 2H), 2.55-2.43 (m, 1H), 2.00-1.91 (m, 3H), 1.89-1.79 (m, 2H), 0.92-0.86 (m, 6H). | I-162 and I-94 |
| 225 | 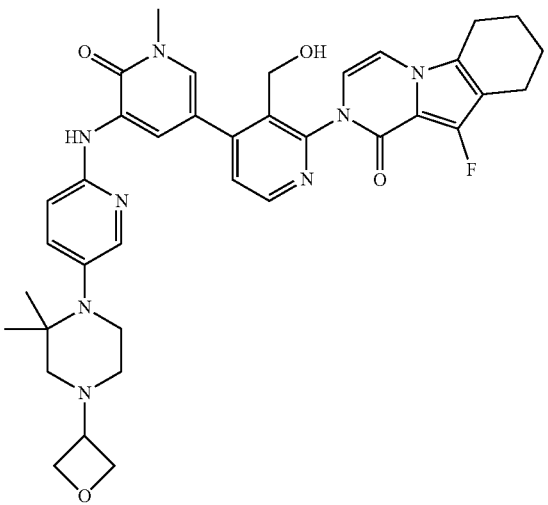 [SMILES: Cn1cc(-c2ccnc(-n3ccn4c5c(c(F)c4c3=O)CCCC5)c2CO)cc(Nc2ccc(N3CCN(C4COC4)CC3(C)C)cn2)c1=O] | 681.2 | ¹H NMR (400 MHz, CD₃OD) δ 8.73 (d, J = 2.2 Hz, 1H), 8.55 (d, J = 5.1 Hz, 1H), 8.02 (d, J = 2.3 Hz, 1H), 7.58 (d, J = 5.1 Hz, 1H), 7.53 (d, J = 2.3 Hz, 1H), 7.49-7.47 (m, 1H), 7.16-7.14 (m, 1H), 7.00 (d, J = 8.8 Hz, 1H), 6.70 (d, J = 6.0 Hz, 1H), 4.70-4.50 (m, 6H), 3.71 (s, 3H), 3.47-3.43 (m, 1H), 3.15-3.11 (m, 2H), 2.78-2.69 (m, 2H), 2.65-2.61 (m, 2H), 2.45-2.41 (m, 2H), 2.21-2.17 (m, 2H), 2.00-1.78 (m, 4H), 1.08-1.04 (m, 6H). | I-166 and I-91 |

| Compound | Structural formula | LC-MS [M + H]+ | 1HNMR | Intermediate |
|---|---|---|---|---|
| 227 | 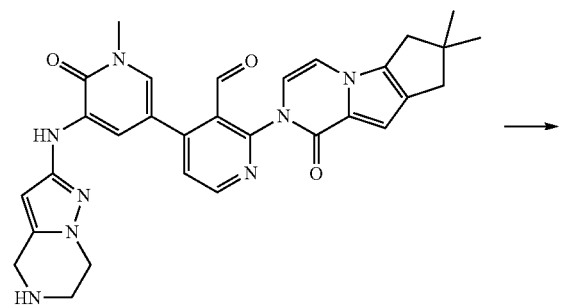 | 681.4 | $^1$H NMR (400 MHz, CD$_3$OD): δ 8.61 (s, 1H), 8.53 (d, J = 5.0 Hz, 1H), 7.96-7.85 (m, 1H), 7.57 (d, J = 5.2 Hz, 1H), 7.52-7.46 (m, 1H), 7.42-7.35(m, 1H), 7.14 (d, J = 5.7 Hz, 1H), 7.01 (d, J = 8.9 Hz, 1H), 6.69 (d, J = 5.9 Hz, 1H), 4.72-4.47 (m, 6H), 3.69 (s, 3H), 3.53-3.45 (m, 1H), 3.41-3.35 (m, 1H), 3.18-3.05 (m, 2H), 2.80-2.67 (m, 2H), 2.66-2.53 (m, 3H), 2.50-2.37 (m, 2H), 2.35-2.27 (m, 1H), 1.98-1.88 (m, 2H), 1.87-1.77 (m, 2H), 1.73-1.59 (m, 1H), 1.46-1.33 (m, 1H), 0.87-0.77 (m, 3H). | I-167 and I-91 |

Compound 68

2-(5-((5-acetyl-4,5,6,7-tetrahydropyrazolo[1,5-a]pyrazin-2-yl)amino)-3'-(hydroxymethyl)-1-methyl-6-oxo-1,6-dihydro-[3,4'-bispyridin]-2'-yl)-7,7-dimethyl-7,8-dihydro-2H-cyclopenta[4,5]pyrrolo[1,2-a]pyrazin-1(6H)-one

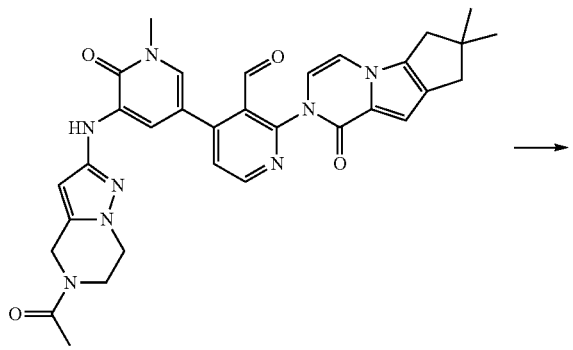

→

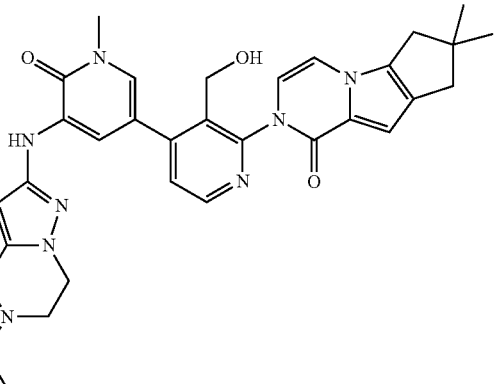

The compound 68 was prepared with compound 68a and corresponding reagents according to step 2 of intermediate I-4 and step 2 of compound 2. [M+H]+ 595.3

$^1$H NMR (400 MHz, CD$_3$OD): δ 8.55-8.50 (m, 1H), 8.07-8.01 (m, 1H), 7.58-7.54 (m, 1H), 7.43 (s, 1H), 7.24-7.19 (m, 1H), 6.93 (s, 1H), 6.81-6.74 (m, 1H), 5.98-5.91 (m, 1H), 4.77-4.70 (m, 2H), 4.62-4.52 (m, 1H), 4.51-4.40 (m, 1H), 4.10-4.07 (m, 1H), 4.06-3.93 (m, 3H), 3.68 (s, 3H), 2.78-2.70 (m, 2H), 2.64-2.59 (m, 2H), 2.21-2.16 (m, 3H), 1.30-1.27 (m, 6H).

489
Compound 69

2-(3'-(hydroxymethyl)-1-methyl-5-((5-methyl-4,5,6,7-tetrahydropyrazolo[1,5-a]pyrazin-2-yl)amino)-6-oxo-1,6-dihydro-[3,4'-bispyridin]-2'-yl)-7,7-dimethyl-7,8-dihydro-2H-cyclopenta[4,5]pyrrolo[1,2-a]pyrazin-1(6H)-one

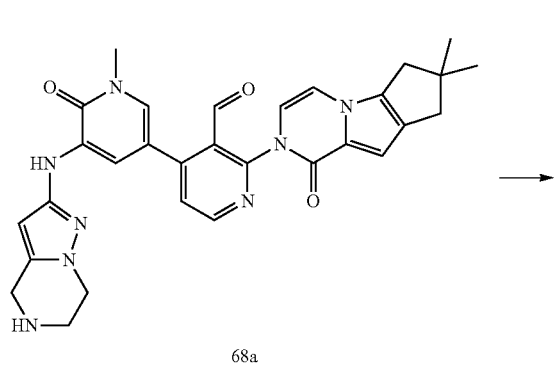

68a

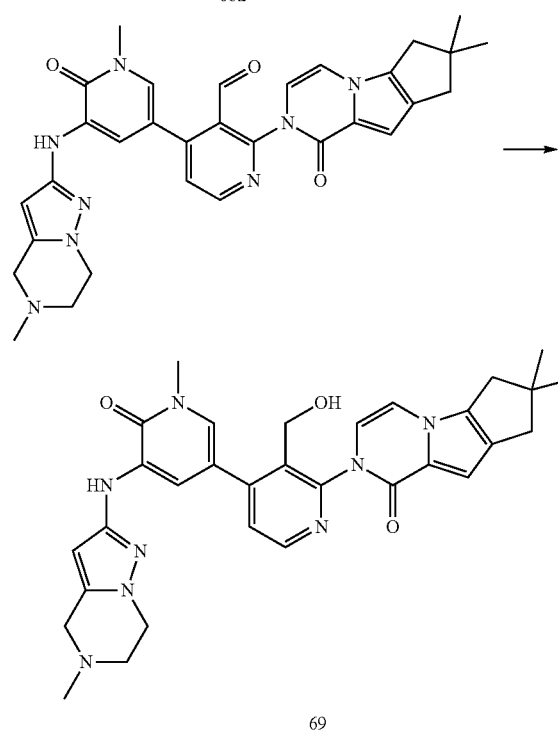

69

The compound 69 was prepared with compound 68a and corresponding reagents according to step 3 of intermediate I-2 and step 2 of compound 2. [M+H]+ 576.2

$^1$H NMR (400 MHz, CD$_3$OD): δ 8.57-8.50 (m, 1H), 8.04-7.96 (m, 1H), 7.59-7.55 (m, 1H), 7.46-7.41 (m, 1H), 7.24-7.19 (m, 1H), 6.93 (s, 1H), 6.81-6.73 (m, 1H), 5.86 (s, 1H), 4.60-4.53 (m, 1H), 4.50-4.41 (m, 1H), 4.09-3.97 (m, 2H), 3.68 (s, 3H), 3.64-3.58 (m, 2H), 2.98-2.88 (m, 2H), 2.78-2.69 (m, 2H), 2.66-2.58 (m, 2H), 2.46 (s, 3H), 1.30-1.27 (m, 6H).

490
Compound 70

2-(3'-(hydroxymethyl)-5-((5-(2-methoxymethyl)-4,5,6,7-tetrahydropyrazolo[1,5-a]pyrazin-2-yl)amino)-1-methyl-6-oxo-1,6-dihydro-[3,4'-bispyridin]-2'-yl)-7,7-dimethyl-7,8-dihydro-2H-cyclopenta[4,5]pyrrolo[1,2-a]pyrazin-1(6H)-one

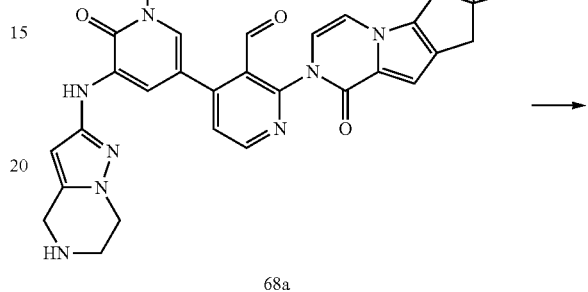

68a

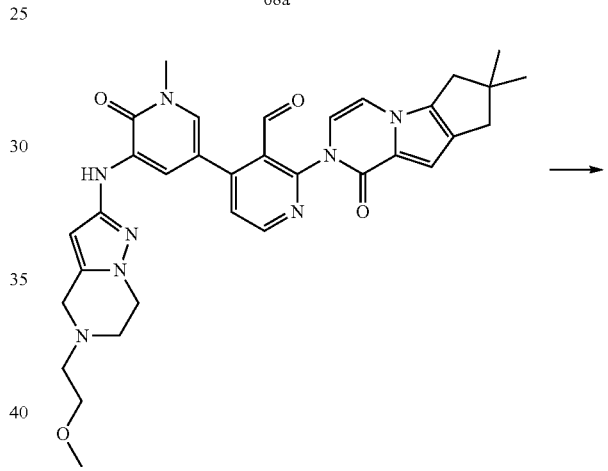

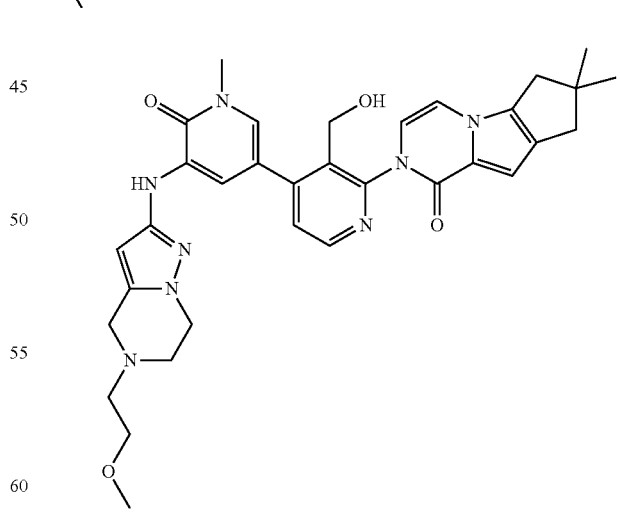

70

The compound 70 was prepared with compound 68a and corresponding reagents according to step 2 of intermediate I-10 and compound 2. [M+H]+ 611.3

¹H NMR (400 MHz, CD₃OD): δ 8.51 (d, J=5.1 Hz, 1H), 7.96 (d, J=2.2 Hz, 1H), 7.54 (d, J=5.1 Hz, 1H), 7.41 (d, J=2.2 Hz, 1H), 7.19 (d, J=5.9 Hz, 1H), 6.92 (s, 1H), 6.76 (d, J=5.9 Hz, 1H), 5.84 (s, 1H), 4.55 (d, J=12.0 Hz, 1H), 4.44 (d, J=12.0 Hz, 1H), 4.03-3.98 (m, 2H), 3.71-3.68 (m, 2H), 3.66 (s, 3H), 3.59-3.55 (m, 2H), 3.33 (s, 3H), 3.03-2.97 (m, 2H), 2.78-2.73 (m, 2H), 2.73-2.70 (m, 2H), 2.62-2.58 (m, 2H), 1.29-1.26 (m, 6H).

Compound 96

(S)-2-(3'-(hydroxymethyl)-1-methyl-5-((5-(2-methylpiperazine)-1-yl)pyridin-2-yl)amino)-6-oxo-1,6-dihydro-[3,4'-bispyridin]-2'-yl)-7,7-dimethyl-7,8-dihydro-2H-cyclopenta[4,5]pyrrolo[1,2-a]pyrazin-1(6H)-one

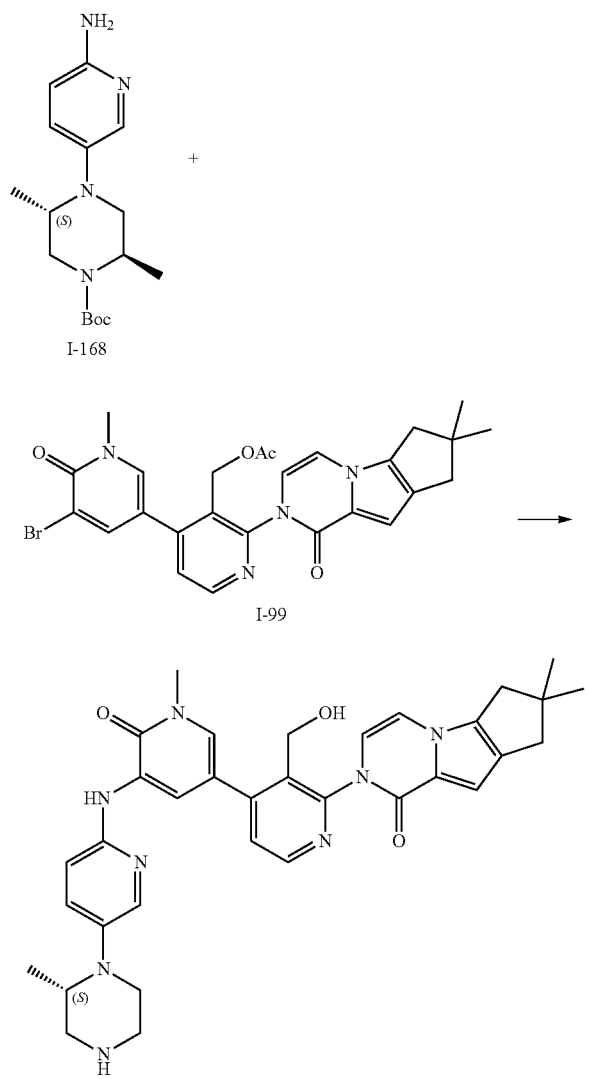

Under nitrogen, a solution of intermediate I-168 (108 mg, 0.37 mmol), intermediate I-99 (200 mg, 0.37 mmol), Pd₂(dba)₃ (37 mg, 0.04 mmol), Xant-phos (23 mg, 0.04 mmol) and cesium carbonate (241 mg, 0.74 mmol) in 1,4-dioxane (20 mL) was reacted at 100° C. for 12 hours.

The reaction solution was concentrated in vacuum under reduced pressure, potassium carbonate (276 mg, 5.0 mmol) and methanol (10 mL) were added, and the mixture was stirred at room temperature for 15 minutes. The reaction solution was concentrated in vacuum under reduced pressure, and the resulting residue was purified with silica gel column chromatography (methanol/water) to give yellow solid (120 mg, two-step yield 42%). [M+H]⁺ 707.4.

To a solution of the yellow solid in methanol (2 mL) was added concentrated hydrochloric acid, and stirred at room temperature for 30 minutes. The reaction solution was concentrated in vacuum under reduced pressure, and the resulting residue was purified with silica gel column chromatography (methanol/dichloromethane) to give compound 96 (50 mg, yield 49%). [M+H]⁺ 607.3

¹H NMR (400 MHz, CD₃OD) δ 8.67 (d, J=1.8 Hz, 1H), 8.53 (d, J=5.1 Hz, 1H), 7.94 (d, J=2.6 Hz, 1H), 7.56-7.52 (m, 2H), 7.44-7.42 (m, 1H), 7.20 (d, J=5.9 Hz, 1H), 7.01 (d, J=8.9 Hz, 1H), 6.92 (s, 1H), 6.77 (d, J=5.9 Hz, 1H), 4.55-4.41 (m, 2H), 3.68 (s, 3H), 3.38-3.32 (m, 1H), 3.07-2.86 (m, 5H), 2.77-2.55 (m, 5H), 1.29-1.27 (m, 6H), 0.90 (d, J=6.3 Hz, 3H).

The compounds in the following table were prepared with intermediate I-99 and corresponding amine intermediates and reagents according to the preparation steps of compound 96:

| Compound | Structural formula | LC-MS [M+H]+ | 1HNMR | Amine intermediate |
|---|---|---|---|---|
| 103 | | 680.3 | 1H NMR (400 MHz, CD3OD) δ 8.51 (d, J = 5.1 Hz, 1H), 7.63-7.48 (m, 3H), 7.39 (s, 1H), 7.21 (d, J = 5.9 Hz, 1H), 7.06-7.04 (m, 1H), 6.97-6.80 (m, 2H), 6.76-6.74 (m, J = 5.8, 2.5 Hz, 1H), 4.77-4.40 (m, 6H), 3.76-3.54 (m, 4H), 3.18-3.16 (m, 1H), 2.90-2.52 (m, 8H), 2.38-2.36 (m, 1H), 2.05-2.04 (m, 1H), 1.29-1.25 (m, 6H), 0.84 (d, J = 6.1 Hz, 3H). | I-169 |
| 123 | | 663.2 | 1H NMR (400 MHz, CD3OD): δ 8.84-8.78 (m, 1H), 8.55 (d, J = 5.1 Hz, 1H), 8.18 (d, J = 2.5 Hz, 1H), 7.66-7.54 (m, 3H), 7.22 (d, J = 5.9 Hz, 1H), 7.08 (d, J = 9.0 Hz, 1H), 6.93 (s, 1H), 6.78 (d, J = 6.0 Hz, 1H), 5.12-5.03 (m, 1H), 4.88-4.85 (m, 2H), 4.83-4.77 (m, 2H), 4.64-4.56 (m, 1H), 4.51-4.44 (m, 1H), 4.40-4.31 (mz, 1H), 4.00-3.92 (m, 1H), 3.70 (s, 3H), 3.39-3.33 (m, 1H), 2.78-2.70 (m, 2H), 2.64-2.58 (m, 2H), 1.29-1.25 (m, 9H). | I-170 |
| 127 | | 637.2 | 1H NMR (400 MHz, CD3OD): δ 8.75 (d, J = 2.2 Hz, 1H), 8.56 (d, J = 5.2 Hz, 1H), 8.03 (d, J = 2.6 Hz, 1H), 7.62-7.49 (m, 3H), 7.22 (d, J = 5.9 Hz, 1H), 7.04 (d, J = 8.8 Hz, 1H), 6.93 (s, 1H), 6.79 (d, J = 5.8 Hz, 1H), 4.60 (d, J = 12.0 Hz, 1H), 4.48 (d, J = 12.1 Hz, 1H), 3.70 (s, 3H), 3.51-3.45 (m, 2H), 3.08-2.92 (m, 4H), 2.77-2.69 (m, 2H), 2.63-2.55 (m, 4H), 1.28-1.27 (m, 6H), 0.84 (d, J = 6.1 Hz, 3H). | I-171 |

-continued

| Compound | Structural formula | LC-MS [M + H]+ | 1HNMR | Amine intermediate |
|---|---|---|---|---|
| 135a | | 695.3 | | Commercial |
| 179 | | 681.4 | 1H NMR (400 MHz, CD3OD) δ 8.64-8.58 (m, 1H), 8.51 (d, J = 5.1 Hz, 1H), 7.90 (d, J = 2.7 Hz, 1H), 7.55 (d, J = 5.1 Hz, 1H), 7.48 (d, J = 2.2 Hz, 1H), 7.39-7.35 (m, 1H), 7.20 (d, J = 5.9 Hz, 1H), 6.98 (d, J = 9.0 Hz, 1H), 6.92 (s, 1H), 6.77 (d, J = 5.9 Hz, 1H), 4.61-4.54 (m, 2H), 3.99-3.97 (m, 1H), 3.78-3.74 (m, 2H), 3.67 (s, 3H), 3.46-3.31 (m, 2H), 3.26-3.22 (m, 1H), 3.01-2.68 (m, 7H), 2.62-2.50 (m, 3H), 1.29-1.25 (m, 6H), 1.17-1.15 (m, 3H). | I-172 |
| 185 | | 681.2 | 1H NMR (400 MHz, CD3OD) δ 8.79-8.71 (m, 1H), 8.58-8.53 (m, 1H), 8.37-8.28 (m, 1H), 8.05-7.99 (m, 1H), 7.60-7.56 (m, 1H), 7.56-7.52 (m, 1H), 7.51-7.46 (m, 1H), 7.26-7.21 (m, 1H), 7.09-7.02 (m, 1H), 6.93 (s, 1H), 6.82-6.76 (m, 1H), 4.64-4.58 (m, 1H), 4.53-4.45 (m, 1H), 3.91-3.80 (m, 4H), 3.70 (s, 3H), 3.52-3.34 (m, 4H), 3.26-3.14 (m, 3H), 3.11-3.03 (m, 1H), 2.79-2.69 (m, 2H), 2.66-2.58 (m, 2H), 1.30-1.27 (m, 6H), 1.01-0.93 (m, 3H). | I-173 |

-continued

| Compound | Structural formula | LC-MS [M+H]+ | 1HNMR | Amine intermediate |
|---|---|---|---|---|
| 203 | | 609.2 | 1H NMR (400 MHz, CD3OD) δ 8.78-8.74 (m, 1H), 8.53-8.49 (m, 1H), 7.62-7.58 (m, 2H), 7.32-7.28 (m, 1H), 7.24-7.18 (m, 2H), 6.91 (s, 1H), 6.78-6.73 (m, 1H), 4.58-4.51 (m, 1H), 4.49-4.40 (m, 1H), 4.17-4.10 (m, 1H), 3.98-3.93 (m, 1H), 3.77-3.73 (m, 2H), 3.70-3.65 (m, 4H), 3.62-3.55 (m, 1H), 3.26-3.16 (m, 1H), 2.76-2.67 (m, 2H), 2.64-2.56 (m, 2H), 1.29-1.25 (m, 6H), 1.19-1.15 (m, 3H). | I-174 |
| 204 | | 664.2 | 1H NMR (400 MHz, CD3OD) δ 8.79 (d, J = 2.3 Hz, 1H), 8.57-8.55 (m, 1H), 7.65-7.61 (m, 2H), 7.32-7.29 (m, 2H), 7.24-7.22 (m, 1H), 6.93-6.91 (m, 1H), 6.77 (d, J = 5.9 Hz, 1H), 4.70-4.63 (m, 6H), 4.37-4.35 (m, 1H), 3.89-3.87 (m, 1H), 3.71 (s, 3H), 3.48-3.46 (m, 1H), 3.36-3.34 (m, 1H), 3.24-3.22 (m, 1H), 2.84-2.82 (m, 1H), 2.75-2.73 (m, 2H), 2.69-2.67 (m, 1H), 2.63-2.61 (m, 2H), 2.23-2.21 (m, 1H), 1.31-1.27 (m, 9H). | I-175 |
| 217 | | 678.2 | 1H NMR (400 MHz, CD3OD): δ 8.78 (d, J = 2.2 Hz, 1H), 8.55 (d, J = 5.1 Hz, 1H), 7.68-7.58 (m, 2H), 7.33-7.18 (m, 3H), 6.93 (s, 1H), 6.77 (d, J = 5.9 Hz, 1H), 4.72-4.45 (m, 6H), 4.14-4.06 (m, 1H), 4.01-3.91 (m, 1H), 3.71 (s, 3H), 3.49-3.40 (m, 1H), 3.27-3.17 (m, 1H), 2.85-2.77 (m, 2H), 2.76-2.68 (m, 2H), 2.66-2.57 (m, 2H), 2.13-2.04 (m, 1H), 2.03-1.88 (m, 2H), 1.73-1.56 (m, 1H), 1.30-1.27 (m, 6H), 0.89 (t, J = 7.4 Hz, 3H). | I-176 |

| Compound | Structural formula | LC-MS [M+H]+ | 1HNMR | Amine intermediate |
|---|---|---|---|---|
| 222 | 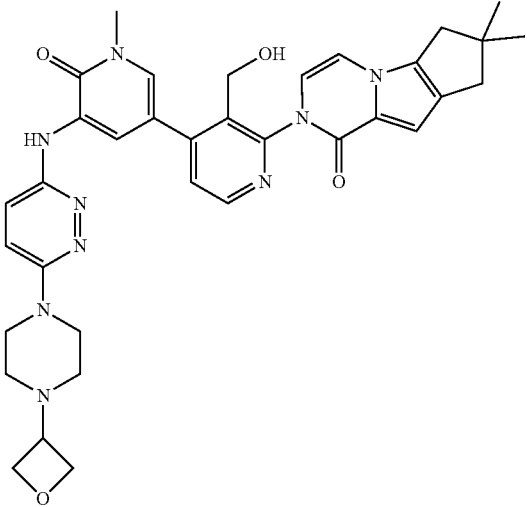 | 650.2 | 1H NMR (400 MHz, CD3OD/CDCl3 = 1/1) δ 8.82-8.76 (m, 1H), 8.57-8.50 (m, 1H), 7.69-7.63 (m, 1H), 7.63-7.57 (m, 1H), 7.27-7.20 (m, 2H), 7.16-7.10 (m, 1H), 6.95 (s, 1H), 6.75-6.68 (m, 1H), 4.73-4.69 (m, 2H), 4.66-4.61 (m, 2H), 4.57-4.51 (m, 1H), 4.46-4.45 (m, 1H), 3.71 (s, 3H), 3.57-3.49 (m, 5H), 2.77-2.67 (m, 2H), 2.65-2.57 (m, 2H), 2.52-2.42 (m, 4H), 1.30-1.26 (m, 6H). | I-177 |
| 229 | 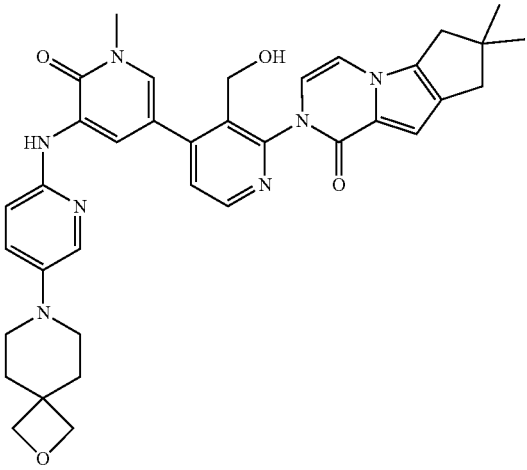 [SMILES: Cn1cc(-c2ccnc(-n3ccn4c5c(cc4c3=O)CC(C)(C)C5)c2CO)cc(Nc2ccc(N3CCC4(CC3)COC4)cn2)c1=O] | 634.3 | 1H NMR (400 MHz, CDCl3) δ 8.63 (s, 1H), 8.54 (d, J = 5.1 Hz, 1H), 7.91-7.74 (m, 3H), 7.47 (d, J = 5.0 Hz, 1H), 7.24-7.22 (m, 1H), 7.01 (s, 1H), 6.90 (d, J = 6.5 Hz, 1H), 6.78 (d, J = 8.9 Hz, 1H), 6.63 (d, J = 5.9 Hz, 1H), 5.08 (d, J = 11.3 Hz, 1H), 4.53-4.43 (m, 5H), 4.36-4.32 (m, 1H), 3.70 (s, 3H), 3.03-2.90 (m, 4H), 2.72-2.57 (m, 4H), 2.03-1.94 (m, 4H), 1.30-1.26 (s, 6H). | I-178 |
| 230 | 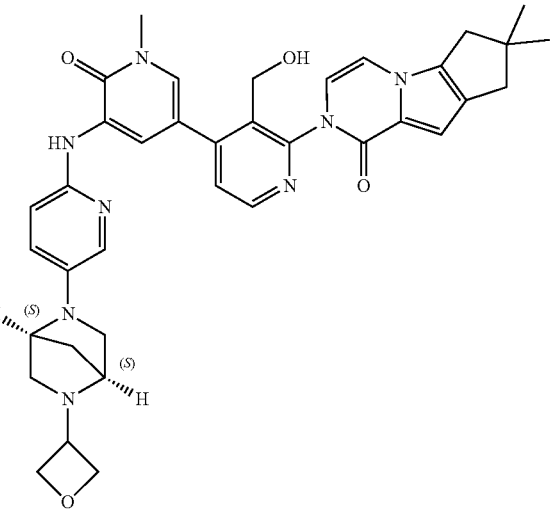 | 661.2 | 1H NMR (400 MHz, CD3OD) δ 8.57-8.50 (m, 1H), 8.46-8.40 (m, 1H), 7.66-7.60 (m, 1H), 7.60-7.55 (m, 1H), 7.49-7.43 (m, 1H), 7.24-7.19 (m, 1H), 7.09-7.02 (m, 1H), 7.03-6.96 (m, 1H), 6.93 (s, 1H), 6.80-6.74 (m, 1H), 4.69-4.63 (m, 2H), 4.62-4.55 (m, 1H), 4.52-4.44 (m, 2H), 4.41-4.36 (m, 1H), 4.31 (s, 1H), 3.98-3.86 (m, 1H), 3.69 (s, 3H), 3.54 (s, 1H), 3.44-3.38 (m, 1H), 3.09-2.97 (m, 1H), 2.86-2.78 (m, 2H), 2.76-2.69 (m, 2H), 2.65-2.58 (m, 2H), 1.98-1.83 (m, 2H), 1.29-1.27 (m, 6H). | I-179 |

-continued

| Compound | Structural formula | LC-MS [M+H]+ | 1HNMR | Amine intermediate |
|---|---|---|---|---|
| 231 | | 675.3 | 1H NMR (400 MHz, CD3OD) δ 8.57-8.53 (m, 2H), 8.01 (d, J = 2.9 Hz, 1H), 7.58 (d, J = 5.1 Hz, 1H), 7.49 (d, J = 2.3 Hz, 1H), 7.40-7.36 (m, 1H), 7.22 (d, J = 5.9 Hz, 1H), 7.00-6.90 (m, 2H), 6.77 (d, J = 5.8 Hz, 1H), 4.64-4.45 (m, 6H), 3.74-3.61 (m, 5H), 3.43-3.41 (m, 1H), 2.79-2.57 (m, 4H), 2.51-2.13 (m, 4H), 1.30-1.26 (m, 6H), 0.94-0.72 (m, 4H). | I-180 |
| 232 | | 649.4 | 1H NMR (400 MHz, CD3OD) δ 8.65-8.60 (m, 1H), 8.57-8.51 (m, 1H), 7.93-7.86 (m, 1H), 7.60-7.55 (m, 1H), 7.53-7.46 (m, 1H), 7.41-7.35 (m, 1H), 7.24-7.18 (m, 1H), 7.03-6.96 (m, 1H), 6.93 (s, 1H), 6.82-6.75 (m, 1H), 4.63-4.56 (m, 1H), 4.51-4.44 (m, 1H), 3.87-3.81 (m, 1H), 3.79-3.74 (m, 1H), 3.69 (s, 3H), 3.68-3.62 (m, 1H), 3.51-3.44 (m, 1H), 3.35-3.32 (m, 1H), 3.29-3.24 (m, 1H), 2.91-2.81 (m, 2H), 2.78-2.69 (m, 3H), 2.66-2.58 (m, 2H), 2.50-2.33 (m, 4H), 1.30-1.27 (m, 6H). | I-181 |
| 233 | | 648.4 | 1H NMR (400 MHz, CD3OD) δ 8.65 (d, J = 2.2 Hz, 1H), 8.61-8.55 (m, 1H), 7.99-7.92 (m, 1H), 7.66-7.58 (m, 1H), 7.54 (d, J = 2.2 Hz, 1H), 7.47-7.39 (m, 1H), 7.30-7.22 (m, 1H), 7.07-7.01 (m, 1H), 6.97 (s, 1H), 6.86-6.78 (m, 1H), 4.64 (d, J = 12.0 Hz, 1H), 4.52 (d, J = 12.0 Hz, 1H), 3.99-3.83 (m, 2H), 3.73 (s, 3H), 3.62-3.60 (m, 2H), 3.18-3.01 (m, 4H), 2.83-2.57 (m, 4H), 1.88-1.83 (m, 2H), 1.81-1.74 (m, 4H), 1.34-1.31 (m, 6H). | I-182 |

-continued

| Compound | Structural formula | LC-MS [M+H]+ | 1HNMR | Amine intermediate |
|---|---|---|---|---|
| 234 | | 677.4 | 1H NMR (400 MHz, CD3OD) δ 8.58 (d, J = 2.3 Hz, 1H), 8.51 (d, J = 5.1 Hz, 1H), 7.82 (d, J = 2.7 Hz, 1H), 7.55 (d, J = 5.1 Hz, 1H), 7.47 (d, J = 2.2 Hz, 1H), 7.33-7.29 (m, 1H), 7.18 (d, J = 5.9 Hz, 1H), 6.98 (d, J = 9.0 Hz, 1H), 6.92 (s, 1H), 6.76 (d, J = 5.9 Hz, 1H), 4.74-4.43 (m, 6H), 3.74-3.53 (m, 5H), 3.16-3.00 (m, 2H), 2.78-2.47 (m, 6H), 2.10-2.06 (m, 1H), 1.29-1.25 (m, 6H), 0.92-0.88 (m, 6H). | I-183 |
| 235 | | 661.3 | 1H NMR (400 MHz, CD3OD) δ 8.58-8.49 (m, 2H), 7.61-7.52 (m, 2H), 7.50-7.45 (m, 1H), 7.24-7.18 (m, 1H), 7.03-6.94 (m, 2H), 6.92 (s, 1H), 6.80-6.74 (m, 1H), 4.61-4.41 (m, 6H), 4.34-4.24 (m, 2H), 3.75-3.67 (m, 4H), 3.20-3.15 (m, 2H), 2.96-2.83 (m, 2H), 2.78-2.68 (m, 2H), 2.68-2.56 (m, 3H), 2.10-2.02 (m, 1H), 1.29-1.27 (m, 6H). | I-184 |
| 236 | | 663.3 | 1H NMR (400 MHz, CD3OD) δ 8.62-8.46 (m, 2H), 7.86-7.76 (m, 1H), 7.61-7.54 (m, 1H), 7.52-7.44 (m, 1H), 7.36-7.28 (m, 1H), 7.25-2.17 (m, 1H), 7.06-6.96 (m, 1H), 6.96-6.87 (m, 1H), 6.83-6.71 (m, 1H), 4.62-4.57 (m, 1H), 4.52-4.44 (m, 1H), 4.02-3.91 (m, 1H), 3.85-3.66 (m, 6H), 3.38-3.33 (m, 1H), 3.09-2.97 (m, 1H), 2.76-2.53 (m, 8H), 2.35-2.18 (m, 2H), 1.28 (s, 6H), 1.09 (s, 3H). | I-185 |

Compound 98

2-(5-amino-3'-(hydroxymethyl)-1-methyl-6-oxo-1,6-dihydro-[3,4'-bispyridin]-2'-yl)-7,7-dimethyl-7,8-dihydro-2H-cyclopenta[4,5]pyrrolo[1,2-a]pyrazin-1(6H)-one

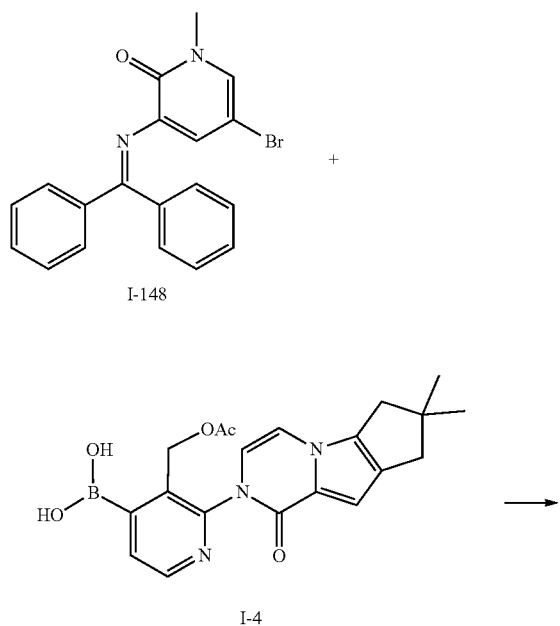

Under nitrogen, a solution of intermediate I-148 (220 mg, 0.60 mmol), intermediate I-4 (237 mg, 0.60 mmol), Pd(dppf)Cl$_2$ CH$_2$Cl$_2$ (49 mg, 0.06 mmol), Xphos(57 mg, 0.12 mmol) and potassium phosphate trihydrate (479 mg, 1.80 mmol) in 1,4-dioxane (10 mL) and water (1 mL) was reacted at 100° C. for 4 hours. The reaction solution was concentrated in vacuum under reduced pressure, and the resulting residue was purified with silica gel column chromatography (methanol/water) to give yellow solid (268 mg, yield 70%). [M+H]$^+$ 638.3.

To a solution of the yellow solid in methanol (5 mL) was added trifluoroacetic acid (2 mL), and stirred at room temperature for 2 hours. The reaction solution was concentrated in vacuum under reduced pressure, and potassium carbonate (174 mg, 1.26 mmol) and methanol (5 mL) were added to the resulting residue, and the mixture was stirred at room temperature for 15 minutes. The reaction solution was concentrated in vacuum under reduced pressure, and purified with silica gel column chromatography (methanol/water) to give compound 98 (48 mg, yield 26%). [M+H]$^+$ 432.2

$^1$H NMR (400 MHz, CD$_3$OD) δ 8.55-8.48 (m, 1H), 7.52-7.48 (m, 1H), 7.36-7.30 (m, 1H), 7.24-7.20 (m, 1H), 6.95-6.91 (m, 1H), 6.91-6.86 (m, 1H), 6.78-6.72 (m, 1H), 4.55-4.49 (m, 1H), 4.47-4.41 (m, 1H), 3.64 (s, 3H), 2.79-2.68 (m, 2H), 2.66-2.56 (m, 2H), 1.30-1.27 (m, 6H).

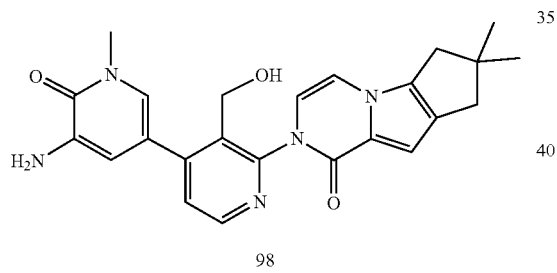

Compounds 119 and 120

2-(3'-(hydroxymethyl)-5-((5-(2-methoxyethyl)-4-methyl-4,5,6,7-tetrahydropyrazolo[1,5-a]pyrazin-2-yl)amido)-1-methyl-6-oxo-1,6-dihydro-[3,4'-bispyridin]-2'-yl)-7,7-dimethyl-7,8-dihydro-2H-cyclopenta[4,5]pyrrolo[1,2-d][1,2,4]triazin-1(6H)-one optically Pure

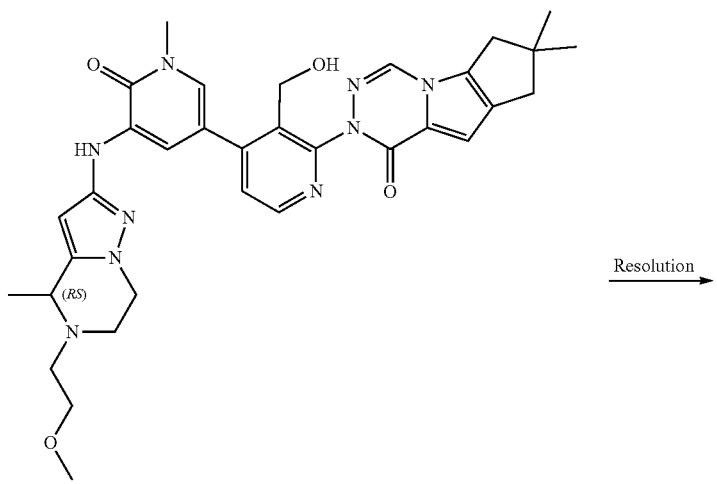

Resolution →

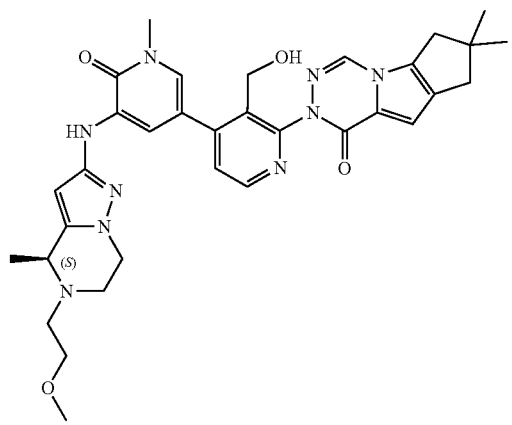

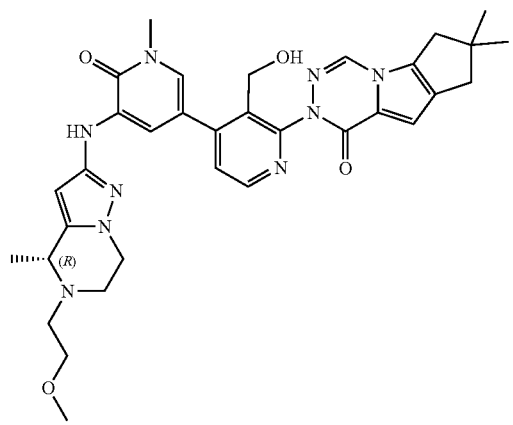

119 & 120

(RS)-2-(3'-(hydroxymethyl)-5-((5-(2-methoxyethyl)-4-methyl-4,5,6,7-tetrahydropyrazolo[1,5-a]pyrazin-2-yl)amido)-1-methyl-6-oxo-1,6-dihydro-[3,4'-bispyridin]-2'-yl)-7,7-dimethyl-7,8-dihydro-2H-cyclopenta[4,5]pyrrolo[1,2-d][1,2,4]triazin-1(6H)-one (compound 110, 110 mg) was resolved by chiral HPLC to give a pair of optically pure enantiomers, (R)-2-(3'-(hydroxymethyl)-5-((5-(2-methoxyethyl)-4-methyl-4,5,6,7-tetrahydropyrazolo[1,5-a]pyrazin-2-yl)amido)-1-methyl-6-oxo-1,6-dihydro-[3,4'-bispyridin]-2'-yl)-7,7-dimethyl-7,8-dihydro-2H-cyclopenta[4,5]pyrrolo[1,2-d][1,2,4]triazin-1(6H)-one and (S)-2-(3'-(hydroxymethyl)-5-((5-(2-methoxyethyl)-4-methyl-4,5,6,7-tetrahydropyrazolo[1,5-a]pyrazin-2-yl)amido)-1-methyl-6-oxo-1,6-dihydro-[3,4'-bispyridin]-2'-yl)-7,7-dimethyl-7,8-dihydro-2H-cyclopenta[4,5]pyrrolo[1,2-d][1,2,4]triazin-1(6H)-one. Chiral HPLC resolution conditions: column: AD-H (0.46 cm I.D.×15 cm L); Mobile phase: $CO_2$/ethanol=60:40; Flow rate: 2.5 mL; Detector wavelength: UV 254 nm).

Under the above conditions, the compound obtained after removing the solvent from the first eluent obtained was named compound 119 (40 mg, yield 36%), ee %=100%, MS (m/z): 626.3 [M+H]$^+$. $^1$H NMR (400 MHz, CD$_3$OD) δ 8.57-8.51 (m, 1H), 8.43-8.38 (m, 1H), 7.97-7.91 (m, 1H), 7.60-7.57 (m, 1H), 7.41-7.38 (m, 1H), 7.07-7.01 (m, 1H), 5.93-5.89 (m, 1H), 4.60-4.51 (m, 2H), 4.04-3.91 (m, 2H), 3.83-3.76 (m, 1H), 3.68 (s, 3H), 3.60-3.53 (m, 2H), 3.40-3.35 (m, 1H), 2.99-2.87 (m, 2H), 2.86-2.81 (m, 2H), 2.73-2.62 (m, 3H), 1.43-1.39 (m, 3H), 1.31 (s, 6H).

Under the above conditions, the compound obtained after removing the solvent from the second eluent obtained was named compound 120 (42 mg, yield 38%), ee %=99.68%, MS (m/z): 626.3 [M+H]$^+$. $^1$H NMR (400 MHz, CD$_3$OD) δ 8.56-8.52 (m, 1H), 8.42-8.38 (m, 1H), 7.95-7.92 (m, 1H), 7.60-7.57 (m, 1H), 7.41-7.38 (m, 1H), 7.06-7.02 (m, 1H), 5.93-5.89 (m, 1H), 4.60-4.49 (m, 2H), 4.03-3.93 (m, 2H), 3.82-3.76 (m, 1H), 3.68 (s, 3H), 3.59-3.52 (m, 2H), 3.40-3.34 (m, 1H), 2.99-2.87 (m, 2H), 2.86-2.81 (s, 2H), 2.73-2.62 (m, 3H), 1.43-1.39 (m, 3H), 1.30 (s, 6H).

| Compound | Structural formula | LC-MS [M + H]$^+$ | $^1$H NMR | Original compound |
|---|---|---|---|---|
| 116 | | 625.3 | $^1$H NMR (400 MHz, CD$_3$OD) δ 8.53 (d, J = 5.1 Hz, 1H), 7.97-7.95 (m, 1H), 7.56 (d, J = 5.1 Hz, 1H), 7.42 (d, J = 2.2 Hz, 1H), 7.21 (d, J = 5.9 Hz, 1H), 6.92 (s, 1H), 6.76 (d, J = 5.9 Hz, 1H), 5.90 (s, 1H), 4.60-4.39 (m, 2H), 4.01-3.97 (m, 2H), 3.79 (q, J = 6.6 Hz, 1H), 3.67 (s, 3H), 3.61-3.52 (m, 2H), 3.39-3.32 (m, 4H), 2.94-2.90 (m, 2H), 2.79-2.53 (m, 5H), 1.40 (d, J = 6.5 Hz, 3H), 1.30-1.26 (m, 6H). | 111 |

+

-continued

| Compound | Structural formula | LC-MS [M+H]+ | 1H NMR | Original compound |
|---|---|---|---|---|
| 117 | | 625.3 | 1H NMR (400 MHz, CD3OD) δ 8.52 (d, J = 5.1 Hz, 1H), 7.97-7.95 (m, 1H), 7.56 (d, J = 5.1 Hz, 1H), 7.41 (d, J = 2.1 Hz, 1H), 7.21 (d, J = 5.9 Hz, 1H), 6.92 (s, 1H), 6.76 (d, J = 5.9 Hz, 1H), 5.90 (s, 1H), 4.62-4.39 (m, 2H), 4.06-3.89 (m, 2H), 3.78 (q, J = 6.6 Hz, 1H), 3.67 (s, 3H), 3.60-3.48 (m, 2H), 3.42-3.32 (m, 4H), 3.00-2.84 (m, 2H), 2.79-2.54 (m, 5H), 1.40 (d, J = 6.5 Hz, 3H), 1.30-1.26 (m, 6H). | |
| 136 | | 623.2 | 1H NMR (400 MHz, CD3OD) δ 8.50 (d, J = 5.1 Hz, 1H), 7.97 (t, J = 2.4 Hz, 1H), 7.53 (d, J = 5.1 Hz, 1H), 7.40 (d, J = 2.2 Hz, 1H), 7.19 (d, J = 6.4 Hz, 1H), 6.91 (s, 1H), 6.75 (d, J = 5.8 Hz, 1H), 5.88 (s, 1H), 4.72-4.39 (m, 6H), 4.03-3.90 (m, 3H), 3.78-3.76 (m, 1H), 3.65 (s, 3H), 3.19-3.08 (m, 1H), 2.84-2.51 (m, 5H), 1.28-1.24 (m, 9H). | 112 |
| 137 | | 623.2 | 1H NMR (400 MHz, CD3OD) δ 8.53 (d, J = 5.2 Hz, 1H), 8.02-7.96 (m, 1H), 7.57 (d, J = 5.1 Hz, 1H), 7.41 (d, J = 6.4 Hz, 1H), 7.25-7.18 (m, 1H), 6.92 (s, 1H), 6.76 (d, J = 5.9 Hz, 1H), 5.90 (s, 1H), 4.70-4.48 (m, 6H), 4.05-3.95 (m, 3H), 3.83-3.79 (m, 1H), 3.68 (s, 3H), 3.21-3.17 (m, 1H), 2.84-2.60 (m, 5H), 1.32-1.24 (m, 9H). | |

| Compound | Structural formula | LC-MS [M+H]+ | 1H NMR | Original compound |
|---|---|---|---|---|
| 198 | | 679.3 | 1H NMR (400 MHz, CD3OD): δ 8.69 (t, J = 2.4 Hz, 1H), 8.56 (dd, J = 5.1, 1.2 Hz, 1H), 7.97 (d, J = 2.5 Hz, 1H), 7.59 (d, J = 5.1 Hz, 1H), 7.55-7.51 (m, 1H), 7.47 (dd, J = 8.9, 2.8 Hz, 1H), 7.39 (d, J = 6.0 Hz, 1H), 7.04 (d, J = 8.9 Hz, 1H), 6.91 (s, 1H), 6.83 (dd, J = 5.9, 2.1 Hz, 1H), 4.76-4.46 (m, 7H), 3.78-3.63(m, 4H), 3.55-3.44 (m, 1H), 3.17-3.07 (m, 2H), 2.92-2.55 (m, 4H), 2.54-2.46 (m, 1H), 2.44-2.25 (m, 1H), 1.23-1.17 (m, 6H), 0.97 (d, J = 6.3 Hz, 3H). | 183 |
| 199 | | 679.3 | 1H NMR (400 MHz, CD3OD): δ 8.67 (t, J = 2.1 Hz, 1H), 8.55 (dd, J = 5.1, 1.7 Hz, 1H), 7.95 (d, J = 2.7 Hz, 1H), 7.59 (d, J = 5.2 Hz, 1H), 7.51 (dd, J = 3.8, 2.3 Hz, 1H), 7.44 (dd, J = 8.9, 2.9 Hz, 1H), 7.39 (d, J = 5.9 Hz, 1H), 7.03 (d, J = 8.9 Hz, 1H), 6.91 (s, 1H), 6.83 (dd, J = 5.9, 2.1 Hz, 1H), 4.77-4.46 (m, 7H), 3.76-3.65 (m, 3H), 3.56-3.44 (m, 2H), 3.13-3.00 (m, 2H), 2.76-2.39 (m, 5H), 2.26-2.14 (m, 1H), 1.24-1.18 (m, 6H), 0.97 (d, J = 6.3 Hz, 3H). | |

The optically pure enantiomeric/diastereomeric compounds in the above table were obtained by chiral HPLC resolution. The resolution conditions were: flow rate: 2.5 mL, detector wavelength: UV 254 nm; the chiral column and mobile phase used, and the ee(de) values of the obtained compounds were shown in the table below (wherein in each pair of enantiomeric compounds, the earlier numbered compounds were the compounds obtained after removing the solvent from the first eluent obtained from the chiral column, and the later numbered compounds were the compounds obtained after removing the solvent from the second eluent obtained from the chiral column):

| Compound | Column | Mobile phase | ee(de) % |
|---|---|---|---|
| 116 | AD-H (0.46 cm I.D. × 15 cm L) | $CO_2$/ethanol (0.1% DEA) = 60:40 | 100% |
| 117 | | | 99.76% |
| 136 | AS-H (0.46 cm I.D. × 15 cm L) | $CO_2$/isopropyl alcohol (0.1% DEA) = 60:40 | 100% |
| 137 | | | 98.50% |
| 198 | AD-H (0.46 cm I.D. × 15 cm L) | $CO_2$/isopropyl alcohol (0.1% DEA) = 50:50 | 99.38% |
| 199 | | | 98.42% |

Compound 135

2-((2'-(7,7-dimethyl-1-oxo-1,6,7,8-tetrahydro-2H-cyclopenta[4,5]pyrrolo[1,2-a]pyrazin-2-yl)-3'-(hydroxymethyl)-1-methyl-6-oxo-1,6-dihydro-[3,4'-bispyridin]-5-yl)amino)-6,7-dihydropyrazolo[1,5-a]pyrazin-5(4H)-nitrile

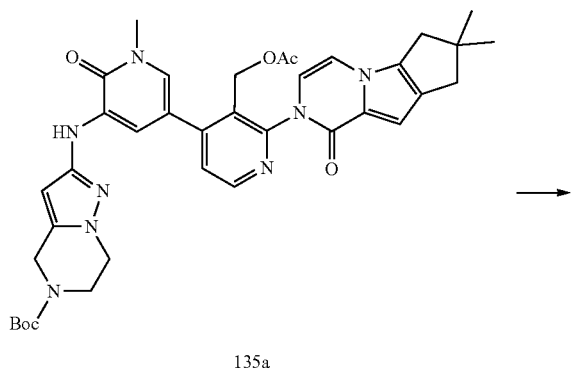

135a

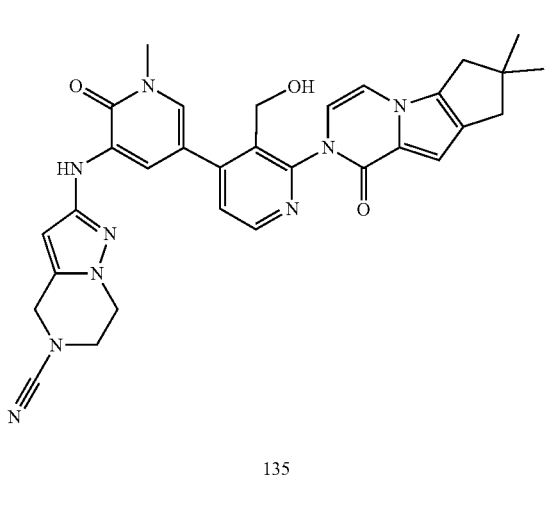

135

To a solution of compound 135a (250 mg, 0.36 mmol) in methanol (5 mL) was added concentrated hydrochloric acid (2 mL), and stirred at 50° C. for 30 minutes. The reaction solution was concentrated in vacuum under reduced pressure, acetonitrile (20 mL), potassium carbonate (150 mg, 1.08 mmol) and cyanogen bromide (45 mg, 0.43 mmol) were added to the reaction solution, and the mixture was stirred at room temperature for 1 hour. The reaction solution was poured into water, and extracted with dichloromethane, the organic phase was collected, and concentrated in vacuum under reduced pressure, and the resulting residue was purified with silica gel column chromatography (methanol/water) to give compound 135 (60 mg, yield 29%). [M+H]$^+$ 578.3

$^1$H NMR (400 MHz, CD$_3$OD) δ8.49 (d, J=5.1 Hz, 1H), 8.05 (d, J=1.8 Hz, 1H), 7.51 (d, J=7.2 Hz, 1H), 7.41 (d, J=1.8 Hz, 1H), 7.18 (d, J=5.9 Hz, 1H), 6.90 (s, 1H), 6.75 (d, J=5.9 Hz, 1H), 5.89 (s, 1H), 4.57-4.37 (m, 4H), 4.10 (t, J=5.3 Hz, 2H), 3.77-3.58 (m, 5H), 2.78-2.53 (m, 4H), 1.28-1.24 (m, 6H).

The compounds in the following table were prepared with corresponding intermediates and reagents according to the preparation steps of compound 135:

| Compound | Structural formula | LC-MS [M + H]$^+$ | $^1$HNMR | Intermediate |
|---|---|---|---|---|
| 142 | | 550.2 | $^1$H NMR (400 MHz, CD$_3$OD/CDCl$_3$ = 1/2) δ 8.60-8.56 (m, 1H), 8.05-8.01 (m, 1H), 7.62-7.61 (m, 1H), 7.56-7.53 (m, 1H), 7.10-7.06 (m, 1H), 7.06-7.03 (m, 1H), 6.71-6.65 (m, 1H), 5.94-5.88 (m, 1H), 4.54-4.52 (m, 2H), 4.45-4.41 (m, 2H), 4.25-4.17 (m, 2H), 3.78-3.72 (m, 5H), 2.95-2.89 (m, 2H), 2.86-2.80 (m, 2H), 2.64-2.55 (m, 2H). | I-187 and I-129 |

| Compound | Structural formula | LC-MS [M + H]+ | 1HNMR | Intermediate |
|---|---|---|---|---|
| 143 | | 579.3 | 1H NMR (400 MHz, CD3OD/CDCl3 = 2/1) δ 8.60-8.55 (m, 1H), 8.34-8.31 (m, 1H), 8.06-8.02 (m, 1H), 7.59-7.56 (m, 1H), 7.48-7.45 (m, 1H), 7.11-7.08 (m, 1H), 5.98-5.93 (m, 1H), 4.58-4.52 (m, 4H), 4.21-4.16 (m, 2H), 3.78-3.74 (m, 2H), 3.72 (s, 3H), 2.86-2.84 (m, 2H), 2.69-2.65 (m, 2H), 1.34 (s, 6H). | I-187 and I-114 |

Compound 223

(S)-2-(3'-(methoxymethyl)-1-methyl-5-(methyl(5-(2-methyl-4-(oxetan-3-yl)piperazin-1-yl)pyridin-2-yl)amino)-6-oxo-1,6-dihydro-[3,4'-bispyridin]-2'-yl)-7,7-dimethyl-7,8-dihydro-2H-cyclopenta[4,5]pyrrolo[1,2-a]pyrazin-1(6H)-one

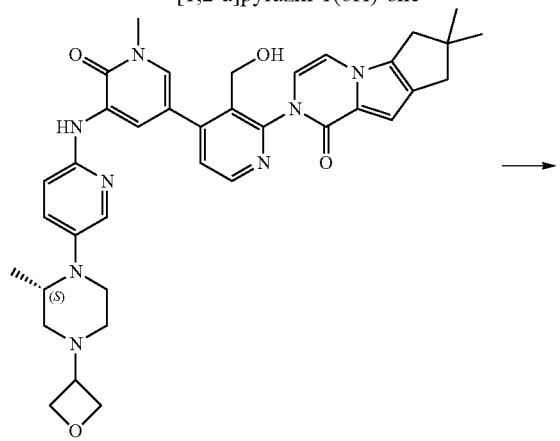

At 0-5° C., to a solution of compound 19 (100 mg, 0.15 mmol) in DMF(10 mL) was added 60% NaH (38 mg, 0.95 mmol), and stirred at this temperature for 30 minutes. Iodomethane (123 mg, 0.87 mmol) was further added, and the reaction solution was reacted at room temperature for 30 minutes. The reaction solution was poured into water, and extracted with ethyl acetate, the organic phase was collected, and concentrated in vacuum under reduced pressure, and the resulting residue was purified with silica gel column chromatography (methanol/water) to give compound 223 (18 mg, yield 7%). [M+H]+ 691.2.

1H NMR (400 MHz, CD3OD) δ 8.61-8.54 (m, 1H), 7.96-7.89 (m, 1H), 7.85-7.79 (m, 1H), 7.78-7.71 (m, 1H), 7.62-7.56 (m, 1H), 7.47-7.39 (m, 1H), 7.24-7.17 (m, 1H), 6.91 (s, 1H), 6.77-6.66 (m, 2H), 4.72-4.67 (m, 2H), 4.64-4.58 (m, 3H), 4.42-4.35 (m, 1H), 4.27-4.19 (m, 1H), 3.68 (s, 3H), 3.54-3.47 (m, 1H), 3.34 (s, 3H), 3.14 (s, 3H), 3.07-2.96 (m, 2H), 2.78-2.71 (m, 2H), 2.67-2.59 (m, 3H), 2.59-2.51 (m, 1H), 2.43-2.34 (m, 1H), 2.14-2.05 (m, 1H), 1.29 (s, 6H), 0.93-0.90 (m, 3H).

Compound 228

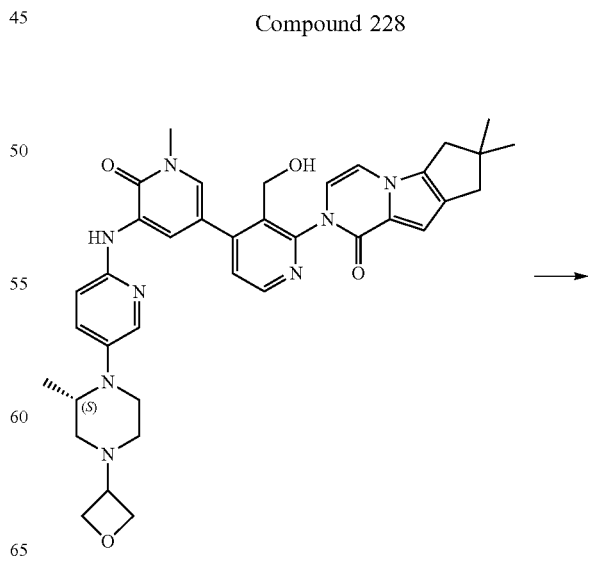

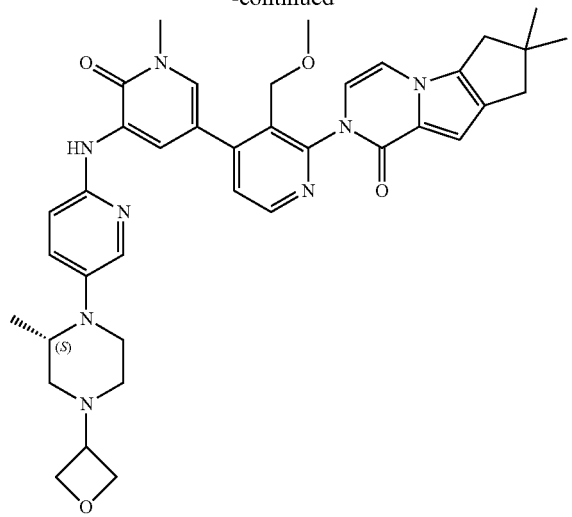

228

At 0-5° C., to a solution of compound 19 (200 mg, 0.30 mmol) in DMF(10 mL) was added 60% NaH (38 mg, 0.95 mmol), and stirred at this temperature for 30 minutes. Iodomethane (111 mg, 0.78 mmol) was further added, and the reaction solution was reacted at room temperature for 30 minutes. The reaction solution was poured into water, and extracted with ethyl acetate, the organic phase was collected, and concentrated in vacuum under reduced pressure, and the resulting residue was purified with silica gel column chromatography (methanol/water) to give compound 228 (45 mg, yield 9%). [M+H]$^+$ 677.3.

$^1$H NMR (400 MHz, CD$_3$OD) δ 8.74-8.68 (m, 1H), 8.55-8.49 (m, 1H), 7.98-7.89 (m, 1H), 7.57-7.51 (m, 1H), 7.43-7.39 (m, 1H), 7.37-7.32 (m, 1H), 7.22-7.14 (m, 1H), 7.01-6.95 (m, 1H), 6.91 (s, 1H), 6.79-6.71 (m, 1H), 4.70-4.65 (m, 2H), 4.63-4.55 (m, 2H), 4.42-4.34 (m, 1H), 4.28-4.21 (m, 1H), 3.68 (s, 3H), 3.51-3.44 (m, 2H), 3.11 (s, 3H), 3.09-2.98 (m, 2H), 2.76-2.69 (m, 2H), 2.63-2.58 (m, 2H), 2.56-2.50 (m, 1H), 2.49-2.38 (m, 2H), 2.23-2.15 (m, 1H), 1.27 (s, 6H), 0.97-0.91 (m, 3H).

Example 2 Determination of Biochemical BTK

1. Reagents and Materials

BTK recombinant protein: Invitrogen, Cat #PV3363;
Z'-LYTE® kinase test kit-tyrosine 1 peptide: Invitrogen, Cat #PV3190;
384-well low-flange black flat-bottomed polystyrene NBS microplate, no lid, no sterilization: Corning, Cat #3575;
96-well polystyrene conical-bottomed MicroWell™ plate, sealed with a lid: Thermo Scientific™ Nunc™, Cat #277143;
Envision multi-mode plate reader: PerkinElmer;
Mixmate® shaker: Eppendorf;
TS-2102 shaking incubator: TENSUC;

2. Methods

Z'-LYTE® biochemical assay employs a fluorescence resonance energy transfer (FRET)—based, coupled-enzyme format and is based on the differential sensitivity of phosphorylated and non-phosphorylated peptides to proteolytic cleavage. Both ends of the short peptide substrate are labeled with two fluorescent groups to form a FRET paired combination. In the primary reaction (the Kinase Reaction), the kinase transfers the γ-phosphate of ATP to a single serine or threonine residue on the short peptide substrate. In the secondary reaction (the development reaction), the non-phosphorylated short peptides were recognized and cleaved by a site-specific protease (the development reagent). Phosphorylated short peptides can resist such cleavage. Cleavage of short peptides can disrupt the donor (such as coumarin) and receptor fluorophores (fluorescein) on the short peptides, while the phosphorylated short peptides can maintain FRET. The calculation method of the ratio is as follows, and the ratio of the respective emission signals generated by the donor fluorophores emitted (after excitation at 400 nm) to the receptors is calculated. Emission signal ratio=emitted light by coumarin (445 nm)/emitted light by fluorescein (520 nm). If the FRET short peptide is phosphorylated (such as no kinase inhibitor), the emitted light ratio will remain in a lower level. If the FRET short peptide is non-phosphorylated (such as kinase inhibitor), the emitted light ratio will be in a higher level. In this way, the inhibitory effects of different compound inhibitors on BTK kinase activity would be distinguished.

The experiment were carried out according to the instructions of the Z'-LYTE® kinase test kit-tyrosine 1 peptide. Reagent preparation: 1.33× kinase buffer: 5× kinase buffer was diluted with water to 1.33× kinase buffer; an enzyme solution: the kinase was dissolved in 1.33× kinase buffer with the final working concentration being 3.32 nM; a short peptide solution: a short peptide stock solution (1 mM dissolved in DMSO) was dissolved in 1.33× kinase buffer with the final working concentration being 2 μM; Z'-LYTE Tyr01 phosphorylated short peptide solution, 0.6 μl of stock solution (1 mM dissolved in DMSO) was dissolved in 149.4 μl of 1.33× kinase buffer; an ATP solution: an ATP stock solution (10 mM aqueous solution) was dissolved in 1.33× kinase buffer with the final working concentration being 32 μM; a color-developing solution: color-developing solution B was dissolved in color-developing buffer with the final working concentration being 1× color-developing solution; 4× compound preparation: the compound was diluted in 3-fold gradient concentration to finally obtain 4% DMSO aqueous solution containing different concentrations of the compound, with the final working concentration being 3000, 1000, 333.33, 111.11, 37.04, 12.35, 4.12, 1.37 nM, 8 concentration points in total.

Specific steps of the experiment: In the experiment, there were three control groups, each with 8 replicate wells, which were C1 100% inhibition group (no ATP), C2 0% inhibition group (with ATP), and C3 100% phosphorylation group, respectively. 2.5 μl of serially diluted compound was added to each well of a 384-well plate, with double replicate wells, and 4% DMSO solution was added to wells C1, C2, and C3. After that, except for wells C3, 2.5 μl of BTK enzyme solution was added to each remaining well, which was left to stand at 4° C. for 30 minutes. After that, except for wells C3, 2.5 μl of short peptide solution was added to each well, and 5 μl of phosphorylated short peptide solution was added to each of wells C3. 2.5 μl of 1.33× kinase buffer was added to each of wells C1 and C3, and 2.5 μl of ATP solution was added to each of the remaining wells. The wells were centrifuged transiently, and the plate was shaken at 1000 rpm for 30 seconds to perform transient centrifuge. The 384-well plate was placed in a shaking incubator protected from light and incubated at room temperature for 1 hour. After the enzymatic reaction was completed, 5 μl of development solution was added to each well, which was centrifuged transiently, and the plate was shaken at 1000 rpm for 30 seconds to perform transient centrifuge. The 384-well plate was placed in a shaking incubator protected from light and incubated at room temperature for 1 hour until the color-developing reaction was completed.

3. Detection

After the development reaction was completed, the 384-well plate was taken out to perform plate reading using the Envision multi-mode plate reader, and the optical signal was detected at the emission wavelength of 405 nm and the excitation wavelength of 460 nm/535 nm. The reading value at 460 nm/535 nm of each well was used as the signal value of each well.

4. Calculation

The average signal value of C3 was regarded as 100% phosphorylation, the average signal value of C1 was regarded as 0% phosphorylation, and the average signal value of C2 was used to calculate the phosphorylation ratio of short peptides in the presence of BTK kinase. According to the signal value in each well, the inhibition ratio (%) of each concentration of compounds was calculated, and the 205 model in XL-Fit 5.3 software (ID Business Solutions Limited) was used to obtain an $IC_{50}$ value.

The phosphorylation ratio is calculated as follows:

Phosphorylation ratio (%)=100-100×[(emission signal ratio×$F_{100\%}$)−$C_{100\%}$]/{($C_{0\%}$−$C_{100\%}$)+[emission signal ratio×($F_{100\%}$-$F_{0\%}$)]} wherein, the emission signal ratio=coumarin emission signal (460 nm)/fluorescein emission signal (535 nm); $C_{100\%}$=average value of coumarin emission signal in C3; $C_{0\%}$=average value of coumarin emission signal in C1; $F_{100\%}$=average value of fluorescein emission signal in C3; $F_{0\%}$=average value of fluorescein emission signal in C1.

The inhibition ratio is calculated as follows:

Inhibition ratio (%)=100×(phosphorylation ratio in C2−phosphorylation ratio in testing well)/phosphorylation ratio in C2

5. Test Results

| Compound No. | $IC_{50}$ (μM) |
| --- | --- |
| 1 | 0.035 |
| 2 | 0.009 |
| 3 | 0.224 |
| 4 | 0.756 |
| 5 | 0.009 |
| 6 | 0.002 |
| 7 | <0.001 |
| 8 | 0.012 |
| 9 | <0.001 |
| 10 | 0.018 |
| 11 | 0.106 |
| 12 | 0.230 |
| 13 | — |
| 14 | 0.051 |
| 15 | 0.017 |
| 16 | — |
| 17 | — |
| 18 | 0.004 |
| 19 | 0.008 |
| 20 | 0.027 |
| 21 | 0.008 |
| 22 | 0.010 |
| 23 | 0.044 |
| 24 | 0.003 |
| 25 | 0.008 |
| 26 | 0.007 |
| 27 | 0.007 |
| 28 | 0.003 |
| 29 | 0.008 |
| 30 | 0.009 |
| 31 | 0.009 |
| 32 | 0.017 |
| 33 | 0.025 |
| 34 | 0.005 |
| 35 | 0.017 |
| 36 | 0.031 |
| 37 | 0.132 |
| 38 | <0.001 |
| 39 | 0.024 |
| 40 | >3 |
| 41 | 0.012 |
| 42 | 0.269 |
| 43 | 0.009 |
| 44 | 0.022 |
| 45 | 0.011 |
| 46 | 0.008 |
| 47 | 0.003 |
| 48 | 0.004 |
| 49 | 0.006 |
| 50 | 0.024 |
| 51 | 0.01 |
| 52 | 0.018 |
| 53 | 0.033 |
| 54 | 0.015 |
| 55 | 0.019 |
| 56 | 0.020 |
| 57 | 0.006 |
| 58 | 0.008 |
| 59 | 0.005 |
| 60 | 0.004 |
| 61 | 0.004 |
| 62 | 0.021 |
| 63 | 0.008 |
| 64 | 0.020 |
| 65 | 0.014 |
| 66 | 0.011 |
| 67 | 0.082 |
| 68 | 0.005 |
| 69 | 0.007 |
| 70 | 0.010 |
| 71 | 0.006 |
| 72 | 0.058 |
| 73 | 0.216 |
| 74 | 0.017 |
| 75 | 0.011 |
| 76 | 0.123 |
| 77 | 0.441 |
| 78 | 0.008 |
| 79 | <0.001 |
| 80 | 0.005 |
| 81 | 0.008 |
| 82 | 0.006 |
| 83 | 0.013 |
| 84 | 0.009 |
| 85 | 0.011 |
| 86 | 0.016 |
| 87 | 0.011 |
| 88 | 0.134 |
| 89 | 0.011 |
| 90 | 0.026 |
| 91 | 0.017 |
| 92 | 0.010 |
| 93 | 0.049 |
| 94 | 0.007 |
| 95 | 0.010 |
| 96 | 0.007 |
| 97 | 0.009 |
| 98 | 1.269* |
| 99 | 0.006 |
| 100 | 0.005 |
| 101 | 0.006 |
| 102 | 0.011 |
| 103 | >3 |
| 104 | 0.010 |
| 105 | 0.067 |
| 106 | 0.012 |
| 107 | 0.012 |
| 108 | 0.007 |

| Compound No. | IC$_{50}$ (μM) |
|---|---|
| 109 | 0.020 |
| 110 | 0.002 |
| 111 | 0.008 |
| 112 | 0.005 |
| 114 | >3 |
| 115 | 0.012 |
| 116 | 0.010 |
| 117 | 0.004 |
| 118 | 0.005 |
| 119 | 0.007 |
| 120 | 0.008 |
| 121 | 0.023 |
| 122 | <0.001 |
| 123 | 0.013 |
| 124 | 0.006 |
| 125 | 0.033 |
| 126 | 0.026 |
| 127 | 0.010 |
| 130 | 0.316 |
| 131 | 2.007 |
| 132 | 0.051 |
| 133 | 0.033 |
| 134 | 0.059 |
| 135 | 0.008 |
| 136 | 0.004 |
| 137 | 0.006 |
| 138 | 0.218 |
| 139 | 0.039 |
| 140 | <0.001 |
| 141 | 0.014 |
| 142 | 0.051 |
| 143 | 0.004 |
| 144 | 0.018 |
| 145 | 0.033 |
| 146 | 0.624 |
| 147 | 1.563 |
| 148 | 0.112 |
| 149 | 0.019 |
| 150 | 0.012 |
| 151 | 0.002 |
| 152 | 0.353 |
| 153 | 0.117 |
| 154 | 0.008 |
| 155 | 0.122 |
| 156 | 0.006 |
| 157 | 0.016 |
| 158 | 0.194 |
| 159 | 0.006 |
| 160 | 0.003 |
| 161 | 0.004 |
| 162 | 0.001 |
| 163 | 0.008 |
| 164 | 0.012 |
| 165 | 0.004 |
| 166 | 0.035 |
| 167 | 0.016 |
| 168 | 0.028 |
| 169 | 0.060 |
| 170 | 0.018 |
| 171 | 0.013 |
| 172 | 0.041 |
| 173 | 0.080 |
| 174 | 0.002 |
| 175 | 0.071 |
| 176 | 0.003 |
| 177 | 0.006 |
| 178 | 0.006 |
| 179 | 0.019 |
| 180 | 0.016 |
| 181 | 0.012 |
| 182 | 0.008 |
| 183 | 0.025 |
| 184 | 0.077 |
| 185 | 0.013 |
| 186 | 0.014 |
| 187 | 0.014 |
| 188 | 0.041 |
| 189 | 0.039 |
| 190 | 0.029 |
| 191 | 0.011 |
| 192 | 0.009 |
| 193 | 0.012 |
| 194 | 0.065 |
| 195 | 0.038 |
| 196 | 0.002 |
| 197 | 0.066 |
| 198 | 0.004 |
| 199 | 0.008 |
| 200 | 0.004 |
| 201 | 0.005 |
| 202 | 0.008 |
| 203 | <0.001 |
| 204 | 0.011 |
| 205 | 0.015 |
| 206 | 0.013 |
| 207 | 0.011 |
| 208 | 0.004 |
| 209 | 0.011 |
| 210 | 0.021 |
| 211 | 0.017 |
| 212 | 0.010 |
| 213 | 0.015 |
| 214 | 0.031 |
| 215 | 0.031 |
| 216 | 0.011 |
| 217 | 0.008 |
| 218 | 0.006 |
| 219 | 0.004 |
| 220 | 0.005 |
| 221 | 0.008 |
| 222 | 0.008 |
| 223 | >3 |
| 224 | 0.009 |
| 225 | 0.011 |
| 226 | 0.017 |
| 227 | 0.008 |
| 228 | 0.171 |
| 229 | 0.012 |
| 230 | 0.029 |
| 231 | 0.005 |
| 232 | 0.012 |
| 233 | 0.040 |
| 234 | 0.032 |
| 235 | 0.022 |
| 236 | 0.024 |

Example 3

Determination of Phosphorylated BTK in Ramos Cells

1. Reagents and Materials

Ramos cells: Ramos cells were purchased from American Standard Biological Collection Center ATCC Cell Bank, PRMI 1640 medium containing L-glutamine, 1.5 g/L of sodium bicarbonate, 2.383 g/L of HEPES solution, 0.11 g/L of sodium pyruvate and 4.5 g/L of glucose was used, added 10% fetal bovine serum FBS, and placed in a 5% $CO_2$, 37° C. cell incubator for normal culture;

PRMI 1640 medium: GIBCO, Cat #A10491-01;

Fetal bovine serum (FBS): GIBCO, Cat #100100-147;

Hank's balanced salt solution (HBSS): GIBCO, Cat #14025-092;

Immunoglobulin M (IgM): Jackson Immuno, Cat #109-006-129;

3% hydrogen peroxide (3% $H_2O_2$): Sigma, Cat #88597-100ML-F;

Phosphorylated BTK HTRF detection kit (BTK phospho-Y223 HTRF kit): Cisbio, Cat #63ADK017PEH;

Microwell plate reader: Envision, Perkin Elmer;

384-well plate CulturPlate™384: Perkin Elmer, Cat #6007680

96-well plate: Corning, Cat #3799.

2. Methods

Ramos cells were starved in PRMI 1640 medium with 1% FBS for 2 hours. The starved Ramos cells were diluted with Hank's balanced salt solution to $5.0 \times 10^6$ cells/ml, seeded in a 96-well plate with 20 μL/well ($1.0 \times 10^5$ cells/well), and cultured in a 5% $CO_2$, 37° C. cell incubator. After culturing for 1 hour, the test compound was diluted with Hank's balanced salt solution in 4-fold gradient to the corresponding concentrations, and then 5 μL/well of the diluted test compound with different concentrations (the final concentrations of the test compound were 3.0, 0.75, 0.188, 0.047, 0.012, 0.0029, 0.0007 and 0.00018 μM, and the final concentration of DMSO was 0.3%, double replicate wells) or 5 μL/well of control solution (1.5% DMSO, 8 replicate wells) were added to 20 μL/well of cell culture system, which incubated together for another hour, then 5 μL/well of a mixed solution of human immunoglobulin M (final concentration was 10 μg/mL) and hydrogen peroxide (final concentration was 3.3 mM) diluted with Hank's balanced salt solution was added to the treating wells for the test compound and the control treating wells for anti-human immunoglobulin M, and 5 μL/well of Hank's balanced salt solution was added to negative control treating wells. The plate was incubated in a 5% $CO_2$, 37° C. cell incubator for 10 minutes.

10 μL/well of cell lysis buffer was added to each well of a 96-well plate, which was mixed well and lysed at room temperature for 30 minutes. 16 μL/well of lysis buffer was pipetted to a new 384 well plate, and then added 4 μL/well of phosphorylated BTK antibody, centrifuged (1000 rpm) for 1 minute, then shaken for 1 minute, further centrifuged (1000 rpm) for 1 minute, and finally placed in a constant temperature incubator overnight. Detection was performed on the next day.

3. Detection

The 384 well plate incubated overnight in the constant temperature incubator was taken out to detect the luminescence signal using the Envision microwell plate reader at the emission wavelength of 320 nm and excitation wavelength of 665 nm/615 nm. The reading value at 665 nm/615 nm of each well multiplied by 104 was used as the signal value of each well.

4. Calculation

The average signal value of the wells supplemented with the mixed solution of human immunoglobulin M (final concentration was 10 μg/mL) and hydrogen peroxide (final concentration was 3.3 mM) without the test compound was regarded as the high value, and the average signal value of the wells without immunoglobulin M stimulation and without the test compound was regarded as the low value. According to the signal value in each well, the inhibition ratio (%) of each concentration of compounds was calculated, and the 205 model in XL-Fit 5.3 software (ID Business Solutions Limited) was used to obtain an $IC_{50}$ value.

The inhibition ratio is calculated as follows:

inhibition ratio (%)=100%−{(treating well for the test compound−negative control treating well)/(control treating well for anti-human immunoglobulin M−negative control treating well)}× 100%, wherein, Treating well for the test compound: represents the signal value of Ramos cells treated with anti-human immunoglobulin M, hydrogen peroxide and the test compound.

Control treating well for anti-human immunoglobulin M: represents the signal value of Ramos cells treated with anti-human immunoglobulin M, hydrogen peroxide but without the test compound.

Negative control treating well: represents the signal value of Ramos cells without the test compound and without immunoglobulin stimulation.

5. Test Results

| Compound No. | $IC_{50}$ (μM) |
| --- | --- |
| 1 | 0.005 |
| 2 | 0.010 |
| 3 | 0.339 |
| 4 | 0.480 |
| 5 | 0.002 |
| 6 | 0.002 |
| 7 | 0.003 |
| 8 | 0.002 |
| 9 | 0.004 |
| 10 | 0.010 |
| 11 | 0.155 |
| 12 | 0.013 |
| 13 | 0.001 |
| 14 | 0.014 |
| 15 | 0.012 |
| 16 | 0.002 |
| 17 | 0.004 |
| 18 | 0.004 |
| 19 | 0.004 |
| 20 | 0.017 |
| 21 | 0.015 |
| 22 | 0.018 |
| 23 | 0.030 |
| 24 | 0.014 |
| 25 | 0.024 |
| 26 | 0.007 |
| 27 | 0.001 |
| 28 | 0.002 |
| 29 | 0.030 |
| 30 | 0.008 |
| 31 | 0.006 |
| 32 | 0.030 |
| 33 | 0.026 |
| 34 | 0.010 |
| 35 | 0.006 |
| 36 | 0.012 |
| 37 | 0.011 |
| 38 | — |
| 39 | 0.003 |
| 40 | >3 |
| 41 | 0.002 |
| 42 | 0.341 |
| 43 | 0.002 |
| 44 | 0.018 |
| 45 | 0.005 |
| 46 | 0.005 |
| 47 | 0.003 |
| 48 | 0.006 |
| 49 | 0.001 |
| 50 | 0.002 |
| 51 | 0.008 |
| 52 | 0.018 |
| 53 | 0.025 |
| 54 | 0.016 |
| 55 | 0.008 |
| 56 | 0.024 |
| 57 | 0.003 |
| 58 | 0.004 |
| 59 | 0.001 |
| 60 | 0.003 |
| 61 | 0.002 |
| 62 | 0.003 |
| 63 | 0.005 |

| Compound No. | IC$_{50}$ (μM) |
|---|---|
| 64 | 0.010 |
| 65 | 0.002 |
| 66 | 0.002 |
| 67 | 0.060 |
| 68 | 0.002 |
| 69 | 0.002 |
| 70 | 0.002 |
| 71 | 0.006 |
| 72 | 0.097 |
| 73 | 0.116 |
| 74 | 0.011 |
| 75 | 0.007 |
| 76 | 0.060 |
| 77 | 0.132 |
| 78 | 0.003 |
| 79 | 0.002 |
| 80 | 0.002 |
| 81 | 0.002 |
| 82 | 0.002 |
| 83 | 0.013 |
| 84 | 0.011 |
| 85 | 0.002 |
| 86 | 0.006 |
| 87 | 0.003 |
| 88 | — |
| 89 | 0.008 |
| 90 | 0.007 |
| 91 | 0.004 |
| 92 | 0.007 |
| 93 | 0.046 |
| 94 | 0.002 |
| 95 | 0.003 |
| 96 | 0.005 |
| 97 | 0.003 |
| 98 | — |
| 99 | 0.004 |
| 100 | 0.002 |
| 101 | 0.002 |
| 102 | 0.002 |
| 103 | — |
| 104 | 0.006 |
| 105 | 0.011 |
| 106 | 0.001 |
| 107 | 0.002 |
| 108 | 0.001 |
| 109 | 0.004 |
| 110 | 0.002 |
| 111 | 0.002 |
| 112 | 0.003 |
| 113 | — |
| 114 | — |
| 115 | 0.010 |
| 116 | 0.011 |
| 117 | 0.007 |
| 118 | 0.001 |
| 119 | 0.002 |
| 120 | 0.005 |
| 121 | 0.021 |
| 122 | 0.007 |
| 123 | 0.009 |
| 124 | 0.007 |
| 125 | 0.021 |
| 126 | 0.020 |
| 127 | 0.018 |
| 128 | — |
| 129 | — |
| 130 | — |
| 131 | — |
| 132 | 0.028 |
| 133 | 0.013 |
| 134 | 0.054 |
| 135 | 0.005 |
| 136 | 0.005 |
| 137 | 0.004 |
| 138 | — |
| 139 | 0.011 |

| Compound No. | IC$_{50}$ (μM) |
|---|---|
| 140 | 0.011 |
| 141 | 0.013 |
| 142 | 0.060 |
| 143 | 0.005 |
| 144 | 0.038 |
| 145 | 0.016 |
| 146 | — |
| 147 | — |
| 148 | — |
| 149 | 0.008 |
| 150 | 0.012 |
| 151 | 0.028 |
| 152 | — |
| 153 | — |
| 154 | 0.013 |
| 155 | — |
| 156 | 0.012 |
| 157 | 0.025 |
| 158 | — |
| 159 | 0.026 |
| 160 | 0.011 |
| 161 | 0.007 |
| 162 | 0.006 |
| 163 | 0.034 |
| 164 | 0.023 |
| 165 | 0.031 |
| 166 | 0.121 |
| 167 | 0.012 |
| 168 | 0.020 |
| 169 | 0.030 |
| 170 | 0.016 |
| 171 | 0.011 |
| 172 | 0.011 |
| 173 | 0.028 |
| 174 | 0.044 |
| 175 | 0.040 |
| 176 | 0.016 |
| 177 | 0.021 |
| 178 | 0.012 |
| 179 | 0.070 |
| 180 | 0.084 |
| 181 | 0.038 |
| 182 | 0.034 |
| 183 | 0.067 |
| 184 | 0.080 |
| 185 | 0.013 |
| 186 | 0.010 |
| 187 | 0.028 |
| 188 | 0.039 |
| 189 | 0.051 |
| 190 | 0.040 |
| 191 | 0.010 |
| 192 | 0.016 |
| 193 | 0.006 |
| 194 | — |
| 195 | — |
| 196 | 0.007 |
| 197 | — |
| 198 | 0.012 |
| 199 | 0.025 |
| 200 | 0.021 |
| 201 | 0.008 |
| 202 | 0.017 |
| 203 | 0.007 |
| 204 | 0.007 |
| 205 | 0.015 |
| 206 | 0.007 |
| 207 | 0.008 |
| 208 | 0.004 |
| 209 | 0.005 |
| 210 | 0.019 |
| 211 | 0.020 |
| 212 | 0.011 |
| 213 | 0.015 |
| 214 | 0.024 |
| 215 | 0.051 |

-continued

| Compound No. | IC$_{50}$ (μM) |
|---|---|
| 216 | 0.007 |
| 217 | 0.010 |
| 218 | 0.012 |
| 219 | 0.011 |
| 220 | 0.016 |
| 221 | 0.012 |
| 222 | 0.008 |
| 223 | — |
| 224 | 0.007 |
| 225 | 0.009 |
| 226 | 0.011 |
| 227 | 0.005 |
| 228 | 0.139 |
| 229 | 0.010 |
| 230 | 0.020 |
| 231 | 0.004 |
| 232 | 0.008 |
| 233 | 0.008 |
| 234 | 0.010 |
| 235 | 0.013 |
| 236 | 0.004 |

Example 4 Determination of B Cell Activity in Whole Blood of Rats

1. Reagents and Materials

Peripheral whole blood of female Wistar rats;
phosphate buffer PBS: GIBCO, Cat #C20012500BT;
anti-rat B220PE antibody (PE anti-rat B220): eBioscience, Cat #12-0460-82;
anti-rat CD86 FITC antibody (FITC anti-rat CD86): eBioscience, Cat #11-0860-82;
times lysis buffer (10× lysis buffer): BD Biosciences, Cat #555899;
fixation buffer (IC fixation buffer): Invitrogen, Cat #00-8222-49;
96 well U-shaped bottom plate: Nunc, Cat #163320;
96 well V-shaped bottom plate: Nunc, Cat #49952;
dimethyl sulfoxide (DMSO): Sigma-Aldrich, Cat #34869-4L;
anti-rat immunoglobulin D (Mouse Anti-rat IgD): Biorad, Cat #MCA190;
flow cytometer: BD FACS Canto II, BD.

2. Methods

In the determination of the compound activity, the collected peripheral whole blood of rat was added to a 96 well plate at 80 μL/well and cultured in a 5% CO$_2$, 37° C. cell incubator. After half an hour, the test compound was diluted with PBS in a 3-fold gradient to the corresponding concentrations, and then the diluted test compound with different concentrations was added to the culture system of rat whole blood at 10 μL/well (the final concentration of the test compound was 1.0, 0.33, 0.11, 0.037, 0.012, 0.0041, 0.0014, and 0.0005 μM, the final concentration of DMSO was 0.3%, double replicate wells), or the control solution (0.3% DMSO, 6 replicate wells) was added to the corresponding well at 10 μL/well, which were incubated in the cell incubator for one hour. Then 10 μL/well of anti-rat immunoglobulin D diluted in PBS (the final concentration was 10 μg/mL) was add to the treating wells of the test compound and control wells for anti-rat immunoglobulin D, or 10 μL/well of PBS was added to the negative control wells, which were mixed well to continue the culture in a 5% CO$_2$, 37° C. cell incubator, and incubated for 18 hours.

On the second day, the 96-well plates were taken out and the flow cytometry antibody mixture (the final concentration of anti-rat B220PE antibody was 1 μg/mL and the final concentration of anti-rat CD86 FITC antibody was 1 μg/mL) diluted with PBS was added to each well of plate, which were incubated for 30 minutes in the dark, and then 50 μL of blood from each well was pipetted to the freshly prepared 500 μL of lysis buffer to lyse red blood cells. The plates were shaken for 20 minutes, centrifuged to remove the supernatant, then washed, fixed, and detected on a flow cytometer.

3. Detection

The B cell activation in the sample was determined by flow dyeing method.

4. Calculation

The average value of the proportion of activated B cells in the wells with anti-rat immunoglobulin D but without the test compound was used as the control treating well for anti-rat immunoglobulin D, and the average value of the proportion of activated B cells in the wells without immunoglobulin D stimulation and without the test compound was used as the negative control treating well. According to the B cell activation ratio in each well, the inhibition ratio (%) of each concentration was calculated, and then the IC$_{50}$ value was obtained by using the 205 model in XL-Fit 5.3 software (ID Business Solutions Limited).

The inhibition ratio is calculated as follows:

inhibition ratio (%)=100%−{(treating well for the test compound−negative control treating well)/(control treating well for anti-rat immunoglobulin D−negative control treating well)}×100%, wherein, Treating well for the test compound: represents the B cell activation ratio in rat whole blood treated with anti-rat immunoglobulin D and the test compound.

Control treating well for anti-rat immunoglobulin D: represents the B cell activation ratio in rat whole blood treated with anti-rat immunoglobulin D but without the test compound.

Negative control treating well: represents the B cell activation ratio in rat whole blood without the test compound and without immunoglobulin stimulation.

Through the above-mentioned test, the compound of the present invention has a potency to inhibit B cell activation in rat whole blood.

| Compound No. | IC$_{50}$ (μM) |
|---|---|
| 2 | 0.054 |
| 5 | 0.002 |
| 8 | 0.017 |
| 13 | 0.005 |
| 16 | 0.008 |
| 17 | 0.026 |
| 19 | 0.003 |
| 20 | 0.462 |
| 21 | 0.024 |
| 22 | 0.034 |
| 23 | 0.277 |
| 24 | 0.085 |
| 25 | 0.029 |
| 26 | 0.019 |
| 27 | 0.005 |
| 28 | 0.078 |
| 31 | 0.093 |
| 43 | 0.052 |
| 48 | 0.026 |
| 49 | 0.010 |
| 50 | 0.084 |
| 57 | 0.021 |

-continued

| Compound No. | IC$_{50}$ (μM) |
|---|---|
| 58 | 0.006 |
| 59 | 0.019 |
| 60 | 0.034 |
| 63 | 0.044 |
| 64 | 0.052 |
| 71 | 0.092 |
| 75 | 0.085 |
| 78 | 0.041 |
| 79 | 0.006 |

Example 5 Stability Test in Liver Microsomes

1. Experiment Materials:

Both male CD-1 mouse pooled liver microsomes and male SD rat pooled liver microsomes were purchased from BioreclamationIVT Corporation, USA.

Phenacetin, glucose-6-phosphate dehydrogenase (G-6-PDH) and nicotinamide adenine dinucleotide phosphate (NADP) were all purchased from Sigma-Aldrich Corporation, USA. Glucose-6-phosphate (G-6-P) was purchased from Shanghai Eybridge Chemical Technology Co., Ltd.

2. Solution Preparation:

Ten mM test compound stock solution: a certain amount of test compound was weighed, and dissolved with an appropriate volume of DMSO to prepare a stock solution with a concentration of 10 mM for use.

Reaction stopping solution: an appropriate amount of internal standard compound phenacetin was dissolved in acetonitrile to prepare a reaction stopping solution with a concentration of 1000 ng/mL for use at room temperature.

3. Experiment Method:

The test compound stock solution was diluted with an organic solvent (usually a mixture of acetonitrile, methanol and water with various ratios, depending on the solubility of the compound, if necessary, 1 N hydrochloric acid or 1 N sodium hydroxide would be added to facilitate solubilization) to the 0.1 mM (the final concentration of the compound in the reaction system was 1 μM) and the concentration percentage of the organic solvents in the incubation system no more than 1% (wherein the percentage of DMSO was required to be no more than 0.1%). An appropriate amount of 100 mM NADP, 500 mM G-6-P and 100 Unit/mL G-6-PDH were mixed and diluted with ultrapure water (the final system contains 1 mM NADP, 5 mM G-6-P and 1 Unit/mL G-6-PDH), pre-incubated in a 37° C. water bath for 10 minutes and then placed on ice for use as a NADPH regeneration solution. 20 mg/mL liver microsomes solution and 200 mM phosphate buffer was mixed, and diluted with ultrapure water to give a liver microsomes solution containing 2.5 mg/mL liver microsomes (the final concentration of the reaction system is 0.5 mg/mL) and 50 mM phosphate buffer. The diluted liver microsomes solution was mixed with 0.1 mM compound solution, a mixture of 100 mM EDTA, 300 mM MgCl$_2$ solution, 200 mM phosphate buffer (the final system was 3 mM MgCl$_2$, 1 mM EDTA and 50 mM phosphate buffer) and water in an appropriate volume was added. Finally, the NADPH regeneration solution was added, then the reaction solution was placed in a 37° C. water bath to start the reaction (the reaction time was 30 minutes), and the reaction was stopped by adding the ice-cold acetonitrile reaction stopping solution containing the internal standard. The 0-minute sample was not incubated in a 37° C. water bath, and its difference from the 30-minute sample further lies in that the ice-cold acetonitrile reaction stopping solution containing the internal standard was added first, and then the NADPH regeneration solution was added. The sample added with the reaction stopping internal standard solution was vortexed and mixed well, and then centrifuged at 4400 rpm for 10 minutes. The supernatant was taken and diluted ten times with 50% methanol for LC-MS/MS analysis.

4. Analysis Method:

LC-MS/MS was used to determine the concentration of the compound in the sample. The percentage of the remaining compound after 30 minutes of incubation comparing with that in the 0-minute sample was calculated using the peak area ratio of the compound to the internal standard as an indicator, to evaluate the metabolic stability of the compound.

Instrument: API4500, API4000 or LTQ Mass Spectrometer; the liquid phase is UHPLC system (Shimadzu LC-30 AD, model Nexra X2) including liquid delivery unit, column thermostat, detector and autosampler; or Agilent 1200 Binary Pump series HPLC and CTC Autosampler.

Chromatographic column: Waters XSELECT Hss T3 C$_{18}$ (2.5 μm, 2.1×50 mm) or CAPCELLPAK MG (5 μm, 2.0×50 mm)

Mobile Phase:

A: water with 0.1% FA (formic acid) (with or without 0.1% ACN (acetonitrile))

B: acetonitrile with 0.1% FA (formic acid).

As results, the stability of the compounds 2, 9, 19, 22, 34, 44, 56, 58, 63, 64, 74, 75, 78, 79 of the present invention in rat & mouse liver microsomes is better than that of the reference GDC-0853.

| Compound No. | RLM* | MLM** | Compound No. | RLM* | MLM** |
|---|---|---|---|---|---|
| GDC-0853 | 81.0% | 76.3% | 58 | ~100% | 97.1% |
| 2 | 98.9% | 90.5% | 63 | 89.6% | 85.8% |
| 9 | 89.5% | 95.7% | 64 | 92.1% | 95.6% |
| 19 | 92.7% | 91.8% | 74 | 87.7% | 97.5% |
| 22 | 95.6% | 83.4% | 75 | 84.0% | 83.0% |
| 34 | ~100% | 89.5% | 78 | 91.8% | 83.4% |
| 44 | 97.1% | 93.1% | 79 | ~100% | ~100% |
| 56 | 93.7% | 89.5% | | | |

*RLM, rat liver microsomes.
**MLM, mouse liver microsomes.

Example 6 Study on In Vivo Pharmacokinetics in Mice

1. Experiment Materials:

Solutol HS15 was purchased from BASF, Germany, ethanol (anhydrous) was purchased from Nanjing Chemical Reagent Co., Ltd., physiological saline was purchased from Huayu (Wuxi) Pharmaceutical Co., Ltd., dimethyl sulfoxide (DMSO) and sodium carboxymethyl cellulose 800-1200 (CMC-Na) were purchased from Sinopharm Chemical Reagent Co., Ltd.

2. Solution Preparation:

Preparation of ethanol/Solutol mixed solution (1:1, v/v): taking an appropriate amount of Solutol HS15 in a centrifuge tube and placing in a 37° C. water bath until dissolved, placing on the bench top to room temperature, taking 1 mL of Solutol in a centrifuge tube containing 1 mL of ethanol and mixing well to obtain the mixed solution.

Preparation of the formulation for intravenous administration: accurately weighing an appropriate amount of compound 19 powder and GDC-0853 and placing in a centrifuge tube respectively, then adding an appropriate amount of dimethyl sulfoxide, vortexing to completely dissolve to obtain a stock solution. Taking an appropriate amount of stock solution and placing in a blank centrifuge tube, adding an appropriate amount of ethanol/Solutol mixed solution prepared in advance, vortexing, then adding an appropriate amount of physiological saline, and mixing well until a transparent liquid.

Preparation of the formulations for intragastric administration: accurately weighing an appropriate amount of compound 19 powder and GDC-0853 and placing in a centrifuge tube respectively, adding an appropriate amount of CMC-Na whose pH value was adjusted to 2.1 with hydrochloric acid, vortexing and sonicating to a uniform suspension liquid.

3. Administration to Animals and Sample Collection:

Male ICR mice were purchased from Shanghai Lingchang Biotechnology Co., Ltd. 18 mice were randomly divided into intravenous administration group and intragastric administration group. The mice were fasted overnight before administration. The mice were withheld food but allowed to access water freely within 4 hours after administration, and allowed to freely access food and water after 4 hours. After anesthesia with isoflurane, blood was collected from the retroorbital venous plexus and placing in an centrifuge tube containing anticoagulant, and the centrifuge tube was stored in an box containing wet ice until the plasma was centrifuged.

4. Sample Analysis:

The plasma samples were pre-treated and then analyzed by liquid chromatography-tandem mass spectrometry (LC-MS/MS), the instrument model was API5500. The analytical chromatographic column was Waters XSELECT HSS T3 C18 column (50×2.1 mm, 2.5 μm). In the mobile phases, deionized water containing 0.1% formic acid and 0.1% acetonitrile was used as the aqueous phase and acetonitrile containing 0.1% formic acid was used as the organic phase. The concentrations of the compound in the samples were determined as follows. Firstly, a standard curve was established, and the peak area ratios of the compound 19 to the internal standard in the standard curve were used as indexes. The theoretical concentrations of compound 19 and the peak area ratios of compound 19 to the internal standard were fitted with a quadratic regression equation to obtain the regression equation. The sample concentrations were calculated by measuring the peak area ratio of the compound of the test sample to the internal standard according to the standard curve. The concentrations of GDC-0853 in the samples were determined following the same procedure.

5. Data Analysis:

The pharmacokinetic parameters of compound 19 and GDC-0853 in mice were calculated by Thermo Kinetica software using the average drug concentration in plasma at each time point by non-compartmental analysis.

As results, the compound 19 of the present invention has a higher plasma exposure ($AUC_{0-\infty}$) after oral administration in mice, which is about 1.7 times that of the reference GDC-0853. The average value of maximum plasma concentration ($C_{max}$) of compound 19 of the present invention is similar to that of GDC-0853 ($C_{max}$ of compound 19 is 3807 ng/mL, and $C_{max}$ of GDC-0853 is 4063 ng/mL), but compound 19 has a longer elimination half-life ($T_{1/2}$) (the $T_{1/2}$ of compound 19 is 2.7 h, and $T_{1/2}$ of GDC-0853 is 1.5 h). The plasma concentration of compound 19 at 8 h is about 3.9-folds higher than that of GDC-0853 (555 ng/mL for compound 19, and 143 ng/mL for GDC-0853), and the plasma concentration of compound 19 at 24 h can still be detected (the average concentration is 8.5 ng/mL), but the plasma concentration of GDC-0853 at 24 h is below the lower limit of quantification (2.4 ng/mL). The test results are shown in the following Table:

|  | Compound 19 | GDC-0853 |
| --- | --- | --- |
| Dosage (mg/kg) | 10 | 10 |
| $AUC_{0-\infty}$ (ng/mL*h) | 17806 | 10268 |
| $T_{1/2}$ (h) | 2.7 | 1.5 |
| $C_{max}$ (ng/mL) | 3807 | 4063 |
| $C_{8\,h}$ (ng/mL) | 555 | 143 |
| $C_{24\,h}$ (ng/mL) | 8.5 | <2.4 |

Example 7 Evaluation of In Vivo Efficacy of the Compound of the Present Invention in TMD8 Subcutaneous Xenograft Model Objects: To investigate the anti-tumor activity of compound 19 in TMD8 subcutaneous xenograft model in nude mice.

Methods: Human diffuse large B-cell lymphoma cells TMD8 (acquired under license from Tokyo Medical and Dental University) were cultured in RPMI1640 medium containing 10% fetal bovine serum. $1 \times 10^7$ tumor cells suspended in RPMI1640 medium mixed well with Matrigel (purchased from Corning, USA) at 1:1 were implanted subcutaneously on the right flank of each male Balb/c nude mouse (Shanghai Lingchang Biotechnology Co., Ltd.), pretreated with cyclophosphamide (at a dose of 200 mg/kg, intraperitoneal injection 24 h before cell inoculation). When the average tumor volume reached about 400 mm³, animals were randomly assigned to the following groups with 8 animals per group according to the tumor volume: vehicle control, positive reference compound Ibrutinib (Shanghai Tianxi Chemical Co., LTD) (50 mg/kg), reference compound GDC-0853 (10 mg/kg), compound 19 (10 mg/kg and 30 mg/kg). Ibrutinib was formulated in 0.5% sodium methylcellulose solution, and GDC-0853 and compound 19 were prepared in 0.5% hydroxypropyl methylcellulose solution (pH=3). All drugs were administered by oral gavage, once a day, and the vehicle control group was administered orally with 0.5% hydroxypropyl methylcellulose solution (pH=3).

Tumor volumes (tumor volume=0.5×long diameter×short diameter²) and body weights of the mice were measured regularly. The tumor volume change and body weight were statistically analyzed, with p<0.05 considered statistically significant, and p<0.01 as extremely statistically significant.

The anti-tumor activity was evaluated by tumor growth inhibition.

Tumor growth inhibition (TGI %)=100%×(1−
($TV_{Dt\,(treatment\,group)} - TV_{D0\,(treatment\,group)}$)/
($TV_{Dt\,(control\,group)} - TV_{D0\,(control\,group)}$))

Relative body weight (RBW %)=$BW_{Dt}/BW_{D0} \times 100\%$ wherein, $TV_{D0}$ represents the tumor volume obtained at first measurement, namely, the tumor volume before drug administration, and $TV_{Dt}$ represents the tumor volume on the day of measurement; $BW_{D0}$ represents the body weight of the animal obtained at first measurement, namely, the body weight of the animal before drug administration; $BW_{Dt}$ represents the body weight of the animal on the day of measurement.

Results: The experimental results were shown in Table 1 and FIG. 1.

21 days after treatment, compared with the vehicle control group, ibrutinib at 50 mg/kg led to a 42.4% reduction in tumor growth; GDC-0853 at 10 mg/kg was associated with a TGI of −12.8%. Compound 19 of the present invention showed a dose-dependent anti-tumor efficacy with TGIs of 76.5% and 114% at 10 mg/kg and 30 mg/kg, respectively, which had extremely significant statistical difference compared with the vehicle control group. All 8 mice in the compound 19 (30 mg/kg) treated group showed complete tumor regression (CR) on Day 21. Therefore, compound 19 exhibited statistically significant superior efficacy to Ibrutinib or GDC-0853 at tested dose in TMD-8 model. In addition, the tumor volume changes in the two dose groups of compound 19 had statistically significant or extremely significant difference compared with the two references, indicating that compound 19 of the present invention exhibited significantly superior anti-tumor efficacy to the two references at the tested doses. In addition, the tumor volume changes in the two dose groups of compound 19 had statistically significant or extremely significant statistical difference compared with the two references, indicating that the anti-tumor effect of compound 19 of the present invention is significantly better than that of the two reference compounds at the tested doses. In this experiment, no body weight loss was observed in mice regardless of treatment, indicating that all the compounds at tested doses were well tolerated.

The results showed that compound 19 of the present invention displayed a dose-dependent anti-tumor activity in the TMD8 subcutaneous xenograft model, and complete tumor regression would be achievable by continuous daily dosing of compound 19 at 30 mg/kg.

TABLE 1

The effect of each compound on the growth of TMD8 subcutaneous transplantation xenograft model

| Groups | Tumor volume (mm$^3$) ± SD Day 0 | Tumor volume (mm$^3$) ± SD Day 21 | TGI (%) | Number of animals with CR (Day 21) | RBW (%) (Day 21) |
|---|---|---|---|---|---|
| Vehicle group | 403 ± 40 | 3229 ± 1227 | — | — | 116.0 |
| Ibrutinib 50 mg/kg | 397 ± 42 | 2027 ± 991 | 42.4 | 1 | 111.4 |
| GDC-0853 10 mg/kg | 397 ± 46 | 3585 ± 494 | −12.8 | 0 | 115.5 |
| Compound 19 10 mg/kg | 400 ± 41 | 1065 ± 763**, #, $$ | 76.5 | 0 | 111.0 |
| Compound 19 30 mg/kg | 396 ± 47 | 0 ± 0**, #, $$ | 114 | 8 | 109.8 |

Compared with the vehicle group: **p < 0.01;
Compared with ibrutinib treatment group: #p < 0.05, ##p < 0.01;
Compared with GDC-0853 treatment group: $$p < 0.01.

Example 8 Evaluation for in vivo efficacy of the inhibitory effect on BTK target Objects: B cells in mice whole blood were induced and activated by the anti-IgD antibody, and the inhibitory effect of the compound of the present invention on B cell activation in vivo was studied, so as to determine the inhibitory effect of the compound of the present invention on the BTK target in vivo.

Methods: C57BL/6 mice (female, 18-20 g, purchased from Shanghai Lingchang Biotechnology Co., Ltd.) were grouped according to Table 2.

TABLE 2

Grouping information of in vivo administration

| Groups | Dosage (mg/kg) | Number of animals | Vehicle | Mode of administration | Administration volume | Time for blood collection after administration | Dosage form |
|---|---|---|---|---|---|---|---|
| Vehicle group | 0 | 6 | 0.5% HPMC, pH = 3 | Oral gavage, single administration | 10 mL/kg in weight | 16 h | — |
| GDC-0853 | 20 | 3 | | | | 16 h | Solution |
| Compound 232 | 20 | 3 | | | | 16 h | Solution |

The animals of each group were administered, then were placed in $CO_2$ for anesthesia at designated time points, blood samples were taken from rats via retro-orbital bleeding, and heparin was used for anticoagulation; 90 μL of whole blood was taken from mice of each group, and added to a 96 well culture plate, and anti-mouse IgD antibody (BIO-RAD, Cat #MCA4693) was added to each well to a final concentration of 0.01 μg/μL (respectively for the each drug-treated group and anti-IgD antibody-inducted vehicle group); in addition, 90 μL of whole blood of mice in the vehicle group was taken and added to the 96-well culture plate, and PBS (phosphate buffer, GIBCO, Cat #C20012500BT) was added to each well to a final concentration of 0.01 μg/μL (namely, the vehicle control group); Each group was mixed well and incubated in a 37° C./5% $CO_2$ incubator for 4 hours. In addition, the blood of mice in the drug-treated group was centrifuged to separate plasma for blood concentration analysis.

The cultured whole blood was added with fluorescently labeled antibodies including anti-CD19-APC (BD Biosciences, Cat #550992) and anti-CD69-PE (BD Biosciences, Cat #553237), mixed well, and incubated at room temperature in the dark for 30 minutes; 50 μL of the sample was transferred to a 96-well deep V-shaped culture plate containing 380 μL of fresh lysis buffer (BD Biosciences, Cat #555899), shaken, and placed at room temperature in the dark for 15 minutes to remove red blood cells; which was added with 400 μL of FACS buffer (2% FBS/PBS, FBS: fetal bovine serum, GIBCO, Cat #100100-147; PBS: GIBCO, Cat #C20012500BT), centrifuged at 1200 rpm at 4° C. for 8 minutes; the supernatant was removed, the cell clumps were washed twice with FACS buffer, and centrifuged; then the cells were resuspended with 400 μL of FACS buffer, the expression of CD69+ in CD19+ positive cells (B cells) was detected using BD FACS LSRFortessa flow cytometer and the data was analyzed.

Calculation for B Cell Activation Ratio:

B cell activation ratio=percentage of CD69+CD19+ double positive B cells/percentage of CD19+ single positive B cells Calculation for Inhibition Ratio:

Inhibition ratio=(percentage of B cell activation ratio in anti-IgD antibody-induced vehicle group-percentage of B cell activation ratio in drug-treated group)/(percentage of B cell activation ratio in anti-IgD antibody-induced vehicle group-percentage of B cell activation ratio in vehicle control group)×100%

All data are represented by mean±standard error. For the comparison between each drug-treated group and the anti-IgD antibody-induced vehicle group, p value was calculated by Graphpad Prism using one-way ANOVA analysis of variance and Dunnett's test, and for the comparison between each drug-treated group, p value was calculated by using unpaired t test.

Figure 2:
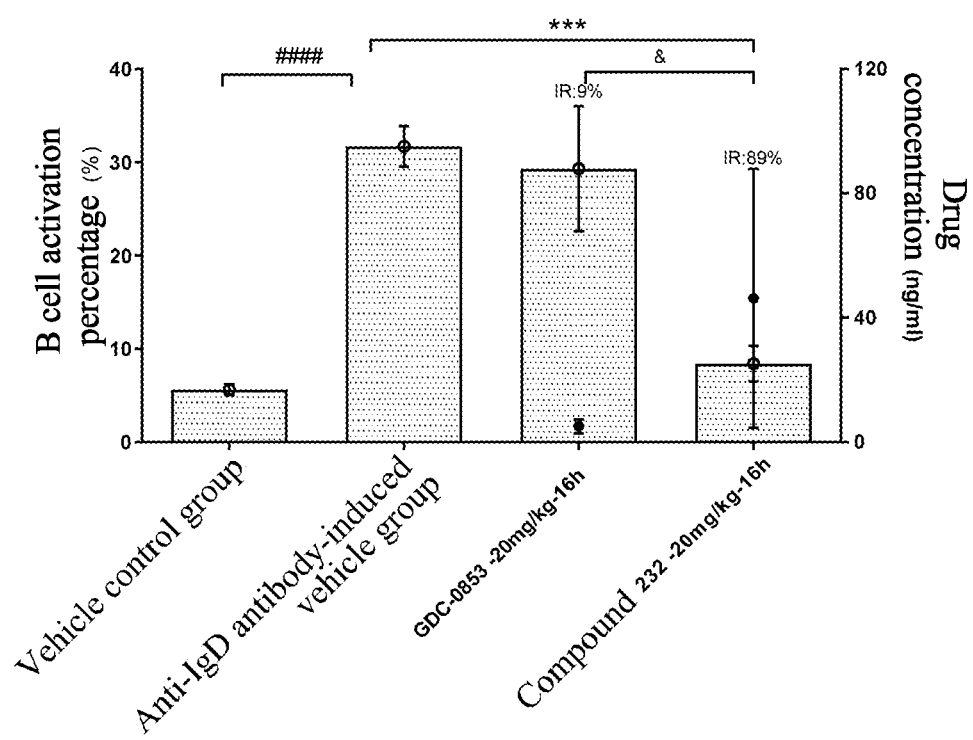
FIG. 2: The inhibiting effect of the compounds of the present invention on B cell activation in mouse whole blood induced by anti-IgD antibodies.

Results: The experimental results are shown in FIG. 2 and Table 3.

In this experiment, after 16 hours of administration, the inhibition ratio of GDC-0853 20 mg/kg on B cell activation is 9%. The inhibition ratio of the compound 232 of the present invention at a dose of 20 mg/kg on B cell activation is 89%, which has a significantly statistical difference compared with the anti-IgD antibody-induced vehicle group.

TABLE 3

Effect of in vivo administration on anti-IgD antibody-induced B cell activation in mice whole blood

| Groups | Dosage (mg/kg) | Time (h) | B cell activation ratio (the proportion of activated B cells to total B cells) | Inhibition ratio (%) | Drug concentration in plasma (ng/mL) |
|---|---|---|---|---|---|
| Vehicle control group | / | 16 | 5.6 ± 0.6 | 100% | / |
| Anti-IgD antibody-inducted vehicle group | / | 16 | 31.7 ± 2.2[####] | 0% | / |
| GDC-0853 | 20 | 16 | 29.3 ± 6.7 | 9% | 5.01 ± 2.26 |
| Compound 232 | 20 | 16 | 8.4 ± 1.9[***&] | 89% | 76.2 ± 41.7 |

[####] represents $p < 0.0001$ compared with the vehicle control group;
[***] represents $p < 0.001$ compared with the anti-IgD antibody-induced vehicle group;
[&] represents $p < 0.05$ compared with the reference GDC-0853-treated group.

According to the above-mentioned method, the inhibitory effect on BTK target in vivo was further measured between compound 19 and compound 176 (referred to "reference compound 176") in PCT patent application WO 2013067274, and grouping was performed according to table 4 below.

TABLE 4

Grouping information of in vivo administration

| Groups | Dosage (mg/kg) | Number of animals | Vehicle | Mode of administration | Administration volume | Time for blood collection after administration | Dosage form |
|---|---|---|---|---|---|---|---|
| Vehicle group | 0 | 6 | 0.5% HPMC, pH = 3 | Oral gavage, single administration | 10 mL/kg in weight | 16 h | — |
| Reference compound 176 | 5 | 3 | | | | 16 h | Solution |
| Compound 19 | 5 | 3 | | | | 16 h | Solution |

Figure 3:
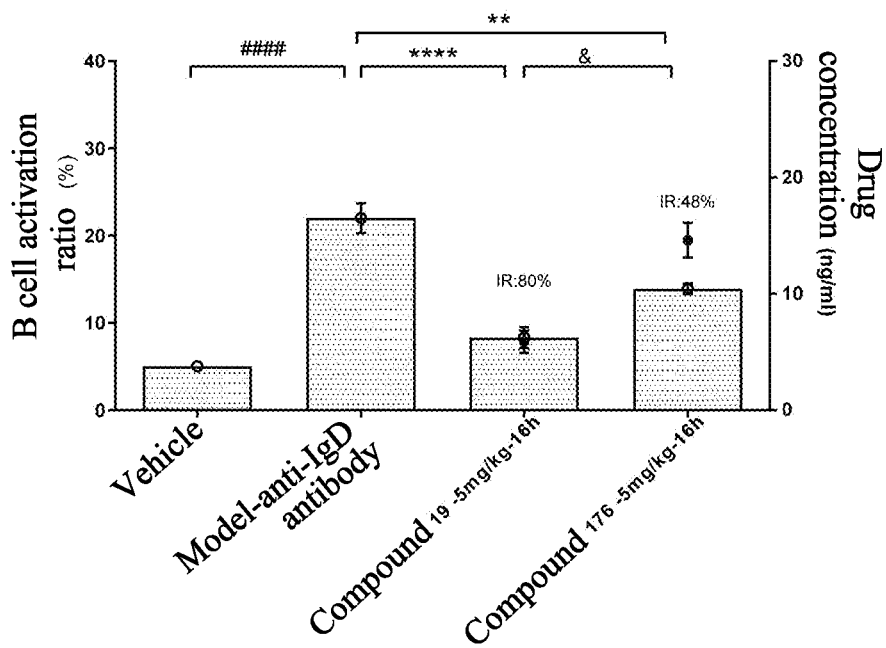
FIG. 3: The inhibiting effect of the compounds of the present invention on B cell activation in mouse whole blood induced by anti-IgD antibodies.

Results: The experimental results are shown in FIG. 3 and Table 5.

In this experiment, after 16 hours of administration, the inhibition ratio of reference compound 176 at a dose of 5 mg/kg on B cell activation is 48%; The inhibition ratio of the compound 19 of the present invention at a dose of 5 mg/kg on B cell activation is 80%, which has a remarkable statistical difference compared with the anti-IgD antibody-induced vehicle group.

TABLE 5

Effect of in vivo administration on anti-IgD antibody-induced B cell activation in mice whole blood

| Groups | Dosage (mg/kg) | Time (h) | B cell activation ratio (the proportion of activated B cells to total B cells) | Inhibition ratio (%) |
|---|---|---|---|---|
| Vehicle control group | / | 16 | 5.0 ± 0.5 | 100% |
| Anti-IgD antibody-inducted vehicle group | / | 16 | 22.0 ± 1.7[####] | 0% |
| Compound 19 | 5 | 16 | 8.3 ± 1.2[****] | 80% |
| Reference compound 176 | 5 | 16 | 13.9 ± 0.6[**&] | 48% |

[####] represents $p < 0.0001$ compared with the vehicle control group;
[**] represents $p < 0.01$ compared with the anti-IgD antibody-induced vehicle group;
[****] represents $p < 0.0001$ compared with the anti-IgD antibody-induced vehicle group;
& represents $p < 0.05$ compared with compound 19-treated group.

Example 9 Therapeutic Effect of the Compound of the Present Invention on a Rat Arthritis Model Induced by Type II Collagen Study Methods An appropriate amount of bovine type II collagen (CII, Chondrex (Redmond, Wash., USA), Cat #20021) was weighed and dissolved in 0.1 mole of acetic acid (SPGC Sinopharm Chemical Reagent Co., Ltd (Shanghai, P. R. China), Cat #: 10000218.), which was formulated into a solution with a concentration of 6 mg/mL, stirred at 4° C. overnight, and added with an equal volume of Freund's incomplete adjuvant (Sigma-Aldrich. (St. Louis, Mo., USA), Cat #: SLBW0366.), fully emulsified to prepare an emulsion with a CII concentration of 3 mg/mL.

Female Lewis rats were purchased from Beijing Vital River Laboratory Animal Technology Co., Ltd (certificate number 1100111911070522, initial body weight of 110-130 grams), and 3 rats were randomly selected as normal group, and the remaining rats were grouped according to the following table. In the first immunization on day 0, the rats except that in the normal group were anesthetized with isoflurane (Hebei Yipin Pharmaceutical Co., Ltd., Lot: C002170601.), and then disinfected with 75% alcohol. 0.2 mL of emulsion was injected intradermally at the base of the tail thereof. A second challenge was carried out on day 7, and 0.2 mL of emulsion was intradermally injected using the same method.

TABLE 6

Grouping Information of modeling administration

| Groups | Modeling | Dosage of administration | Mode of administration | Number of animals | Vehicle |
|---|---|---|---|---|---|
| Normal group | / | / | / | 3 | / |
| Vehicle control group | Day 0 and Day 7, 600 µg CII + IFA | 0 mg/kg | Once a day, from Day 0 to Day 19 | 8 rats in each group | 0.5% HPMC-Na pH 3 |
| GDC-0853-4 | | 4 mg/kg | | | |
| Compound 19-0.06 | | 0.06 mg/kg | | | |
| Compound 19-0.25 | | 0.25 mg/kg | | | |
| Compound 19-1 | | 1 mg/kg | | | |
| Compound 19-4 | | 4 mg/kg | | | |
| Compound 19-16 | | 16 mg/kg | | | |

After grouping and modeling, the normal group was not administered, and the rats in the other groups were administered with the control vehicle, 4 mg/kg of the reference GDC-0853, and each dose of compound 19 orally once a day until the end of the experiment. Grouping and dosage regimen are shown in Table 6.

The paw volume was measured on day 8 after immunization, and the left and right hind paw volumes (V) were measured every day after the paw volume increase was detected.

The arthrosis paw volumes of the left and right hind limbs of each animal were measured, and the average paw volume (APV, which shows the swelling change of the paw of the animal) was calculated according to the following formula:

Average paw volume APV=$(V_{left}+V_{right})/2$

Effect of drugs on the average paw volume was subjected to significance analysis by GraphPad with repeated measure ANOVA and Dunnett's multiple comparisons test, and the p value was calculated, wherein #P<0.01 indicated that there was a significant difference compared with the normal group, and **p<0.01 indicated that there was a significant difference compared with the vehicle control group.

The average arthrosis paw volume of each animal before administration was used as the baseline (or considered 100% inhibition of inflammation). The averaged paw swelling (APS) of each animal is calculated according to the following formula, wherein, $APV_{d1}$ is the average paw volume of the animal administered on day 1, and $APV_{dt}$ is the average paw volume of the animal administered on day t:

The averaged paw swelling $APS_{dt}=(APV_{dt}-APV_{d1})$

The area under the curve (AUC) of the average paw volume change is the area under the curve of the arthrosis score change calculated by the trapezoid method, and the calculation formula is:

$AU_{Cpaw\ volume}=1/2\times(APS_{d1}+APS_{d2})\times(d_2-d_1)+1/2\times(APS_{d2}+APS_{d3})\times(d_3-d_2)+\ldots+1/2\times(APS_{dn}+APS_{d(n-1)})\times(d_n-d_{n-1})$ $ED_{50}$ is calculated by XLfit software according to the AUC inhibition ratio of the area under the curve of the average paw volume change. The selected model is "log (inhibitor) vs. response–Variable slope":

$$y = A + \frac{B-A}{1+\left(\frac{C}{x}\right)^D}.$$

Results

Figure 4:
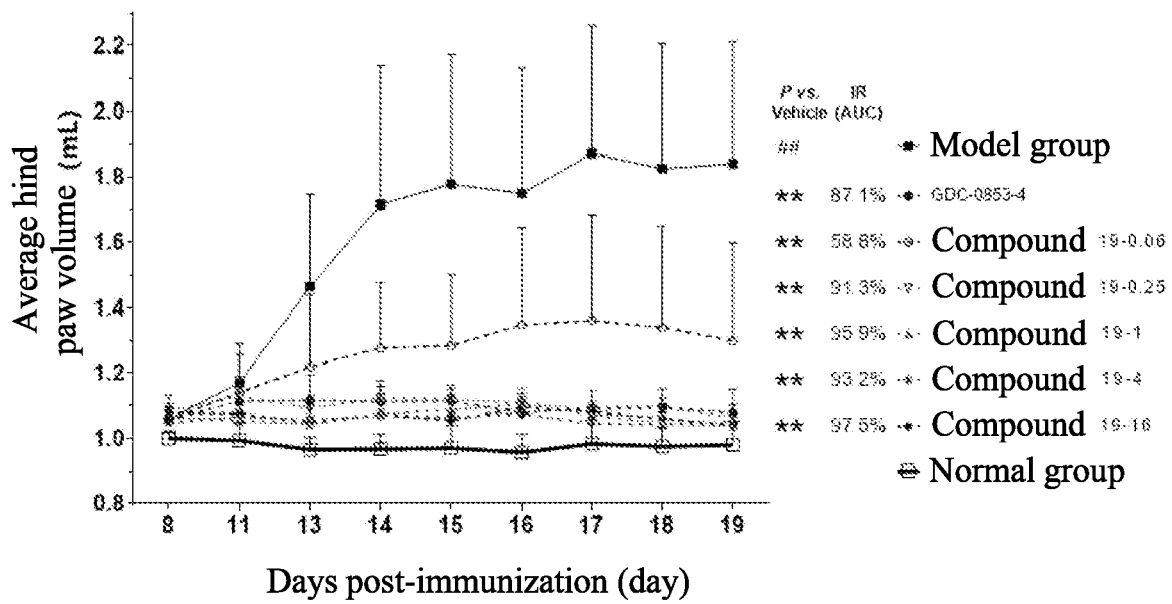
FIG. 4: Effects of the compounds of the present invention on the arthrosis paw volume in CIA (collagen induced arthritis) rats (the hind paw volume was measured by a Paw Volume Meter, the data were represented by mean±standard error, and each group respectively represented a normal group, a vehicle control group (i.e., the model group in the figure), compound 19 QD groups in different doses, and a 4 mg/kg GDC-0853 group (normal group: n=3, other groups: n=8)).

Lewis rats started to develop symptoms on day 11 after the first immunization with bovine type II collagen, and the paw volume of the right hind limb gradually increased with the developing of course of the disease. The paw volume increase of the rat in the vehicle control group was compared with that in the normal group, there was a statistically significant difference (##p<0.01). The paw volume of the rat with GDC-0853 was significantly reduced (**p<0.01) compared with that in the vehicle control group. Oral administration of 0.06, 0.25, 1, 4 and 16 mg/kg QD of compound 19 solution once a day dose-dependently inhibited paw swelling, and the inhibition ratios of area under the curve were 58.8%, 91.3%, 95.9%, 93.2% and 97.5%, respectively; The minimum effective dose was 0.06 mg/kg/day, with $ED_{50}$<0.06 mg/kg/day, $ED_{90}$=0.26 mg/kg. 0.25 mg/kg/day of compound 19 (inhibition ratio of area under the curve was 91.3%) has the similar efficacy to 4 mg/kg/day of GDC-0853 (inhibition ratio of area under the curve was 87.1%), there was no statistical difference between the two groups, and both of the compounds can significantly improve paw volume swelling compared with the model group (p<0.001, paired t test by Graphpad). There was a statistical difference between 4 mg/kg/day of compound 19 (inhibition ratio of area under the curve was 93.2%) and the same dose of GDC-0853 (inhibition ratio of area under the curve was 87.1%), and the compound 19 significantly increased the improvement in paw volume swelling (p<0.001, paired t test by Graphpad). The results are as shown in FIG. 4.

The invention claimed is:

1. A compound of the following formula:

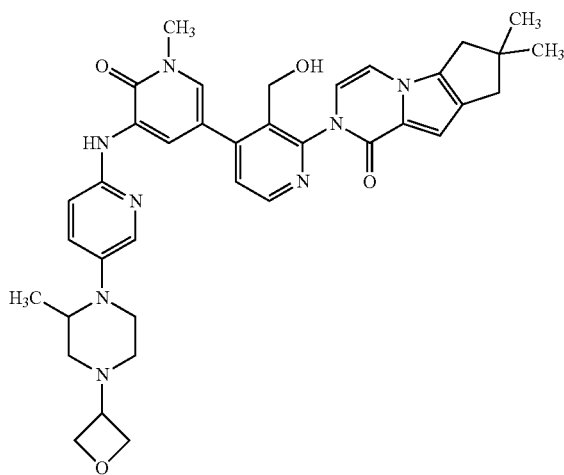

or a pharmaceutically acceptable salt, stereoisomer, or deuterated isotope thereof.

2. A pharmaceutical composition comprising a pharmaceutically acceptable excipient and the compound of claim 1, or a pharmaceutically acceptable salt, stereoisomer, or deuterated isotope thereof.

3. The pharmaceutical composition of claim 2, wherein the pharmaceutical composition further comprises one or more additional therapeutic agents.

4. The pharmaceutical composition of claim 3, wherein the one or more additional therapeutic agents are selected from the group consisting of an anti-inflammatory agent, an anti-tumor active agent, and an immunomodulator.

5. The pharmaceutical composition of claim 4, wherein the anti-tumor active agent is selected from the group consisting of a chemotherapeutic agent, an immune checkpoint agonist, an immune checkpoint inhibitor, and a targeted therapeutic agent.

6. A compound of the following formula:

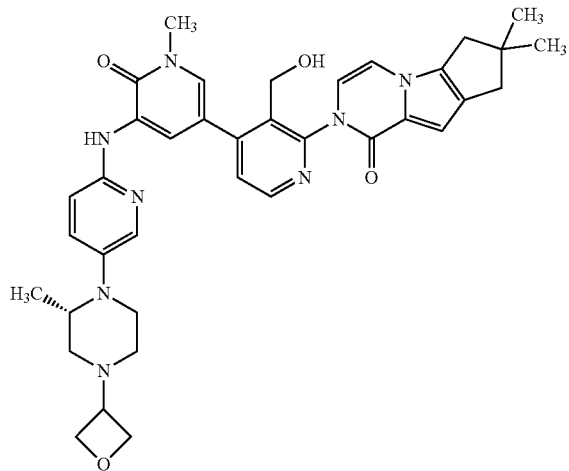

or a pharmaceutically acceptable salt or deuterated isotope thereof.

7. A pharmaceutical composition comprising a pharmaceutically acceptable excipient and the compound of claim 6, or a pharmaceutically acceptable salt or deuterated isotope thereof.

8. The pharmaceutical composition of claim 7, wherein the pharmaceutical composition further comprises one or more additional therapeutic agents.

9. The pharmaceutical composition of claim 8, wherein the one or more additional therapeutic agents are selected from the group consisting of an anti-inflammatory agent, an anti-tumor active agent, and an immunomodulator.

10. The pharmaceutical composition of claim 9, wherein the anti-tumor active agent is selected from the group consisting of a chemotherapeutic agent, an immune checkpoint agonist, an immune checkpoint inhibitor, and a targeted therapeutic agent.

11. A pharmaceutically acceptable salt of a compound of the following formula:

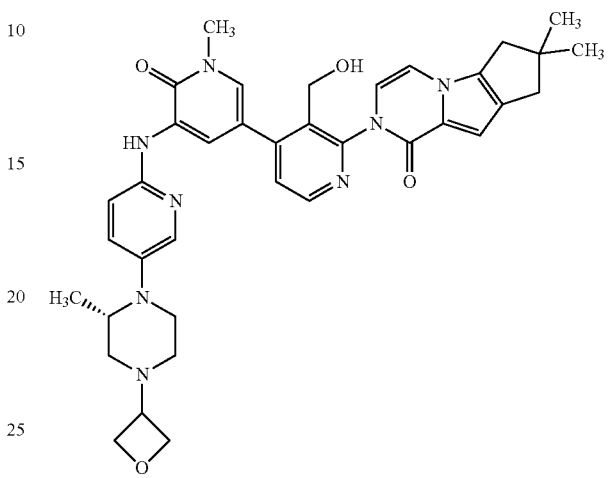

or a deuterated isotope thereof.

12. A pharmaceutical composition comprising a pharmaceutically acceptable excipient and the pharmaceutically acceptable salt of the compound of claim 11, or a deuterated isotope thereof.

13. The pharmaceutical composition of claim 12, wherein the pharmaceutical composition further comprises one or more additional therapeutic agents.

14. The pharmaceutical composition of claim 13, wherein the one or more additional therapeutic agents are selected from the group consisting of an anti-inflammatory agent, an anti-tumor active agent, and an immunomodulator.

15. The pharmaceutical composition of claim 14, wherein the anti-tumor active agent is selected from the group consisting of a chemotherapeutic agent, an immune checkpoint agonist, an immune checkpoint inhibitor, and a targeted therapeutic agent.

* * * * *

UNITED STATES PATENT AND TRADEMARK OFFICE
CERTIFICATE OF CORRECTION

PATENT NO. : 11,478,474 B2
APPLICATION NO. : 17/506220
DATED : October 25, 2022
INVENTOR(S) : Guangxiu Dai and Kun Xiao Page 1 of 4

It is certified that error appears in the above-identified patent and that said Letters Patent is hereby corrected as shown below:

In the Specification

In Column 38, Line 47:
"$R_1$" should be changed to "$R_{11}$".

In Column 55, the structure of Compound 19:

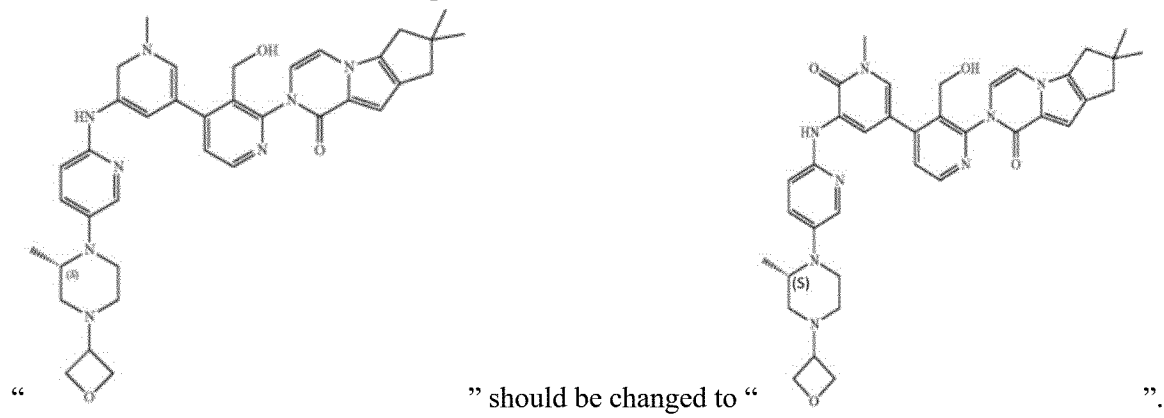

Signed and Sealed this
Eleventh Day of June, 2024

Katherine Kelly Vidal
*Director of the United States Patent and Trademark Office*

CERTIFICATE OF CORRECTION (continued)
U.S. Pat. No. 11,478,474 B2

In Column 55, the structure of Compound 20:

" 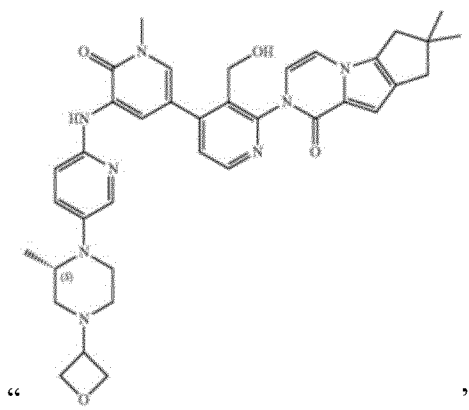 " should be changed to " 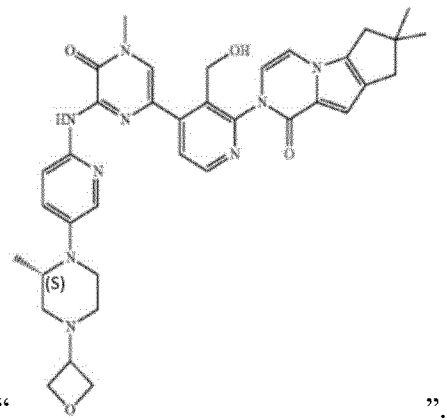 ".

In Column 57, the structure of Compound 22:

" 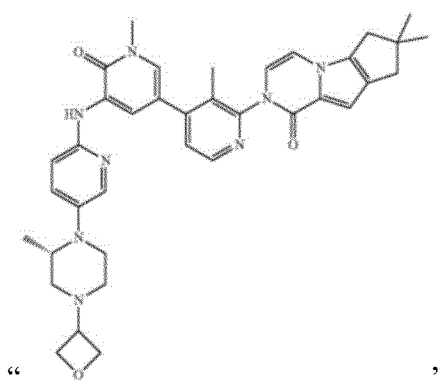 " should be changed to " 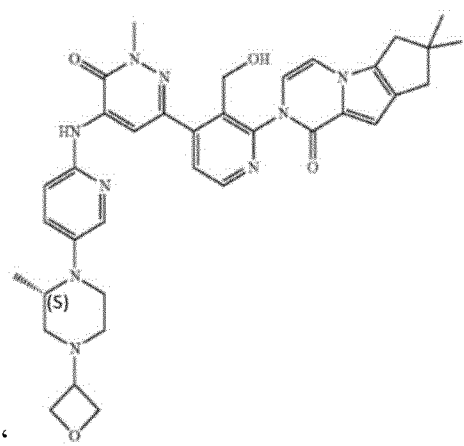 ".

In Column 59, the structure of Compound 24:

" 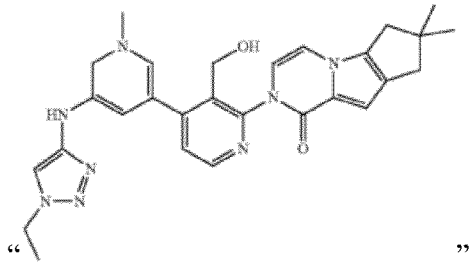 " should be changed to " 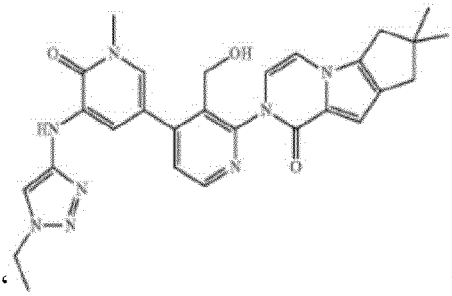 ".

CERTIFICATE OF CORRECTION (continued)
U.S. Pat. No. 11,478,474 B2

Page 3 of 4

In Column 59, the structure of Compound 25:

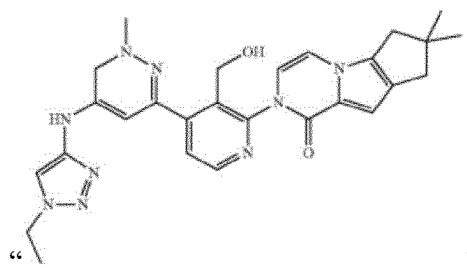  " should be changed to " 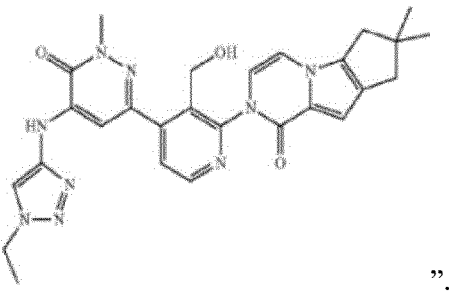 ".

In Columns 361 and 362, the structure of Compound 5:

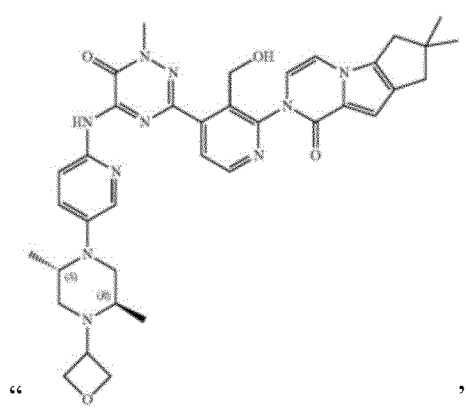  " should be changed to " 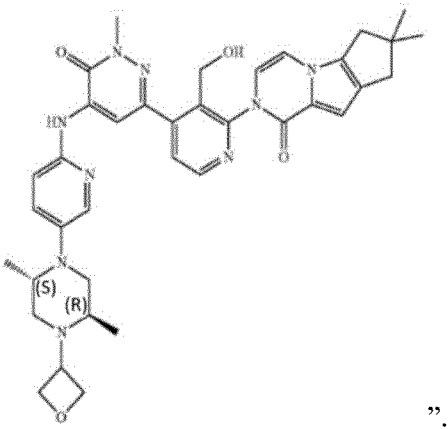 ".

In Columns 363 and 364, the structure of Compound 6:

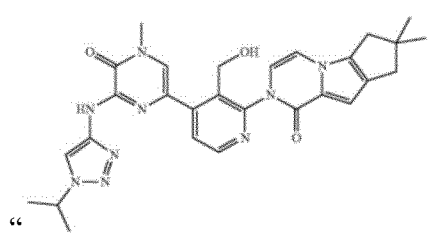  " should be changed to " 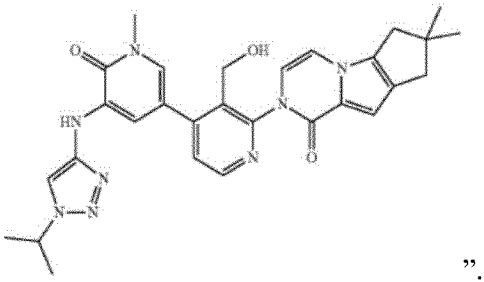 ".

CERTIFICATE OF CORRECTION (continued)
U.S. Pat. No. 11,478,474 B2

Page 4 of 4

In Columns 363 and 364, the structure of Compound 8:

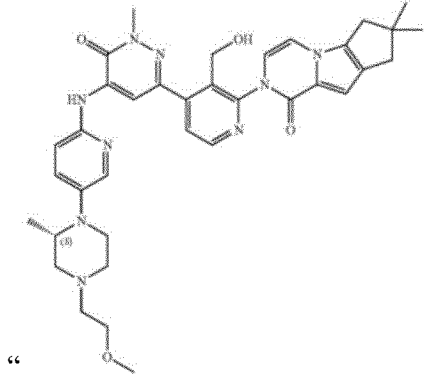 " should be changed to " 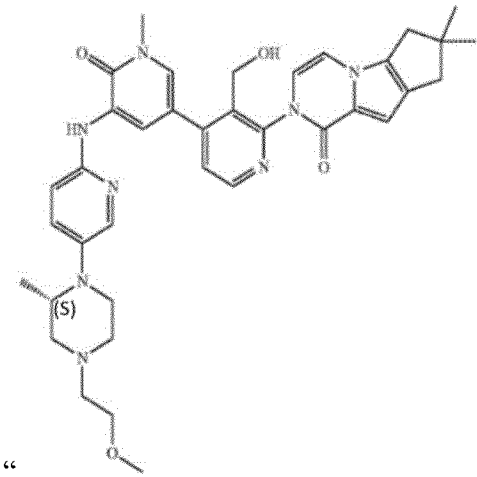 ".

In Columns 383 and 384, the structure of Compound 42:

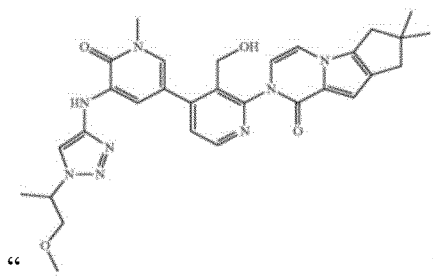 " should be changed to " 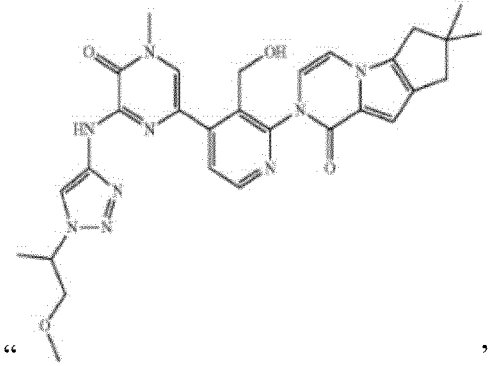 ".

In Column 515, Lines 45-65, the structure of Compound 223:

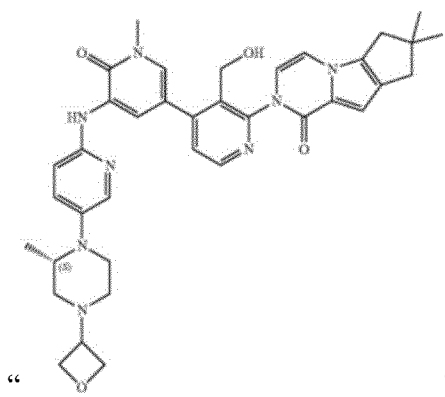 " should be changed to " 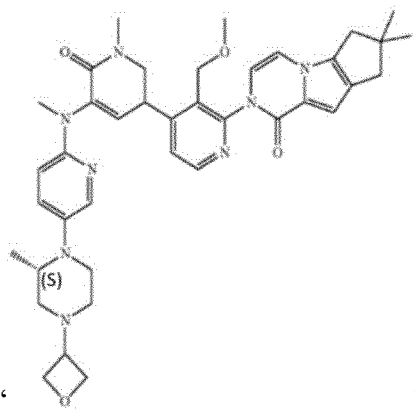 ".